US011529407B2

(12) United States Patent
Rümenapf et al.

(10) Patent No.: US 11,529,407 B2
(45) Date of Patent: Dec. 20, 2022

(54) ISOLATION OF A NOVEL PESTIVIRUS CAUSING CONGENITAL TREMOR A

(71) Applicant: VETERINÄRMEDIZINISCHE UNIVERSITÄT WIEN, Vienna (AT)

(72) Inventors: Hans Tillmann Rümenapf, Vienna (AT); Benjamin Lamp, Vienna (AT); Lukas Schwarz, Vienna (AT)

(73) Assignee: VETERINÄRMEDIZINISCHE UNIVERSITÄT WIEN, Vienna (AT)

( * ) Notice: Subject to any disclaimer, the term of this patent is extended or adjusted under 35 U.S.C. 154(b) by 472 days.

(21) Appl. No.: 16/472,846

(22) PCT Filed: Dec. 22, 2017

(86) PCT No.: PCT/EP2017/084453
§ 371 (c)(1),
(2) Date: Jun. 21, 2019

(87) PCT Pub. No.: WO2018/115474
PCT Pub. Date: Jun. 28, 2018

(65) Prior Publication Data
US 2021/0308248 A1    Oct. 7, 2021

Related U.S. Application Data

(60) Provisional application No. 62/437,888, filed on Dec. 22, 2016.

(51) Int. Cl.
| | | |
|---|---|---|
| *A61K 39/12* | (2006.01) | |
| *C12N 7/02* | (2006.01) | |
| *C12N 15/86* | (2006.01) | |
| *C12N 7/00* | (2006.01) | |
| *A61K 39/00* | (2006.01) | |

(52) U.S. Cl.
CPC ............... *A61K 39/12* (2013.01); *C12N 7/00* (2013.01); *C12N 15/86* (2013.01); *A61K 2039/5252* (2013.01); *A61K 2039/5254* (2013.01); *A61K 2039/552* (2013.01); *C12N 2770/24334* (2013.01); *C12N 2770/24341* (2013.01)

(58) Field of Classification Search
None
See application file for complete search history.

(56) References Cited

U.S. PATENT DOCUMENTS

| | | |
|---|---|---|
| 2010/0203063 A1 | 8/2010 | Frost et al. |
| 2011/0117126 A1 | 5/2011 | Meyers et al. |
| 2013/0039946 A1 | 2/2013 | Meyers et al. |

FOREIGN PATENT DOCUMENTS

| | | |
|---|---|---|
| WO | 2007/121522 | 11/2007 |

OTHER PUBLICATIONS

KP941585, Bovine viral diarrhea virus 2 strain USMARC-55476 polyprotein gene, complete cds, 2015.*
Ad de Groof, et al., "Atypical Porcine Pestivirus: A Possible Cause of Congenital Tremor Type A-II in Newborn Piglets," Viruses 2016, 8(12):271 (2016), 13 pages.
International Search Report, corresponding International Patent Application No. PCT/EP2017/084453, dated Mar. 22, 2018, 5 pages.
International Written Opinion, corresponding International Patent Application No. PCT/EP2017/084453, dated Mar. 22, 2018, 5 pages.
Glotov AG et al., Agricultural Biology, 2015, vol. 50, No. 4, pp. 399-408.
Kumar R et al, Veterinary World, 2015, vol. 8, No. 9, pp. 1059-1062.
Schwarz et al., "Congenital infection with atypical porcine pestivirus (APPV) is associated with disease and viral persistence", Vet Res (2017) 48:1 DOI 10.1186/s13567-016-0406-1. (14 pages).

* cited by examiner

*Primary Examiner* — Benjamin P Blumel
(74) *Attorney, Agent, or Firm* — Loza & Loza, LLP; Michael F. Fedrick

(57) ABSTRACT

The present invention relates to a new pestivirus useful in the fields of veterinary virology and vaccines. Specifically, it relates to an isolated polynucleotide originating from pestivirus and a pestivirus, to vaccines and medical uses thereof, to chimeric virus comprising the polynucleotide and to expression vectors for heterologous expression of polypeptides.

Figure 3:
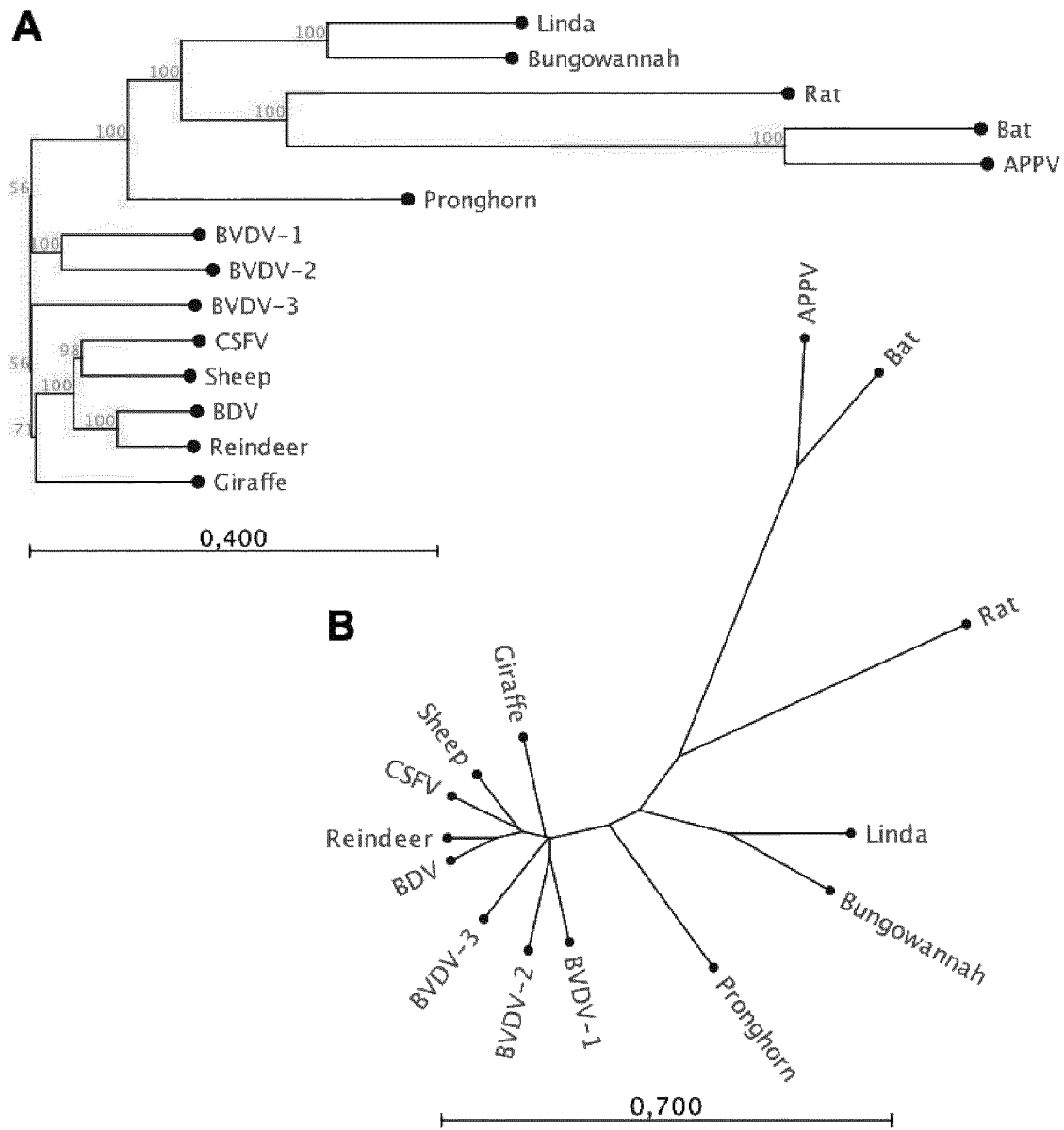

18 Claims, 28 Drawing Sheets
Specification includes a Sequence Listing.

Figure 1:
a
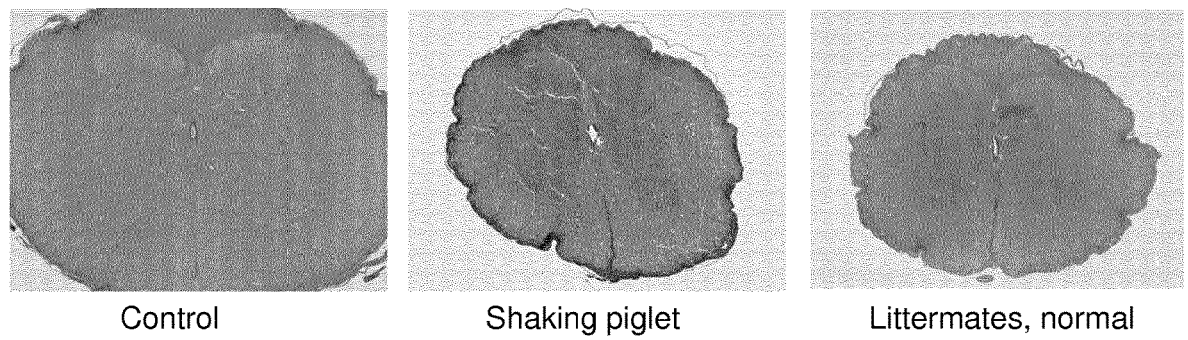
Control     Shaking piglet     Littermates, normal
b
Cerebellum
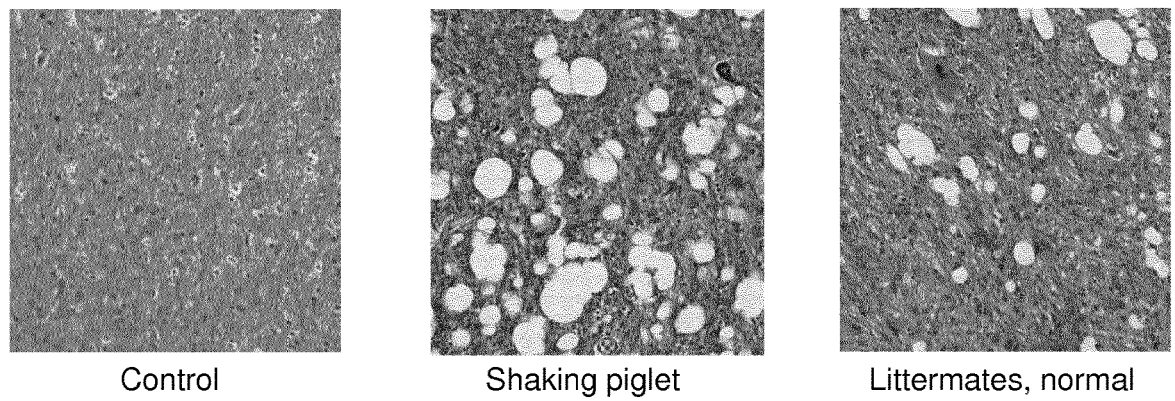
Control     Shaking piglet     Littermates, normal
c
Spinal Ganglion
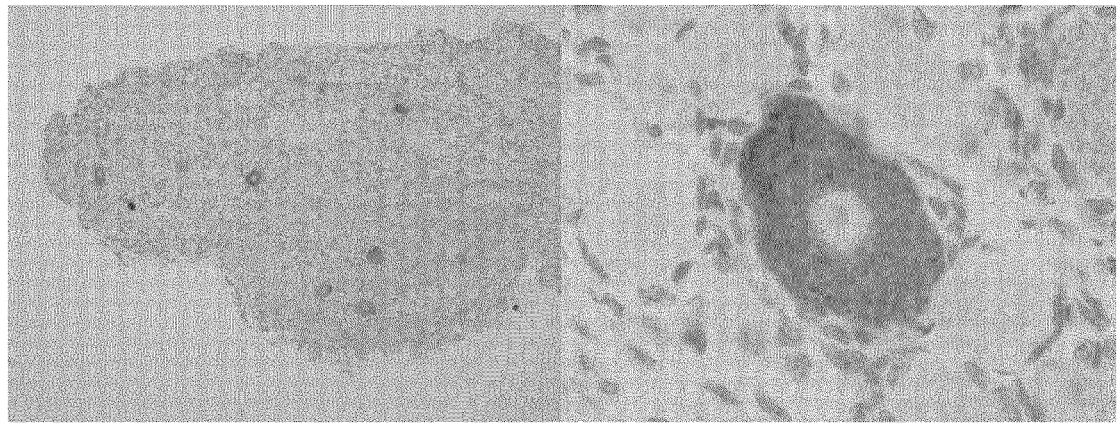

Figure 2

Figure 4

```
                                  20                                 40                                 60
                                   |                                  |                                  |
      LindaE2  - LEC - - - - NF  ELQYALAGNT  SMSLLGPTAL  - - - - - KTQWY  QAADGVKITD  GVVTVIC - - -  47
 Bungowannah E2 - QTC - - - - NP  EFMYALAKNT  SIGSLGPESL  - - - - - TTRWY  QLTSGFKLTD  STIEVTCVGA  50
   Pronghorn E2 - LEC - - - - DT  NFQYALAKGT  KIGPLGAEEL  - - - - - TTTYR  RLQPGEQLTD  GLVTITC - - -  47
     Giraffe E2  AITC - - - - EP  EYQYALARSK  RIGPLGAEDL  - - - - - VTTWH  DYKFDLKIQD  PLVMVYC - - -  48
        BDV E2  QFAC - - - - RE  DYRYALARTK  EIGALGAESL  - - - - - TTTWT  DYRGNLELDD  GTVRATC - - -  48
   Reindeer E2  QFSC - - - - RE  GYRYALAKTK  DVGPLGAESL  - - - - - TTTWV  DYKRNLQLDD  GTVRAVC - - -  48
      Sheep E2  QFTC - - - - EK  NYRYAIAKTT  DVGLLGAESL  - - - - - TTTWR  EYKNNFELDD  GLLRAVC - - -  48
       CSFV E2  QLAC - - - - KE  DYRYAISSTN  EIGLLGAGGL  - - - - - TTTWK  EYNHDLQLND  GTVKAIC - - -  48
     BVDV-1 E2  HLDC - - - - KP  EFSYAIAKDE  RIGQLGAEGL  - - - - - TTTWK  EYSPGMKLED  TMVIAWC - - -  48
     BVDV-2 E2  FPEC - - - - KE  GFQYAISKDR  KMGLLGPESL  - - - - - TTTW -  - HRPTKKLVD  SMVQVWC - - -  46
     BVDV-3 E2  - LSC - - - - KP  EFQYAISETD  EINLLGPTGL  - - - - - TTTWH  AYSEKLHITD  SSVDLTC - - -  47
        Rat E2  RYNQVKVDRP  DWHTLLQKDL  KGVLSGKDGL  YILRSNKVWT  - - GGSVIITD  EFAVTTFIGD  58
        Bat E2  - - NCITRVDY  - YNYSLKVEK  NTGN - - - - - -  - - - - - - - - - -  - - - - EVTAYD  GTYFVITLKD  37
       APPV E2  - - SCHKRQDY  - YSIQLVVDG  KTGV - - - - - -  - - - - - - - - - -  - - - - EKRSIV  GKWTVITREG  37
     Consensus  - LXC - - - - KP  EYQYALAKTX  KIGLLGAEGL  - - - - - TTTW -  - YKPGLKLTD  GTVXVTC - - -
                                  80                                100                                120
                                   |                                  |                                  |
      LindaE2  NKGIFSVTPR  CKEAPVRYLA  INHPRSLSTS  AWFKKIHDPA  DHPTETLMGE  KGRAYLCPCG  107
 Bungowannah E2 NMRIHVVCPL  VSD - - - RYLA  INHPRALPTT  AWFRKIHTQH  EVPRERIMSE  SKRRYTCPCG  107
   Pronghorn E2 TNHDIIIHDQ  CSIER - RWIA  KIHPQALPTS  VQFYLAAEPK  EAPKIIEMSD  EFEFAICPCD  106
     Giraffe E2 KNDQFFVGKR  CKAGEARYLA  KIHWRALPTS  VVFEKVLE - E  NPPEELPLED  NFEFGLCPCD  107
        BDV E2  SRGFFRFRGH  CMIGP - RYLA  SLHLRALPTS  VTFELIPGGS  AMTEE - EMGD  DFEFGLCPCD  106
   Reindeer E2 SNGYFRIRPT  CLIGS - RFIA  SLHQRALPTS  VTFELIPRGS  AMVTE - EMND  SFEFGLCPCD  106
      Sheep E2  KSGFFTFRFH  CDMGT - RYLA  KLHAQALPTS  VVFEKVGQQP  GAREI - TMED  NFEFGLCPCD  106
       CSFV E2  VAGSFKVTAL  NVVSR - RYLA  SLHKEALPTS  VTFELLFDGT  NPSTE - EMGD  DFGFGLCPFD  106
     BVDV-1 E2  EDGKLMYLQR  CTRET - RYLA  ILHTRALPTS  VVFKKLFDGR  KQEDVVEMND  NFEFGLCPCD  107
     BVDV-2 E2  EGKDLKILKT  CPKEE - RYLV  AVHERALSTS  AEFMPISDGT  IGPDVIDMPD  DFEFGLCPCD  105
     BVDV-3 E2  VDGNFLVYRR  CVRKR - RYLA  TVHERALSTS  VRFTLVADPQ  DLEDV - QMGD  DFEFGLCPCD  105
        Rat E2  HTGNFKFSVK  VMTTPIEMDY  CI - - KVIDTA  KFFCVMVGTP  TQRDLVKPPE  M - - - - LCGCG  112
        Bat E2  EEPKLM - - - -  - - - - - - EKVV  KVNGNATKDE  YCYQAI - - - -  - - - - - - - - - -  - - - - - - - - - -  63
       APPV E2  REPRLM - - - -  - - - - - - EQIS  MVSNDSLSET  YCYNRL - - - -  - - - - - - - - - -  - - - - - - - - - -  63
     Consensus  ENGXFXVRPR  CXIGX - RYLA  KLHPRALPTS  VXFEXIXDGX  XXPDE - EMGD  DFEFGLCPCD
                                 140                                160                                180
                                   |                                  |                                  |
      LindaE2  ATPLPKPKVP  FNPITIQ - GS  AFSLTC - - - -  PKNWQGDIEC  NLLSPDTLAI  ETIYTFRKHK  162
 Bungowannah E2 SKPVVRSTTQ  FNPISIS - TP  SFELEC - - - -  PRGWTGAVEC  TLVSPSTLTT  ETIFTYRKPK  162
   Pronghorn E2 ALPLVKGN - -  FNCTLTN - AQ  AFQMVC - - - -  PYGWVGTIEC  VKYSPTTLST  TVVQVYKRGR  159
     Giraffe E2 SRPVVKGN - -  FNTTLIN - HS  AFQLVC - - - -  PIGWVGTIEC  TLVNTDTLAT  TVVKRYTRTT  160
        BDV E2  SRPVVKGK - -  YNTTLLN - GS  AFQLIC - - - -  PYGWVGRVEC  TTVSKSTLAT  EVVKIYKKTK  159
   Reindeer E2 SKPVVKGK - -  YNATLLN - GS  AFQLVC - - - -  PFGWVGRVEC  TAVSTSTLAT  EVIKIYKRST  159
      Sheep E2  SKPVVKGK - -  YNATLLN - GS  AFNLVC - - - -  PIGWTGVVEC  TVISESTLHT  EVVKVFRRDK  159
       CSFV E2  TSPVVKGK - -  YNTTLLN - GS  AFYLVC - - - -  PIGWTGVIEC  TAVSPTTLRT  EVVKTFRRDK  159
     BVDV-1 E2  AKPIVRGK - -  FNTTLLN - GP  AFQMVC - - - -  PIGWTGTVSC  TSFNMDTLAT  TVVRTYRRSK  160
     BVDV-2 E2  AKPVIKGK - -  FNASLLN - GP  AFQMVC - - - -  PQGWTGTIEC  TLANQDTLDT  TVVRTYRRTT  158
     BVDV-3 E2  SVPIIRGK - -  FNTTLLN - GS  AFQLVC - - - -  PYGWTGTIEC  TVVSDSTLKT  QVVKRFARYK  158
        Rat E2  ALEVQDNN - -  - STGLISPGN  VLPSKC - - - -  INGWTGVVTC  HCPYTDI - - -  - KMKFLENTT  161
        Bat E2  - - - - - - - - - -  - NITKWNRKP  DKLRWCGQTF  PY - WLG - - - -  - - - - - - - - - -  - - - - - - - - - -  87
       APPV E2  - - - - - - - - - -  - NTSSWGRQP  ARQRGCGQTV  PF - WPG - - - -  - - - - - - - - - -  - - - - - - - - - -  87
     Consensus  SKPVVKGK - -  FNTTLLN - GS  AFQLVC - - - -  PXGWTGTXEC  TLVSPXTLAT  EVVKTYRRTK
                                 200                                220                                240
                                   |                                  |                                  |
      LindaE2  PYKEEPYCSY  TKVVDGYLRN  - VHLWGHDTC  VAGDIIN - - G  SQDDSVTKCK  WCGYEFNSAT  219
 Bungowannah E2 PFGLENWCKY  TVVEKGILYS  - CKFGGNSTC  IKGLIVK - - G  QREDVKRYCE  WCGYKFSSPN  219
   Pronghorn E2 PFPRRRHCTT  EEVFQGNYYT  - CEKGGNWTC  QPGHISH - - G  HNSDEVEECE  WCGFRSLK - -  214
     Giraffe E2 PFPMRAGCVV  YKLIGEDLHH  - CTLGGNWTC  VPEDDGT - - -  YTGGELEKCK  WCGFKFRIPD  216
        BDV E2  PFPQRVGCDH  TTVYKQDLYH  - CQMGGNWTC  MRGEVVK - - -  YVGGPVKKCE  WCGYVFKKRE  215
   Reindeer E2 PFPYRTGCDH  TTVINKDLYR  - CSMGGNWTC  IKGEQVR - - -  YTGGVVTKCK  WCDYVFKEGD  215
      Sheep E2  PFPSRKYCVD  TKVIGEDLFH  - CKLGGNWTC  IPGEQVA - - -  YRGGQVKNCK  WCGFTFETPE  215
       CSFV E2  PFPHRMDCVT  TTVENEDLFY  - CKLGGNWTC  VKGEPVV - - -  YTGGLVKQCR  WCGFDFNEPD  215
     BVDV-1 E2  PFPHRQGCIT  QKNLGEDLHN  - CILGGNWTC  VPGDQLL - - -  YKGGSIESCK  WCGYQFKESE  216
     BVDV-2 E2  PFQRRKWCSY  EKIIGEDIHE  - CILGGNWTC  ITGDHSK - - -  LKDGPIKKCK  WCGYDFVNSE  214
     BVDV-3 E2  PFPHRKHCMD  QMVVGEDLYE  - CLYGGNWTC  IPGDRVL - - -  YQGGEVKDCK  WCGFTFEEPS  214
        Rat E2  PQKYSKNCPG  TYLSDQNFHH  DCKYGSQESC  IDPEPTKLPP  ETYEDIQECF  WCSYYIKDAN  221
        Bat E2  - - - - - - - - - -  DTVNGEAYFQ  K - - - - GYWN  ITTEP - - - - -  - - - - - - - - - -  - - - - - - - - - -  108
       APPV E2  - - - - - - - - - -  DNVLEEQYYS  T - - - - GYWN  AT - - - - - - - -  - - - - - - - - - -  - - - - - - - - - -  105
     Consensus  PFPHRKGCVX  TKVIGEDLYH  - CKLGGNWTC  IPGEXVK - - -  YTGGEVKKCK  WCGYXFKEPE
```

Figure 4 contd.

```
                       260                                    280                                    300
                        |                                      |                                      |
    LindaE2   DLPDY-PIGY  CTKRGTNYLI  RYKQVPCEVG  GVRIGS-GKV  EC-TIGSTRV  KVE-QTS-NE  274
Bungowannah E2  GLPQY-PLGL  CEKEQSEGLR  DYGDFPCCNN  GTCIDKEGSV  QC-YIGDKKV  TVKLYNA-SL  276
 Pronghorn E2  --PSA-KLGR  CIRRGEKAHR  LYDTRPCKEK  AFTFSPAGEV  EC-LLGGFKV  RVDRSDTTNE  270
   Giraffe E2  GLPTY-PIGR  CMKRGKAGYR  FVSEEPCNRE  GVEISTKGKL  KC-IIEKTQV  KVYAAD--NT  272
      BDV E2   GLPHY-PIGR  CMLRNETGYR  SVDDTPCDRG  GVVISKTGEL  EC-LIGKTTV  KVFSSD--KK  271
  Reindeer E2  GLDHY-PIGK  CMLKNETGYR  LVDDTPCDRG  GVVISKTGTL  EC-LIGKTTV  KVYSSN--DK  271
     Sheep E2  DLPHY-PIGK  CVLSNETGYR  LVDGTTCNRH  GVIIDQTGSH  EC-LIGKTKI  KVYPVD--DK  271
      CSFV E2  GLPHY-PIGK  CILANETGYR  IVDSTDCNRD  GVVISTEGSH  EC-LIGNTTV  KVHASD--ER  271
    BVDV-1 E2  GLPHY-PIGK  CKLENETGYR  LVDSTSCNRE  GVAIVPQGTL  KC-KIGKTTV  QVIAMD--TK  272
    BVDV-2 E2  GLPHY-PIGK  CMLINESGYR  YVDDTSCDRG  GVAIVPTGTV  KC-RIGDVTV  QVVASN--ND  270
    BVDV-3 E2  DLPHF-PLGK  CRLTNETGYR  YVDNTTCDRD  GVAIMEQGTL  KC-KIGKVEV  RVSALN--KN  270
       Rat E2  FTPHKGPLGW  CRVGENEPYY  LTNRKSCVQG  GVQIG-SGEV  TC-LIGTTKI  KVGNFN-ETA  278
       Bat E2  --------DN  CEL-------  -------RK   GVFLSKNGAV  SCTRNGTRLV  LQLKNLNSTN  145
      APPV E2  --------GG  CQL-------  -------RE   GVWLSRKGNV  QCQRNGSSLI  LQLAIKEEND  142
    Consensus  GLPHY-PIGK  CMLRNETGYR  LVDDTPCXRG  GVXISKTGTV  EC-LIGKTTV  KVYASD--NK 320                                    340                                    360
                        |                                      |                                      |
    LindaE2   LGPMPCKPI-  VYSSQGPPNP  KTCTFKWSYT  LNNKYYEPRD  EFFQQYITSG  GYQYWFDLTA  333
Bungowannah E2  LAPMPCKPI-  VYNSQGPPAP  KTCTYRWAST  LENKYYEPRD  SYYQQYIIKS  GYQYWFDLTA  335
 Pronghorn E2  LLPMPCNPIK  V-GSQGPVSR  AACTYNYSQV  LRNSYYEERD  KFWQQYMIKD  GYQYWFDLEA  329
   Giraffe E2  LGPMPCKPME  IISSEGPVSK  TACTFNYTET  LENKYFEPRD  EYFQQYMLKG  KYQYWFDLKA  332
      BDV E2   LGPMPCKPKE  VISSEGPVSK  IACTFNYSKT  LENKYYEPRD  SYFQQYMLKG  QYQYWFDLEA  331
  Reindeer E2  LGAMPCKPKE  IISSEGPISK  TACTFNYSKT  LKNKYYEPRD  SYFQQYMLKG  EYQYWFDLDA  331
     Sheep E2  LGPMPCRPKE  IISSEGPISK  TACTFNYTKT  LKNKYYEPRD  SYFQQYMLKG  EYQYWFDLDV  331
      CSFV E2  LGPMPCRPKE  IVSSAGPVRK  TSCTFNYAKT  LKNKYYEPRD  SYFQQYMLKG  EYQYWFDLDV  331
    BVDV-1 E2  LGPMPCRPYE  IISSEGPVEK  TACTFNYTKT  LKNKYFEPRD  SYFQQYMLKG  EYQYWFDLEV  332
    BVDV-2 E2  LGPMPCSPAE  VIASEGPVEK  TACTFNYSRT  LPNKYYEPRD  RYFQQYMLKG  EWQYWFDLDH  330
    BVDV-3 E2  LGPMPCKPSH  VTQSEGPVSK  TACTFNWTET  LENKYFEPRD  NYFQQYMLKG  KYQYWFDLEA  330
       Rat E2  ISFMPCNPIK  -EASRGPPSR  TTCTYKYAKT  LKNIYDEKD   RYWGQYMVKG  EYQYWFDLEQ  337
       Bat E2  KEEIPCDPIE  T-SSLGPAEN  GACVYTWAPA  PEGWYYDKKD  DYWLQYVKKG  GYQYWTQIPS  204
      APPV E2  TMEIPCDPVE  T-ESMGPVTQ  GTCVYSWAFA  PRGWYYNRKD  GYWLQYVKKN  DYQYWTKMPT  201
    Consensus  LGPMPCKPIE  VISSEGPVSK  TACTFNYXKT  LXNKYYEPRD  SYFQQYMLKG  EYQYWFDLEA 380                                    400
                        |                                      |
    LindaE2   KDHVMDWVTR  YFPIIVVALL  GGRAVLWILI  AYELLNHYQV  GAD---  376
Bungowannah E2  KDHVADWITK  YFPIIIVALL  GGRGTLWVLI  AYELLTQYEV  VGDENI  381
 Pronghorn E2  DDHHKNWFNE  FLVVVVVALL  GGRYILWLII  IYMTLTYYPD  DA----  371
   Giraffe E2  TDNRKDYFAE  FLVIAVVALL  GGRYVLWLLV  TYFVITEQEA  SG----  374
      BDV E2   TDHHSDYFAE  FIMLAVVALL  GGRYVLWLMV  VYMILADQMT  SA----  373
  Reindeer E2  TDHHTDYFAE  FIVLAVVALL  GGRYVLWLLV  IYTVLTEQMA  AA----  373
     Sheep E2  TDHHTDYFAE  FIVVVVVALL  GGRYVLWLMV  VYIVLTDQMA  SG----  373
      CSFV E2  TDRHSDYFAE  FVVLVVVALL  GGRYILWLIV  TYIVLTEQLA  AG----  373
    BVDV-1 E2  TDHHRDYFAE  SILVVVVALL  GGRYVLWLLV  TYMVLSEQKA  LG----  374
    BVDV-2 E2  VDHHKDYFSE  FIIIAVVALL  GGKYVLWLLI  TYTILSEQMA  MG----  372
    BVDV-3 E2  TDHHQDYFAE  FIVIIVVALL  GGRYVLWLLI  VYYVATEQGA  RG----  372
       Rat E2  DDHVTGGLLK  YLPLIMVLLL  GGKMVAWLLT  AYYLMEVVEA  T----R  379
       Bat E2  LESSANIYRH  LLPILIACLL  GGRLSVWILA  MILSLQVEAS  E----V  246
      APPV E2  ASSATTMYRH  LLPLLVACLM  GGRISVWIVA  MLLSLQVEAS  E----V  243
    Consensus  TDHHTDYFAE  FIVIXVVALL  GGRYVLWLLV  TYMVLTEQMA  SG----
```

Figure 7

SEQ ID NO 1

GTATAGCAGCAGTAGCTCAAGGCTGCTATACGATTGGACATACCAAATTC
CAATTGGTGTTAGGGACCACCTAGGTGAAGGCCGACGACAGGTAGCCATT
CCTGTTAGTAGGACGAACCGTTATGGTGGACTGGTTGCTCAGGTGAGCAG
GCTGCAATGCGTAAGTGGTGAGTACACCACAGCCGTCAAAGGTGCCACTG
GTAAGGATCACCCACTGGCGATGCCTTGTGGACGGGGGCGTGCCCAACGC
AATGTTAGCGGTGGCGGGGGCTGCCATCGTGAAAGCTAGGTCTTGATGGA
CCTTGTTGCCTGTACAGTCTGATAGGATGCCGGCGGATGCCCTGTGACAG
CCAGTATAAAGAATATCCGTTGTGATTGCACATGGAGTTTAAAATTCTCA
ACAACACAAAGAAAAAAATAATAATGAGGAGGAAGCTGAGGGGAACATG
TTCTGGCGGATGTACCGAAGACCTCCGCCTGGTTGCTACGAACCAACTTA
CAACCTAAGTGGGACACCTAGCTTCGGACCCATGCACCCACCACTGAGGA
AAGGGAGTACATTACGTTTACCCCACTGGAGAGGCATAGCCACGGTTGGA
TGTGAGCTTAAAAACCTGCCACGCAAGGGTGATTGTACTAAGTGCCACGC
TAACCCAACATCTGGCATCTACCTCAACCTGGGTGCGGTGTTTTATAAAG
ATTACGAGGGGGAGGTATACCATAGAGTCCCCCTTGAACACTGTGAGGAA
CAGCAGAGGTGCGAAGTCGTCAAGCGTGTAGGGAGAATGACTGCTAGCGA
TGGATCCTTGGTGGGAGTGCTAGTATGCAGTGACGACTGCGTGCTGTTTG
AGAGAAGAAGAGGGGAACACACAGTGTTGAAGTGGGTAAAGAACCCTATC
GGGGCGCCACTCTGGGTACAGAGCTGCTCCGACGAGAAGGGGGCCAAACC
AAAAAACAAGTCTAAACAACAAAACGATCGAATGGCACCGGGTAAAATGG
TGACAAAACCTAAGGAAGTGGAAGCTGATCAGAAAACTAGACCGCCAGAC
GCTACAATTGTGGTGGATGGACAGAAATATCAAGTAAGGAAGAAAGGGAA
GGCAAAACCAAAGACACCAGATGGCCTGTACCACAATAAAAACAAGCCGG
AGGCATCTAGAAAGAAATTAGAAAAGCGCTACTAGCTTGGGCAGTCATT
GCAATAATATTGATTCAGCAGACCACAGCAAACAATGTGACGCAGTGGAA
CTTGTGGGACGACAAGAACGCAACAGATGTGCACTCAGTGATGCATCAGA
GACAAATCAAGCGCAGCCTCCACGGCATCTGGCCTGAAAGAATCTGCAAA
GGGGTCCCAGGTCATCTGGCTACTGACTATGAGCTAAAACGGATAGAGGG
GATGTTGGATGCCAGCGAAAAAACTAATTTTACCTGTTGCAGGCTGCAAA
GACACGAATGGAACAAACATGGCTGGTGTAACTGGTACAATATAGACCCC
TGGGTCGCCATTATGAACAGGACCCAAGCCCTTCTATCTAGTGGCCAAAA
CTTTACAGAGTGTGCCGTTACATGTAGGTATGACACAGAACAGCAGATAA
ACATAGTAACTCAAGCCCGCATGACACCAACGATTTTAACAGGGTGTAAG
AAGGACGTAAACTTCTCTTTCTCAGGGGAGGTGAGGACTGGGCCTTGCAA
CTATGAACTGAAGCCAGAAGACTTAATGAGGATTCTGGACCATACCAACT
GCAAAGATTTCAGCTATTTCGGAGAAGGTCTGGTGGATGATTTCACAGAA
GCCACGGAAAAATTAGATCTAGTGGGTACAGGGCCCTGTCGTGGCTGCA
AGACAAGCTAGAGAAAACTAAGAAGAAGGTGTTTGGAGCTGAAGCAACAC
CATACTGCAATGTGACAAGGAGGGTTTTCAACATCATATACACCAACAAC
TGCACCCCGCTGGACTGCCAGATAACACGAGGATAGTTGGGCCAGGGAC
ATTTGACATCAGTGAAATGGAAATAAAAACTGTTACCCAACTTGGACT
ACCACTTGGCAGATTTCATGGTACTGGGCTTAGTGGCTTTATCCGACTTT
GCCCCAGAAACTGCTAGTACAATCTATCTGGTATTGCACTACTGGCTGCC
TCAGGCAGAGGTGCATACATTGGACACCCACTTGACACCAACAAGCTGA
ATCTAACAAGGAACAGGCAGGTTAGTAGTGTAGTCCCTAATTCAATATGG
TTGGGAGGGCAGCTGGTGTGCGTCAAGCCAAGGTGGTGGCCCTACTCAGC
AGAAATTACAACAGTGATTAGCGGACTGACCACTGTAACCGACCTAGTGG
TCAAGACCATAGAGGAACTTGTGAGCTTGTGGACAGAGGCAACAGCAGTA
GCCTTCTTGGCAGCCCTGATAAAGATCTTCAGAGGACAACCAATACAAGCAC

Figure 7 contd.

```
TAGCATGGCTCATAATAATAGGGGGAGCCCAGGGTCTTGAATGCAACT
TCGAACTGCAATACGCTCTGGCCGGGAACACATCCATGAGCCTACTAGGG
CCAACTGCCTTAAAGACTCAATGGTACCAAGCGGCAGACGGGGTCAAAAT
AACGGATGGGGTAGTAACTGTGATATGCAACAAGGGCATTTTCTCGGTGA
CTCCTAGGTGCAAAGAGGCACCTGTAAGGTACCTGGCAATCAACCACCCC
AGGTCCTTATCAACCAGTGCTTGGTTCAAGAAAATACACGACCCGGCAGA
CCATCCGACTGAGACACTGATGGGCGAAAAGGGAAGGGCATACCTCTGCC
CTTGCGGGGCTACACCACTACCAAAACCCAAGGTTCCGTTTAACCCAATC
ACAATACAAGGTTCGGCGTTCTCCCTAACATGCCCAAAAAACTGGCAAGG
TGACATAGAATGCAATCTCTTAAGCCCAGACACACTAGCAATTGAAACCA
TATACACCTTCAGAAAACATAAGCCATACAAAGAAGAACCCTACTGCTCG
TACACTAAGGTAGTGGACGGGTACTTGCGCaACGTGCACCTATGGGGGCA
TGATACATGTGTGGCAGGAGATATAATCAATGGCAGTCAAGATGACAGTG
TGACCAAGTGCAAATGGTGTGGGTATGAGTTCAATTCAGCAACTGACTTA
CCTGACTACCCAATTGGTTACTGCACGAAGCGAGGCACCAATTATCTAAT
CAGGTACAAGCAGGTGCCTTGTGAGGTAGGAGGAGTCCGCATCGGGTCAG
GAAAAGTAGAGTGTACCATTGGCTCCACGAGAGTAAAAGTAGAACAAACC
AGTAATGAGTTGGGTCCGATGCCCTGCAAGCCAATAGTATATTCATCTCA
AGGACCGCCTAATCCAAAAACGTGTACATTCAAATGGAGCTACACATTAA
ACAACAAGTACTACGAGCCAAGGGATGAATTCTTCCAACAGTACATAACC
TCAGGTGGCTATCAGTATTGGTTTGACCTGACAGCAAAGATCACGTGAT
GGATTGGGTAACACGATACTTCCCCATTATAGTTGTAGCATTACTGGGGG
GTAGAGCAGTGCTGTGGATCCTAATTGCGTACGAGTTGCTAAATCACTAC
CAAGTGGGCGCAGACCAGAACACATTGCTGCAGGCCGAAGCACTAGTGAT
AGGTAACATCCTGATGACAAGAGACCTGGAAGTGATGGTGTGCTTTCTGT
TGCTGATGGTCTTGATAAGAAGACAGCAGGCTAGAAGGGCTTTGGCCTTG
GTTTTCCATTGGATGGTAATGCATCCCGCCCAATCAGCCATCGCAACATT
GGTGTACGTAATAGGCATCGTGAGAGCTGAAGAGGGACAGGTTAACTCTG
ACAGTTCTACGCAAGCACACGTGGTGGCCATTTTGTTGTTTCTAATTTAC
CACACACTAAAAGAAAGGGACCTTCACACAGCTATGACATTACTGTTGAC
ATTTTCCATAAAGAGCACTGACTATGTAGACACACATTATTATGAAATAC
CGATGCTCTTCACAGTTATTTCGTTGGTCATTTCCATTTACATATTCAAC
ATACACATAAAAACCAAGTGGGTAGCTCTGGTGCTCAGTATGGTGGGCAT
GGTCACCTTTATAAGGTGCCTTTGGTTGATCAGGAACATACAAATAACAC
CCCCTTCCATACCACTAACATACATCAGTCCAAAAATATTGATCATAGCT
TACCTGGTTTCTCTGACTGTCTTGGTGAATAACAACCTAGACCTCGCCAG
CTACGTGATCAGGGCTGGCCCGATACTAATGTCCTACTTAACTTTATGGG
TGGACATCCTGATGTTGCTAGTTCTACTACCTTGGTATGAATTGATTAAA
GTCTATTACCTAAAGAAGAAGAAAGACGACATAGAAGACTGCTTCCAATA
CAGCGGGATAGCCACTCAAGGGTTATCCCCGTACAATCAGGACTTCGTGG
ACCCAAAAGAGGGGGTACACTTGATCCCCTCACAAAACAAGAGCAATTTC
ACCCGGACCGCATATCTGACTATCCTGAGGGCCCTAGTTCTCACAGCTTT
CAGCAGCATTTGGAAGCCTCTAATCCTAGCCGAACTGCTATTGGAATCCA
TTTATTGGACACACATCAAAGTTGCAAAAGAAGTGGCGGGATCTACGAGG
CTTATAGGTAGGTTTGTAGCGGCCCTGATAGAACTAAATTGGGTTTTTGA
TGACAAGGAAGCAGCAAGATACAAAAAATTCTTTGTTTTAACCTCAAGAG
TGAGAGACCTCATGGTAAAACACAAGGTGCAGAACGACACAATGAGGCAG
TGGTTTGAAGAGACGGAAATATTCGGCTTACAAAAAGTTGCCTTGGTGGT
CAGAGCACACTCACTGACAGCAGACAGCAACAGTATACTATGCTCAGTGT
GTGAGGAAAACAGAACATAGAAGCCAAGAGGGTATGTCCCAAGTGTGGA
AACAGAGGAACAGGAATCAAGTGCGGGATGACCTTGGCTGAGTTTGAAGA
AAAATATTACAAAAAGATCTATCTAGTGGATGGAGACAATACGCAAGCAT
ATCGCAGAGAGGAGAGAGGAGAAGTCACGTACACAGCTAGGGGCGCCTTC
```

Figure 7 contd.

```
TTCTTGAGGAACTTACCCATTCTGGCCACAAAAAACAAGTATATACTGGT
AGGTAACTTAGGTATGGAATTACAAGACCTTGAGTCCATGGGGTGGATTA
TCAGGGGCCCAGCTGTCTGCAAAAAGATAGTGCACCATGAACGCTGCAGG
CCCACCATCCCTGATAAACTTATGGCTTTCTTTGGGCTCATGCCAAGAGG
CGTAGTCCCCGGGCACCAACCCGCTTCCCTGTATCATTACTGAAAATTA
AAAGGGGTTTCGAAACGGGGTGGGCATATACACACCCTGGAGGGATCAGC
AGCGTAATGCATGTAACAGCAGGCTTGGACATGTACGTCAATGATGCCAT
GGGTAGAACCAAGGTGCAGTGCCAAGAGAGAAACAAGCTGACAGACGAAT
GTGAGTATGGCATTAAAACTGACTCAGGCTGCTCTGAAGGGGCACGCTGC
TATGTAATAAATCCCGAAGCCGTCAACATAGCAGGCACCAGGGGCGCTAT
GGTACACCTCAGAAAACAGGTCCAGAATTTACCTGTGTGACAGCCCAAG
GAACCCCAGCCTTCTACAATTTGAGGAATCTTAAAGGTTGGTCAGGGCTA
CCAATATTCGAGGCAGCTACGGGAAGGGTGGTAGGCAGAGTGAAAGCAGG
CAAGAATGCAGAGGATAGTCCAACAACTATAATGTCTGGCACCCAGGCAG
CCAAACCGACAGAGTGTGACCTGGAGTCGGTCGTAAGGAAGCTGGAAACC
ATGAACAGAGGGGAGTTCAAGCAGGTGGTGCTAGCAACTGGGGCAGGGAA
GACAACAGAACTGCCAAGGAAGCTAATAGAAGCCGTGGGGCGGCACAAGA
GGGTTTTAGTCCTAATCCCCCTGAGAGCAGCAGCAGAGGGGGTTTATAAC
TATATGAGAACAAAGCATCCAAGCATAGCATTCAACCTGAGGATAGGGGA
CTTAAAAGAAGGAGACATGGCAACTGGTATAACTTATGCCTCATATGGTT
ATTTTTGTCAAATGGACATGCCACGGCTAGATGCAGCTATGAAGGAGTAC
AACTACATATTCCTGGACGAATATCATTGTGCAACACCAGAGCAATTGGC
TGTGATGTCAAAAATACACAGGATCAGTGCTGACCTAAGAGTGGTGGCCA
TGACAGCTACCCCTGCAGGCGCTGTGTCAAAGGTGGGCCAGAAATTCTCC
ATAGAAGAAGTGGTGGTGCCAGAGGTAATGAAAGGGGAAGACCTAGGCGA
GGATTATTTGGACATAGCCGGACTAAAAATACCAAAATCGGAACTACAAG
GGAATGTCTTAACGTTTGTTCCGACAAAAAGTTGGCGTCAGACACTGCT
AAGAAACTAACCACCCAGGGCTACAACGCTGGGTATTACTTTAGTGGTGA
AGACCCAAGCTCGCTGCGCACCATAACATCAAAATCCCCGTACATCATAA
TAGCCACCAATGCAATAGAGTCAGGGGTGACATTACCAGACCTAGACACA
GTAATTGACACAGGGATGAAGTGTGAAAAGAGGGTGAGAATAGAGAACAA
GGCTCCATACATAATAACAGGCCTAAAAAGAATGGCCATCACCACAGGGG
AGCAAGCCCAGAGGAAGGGAAGAGTAGGTAGAGTCAAACCAGGGAGATAC
CTAAGAGGGCCTGAAAATGCAGGTGGAGAGAGAGATTATCACTATGACCT
GCTGCAGGCACAACGTTATGGGCTCCAGGATGCTATCAACATCACCAAAT
CATTCAGGGAGATGAACTATGACTGGGCACTCTATGAGGAAGACCCACTG
AGAATAACACAATTGGAGGTATTAAATACCCTACTCATATCCAAAGATCT
GCCAACAGTCACAAAGAATTTGATGACCAGGACCACACACCCAGAACCAA
TTCAATTAGCTTACAATAGCATAGAAACCCCGTCCCAGTGCTGTTCCCG
AAAGTGAAGGGTGGAGAGGTGACCGATGCTTATGAGACCTATGAACTGAT
GATGTGTCGGAAGCTGGATAACGACCCCCGATTTATCTGTATGCCACGG
AAGATGAAGACCTAGCAGTGGACCTCCTGAACCTGAAATGGCCCGCAGTG
TCAACAGCCTCGGCCATAGAAACAGAGGACGCCCTCAACAAGTTATCGGG
GCTTTCGGCAGGGGAAACAGCCCTGCTAGTGGCTCTGCTAGGTTGGGTCG
GTTACGAGGCTCTGGTGAAAGACACATACCAATAGTGACTGACATATAT
ACAATTGAAGATGAAAACTTGAGGACACCACCCACCTCCAGTATTCACC
AGATGAACTGCAAAACACCGAGACAGTGGAGCTGAAAGACCTGTCGGCAC
ACGAACTGAAAGAAGCCCTGGAAAGCGGAAAAGTTATGTCAAAGACGCC
TTTGAATTCGTAAAATCACAGGTTGAGAAGCTCCCGACACAAAAATTTAC
AAGCAAGTCCAAGAGAAGTCACCCGGTCTTTTAGAAAAATTTTTGGCCT
ATCTGTCAGAACACAGTAGTGACATAAAGAAATATGGATTGTGGGGGGTC
CATACCTCTCTGTACAATAGTATCAAAGAGAGATTGGGGCACGAAACTGC
CTTCGCTTCATTGATCATCAAGTGGATAGCATTTTCCAGCGAAGGGCTGC
```

Figure 7 contd.

```
CTGGAATGGTGAAACAAGCTGCTGTAGACTTGGTGGTATATTATCTGATC
AACAAACCAGATTTCAAAGGTGACAAAGACACCCAAGATGATGGAAGGAA
GTTCGTAGGAGCCCTGTTCGTGTCAGCTCTGGCCAATTACACATTTAAAA
ATTTTAATAAGTCAACACTTGAAGGCTTAGTAATGCCAGCATTGAACTAC
CTACCATATGCAGGGGCTGCACTAAAAATATTTGTGCCTACTAAATTAGA
GAGCTTAGTAATACTGTCAACAACCATCTACAGGACCTACCTCTCCATTA
AGAAAGGCTCTAGTCAAGGACTGGCTGGGTTAGCAGTGAGCTCAGGTATG
GAAATTATGAATCAGAATCCAATATCAGTGGCCATTGCGGTGGCATTGGG
AGTCGGTGCCATAGCTGCACACAATGCGATCGAGAGCAGCGAGGCAAAGA
GGACCCTGTTGATGAAGGTATTTGTGAAAAACTTTCTAGACCAGGCAGCG
ACAGACGAGCTGGTAAAGAGAACCCAGAAAAAATAATAATGGCAGTATT
TGAAGCAATCCAGACAGCAGGTAATCCAATAAGGCTAATATACCACCTAT
ATGCCATGTTCTACAAAGGTTGGAACGCCTCCCAGATAGCAGATAAGACA
GCGGGGAGGAACATATTCGTGCTGACAATATTCGAGGGTTTAGAACTGTT
GGGACTAGACAAGGATTCCAAGTGGAGGGATTTGAGCTCAAATTATTTAG
TGGATGCAATCAGGAAGCTCATTGAAAAATTGACTAAAATACTCAGAAAC
ACCACCAAGTCATTAATCAAATCCTTGCTGCCAGCTCCATTCTCTTGCAC
GAGATTCACAAGAGACAACAGAATTGGATGGCCACATTTAAATTTTGATT
ATTACGAGATAAATTGTGCATGTGGGTACCGGAGGAGAGTGGTAAAAACT
GTCATCGACCCAGTCACCTGGGAGACTTTGGAAGAAGAAGGCCCTGAGTT
CTGCTTCAACAGGGGGACTAACGCCCTGGCAAACCCAAGAGTTGCAAGTT
ATTACTCAGCTGGAGAGCCAGTTCTCCCAGTGGTAAAAGAGAGGGGGTT
GGCGAAATCCTGGTAAGGGGGTGACAATCCAGATGCATTATGACCACAA
CAAGATACTCGCCACTGACAACTGGCAAGTGCCATTCCAGGCAGTGACGA
AGATATTTACAGATTACCAGGGCATAGGGTACCAAGAAGCATATCTGGGA
ACCCAGCCAAACTACAAAGCACTGGTGAAGAGGTCATCCGTCACGATTAC
AAAAGAAGGCCTGAAATTTATAAGATGCAAGAAAGGGATCGCGTATACGA
CCAATCTAAACTTAACCCACATCCAAAAGCTGGTGCAGGTGTGCAGAATG
AATGAATTGCAAGAAGGCGTCATACCTGAGACCTTGGATGGCGACACCTG
GATTAACTACATGGCAATCATCGAAGATGTGGGGGCCACAAAACCAAGCT
TGGAGAGAGAGTcATACCCGAAACCATACGAGGAGGATCCCCTCGAAGGC
CCCAGTGTGATCGTGGAAACAGGGGACGTGGACATCACAAAAGTGGGCGT
AAATCAACAATCCAGTTCATCAGGAACCGTCTTTCAAGTAGTGGAGAAGA
TCTATACTAAACTGGTCAATACAAATGTAATAAAGATAGGATTCAAAGAA
GGCTGTTTCCCGGGACCCACAAAGAATGTGAATTCATTGAATGAGCACAT
AGAAGATAAAGACAGTAAACCATACATCTTCATATGCTCTTCCGACAAAG
CAATGTCCAACAGAGTAAAGACTGCAAGGAACATTAAGAAACTCAACACA
AATTCGGCAATAGTAGCCCGTAATTTGGCCAGGGAAGGGAAATTGATCAT
AATAGTACTAGGAGAGAAGTACCATGAGGACATCTACAAACATGCTGACT
TCAAGGGGACTTTCCTCGACAGGAAGGCACTGGAAGCCCTGTCCAAGGCC
AAGCCTGTAAAAAAGAACATGACTAGGAGAGAGGCTCAATATCTGCTGGA
AAAGAAGCTTAGTGAAGACATAGAGGTACCAGAATGGCTGGGATCTGAAA
AACCTATGTTTTTGGATGTAACCAAAAGTGGTGAAACATACCATCTGTTA
GGGGATCTAAATCACTTGAAGGCACAAGCGGAACAACTTGGTGCCAAGGC
AACCACTACAATAAATAAAGTAGGGAAGACGTATACAATGAACCTCAGTA
CATGGTGGGAGAGTGAAAGAACCCCCACATTCAGACCCCTGTTCCAGGAA
CTGCTGTTACGCTGCAGGCCATGCACTAGGGAGGAGTATAAGAGCTGCCAT
TTTGTAGGGGCTACACAATTGGCCGGAGGAAACTGGAAACCAGTAGCCC
CTGTGGTGCACCTAGGAACTATACCAGCAAAAGAGAGAAATGCCTGCCA
TATGAAGCATATATATCACTTAAGAATATGGTGGAAAACCTAAAAATAGA
GAATCCTGGAGTGTGCAAGAAGAAACATCAGTGGCTCTTAAATAAAATTA
AAAAACAAGGGGAATTAGGCTTGAAGAATCTCGTATCTCCTGGGAGTGTA
GGGGGATCACGTGGTTACAGAAAGAAAGAATTCAACATTTACAACAAACA
```

Figure 7 contd.

GATTACGAGCACAATGCTGGCTGTGGGGATCAAGCCAGAGAAGTTTCCAG
TCGTCAGAGCTCAAACGTCCAAGAGAGAATTCCATCAAGCAATTAGAGAG
AAGATTGATAAGCTGCCCAACCCCAGAATAGGGACCTCCATAAGGAACT
GAAAGAAATATTTGACTCGGTGTGCGCTGTAAAAGATTTGAAACATACCT
ACGAAGAAGTCAGCTGGGATGTACTGACGGTGGGGATCAACAGGAAAGGA
GCAGCTGGCTATTTCGAAAAGAAGAATGTGGGTGAGATAATAGACACTGA
CAGGAGAGGGGTCGAGAAACTTATCAAGGTAATGAAAACCGGGGGACCTA
TAGACTACTATGAGACAGCAATACCTAAGAATGAGAAGAGAGCAGTTGTA
GATGACTGGCTGGAAGGAGATTTCGTTGAAGAGAAAAGCCACGAGTGAT
CCAATACCCAGAAGCAAAATGCGTTTGGCAATAACCAAAGTTATGTACA
ATTGGGTCAAGCAAAAACCAGTGGTGATACCCGGGTACGAGGGGAAGACA
CCTTTGTTTAAAGTGTTTGATAAGGTTTTTGATGAATGGAAACAACTGAG
AGACCCGGTTGCAGTCAGTTTCGACACTAAAGCATGGGATACACAAGTGA
CACCTGAGGACTTACAATTGATATCGGAAATCCAAAAGTATTACTTTAAA
CCAAAATACCACAAATTTATTGAAACATTGACTGCGGAGATGAAAGAAGT
GCCAGTCGTGTGCCAGGATGGGGAGGTTTACATCAGGCTAGGACAGAGAG
GAAGTGGCCAGCCAGATACCAGTGCAGGAAATAGCATGTTGAATGTGTTG
ACAATGATATATGCTTTTTGCAAATCCAATGACATCCCGTACAAGGCATT
CCGAAGGGTGGCAAAATACACGTCTGTGGCGACGATGGGTTCCTAATTA
CAGAGAGGCGCCTAGGAGAGAACTTTGCTGCGATGGGGCCACAAATACTG
ATGGAAGCCGGGAAACCACAGAAACTGGTAGGAGAGATGGGACTGAAGCT
AGCCTACAAGTTCCAGGACATAGAGTTCTGCTCCCACACGCCTATACAAG
TAAGGTGGGATGACAACACAACTAGTTATTTACCAGGCAGAGACACGGCA
ACCATCTTAGCAAAGATGTGTACCAGGCTGGACTCCGCAGGGGAGCGGGG
TACCAGTTCCTATGAACTTGCTGTTGTGTTTAGTTTCCTCCTAATGTACT
CCTGGAACCCAATAGTTAGAAGGATCTGCCTATTAGTTATGGCAACAATC
GGAGTAAAAGACCCAGATAAATCAGGAACAATATTCACCTTCTCTGGAGA
CCCACTAGGGGCGTACAAGGAAGTAATAGGACACCGATTGGGCCAACTAA
AACAAACTGAATTTTCAAAATTGGCAAGTTGCAATTTATCAATGTCACTG
TTAGGGATTTACAGTAGGCACACCTCAAAAAGAATCATAGAGGACTGTGT
GAAGATTGGAACCCTAAACCGACAGAGCCCCGTGAATGCAGATCGCTTGA
TAGCAAAGAAGACTGGTTTTGTATACGAACCGTCAAGGGGCAGTGTTAGG
GTGGGAAAACACTAtGAAGaATTGGAATTGGACAAATGGAAAAGAAGAC
GCCACTCATAGAAGGGGCGGAAAGGTACATTCCAGGCCCGATTAAGACCT
TTATACTGAAAAGACTCAAAGTGTTACAGATGATAGGCCTGAAATTCTTC
TAATATATAGGGAGTACAGGTTACAGCTGTGTTTCACAGAAAGTGGGTGG
CGACACTTACCTCTGGAGCCAACTTGTAAATAGGTTAGTAATATTTATTT
AATAGACGTTATTTACTTATTTATTTATTTATTTGATTATTTATTAATTA
TTTAAAAACGCTACTGCATGAGCTGGTTAGTCAGCTTATGAAAGTGGGTT
GTGTCACTTGCGTCAGGAGCAAATACCTCAATAACAACGCTACCACATAG
CCTGAGACCAGGTTGTGAAAGAGAGTTGCGCCTCTTGCGTTGGGAGCTAT
CTACCTCAAGTACCCAGCTGCTGAAGCTGGTTACCTCAATTCCAATGGAT
GACCGTAGCCATTGGTCTTATTAATTCGGTCATTTATAATTAGCACTTTA
AAGCTAATTGGGACATAAAGTAAGGACGTCCTAGGGAGGACTACTTACAG
TTCCAAGAGGCCCC

Figure 8

SEQ ID NO: 2 full length RNA of Linda pastivirus

```
GUAUAGCAGC AGUAGCUCAA GGCUGCUAUA CGAUUGGACA UACCAAAUUC CAAUUGGUGU
UAGGGACCAC CUAGGUGAAG GCCGACGACA GGUAGCCAUU CCUGUUAGUA GGACGAACCG
UUAUGGUGGA CUGGUUGCUC AGGUGAGCAG GCUGCAAUGC GUAAGUGGUG AGUACACCAC
AGCCGUCAAA GGUGCCACUG GUAAGGAUCA CCCACUGGCG AUGCCUUGUG GACGGGGGCG
UGCCCAACGC AAUGUUAGCG GUGGCGGGGG CUGCCAUCGU GAAAGCUAGG UCUUGAUGGA
CCUUGUUGCC UGUACAGUCU GAUAGGAUGC CGGCGGAUGC CCUGUGACAG CCAGUAUAAA
GAAUAUCCGU UGUGAUUGCA CAUGGAGUUU AAAAUUCUCA ACAACACAAA GAAAAAAAAU
AAUAAUGAGG AGGAAGCUGA GGGGAACAUG UUCUGGCGGA UGUACCGAAG ACCUCCGCCU
GGUUGCUACG AACCAACUUA CAACCUAAGU GGGACACCUA GCUUCGGACC CAUGCACCCA
CCACUGAGGA AAGGGAGUAC AUUACGUUUA CCCCACUGGA GAGGCAUAGC CACGGUUGGA
UGUGAGCUUA AAAACCUGCC ACGCAAGGGU GAUUGUACUA AGUGCCACGC UAACCCAACA
UCUGGCAUCU ACCUCAACCU GGGUGCGGUG UUUUAUAAAG AUUACGAGGG GGAGGUAUAC
CAUAGAGUCC CCCUUGAACA CUGUGAGGAA CAGCAGAGGU GCGAAGUCGU CAAGCGUGUA
GGGAGAAUGA CUGCUAGCGA UGGAUCCUUG GUGGGAGUGC UAGUAUGCAG UGACGACUGC
GUGCUGUUUG AGAGAAGAAG AGGGGAACAC ACAGUGUUGA AGUGGGUAAA GAACCCUAUC
GGGGCGCCAC UCUGGGUACA GAGCUGCUCC GACGAGAAGG GGGCCAAACC AAAAAACAAG
UCUAAACAAC AAAACGAUCG AAUGGCACCG GGUAAAAUGG UGACAAAACC UAAGGAAGUG
GAAGCUGAUC AGAAAACUAG ACCGCCAGAC GCUACAAUUG UGGUGGAUGG ACAGAAAUAU
CAAGUAAGGA AGAAAGGGAA GGCAAAACCA AAGACACCAG AUGGCCUGUA CCACAAUAAA
AACAAGCCGG AGGCAUCUAG AAAGAAAUUA GAAAAGCGC UACUAGCUUG GGCAGUCAUU
GCAAUAAUAU UGAUUCAGCA GACCACAGCA AACAAUGUGA CGCAGUGGAA CUUGUGGGAC
GACAAGAACG CAACAGAUGU GCACUCAGUG AUGCAUCAGA GACAAAUCAA GCGCAGCCUC
CACGGCAUCU GGCCUGAAAG AAUCUGCAAA GGGGUCCCAG GUCAUCUGGC UACUGACUAU
GAGCUAAAAC GGAUAGAGGG GAUGUUGGAU GCCAGCGAAA AAACUAAUUU UACCUGUUGC
AGGCUGCAAA GACACGAAUG GAACAAACAU GGCUGGUGUA ACUGGUACAA UAUAGACCCC
UGGGUCGCCA UUAUGAACAG GACCCAAGCC CUUCUAUCUA GUGGCCAAAA CUUUACAGAG
UGUGCCGUUA CAUGUAGGUA UGACACAGAA CAGCAGAUAA ACAUAGUAAC UCAAGCCCGC
AUGACACCAA CGAUUUUAAC AGGGUGUAAG AAGGACGUAA ACUUCUCUUU CUCAGGGGAG
GUGAGGACUG GGCCUUGCAA CUAUGAACUG AAGCCAGAAG ACUUAAUGAG GAUUCUGGAC
CAUACCAACU GCAAAGAUUU CAGCUAUUUC GGAGAAGGUC UGGUGGAUGA UUUCACAGAA
GCCACGGAAA AAAUUAGAUC UAGUGGGUAC AGGGCCCUGU CGUGGCUGCA AGACAAGCUA
GAGAAAACUA AGAAGAAGGU GUUUGGAGCU GAAGCAACAC CAUACUGCAA UGUGACAAGG
AGGGUUUUCA ACAUCAUAUA CACCAACAAC UGCACCCCG CUGGACUGCC AGAUAACACG
AGGAUAGUUG GGCCAGGGAC AUUUGACAUC AGUGAAAUGG AAAAUAAAAA ACUGUUACCC
AACUUGGACU ACCACUUGGC AGAUUUCAUG GUACUGGGCU UAGUGGCUUU AUCCGACUUU
GCCCCAGAAA CUGCUAGUAC AAUCUAUCUG GUAUUGCACU ACUGGCUGCC UCAGGCAGAG
GUGCAUACAU UGGACACCCC ACUUGACACC AACAAGCUGA AUCUAACAAG GAACAGGCAG
GUUAGUAGUG UAGUCCCUAA UUCAAUAUGG UUGGGAGGGC AGCUGGUGUG CGUCAAGCCA
AGGUGGUGGC CCUACUCAGC AGAAAUUACA ACAGUGAUUA GCGGACUGAC CACUGUAACC
GACCUAGUGG UCAAGACCAU AGAGGAACUU GUGAGCUUGU GGACAGAGGC AACAGCAGUA
GCCUUCUUGG CAGCCCUGAU AAAGAUCUUC AGAGGACAAC CAAUACAAGC ACUAGCAUGG
CUCAUAAUAA UAGGGGGAGC CCAGGGUCUU GAAUGCAACU UCGAACUGCA AUACGCUCUG
GCCGGGAACA CAUCCAUGAG CCUACUAGGG CCAACUGCCU UAAAGACUCA AUGGUACCAA
GCGGCAGACG GGGUCAAAAU AACGGAUGGG GUAGUAACUG UGAUAUGCAA CAAGGGCAUU
UUCUCGGUGA CUCCUAGGUG CAAAGAGGCA CCUGUAAGGU ACCUGGCAAU CAACCACCCC
AGGUCCUUAU CAACCAGUGC UUGGUUCAAG AAAAUACACG ACCCGGCAGA CCAUCCGACU
GAGACACUGA UGGGCGAAAA GGGAAGGGCA UACCUCUGCC CUUGCGGGGC UACACCACUA
CCAAAACCCA AGGUUCCGUU UAACCCAAUC ACAAUACAAG GUUCGGCGUU CUCCCUAACA
UGCCCAAAAA ACUGGCAAGG UGACAUAGAA UGCAAUCUCU UAAGCCCAGA CACACUAGCA
AUUGAAACCA UAUACACCUU CAGAAAACAU AAGCCAUACA AAGAAGAACC CUACUGCUCG
UACACUAAGG UAGUGGACGG GUACUUGCGC AACGUGCACC UAUGGGGCA UGAUACAUGU
```

Figure 8 contd.

```
GUGGCAGGAG  AUAUAAUCAA  UGGCAGUCAA  GAUGACAGUG  UGACCAAGUG  CAAAUGGUGU
GGGUAUGAGU  UCAAUUCAGC  AACUGACUUA  CCUGACUACC  CAAUUGGUUA  CUGCACGAAG
CGAGGCACCA  AUUAUCUAAU  CAGGUACAAG  CAGGUGCCUU  GUGAGGUAGG  AGGAGUCCGC
AUCGGGUCAG  GAAAAGUAGA  GUGUACCAUU  GGCUCCACGA  GAGUAAAAGU  AGAACAAACC
AGUAAUGAGU  UGGGUCCGAU  GCCCUGCAAG  CCAAUAGUAU  AUUCAUCUCA  AGGACCGCCU
AAUCCAAAAA  CGUGUACAUU  CAAAUGGAGC  UACACAUUAA  ACAACAAGUA  CUACGAGCCA
AGGGAUGAAU  UCUUCCAACA  GUACAUAACC  UCAGGUGGCU  AUCAGUAUUG  GUUUGACCUG
ACAGCAAAAG  AUCACGUGAU  GGAUGGGUA   ACACGAUACU  UCCCCAUUAU  AGUUGUAGCA
UUACUGGGGG  GUAGAGCAGU  GCUGUGGAUC  CUAAUUGCGU  ACGAGUUGCU  AAAUCACUAC
CAAGUGGGCG  CAGACCAGAA  CACAUUGCUG  CAGGCCGAAG  CACUAGUGAU  AGGUAACAUC
CUGAUGACAA  GAGACCUGGA  AGUGAUGGUG  UGCUUUCUGU  UGCUGAUGGU  CUUGAUAAGA
AGACAGCAGG  CUAGAAGGGC  UUUGGCCUUG  GUUUUCCAUU  GGAUGGUAAU  GCAUCCCGCC
CAAUCAGCCA  UCGCAACAUU  GGUGUACGUA  AUAGGCAUCG  UGAGAGCUGA  AGAGGGACAG
GUUAACUCUG  ACAGUUCUAC  GCAAGCACAC  GUGGUGGCCA  UUUUGUUGUU  UCUAAUUUAC
CACACACUAA  AAGAAAGGGA  CCUUCACACA  GCUAUGACAU  UACUGUUGAC  AUUUUCCAUA
AAGAGCACUG  ACUAUGUAGA  CACACAUUAU  UAUGAAAUAC  CGAUGCUCUU  CACAGUUAUU
UCGUUGGUCA  UUUCCAUUUA  CAUAUUCAAC  AUACACAUAA  AAACCAAGUG  GGUAGCUCUG
GUGCUCAGUA  UGGUGGGCAU  GGUCACCUUU  AUAAGGUGCC  UUUGGUUGAU  CAGGAACAUA
CAAAUAACAC  CCCCUUCCAU  ACCACUAACA  UACAUCAGUC  CAAAAAUAUU  GAUCAUAGCU
UACCUGGUUU  CUCUGACUGU  CUUGGUGAAU  AACAACCUAG  ACCUCGCCAG  CUACGUGAUC
AGGGCUGGCC  CGAUACUAAU  GUCCUACUUA  ACUUUAUGGG  UGGACAUCCU  GAUGUUGCUA
GUUCUACUAC  CUUGGUAUGA  AUUGAUUAAA  GUCUAUUACC  UAAAGAAGAA  GAAAGACGAC
AUAGAAGACU  GCUUCCAAUA  CAGCGGGAUA  GCCACUCAAG  GGUUAUCCCC  GUACAAUCAG
GACUUCGUGG  ACCCAAAAGA  GGGGGUACAC  UUGAUCCCCU  CACAAAACAA  GAGCAAUUUC
ACCCGGACCG  CAUAUCUGAC  UAUCCUGAGG  GCCCUAGUUC  UCACAGCUUU  CAGCAGCAUU
UGGAAGCCUC  UAAUCCUAGC  CGAACUGCUA  UUGGAAUCCA  UUUAUUGGAC  ACACAUCAAA
GUUGCAAAAG  AAGUGGCGGG  AUCUACGAGG  CUUAUAGGUA  GGUUUGUAGC  GGCCCUGAUA
GAACUAAAUU  GGGUUUUUGA  UGACAAGGAA  GCAGCAAGAU  ACAAAAAAUU  CUUUGUUUUA
ACCUCAAGAG  UGAGAGACCU  CAUGGUAAAA  CACAAGGUGC  AGAACGACAC  AAUGAGGCAG
UGGUUUGAAG  AGACGGAAAU  AUUCGGCUUA  CAAAAAGUUG  CCUUGGUGGU  CAGAGCACAC
UCACUGACAG  CAGACAGCAA  CAGUAUACUA  UGCUCAGUGU  GUGAGGAAAA  ACAGAACAUA
GAAGCCAAGA  GGGUAUGUCC  CAAGUGUGGA  AACAGAGGAA  CAGGAAUCAA  GUGCGGGAUG
ACCUUGGCUG  AGUUUGAAGA  AAAAUAUUAC  AAAAAGAUCU  AUCUAGUGGA  UGGAGACAAU
ACGCAAGCAU  AUCGCAGAGA  GGAGAGAGGA  GAAGUCACGU  ACACAGCUAG  GGGCGCCUUC
UUCUUGAGGA  ACUUACCCAU  UCUGGCCACA  AAAAACAAGU  AUAUACUGGU  AGGUAACUUA
GGUAUGGAAU  UACAAGACCU  UGAGUCCAUG  GGGUGGAUUA  UCAGGGCCC   AGCUGUCUGC
AAAAAGAUAG  UGCACCAUGA  ACGCUGCAGG  CCCACCAUCC  CUGAUAAACU  UAUGGCUUUC
UUUGGGCUCA  UGCCAAGAGG  CGUAGUCCCC  CGGGCACCAA  CCCGCUUCCC  UGUAUCAUUA
CUGAAAAUUA  AAAGGGGUUU  CGAAACGGGG  UGGGCAUAUA  CACACCCUGG  AGGGAUCAGC
AGCGUAAUGC  AUGUAACAGC  AGGCUUGGAC  AUGUACGUCA  AUGAUGCCAU  GGGUAGAACC
AAGGUGCAGU  GCCAAGAGAG  AAACAAGCUG  ACAGACGAAU  GUGAGUAUGG  CAUUAAAACU
GACUCAGGCU  GCUCUGAAGG  GGCACGCUGC  UAUGUAAUAA  AUCCCGAAGC  CGUCAACAUA
GCAGGCACCA  GGGGCGCUAU  GGUACACCUC  AGAAAACAG   GUCCAGAAUU  UACCUGUGUG
ACAGCCCAAG  GAACCCCAGC  CUUCUACAAU  UUGAGGAAUC  UUAAAGGUUG  GUCAGGGCUA
CCAAUAUUCG  AGGCAGCUAC  GGGAAGGGUG  GUAGGCAGAG  UGAAAGCAGG  CAAGAAUGCA
GAGGAUAGUC  CAACAACUAU  AAUGUCUGGC  ACCCAGGCAG  CCAAACCGAC  AGAGUGUGAC
CUGGAGUCGG  UCGUAAGGAA  GCUGGAAACC  AUGAACAGAG  GGGAGUUCAA  GCAGGUGGUG
CUAGCAACUG  GGGCAGGGAA  GACAACAGAA  CUGCCAAGGA  AGCUAAUAGA  AGCCGUGGGG
CGGCACAAGA  GGGUUUUAGU  CCUAAUCCCC  CUGAGAGCAG  CAGCAGAGGG  GGUUUAUAAC
UAUAUGAGAA  CAAAGCAUCC  AAGCAUAGCA  UUCAACCUGA  GGAUAGGGA   CUUAAAAGAA
GGAGACAUGG  CAACUGGUAU  AACUUAUGCC  UCAUAUGGUU  AUUUUUGUCA  AAUGGACAUG
CCACGGCUAG  AUGCAGCUAU  GAAGGAGUAC  AACUACAUAU  UCCUGGACGA  AUAUCAUUGU
GCAACACCAG  AGCAAUGGGC  UGUGAUGUCA  AAAAUACACA  GGAUCAGUGC  UGACCUAAGA
GUGGUGGCCA  UGACAGCUAC  CCCUGCAGGC  GCUGUGUCAA  AGGUGGGCCA  GAAAUUCUCC
```

Figure 8 contd.

```
AUAGAAGAAG  UGGUGGUGCC  AGAGGUAAUG  AAAGGGGAAG  ACCUAGGCGA  GGAUUAUUUG
GACAUAGCCG  GACUAAAAAU  ACCAAAAUCG  GAACUACAAG  GGAAUGUCUU  AACGUUUGUU
CCGACAAAAA  AGUUGGCGUC  AGACACUGCU  AAGAAACUAA  CCACCCAGGG  CUACAACGCU
GGGUAUUACU  UUAGUGGUGA  AGACCCAAGC  UCGCUGCGCA  CCAUAACAUC  AAAAUCCCCG
UACAUCAUAA  UAGCCACCAA  UGCAAUAGAG  UCAGGGGUGA  CAUUACCAGA  CCUAGACACA
GUAAUUGACA  CAGGGAUGAA  GUGUGAAAAG  AGGGUGAGAA  UAGAGAACAA  GGCUCCAUAC
AUAAUAACAG  GCCUAAAAAG  AAUGGCCAUC  ACCACAGGGG  AGCAAGCCCA  GAGGAAGGGA
AGAGUAGGUA  GAGUCAAACC  AGGGAGAUAC  CUAAGAGGGC  CUGAAAAUGC  AGGUGGAGAG
AGAGAUUAUC  ACUAUGACCU  GCUGCAGGCA  CAACGUUAUG  GGCUCCAGGA  UGCUAUCAAC
AUCACCAAAU  CAUUCAGGGA  GAUGAACUAU  GACUGGGCAC  UCUAUGAGGA  AGACCCACUG
AGAAUAACAC  AAUUGGAGGU  AUUAAAUACC  CUACUCAUAU  CCAAAGAUCU  GCCAACAGUC
ACAAAGAAUU  UGAUGACCAG  GACCACACAC  CCAGAACCAA  UUCAAUUAGC  UUACAAUAGC
AUAGAAACCC  CCGUCCAGU   GCUGUUCCCG  AAAGUGAAGG  GUGGAGAGGU  GACCGAUGCU
UAUGAGACCU  AUGAACUGAU  GAUGUGUCGG  AAGCUGGAUA  ACGACCCCCC  GAUUUAUCUG
UAUGCCACGG  AAGAUGAAGA  CCUAGCAGUG  GACCUCCUGA  ACCUGAAAUG  GCCCGCAGUG
UCAACAGCCU  CGGCCAUAGA  AACAGAGGAC  GCCCUCAACA  AGUUAUCGGG  GCUUUCGGCA
GGGGAAACAG  CCCUGCUAGU  GGCUCUGCUA  GGUUGGGUCG  GUUACGAGGC  UCUGGUGAAA
AGACACAUAC  CAAUAGUGAC  UGACAUAUAU  ACAAUUGAAG  AUGAAAAACU  UGAGGACACC
ACCCACCUCC  AGUAUUCACC  AGAUGAACUG  CAAAACACCG  AGACAGUGGA  GCUGAAAGAC
CUGUCGGCAC  ACGAACUGAA  AGAAGCCCUG  GAAAGCGGAA  AAAGUUAUGU  CAAAGACGCC
UUUGAAUUCG  UAAAAUCACA  GGUUGAGAAG  CUCCCCGACA  CAAAAAUUUA  CAAGCAAGUC
CAAGAGAAGU  CACCCGGUCU  UUUAGAAAAA  UUUUUGGCCU  AUCUGUCAGA  ACACAGUAGU
GACAUAAAGA  AAUAUGGAUU  GUGGGGGGUC  CAUACCUCUC  UGUACAAUAG  UAUCAAGAG
AGAUUGGGGC  ACGAAACUGC  CUUCGCUUCA  UUGAUCAUCA  AGUGGAUAGC  AUUUUCCAGC
GAAGGCUGC   CUGGAAUGGU  GAAACAAGCU  GCUGUAGACU  UGGUGGUAUA  UUAUCUGAUC
AACAAACCAG  AUUUCAAAGG  UGACAAAGAC  ACCCAAGAUG  AUGGAAGGAA  GUUCGUAGGA
GCCCUGUUCG  UGUCAGCUCU  GGCCAAUUAC  ACAUUUAAAA  AUUUUAAUAA  GUCAACACUU
GAAGGCUUAG  UAAUGCCAGC  AUUGAACUAC  CUACCAUAUG  CAGGGGCUGC  ACUAAAAAUA
UUUGUGCCUA  CUAAAUUAGA  GAGCUUAGUA  AUACUGUCAA  CAACCAUCUA  CAGGACCUAC
CUCUCCAUUA  AGAAAGGCUC  UAGUCAAGGA  CUGGCUGGGU  UAGCAGUGAG  CUCAGGUAUG
GAAAUUAUGA  AUCAGAAUCC  AAUAUCAGUG  GCCAUUGCGG  UGGCAUUGGG  AGUCGGUGCC
AUAGCUGCAC  ACAAUGCGAU  CGAGAGCAGC  GAGGCAAAGA  GGACCCUGUU  GAUGAAGGUA
UUUGUGAAAA  ACUUUCUAGA  CCAGGCAGCG  ACAGACGAGC  UGGUAAAAGA  GAACCCAGAA
AAAAUAAUAA  UGGCAGUAUU  UGAAGCAAUC  CAGACAGCAG  GUAAUCCAAU  AAGGCUAAUA
UACCACCUAU  AUGCCAUGUU  CUACAAAGGU  UGGAACGCCU  CCCAGAUAGC  AGAUAAGACA
GCGGGGAGGA  ACAUAUUCGU  GCUGACAAUA  UUCGAGGGUU  UAGAACUGUU  GGGACUAGAC
AAGGAUUCCA  AGUGGAGGGA  UUUGAGCUCA  AAUUAUUUAG  UGGAUGCAAU  CAGGAAGCUC
AUUGAAAAAU  UGACUAAAAU  ACUCAGAAAC  ACCACCAAGU  CAUUAAUCAA  AUCCUUGCUG
CCAGCUCCAU  UCUCUUGCAC  GAGAUUCACA  AGAGACAACA  GAAUUGGAUG  GCCACAUUUA
AAUUUUGAUU  AUUACGAGAU  AAAUUGUGCA  UGUGGGUACC  GGAGGAGAGU  GGUAAAAACU
GUCAUCGACC  CAGUCACCUG  GGAGACUUUG  GAAGAAGAAG  GCCCUGAGUU  CUGCUUCAAC
AGGGGGACUA  ACGCCCUGGC  AAACCCAAGA  GUUGCAAGUU  AUUACUCAGC  UGGAGAGCCA
GUUCUCCCAG  UGGUAAAAAG  AGAGGGGGUU  GGCGAAAUCC  UGGUAAGGGG  GGUGACAAUC
CAGAUGCAUU  AUGACCACAA  CAAGAUACUC  GCCACUGACA  ACUGGCAAGU  GCCAUCCAG
GCAGUGACGA  AGAUAUUUAC  AGAUUACCAG  GGCAUAGGGU  ACCAAGAAGC  AUAUCUGGGA
ACCCAGCCAA  ACUACAAAGC  ACUGGUGAAG  AGGUCAUCCG  UCACGAUUAC  AAAAGAAGGC
CUGAAAUUUA  UAAGAUGCAA  GAAAGGGAUC  GCGUAUACGA  CCAAUCUAAA  CUUAACCCAC
AUCCAAAAGC  UGGUGCAGGU  GUGCAGAAUG  AAUGAAUUGC  AAGAAGGCGU  CAUACCUGAG
ACCUUGGAUG  GCGACACCUG  GAUUAACUAC  AUGGCAAUCA  UCGAAGAUGU  GGGGGCCACA
AAACCAAGCU  UGGAGAGAGA  GUCAUACCCG  AAACCAUACG  AGGAGGAUCC  CCUCGAAGGC
CCCAGUGUGA  UCGUGGAAAC  AGGGGACGUG  GACAUCACAA  AAGUGGGCGU  AAAUCAACAA
UCCAGUUCAU  CAGGAACCGU  CUUUCAAGUA  GUGGAGAAGA  UCUAUACUAA  ACUGGUCAUU
ACAAAUGUAA  UAAAGAUAGG  AUUCAAAGAA  GGCUGUUUCC  CGGGACCCAC  AAAGAAUGUG
AAUUCAUUGA  AUGAGCACAU  AGAAGAUAAA  GACAGUAAAC  CAUACACUCUU  CAUAUGCUCU
```

Figure 8 contd.

```
UCCGACAAAG  CAAUGUCCAA  CAGAGUAAAG  ACUGCAAGGA  ACAUUAAGAA  ACUCAACACA
AAUUCGGCAA  UAGUAGCCCG  UAAUUUGGCC  AGGGAAGGGA  AAUUGAUCAU  AAUAGUACUA
GGAGAGAAGU  ACCAUGAGGA  CAUCUACAAA  CAUGCUGACU  UCAAGGGGAC  UUUCCUCGAC
AGGAAGGCAC  UGGAAGCCCU  GUCCAAGGCC  AAGCCUGUAA  AAAAGAACAU  GACUAGGAGA
GAGGCUCAAU  AUCUGCUGGA  AAAGAAGCUU  AGUGAAGACA  UAGAGGUACC  AGAAUGGCUG
GGAUCUGAAA  AACCUAUGUU  UUUGGAUGUA  ACCAAAAGUG  GUGAAACAUA  CCAUCUGUUA
GGGGAUCUAA  AUCACUUGAA  GGCACAAGCG  GAACAACUUG  GUGCCAAGGC  AACCACUACA
AUAAAUAAAG  UAGGGAAGAC  GUAUACAAUG  AACCUCAGUA  CAUGGUGGGA  GAGUGAAAGA
ACCCCCACAU  UCAGACCCCU  GUUCCAGGAA  CUGCUGUUAC  GCUGCAGGCC  AUGCACUAGG
GAGGAGUAUA  AGAGCUGCCA  UUUUGUAGGG  GCUACACAAU  UGGCCGGAGG  AAACUGGAAA
CCAGUAGCCC  CUGUGGUGCA  CCUAGGAACU  AUACCAGCAA  AAAGAGAGAA  AUGCCUGCCA
UAUGAAGCAU  AUAUAUCACU  UAAGAAUAUG  GUGGAAAACC  UAAAAAUAGA  GAAUCCUGGA
GUGUGCAAGA  AGAAACAUCA  GUGGCUCUUA  AAUAAAAUUA  AAAAACAAGG  GGAAUUAGGC
UUGAAGAAUC  UCGUAUCUCC  UGGGAGUGUA  GGGGGAUCAC  GUGGUUACAG  AAAGAAAGAA
UUCAACAUUU  ACAACAAACA  GAUUACGAGC  ACAAUGCUGG  CUGUGGGGAU  CAAGCCAGAG
AAGUUUCCAG  UCGUCAGAGC  UCAAACGUCC  AAGAGAGAAU  UCCAUCAAGC  AAUUAGAGAG
AAGAUUGAUA  AGCUGCCCAA  CCCCCAGAAU  AGGGACCUCC  AUAAGGAACU  GAAAGAAAUA
UUUGACUCGG  UGUGCGCUGU  AAAAGAUUUG  AAACAUACCU  ACGAAGAAGU  CAGCUGGGAU
GUACUGACGG  UGGGGAUCAA  CAGGAAAGGA  GCAGCUGGCU  AUUUCGAAAA  GAAGAAUGUG
GGUGAGAUAA  UAGACACUGA  CAGGAGAGGG  GUCGAGAAAC  UUAUCAAGGU  AAUGAAAACC
GGGGGACCUA  UAGACUACUA  UGAGACAGCA  AUACCUAAGA  AUGAGAAGAG  AGCAGUUGUA
GAUGACUGGC  UGGAAGGAGA  UUUCGUUGAA  GAGAAAAAGC  CACGAGUGAU  CCAAUACCCA
GAAGCAAAAA  UGCGUUUGGC  AAUAACCAAA  GUUAUGUACA  AUUGGGUCAA  GCAAAAACCA
GUGGUGAUAC  CCGGGUACGA  GGGGAAGACA  CCUUUGUUUA  AAGUGUUUGA  UAAGGUUUUU
GAUGAAUGGA  AACAACUGAG  AGACCCGGUU  GCAGUCAGUU  UCGACACUAA  AGCAUGGGAU
ACACAAGUGA  CACCUGAGGA  CUUACAAUUG  AUAUCGGAAA  UCCAAAGUA  UUACUUUAAA
CCAAAAUACC  ACAAAUUUAU  UGAAACAUUG  ACUGCGGAGA  UGAAAGAAGU  GCCAGUCGUG
UGCCAGGAUG  GGGAGGUUUA  CAUCAGGCUA  GGACAGAGAG  GAAGUGGCCA  GCCAGAUACC
AGUGCAGGAA  AUAGCAUGUU  GAAUGUGUUG  ACAAUGAUAU  AUGCUUUUUG  CAAAUCCAAU
GACAUCCCGU  ACAAGGCAUU  CCGAAGGGUG  GCAAAAAUAC  ACGUCUGUGG  CGACGAUGGG
UUCCUAAUUA  CAGAGAGGCG  CCUAGGAGAG  AACUUUGCUG  CGAUGGGGCC  ACAAAUACUG
AUGGAAGCCG  GGAAACCACA  GAAACUGGUA  GGAGAGAUGG  GACUGAAGCU  AGCCUACAAG
UUCCAGGACA  UAGAGUUCUG  CUCCCACACG  CCUAUACAAG  UAAGGUGGGA  UGACAACACA
ACUAGUUAUU  UACCAGGCAG  AGACACGGCA  ACCAUCUUAG  CAAAGAUGUG  UACCAGGCUG
GACUCCGCAG  GGGAGCGGGG  UACCAGUUCC  UAUGAACUUG  CUGUUGUGUU  UAGUUUCCUC
CUAAUGUACU  CCUGGAACCC  AAUAGUUAGA  AGGAUCUGCC  UAUUAGUUAU  GGCAACAAUC
GGAGUAAAAG  ACCCAGAUAA  AUCAGGAACA  AUAUUCACCU  UCUCUGGAGA  CCCACUAGGG
GCGUACAAGG  AAGUAAUAGG  ACACCGAUUG  GGCCAACUAA  AACAAACUGA  AUUUUCAAAA
UUGGCAAGUU  GCAAUUUAUC  AAUGUCACUG  UUAGGGAUUU  ACAGUAGGCA  CACCUCAAAA
AGAAUCAUAG  AGGACUGUGU  GAAGAUUGGA  ACCCUAAACC  GACAGAGCCC  CGUGAAUGCA
GAUCGCUUGA  UAGCAAAGAA  GACUGGUUUU  GUAUACGAAC  CGUCAAGGGG  CAGUGUUAGG
GUGGGAAAAC  ACUAUGAAGA  AUUGGAAUUG  GACAAAUGGA  AAAAGAAGAC  GCCACUCAUA
GAAGGGGCGG  AAAGGUACAU  UCCAGGCCCG  AUUAAGACCU  UUAUACUGAA  AAGACUCAAA
GUGUUACAGA  UGAUAGGCCU  GAAAUUCUUC  UAAUAUAUAG  GGAGUACAGG  UUACAGCUGU
GUUUCACAGA  AAGUGGGUGG  CGACACUUAC  CUCUGGAGCC  AACUUGUAAA  UAGGUUAGUA
AUAUUUAUUU  AAUAGACGUU  AUUUACUUAU  UUAUUUAUUU  AUUUGAUUAU  UUAUUAAUUA
UUUAAAAACG  CUACUGCAUG  AGCUGGUUAG  UCAGCUUAUG  AAAGUGGGUU  GUGUCACUUG
CGUCAGGAGC  AAAUACCUCA  AUAACAACGC  UACCACAUAG  CCUGAGACCA  GGUUGUGAAA
GAGAGUUGCG  CCUCUUGCGU  UGGGAGCUAU  CUACCUCAAG  UACCCAGCUG  CUGAAGCUGG
UUACCUCAAU  UCCAAUGGAU  GACCGUAGCC  AUUGGUCUUA  UUAAUUCGGU  CAUUUAUAAU
UAGCACUUUA  AAGCUAAUUG  GGACAUAAAG  UAAGGACGUC  CUAGGGAGGA  CUACUUACAG
UUCCAAGAGG  CCCC
```

Figure 9:

SEQ ID NO: 3 amino acid sequence of Linda virus

*MEFKILNNTKKKNNNEEEAEGNMFWRMYRRPPPGCYEPTYNLSGTPSFGP*
*MHPPLRKGSTLRLPHWRGIATVGCELKNLPRKGDCTKCHANPTSGIYLNL*
*GAVFYKDYEGEVYHRVPLEHCEEQQRCEVVKRVGRMTASDGSLVGVLVCS*
*DDCVLFERRRGEHTVLKWVKNPIGAPLWVQSCS*DEKGAKPKNKSKQQNDR
MAPGKMVTKPKEVEADQKTRPPDATIVVDGQKYQVRKKGKAKPKTPDGLY
HNKNKPEASRKKLEKALLAWAVIAIILIQQTTANNVTQWNLWDDKNATDV
HSVMHQRQIKRSLHGIWPERICKGVPGHLATDYELKRIEGMLDASEKTNF
TCCRLQRHEWNKHGWCNWYNIDPWVAIMNRTQALLSSGQNFTECAVTCRY
DTEQQINIVTQARMTPTILTGCKKDVNFSFSGEVRTGPCNYELKPEDLMR
ILDHTNCKDFSYFGEGLVDDFTEATEKIRSSGYRALSWLQDKLEKTKKKV
FGAEATPYCNVTRRVFNIIYTNNCTPAGLPDNTRIVGPGTFDISEMENKK
LLPNLDYHLADFMVLGLVALSDFAPETASTIYLVLHYWLPQAEVHTLDTP
LDTNKLNLTRNRQVSSVVPNSIWLGGQLVCVKPRWWPYSAEITTVISGLT
TVTDLVVKTIEELVSLWTEATAVAFLAALIKIFRGQPIQALAWLIIIGGA
QGLECNFELQYALAGNTSMSLLGPTALKTQWYQAADGVKITDGVVTVICN
KGIFSVTPRCKEAPVRYLAINHPRSLSTSAWFKKIHDPADHPTETLMGEK
GRAYLCPCGATPLPKPKVPFNPITIQGSAFSLTCPKNWQGDIECNLLSPD
TLAIETIYTFRKHKPYKEEPYCSYTKVVDGYLRNVHLWGHDTCVAGDIIN
GSQDDSVTKCKWCGYEFNSATDLPDYPIGYCTKRGTNYLIRYKQVPCEVG
GVRIGSGKVECTIGSTRVKVEQTSNELGPMPCKPIVYSSQGPPNPKTCTF
KWSYTLNNKYYEPRDEFFQQYITSGGYQYWFDLTAKDHVMDWVTRYFPII
VVALLGGRAVLWILIAYELLNHYQVGADQNTLLQAEALVIGNILMTRDLE
VMVCFLLLMVLIRRQQARRALALVFHWMVMHPAQSAIATLVYVIGIVRAE
EGQVNSDSSTQAHVVAILLFLIYHTLKERDLHTAMTLLLTFSIKSTDYVD
THYYEIPMLFTVISLVISIYIFNIHIKTKWVALVLSMVGMVTFIRCLWLI
RNIQITPPSIPLTYISPKILIIAYLVSLTVLVNNNLDLASYVIRAGPILM
SYLTLWVDILMLLVLLPWYELIKVYYLKKKKDDIEDCFQYSGIATQGLSP
YNQDFVDPKEGVHLIPSQNKSNFTRTAYLTILRALVLTAFSSIWKPLILA
ELLLESIYWTHIKVAKEVAGSTRLIGRFVAALIELNWVFDDKEAARYKKF
FVLTSRVRDLMVKHKVQNDTMRQWFEETEIFGLQKVALVVRAHSLTADSN
SILCSVCEEKQNIEAKRVCPKCGNRGTGIKCGMTLAEFEEKYYKKIYLVD
GDNTQAYRREERGEVTYTARGAFFLRNLPILATKNKYILVGNLGMELQDL
ESMGWIIRGPAVCKKIVHHERCRPTIPDKLMAFFGLMPRGVVPRAPTRFP
VSLLKIKRGFETGWAYTHPGGISSVMHVTAGLDMYVNDAMGRTKVQCQER
NKLTDECEYGIKTDSGCSEGARCYVINPEAVNIAGTRGAMVHLRKTGPEF
TCVTAQGTPAFYNLRNLKGWSGLPIFEAATGRVVGRVKAGKNAEDSPTTI
MSGTQAAKPTECDLESVVRKLETMNRGEFKQVVLATGAGKTTELPRKLIE
AVGRHKRVLVLIPLRAAAEGVYNYMRTKHPSIAFNLRIGDLKEGDMATGI
TYASYGYFCQMDMPRLDAAMKEYNYIFLDEYHCATPEQLAVMSKIHRISA
DLRVVAMTATPAGAVSKVGQKFSIEEVVVPEVMKGEDLGEDYLDIAGLKI
PKSELQGNVLTFVPTKKLASDTAKKLTTQGYNAGYYFSGEDPSSLRTITS
KSPYIIIATNAIESGVTLPDLDTVIDTGMKCEKRVRIENKAPYIITGLKR
MAITTGEQAQRKGRVGRVKPGRYLRGPENAGGERDYHYDLLQAQRYGLQD
AINITKSFREMNYDWALYEEDPLRITQLEVLNTLLISKDLPTVTKNLMTR
TTHPEPIQLAYNSIETPVPVLFPKVKGGEVTDAYETYELMMCRKLDNDPP
IYLYATEDEDLAVDLLNLKWPAVSTASAIETEDALNKLSGLSAGETALLV
ALLGWVGYEALVKRHIPIVTDIYTIEDEKLEDTTHLQYSPDELQNTETVE

Figure 9 contd.

LKDLSAHELKEALESGKSYVKDAFEFVKSQVEKLPDTKIYKQVQEKSPGL
LEKFLAYLSEHSSDIKKYGLWGVHTSLYNSIKERLGHETAFASLIIKWIA
FSSEGLPGMVKQAAVDLVVYYLINKPDFKGDKDTQDDGRKFVGALFVSAL
ANYTFKNFNKSTLEGLVMPALNYLPYAGAALKIFVPTKLESLVILSTTIY
RTYLSIKKGSSQGLAGLAVSSGMEIMNQNPISVAIAVALGVGAIAAHNAI
ESSEAKRTLLMKVFVKNFLDQAATDELVKENPEKIIMAVFEAIQTAGNPI
RLIYHLYAMFYKGWNASQIADKTAGRNIFVLTIFEGLELLGLDKDSKWRD
LSSNYLVDAIRKLIEKLTKILRNTTKSLIKSLLPAPFSCTRFTRDNRIGW
PHLNFDYYEINCACGYRRRVVKTVIDPVTWETLEEEGPEFCFNRGTNALA
NPRVASYYSAGEPVLPVVKREGVGEILVRGVTIQMHYDHNKILATDNWQV
PFQAVTKIFTDYQGIGYQEAYLGTQPNYKALVKRSSVTITKEGLKFIRCK
KGIAYTTNLNLTHIQKLVQVCRMNELQEGVIPETLDGDTWINYMAIIEDV
GATKPSLERESYPKPYEEDPLEGPSVIVETGDVDITKVGVNQQSSSSGTV
FQVVEKIYTKLVNTNVIKIGFKEGCFPGPTKNVNSLNEHIEDKDSKPYIF
ICSSDKAMSNRVKTARNIKKLNTNSAIVARNLAREGKLIIIVLGEKYHED
IYKHADFKGTFLDRKALEALSKAKPVKKNMTRREAQYLLEKKLSEDIEVP
EWLGSEKPMFLDVTKSGETYHLLGDLNHLKAQAEQLGAKATTTINKVGKT
YTMNLSTWWESERTPTFRPLFQELLLRCRPCTREEYKSCHFVGATQLAGG
NWKPVAPVVHLGTIPAKREKCLPYEAYISLKNMVENLKIENPGVCKKKHQ
WLLNKIKKQGELGLKNLVSPGSVGGSRGYRKKEFNIYNKQITSTMLAVGI
KPEKFPVVRAQTSKREFHQAIREKIDKLPNPQNRDLHKELKEIFDSVCAV
KDLKHTYEEVSWDVLTVGINRKGAAGYFEKKNVGEIIDTDRRGVEKLIKV
MKTGGPIDYYETAIPKNEKRAVVDDWLEGDFVEEKKPRVIQYPEAKMRLA
ITKVMYNWVKQKPVVIPGYEGKTPLFKVFDKVFDEWKQLRDPVAVSFDTK
AWDTQVTPEDLQLISEIQKYYFKPKYHKFIETLTAEMKEVPVVCQDGEVY
IRLGQRGSGQPDTSAGNSMLNVLTMIYAFCKSNDIPYKAFRRVAKIHVCG
DDGFLITERRLGENFAAMGPQILMEAGKPQKLVGEMGLKLAYKFQDIEFC
SHTPIQVRWDDNTTSYLPGRDTATILAKMCTRLDSAGERGTSSYELAVVF
SFLLMYSWNPIVRRICLLVMATIGVKDPDKSGTIFTFSGDPLGAYKEVIG
HRLGQLKQTEFSKLASCNLSMSLLGIYSRHTSKRIIEDCVKIGTLNRQSP
VNADRLIAKKTGFVYEPSRGSVRVGKHYEELELDKWKKKTPLIEGAERYI
PGPIKTFILKRLKVLQMIGLKFF*

Figure 10:

a) SEQ ID NO. 4: Npro of Linda pastivirus

MEFKILNNTKKKNNNEEEAEGNMFWRMYRRPPPGCYEPTYNLSGTPSFGP
MHPPLRKGSTLRLPHWRGIATVGCELKNLPRKGDCTKCHANPTSGIYLNL
GAVFYKDYEGEVYHRVPLEHCEEQQRCEVVKRVGRMTASDGSLVGVLVCS
DDCVLFERRRGEHTVLKWVKNPIGAPLWVQSC b) SEQ ID NO. 5: Core of Linda pastivirus SDEKGAKPKNKSKQQNDRMAPGKMVTKPKEVEADQKTRPPDATIVVDGQKY
QVRKKGKAKPKTPDGLY
HNKNKPEASRKKLEKALLAWAVIAIILIQQTTA c) SEQ ID NO. 6: Erns of Linda pastivirus NNVTQWNLWDDKNATDV
HSVMHQRQIKRSLHGIWPERICKGVPGHLATDYELKRIEGMLDASEKTNF
TCCRLQRHEWNKHGWCNWYNIDPWVAIMNRTQALLSSGQNFTECAVTCRY
DTEQQINIVTQARMTPTILTGCKKDVNFSFSGEVRTGPCNYELKPEDLMR
ILDHTNCKDFSYFGEGLVDDFTEATEKIRSSGYRALSWLQDKLEKTKKKV
FGAE d) SEQ ID NO. 7: E1 of Linda pastivirus ATPYCNVTRRVFNIIYTNNCTPAGLPDNTRIVGPGTFDISEMENKK
LLPNLDYHLADFMVLGLVALSDFAPETASTIYLVLHYWLPQAEVHTLDTP
LDTNKLNLTRNRQVSSVVPNSIWLGGQLVCVKPRWWPYSAEITTVISGLT
TVTDLVVKTIEELVSLWTEATAVAFLAALIKIFRGQPIQALAWLIIIGGA
QG e) SEQ ID NO. 8: E2 of Linda pastivirus LECNFELQYALAGNTSMSLLGPTALKTQWYQAADGVKITDGVVTVICN
KGIFSVTPRCKEAPVRYLAINHPRSLSTSAWFKKIHDPADHPTETLMGEK
GRAYLCPCGATPLPKPKVPFNPITIQGSAFSLTCPKNWQGDIECNLLSPD
TLAIETIYTFRKHKPYKEEPYCSYTKVVDGYLRNVHLWGHDTCVAGDIIN
GSQDDSVTKCKWCGYEFNSATDLPDYPIGYCTKRGTNYLIRYKQVPCEVG
GVRIGSGKVECTIGSTRVKVEQTSNELGPMPCKPIVYSSQGPPNPKTCTF
KWSYTLNNKYYEPRDEFFQQYITSGGYQYWFDLTAKDHVMDWVTRYFPII
VVALLGGRAVLWILIAYELLNHYQVGA f) SEQ ID NO. 9: P7 of Linda pastivirus

DQNTLLQAEALVIGNILMTRDLE
VMVCFLLLMVLIRRQQARRALALVFHWMVMHPAQSAIATLVYVIGIVRAE
EG

Figure 10 contd.

g) SEQ ID NO. 10: NS2 of Linda pastivirus
QVNSDSSTQAHVVAILLFLIYHTLKERDLHTAMTLLLTFSIKSTDYVD
THYYEIPMLFTVISLVISIYIFNIHIKTKWVALVLSMVGMVTFIRCLWLI
RNIQITPPSIPLTYISPKILIIAYLVSLTVLVNNNLDLASYVIRAGPILM
SYLTLWVDILMLLVLLPWYELIKVYYLKKKKDDIEDCFQYSGIATQGLSP
YNQDFVDPKEGVHLIPSQNKSNFTRTAYLTILRALVLTAFSSIWKPLILA
ELLLESIYWTHIKVAKEVAGSTRLIGRFVAALIELNWVFDDKEAARYKKF
FVLTSRVRDLMVKHKVQNDTMRQWFEETEIFGLQKVALVVRAHSLTADSN
SILCSVCEEKQNIEAKRVCPKCGNRGTGIKCGMTLAEFEEKYYKKIYLVD
GDNTQAYRREERGEVTYTARGAFFLRNLPILATKNKYILVGNLGMELQDL
ESMGWIIR h) SEQ ID NO. 11: NS3 of Linda pastivirus GPAVCKKIVHHERCRPTIPDKLMAFFGLMPRGVVPRAPTRFP
VSLLKIKRGFETGWAYTHPGGISSVMHVTAGLDMYVNDAMGRTKVQCQER
NKLTDECEYGIKTDSGCSEGARCYVINPEAVNIAGTRGAMVHLRKTGPEF
TCVTAQGTPAFYNLRNLKGWSGLPIFEAATGRVVGRVKAGKNAEDSPTTI
MSGTQAAKPTECDLESVVRKLETMNRGEFKQVVLATGAGKTTELPRKLIE
AVGRHKRVLVLIPLRAAAEGVYNYMRTKHPSIAFNLRIGDLKEGDMATGI
TYASYGYFCQMDMPRLDAAMKEYNYIFLDEYHCATPEQLAVMSKIHRISA
DLRVVAMTATPAGAVSKVGQKFSIEEVVVPEVMKGEDLGEDYLDIAGLKI
PKSELQGNVLTFVPTKKLASDTAKKLTTQGYNAGYYFSGEDPSSLRTITS
KSPYIIIATNAIESGVTLPDLDTVIDTGMKCEKRVRIENKAPYIITGLKR
MAITTGEQAQRKGRVGRVKPGRYLRGPENAGGERDYHYDLLQAQRYGLQD
AINITKSFREMNYDWALYEEDPLRITQLEVLNTLLISKDLPTVTKNLMTR
TTHPEPIQLAYNSIETPVPVLFPKVKGGEVTDAYETYELMMCRKLDNDPP
IYLYATEDEDLAVDLLNLKWPAVSTASAIETEDALNKLSGL i) SEQ ID NO. 12: NS4A of Linda pastivirus

SAGETALLVALLGWVGYEALVKRHIPIVTDIYTIEDEKLEDTTHLQYSPDELQNT
ETVELKDL j) SEQ ID NO. 13: NS4B of Linda pastivirus SAHELKEALESGKSYVKDAFEFVKSQVEKLPDTKIYKQVQEKSPGL
LEKFLAYLSEHSSDIKKYGLWGVHTSLYNSIKERLGHETAFASLIIKWIA
FSSEGLPGMVKQAAVDLVVYYLINKPDFKGDKDTQDDGRKFVGALFVSAL
ANYTFKNFNKSTLEGLVMPALNYLPYAGAALKIFVPTKLESLVILSTTIY
RTYLSIKKGSSQGLAGLAVSSGMEIMNQNPISVAIAVALGVGAIAAHNAI
ESSEAKRTLLMKVFVKNFLDQAATDELVKENPEKIIMAVFEAIQTAGNPI
RLIYHLYAMFYKGWNASQIADKTAGRNIFVLTIFEGLELLGLDKDSKWRD
L

Figure 10 contd.

k) SEQ ID NO. 14: NS5A of Linda pastivirus

SSNYLVDAIRKLIEKLTKILRNTTKSLIKSLLPAPFSCTRFTRDNRIGW
PHLNFDYYEINCACGYRRRVVKTVIDPVTWETLEEEGPEFCFNRGTNALA
NPRVASYYSAGEPVLPVVKREGVGEILVRGVTIQMHYDHNKILATDNWQV
PFQAVTKIFTDYQGIGYQEAYLGTQPNYKALVKRSSVTITKEGLKFIRCK
KGIAYTTNLNLTHIQKLVQVCRMNELQEGVIPETLDGDTWINYMAIIEDV
GATKPSLERESYPKPYEEDPLEGPSVIVETGDVDITKVGVNQQSSSSGTV
FQVVEKIYTKLVNTNVIKIGFKEGCFPGPTKNVNSLNEHIEDKDSKPYIF
ICSSDKAMSNRVKTARNIKKLNTNSAIVARNLAREGKLIIIVLGEKYHED
IYKHADFKGTFLDRKALEALSKAKPVKKNMTRREAQYLLEKKLSEDIEVP
EWLGSEKPMFLDVTKSGETYHLLGDLNHLKAQAEQLGAKATTTINKVGKT
YTMNL l) SEQ ID NO. 15: NS5B of Linda pastivirus STWWESERTPTFRPLFQELLLRCRPCTREEYKSCHFVGATQLAGGNWKPV
APVVHLGTIPAKREKCLPYEAYISLKNMVENLKIENPGVCKKKHQWLLNK
IKKQGELGLKNLVSPGSVGGSRGYRKKEFNIYNKQITSTMLAVGIKPEKF
PVVRAQTSKREFHQAIREKIDKLPNPQNRDLHKELKEIFDSVCAVKDLKH
TYEEVSWDVLTVGINRKGAAGYFEKKNVGEIIDTDRRGVEKLIKVMKTGG
PIDYYETAIPKNEKRAVVDDWLEGDFVEEKKPRVIQYPEAKMRLAITKVM
YNWVKQKPVVIPGYEGKTPLFKVFDKVFDEWKQLRDPVAVSFDTKAWDTQ
VTPEDLQLISEIQKYYFKPKYHKFIETLTAEMKEVPVVCQDGEVYIRLGQ
RGSGQPDTSAGNSMLNVLTMIYAFCKSNDIPYKAFRRVAKIHVCGDDGFL
ITERRLGENFAAMGPQILMEAGKPQKLVGEMGLKLAYKFQDIEFCSHTPI
QVRWDDNTTSYLPGRDTATILAKMCTRLDSAGERGTSSYELAVVFSFLLM
YSWNPIVRRICLLVMATIGVKDPDKSGTIFTFSGDPLGAYKEVIGHRLGQ
LKQTEFSKLASCNLSMSLLGIYSRHTSKRIIEDCVKIGTLNRQSPVNADR
LIAKKTGFVYEPSRGSVRVGKHYEELELDKWKKKTPLIEGAERYIPGPIK
TFILKRLKVLQMIGLKFF

Figure 11

DNA sequences of Linda virus proteins and untranslated regions a) SEQ ID 16: 5'-UTR GTATAGCAGCAGTAGCTCAAGGCTGCTATACGATTGGACATACCAAATTC
CAATTGGTGTTAGGGACCACCTAGGTGAAGGCCGACGACAGGTAGCCATT
CCTGTTAGTAGGACGAACCGTTATGGTGGACTGGTTGCTCAGGTGAGCAG
GCTGCAATGCGTAAGTGGTGAGTACACCACAGCCGTCAAAGGTGCCACTG
GTAAGGATCACCCACTGGCGATGCCTTGTGGACGGGGGCGTGCCCAACGC
AATGTTAGCGGTGGCGGGGGCTGCCATCGTGAAGCTAGGTCTTGATGGA
CCTTGTTGCCTGTACAGTCTGATAGGATGCCGGCGGATGCCCTGTGACAG
CCAGTATAAAGAATATCCGTTGTGATTGCAC b) SEQ ID NO: 17 Npro:

ATGGAGTTTAAAATTCTCAACAACACAAAGAAAAAAAATAATAATGAGGA
GGAAGCTGAGGGGAACATGTTCTGGCGGATGTACCGAAGACCTCCGCCTG
GTTGCTACGAACCAACTTACAACCTAAGTGGGACACCTAGCTTCGGACCC
ATGCACCCACCACTGAGGAAAGGGAGTACATTACGTTTACCCCACTGGAG
AGGCATAGCCACGGTTGGATGTGAGCTTAAAAACCTGCCACGCAAGGGTG
ATTGTACTAAGTGCCACGCTAACCCAACATCTGGCATCTACCTCAACCTG
GGTGCGGTGTTTTATAAAGATTACGAGGGGGAGGTATACCATAGAGTCCC
CCTTGAACACTGTGAGGAACAGCAGAGGTGCGAAGTCGTCAAGCGTGTAG
GGAGAATGACTGCTAGCGATGGATCCTTGGTGGGAGTGCTAGTATGCAGT
GACGACTGCGTGCTGTTTGAGAGAAGAAGAGGGGAACACACAGTGTTGAA
GTGGGTAAAGAACCCTATCGGGGCGCCACTCTGGGTACAGAGCTGC c) SEQ ID NO: 18 Core TCCGACGAGAAGGGGGCCAAACCAAAAAACAAGTCTAAACAACAAAACGA
TCGAATGGCACCGGGTAAAATGGTGACAAAACCTAAGGAAGTGGAAGCTG
ATCAGAAAACTAGACCGCCAGACGCTACAATTGTGGTGGATGGACAGAAA
TATCAAGTAAGGAAGAAAGGGAAGGCAAAACCAAAGACACCAGATGGCCT
GTACCACAATAAAAACAAGCCGGAGGCATCTAGAAAGAAATTAGAAAAAG
CGCTACTAGCTTGGGCAGTCATTGCAATAATATTGATTCAGCAGACCACA
GCA d) SEQ ID NO: 19 Erns AACAATGTGACGCAGTGGAACTTGTGGGACGACAAGAACGCAACAGATGT
GCACTCAGTGATGCATCAGAGACAAATCAAGCGCAGCCTCCACGGCATCT
GGCCTGAAAGAATCTGCAAAGGGGTCCCAGGTCATCTGGCTACTGACTAT
GAGCTAAAACGGATAGAGGGGATGTTGGATGCCAGCGAAAAACTAATTT
TACCTGTTGCAGGCTGCAAAGACACGAATGGAACAAACATGGCTGGTGTA
ACTGGTACAATATAGACCCCTGGGTCGCCATTATGAACAGGACCCAAGCC
CTTCTATCTAGTGGCCAAAACTTTACAGAGTGTGCCGTTACATGTAGGTA
TGACACAGAACAGCAGATAAACATAGTAACTCAAGCCCGCATGACACCAA
CGATTTTAACAGGGTGTAAGAAGGACGTAAACTTCTCTTTCTCAGGGGAG

Figure 11 contd.

GTGAGGACTGGGCCTTGCAACTATGAACTGAAGCCAGAAGACTTAATGAG
GATTCTGGACCATACCAACTGCAAAGATTTCAGCTATTTCGGAGAAGGTC
TGGTGGATGATTTCACAGAAGCCACGGAAAAAATTAGATCTAGTGGGTAC
AGGGCCCTGTCGTGGCTGCAAGACAAGCTAGAGAAAACTAAGAAGAAGGT
GTTTGGAGCTGAA e) SEQ ID NO: 20 E1

GCAACACCATACTGCAATGTGACAAGGAGGGTTTTCAACATCATATACAC
CAACAACTGCACCCCGCTGGACTGCCAGATAACACGAGGATAGTTGGGC
CAGGGACATTTGACATCAGTGAAATGGAAATAAAAAACTGTTACCCAAC
TTGGACTACCACTTGGCAGATTTCATGGTACTGGGCTTAGTGGCTTTATC
CGACTTTGCCCCAGAAACTGCTAGTACAATCTATCTGGTATTGCACTACT
GGCTGCCTCAGGCAGAGGTGCATACATTGGACACCCACTTGACACCAAC
AAGCTGAATCTAACAAGGAACAGGCAGGTTAGTAGTGTAGTCCCTAATTC
AATATGGTTGGGAGGGCAGCTGGTGTGCGTCAAGCCAAGGTGGTGGCCCT
ACTCAGCAGAAATTACAACAGTGATTAGCGGACTGACCACTGTAACCGAC
CTAGTGGTCAAGACCATAGAGGAACTTGTGAGCTTGTGGACAGAGGCAAC
AGCAGTAGCCTTCTTGGCAGCCCTGATAAAGATCTTCAGAGGACAACCAA
TACAAGCACTAGCATGGCTCATAATAATAGGGGGAGCCCAGGGT f) SEQ ID NO: 21 E2

CTTGAATGCAACTTCGAACTGCAATACGCTCTGGCCGGGAACACATCCAT
GAGCCTACTAGGGCCAACTGCCTTAAAGACTCAATGGTACCAAGCGGCAG
ACGGGGTCAAAATAACGGATGGGGTAGTAACTGTGATATGCAACAAGGGC
ATTTTCTCGGTGACTCCTAGGTGCAAAGAGGCACCTGTAAGGTACCTGGC
AATCAACCACCCCAGGTCCTTATCAACCAGTGCTTGGTTCAAGAAAATAC
ACGACCCGGCAGACCATCCGACTGAGACACTGATGGGCGAAAAGGGAAGG
GCATACCTCTGCCCTTGCGGGGCTACACCACTACCAAAACCCAAGGTTCC
GTTTAACCCAATCACAATACAAGGTTCGGCGTTCTCCCTAACATGCCCAA
AAAACTGGCAAGGTGACATAGAATGCAATCTCTTAAGCCCAGACACACTA
GCAATTGAAACCATATACACCTTCAGAAAACATAAGCCATACAAAGAAGA
ACCCTACTGCTCGTACACTAAGGTAGTGGACGGGTACTTGCGCaACGTGC
ACCTATGGGGGCATGATACATGTGTGGCAGGAGATATAATCAATGGCAGT
CAAGATGACAGTGTGACCAAGTGCAAATGGTGTGGGTATGAGTTCAATTC
AGCAACTGACTTACCTGACTACCCAATTGGTTACTGCACGAAGCGAGGCA
CCAATTATCTAATCAGGTACAAGCAGGTGCCTTGTGAGGTAGGAGGAGTC
CGCATCGGGTCAGGAAAGTAGAGTGTACCATTGGCTCCACGAGAGTAAA
AGTAGAACAAACCAGTAATGAGTTGGGTCCGATGCCCTGCAAGCCAATAG
TATATTCATCTCAAGGACCGCCTAATCCAAAAACGTGTACATTCAAATGG
AGCTACACATTAAACAACAAGTACTACGAGCCAAGGGATGAATTCTTCCA
ACAGTACATAACCTCAGGTGGCTATCAGTATTGGTTTGACCTGACAGCAA
AAGATCACGTGATGGATTGGGTAACACGATACTTCCCCATTATAGTTGTA
GCATTACTGGGGGGTAGAGCAGTGCTGTGGATCCTAATTGCGTACGAGTT
GCTAAATCACTACCAAGTGGGCGCA

Figure 11 contd.

g) SEQ ID NO: 22: P7

GACCAGAACACATTGCTGCAGGCCGAAGCACTAGTGATAGGTAACATCCT
GATGACAAGAGACCTGGAAGTGATGGTGTGCTTTCTGTTGCTGATGGTCT
TGATAAGAAGACAGCAGGCTAGAAGGGCTTTGGCCTTGGTTTTCCATTGG
ATGGTAATGCATCCCGCCCAATCAGCCATCGCAACATTGGTGTACGTAAT
AGGCATCGTGAGAGCTGAAGAGGGA h) SEQ ID NO: 23: NS2

CAGGTTAACTCTGACAGTTCTACGCAAGCACACGTGGTGGCCATTTTGTT
GTTTCTAATTTACCACACACTAAAAGAAAGGGACCTTCACACAGCTATGA
CATTACTGTTGACATTTTCCATAAAGAGCACTGACTATGTAGACACACAT
TATTATGAAATACCGATGCTCTTCACAGTTATTTCGTTGGTCATTTCCAT
TTACATATTCAACATACACATAAAAACCAAGTGGGTAGCTCTGGTGCTCA
GTATGGTGGGCATGGTCACCTTTATAAGGTGCCTTTGGTTGATCAGGAAC
ATACAAATAACACCCCCTTCCATACCACTAACATACATCAGTCCAAAAAT
ATTGATCATAGCTTACCTGGTTTCTCTGACTGTCTTGGTGAATAACAACC
TAGACCTCGCCAGCTACGTGATCAGGGCTGGCCCGATACTAATGTCCTAC
TTAACTTTATGGGTGGACATCCTGATGTTGCTAGTTCTACTACCTTGGTA
TGAATTGATTAAAGTCTATTACCTAAAGAAGAAGAAAGACGACATAGAAG
ACTGCTTCCAATACAGCGGGATAGCCACTCAAGGGTTATCCCCGTACAAT
CAGGACTTCGTGGACCCAAAAGAGGGGGTACACTTGATCCCCTCACAAAA
CAAGAGCAATTTCACCCGGACCGCATATCTGACTATCCTGAGGGCCCTAG
TTCTCACAGCTTTCAGCAGCATTTGGAAGCCTCTAATCCTAGCCGAACTG
CTATTGGAATCCATTTATTGGACACACATCAAAGTTGCAAAAGAAGTGGC
GGGATCTACGAGGCTTATAGGTAGGTTTGTAGCGGCCCTGATAGAACTAA
ATTGGGTTTTTGATGACAAGGAAGCAGCAAGATACAAAAAATTCTTTGTT
TTAACCTCAAGAGTGAGAGACCTCATGGTAAAACACAAGGTGCAGAACGA
CACAATGAGGCAGTGGTTTGAAGAGACGGAAATATTCGGCTTACAAAAAG
TTGCCTTGGTGGTCAGAGCACACTCACTGACAGCAGACAGCAACAGTATA
CTATGCTCAGTGTGTGAGGAAAAACAGAACATAGAAGCCAAGAGGGTATG
TCCCAAGTGTGGAAACAGAGGAACAGGAATCAAGTGCGGGATGACCTTGG
CTGAGTTTGAAGAAAATATTACAAAAGATCTATCTAGTGGATGGAGAC
AATACGCAAGCATATCGCAGAGAGGAGAGAGGAGAAGTCACGTACACAGC
TAGGGGCGCCTTCTTCTTGAGGAACTTACCCATTCTGGCCACAAAAAACA
AGTATATACTGGTAGGTAACTTAGGTATGGAATTACAAGACCTTGAGTCC
ATGGGGTGGATTATCAGG i) SEQ ID NO: 24: NS3

GGCCCAGCTGTCTGCAAAAGATAGTGCACCATGAACGCTGCAGGCCCAC
CATCCCTGATAAACTTATGGCTTTCTTTGGGCTCATGCCAAGAGGCGTAG
TCCCCGGGCACCAACCCGCTTCCTGTATCATTACTGAAAATTAAAAGG
GGTTTCGAAACGGGGTGGGCATATACACACCCTGGAGGGATCAGCAGCGT
AATGCATGTAACAGCAGGCTTGGACATGTACGTCAATGATGCCATGGGTA
GAACCAAGGTGCAGTGCCAAGAGAGAAACAAGCTGACAGACGAATGTGAG
TATGGCATTAAAACTGACTCAGGCTGCTCTGAAGGGGCACGCTGCTATGT

Figure 11 contd.

AATAAATCCCGAAGCCGTCAACATAGCAGGCACCAGGGGCGCTATGGTAC
ACCTCAGAAAAACAGGTCCAGAATTTACCTGTGTGACAGCCCAAGGAACC
CCAGCCTTCTACAATTTGAGGAATCTTAAAGGTTGGTCAGGGCTACCAAT
ATTCGAGGCAGCTACGGGAAGGGTGGTAGGCAGAGTGAAAGCAGGCAAGA
ATGCAGAGGATAGTCCAACAACTATAATGTCTGGCACCCAGGCAGCCAAA
CCGACAGAGTGTGACCTGGAGTCGGTCGTAAGGAAGCTGGAAACCATGAA
CAGAGGGGAGTTCAAGCAGGTGGTGCTAGCAACTGGGGCAGGGAAGACAA
CAGAACTGCCAAGGAAGCTAATAGAAGCCGTGGGGCGGCACAAGAGGGTT
TTAGTCCTAATCCCCTGAGAGCAGCAGCAGAGGGGGTTTATAACTATAT
GAGAACAAAGCATCCAAGCATAGCATTCAACCTGAGGATAGGGGACTTAA
AAGAAGGAGACATGGCAACTGGTATAACTTATGCCTCATATGGTTATTTT
TGTCAAATGGACATGCCACGGCTAGATGCAGCTATGAAGGAGTACAACTA
CATATTCCTGGACGAATATCATTGTGCAACACCAGAGCAATTGGCTGTGA
TGTCAAAAATACACAGGATCAGTGCTGACCTAAGAGTGGTGGCCATGACA
GCTACCCCTGCAGGCGCTGTGTCAAAGGTGGGCCAGAAATTCTCCATAGA
AGAAGTGGTGGTGCCAGAGGTAATGAAAGGGGAAGACCTAGGCGAGGATT
ATTTGGACATAGCCGGACTAAAAATACCAAAATCGGAACTACAAGGGAAT
GTCTTAACGTTTGTTCCGACAAAAAGTTGGCGTCAGACACTGCTAAGAA
ACTAACCACCCAGGGCTACAACGCTGGGTATTACTTTAGTGGTGAAGACC
CAAGCTCGCTGCGCACCATAACATCAAAATCCCCGTACATCATAATAGCC
ACCAATGCAATAGAGTCAGGGGTGACATTACCAGACCTAGACACAGTAAT
TGACACAGGGATGAAGTGTGAAAAGAGGGTGAGAATAGAGAACAAGGCTC
CATACATAATAACAGGCCTAAAAGAATGGCCATCACCACAGGGGAGCAA
GCCCAGAGGAAGGGAAGAGTAGGTAGAGTCAAACCAGGGAGATACCTAAG
AGGGCCTGAAAATGCAGGTGGAGAGAGAGATTATCACTATGACCTGCTGC
AGGCACAACGTTATGGGCTCCAGGATGCTATCAACATCACCAAATCATTC
AGGGAGATGAACTATGACTGGGCACTCTATGAGGAAGACCCACTGAGAAT
AACACAATTGGAGGTATTAAATACCCTACTCATATCCAAAGATCTGCCAA
CAGTCACAAAGAATTTGATGACCAGGACCACACACCCAGAACCAATTCAA
TTAGCTTACAATAGCATAGAAACCCCGTCCCAGTGCTGTTCCCGAAAGT
GAAGGGTGGAGAGGTGACCGATGCTTATGAGACCTATGAACTGATGATGT
GTCGGAAGCTGGATAACGACCCCCGATTTATCTGTATGCCACGGAAGAT
GAAGACCTAGCAGTGGACCTCCTGAACCTGAAATGGCCCGCAGTGTCAAC
AGCCTCGGCCATAGAAACAGAGGACGCCCTCAACAAGTTATCGGGGCTT j) SEQ ID NO: 25: NS4A

TCGGCAGGGGAAACAGCCCTGCTAGTGGCTCTGCTAGGTTGGGTCGGTTA
CGAGGCTCTGGTGAAAAGACACATACCAATAGTGACTGACATATATACAA
TTGAAGATGAAAAACTTGAGGACACCACCCACCTCCAGTATTCACCAGAT
GAACTGCAAAACACCGAGACAGTGGAGCTGAAAGACCTG k) SEQ ID NO: 26 NS4B

TCGGCACACGAACTGAAAGAAGCCCTGGAAAGCGGAAAAAGTTATGTCAA
AGACGCCTTTGAATTCGTAAAATCACAGGTTGAGAAGCTCCCCGACACAA
AAATTTACAAGCAAGTCCAAGAGAAGTCACCCGGTCTTTTAGAAAAATTT
TTGGCCTATCTGTCAGAACACAGTAGTGACATAAAGAAATATGGATTGTG

Figure 11 contd.

GGGGGTCCATACCTCTCTGTACAATAGTATCAAAGAGAGATTGGGGCACG
AAACTGCCTTCGCTTCATTGATCATCAAGTGGATAGCATTTTCCAGCGAA
GGGCTGCCTGGAATGGTGAAACAAGCTGCTGTAGACTTGGTGGTATATTA
TCTGATCAACAAACCAGATTTCAAAGGTGACAAAGACACCCAAGATGATG
GAAGGAAGTTCGTAGGAGCCCTGTTCGTGTCAGCTCTGGCCAATTACACA
TTTAAAAATTTTAATAAGTCAACACTTGAAGGCTTAGTAATGCCAGCATT
GAACTACCTACCATATGCAGGGGCTGCACTAAAATATTTGTGCCTACTA
AATTAGAGAGCTTAGTAATACTGTCAACAACCATCTACAGGACCTACCTC
TCCATTAAGAAAGGCTCTAGTCAAGGACTGGCTGGGTTAGCAGTGAGCTC
AGGTATGGAAATTATGAATCAGAATCCAATATCAGTGGCCATTGCGGTGG
CATTGGGAGTCGGTGCCATAGCTGCACACAATGCGATCGAGAGCAGCGAG
GCAAAGAGGACCCTGTTGATGAAGGTATTTGTGAAAAACTTTCTAGACCA
GGCAGCGACAGACGAGCTGGTAAAAGAGAACCCAGAAAAATAATAATGG
CAGTATTTGAAGCAATCCAGACAGCAGGTAATCCAATAAGGCTAATATAC
CACCTATATGCCATGTTCTACAAAGGTTGGAACGCCTCCCAGATAGCAGA
TAAGACAGCGGGGAGGAACATATTCGTGCTGACAATATTCGAGGGTTTAG
AACTGTTGGGACTAGACAAGGATTCCAAGTGGAGGGATTTG l)   SEQ ID NO: 27: NS5A

AGCTCAAATTATTTAGTGGATGCAATCAGGAAGCTCATTGAAAAATTGAC
TAAAATACTCAGAAACACCACCAAGTCATTAATCAAATCCTTGCTGCCAG
CTCCATTCTCTTGCACGAGATTCACAAGAGACAACAGAATTGGATGGCCA
CATTTAAATTTTGATTATTACGAGATAAATTGTGCATGTGGGTACCGGAG
GAGAGTGGTAAAAACTGTCATCGACCCAGTCACCTGGGAGACTTTGGAAG
AAGAAGGCCCTGAGTTCTGCTTCAACAGGGGGACTAACGCCCTGGCAAAC
CCAAGAGTTGCAAGTTATTACTCAGCTGGAGAGCCAGTTCTCCCAGTGGT
AAAAAGAGAGGGGGTTGGCGAAATCCTGGTAAGGGGGGTGACAATCCAGA
TGCATTATGACCACAACAAGATACTCGCCACTGACAACTGGCAAGTGCCA
TTCCAGGCAGTGACGAAGATATTTACAGATTACCAGGGCATAGGGTACCA
AGAAGCATATCTGGGAACCCAGCCAAACTACAAAGCACTGGTGAAGAGGT
CATCCGTCACGATTACAAAAGAAGGCCTGAAATTTATAAGATGCAAGAAA
GGGATCGCGTATACGACCAATCTAAACTTAACCCACATCCAAAAGCTGGT
GCAGGTGTGCAGAATGAATGAATTGCAAGAAGGCGTCATACCTGAGACCT
TGGATGGCGACACCTGGATTAACTACATGGCAATCATCGAAGATGTGGGG
GCCACAAAACCAAGCTTGGAGAGAGTcATACCCGAAACCATACGAGGA
GGATCCCCTCGAAGGCCCAGTGTGATCGTGGAAACAGGGGACGTGGACA
TCACAAAAGTGGGCGTAAATCAACAATCCAGTTCATCAGGAACCGTCTTT
CAAGTAGTGGAGAAGATCTATACTAAACTGGTCAATACAAATGTAATAAA
GATAGGATTCAAAGAAGGCTGTTTCCCGGGACCCACAAAGAATGTGAATT
CATTGAATGAGCACATAGAAGATAAAGACAGTAAACCATACATCTTCATA
TGCTCTTCCGACAAAGCAATGTCCAACAGAGTAAAGACTGCAAGGAACAT
TAAGAAACTCAACACAAATTCGGCAATAGTAGCCCGTAATTTGGCCAGGG
AAGGGAAATTGATCATAATAGTACTAGGAGAGAAGTACCATGAGGACATC
TACAAACATGCTGACTTCAAGGGGACTTTCCTCGACAGGAAGGCACTGGA
AGCCCTGTCCAAGGCCAAGCCTGTAAAAAGAACATGACTAGGAGAGAGG
CTCAATATCTGCTGGAAAAGAAGCTTAGTGAAGACATAGAGGTACCAGAA
TGGCTGGGATCTGAAAAACCTATGTTTTGGATGTAACCAAAAGTGGTGA

Figure 11 contd.

AACATACCATCTGTTAGGGGATCTAAATCACTTGAAGGCACAAGCGGAAC
AACTTGGTGCCAAGGCAACCACTACAATAAATAAAGTAGGGAAGACGTAT
ACAATGAACCTC m) SEQ ID NO: 28: NS5B

AGTACATGGTGGGAGAGTGAAAGAACCCCCACATTCAGACCCCTGTTCCA
GGAACTGCTGTTACGCTGCAGGCCATGCACTAGGGAGGAGTATAAGAGCT
GCCATTTTGTAGGGGCTACACAATTGGCCGGAGGAAACTGGAAACCAGTA
GCCCCTGTGGTGCACCTAGGAACTATACCAGCAAAAGAGAGAAATGCCT
GCCATATGAAGCATATATCACTTAAGAATATGGTGGAAAACCTAAAAA
TAGAGAATCCTGGAGTGTGCAAGAAGAAACATCAGTGGCTCTTAAATAAA
ATTAAAAAACAAGGGGAATTAGGCTTGAAGAATCTCGTATCTCCTGGGAG
TGTAGGGGGATCACGTGGTTACAGAAGAAAGAATTCAACATTTACAACA
AACAGATTACGAGCACAATGCTGGCTGTGGGGATCAAGCCAGAGAAGTTT
CCAGTCGTCAGAGCTCAAACGTCCAAGAGAGAATTCCATCAAGCAATTAG
AGAGAAGATTGATAAGCTGCCCAACCCCCAGAATAGGGACCTCCATAAGG
AACTGAAAGAAATATTTGACTCGGTGTGCGCTGTAAAAGATTTGAAACAT
ACCTACGAAGAAGTCAGCTGGGATGTACTGACGGTGGGGATCAACAGGAA
AGGAGCAGCTGGCTATTTCGAAAAGAAGAATGTGGGTGAGATAATAGACA
CTGACAGGAGAGGGGTCGAGAAACTTATCAAGGTAATGAAAACCGGGGGA
CCTATAGACTACTATGAGACAGCAATACCTAAGAATGAGAAGAGAGCAGT
TGTAGATGACTGGCTGGAAGGAGATTTCGTTGAAGAGAAAAAGCCACGAG
TGATCCAATACCCAGAAGCAAAAATGCGTTTGGCAATAACCAAAGTTATG
TACAATTGGGTCAAGCAAAAACCAGTGGTGATACCCGGGTACGAGGGGAA
GACACCTTTGTTTAAAGTGTTTGATAAGGTTTTTGATGAATGGAAACAAC
TGAGAGACCCGGTTGCAGTCAGTTCGACACTAAAGCATGGGATACACAA
GTGACACCTGAGGACTTACAATTGATATCGGAAATCCAAAAGTATTACTT
TAAACCAAAATACCACAAATTTATTGAAACATTGACTGCGGAGATGAAAG
AAGTGCCAGTCGTGTGCCAGGATGGGGAGGTTTACATCAGGCTAGGACAG
AGAGGAAGTGGCCAGCCAGATACCAGTGCAGGAAATAGCATGTTGAATGT
GTTGACAATGATATATGCTTTTTGCAAATCCAATGACATCCCGTACAAGG
CATTCCGAAGGGTGGCAAAAATACACGTCTGTGGCGACGATGGGTTCCTA
ATTACAGAGAGGCGCCTAGGAGAGAACTTTGCTGCGATGGGGCCACAAAT
ACTGATGGAAGCCGGGAAACCACAGAAACTGGTAGGAGAGATGGGACTGA
AGCTAGCCTACAAGTTCCAGGACATAGAGTTCTGCTCCCACACGCCTATA
CAAGTAAGGTGGGATGACAACACAACTAGTTATTTACCAGGCAGAGACAC
GGCAACCATCTTAGCAAAGATGTGTACCAGGCTGGACTCCGCAGGGGAGC
GGGGTACCAGTTCCTATGAACTTGCTGTTGTGTTTAGTTTCCTCCTAATG
TACTCCTGGAACCCAATAGTTAGAAGGATCTGCCTATTAGTTATGGCAAC
AATCGGAGTAAAAGACCCAGATAAATCAGGAACAATATTCACCTTCTCTG
GAGACCCACTAGGGGCGTACAAGGAAGTAATAGGACACCGATTGGGCCAA
CTAAAACAAACTGAATTTTCAAAATTGGCAAGTTGCAATTTATCAATGTC
ACTGTTAGGGATTTACAGTAGGCACACCTCAAAAAGAATCATAGAGGACT
GTGTGAAGATTGGAACCCTAAACCGACAGAGCCCCGTGAATGCAGATCGC
TTGATAGCAAAGAAGACTGGTTTTGTATACGAACCGTCAAGGGGCAGTGT
TAGGGTGGGAAAACACTAtGAAGaATTGGAATTGGACAAATGGAAAAGA
AGACGCCACTCATAGAAGGGGCGGAAAGGTACATTCCAGGCCCGATTAAG

Figure 11 contd.

ACCTTTATACTGAAAAGACTCAAAGTGTTACAGATGATAGGCCTGAAATTCTTC n) SEQ ID NO: 29: 3'-UTR

TAATATATAGGGAGTACAGGTTACAGCTGTGTTTCACAGAAAGTGGGTGGCGACACTTACCTCTGGAGCCAACTTGTAAATAGGTTAGTAATATTTATTTAATAGACGTTATTTACTTATTTATTTATTTATTTGATTATTTATTAATTATTTAAAAACGCTACTGCATGAGCTGGTTAGTCAGCTTATGAAAGTGGGTTGTGTCACTTGCGTCAGGAGCAAATACCTCAATAACAACGCTACCACATAGCCTGAGACCAGGTTGTGAAAGAGAGTTGCGCCTCTTGCGTTGGGAGCTATCTACCTCAAGTACCCAGCTGCTGAAGCTGGTTACCTCAATTCCAATGGATGACCGTAGCCATTGGTCTTATTAATTCGGTCATTTATAATTAGCACTTTAAAGCTAATTGGGACATAAAGTAAGGACGTCCTAGGGAGGACTACTTACAGTTCCAAGAGGCCCC

ISOLATION OF A NOVEL PESTIVIRUS CAUSING CONGENITAL TREMOR A

CROSS-REFERENCE TO RELATED APPLICATIONS

This application is the U.S. national stage of International Patent Application No. PCT/EP2017/084453, filed on Dec. 22, 2017 and titled ISOLATION OF A NOVEL PESTIVIRUS CAUSING CONGENITAL TREMOR A, which claims the benefit of priority under 35 U.S.C. § 119(e) from U.S. Patent Application No. 62/437,888, filed on Dec. 22, 2016. The disclosures of the foregoing applications are incorporated herein by reference in their entirety.

SEQUENCE LISTING

The entire content of a Sequence Listing titled "Sequence_ Listing.txt," created on Jul. 3, 2020 and having a size of 578 kilobytes, which has been submitted in electronic form in connection with the present application, is hereby incorporated by reference herein in its entirety.

FIELD OF THE INVENTION

The present invention relates to a new pestivirus useful in the fields of veterinary virology and vaccines. Specifically, it relates to an isolated polynucleotide originating from pestivirus, to vaccines and medical uses thereof, to chimeric virus comprising the polynucleotide and to the use of said virus as viral vector for expression of heterologous polypeptides.

BACKGROUND OF THE INVENTION

Pestiviruses are single-stranded, positive-sense RNA viruses. The pestiviral genome has a length of about 11.5 to 12.5 kb and contains one large open reading frame, which is flanked by non-translated regions (NTR) at the 5' and 3' genome ends. The resulting large polyprotein is co- and post-translationally processed into 12 mature viral proteins: an autoprotease (Npro), capsid protein (C), three envelope proteins (Erns, E1, E2) and the non-structural proteins (p7, NS2, NS3, NS4A, NS4B, NS5A, NS5B) which are conserved among pestiviruses regarding genome localization and catalytic residues.

The genus pestivirus is classified within the family Flaviviridae and consists of four species approved by the International Committee on Taxonomy of Viruses. The classification of pestiviruses is based on nucleotide sequence, host range and serological differences. The 5' NTR is the region most frequently used for the phylogenetic analysis of pestiviruses but more variable genes (Npro or E2) have also been employed. Nevertheless, a comparison of full genome sequences enables the most precise phylogenetic typing. Besides Bovine viral diarrhea virus-1 (BVDV-1) and BVDV-2, Border disease virus (BDV) and Classical swine fever virus (CSFV), several unassigned strains and/or tentative species are represented by the so called atypical pestivirus strains. Atypical pestiviruses have been isolated from exotic species within the order Artiodactyla, especially bovine, ovine and porcine hosts. Recent studies detected pestiviral sequences in rats and bats suggesting a broader host range of pestiviruses. However, until now all isolated pestiviruses originate from ungulates.

One of the most dangerous viral epidemics in swine, CSFV, has been eradicated from the domesticated swine population in most developed countries since decades. Infections of swine with other pestivirus species have been detected, for example the introduction of certain BDV and BVDV strains pointing at the capacity of adaptation. An "atypical" porcine pestivirus was identified in 2003 in a commercial pig breeding farm in Australia, later termed Bungowannah virus. This well studied virus caused reproductive disorders, stillbirth and sudden death in piglets due to myocarditis. The marked sequence diversity of this virus resulted in the failure of its detection by the established pan-pestivirus diagnostic methods (ELISA, cross-neutralization tests, RT-PCRs). The documented pathogenicity of Bungowannah virus alarmed the pork-producing industry because of the potential economic impact. The loss of about 50,000 animals was only reported from two affected farms in Australia. Bungowannah virus is still present in one farm but this virus or relatives were never found at other locations.

A novel group of closely related porcine pestiviruses has been discovered recently forming the tentative species of "atypical porcine pestiviruses (APPV)". These viruses were first identified in North America and subsequently also found in Germany, the Netherlands and Austria (Schwarz et al., 2017. Congenital infection with atypical porcine pestivirus (APPV) is associated with disease and viral persistence. Veterinary Research 48:1). There is strong evidence that APPVs are representing the infectious agents behind the type A-II congenital tremor (CT) syndrome of piglets. A-II CT is prevalent worldwide and a common syndrome in newborn piglets. APPV is very difficult to propagate in vitro and hence Koch's postulates have only partly been fulfilled. Nevertheless, transmission of the agent from affected piglets to pregnant sows reproduced the clinical signs. The clinical features are characterized by a generalized mild to severe shaking of the whole body that pathohistologically is associated with variable hypomyelination of brain and spinal cord. Hypomyelination is a characteristic lesion apparent in the brain of sheep, cattle and pigs after late gestation state in utero infection with BDV, BVDV and CSFV yielding newborn "hairy shaker" lambs. shaking calves and A-I CT affected piglets. Infections with most if not all pestiviruses during gestation may have a detrimental effect on the embryo or fetus, causing stillbirth, malformations or neurological defects.

In view of the importance of an effective and safe as well as detectable prophylaxis and treatment of pestiviral infections, there is still a strong and unmet need for an immunogenic pestivirus, with good viral replication and high potential for induction of immunity.

SHORT DESCRIPTION OF THE INVENTION

The object is met by the subject matter of the invention as claimed.

The novel isolated pestivirus has low pathogenicity in animals and can lead to fast and reliable sero-conversion even after natural infection routes. Therefore the virus is highly applicable for vaccination purposes.

The inventors have named the novel pestivirus Linda virus.

According to the invention there is provided an isolated polynucleotide comprising a nucleotide sequence of SEQ ID NO: 1 or SEQ ID NO: 2 or a sequence with at least 60%, specifically at least 70% identity thereto.

Specifically, said polynucleotide is an infectious polynucleotide.

In an embodiment of the invention, the polynucleotide is present in a cell, specifically in a host cell.

According to the invention there is also provided an RNA polymerase promoter operably linked to the polynucleotide.

According to a further embodiment, the polynucleotide further comprises an exogenous, heterologous polynucleotide.

According to an embodiment, the polynucleotide is present in a vector.

In a further embodiment there is provided a cDNA polynucleotide of SEQ ID NO: 1.

In a further embodiment there is provided a cDNA polynucleotide having at least 60%, at least 65%, at least 70%, at least 80%, at least 85%, at least 90%, at least 95%, at least 99%, at least 99.5% identity to SEQ ID NO: 1.

In a further embodiment there is provided a polynucleotide having at least 70%, 75%, 80%, 85%, 90%, 95%, 99%, 99.5% identity to SEQ ID NO: 1 or SEQ ID NO: 2.

Provided herein is also a polynucleotide comprising a sequence selected from the group of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 or any combinations thereof or a sequence with at least 90%, specifically at least 95% identity thereto or any combinations thereof.

It is highly advantageous that the pestivirus of the invention is clearly distinct from other viruses such as Bungowannah or APPV. The pestivirus of the invention may easily be propagated on host cells such as SK-6 or PK-15 cells to high titers, such as a titer of >$10^7$ TCID$_{50}$, without the need for adaptation.

Provided herein is also a composition comprising a porcine pestivirus having a nucleotide sequence of SEQ ID NO: 1 or SEQ ID NO: 2 or a sequence having at least 60%, specifically at least 70%, 75%, 80%, 85%, 90%, 95%, 99% identity to SEQ ID NO: 1 or SEQ ID NO: 2. According to a specific embodiment, the at least 60%, specifically at least 70%, 75%, 80%, 85%, 90%, 95%, 99% identity to SEQ ID NO: 1 or SEQ ID NO: 2 is given over the entire length of the sequences.

According to the invention there is also provided a composition comprising a porcine pestivirus comprising an amino acid sequence of SEQ ID NO: 3 or a sequence with at least 60%, 65%, 70%, 75%, 80%, 85%, 90%, 95%, 99%, 99.5% identity to SEQ ID NO: 3. According to a specific embodiment, the at least 60%, 65%, 70%, 75%, 80%, 85%, 90%, 95%, 99%, 99.5% identity to SEQ ID NO: 3 is given over the entire length of the sequence.

According to the invention there is also provided a composition comprising a porcine pestivirus having an amino acid sequence selected from SEQ ID NO: 4 (Npro), SEQ ID NO: 5 (Core), SEQ ID NO: 6 (Erns), SEQ ID NO: 7 (E1), SEQ ID NO: 8 (E2), SEQ ID NO: 9 (P7), SEQ ID NO: 10 (NS2), SEQ ID NO: 11 (NS3), SEQ ID NO: 12 (NS4A), SEQ ID NO: 13 (NS4B), SEQ ID NO: 14 (NS5A), SEQ ID NO: 15 (NS5B), or any combinations thereof.

Specifically, the composition comprises 2, 3, 4, 5, 6, 7, 8, 9, 10, 11 or 12 sequences of SEQ ID NO: 4 (Npro), SEQ ID NO: 5 (Core), SEQ ID NO: 6 (Erns), SEQ ID NO: 7 (E1), SEQ ID NO: 8 (E2), SEQ ID NO: 9 (P7), SEQ ID NO: 10 (NS2), SEQ ID NO: 11 (NS3), SEQ ID NO: 12 (NS4A), SEQ ID NO: 13 (NS4B), SEQ ID NO: 14 (NS5A), SEQ ID NO: 15 (NS5B).

According to a further embodiment of the invention, there is provided a composition wherein the porcine pestivirus is inactivated or attenuated, specifically there is provided a chemically inactivated virus which is inactivated by treatment with an inactivating agent selected from the group consisting of binary ethyleneimine, ethyleneimine, acetylethyleneimine, beta-ethyleneimine, beta-propiolactone, glutaraldehyde, ozone, and formaldehyde.

There is also provided a composition containing a pestivirus of the invention, wherein the pestivirus is a physically inactivated pestivirus, specifically inactivated by treatment with UV radiation, X-ray radiation, gamma-radiation, freeze-thawing, and/or heating.

According to an alternative embodiment of the invention, the pestivirus is attenuated by modifying the Npro, Erns or N2-3 gene.

According to a specific embodiment, the pestivirus is in freeze-dried form.

For administration, the composition comprises a titer of at least about $10^4$, specifically at least $10^5$, $10^6$, $10^7$, $10^8$ TCID$_{50}$ per dose.

According to a further embodiment of the invention, there is also provided a pharmaceutical composition comprising a polynucleotide, a composition, a vector or a chimeric pestivirus as described herein.

The present invention also provided a porcine pestivirus vector comprising a nucleotide sequence of SEQ ID NO: 1 or a sequence having at least 60%, specifically at least 70%, 75%, 80%, 85%, 90%, 95%, 99% identity to SEQ ID NO: 1 and a sequence encoding a heterologous sequence.

The present invention also provided a porcine pestivirus vector comprising a nucleotide sequence of SEQ ID NO: 2 or a sequence having at least 60%, specifically at least 70%, 75%, 80%, 85%, 90%, 95%, 99% identity to SEQ ID NO: 2 and a sequence encoding a heterologous sequence. Said heterologous sequences can be any regulatory sequence or sequence encoding selection markers. Specifically, a heterologous sequence is selected from one or more viruses consisting of the group of bovine viral diarrhea virus-1 (BVDV-1) and BVDV-2, border disease virus (BDV), classical swine fever virus (CSFV), atypical pestivirus (APPV), specifically NRPV, PEDV, RaPV, border disease virus, isolates from reindeer, giraffe, HoBi pestivirus and Bungowannah virus.

Specifically, said heterologous sequence encodes a surface antigen from said viruses. More specifically, the heterologous sequence encodes a surface antigen selected from the group of sequences comprising SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 and SEQ ID NO: 48 or any combination or fragment or part thereof.

According to an alternative embodiment, said heterologous sequence encodes a surface antigen from any virus of interest such as, but not limited to PEDV, African swine fever porcine circovirus and PRRSV.

Specifically, the heterologous sequence is inserted within the 5' or 3' terminal region or at the 5' or 3' terminus of Npro or E2.

According to an alternative embodiment, the heterologous sequence encodes a fusion peptide with Npro, E2 or E1 protein of the pestivirus.

The invention also provides a chimeric pestivirus comprising a nucleotide sequence of SEQ ID NO: 1 or SEQ ID NO: 2 or a sequence having at least 60%, specifically at least 65%, 70%, 75%, 80%, 85%, 90%, 95%, 99% identity to SEQ ID NO: 1 or SEQ ID NO: 2, and a foreign polypeptide.

According to the invention there is provided a vaccine for animals comprising a polynucleotide, a composition, a vector, or a chimeric pestivirus as described herein.

Further provided herein is a kit for inducing an immune response against porcine pestivirus infection in an animal, specifically in a pig, said kit comprising a composition or vaccine as described herein and instructions for administering said composition to said animal.

Further provided herein is a method for protecting an animal, specifically a pig, specifically a piglet, against a disease associated with pestivirus, wherein the method comprises administering to a pregnant sow, a boar, a post weaner or a gilt, or to a sow or gilt prior to breeding, the composition or vaccine as described herein, in an amount sufficient to protect the animal, specifically for protecting or treating the animal against congenital tremor, specifically congenital tremor A-II.

According to a specific embodiment of the invention, the composition is parenterally administered, specifically intramuscularly, subcutaneously, intradermally, or intravenously using a needle and syringe, or a needleless injection device; and mucosal administration nasally or orally.

According to an embodiment of the invention, a method for detecting pestivirus is provided, wherein a sample is tested with RT PCR using at least one of the primers selected from 5'-GTKATHCAATACCCTGARGC-3' (SEQ ID NO: 32) and 5'-GGRTTCCAGGARTACATCA-3' (SEQ ID NO: 33).

Further provided herein is a diagnostic assay for detecting pestivirus, comprising at least one of the primers selected from SEQ ID NO: 32 and SEQ ID NO: 33.

Also provided herein is a diagnostic kit for detecting pestivirus, comprising at least one of the primers selected from SEQ ID NO: 32 and SEQ ID NO: 33, further comprising devices and instructions.

According to a further embodiment also a method for detecting pestivirus antigen having an amino acid sequence of SEQ ID NO: 3 or an amino acid sequence of at least 60% identity in a biological sample is provided, said method comprising contacting a biological sample, specifically blood, organ or excretion samples, with an antibody specifically binding to an antigen of said pestivirus if present in said sample; and detecting said antibody binding to said antigen in said sample.

According to a specific embodiment, the antibody is a monoclonal antibody, specifically it is monoclonal antibody 6A5 as described by Gilmartin A. A. et al., 2012, Protein Eng Des Sel 25.

According to the invention there is also provided a method for preparing the inventive vaccine comprising the sequential steps of
a) infecting a host cell culture with a polynucleotide, a vector, or a chimeric pestivirus as described herein,
b) incubating said host cell culture for virus propagation,
c) harvesting the host cell culture, and optionally
d) isolating the virus from the culture and
e) admixing to the culture with a pharmaceutically acceptable carrier.

The embodiment of the invention also provides the use of a polynucleotide, a vector, a composition, or a chimeric pestivirus as described herein, for preparing a vaccine for animals.

Further provided herein is a polynucleotide, a vector, a composition, or a chimeric pestivirus as described herein or any combinations thereof, for use in a vaccine or for the treatment of animals.

Also provided herein is a method for controlling an infection with a pestivirus in animals, wherein the vaccine as described herein is combined with a diagnostic kit or assay as described herein.

FIGURES

FIG. 1: Histopathological examination in piglets with congenital tremor (CT).

Figure 2:
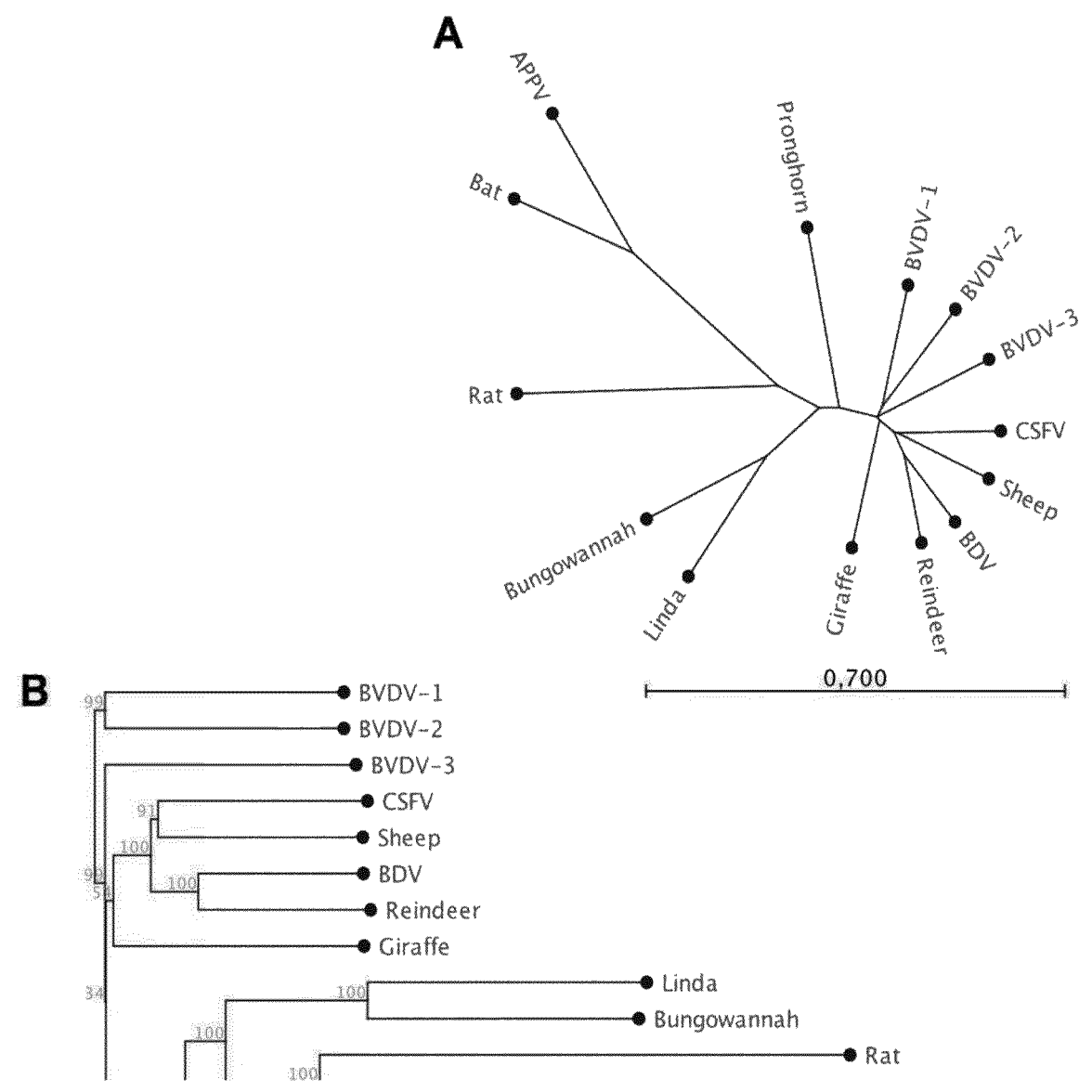

FIG. 2: Phylogenetic genome analysis of Linda virus, atypical pestivirus strains and the pestiviral type strains.

FIG. 3: Phylogenetic analysis of pestiviral polyproteins.

FIG. 4: Amino acid comparison of Linda virus E2 protein. E2 sequences of Linda virus (SEQ ID NO: 8) Bungowannah virus (SEQ ID NO: 36), Pronghorn (SEQ ID NO: 37), Giraffe (SEQ ID NO: 38), BDV (SEQ ID NO: 39), Reindeer (SEQ ID NO: 40), Sheep (SEQ ID NO: 41), CSFV (SEQ ID NO: 42), BVDV-1 (SEQ ID NO: 43), BVDV-2 (SEQ ID NO: 44), BVDV-3 (SEQ ID NO: 45), Rat E2 (SEQ ID NO: 46), Bat E2 (SEQ ID NO: 47), APPV E2 (SEQ ID NO: 48)

Figure 5:
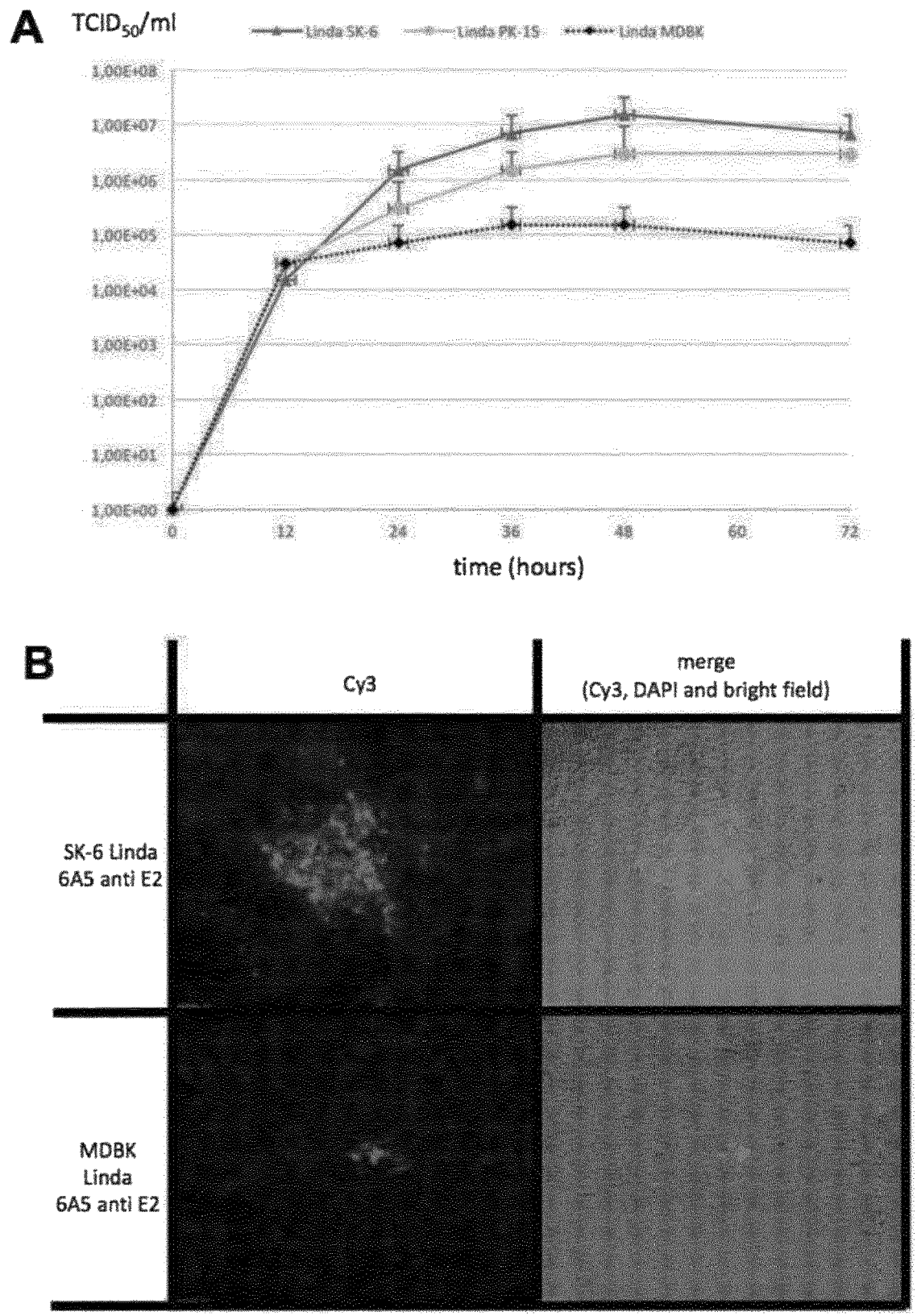

FIG. 5: Propagation of Linda pestivirus in cell culture.

Figure 6:
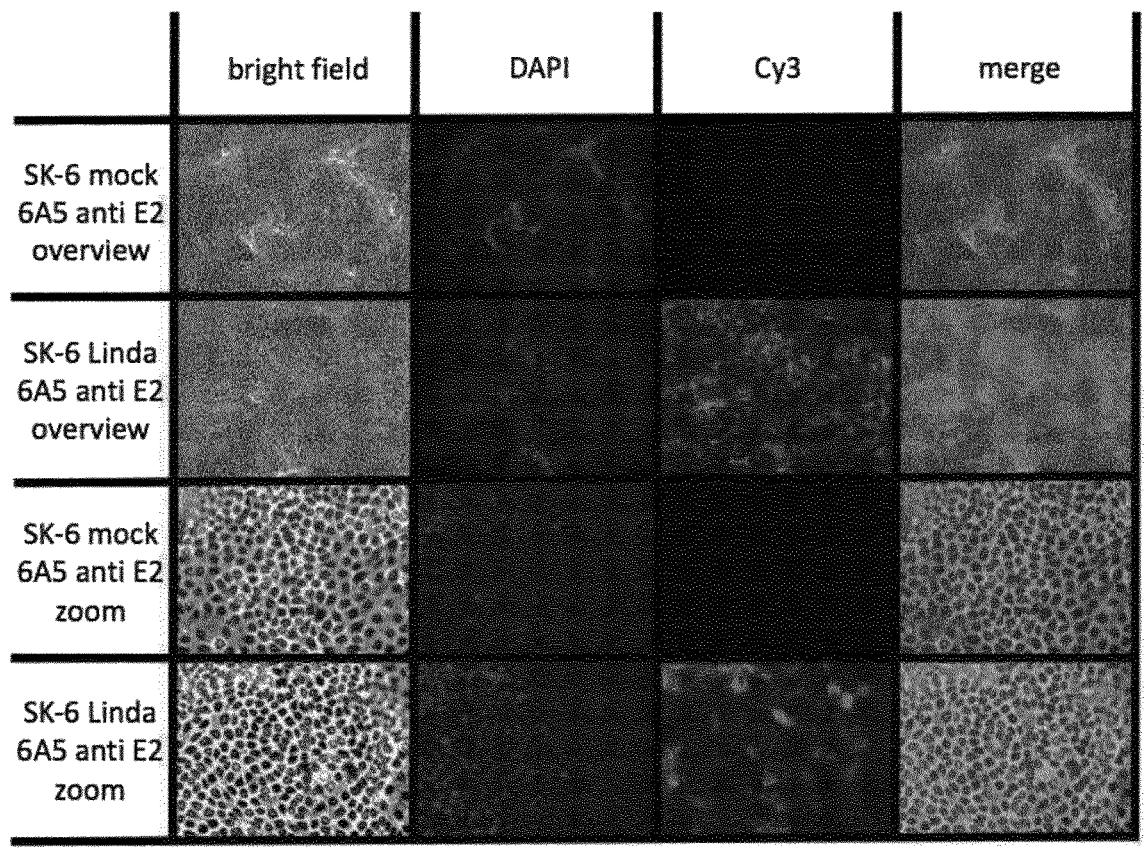

FIG. 6: Validation of a cross-reactive monoclonal antibody

FIG. 7: Full length DNA sequence of Linda virus (SEQ ID NO: 1).

FIG. 8: Full length RNA sequence of Linda virus (SEQ ID NO: 2).

FIG. 9: Amino acid sequence of Linda virus (SEQ ID NO: 3), amino acids in bold letters mark possible insertion sites. Npro sequence is in italic letters.

FIG. 10: Amino acid sequences of Linda virus a) Npro (SEQ ID NO: 4), b) Core (SEQ ID NO: 5), c) Erns (SEQ ID NO: 6), d) E1 (SEQ ID NO: 7), e) E2 (SEQ ID NO: 8), f) P7 (SEQ ID NO: 9), g) NS2 (SEQ ID NO: 10), h) NS3 (SEQ ID NO: 11), i) NS4A (SEQ ID NO: 12), j) NS4B (SEQ ID NO: 13), k) NS5A (SEQ ID NO: 14), l) NS5B (SEQ ID NO: 15).

FIG. 11: DNA sequences of Linda virus proteins and untranslated regions. a) 5'-UTR (SEQ ID 16), Npro (SEQ ID 17), c) Core (SEQ ID 18), d) Erns (SEQ ID 19), e) E1 (SEQ ID 20), f) E2 (SEQ ID 21), g) P7 (SEQ ID 22), h) NS2 (SEQ ID 23), i) NS3 (SEQ ID 24), j) NS4A (SEQ ID 25), k) NS4B (SEQ ID 26), l) NS5A (SEQ ID 27), m) NS5B (SEQ ID 28), n) 3'-UTR (SEQ ID 29).

DETAILED DESCRIPTION

Specific terms as used throughout the specification have the following meaning.

The terms "comprise", "contain", "have" and "include" as used herein can be used synonymously and shall be understood as an open definition, allowing further members or parts or elements. "Consisting" is considered as a closest definition without further elements of the consisting definition feature. Thus "comprising" is broader and contains the "consisting" definition.

The term "about" as used herein refers to the same value or a value differing by +/−5% of the given value.

In the sequence identifiers presented herewith, nucleotides are represented in standard IUPAC-IUB code of DNA. However, as the skilled person will understand, the pestivirus genomic sequences in nature are in RNA form, where a T will be a U. The pestivirus RNA sequence of the invention specifically is SEQ ID NO: 2.

The term "infectious" refers to a polynucleotide having the sequence of SEQ ID NO. 2 or at least parts or fragments thereof such as the NSP encoding region that can be fully replicated in a host cell or an animal.

The terms "homology" or "identity" can be used interchangeably and refer to the identity of the respective nucleic acid residues. The percentage of identical residues (percent identity) is used to quantify the homology/identity.

The term "attenuated" as used herein refers to a virus having a polynucleotide sequence derived from or originating from pestivirus having a nucleotide sequence of SEQ ID No. 1 or SEQ ID NO. 2 or at least parts or fragments thereof, wherein the virus has a reduced virulence as compared to another virus of the same species or isolate, such as a wild type virus or isolate. In fact, attenuated means to display a reduced dissemination through the body of an infected target animal, e.g. fetal infection; to induce less pathology such as (signs of) disease; and/or to display a reduced spread into the environment. Whether the pestivirus is attenuated, and whether that level of attenuation is sufficient for use according to the invention, e.g. regarding its use in a live vaccine, can be determined using standard procedures either in vitro or in vivo. For example, by comparing viruses, comparing the effect of a modification on the viral replication rate in cell culture, or in an infected animal by checking viral presence in different tissues or organs or in the feces of said animal, and monitoring clinical, macroscopic, or microscopic signs of disease in an animal or a fetus.

Attenuation can be established but is not limited by modifying the Npro gene or the NS2-3 gene of the inventive virus, whereby the pestivirus has a modification, especially a mutation of an epitope located in the Npro protein, the NS2 protein, or a duplication of certain genome regions so that the NS2-3 cleavage is enhanced. This is not affected by mutations of an epitope located in a helicase domain of the NS3 protein, so that the epitope is not or less reactive with an antibody against that epitope compared to a wild-type pestivirus.

The term "inactivated" as used herein refers to a virus having a polynucleotide sequence derived from or originating from pestivirus having a nucleotide sequence of SEQ ID No. 1 or SEQ ID NO. 2 or at least parts or fragments thereof, wherein the virus has lost its virulence as compared to another virus of the same species or isolate, such as a wild type virus or isolate by killing the virus with chemicals, heat, or radiation.

Inactivation can be established by, but is not limited to, the methods such as treatment with an inactivating agent selected from the group consisting of binary ethyleneimine, ethyleneimine, acetylethyleneimine, beta-ethyleneimine, beta-propiolactone, glutaraldehyde, ozone, and formaldehyde.

As an alternative, physical inactivation can be performed such as but not limited to treatment with UV radiation, X-ray radiation, gamma-radiation, freeze-thawing, and/or heating.

A polynucleotide molecule is a biopolymer composed of 13 or more nucleotide monomers covalently bonded in a chain. DNA (deoxyribonucleic acid) and RNA (ribonucleic acid) are examples of the polynucleotides. As used herein, the term "exogenous polynucleotide" or "heterologous polynucleotide" refers to any polynucleotide sequence not naturally occurring in the pestivirus encoded by the sequences of the invention.

As used in this application, the term "amino acid" means one of the naturally occurring amino carboxylic acids of which proteins are comprised. The term "polypeptide" as described herein refers to a polymer of amino acid residues joined by peptide bonds, whether produced naturally or synthetically. Polypeptides of less than about 10 amino acids residues are commonly referred to as "peptides".

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 15 amino acids, specifically at least 20 amino acids, more specifically at least 30 amino acids, more specifically at least 50 amino acids, or which is immunologically identifiable with a polypeptide encoded in the sequence. This terminology also includes a polypeptide expressed from a designated nucleic acid sequence.

Specifically, the heterologous polypeptide is an immunogenic polypeptide.

In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th1-type response (cell-mediated response), and Th2-type immune response (humoral response). Stimulation of an immune response can result from a direct or indirect response of a cell or component of the immune system to exposure to an immunogen. Immune responses can be measured in many ways including activation, proliferation or differentiation of cells of the immune system (e.g., B cells, T cells, dendritic cells, APCs, macrophages, NK cells, NKT cells, etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

An "RNA polymerase promoter" according to the invention can be any region containing a sequence specifically recognized by an RNA polymerase (RNAP). The promoter can be operably linked to a sequence encoding a target RNA. One feature of present embodiments is the use of an RNA polymerase promoter and RNA polymerase such as any RNA polymerase and promoter known in the art. Certain examples herein, while not intended to be limiting, are T7 RNAP and T7 RNAP promoter. Other examples of polymerases with promoters include T7 RNAP with T7 Class III RNAP promoter or T7 phi 2.5 RNAP promoter, SP6 RNAP with SP6 RNAP promoter, T3 RNAP with T3 RNAP promoter, Syn5 RNAP with Syn5 RNAP promoter, *E. coli* RNAP with T5 promoter.

The term vector or plasmid vector as used herein defines a system comprising at least one vector suitable for transformation, transfection or transduction of a host cell. A vector per se thus denotes a cargo for the delivery of a biomolecule into a host cell of interest, wherein the biomolecule includes a nucleic acid molecule, including DNA, RNA and cDNA, or, in the case of a transfection system as vector, an amino acid molecule, or a combination thereof. The pestivirus of the invention can be used as vector according to the invention as it contains all regulatory elements necessary for replication. An alternative vector according to the present invention is a plasmid or expression vector that can be circular or linear. An expression vector can comprise one vector encoding at least one target molecule, preferably a nucleic acid molecule, to be introduced into a host cell. A vector of the vector system can also comprise more than one target molecules to be introduced. Alternatively, the vector system can be built from several individual vectors carrying at least one target molecule to be introduced. An expression vector additionally comprises all elements necessary for driving transcription and/or translation of a sequence of interest in a host cell, the expression vector is designed for. These elements comprise, inter alia, regulatory elements, which are involved in the regulation of transcription, including promoters and the like functional in the host cell of interest. Furthermore, an expression vector comprises an origin of replication and optionally depending on the type of vector and the intended use a selectable marker gene, a multiple cloning site, a tag to be attached to a sequence of interest, a chromosomal integration cassette and the like. The choice and possible modification of a suitable expression vector for use with a respective host cell and sequence of interest to be inserted into the expression vector is well within the capabilities of the person skilled in the art.

The term "cDNA" stands for a complementary DNA and refers to a nucleic acid sequence/molecule obtained by reverse transcription from an RNA molecule. As it is a standard method for the person skilled in the art to obtain cDNAs from a given sequence and to further use this cDNA or to clone said cDNA into a vector, preferably a plasmid vector, of interest.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The polynucleotide of the invention comprises a nucleotide sequence having at least 60%, specifically at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identity to SEQ ID NO: 1 or SEQ ID NO: 2.

In a certain embodiment, the polynucleotide consists of a nucleotide sequence of SEQ ID NO: 1 or SEQ ID NO: 2.

Herein provided is further a composition comprising a porcine pestivirus having a nucleotide sequence with at least 60%, specifically at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identity to SEQ ID NO: 1 or SEQ ID NO: 2.

The polynucleotide sequences of the invention can be used for encoding pestivirus proteins or polypeptides, specifically Npro, Core, Erns, E1, E2, P7, NS2, NS3, NS4A, NS4B, NS5A, NS5B of the pestivirus of the invention.

Herein provided is a porcine pestivirus comprising a polyprotein having an amino acid sequence with at least 55% identity to SEQ ID NO: 3, specifically having at least 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 100% identity to SEQ ID NO: 3.

Herein provided is also a polypeptide comprising an amino acid sequence of SEQ ID NO:4 (Npro) or an amino acid sequence having at least 65%, specifically having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% to SEQ ID NO: 4.

Herein provided is also a polypeptide comprising an amino acid sequence of SEQ ID NO: 5 (Core protein) or an amino acid sequence having at least 85%, specifically having at least 86%, 87%, 88%, 89%, 90%, 91%, 92%, 93%, 94%, 95%, 96%, 97%, 98%, 99%, 99.5% sequence identity to SEQ ID NO: 5.

Herein provided is also a polypeptide comprising an amino acid sequence of SEQ ID NO: 6 (Erns protein) or an amino acid sequence having at least 75%, specifically having at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% to SEQ ID NO. 6.

Herein provided is also a polypeptide comprising an amino acid sequence of SEQ ID NO: 7 (E1 protein) or an amino acid sequence having at least 75%, specifically having at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% to SEQ ID NO: 7.

Herein provided is also a polypeptide comprising an amino acid sequence of SEQ ID NO: 8 (E2) or an amino acid sequence having at least 55%, specifically having at least 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% to SEQ ID NO: 8.

Herein provided is also a polypeptide comprising an amino acid sequence of SEQ ID NO: 9 (P7) or an amino acid sequence having at least 65%, specifically having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% to SEQ ID NO: 9.

Herein provided is also a polypeptide comprising an amino acid sequence of SEQ ID NO: 10 (NS2) or an amino acid sequence having at least 65%, specifically having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% to SEQ ID NO: 10.

Herein provided is also a polypeptide comprising an amino acid sequence of SEQ ID NO: 11 (NS3) or an amino acid sequence having at least 90%, specifically having at least 91%, 92%, 93%, 94%, 95%, 96%, 97%, 98%, 99%, 99.5% to SEQ ID NO: 11.

Herein provided is also a polypeptide comprising an amino acid sequence of SEQ ID NO: 12 (NS4A) or an amino acid sequence having at least 85%, specifically having at least 86%, 87%, 88%, 89%, 90%, 91%, 92%, 93%, 94%, 95%, 96%, 97%, 98%, 99%, 99.5% to SEQ ID NO: 12.

Herein provided is also a polypeptide comprising an amino acid sequence of SEQ ID NO: 13 (NS4B) or an amino acid sequence having at least 80%, specifically having at least 81%, 82%, 83%, 84%, 85%, 86%, 87%, 88%, 89%, 90%, 91%, 92%, 93%, 94%, 95%, 96%, 97%, 98%, 99%, 99.5% to SEQ ID NO: 13.

Herein provided is also a polypeptide comprising an amino acid sequence of SEQ ID NO: 14 (NS5A) or an amino acid sequence having at least 55%, specifically having at least 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% to SEQ ID NO: 14.

Herein provided is also a polypeptide comprising an amino acid sequence of SEQ ID NO: 15 (NS5B) or an amino acid sequence having at least 75%, specifically having at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% to SEQ ID NO: 15.

As described herein, the pestivirus of the invention and the polynucleotide encoding said virus can be used for expressing one or more heterologous sequences.

Said heterologous sequence can be any sequence which is not originating or derived from the inventive pestivirus or from the polynucleotide of SEQ ID NO: 1 or SEQ ID NO: 2. Said heterologous sequence can encode a heterologous polypeptide or protein or part thereof from porcine circovirus 2 (PCV2), bovine viral diarrhea virus-1 (BVDV-1) and BVDV-2, border disease virus (BDV), classical swine fever virus (CSFV), atypical pestivirus (APPV), specifically NRPV, RaPV and border disease virus. The heterologous sequence can encode a surface antigen from any viruses or synthetic sequences derived therefrom as listed above. Specifically, the heterologous sequence is inserted at the 5' or 3' end of Npro or E2. More specifically, the heterologous sequence encodes a fusion peptide with Npro, E2 or E1 or a part or fragment of Npro, E2 or E1 of the pestivirus.

Even more specifically, the sequences can comprise any one of SEQ ID NO: 61 (Bungowannah), SEQ ID NO: 49 (pronghorn), SEQ ID NO: 50 (giraffe), SEQ ID NO: 51 (BDV), SEQ ID NO: 52 (reindeer), SEQ ID NO: 53 (sheep), SEQ ID NO: 54 (CSFV), SEQ ID NO: 55 (BVDV-1), SEQ ID NO: 56 (BVDV-2), SEQ ID NO: 57 (BVDV-3), SEQ ID NO: 58 (rat), SEQ ID NO: 59 (bat), SEQ ID NO: 60 (APPV) or any combination thereof or the part of the respective sequence encoding Npro, core, Erns, E1, E2, P7, NS2, NS3, NS4A, NS4B, NS5A and NS5B protein of any of above listed pestivirus. Thus although full length amino acid sequence is given in any of SEQ ID Nos: 48 to SEQ ID NO: 60, the skilled person can easily determine the respective partial sequence of the protein of interest. Within the scope of the invention there is thus also a heterologous protein or polypeptide encoded by the virus of the invention having a sequence of Npro, core, Erns, E1, E2, P7, NS2, NS3, NS4A, NS4B, NS5A and NS5B protein of SEQ ID Nos: 48 to 60, or a sequence having at least 90%, specifically at least 95, more specifically at least 99% identity therewith.

The heterologous sequence can be inserted into the polynucleotide of SEQ ID NO: 1 or SEQ ID NO: 2 of the invention. Insertion can be performed by any method known to the skilled person.

According to an embodiment, the heterologous polypeptide is inserted within the N-terminal or C-terminal region.

As referred herein, the term "region" in connection with the N-terminus specifically means that the polypeptide is inserted within the first 15, specifically 10, specifically 5 N-terminal amino acids. In connection with the C-terminus, the heterologous sequence is inserted within 15, specifically 10, specifically 5 of the C-terminal amino acids.

For the invention, the heterologous polypeptide can be inserted within the N-terminal sequence MEFK (SEQ ID NO: 30) of Npro or the C-terminal sequence SCSD (SEQ ID NO: 31) of NPro. The heterologous sequence can also be inserted between the N-terminal methionine and glutamic acid (ME) and/or between the C-terminal cysteine and serine (CS) of Npro.

To allow sufficient cleavage of the heterologous polypeptide, proliferation sequences are additionally inserted at the C-terminal region of the heterologous polypeptide, for example, but not limited to, ubiquitin or picornavirus 2A protein is additionally inserted.

Alternatively, the heterologous polypeptide can also be inserted within the N-terminal 11, 10, 9, 8, 7, 6, 5, 4, 3, 2 amino acids of the E2 sequence, specifically between the N-terminal amino acids leucine and glutamic acid.

A gene is "chimeric" if it is an assembly of parts that were not originally connected. For example, an assembly of parts of the same gene from different virus isolates or species. A chimeric gene encodes a chimeric protein that is effectively a fusion protein.

The term "chimeric pestivirus" according to the invention refers to the pestivirus of the invention comprising one or more of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 or any combinations thereof or a sequence with at least 90%, specifically at least 95%. At least 99% identity thereto or any combinations thereof any further comprising a nucleotide sequence from a foreign polypeptide. Said foreign polypeptide can be originating from a genetically different pestivirus. The foreign polypeptide can be, but is not limited to, from bovine viral diarrhea virus-1 (BVDV-1) and BVDV-2, border disease virus (BDV), classical swine fever virus (CSFV), atypical pestivirus (APPV), specifically NRPV, PEDV, RaPV, border disease virus, isolates from reindeer, giraffe, HoBi pestivirus and Bungowannah virus or any fragment or derivative thereof.

The pestivirus, composition, vector or chimeric virus as described herein can be used for preparing a pharmaceutical composition, specifically a vaccine.

A "vaccine" is an immunogenic composition that has an inherent medical effect. A vaccine comprises an immunologically active component, and a pharmaceutically acceptable carrier. The 'immunologically active component', is one or more antigenic molecule(s) that is recognized by the immune system of a target, i.e. the pestivirus according to the invention per se or a vector or chimeric pestivirus as described herein, and that induces a protective immunological response. A vaccine generally is efficacious in reducing the level or the extent of an infection, for example by reducing the viral load or shortening the duration of viral replication in a host animal. Also a vaccine generally is effective in reducing or ameliorating the symptoms of disease that may be caused by, or may be the result of, such viral infection or replication, or by the animal's response to that infection.

The effect of the vaccine according to the invention is the prevention or reduction in animals of an infection by a pestivirus and/or of signs of disease that are associated with such virus infection or replication, through the induction of an immunological response, such as the induction of virus-neutralizing antibodies, and/or the induction of a cellular immune response.

The vaccines, specifically live attenuated or inactivated vaccines can be prepared in freeze-dried form. Freeze drying methods are well known in the art. The freeze-dried form can be, but is not limited to a cake, or a lyosphere. For reconstitution, the vaccine can be resuspended in a physiologically acceptable diluent. The diluent may contain additional compounds, such as an adjuvant.

The "animals" for which the vaccine according to the invention is intended are animals that are susceptible to infection with a pestivirus. Mainly these will be mammalian (non-human) animals, and will be members of the order Artiodactyla. Preferred target animals for the vaccine according to the invention are ruminants and swine; especially piglets. The term piglets specifically refers to post weaners, more specifically early weaners, having an age of about 10 days to 3 weeks, having about 4-5 kg, or conventional weaners, of about 3 to 5 weeks, having about 5 to 10 kg. Post weaners, however, may also have an age of about 12 weeks.

The term "boar" refers to an uncastrated male pig.

The term "gilt" refers to a young female pig. As used herein, a gilt is a pig that has not yet been bred, whether only a few months old or approaching a year. A gilt is intact, or capable of breeding and producing young, and her reproductive organs are not surgically or chemically altered. The term "sow" refers to an adult female swine.

A vaccine according to the invention may be a live-, a live-attenuated, an inactivated-, or a subunit vaccine, or any combination thereof.

Alternatively, a vaccine according to the invention, or a part thereof, may be a subunit vaccine. This can be prepared either from live- or from inactivated virus, by applying one or more (additional) steps for the fractionation or isolation of one or more parts of the viral particle. This comprises for instance preparing an extract, fraction, homogenate, or sonicate, all well known in the art.

The vaccine of the invention can also be a live vaccine. For the invention the term 'live' refers to the pestivirus of the invention that is capable of replication.

A vaccine according to the invention may also comprise an adjuvant. This is particularly useful when the vaccine is an inactivated- or a subunit vaccine. However, also live vaccines can comprise an adjuvant, although that should be carefully selected not to reduce the viability of the vaccine virus, even upon prolonged storage.

An "adjuvant" is a well-known vaccine ingredient, which in general is a substance that stimulates the immune response of a target in a non-specific manner. Examples of adjuvants for inactivated/subunit vaccines are, but are not limited to Freund's Complete or Incomplete adjuvants, vitamin E, aluminium compositions such as aluminium-phosphate or aluminium-hydroxide, Polygen™, non-ionic block polymers and polyamines such as dextran sulphate, polyacrylic acid, Saponin. Furthermore, peptides such as muramyldipeptides, dimethylglycine, tuftsin, are often used as adjuvant, and oil-emulsions, using mineral oil or light mineral (paraffin) oil; or non-mineral oil such as squalene, squalane, or vegetable oils, e.g. ethyl-oleate. A vaccine-emulsion can be in the form of a water-in-oil (w/o), oil-in-water (o/w), water-in-oil-in-water (w/o/w), or a double oil-emulsion (DOE), etc. Alternatively, and more suitable for use with a live vaccine, other immuno-stimulatory components may be added to the vaccine according to the invention, such as a cytokine or an immunostimulatory oligodeoxynucleotide. The immunostimulatory oligodeoxynucleotide is preferably an immunostimulatory non-methylated CpG-containing oligodeoxynucleotide (INO).

The vaccine can be formulated as an injectable liquid, such as: a suspension, solution, dispersion, or emulsion. Alternatively the vaccine can be formulated in a freeze-dried form. Commonly vaccines are prepared sterile. Proper formulation may depend on various factors, such as the route of administration chosen.

An animal, specifically a piglet can be protected by vaccination against any disease associated with pestivirus by administering to an animal, especially to a pregnant sow, a boar, a post weaner, a gilt, or to a sow or gilt prior to breeding, the composition described herein in an amount sufficient to protect the piglet.

The disease is any disease caused by pestivirus, specifically it is congenital tremor, more specifically congenital tremor A-II, classical swine fever and bovine diarrhea.

For administration, the composition, e.g. the vaccine can comprise a virus titer of a $TCID_{50}$ of at least about $1\times10^4$, specifically at least $1\times10^5$, $1\times10^6$, $1\times10^7$, $1\times10^8$. The determination of the dosage, i.e. the amount of virus which is administered may depend on the mode of administration. For example, when administering the virus by oral or intranasal route, a $TCID_{50}$ of at least $1\times10^6$ shall be administered per dose, when administering the virus via intramuscular route, a $TCID_{50}$ of at least $1\times10^4$ shall be administered per dose, however higher titers are also encompassed, such as a titer of $1\times10^5$, $1\times10^6$, $1\times10^7$ or more. The respective dose can be determined by the skilled person.

The present invention further provides a novel pan-pestivirus RT-PCR assay for detection of APPV, BDV, CSFV, BVDV-1, BVDV-2, and Linda-Virus. Specifically detection of genomes is with regard to the presence of pestivirus specific genes (Npro and Erns) as well as sequence homology to other pestiviruses in conserved genomic regions (NS3 and NS5B). The overall nucleotide identity between the isolated pestivirus of the invention (Linda virus) and the closest related known pestivirus (Bungowannah virus) is below 68.0%.

As an alternative, an assay can be devised for specifically detecting the pestivirus according to the invention, as a positive marker, screening for effective vaccination. Such an assay would use antibodies against a protein expressed by the pestivirus according to the invention, or would use the pestivirus as detection antigen for antibodies.

For the invention, "antibodies" are immunoglobulin proteins or parts thereof that can specifically bind to an epitope. For sero-diagnosis, antibodies will typically be of IgG or IgM type. The antibodies can be intact or partial antibodies, e.g. a single chain antibody, or a part of an immunoglobulin containing the antigen-binding region. They can be of a different form: a (synthetic) construct of such parts, provided the antibody-parts still contain an antigen-binding site. Well known sub-fragments of immunoglobulins are: Fab, Fv, scFv, dAb, or Fd fragments, Vh domains, or multimers of such fragments or domains. Also the antibodies can be labelled in one or more ways to facilitate or amplify detection.

Therefore, in an embodiment of the method, differentiating vaccinated and non-vaccinated or infected and non-infected animals is allowed, using either the primer described herein, antibody 6A5 or serum neutralization assays employing the Linda virus and susceptible cell cultures. The method for differentiating according to the invention can be performed using any suitable method of immune-diagnostic assays. Often such immune-diagnostic assays will have a step for amplifying the signal strength, and one or more steps for washing away unbound, unspecific or unwanted components. The detection of a positive signal can be done in a variety of ways such as optically by detecting a color change, a fluorescence, or a change in particle size, or alternatively by the detection of radioactively labelled antigens or antibodies in immune-complexes. Similarly, the physical form of the test can vary widely and can e.g. employ a microtitration plate, a membrane, a dipstick, a biosensor chip, a gel matrix, or a solution comprising (micro-)carrier particles such as latex, metal, or polystyrene, etc.

The choice for a particular set-up of such an immune-diagnostic assay is usually determined by the type of input sample, the desired test sensitivity (correctly identifying a positive sample), and test specificity (correctly discriminating between true positive and true negative samples). Such properties are dependent of the strength and timing of an immune response, or the presence of a micro-organism. Further the requirements for test-economy such as the applicability on a large scale and the costs may be decisive for selection of a particular format.

Well-known immuno-diagnostic tests are: radioimmuno-assays, immune-diffusion, immunofluorescence, immune-precipitation, agglutination, haemolysis, neutralization, and "enzyme-linked immuno-sorbent assay" or ELISA. Especially for large scale testing, the automation of the liquid handling, and/or of the result reading and processing, may be a requirement. ELISA's are easily scalable, and can be very sensitive. A further advantage is the dynamic range of its results because samples can be tested in a dilution range. Results are expressed in arbitrary units of absorbance, typically between 0.1 and 2.5 optical density (OD) units, or as 'blocking %', depending on the test properties and the settings of the technical equipment used for the readout. Routinely appropriate positive and negative control samples are included, and most-times samples are tested in multifold. Standardization is obtained by including (a dilution range of) a defined reference sample, which also allows matching a certain score to pre-set values for determining positives or negatives, and allows correlation to a biological meaning, for example: an amount of antigen to potency, or an amount of antibody to a level of immune protection.

Many variants of an ELISA set-up are known, but typically these employ immobilizing an antigen or an antibody to a solid phase, e.g. to a well of a microtitration plate. When an antibody is immobilized the test is called a 'capture' or 'sandwich' ELISA. Next a test sample is added, allowing the ligand (e.g. an antigen or antibody to be detected) to bind. Then a detector (an antibody, antigen, or other binding component) is added which often is conjugated to a label, for instance to an enzyme that can induce a color reaction, which can be read spectrophotometrically. Other types of label could be using luminescence, fluorescence, or radioactivity. The use of a labelled detector is intended to provide amplification of signal strength to enhance test sensitivity, however, it may also introduce background signal, reducing the signal to noise ratio.

Methods for collection and preparation of samples are well known in the art. Such samples can be any type of biological sample in which sufficient amounts of the virus or of the antibody to be detected is present. Typically these samples can be: blood, serum, milk, semen, urine, feces, or a tissue sample such as an ear-puncture.

What constitutes an "appropriate immuno-assay" e.g. for the detection of non-vaccine pestivirus may depend on the particulars of the sample, the virus, or other parameters of the test to be performed.

A "diagnostic kit" is also provided to perform the diagnostic assay and relates to a kit of parts for performing the methods for differentiating, or the method for diagnosing, both according to the invention. The kit comprises one or more components for applying the methods, in particular all parts needed for performing an RT-PCR and primers selected from SEQ ID NO: 26 and SEQ ID NO: 27. Optionally instructions how to perform the method, and how to read and interpret the results are included in the kit.

As stated above, the pestivirus of the invention can be efficiently propagated in cell culture.

In the method according to the invention, and for the amplification of the pestivirus according to the invention, the virus is produced in suitable host cells. This may be by way of inoculation onto the host cells and amplification by natural replication.

The host cell can be a primary cell, such as prepared from an animal tissue. Suitable host cells for the replication of pestivirus are well known in the art, and are generally publicly available. Methods, media, and materials for preparing and culturing a host cell according to the invention, are well known in the art. Examples of suitable host cells are cell lines such as: bovine cell lines such as: MDBK (Madin Darby bovine kidney); swine cell lines such as: PK15 or SK-6 (porcine kidney, swine kidney), or STE (swine testicular epitheloid); or general-purpose cell lines such as: Vero (African green monkey kidney cells), MDCK (Madin Darby canine kidney), or PT cells (ovine epithelial kidney cells). Preferred host cells are SK-6 or PK-15 cells. Specifically the pestivirus of the invention could be easily propagated on SK-6 or PK-15 cells to high titers ($>10^7$) without the need for adaptation. This makes the inventive pestivirus highly advantageous for efficient preparing of vaccine compositions as well as for use as a viral vector.

At certain points in the viral replication cycle, such a host cells will contain a pestivirus of the invention. Therefore in a further aspect, the invention relates to a host cell comprising a pestivirus according to the invention, or as obtainable by a method of the invention.

For propagation, a host cell culture is infected with a polynucleotide, a vector, or a chimeric pestivirus as described herein, the host cell culture is incubated for virus propagation under appropriate conditions, the host cell culture is harvested completely or partially, and the virus is isolated from the cell culture or its supernatant. Optionally a pharmaceutically acceptable carrier is added to the virus or cell culture.

The present invention also refers to following items:

1. An isolated polynucleotide comprising a nucleotide sequence of SEQ ID NO: 1 or SEQ ID NO: 2 or a sequence with at least 60%, specifically at least 70% identity thereto.

2. The polynucleotide of item 1 which is an infectious polynucleotide.

3. The polynucleotide according to item 1 or 2, wherein the polynucleotide is present in a cell.

4. The polynucleotide according to any one of items 1 to 3, wherein an RNA polymerase promoter is operably linked to the polynucleotide.

5. The polynucleotide according to any one of items 1 to 4, wherein the polynucleotide further comprises an exogenous polynucleotide.

6. The polynucleotide according to any one of items 1 to 4, wherein the polynucleotide is present in a vector.

7. A cDNA polynucleotide of SEQ ID NO: 1.

8. A cDNA polynucleotide having at least 65%, at least 70%, at least 80%, at least 85%, at least 90%, at least 95% homology to SEQ ID NO: 1.

9. An infectious polynucleotide comprising a sequence selected from the group of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 or any combinations thereof or a sequence with at least 95% identity thereto.

10. A composition comprising a porcine pestivirus having a nucleotide sequence of SEQ ID NO: 1 or SEQ ID NO: 2 or a sequence with at least 60%, specifically at least 70% identity thereto.

11. A composition comprising a porcine pestivirus comprising an amino acid sequence of SEQ ID NO: 3 or a sequence having at least 60% identity thereto.

12. A composition comprising a porcine pestivirus comprising one or more amino acid sequences selected from the group consisting of SEQ ID NO: 4 (Npro), SEQ ID NO: 5 (Core), SEQ ID NO: 6 (Erns), SEQ ID NO: 7 (E1), SEQ ID NO: 8 (E2), SEQ ID NO: 9 (P7), SEQ ID NO: 10 (NS2), SEQ ID NO: 11 (NS3), SEQ ID NO: 12 (NS4A), SEQ ID NO: 13 (NS4B), SEQ ID NO: 14 (NS5A) and SEQ ID NO: 15 (NS5B).

13. The composition according to any one of items 10 to 12, wherein the porcine pestivirus is inactivated or attenuated.

14. The composition of item 13, wherein said pestivirus is a chemically inactivated virus which is specifically inactivated by treatment with an inactivating agent selected from the group consisting of binary ethyleneimine, ethyleneimine, acetylethyleneimine, beta-ethyleneimine, beta-propiolactone, glutaraldehyde, ozone, and formaldehyde.

15. The composition of item 13, wherein the pestivirus is a physically inactivated pestivirus which is inactivated by treatment with UV radiation, X-ray radiation, gamma-radiation, freeze-thawing, and/or heating.

16. The composition of item 13, wherein the pestivirus is an attenuated by modifying the Npro, Erns or N2-3 genes.

17. The composition according to any one of items 10 to 16, comprising the pestivirus in freeze-dried form.

18. The composition according to any one of items 10 to 17, comprising a $TCID_{50}$ at least about $1\times10^4$.

19. Pharmaceutical composition comprising a composition according to any one of items 10 to 18.

20. Porcine pestivirus vector comprising nucleotide sequence SEQ ID NO: 2, or a sequence having at least 60%, specifically at least 70% identity thereto and a sequence encoding a heterologous sequence.

21. The vector of item 20, wherein the heterologous sequence is selected from a virus selected from the group consisting of APPV, NRPV, porcine circovirus 2 (PCV2), Bungowannah virus, bovine viral diarrhea virus (BVDV) specifically BVDV-1, BVDV-2, classical swine fever virus (CSFV), RaPV and border disease virus, specifically said heterologous sequence encodes a surface antigen from said viruses.

22. The vector according to any one of items 20 or 21, wherein heterologous sequence is inserted at the 5' or 3' end of Npro.

23. The vector according to any one of items 25 or 27, wherein the heterologous sequence encodes a fusion peptide with the Npro, the E2 or the E1 protein of the pestivirus.

24. Chimeric pestivirus having comprising a nucleotide sequence having at least 60%, specifically at least 70% identity to SEQ ID NO: 1 or SEQ ID NO: 2, and a foreign polypeptide.

25. Vaccine for animals comprising a polynucleotide according to any one of items 1 to 9, or a composition according to any one of items 10 to 18, or a vector according to any one of items 20 to 23, or a chimeric pestivirus according to item 24.

26. Kit for inducing an immune response against porcine pestivirus infection in a pig, said kit comprising a composition according to any one of items 10 to 18 and instructions for administering said composition to said pig.

27. A method for protecting a piglet against a disease associated with pestivirus, wherein the method comprises administering to a pregnant sow, a boar, a post weaner, a gilt, or to a sow or gilt prior to breeding, the composition of any one of items 10 to 18, in an amount sufficient to protect the piglet.

28. The method according to item 27, wherein the disease is congenital tremor, specifically congenital tremor A-II.

29. The method according to items 27 or 28, wherein the composition is parenterally administered, specifically intramuscularly, subcutaneously, intradermally, or intravenously using a needle and syringe, or a needleless injection device; or via mucosal administration, specifically nasally or orally.

30. Method for detecting pestivirus, wherein a sample is tested with RT PCR using at least one of the primers selected from SEQ ID NO: 32 and SEQ ID NO: 33.

31. Diagnostic assay for detecting pestivirus, comprising at least one of the primers selected from SEQ ID NO: 32 and SEQ ID NO: 33.

32. Method for detecting pestivirus antigen having an amino acid sequence of SEQ ID NO: 3 or an amino acid sequence of at least 60% identity in a biological sample, said method comprising:

contacting a biological sample with monoclonal antibody 6A5 antibody, said monoclonal antibody specifically binding to an antigen of said pestivirus if present in said sample; and detecting antibody binding to said antigen in said sample.

33. Method for preparing a vaccine according to item 32, comprising the sequential steps of a) Infecting a host cell culture with a polynucleotide according to any one of items 1 to 9, a vector according to any one of items 20 to 23, or a chimeric pestivirus according to item 24, b) Incubating said host cell culture for virus propagation, c) Harvesting the host cell culture, and optionally d) Isolating the virus from the culture and e) Admixing to the culture with a pharmaceutically acceptable carrier.

34. Use of a polynucleotide according to any one of items 1 to 9, or a composition according to any one of items 10 to 18, or a vector according to any one of items 20 to 23, or a chimeric pestivirus according to item 24 or any combination thereof, for preparing a vaccine for animals.

35. A polynucleotide according to any one of items 1 to 8, or a composition according to any one of items 10 to 18, or a vector according to any one of items 20 to 23, or a chimeric pestivirus according to item 24 or any combination thereof, for use in a vaccine for animals.

36. Method for controlling an infection with a pestivirus in animals, wherein the vaccine according to item 25 is combined with a diagnostic kit according to item 26.

The present invention is further illustrated by the following examples without being limited thereto.

EXAMPLES

Example 1

An Austrian piglet-producing farm recorded an outbreak of severe repetitive myoclonia in newborn piglets. Histological examination of the central nervous system (CNS) of affected piglets revealed a hypomyelination of the white substance in cerebellum and spinal cord. During the search for Atypical porcine pestivirus (APPV) genomes in the affected piglets, a previously unknown pestivirus strain—provisionally termed "Linda virus"—was discovered. This virus was isolated from serum samples and could be readily propagated in cultured porcine cells. A full genomic sequence was determined using primer walking together with Sanger sequencing and RACE-PCRs. Pairwise alignment of Linda sequences with other known pestivirus species and unassigned strains revealed a nucleotide identity of less than 68% and an amino acid identity of less than 70% to its closest relative, Bungowannah virus. Within a broad panel of more than hundred monoclonal antibodies raised against the pestivirus species BVDV-1, BVDV-2, CSFV and Bungowannah virus, one E2 specific antibody reactive against Linda virus was identified. Using the E2 specific antibody, the presence of Linda in the CNS of affected piglets at the site of lesions was confirmed. In conclusion, a putative novel pestivirus species is described herein which causes congenital tremor in European domesticated swine clearly distinct from the recently discovered APPVs.

Here, the discovery and molecular characterization of a novel porcine pestiviruses strain is reported that is provisionally termed "Linda" and is unrelated to APPV. The virus was found in an Austrian pig farm reporting major losses due to the "shaking piglet" syndrome. The course of disease was similar to recent APPV outbreaks in Austria (Schwarz et al., 2016, above) but clinical signs and pathological lesions were more pronounced. Histopathological examinations showed that the severe clinical signs were linked to an apparent hypomyelination in the cerebellum and spinal cord. Linda pestivirus was isolated from sera and tissue samples of affected piglets and propagated to high titers on porcine cell lines. The infected tissue cultures were used to identify monoclonal antibodies (mAb) reactive against Linda virus. Using these mAbs, the protein expression of Linda virus was detected by immunohistochemistry at the site of lesions in the central nervous system (CNS). A full genomic sequence of strain Linda was determined by RT-PCR, substantiating the affiliation of Lind virus to the genus pestivirus. Phylogenetic analysis showed that Linda virus is most closely related to Bungowannah virus. However, the divergence observed between Linda and Bungowannah virus was greater than between the approved pestiviral species BDV, BVDV and CSFV. Hence, strain Linda is proposed as a novel species within the genus Pestivirus.

2. Material and Methods

2.1. Sample Collection

All animal use protocols employed in this study are approved by the institutional ethics and animal welfare committee and the national authority according to No endangered or protected species were involved in the study. Solely privately owned land was used for sample collection and accessed only after permission from the owner. In 2015 samples were obtained by the contracted veterinarian from a small scale Austrian piglet-producing farm, which reported major piglet losses due CT. Farm L had not used any vaccines against CSFV or other pestiviruses according to the Austrian legislation. Veterinarians of the University Clinic for Swine in Vienna visited farm L and collected further samples for diagnostic evaluation.

2.2. Description of the Farm L

Farm L is a piglet production site located in Styria in the southern part of Austria. In total 25 Large-white×Landrace crossbred sows are managed in continuous farrowing cycles. CT affected litters solely occurred in gilts and were not observed in following litters. The gilts were obtained from a gilt producer, who was not reporting problems with CT. All gilts were vaccinated against parvovirosis and erysipelas (Parvoruvac®, Merial SAS, Lyon, France) and treated alternately with fenbendazole (Panacur 4%, Intervet, Vienna) and ivermectine (Ivomec, Merial SAS, Lyon, France) to prevent introduction of sarcoptic mange and round worms. This herd was free of PRRSV before and after occurrence of CT.

2.3. Pathology

A complete necropsy was performed on eight piglets of farm L originating from two different litters. The findings from six clinically affected piglets and two healthy littermates without symptoms were compared. The piglets were euthanized; a gross pathological examination was performed and samples were taken. For histological examination brain, spinal cord, and organ samples of all piglets and healthy control animals from a farm without CT problems were fixed in 10% neutral buffered formalin. Formalin fixed brains were cut into coronary sections of 2-3 mm thickness and embedded in paraffin wax. Organ samples and coronary and longitudinal sections of cervical, thoracic and lumbar spinal cord were cut and embedded in paraffin wax, too. Of all embedded organs 1.5 μm thick sections were cut and stained with hematoxylin and eosin (HE). Furthermore, brain and spinal cord samples were stained with a combination of luxol fast blue and HE (LFB-HE) to determine the extent of myelination. Immunohistochemical investigations using a primary anti pan-pestivirus E2 antibody (mAb 6A5, dilution 1:1000) for detection of Linda were performed automatically on an autostainer (Lab Vision AS 360, Thermo Fisher Scientific, Waltham, USA). Briefly, 2 μm paraffin-embedded sections of the piglets' brains and spinal cords were placed on coated slides and dried to enhance tissue adherence. Antigen retrieval was performed on deparaffinized and rehydrated sections by heating in citrate buffer (pH 6). Endogenous peroxidase activity was blocked by incubation in H2O2. After application of the primary antibody a polymer detection system (UltraVision LP Large Volume Detection System; Thermo Fisher Scientific, Waltham, USA), consisting of a universal secondary antibody formulation conjugated to an enzyme-labeled polymer was used. The polymer complex was then visualized with an appropriate substrate/chromogen (diaminobenzidine [DAB]; Labvision/Thermo Fisher Scientific, Waltham, USA). Subsequently, all sections were counterstained with hematoxylin, dehydrated and mounted.

2.4. Detection of APPV Genomes

Total RNA was extracted from field serum or tissue samples using the QIAamp Viral RNA Mini Kit (Qiagen, Hilden, Germany) according to the manufacturer's instructions. RNA was eluted in 60 μl RNase free distilled water and directly used for RT-PCR or stored at −80° C. for subsequent analysis. RT-PCR was carried out using the OneTaq One-Step RT-PCR Kit (NEB, Ipswich, USA) or the One Step RT-PCR Kit (Qiagen, Hilden, Germany) according to the manufacturer's instructions. A pan-pestivirus RT-PCR protocol was developed to detect atypical pestiviruses using the oligonucleotides PPF (5'-GTKATHCAATACCCT-GARGC-3', SEQ ID NO: 32) and PPR (5'-GGRTTCCAG- GARTACATCA-3', SEQ ID NO: 33), an annealing temperature of 55° C., and an elongation time of 1 min.

2.5. Virus Isolation and Growth

For virus isolation, 50 µl serum or 50 µl of homogenized tissue samples of diseased piglets from the affected farm L were used to inoculate 5×10⁶ SK-6 cells on a six-well plate. After three days, the cell culture supernatant was harvested, cleared by centrifugation and passaged on fresh SK-6 cells. All cells were grown in Dulbecco's modified Eagle's medium (DMEM) supplemented with 10% fetal calf serum (FCS Gold Plus, Bio&Sell, Feucht, Germany) and maintained at 37° C. and 5% $CO_2$. Virus infections and passages were analyzed by RT-PCR and immunofluorescence.

2.6. Monoclonal Antibodies Against Strain Linda

Monoclonal antibodies were generated against most proteins of CSFV and BVDV in previous studies. Furthermore, antibodies were raised against E2 and NS3 of Bungowannah virus (unpublished data). Briefly, BALB/c mice were immunized with recombinant proteins until seroconversion was observed. Spleen cells were prepared and fused with sp2/0-AG14 myeloma cells to generate monoclonal antibody producing hybridomas. The resulting mAbs were evaluated using ELISA, immunoblot and immunofluorescence assays as needed. Each of these fusion experiments yielded up to 100 different reactive monoclonal antibodies generating an extensive collection of antibodies against the pestiviral proteins. Several E2-specific and NS3-specific panels of cross-reactive antibodies were screened by an indirect immunofluorescent assay using Linda virus infected cell cultures.

2.7. Determination of the Full Genomic Sequence

Several primer pairs (available upon request) that were hybridizing with highly conserved regions in different pestivirus species (BVDV, BDV, CSFV, Bungowannah, and APPV) were designed according to published sequences available in GenBank. To determine the sequence of the ultimate 5'- and 3'-termini, RACE-PCRs were performed. Total RNA purified from virus infected cell cultures was ligated to two different adapter oligonucleotides using T4 RNA ligase I (NEB, Ipswich, USA). A non-phosphorylated standard oligonucleotide (AD1, 5'-GGC-CACGCGTCGACTAGTAC-3'-OH, SEQ ID NO: 34) was used for 5'-RACE and a phosphorylated oligonucleotide blocked at the 3' end by an amine group for 3'-RACE (AD2, PO3-5'-GGCCACGCGTCGACTAGTAC-3'-AmC3, SEQ ID NO: 35). For cDNA generation and subsequent PCR amplification, primer hybridizing with Linda virus specific sequences and adapter primer (AD1 or AD1rev) were applied together with reverse transcriptase (Superscript II, Thermo Fisher Scientific) and high fidelity Taq-Polymerase (One Taq, NEB). A second PCR was employed using the adapter oligonucleotide (AD1 or AD1rev) together with a nested Linda sequence specific primer to amplify the desired 5'- and 3'-termini. PCR amplicons were subjected to gel electrophoresis, purified by the peqGOLD Gel Extraction Kit (Peqlab, Erlangen, Germany) and sequenced by a commercial provider (Eurofins Genomics, Ebersberg, Germany). In addition, all Linda cDNA fragments were sub-cloned in the pGEM-T easy vector (Promega. Madison, USA) and re-sequenced from the plasmid to obtain high quality sequencing results. The sequence of the pestivirus strain Linda was submitted to GenBank and is listed below as SEQ ID NO: 1. First analyses were carried out using NCBI's basic local alignment search tool for nucleotides (BLASTn) and proteins (BLASTp). Phylogenetic pairwise comparison and identity calculations were carried out with CLC Main Workbench 7.6 (CLCBIO, Aarhus, Denmark). Alignments and phylogenetic trees were generated with the software CLC Sequence Viewer 7.6 (CLCBIO, Aarhus, Denmark) with bootstrap values based on 1,000 replicates. For construction of the phylogenetic trees, sequences of other pestivirus species deposited in GenBank were used as indicated.

3. Results 3.1. Description of the Clinical Signs in the Affected Farm L

In July 2015, first signs of CT were observed in newborn piglets of sows that had farrowed for the first time: between 20% and 100% of the newborn piglets from these litters showed a horizontal shaking involving the whole body. Many newborn piglets were incapable of sucking milk and died before weaning. The shaking vanished in single affected piglets over time, yielding unsuspicious post-weaners. The outbreak of CT ended in September of 2015 with the last litter of newly farrowing gilts.

3.2. Pathology

Piglets from two CT affected litters showed no or only mild lesions on gross examination. Excoriations of the legs, alveolar lung edema and emphysema were found. Some of the CT affected piglets showed scattered petechiae in the renal cortex and in the spinal cord, which were not related to euthanasia. The spinal cord of CT affected piglets appeared slightly hypotrophic. Accentuated vacuoles were present in the white matter of the cerebellum of all clinically affected animals (n=6/6), while fewer vacuoles were found in the unaffected littermates in HE-LFB-staining (FIG. 1A, B). Hypomyelination and hypoplasia were evident in the white matter of the cerebellum and spinal cord of affected piglets and unaffected littermates compared to the healthy control (FIG. 1).

3.3. Detection of Linda Virus

A pan-pestivirus RT-PCR targeting a well conserved NS5B region was developed to detect atypical pestiviruses using a novel set of primers. This assay was successfully evaluated using cultures of BVDV-1, BVDV-2, CSFV, BDV, Bungowannah virus and recently isolated APPV strains (Schwarz et al., 2016). Using this RT-PCR assay and clinical samples of CT affected piglets of farm L, an amplicon of appropriate length was obtained. The 815 bp amplicon was sequenced using the PCR primer yielding an unknown sequence with non-interrupted open reading frame. An initial BLASTn search resulted in "no significant similarity found", but the translated amino acid sequence of 270 amino acid aligned with different pestiviruses. Alignments covered Bungowannah virus (YP_008992092.1, identity 84%, E-value 1e-154), CSFV (NP_777506.1, identity 78%, E-value 2e-153), BDV (NP_777545.1, identity 77%, E-value 9e-151), and BVDV-1 (1S4F_A, identity 75%, E-value 6e-150). The viral RNA sequence was found in clinical samples of all piglets from CT litters examined from farm L (serum, tonsils, lung, liver, spleen and CNS material), whether CT affected or not. In contrast, serum samples of mother sows of farm L were negatively tested for the presence of nucleic acid of strain Linda. 3.4. Genomic sequence and phylogenetic genome analysis The full genome of Linda was determined using the standard primer walking RT-PCR approach together with RACE-PCR to identify the ultimate 5'- and 3'-termini. A total of 12,614 nucleotides (nt) were determined for Linda virus representing 381 nt of the 5'-NTR, 461 nt of the 3'-NTR and 11,772 nt of the coding region (ORF). Nucleotide identity between Linda and its closest relative, Bungowannah virus, was below 68.0% with a sequence alignment coverage of only 88%. Only short stretches of highly similar nucleotide alignments within the conserved genes with other pestiviruses covering less than 42% of their genome were obtained. Consequently, the identities between Linda and BVDV-1, BVDV-2, BDV, APPV or CSFV were below 60%. As apparent, the distance to Bungowannah virus as well as to the classical pestivirus species is considerable. A phylogenetic genome analysis of Linda virus, atypical pestivirus strains and the pestiviral type strains is shown in FIG. 2.

3.5. ORF-Analysis

The ORF of Linda contains 3,924 codons; more codons than the ORF of any other known pestivirus genome, except for BVDV strains with foreign gene insertions. Comparison of the amino acid sequence of Linda with other pestiviruses available in GenBank yields an amino acid identity of 69% with Bungowannah virus (YP_008992092.1), 53% with BVDV-3 (BA004453.1), 53% with BDV (AHM88396.1), 53% with CSFV (AGE89843.1), 52% with BVDV-2 (CDH30717.1), and 52% with BVDV-1 (AEW46241.1) with expected values of 0.0 each. The phylogenetic analysis of pestiviral polyproteins is shown in FIG. 3. All hypothetical polyprotein processing products of Linda virus match best with the mature proteins of Bungowannah virus. The identity score to Bungowannah virus were determined with 63% for Npro (AA1-182), 83% for Core (AA183-283), 74% for Erns (AA284-504), 67% for E1 (AA505-702), 53% for E2 (AA703-1077), 59% for P7 (AA1078-1152), 63% for NS2 (AA1153-1608), 85% for NS3 (AA1609-2291), 81% for NS4A (AA2292-2354), 78% for NS4B (AA2355-2701), 53% for NS5A (AA2702-3205), and 73% for NS5B (AA3206-3923). Signal peptide cleavage sites were annotated in analogy to experimental determined protein borders of classical pestiviruses and confirmed using in silico prediction. In difference to other pestiviruses, the NS3 mediated cleavage between the nonstructural proteins NS4A and NS4B takes place at a leucine/serine site in Linda virus, just like in Bungowannah virus. The specific intramolecular leucine/alanine cleavage site (L1834/A1835) within the NS3 separating protease and helicase domains is present in Linda virus.

3.6. Analysis of Linda Virus E2

The pestiviral envelope protein E2 forms homodimers and E1-E2 heterodimers on the virus surface that mediate attachment and entry into host cells via receptor mediated endocytosis. Convalescent hosts develop an antibody response against the E2 protein that is crucial for virus neutralization. The E2 protein is responsible for the pestivirus species specific host tropism and exhibits the greatest amount of diversity among all pestiviral proteins. Linda virus E2 was 53% identical to the Bungowannah virus E2 (FIG. 4). All E2 proteins, except for the shorter Rat pestivirus and APPV E2 with only 241-244 amino acids, show a comparable length (373-378 AA) and shared a three domain structure. APPV and Bat pestivirus E2 contains 8 cysteines, CSFV E2 15 cysteines, Linda virus E2 16 cysteines, BVDV-1, BVDV-2, BVDV-3, Sheep, Reindeer, Giraffe, Rat pestivirus, and BDV E2 17 cysteines, Pronghorn pestivirus E2 18 cysteines and Bungowannah virus 19 cysteines. The up to eight intramolecular disulfide bonds form the structural units of E2 protein domains and free cysteines mediate intermolecular dimerization of E2-E2 homodimers or E1-E2 heterodimers. The typical cysteine positions are conserved in Linda virus and in analogy to BVDV, the cysteine in the E2 of Linda virus at position 296 is mediating heterodimer formation. N-linked glycosylation (NLG), the addition of oligosaccharides to asparagine residues, requires recognition of the consensus sequence motive Asn-X-Ser/Thr. Pestiviral E2 contains three NLG sites in case of Pronghorn pestivirus, four NLG sites in case of BVDV-1, BVDV-2, Rat pestivirus, Giraffe pestivirus and Bungowannah virus, five NLG sites in BDV, APPV and Sheep pestivirus but up to six NLG sites in case of CSFV, BVDV-3, Reindeer pestivirus and Bat pestivirus. The heavy glycosylation is causing an increase of the molecular mass by glycan attachment and a masking of immunogenic protein surfaces. In contrast to all known pestiviral species, the sequence of Linda pestivirus includes only two potential NLG sites. Linda pestivirus E2 exhibits sequence similarities with the E2 molecules of the classical pestiviruses but shows distinct features.

3.6. Isolation and Propagation of Strain Linda

The availability of the RT-PCR assay allowed for detection of Linda infection of cultured cells. After initial inoculation of SK-6 cells with serum of a CT affected piglet and passage of cell culture supernatant, the successful isolation of Linda virus was shown by RT-PCR. The infection of SK-6 or PK-15 cells with Linda did not lead to an apparent cytopathic effect. Using established serological reagents and immunofluorescence, the presence of Linda antigen in SK-6, PK-15 and MDBK cells after infection was further demonstrated. Considerably high infectious titers of Linda were measured in the supernatant of infected porcine cell cultures (>$10^7$ TCID50 per ml, FIG. 5). In addition, a focus size assay employing porcine and bovine cell lines revealed about 10-fold larger antigen positive foci in SK-6 cells than in MDBK cells (FIG. 5B).

3.7. Serological Reagents Against Strain Linda

Panels of immunofluorescence positive pestivirus specific mAbs, which were established in earlier studies. were screened for reactivity against Linda virus infected cell cultures. A strong reactivity against Linda infected cells was seen using the E2 specific antibody 6A5, generated against BVDV E2 (FIG. 6). The immunofluorescence of this antibody yielded a cytoplasmic signal with a dominant staining of membranes of the endoplasmic reticulum. This staining pattern has also been documented for the homologous proteins of other pestiviruses.

4. Discussion

In the course of investigating typical cases of CT for the presence of APPV, piglet producing farm L stood out because APPVs were not detected using a TaqMan probe based RT-PCR assay (Schwarz et al., 2016). This was surprising as the clinical observations were apparent and the lesions in the spinal cord and cerebellum of infected animals were pronounced.

A novel pan-pestivirus RT-PCR assay was designed to ensure the detection of APPV, BDV, BVDV-1, and BVDV-2, described earlier. Sequence analysis of the amplicons of six CT-affected piglets from farm L revealed a sequence of a so far unknown pestivirus. Further analyses of the assembled genome allowed an unambiguous assignment of Linda virus within the genus pestivirus, both with regard to the presence of pestivirus specific genes (Npro and Erns) as well as sequence homology to other pestiviruses in conserved genomic regions (NS3 and NS5B). The overall nucleotide identity between Linda and the closest related known pestivirus (Bungowannah virus) is below 68.0% suggesting that Linda virus represents a novel pestivirus species. The finding that Linda pestivirus very likely shares a common ancestor with Bungowannah virus is exciting. After its description about 10 years ago, it was intensively searched for Bungowannah virus all over the world but the virus was never detected outside Australia. Another feature of Linda pestivirus was remarkable and clearly distinct from APPV. APPV hardly infects cultured cells at all and isolation is challenging. Linda pestivirus could be easily propagated on SK-6 or PK-15 cells to high titers (>107) without the need for adaptation, similar to what has been reported for Bungowannah virus and CSFV. Worth mentioning is the fact that even though MDBK cell were permissive for Linda pestivirus, its growth was remarkable reduced compared to porcine cell lines. This suggests that Linda pestivirus is a genuine porcine pathogen.

According to the ICTV, the classification of pestiviruses is mainly based on host range, sequence homology and disease. The natural host of CSFV is pigs, the natural host of BDV is sheep, the natural host of BVDVs is cattle, and several atypical pestivirus strains found an ecological niche in different wildlife species. However, most pestivirus species are able to adapt on novel cloven hooved host species and show a broad host range after laboratory infections. In addition to the approved species, three groups of atypical pestiviruses have been described and categorized with respect to the natural hosts. Group 1 comprises all pestiviruses of bovine origin. Group 2 includes the pestiviruses of non-bovine and non-ovine origin, covering wildlife pathogens like the Pronghorn virus and also porcine pathogens like Bungowannah virus. Group 3 comprises the sheep isolates also referred to as the Tunisian pestiviruses. The discovery of Bungowannah virus, APPV and the description of Linda demands the establishment of a group 4 as the "porcine pestivirus group". Regarding these categories, the inclusion of established species seems logical.

Species affiliation or demarcation based on the genetic relationship between different strains depends on the definition of type strains. Type strains exist for the classical pestiviruses (BVDV-1, strain NADL; BVDV-2, strain 890; BDV, strain X818; CSFV, strain A187) but were missing for the tentative species of atypical pestiviruses. The nucleotide sequence divergence between the complete genomes of established pestiviral species and the additional tentative species (Giraffe pestivirus, Pronghorn virus, BVDV-3, Sheep pestivirus, Rat pestivirus, Bungowannah virus, and APPV) exceeds 25%, thereby providing a robust minimal threshold (25%) for the affiliation or demarcation of novel strains. In a practical approach, a total of nine pestivirus species (BVDV-1, BVDV-2, BVDV-3, Giraffe pestivirus, CSFV, BDV, Sheep pestivirus, Antelope pestivirus and Bungowannah pestivirus) have been proposed before APPV was discovered. As a consequence of sequence variance, there is a pronounced antigenic variance between the different pestivirus species. Since sera of convalescent animals show a much higher neutralization titer against pestiviral strains from the homologous species than against pestiviral strains from heterologous species, the species relation can also be grouped by serotypes taken the cross-reactivity of immune sera into account. In the case of Linda virus, sera of defined convalescent animals could not be obtained from the farm L and hence, cross-species neutralization tests could not be performed. Controlled laboratory infection studies would be needed to answer the question if immune sera from Linda infected animals were able to neutralize other pestivirus species. It is planned to investigate, if the available ELISA systems for CSFV and BVDV diagnostics show interference with Linda virus infections. A collection of murine monoclonal antibodies were tested against different pestiviral proteins of different species—except of BDV—and found that most established reagents were not reactive against Linda. Even pan-pestivirus specific IgGs, like mAb 8.12.7. which is reactive against CSFV, BVDV-1, BVDV-2, and BDV, failed to detect Linda infected cells (data not shown). Interestingly, none of the Bungowannah specific mAbs cross reacted with Linda virus. These analyses suggested that Linda virus exhibit a considerable antigenic difference to the established pestiviral species and to Bungowannah virus.

Linda virus was detected retrospectively in a single farm that was tested virus free several months after the clinical signs had ceased. In contrast to the mostly mild form of CT in APPV affected piglets that improve from central nervous defects with age, the clinical signs associated with Linda virus were severe in most piglets and frequently led to death. Strong evidence that Linda virus is the causative pathogen of the CNS damage and the hypomyelination comes from the clear detection of Linda virus E2 in the lesions of the periaxonal space. Currently, there is no link to other forms of disease in pigs so that experimental infections are required to assess pathogenicity and virulence of the new virus. The feasibility to grow Linda virus allows to challenge Koch's postulates and define pathogenesis in controlled animal trials. Because the source of Linda virus introduction into the herd can only be speculation, further work is necessary on the prevalence and epidemiology of Linda virus in Austria.

Example 2

Animal Trial Linda Virus

An animal trial was set up to investigate Linda virus pathogenesis and shedding. 21 post-weaning piglets (*Sus scrofa domestica,* 12 weeks old) were housed in a biological safety unit (BSL2) in three different groups. After one week, 5 animals were intra-nasally and 5 animals were intra-muscularly infected with $1 \times 10^7$ tissue infectious doses 50% ($TCID_{50}$) of Linda virus. A group of 5 animals was mock infected and served as a separated control, while 3 sentinel animals were included in the infection groups at the day post infection. The health status of all animals was assessed daily and the body weight was measured. Viremia and virus shedding was assessed at day 0 (day of infection), 3, 5, 7, 14, 21, and 28 post infection analyzing serum samples, nasal and oral swaps, and fecal samples. The animal trail showed, that:

1. Linda is of low pathogenicity for post-weaners (no obvious fever, no obvious growth retardation, slightly reduced weight gain)

2. Linda leads to fast and reliable sero-conversion (neutralizing antibodies detectable in 10 of 10 infected pigs—5 i.n. and 5 i.m—all SNT titers>1:256) even after natural infection routes (SNT titer>1:100 in the infected sentinel animal)

3. Linda is a contagious pathogen for pigs (1 of 6 sentinels infected)

4. Linda is causing a short-lasting viremia (infectious virus only observed in 2 i.m. animals and in the sentinel, at a single test time point each. test scheme: d3, d7, d14, d21, d28)

5. Linda is secreted via oro-nasal fluids (virus detection via RT-PCR positive in three infected animals at day 7 and/or day 14)

The invention claimed is:

1. An isolated polynucleotide comprising a nucleotide sequence of SEQ ID NO: 1 or SEQ ID NO: 2 or a sequence with at least 80% identity thereto, wherein the polynucleotide further comprises an exogenous polynucleotide.

2. The polynucleotide of claim 1, wherein the polynucleotide is infectious.

3. The polynucleotide according to claim 1, wherein an RNA polymerase promoter is operably linked to the polynucleotide.

4. An infectious polynucleotide comprising a sequence selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, and SEQ ID NO: 29 or any combinations thereof or a sequence with at least 95% identity thereto, wherein the infectious polynucleotide further comprises an exogenous polynucleotide.

5. A composition comprising a porcine pestivirus having a nucleotide sequence of SEQ ID NO: 1 or SEQ ID NO: 2 or a sequence with at least 80% identity thereto, wherein the composition further comprises an exogenous polynucleotide.

6. A composition comprising a porcine pestivirus comprising one or more amino acid sequences selected from the group consisting of SEQ ID NO: 3, SEQ ID NO: 4 (Npro), SEQ ID NO: 5 (Core), SEQ ID NO: 6 (Erns), SEQ ID NO: 7 (E1), SEQ ID NO: 8 (E2), SEQ ID NO: 9 (P7), SEQ ID NO: 10 (NS2), SEQ ID NO: 11 (NS3), SEQ ID NO: 12 (NS4A), SEQ ID NO: 13 (NS4B), SEQ ID NO: 14 (NS5A) and SEQ ID NO: 15 (NS5B), wherein the composition further comprises a heterologous polypeptide.

7. The composition according to claim 5, wherein the porcine pestivirus is inactivated or attenuated.

8. The composition of claim 7, wherein said pestivirus is a chemically inactivated virus by treatment with an inactivating agent selected from the group consisting of binary ethyleneimine, ethyleneimine, acetylethyleneimine, beta-ethyleneimine, beta-propiolactone, glutaraldehyde, ozone, and formaldehyde.

9. The composition of claim 7, wherein the pestivirus is a physically inactivated pestivirus by treatment with UV radiation, X-ray radiation, gamma-radiation, freeze-thawing, and/or heating.

10. The composition according to claim 5, wherein the pestivirus is in freeze-dried form.

11. The composition according to claim 5, wherein the composition has a $TCID_{50}$ of at least about $10^4$.

12. The composition according to claim 5, further comprising a pharmaceutically acceptable carrier.

13. The polynucleotide of claim 1, wherein the exogenous sequence is from a virus selected from the group consisting of APPV, NRPV, porcine circovirus 2 (PCV2), Bungowannah virus, bovine viral diarrhea virus type 1 (BVDV-1) bovine viral diarrhea virus type 2 (BVDV-2), classical swine fever virus (CSFV), RaPV and border disease virus.

14. The composition of claim 5, further comprising a foreign polypeptide.

15. A vaccine comprising a polynucleotide according to claim 1.

16. A method for protecting a piglet against congenital tremor A-II, wherein the method comprises administering to a pregnant sow, a post weaner, or to a sow or gilt prior to breeding, the composition of claim 5 in an amount sufficient to protect the piglet.

17. A cell comprising a polynucleotide, wherein the polynucleotide comprises a nucleotide sequence of SEQ ID NO: 1 or SEQ ID NO: 2 or a sequence with at least 80% identity thereto, the polynucleotide further comprising an exogenous polynucleotide.

18. A vector comprising a nucleotide sequence of SEQ ID NO: 1 or SEQ ID NO: 2 or a sequence with at least 80% identity thereto, wherein the vector further comprises an exogenous polynucleotide.

* * * * *

SEQUENCE LISTING

<160> NUMBER OF SEQ ID NOS: 61

<210> SEQ ID NO 1
<211> LENGTH: 12614
<212> TYPE: DNA
<213> ORGANISM: Porcine pestivirus

<400> SEQUENCE: 1

```
gtatagcagc agtagctcaa ggctgctata cgattggaca taccaaattc caattggtgt 60
tagggaccac ctaggtgaag gccgacgaca ggtagccatt cctgttagta ggacgaaccg 120
ttatggtgga ctggttgctc aggtgagcag gctgcaatgc gtaagtggtg agtacaccac 180
agccgtcaaa ggtgccactg gtaaggatca cccactggcg atgccttgtg gacgggggcg 240
tgcccaacgc aatgttagcg gtggcggggg ctgccatcgt gaaagctagg tcttgatgga 300
ccttgttgcc tgtacagtct gataggatgc cggcggatgc cctgtgacag ccagtataaa 360
gaatatccgt tgtgattgca catggagttt aaaattctca acaacacaaa gaaaaaaaat 420
aataatgagg aggaagctga ggggaacatg ttctggcgga tgtaccgaag acctccgcct 480
ggttgctacg aaccaactta caacctaagt gggacaccta gcttcggacc catgcaccca 540
ccactgagga aagggagtac attacgttta ccccactgga gaggcatagc cacggttgga 600
tgtgagctta aaaacctgcc acgcaagggt gattgtacta agtgccacgc taacccaaca 660
tctggcatct acctcaacct gggtgcggtg ttttataaag attacgaggg ggaggtatac 720
catagagtcc cccttgaaca ctgtgaggaa cagcagaggt gcgaagtcgt caagcgtgta 780
gggagaatga ctgctagcga tggatccttg gtgggagtgc tagtatgcag tgacgactgc 840
gtgctgtttg agagaagaag aggggaacac acagtgttga agtgggtaaa gaaccctatc 900
ggggcgccac tctgggtaca gagctgctcc gacgagaagg gggccaaacc aaaaaaacaag 960
tctaaacaac aaaacgatcg aatggcaccg ggtaaaatgg tgacaaaacc taaggaagtg 1020
gaagctgatc agaaaactag accgccagac gctacaattg tggtggatgg acagaaatat 1080
caagtaagga agaaagggaa ggcaaaacca aagacaccag atggcctgta ccacaataaa 1140
aacaagccgg aggcatctag aaagaaatta gaaaaagcgc tactagcttg ggcagtcatt 1200
gcaataatat tgattcagca gaccacagca aacaatgtga cgcagtggaa cttgtgggac 1260
gacaagaacg caacagatgt gcactcagtg atgcatcaga gacaaatcaa gcgcagcctc 1320
cacggcatct ggcctgaaag aatctgcaaa ggggtcccag gtcatctggc tactgactat 1380
gagctaaaac ggatagaggg gatgttggat gccagcgaaa aaactaattt tacctgttgc 1440
aggctgcaaa gacacgaatg gaacaaacat ggctggtgta actggtacaa tatagacccc 1500
tgggtcgcca ttatgaacag gacccaagcc cttctatcta gtggccaaaa ctttacagag 1560
tgtgccgtta catgtaggta tgacacagaa cagcagataa acatagtaac tcaagcccgc 1620
atgacaccaa cgattttaac agggtgtaag aaggacgtaa acttctcttt ctcaggggag 1680
gtgaggactg ggccttgcaa ctatgaactg aagccagaag acttaatgag gattctggac 1740
cataccaact gcaaagattt cagctatttc ggagaaggtc tggtggatga tttcacagaa 1800
gccacggaaa aaattagatc tagtgggtac agggccctgt cgtggctgca agacaagcta 1860
gagaaaacta agaagaaggt gtttggagct gaagcaacac catactgcaa tgtgacaagg 1920
agggttttca acatcatata caccaacaac tgcacccccg ctggactgcc agataacacg 1980
aggatagttg ggccagggac atttgacatc agtgaaatgg aaaataaaaa actgttaccc 2040
aacttggact accacttggc agatttcatg gtactgggct tagtggcttt atccgacttt 2100
```

```
gccccagaaa ctgctagtac aatctatctg gtattgcact actggctgcc tcaggcagag    2160
gtgcatacat tggacacccc acttgacacc aacaagctga atctaacaag gaacaggcag    2220
gttagtagtg tagtccctaa ttcaatatgg ttgggagggc agctggtgtg cgtcaagcca    2280
aggtggtggc cctactcagc agaaattaca acagtgatta gcggactgac cactgtaacc    2340
gacctagtgg tcaagaccat agaggaactt gtgagcttgt ggacagaggc aacagcagta    2400
gccttcttgg cagccctgat aaagatcttc agaggacaac caatacaagc actagcatgg    2460
ctcataataa tagggggagc ccagggtctt gaatgcaact tcgaactgca atacgctctg    2520
gccgggaaca catccatgag cctactaggg ccaactgcct taaagactca atggtaccaa    2580
gcggcagacg gggtcaaaat aacggatggg gtagtaactg tgatatgcaa caagggcatt    2640
ttctcggtga ctcctaggtg caaagaggca cctgtaaggt acctggcaat caaccacccc    2700
aggtccttat caaccagtgc ttggttcaag aaaatacacg acccggcaga ccatccgact    2760
gagacactga tgggcgaaaa gggaagggca tacctctgcc cttgcggggc tacaccacta    2820
ccaaaaccca aggttccgtt taacccaatc acaatacaag gttcggcgtt ctccctaaca    2880
tgcccaaaaa actggcaagg tgacatgaaa tgcaatctct taagcccaga cacactagca    2940
attgaaacca tatacacctt cagaaaacat aagccataca aagaagaacc ctactgctcg    3000
tacactaagg tagtggacgg gtacttgcgc aacgtgcacc tatgggggca tgatacatgt    3060
gtggcaggag atataatcaa tggcagtcaa gatgacagtg tgaccaagtg caaatggtgt    3120
gggtatgagt tcaattcagc aactgactta cctgactacc caattggtta ctgcacgaag    3180
cgaggcacca attatctaat caggtacaag caggtgcctt gtgaggtagg aggagtccgc    3240
atcgggtcag gaaaagtaga gtgtaccatt ggctccacga gagtaaaagt agaacaaacc    3300
agtaatgagt tgggtccgat gcctgcaag ccaatagtat attcatctca aggaccgcct    3360
aatccaaaaa cgtgtacatt caaatggagc tacacattaa acaacaagta ctacgagcca    3420
agggatgaat tcttccaaca gtacataacc tcaggtggct atcagtattg gtttgacctg    3480
acagcaaaag atcacgtgat ggattgggta acacgatact ccccattat agttgtagca    3540 ttactggggg gtagagcagt gctgtggatc ctaattgcgt acgagttgct aaatcactac    3600
caagtgggcg cagaccagaa cacattgctg caggccgaag cactagtgat aggtaacatc    3660
ctgatgacaa gagacctgga agtgatggtg tgctttctgt tgctgatggt cttgataaga    3720
agacagcagg ctagaaggc tttggccttg gttttccatt ggatggtaat gcatcccgcc    3780
caatcagcca tcgcaacatt ggtgtacgta ataggcatcg tgagagctga agagggacag    3840
gttaactctg acagttctac gcaagcacac gtggtggcca ttttgttgtt tctaattac    3900 cacacactaa aagaaggga ccttcacaca gctatgacat tactgttgac attttccata    3960
aagagcactg actatgtaga cacacattat tatgaaatac cgatgctctt cacagttatt    4020
tcgttggtca tttccatta catattcaac atacacataa aaaccaagtg ggtagctctg    4080
gtgctcagta tggtgggcat ggtcaccttt ataaggtgcc tttggttgat caggaacata    4140
caaataacac ccccttccat accactaaca tacatcagtc caaaaatatt gatcatagct    4200
tacctggttt ctctgactgt cttggtgaat aacaacctag acctcgccag ctacgtgatc    4260
agggctggcc cgatactaat gtcctactta actttatggg tggacatcct gatgttgcta    4320
gttctactac cttggtatga attgattaaa gtctattacc taaagaagaa gaaagacgac    4380
atagaagact gcttccaata cagcgggata gccactcaag ggttatcccc gtacaatcag    4440
```

```
gacttcgtgg acccaaaaga gggggtacac ttgatcccct cacaaaacaa gagcaatttc    4500
acccggaccg catatctgac tatcctgagg gccctagttc tcacagcttt cagcagcatt    4560
tggaagcctc taatcctagc cgaactgcta ttggaatcca tttattggac acacatcaaa    4620
gttgcaaaag aagtggcggg atctacgagg cttataggta ggtttgtagc ggccctgata    4680
gaactaaatt gggttttga tgacaaggaa gcagcaagat acaaaaaatt ctttgtttta    4740
acctcaagag tgagagacct catggtaaaa cacaaggtgc agaacgacac aatgaggcag    4800
tggtttgaag agacggaaat attcggctta caaaaagttg ccttggtggt cagagcacac    4860
tcactgacag cagacagcaa cagtatacta tgctcagtgt gtgaggaaaa acagaacata    4920
gaagccaaga gggtatgtcc caagtgtgga acagaggaa caggaatcaa gtgcgggatg    4980
accttggctg agtttgaaga aaatattac aaaaagatct atctagtgga tggagacaat    5040
acgcaagcat atcgcagaga ggagagagga gaagtcacgt acacagctag ggcgccttc    5100 ttcttgagga acttacccat tctggccaca aaaaacaagt atatactggt aggtaactta    5160
ggtatggaat tacaagacct tgagtccatg gggtggatta tcaggggccc agctgtctgc    5220
aaaaagatag tgcaccatga acgctgcagg cccaccatcc ctgataaact tatggctttc    5280
tttgggctca tgccaagagg cgtagtcccc cgggcaccaa cccgcttccc tgtatcatta    5340
ctgaaaatta aagggtttt cgaaacgggg tgggcatata cacaccctgg agggatcagc    5400
agcgtaatgc atgtaacagc aggcttggac atgtacgtca atgatgccat gggtagaacc    5460
aaggtgcagt gccaagagag aaacaagctg acagacgaat gtgagtatgg cattaaaact    5520
gactcaggct gctctgaagg ggcacgctgc tatgtaataa atcccgaagc cgtcaacata    5580
gcaggcacca ggggcgctat ggtacacctc agaaaaacag gtccagaatt tacctgtgtg    5640
acagcccaag gaaccccagc cttctacaat ttgaggaatc ttaaaggttg gtcagggcta    5700
ccaatattcg aggcagctac gggaagggtg gtaggcagag tgaaagcagg caagaatgca    5760
gaggatagtc aacaactat aatgtctggc acccaggcag ccaaaccgac agagtgtgac    5820
ctggagtcgg tcgtaaggaa gctggaaacc atgaacagag gggagttcaa gcaggtggtg    5880
ctagcaactg ggcagggaa gacaacagaa ctgccaagga agctaataga gccgtgggg    5940 cggcacaaga gggttttagt cctaatcccc ctgagagcag cagcagaggg ggtttataac    6000
tatatgagaa caaagcatcc aagcatagca ttcaacctga ggataggga cttaaaagaa    6060 ggagacatgg caactggtat aacttatgcc tcatatggtt attttttgtca aatggacatg    6120 ccacggctag atgcagctat gaaggagtac aactacatat tcctggacga atatcattgt    6180
gcaacaccag agcaattggc tgtgatgtca aaaatacaca ggatcagtgc tgacctaaga    6240
gtggtggcca tgcagctac ccctgcaggc gctgtgtcaa aggtgggcca gaaattctcc    6300
atagaagaag tggtggtgcc agaggtaatg aaaggggaag acctaggcga ggattatttg    6360
gacatagccg gactaaaaat accaaaatcg gaactacaag ggatgtctt aacgtttgtt    6420 ccgacaaaaa agttggcgtc agacactgct aagaaactaa ccacccaggg ctacaacgct    6480
gggtattact ttagtggtga agacccaagc tcgctgcgca ccataacatc aaaatccccg    6540
tacatcataa tagccaccaa tgcaatagag tcaggggtga cattaccaga cctagacaca    6600
gtaattgaca caggggatgaa gtgtgaaaag agggtgagaa tagagaacaa ggctccatac    6660
ataataacag gcctaaaaag aatggccatc accacagggg agcaagccca gaggaaggga    6720
agagtaggta gagtcaaacc agggagatac ctaagagggc ctgaaaatgc aggtggagag    6780
agagattatc actatgacct gctgcaggca caacgttatg ggctccagga tgctatcaac    6840
```

```
atcaccaaat cattcaggga gatgaactat gactgggcac tctatgagga agacccactg    6900
agaataacac aattggaggt attaaatacc ctactcatat ccaaagatct gccaacagtc    6960
acaaagaatt tgatgaccag gaccacacac ccagaaccaa ttcaattagc ttacaatagc    7020
atagaaaccc ccgtcccagt gctgttccog aaagtgaagg gtggagaggt gaccgatgct    7080
tatgagacct atgaactgat gatgtgtcgg aagctggata cgaccccccc gatttatctg    7140
tatgccacgg aagatgaaga cctagcagtg gacctcctga acctgaaatg cccgcagtg     7200 tcaacagcct cggccataga aacagaggac gccctcaaca agttatcggg gctttcggca    7260
ggggaaacag ccctgctagt ggctctgcta ggttgggtcg gttacgaggc tctggtgaaa    7320
agacacatac caatagtgac tgacatatat acaattgaag atgaaaaact tgaggacacc    7380
acccacctcc agtattcacc agtgaactg caaaacaccg agacagtgga gctgaaagac     7440
ctgtcggcac acgaactgaa agaagccctg gaaagcggaa aaagttatgt caaagacgcc    7500
tttgaattcg taaaatcaca ggttgagaag ctccccgaca caaaaattta caagcaagtc    7560
caagagaagt cacccggtct tttagaaaaa ttttttggcct atctgtcaga acacagtagt    7620
gacataaaga aatatggatt gtgggggtc catacctctc tgtacaatag tatcaaagag     7680
agattggggc acgaaactgc cttcgcttca ttgatcatca agtggatagc attttccagc    7740
gaagggctgc ctggaatggt gaaacaagct gctgtagact tggtggtata ttatctgatc    7800
aacaaaccag atttcaaagg tgacaaagac acccaagatg atggaaggaa gttcgtagga    7860
gccctgttcg tgtcagctct ggccaattac acatttaaaa attttaataa gtcaacactt    7920
gaaggcttag taatgccagc attgaactac ctaccatatg caggggctgc actaaaaata    7980
tttgtgccta ctaaattaga gagcttagta atactgtcaa caaccatcta caggacctac    8040
ctctccatta agaaaggctc tagtcaagga ctggctgggt tagcagtgag ctcaggtatg    8100
gaaattatga atcagaatcc aatatcagtg gccattgcgg tggcattggg agtcggtgcc    8160
atagctgcac acaatgcgat cgagagcagc gaggcaaaga ggaccctgtt gatgaaggta    8220
tttgtgaaaa actttctaga ccaggcagcg acagacgagc tggtaaaaga gaacccagaa    8280
aaaataataa tggcagtatt tgaagcaatc cagacagcag gtaatccaat aaggctaata    8340
taccacctat atgccatgtt ctacaaaggt tggaacgcct cccagatagc agataagaca    8400
gcggggagga acatattcgt gctgacaata ttcgagggtt tagaactgtt gggactagac    8460
aaggattcca gtggagggga tttgagctca aattatttag tggatgcaat caggaagctc    8520
attgaaaaat tgactaaaat actcagaaac accaccaagt cattaatcaa atccttgctg    8580
ccagctccat tctcttgcac gagattcaca agagacaaca gaattggatg ccacatttta    8640
aattttgatt attacgagat aaattgtgca tgtgggtacc ggaggagagt ggtaaaaact    8700
gtcatcgacc cagtcacctg ggagactttg gaagaagaag ccctgagtt ctgcttcaac     8760 aggggggacta cgccctggc aaacccaaga gttgcaagtt attactcagc tggagagcca    8820
gttctcccag tggtaaaaag agagggggtt ggcgaaatcc tggtaagggg ggtgacaatc    8880
cagatgcatt atgaccacaa caagatactc gccactgaca actggcaagt gccattccag    8940
gcagtgacga agatatttac agattaccag ggcataggt accaagaagc atatctggga     9000
acccagccaa actacaaagc actggtgaag aggtcatccg tcacgattac aaaagaaggc    9060
ctgaaattta aagatgcaa gaaagggatc gcgtatacga ccaatctaaa cttaaccccac    9120 atccaaaagc tggtgcaggt gtgcagaatg aatgaattgc aagaaggcgt catacctgag    9180
```

```
accttggatg gcgacacctg gattaactac atggcaatca tcgaagatgt gggggccaca   9240
aaaccaagct tggagagaga gtcatacccg aaaccatacg aggaggatcc cctcgaaggc   9300
cccagtgtga tcgtggaaac aggggacgtg gacatcacaa agtgggcgt aaatcaacaa    9360
tccagttcat caggaaccgt ctttcaagta gtggagaaga tctatactaa actggtcaat   9420
acaaatgtaa taagatagg attcaaagaa ggctgtttcc cgggacccac aaagaatgtg    9480
aattcattga atgagcacat agaagataaa gacagtaaac catacatctt catatgctct   9540
tccgacaaag caatgtccaa cagagtaaag actgcaagga acattaagaa actcaacaca   9600
aattcggcaa tagtagcccg taatttggcc agggaaggga aattgatcat aatagtacta   9660
ggagagaagt accatgagga catctacaaa catgctgact tcaagggac tttcctcgac     9720
aggaaggcac tggaagccct gtccaaggcc aagcctgtaa aaagaacat gactaggaga     9780
gaggctcaat atctgctgga aagaagctt agtgaagaca tagaggtacc agaatggctg     9840
ggatctgaaa aacctatgtt tttggatgta accaaaagtg gtgaaacata ccatctgtta    9900
ggggatctaa atcacttgaa ggcacaagcg gaacaacttg gtgccaaggc aaccactaca    9960
ataaataaag tagggaagac gtatacaatg aacctcagta catggtggga gagtgaaaga  10020
acccccacat tcagaccct gttccaggaa ctgctgttac gctgcaggcc atgcactagg   10080
gaggagtata agagctgcca ttttgtaggg gctacacaat tggccggagg aaactggaaa   10140
ccagtagccc ctgtggtgca cctaggaact ataccagcaa aaagagagaa atgcctgcca   10200
tatgaagcat atatatcact taagaatatg gtggaaaacc taaaaataga gaatcctgga   10260
gtgtgcaaga agaaacatca gtggctctta aataaaatta aaaacaagg ggaattaggc    10320
ttgaagaatc tcgtatctcc tgggagtgta ggggatcac gtggttacag aaagaaagaa   10380
ttcaacattt acaacaaaca gattacgagc acaatgctgg ctgtggggat caagccagag   10440
aagtttccag tcgtcagagc tcaaacgtcc aagagagaat tccatcaagc aattagagag   10500
aagattgata agctgcccaa cccccagaat agggacctcc ataaggaact gaaagaaata   10560
tttgactcgg tgtgcgctgt aaaagatttg aaacatacct acgaagaagt cagctgggat   10620
gtactgacgg tgggatcaa caggaaagga gcagctggcc attcgaaaa gaagaatgtg     10680
ggtgagataa tagacactga caggagaggg gtcgagaaac ttatcaaggt aatgaaaacc   10740
gggggaccta tagactacta tgagacagca ataccaaga atgagaagag agcagttgta    10800
gatgactggc tggaaggaga tttcgttgaa gagaaaagc cacgagtgat ccaataccca   10860
gaagcaaaaa tgcgtttggc aataaccaaa gttatgtaca attgggtcaa gcaaaaacca   10920
gtggtgatac ccgggtacga ggggaagaca cctttgttta aagtgtttga taggttttt    10980
gatgaatgga acaactgag agaccccggtt gcagtcagtt tcgacactaa agcatgggat   11040
acacaagtga cacctgagga cttacaattg atatcggaaa tccaaaagta ttactttaaa   11100
ccaaaatacc acaaatttat tgaaacattg actgcggaga tgaaagaagt gccagtcgtg   11160
tgccaggatg gggaggttta catcaggcta ggacagagag aagtggcca gccagatacc    11220
agtgcaggaa atagcatgtt gaatgtgttg acaatgatat atgcttttg caaatccaat    11280
gacatcccgt acaaggcatt ccgaaggggtg caaaaatac acgtctgtgg cgacgatggg   11340
ttcctaatta cagagaggcg cctaggagag aactttgctg cgatggggcc acaaatactg   11400
atggaagccg ggaaaccaca gaaactggta ggagagatgg gactgaagct agcctacaag   11460
ttccaggaca tagagttctg ctcccacacg cctatacaag taaggtggga tgacaacaca   11520
actagttatt taccaggcag agacacggca accatcttag caaagatgtg taccaggctg   11580
```

```
gactccgcag gggagcgggg taccagttcc tatgaacttg ctgttgtgtt tagtttcctc 11640
ctaatgtact cctggaaccc aatagttaga aggatctgcc tattagttat ggcaacaatc 11700
ggagtaaaag acccagataa atcaggaaca atattcacct tctctggaga cccactaggg 11760
gcgtacaagg aagtaatagg acaccgattg ggccaactaa aacaaactga attttcaaaa 11820
ttggcaagtt gcaatttatc aatgtcactg ttagggattt acagtaggca cacctcaaaa 11880
agaatcatag aggactgtgt gaagattgga accctaaacc gacagagccc cgtgaatgca 11940
gatcgcttga tagcaaagaa gactggtttt gtatacgaac cgtcaagggg cagtgttagg 12000
gtgggaaaac actatgaaga attggaattg gacaaatgga aaaagaagac gccactcata 12060
gaaggggcgg aaaggtacat tccaggcccg attaagacct ttatactgaa aagactcaaa 12120
gtgttacaga tgataggcct gaaattcttc taatatatag ggagtacagg ttacagctgt 12180
gtttcacaga aagtgggtgg cgacacttac ctctggagcc aacttgtaaa taggttagta 12240
atatttattt aatagacgtt atttacttat ttatttattt atttgattat ttattaatta 12300
tttaaaaacg ctactgcatg agctggttag tcagcttatg aaagtgggtt gtgtcacttg 12360
cgtcaggagc aaatacctca ataacaacgc taccacatag cctgagacca ggttgtgaaa 12420
gagagttgcg cctcttgcgt tgggagctat ctacctcaag tacccagctg ctgaagctgg 12480
ttacctcaat tccaatggat gaccgtagcc attggtctta ttaattcggt catttataat 12540
tagcacttta aagctaattg ggacataaag taaggacgtc ctagggagga ctacttacag 12600
ttccaagagg cccc 12614

<210> SEQ ID NO 2
<211> LENGTH: 12614
<212> TYPE: RNA
<213> ORGANISM: Porcine pestivirus
<400> SEQUENCE: 2
guauagcagc aguagcucaa ggcugcuaua cgauuggaca uaccaaauuc caauuggugu 60
uagggaccac cuaggugaag gccgacgaca gguagccauu ccuguuagua ggacgaaccg 120
uuauggugga cugguugcuc aggugagcag gcugcaaugc guaaguggug aguacaccac 180
agccgucaaa ggugccacug guaaggauca cccacuggcg augccuugug gacgggggcg 240
ugcccaacgc aauguuagcg guggcggggg cugccaucgu gaaagcuagg ucuugaugga 300
ccuuguugcc uguacagucu gauaggaugc cggcggaugc ccugugacag ccaguauaaa 360
gaauauccgu ugugauugca cauggaguuu aaaauucuca acaacacaaa gaaaaaaaau 420
aauaaugagg aggaagcuga ggggaacaug uucuggcgga uguaccgaag accuccgccu 480
gguugcuacg aaccaacuua caaccuaagu gggacaccua gcuucggacc caugcaccca 540
ccacugagga aagggaguac auuacguuua ccccacugga gaggcauagc cacgguugga 600
ugugagcuua aaaaccugcc acgcaagggu gauuguacua agugccacgc uaacccaaca 660
ucuggcaucu accucaaccu gggugcggug uuuuauaaag auuacgaggg ggagguauac 720
cauagagucc ccuugaaca cugugaggaa cagcagaggu gcgaagucgu caagcgugua 780
gggagaauga cugcuagcga uggauccuug gugggagugc uaguaugcag ugacgacugc 840
gugcuguuug agagaagaag aggggaacac acaguguuga agugggguaaa gaacccuauc 900
ggggcgccac ucuggguaca gagcugcucc gacgagaagg gggccaaacc aaaaaaacaag 960
ucuaaacaac aaaacgaucg aauggcaccg gguaaaaugg ugacaaaacc uaaggaagug 1020
```

-continued

```
gaagcugauc agaaaacuag accgccagac gcuacaauug ugguggaugg acagaaauau    1080
caaguaagga agaaagggaa ggcaaaacca aagacaccag auggccugua ccacaauaaa    1140
aacaagccgg aggcaucuag aaagaaauua gaaaaagcgc acuagcuug ggcagucauu     1200
gcaauaauau ugauucagca gaccacagca aacaauguga cgcaguggaa cuuguggggac   1260
gacaagaacg caacagaugu gcacucagug augcaucaga gacaaaucaa gcgcagccuc   1320
cacggcaucu ggccugaaag aaucugcaaa gggucccag gucaucuggc uacgacuau    1380
gagcuaaaac ggauagaggg gauguuggau gccagcgaaa aaacuaauuu uaccuguugc   1440
aggcugcaaa gacacgaaug gaacaaacau ggcuggugua acugguacaa uauagacccc   1500
ugggucgcca uuaugaacag gacccaagcc cuucuaucua guggccaaaa cuuuacagag   1560
ugugccguua cauguaggua ugacacagaa cagcagauaa acauaguaac ucaagcccgc   1620
augacaccaa cgauuuuaac aggguguaag aaggacguaa acuucucuuu cucaggggag   1680
gugaggacug ggccuugcaa cuaugaacug aagccagaag acuuaaugag gauucuggac   1740
cauaccaacu gcaaagauuu cagcuauuuc ggagaagguc ugguggauga uuucacagaa   1800
gccacggaaa aaauuagauc uagugggac agggcccugu cguggcugca agacaagcua   1860
gagaaaacua agaagaaggu guuuggagcu gaagcaacac cauacugcaa ugugacaagg   1920
agggauuuca caucauaua caccaacaac ugcacccccg cuggacugcc agauaacacg   1980
aggauaguug ggccagggac auuugacauc agugaaaugg aaaauaaaaa acuguuaccc   2040
aacuuggacu accacuuggc agauuucaug guacugggcu uaguggcuuu auccgacuuu   2100
gccccagaaa cugcuaguac aaucuaucug guauugcacu acuggcugcc ucaggcagag   2160
gugcauacau uggacacccc acuugacacc aacaagcuga aucuaacaag gaacaggcag   2220
guuaguagug uagucccuaa uucaauaugg ugggagggc agcuggugug cgucaagcca   2280
aggugguggc ccuacucagc agaaauuaca acagugauua gcggacugac cacuguaacc   2340
gaccuagugu ucaagaccau agaggaacuu gugagcuugu ggacagaggc aacagcagua   2400
gccuucuugg cagcccugau aaagaucuuc agaggacaac caauacaagc acuagcaugg   2460
cucauaauaa uaggggagc ccagggucuu gaaugcaacu cgaacugca auacgcucug   2520
gccgggaaca cauccaugag ccuacuaggg ccaacugccu uaagacuca augguaccaa   2580
gcggcagacg ggucaaaaau aacggauggg uaguaacug ugauaugcaa caagggcauu   2640
uucucgguga cuccuaggug caaagaggca ccuguaaggu accuggcaau caaccacccc   2700
aggucсcuuau caaccagugc uugguucaag aaaauacacg acccggcaga ccauccgacu   2760
gagacacuga uggggcgaaaa gggaagggca uaccucugcc cuugcggggc uacaccacua   2820
ccaaaaccca agguuccguu uaacccaauc acaauacaag guucggcguu uccccuaaca   2880
ugcccaaaaa acuggcaagg ugacauagaa ugcaaucucu aagcccaga cacacuagca   2940
auugaaacca uauacaccuu cagaaaacau aagccauaca aagaagaacc cuacugcucg   3000
uacacuaagg uaguggacgg guacuugcgc aacgugcacc uauggggca ugauacaugu   3060
guggcaggag auauaaucaa uggcagucaa gaugacagug ugaccaagug caauggugu    3120
ggguaugagu ucaauucagc aacgacuua ccugacuacc caauugguua cugcacgaag   3180
cgaggcacca uuaucuaau cagguacaag caggugccuu gugagguagg aggagцccgc   3240
aucgggucag gaaaaguaga guguaccau ggcuccacga gaguaaaagu agaacaaacc   3300
aguaaugagu uggguccgau gcccugcaag ccaauaguau auucaucuca aggaccgccu   3360
aauccaaaaa cguguacauu caaauggagc uacacauuaa acaacaagua cuacgagcca   3420
```

```
aggaaugaau ucuuccaaca guacauaacc ucagguggcu aucaguauug guuugaccug    3480
acagcaaaag aucacgugau ggauugggua acacgauacu uccccauuau aguuguagca    3540 uuacugggg guagagcagu gcuguggauc cuaauugcgu acgaguugcu aaaucacuac    3600
caagugggcg cagaccagaa cacauugcug caggccgaag cacuagugau agguaacauc    3660
cugaugacaa agaccugga agugauggug ugcuuucugu ugcugauggu cuugauaaga    3720
agacagcagg cuagaagggc uuuggccuug guuuuccauu ggaugguaau gcaucccgcc    3780
caaucagcca ucgcaacauu ggguacgua auaggcaucg ugagagcuga agagggacag    3840
guuaacucug acaguucuac gcaagcacac gugguggcca uuuuguuguu ucuaauuuac    3900
cacacacuaa aagaaaggga ccuucacaca gcaugacau acuguugac auuuuccaua    3960 aagagcacug acuauguaga cacacauuau uaugaaauac cgaugcucuu cacaguauuu    4020
ucguuggcua uuccauuua cauauucaac auacacauaa aaaccaagug gguagcucug    4080
gugcucagua uggugggcau ggucaccuuu auaaggugcc uuugguugau caggaacaua    4140
caaauaacac cccccuuccau accacuaaca uacaucaguc caaaauauau gaucauagcu    4200
uaccugguuu cucugacugu cuuggugaau aacaaccuag accucgccag cuacgugauc    4260
agggcuggcc cgauacuaau guccuacuua acuuuauggg uggacauccu gauguugcua    4320
guucuacuac cuugguauga auugauuaaa gucuauuacc uaagaagaa gaaagacgac    4380 auagaagacu gcuuccaaua cagcgggaua gccacucaag gguaucccc guacaaucag    4440 gacuucgugg acccaaaaga gggguacac uugauccccu cacaaaacaa gagcaauuuc    4500
acccggaccg cauaucugac uauccugagg gcccaguuc ucacagcuuu cagcagcauu    4560
uggaagccuc uaauccuagc cgaacugcua uuggaaucca uuuauuggac acacaucaaa    4620
guugcaaaag aaguggcggg aucacgagg cuuauaggua gguuguagc ggcccugaua    4680 gaacuaaauu gggguuuuga ugacaaggaa gcagcaagau acaaaaauu cuuuguuuua    4740 accucaagag ugagagaccu caugguaaaa cacaaggugc agaacgacac aaugaggcag    4800
ugguuugaag agacggaaau auuccggcuua caaaaguug ccuuggugu cagagcacac    4860 ucacugacag cagacagcaa caguauacua ugcucagugu gugaggaaaa acagaacaua    4920
gaagccaaga ggguaugucc caagugugga aacagaggaa caggaaucaa gugcgggaug    4980 accuggcug aguugaaga aaaauauuac aaaaagaucu aucagugga uggagacaau    5040 acgcaagcau aucgcagaga ggagagagga gaagucacgu acacagcuag gggcgccuuc    5100
uucuugagga acuuacccau ucuggccaca aaaaacaagu auaucuggu agguaacuua    5160 gguauggaau uacaagaccu ugagccaug gggguggauua caggggccc agcugucugc    5220 aaaaagauag ugcaccauga acgcugcagg cccaccaucc cugauaaacu uauggcuuuc    5280
uuugggcuca ugccaagagg cguaguccc cgggccaa cccgcuuccc uguaucauua    5340
cugaaaauua aaggggguuu cgaaacgggu ugggcauaua cacacccugg agggaucagc    5400
agcguaaugc auguaacagc aggcuuggac auguacguca augaugccau ggguagaacc    5460
aaggugcagu gccaagagag aaacaagcug acagacgaau gugaguaugg cauuaaaacu    5520
gacucaggcu gcucugaagg ggcacgcugc uauguaauaa ucccgaagc cgucaacaua    5580 gcaggcacca ggggcgcuau gguacaccuc agaaaaacag guccagaauu uaccugugug    5640
acagcccaag gaacccagc cuucuacaau uugaggaauc uuaaagguug gucagggcua    5700
ccaauauucg aggcagcuac gggaagggug guaggcagag ugaaagcagg caagaaugca    5760
```

```
gaggauaguc caacaacuau aaugucuggc acccaggcag ccaaaccgac agagugugac    5820
cuggagucgg ucguaaggaa gcuggaaacc augaacagag gggaguucaa gcagguggug    5880
cuagcaacug gggcagggaa gacaacagaa cugccaagga agcuaauaga agccgugggg    5940
cggcacaaga ggguuuuagu ccuaauccccc cugagagcag cagcagaggg gguuuauaac    6000
uauaugagaa caaagcaucc aagcauagca uucaaccuga ggauagggga cuuaaaagaa    6060
ggagacaugg caacugguau aacuuaugcc ucauaugguu auuuuuguca aauggacaug    6120
ccacggcuag augcagcuau gaaggaguac aacuacauau uccuggacga auaucauugu    6180
gcaacaccag agcaauuggc ugugaugauca aaaauacaca ggaucagugc ugaccuaaga    6240
gugguggcca ugacagcuac cccugcaggc gcugugucaa agguggccca gaaauucucc    6300
auagaagaag uggguggugcc agagguaaug aaaggggaag accuaggcga ggauuauuug    6360
gacauagccg gacuaaaaau accaaaaucg gaacuacaag ggaaugucuu aacguuuguu    6420
ccgacaaaaa aguuggcguc agacacugcu aagaaacuaa ccacccaggg cuacaacgcu    6480
ggguauuacu uuagugguga agacccaagc ucgcugcgca ccauaacauc aaaauccccg    6540
uacaucauaa uagccaccaa ugcaauagag ucagggguga cauuaccaga ccuagacaca    6600
guaauugaca cagggaugaa gugugaaaag agggugagaa uagagaacaa ggcuccauac    6660
auaauaacag gccuaaaaag aauggccauc accacagggg agcaagccca gaggaaggga    6720
agaguaggua gagucaaacc agggagauac cuaagagggc cugaaaaugc aggugga gag    6780 agagauuauc acuaugaccu gcugcaggca caacguuaug ggcuccagga ugcuaucaac    6840
aucaccaaau cauucaggga gaugaacuau gacugggcac ucuauaagga agacccacug    6900
agaauaacac aauuggaggu auuaaauacc cuacucauau ccaaagaucu gccaacaguc    6960
acaaagaauu ugaugaccag gaccacacac ccagaaccaa ucaauuagc uuacaauagc    7020 auagaacccc ccgucccagu gcuguucccg aaagugaagg uggagagggu gaccgaugcu    7080
uaugagaccu augaacugau gaugugucgg aagcuggaua cgacccccc gauuuaucug    7140 uaugccacgg aagaugaaga ccuagcagug gaccuccuga ccugaaaaug gcccgcagug    7200
ucaacagccu cggccauaga aacagaggac gcccucaaca aguuaucggg gcuuucggca    7260
ggggaaacag cccugcuagu ggcucugcua gguugggucg guuacgaggc ucuggugaaa    7320
agacacauac caauagugac ugacauauau acaauugaag augaaaaacu ugaggacacc    7380
acccaccucc aguauucacc agaugaacug caaaacaccg agacagugga gcugaaagac    7440
cugucggcac acgaacugaa agaagcccug gaaagcggaa aaguuaugu caaagacgcc    7500 uuugaauucg uaaaaucaca gguugagaag cuccccgaca caaaaauuua caagcaaguc    7560
caagagaagu cacccggucu uuuagaaaaa uuuuuggccu aucugucaga acacaguagu    7620
gacauaaaga aauaugguga uggggggguc cauaccucuc uguacaauag uaucaaagag    7680
agauuggggc acgaaacugc cuucgcuuca uugaucauca guggauagc auuuccagc    7740 gaagggcugc cuggaauggu gaaacaagcu gcuagacu uggugguaua uuaucugauc    7800
aacaaaccag auuucaaagg ugacaaagac acccaagaug auggaaggaa guucgu agga    7860 gcccuguucg ugcagcucu ggccaauuac acauuuaaaa auuuuaauaa gucaacacuu    7920
gaaggcuuag uaaugccagc auugaacuac cuaccauaug caggggcugc acuaaaaaua    7980
uuugugccua cuaaauuaga gagcuuagua uacugucaa caaccaucua caggaccuac    8040
cucuccauua gaaaggcuc uagucaagga cuggcuggau uagcagugag cucagguaug    8100
gaaauuauga aucagaaucc aauaucagug gccauugcgg uggcauuggg agucggugcc    8160
```

-continued

```
auagcugcac acaaugcgau cgagagcagc gaggcaaaga ggacccuguu gaugaaggua    8220
uuugugaaaa acuuucuaga ccaggcagcg acagacgagu ugguaaaaga gaacccagaa    8280
aaaauaauaa uggcaguauu ugaagcaauc cagacagcag guaaccaau aaggcuaaua    8340
uaccaccuau augccauguu cuacaaaggu uggaacgccu cccagauagc agauaagaca    8400
gcggggagga acauauucgu gcugacaaua uucgaggguu uagaacuguu gggacuagac    8460
aaggauucca aguggaggga uuugagcuca aauuauuuag uggaugcaau caggaagcuc    8520
auugaaaaau ugacuaaaau acucagaaac accaccaagu cauuaaucaa auccuugcug    8580
ccagcuccau ucucuugcac gagauucaca agagacaaca gaauuggaug gccacauuua    8640
aauuuugauu auuacgagau aaauugugca gugggauacc ggaggagagu gguaaaaacu    8700
gucaucgacc cagucaccug ggagacuuug gaagaagaag gcccugaguu cugcuucaac    8760
aggggacua acgcccuggc aaacccaaga guugcaaguu auuacucagc uggagagcca    8820
guucucccag ugguaaaaag agaggggguu ggcgaaauuc ugguaagggg ggugacaauc    8880
cagaugcauu augaccacaa caagauacuc gccacugaca acuggcaagu gccauuccag    8940
gcagugacga agauauuuac agauuaccag ggcauagggu accaagaagc auaucuggga    9000
acccagccaa acuacaaagc acuggugaag aggucauccg ucacgauuac aaaagaaggc    9060
cugaaauuua uaagaugcaa gaaagggauc gcguauacga ccaaucuaaa cuuaacccac    9120
auccaaaagc ugguugcaggu gugcagaaug aaugaauugc aagaaggcgu cauaccugag    9180
accuuggaug gcgacaccug gauuaacuac auggcaauca ucgaagaugu gggggccaca    9240
aaaccaagcu uggagagaga gucauacccg aaaccauacg aggaggaucc ccucgaaggc    9300
cccaguguga ucguggaaac aggggacgug gacaucacaa aguggggcgu aaaucaacaa    9360
uccaguucau caggaaccgu cuuucaagua guggagaaga ucuauacuaa acuggucaau    9420
acaaauguaa uaaagauagg auucaaagaa ggcuguuucc cgggacccac aaagaaugug    9480
aauucauuga augagcacau agaagauaaa gacaguaaac cauacaucuu cauaugcucu    9540
uccgacaaag caauguccaa cagaguaaag acugcaagga acauuaagaa acucaacaca    9600
aauucggcaa uaguagcccg uaauuuggcc agggaaggga aauugaucau aauaguacua    9660
ggagagaagu accaugagga caucuacaaa caugcugacu ucaaggggac uuuccucgac    9720
aggaaggcac uggaagcccu guccaaggcc aagccguaa aaagaacau dacuaggaga    9780
gaggcucaau aucugcugga aaagaagcuu agugaagaca uagagguacc agaauggcug    9840
ggaucugaaa aaccuauguu uuggauguu accaaaagug gugaaacaua ccaucuguua    9900
ggggaucuaa aucacuugaa ggcacaagcg gaacaacuug ugccaaggc aaccacuaca    9960
auaaauaaag uagggaagac guauacaaug aaccucagua caugguggga gagugaaaga    10020
acccccacau ucagaccccu guuccaggaa cugcuguuac gcugcaggcc augcacuagg    10080
gaggaguaua uagagcugcca uuuuguaggg gcuacacaau uggccggagg aaacuggaaa    10140
ccaguagccc cuguggugca ccuaggaacu auaccagcaa aagagagaa augccugcca    10200
uaugaagcau auauaucacu uaagaauaug guggaaaacc uaaaaauaga gaauccugga    10260
gugugcaaga agaaacauca guggcucuua aauaaaauua aaaacaagg ggaauuaggc    10320
uugaagaauc ucguaucucc ugggagugua ggggaucac guggauacag aaagaaagaa    10380
uucaacauuu acaacaaaca gauuacgagc acaaugcugg cuguggggau caagccagag    10440
aaguuuccag ucgucagagc ucaaacgucc aagagagaau uccaucaagc aauuagagag    10500
```

```
aagauugaua agcugcccaa cccccagaau agggaccucc auaaggaacu gaaagaaaua    10560
uuugacucgg ugugcgcugu aaaagauuug aaacauaccu acgaagaagu cagcugggau    10620
guacugacgg uggggaucaa caggaaagga gcagcuggcu auuucgaaaa gaagaaugug    10680
ggugagauaa uagacacuga caggagaggg gucgagaaac uuaucaaggu aaugaaaacc    10740
gggggaccua uagacuacua ugagacagca auaccuaaga augagaagag agcaguugua    10800
gaugacuggc uggaaggaga uuucguugaa gagaaaaagc cacgagugau ccaauaccca    10860
gaagcaaaaa ugcguuuggc aauaaccaaa guuauguaca auugggucaa gcaaaaacca    10920
guggugauac ccggguacga ggggaagaca ccuuuguuua aguguuuga uaagguuuuu     10980 gaugaaugga acaacugag agacccgguu gcagucaguu cgacacuaa agcaugggau      11040 acacaaguga caccugagga cuuacaauug auaucgaaa uccaaaagua uuacuuuaaa     11100
ccaaaauacc acaaauuuau ugaaacauug acugcggaga ugaaagaagu gccagucgug    11160
ugccaggaug gggaguuuua caucaggcua ggacagagag gaaguggcca gccagauacc    11220
agugcaggaa auagcauguu gaaugucuug acaaugauau augcuuuuug caaauccaau    11280
gacaucccgu acaaggcauu ccgaaggguug caaaaauac acgucugug cgacgauggg     11340 uuccuaauua cagagaggcg ccuaggagag aacuuugcug cgauggggcc acaaauacug    11400
auggaagccg ggaaaccaca gaaacuggua ggagagaugg gacugaagcu agccuacaag    11460
uuccaggaca uagaguucug cucccacacg ccuauacaag uaagguggga ugacaacaca    11520
acuaguuauu uaccaggcag agacacggca accaucuuag caaagaugug uaccaggcug    11580
gacuccgcag gggagcgggg uaccaguucc uaugaacuug cuguugucuu uaguuccuc     11640 cuaauguacu ccuggaaccc aauaguuaga aggaucugcc uauuaguuau ggcaacaauc    11700
ggaguaaaag acccagauaa aucaggaaca auauuccccu ucucuggaga cccacuaggg    11760
gcguacaagg aaguaauagg acaccgauug ggccaacuaa aacaaacuga auuuucaaaa    11820
uuggcaaguu gcaauuuauc aaugucacug uuagggauuu acaguaggca caccucaaaa    11880
agaaucauag aggacugugu gaagauugga acccuaaacc gacagagccc cgugaaugca    11940
gaucgcuuga uagcaaagaa gacuggguuuu guauacgaac cgucaagggg caguguuagg    12000
gugggaaaac acuaugaaga auuggaauug gacaaaugga aaagaagac gccacucaua     12060 gaaggggcgg aaagguacau uccaggcccg auuaagaccu uuauacugaa aagacucaaa    12120
uguuuacaga ugauaggccu gaaauucuuc uaauauauag ggaguacagg uuacagcugu    12180
guuucacaga aagugggugg cgacacuuac cucuggagcc aacuuguaaa uagguuagua    12240
auauuuauuu aauagacguu auuuacuuau uauuuauuu auuugauuau uuauuaauua     12300
uuuaaaaacg cuacugcaug agcugguuga ucagcuaug aaagugggu guugcacuug      12360 cgucaggagc aaauaccuca auaacaacgc uaccacauag ccugagacca gguugugaaa    12420
gagaguugcg ccucuugcgu ugggagcuau cuaccucaag uacccagcug cugaagcugg    12480
uuaccucaau uccaauggau gaccguagcc auuggucuua uuaauucggu cauuuauaau    12540
uagcacuuua aagcuaauug ggacauaaag uaaggacguc cuagggagga cuacuuacag    12600
uuccaagagg cccc                                                    12614
```

<210> SEQ ID NO 3
<211> LENGTH: 3923
<212> TYPE: PRT
<213> ORGANISM: Porcine pestivirus

<400> SEQUENCE: 3

```
Met Glu Phe Lys Ile Leu Asn Asn Thr Lys Lys Asn Asn Asn Glu
1               5                   10                  15

Glu Glu Ala Glu Gly Asn Met Phe Trp Arg Met Tyr Arg Pro Pro
            20                  25                  30

Pro Gly Cys Tyr Glu Pro Thr Tyr Asn Leu Ser Gly Thr Pro Ser Phe
        35                  40                  45

Gly Pro Met His Pro Pro Leu Arg Lys Gly Ser Thr Leu Arg Leu Pro
    50                  55                  60

His Trp Arg Gly Ile Ala Thr Val Gly Cys Glu Leu Lys Asn Leu Pro
65                  70                  75                  80

Arg Lys Gly Asp Cys Thr Lys Cys His Ala Asn Pro Thr Ser Gly Ile
                85                  90                  95

Tyr Leu Asn Leu Gly Ala Val Phe Tyr Lys Asp Tyr Glu Gly Glu Val
            100                 105                 110

Tyr His Arg Val Pro Leu Glu His Cys Glu Glu Gln Gln Arg Cys Glu
    115                 120                 125

Val Val Lys Arg Val Gly Arg Met Thr Ala Ser Asp Gly Ser Leu Val
    130                 135                 140

Gly Val Leu Val Cys Ser Asp Asp Cys Val Leu Phe Glu Arg Arg
145                 150                 155                 160

Gly Glu His Thr Val Leu Lys Trp Val Lys Asn Pro Ile Gly Ala Pro
                165                 170                 175

Leu Trp Val Gln Ser Cys Ser Asp Glu Lys Gly Ala Lys Pro Lys Asn
            180                 185                 190

Lys Ser Lys Gln Gln Asn Asp Arg Met Ala Pro Gly Lys Met Val Thr
        195                 200                 205

Lys Pro Lys Glu Val Glu Ala Asp Gln Lys Thr Arg Pro Pro Asp Ala
    210                 215                 220

Thr Ile Val Val Asp Gly Gln Lys Tyr Gln Val Arg Lys Lys Gly Lys
225                 230                 235                 240

Ala Lys Pro Lys Thr Pro Asp Gly Leu Tyr His Asn Lys Asn Lys Pro
                245                 250                 255

Glu Ala Ser Arg Lys Lys Leu Glu Lys Ala Leu Leu Ala Trp Ala Val
            260                 265                 270

Ile Ala Ile Ile Leu Ile Gln Gln Thr Thr Ala Asn Asn Val Thr Gln
        275                 280                 285

Trp Asn Leu Trp Asp Asp Lys Asn Ala Thr Asp Val His Ser Val Met
    290                 295                 300

His Gln Arg Gln Ile Lys Arg Ser Leu His Gly Ile Trp Pro Glu Arg
305                 310                 315                 320

Ile Cys Lys Gly Val Pro Gly His Leu Ala Thr Asp Tyr Glu Leu Lys
                325                 330                 335

Arg Ile Glu Gly Met Leu Asp Ala Ser Glu Lys Thr Asn Phe Thr Cys
            340                 345                 350

Cys Arg Leu Gln Arg His Glu Trp Asn Lys His Gly Trp Cys Asn Trp
        355                 360                 365

Tyr Asn Ile Asp Pro Trp Val Ala Ile Met Asn Arg Thr Gln Ala Leu
    370                 375                 380

Leu Ser Ser Gly Gln Asn Phe Thr Glu Cys Ala Val Thr Cys Arg Tyr
385                 390                 395                 400

Asp Thr Glu Gln Gln Ile Asn Ile Val Thr Gln Ala Arg Met Thr Pro
                405                 410                 415
```

```
Thr Ile Leu Thr Gly Cys Lys Lys Asp Val Asn Phe Ser Phe Ser Gly
            420                 425                 430

Glu Val Arg Thr Gly Pro Cys Asn Tyr Glu Leu Lys Pro Glu Asp Leu
435                 440                 445

Met Arg Ile Leu Asp His Thr Asn Cys Lys Asp Phe Ser Tyr Phe Gly
    450                 455                 460

Glu Gly Leu Val Asp Asp Phe Thr Glu Ala Thr Glu Lys Ile Arg Ser
465                 470                 475                 480

Ser Gly Tyr Arg Ala Leu Ser Trp Leu Gln Asp Lys Leu Glu Lys Thr
                485                 490                 495

Lys Lys Lys Val Phe Gly Ala Glu Ala Thr Pro Tyr Cys Asn Val Thr
            500                 505                 510

Arg Arg Val Phe Asn Ile Ile Tyr Thr Asn Asn Cys Thr Pro Ala Gly
            515                 520                 525

Leu Pro Asp Asn Thr Arg Ile Val Gly Pro Gly Thr Phe Asp Ile Ser
        530                 535                 540

Glu Met Glu Asn Lys Lys Leu Leu Pro Asn Leu Asp Tyr His Leu Ala
545                 550                 555                 560

Asp Phe Met Val Leu Gly Leu Val Ala Leu Ser Asp Phe Ala Pro Glu
                565                 570                 575

Thr Ala Ser Thr Ile Tyr Leu Val Leu His Tyr Trp Leu Pro Gln Ala
            580                 585                 590

Glu Val His Thr Leu Asp Thr Pro Leu Asp Thr Asn Lys Leu Asn Leu
            595                 600                 605

Thr Arg Asn Arg Gln Val Ser Ser Val Pro Asn Ser Ile Trp Leu
610                 615                 620

Gly Gly Gln Leu Val Cys Val Lys Pro Arg Trp Trp Pro Tyr Ser Ala
625                 630                 635                 640

Glu Ile Thr Thr Val Ile Ser Gly Leu Thr Thr Val Thr Asp Leu Val
            645                 650                 655

Val Lys Thr Ile Glu Glu Leu Val Ser Leu Trp Thr Glu Ala Thr Ala
            660                 665                 670

Val Ala Phe Leu Ala Ala Leu Ile Lys Ile Phe Arg Gly Gln Pro Ile
        675                 680                 685

Gln Ala Leu Ala Trp Leu Ile Ile Gly Gly Ala Gln Gly Leu Glu
    690                 695                 700

Cys Asn Phe Glu Leu Gln Tyr Ala Leu Ala Gly Asn Thr Ser Met Ser
705                 710                 715                 720

Leu Leu Gly Pro Thr Ala Leu Lys Thr Gln Trp Tyr Gln Ala Ala Asp
                725                 730                 735

Gly Val Lys Ile Thr Asp Gly Val Val Thr Val Ile Cys Asn Lys Gly
            740                 745                 750

Ile Phe Ser Val Thr Pro Arg Cys Lys Glu Ala Pro Val Arg Tyr Leu
        755                 760                 765

Ala Ile Asn His Pro Arg Ser Leu Ser Thr Ser Ala Trp Phe Lys Lys
        770                 775                 780

Ile His Asp Pro Ala Asp His Pro Thr Glu Thr Leu Met Gly Glu Lys
785                 790                 795                 800

Gly Arg Ala Tyr Leu Cys Pro Cys Gly Ala Thr Pro Leu Pro Lys Pro
                805                 810                 815

Lys Val Pro Phe Asn Pro Ile Thr Ile Gln Gly Ser Ala Phe Ser Leu
            820                 825                 830

Thr Cys Pro Lys Asn Trp Gln Gly Asp Ile Glu Cys Asn Leu Leu Ser
```

-continued

```
                835                 840                 845
Pro Asp Thr Leu Ala Ile Glu Thr Ile Tyr Thr Phe Arg Lys His Lys
    850                 855                 860
Pro Tyr Lys Glu Glu Pro Tyr Cys Ser Tyr Thr Lys Val Val Asp Gly
865                 870                 875                 880
Tyr Leu Arg Asn Val His Leu Trp Gly His Asp Thr Cys Val Ala Gly
                885                 890                 895
Asp Ile Ile Asn Gly Ser Gln Asp Asp Ser Val Thr Lys Cys Lys Trp
            900                 905                 910
Cys Gly Tyr Glu Phe Asn Ser Ala Thr Asp Leu Pro Asp Tyr Pro Ile
            915                 920                 925
Gly Tyr Cys Thr Lys Arg Gly Thr Asn Tyr Leu Ile Arg Tyr Lys Gln
        930                 935                 940
Val Pro Cys Glu Val Gly Gly Val Arg Ile Gly Ser Gly Lys Val Glu
945                 950                 955                 960
Cys Thr Ile Gly Ser Thr Arg Val Lys Val Glu Gln Thr Ser Asn Glu
                965                 970                 975
Leu Gly Pro Met Pro Cys Lys Pro Ile Val Tyr Ser Ser Gln Gly Pro
            980                 985                 990
Pro Asn Pro Lys Thr Cys Thr Phe Lys Trp Ser Tyr Thr Leu Asn Asn
            995                 1000                1005
Lys Tyr Tyr Glu Pro Arg Asp Glu Phe Phe Gln Gln Tyr Ile Thr
    1010                1015                1020
Ser Gly Gly Tyr Gln Tyr Trp Phe Asp Leu Thr Ala Lys Asp His
    1025                1030                1035
Val Met Asp Trp Val Thr Arg Tyr Phe Pro Ile Ile Val Val Ala
    1040                1045                1050
Leu Leu Gly Gly Arg Ala Val Leu Trp Ile Leu Ile Ala Tyr Glu
    1055                1060                1065
Leu Leu Asn His Tyr Gln Val Gly Ala Asp Gln Asn Thr Leu Leu
    1070                1075                1080
Gln Ala Glu Ala Leu Val Ile Gly Asn Ile Leu Met Thr Arg Asp
    1085                1090                1095
Leu Glu Val Met Val Cys Phe Leu Leu Leu Met Val Leu Ile Arg
    1100                1105                1110
Arg Gln Gln Ala Arg Arg Ala Leu Ala Leu Val Phe His Trp Met
    1115                1120                1125
Val Met His Pro Ala Gln Ser Ala Ile Ala Thr Leu Val Tyr Val
    1130                1135                1140
Ile Gly Ile Val Arg Ala Glu Glu Gly Gln Val Asn Ser Asp Ser
    1145                1150                1155
Ser Thr Gln Ala His Val Val Ala Ile Leu Leu Phe Leu Ile Tyr
    1160                1165                1170
His Thr Leu Lys Glu Arg Asp Leu His Thr Ala Met Thr Leu Leu
    1175                1180                1185
Leu Thr Phe Ser Ile Lys Ser Thr Asp Tyr Val Asp Thr His Tyr
    1190                1195                1200
Tyr Glu Ile Pro Met Leu Phe Thr Val Ile Ser Leu Val Ile Ser
    1205                1210                1215
Ile Tyr Ile Phe Asn Ile His Ile Lys Thr Lys Trp Val Ala Leu
    1220                1225                1230
Val Leu Ser Met Val Gly Met Val Thr Phe Ile Arg Cys Leu Trp
    1235                1240                1245
```

```
Leu Ile Arg Asn Ile Gln Ile Thr Pro Pro Ser Ile Pro Leu Thr
    1250                1255                1260

Tyr Ile Ser Pro Lys Ile Leu Ile Ile Ala Tyr Leu Val Ser Leu
    1265                1270                1275

Thr Val Leu Val Asn Asn Asn Leu Asp Leu Ala Ser Tyr Val Ile
    1280                1285                1290

Arg Ala Gly Pro Ile Leu Met Ser Tyr Leu Thr Leu Trp Val Asp
    1295                1300                1305

Ile Leu Met Leu Leu Val Leu Leu Pro Trp Tyr Glu Leu Ile Lys
    1310                1315                1320

Val Tyr Tyr Leu Lys Lys Lys Asp Asp Ile Glu Asp Cys Phe
    1325                1330                1335

Gln Tyr Ser Gly Ile Ala Thr Gln Gly Leu Ser Pro Tyr Asn Gln
    1340                1345                1350

Asp Phe Val Asp Pro Lys Glu Gly Val His Leu Ile Pro Ser Gln
    1355                1360                1365

Asn Lys Ser Asn Phe Thr Arg Thr Ala Tyr Leu Thr Ile Leu Arg
    1370                1375                1380

Ala Leu Val Leu Thr Ala Phe Ser Ser Ile Trp Lys Pro Leu Ile
    1385                1390                1395

Leu Ala Glu Leu Leu Leu Glu Ser Ile Tyr Trp Thr His Ile Lys
    1400                1405                1410

Val Ala Lys Glu Val Ala Gly Ser Thr Arg Leu Ile Gly Arg Phe
    1415                1420                1425

Val Ala Ala Leu Ile Glu Leu Asn Trp Val Phe Asp Asp Lys Glu
    1430                1435                1440

Ala Ala Arg Tyr Lys Lys Phe Phe Val Leu Thr Ser Arg Val Arg
    1445                1450                1455

Asp Leu Met Val Lys His Lys Val Gln Asn Asp Thr Met Arg Gln
    1460                1465                1470

Trp Phe Glu Glu Thr Glu Ile Phe Gly Leu Gln Lys Val Ala Leu
    1475                1480                1485

Val Val Arg Ala His Ser Leu Thr Ala Asp Ser Asn Ser Ile Leu
    1490                1495                1500

Cys Ser Val Cys Glu Glu Lys Gln Asn Ile Glu Ala Lys Arg Val
    1505                1510                1515

Cys Pro Lys Cys Gly Asn Arg Gly Thr Gly Ile Lys Cys Gly Met
    1520                1525                1530

Thr Leu Ala Glu Phe Glu Glu Lys Tyr Tyr Lys Lys Ile Tyr Leu
    1535                1540                1545

Val Asp Gly Asp Asn Thr Gln Ala Tyr Arg Arg Glu Glu Arg Gly
    1550                1555                1560

Glu Val Thr Tyr Thr Ala Arg Gly Ala Phe Phe Leu Arg Asn Leu
    1565                1570                1575

Pro Ile Leu Ala Thr Lys Asn Lys Tyr Ile Leu Val Gly Asn Leu
    1580                1585                1590

Gly Met Glu Leu Gln Asp Leu Glu Ser Met Gly Trp Ile Ile Arg
    1595                1600                1605

Gly Pro Ala Val Cys Lys Lys Ile Val His His Glu Arg Cys Arg
    1610                1615                1620

Pro Thr Ile Pro Asp Lys Leu Met Ala Phe Phe Gly Leu Met Pro
    1625                1630                1635
```

-continued

Arg Gly Val Val Pro Arg Ala Pro Thr Arg Phe Pro Val Ser Leu
1640                1645                1650

Leu Lys Ile Lys Arg Gly Phe Glu Thr Gly Trp Ala Tyr Thr His
    1655                1660                1665

Pro Gly Gly Ile Ser Ser Val Met His Val Thr Ala Gly Leu Asp
    1670                1675                1680

Met Tyr Val Asn Asp Ala Met Gly Arg Thr Lys Val Gln Cys Gln
    1685                1690                1695

Glu Arg Asn Lys Leu Thr Asp Glu Cys Glu Tyr Gly Ile Lys Thr
    1700                1705                1710

Asp Ser Gly Cys Ser Glu Gly Ala Arg Cys Tyr Val Ile Asn Pro
    1715                1720                1725

Glu Ala Val Asn Ile Ala Gly Thr Arg Gly Ala Met Val His Leu
    1730                1735                1740

Arg Lys Thr Gly Pro Glu Phe Thr Cys Val Thr Ala Gln Gly Thr
    1745                1750                1755

Pro Ala Phe Tyr Asn Leu Arg Asn Leu Lys Gly Trp Ser Gly Leu
    1760                1765                1770

Pro Ile Phe Glu Ala Ala Thr Gly Arg Val Val Gly Arg Val Lys
    1775                1780                1785

Ala Gly Lys Asn Ala Glu Asp Ser Pro Thr Thr Ile Met Ser Gly
    1790                1795                1800

Thr Gln Ala Ala Lys Pro Thr Glu Cys Asp Leu Glu Ser Val Val
    1805                1810                1815

Arg Lys Leu Glu Thr Met Asn Arg Gly Glu Phe Lys Gln Val Val
    1820                1825                1830

Leu Ala Thr Gly Ala Gly Lys Thr Thr Glu Leu Pro Arg Lys Leu
    1835                1840                1845

Ile Glu Ala Val Gly Arg His Lys Arg Val Leu Val Leu Ile Pro
    1850                1855                1860

Leu Arg Ala Ala Ala Glu Gly Val Tyr Asn Tyr Met Arg Thr Lys
    1865                1870                1875

His Pro Ser Ile Ala Phe Asn Leu Arg Ile Gly Asp Leu Lys Glu
    1880                1885                1890

Gly Asp Met Ala Thr Gly Ile Thr Tyr Ala Ser Tyr Gly Tyr Phe
    1895                1900                1905

Cys Gln Met Asp Met Pro Arg Leu Asp Ala Ala Met Lys Glu Tyr
    1910                1915                1920

Asn Tyr Ile Phe Leu Asp Glu Tyr His Cys Ala Thr Pro Glu Gln
    1925                1930                1935

Leu Ala Val Met Ser Lys Ile His Arg Ile Ser Ala Asp Leu Arg
    1940                1945                1950

Val Val Ala Met Thr Ala Thr Pro Ala Gly Ala Val Ser Lys Val
    1955                1960                1965

Gly Gln Lys Phe Ser Ile Glu Glu Val Val Val Pro Glu Val Met
    1970                1975                1980

Lys Gly Glu Asp Leu Gly Glu Asp Tyr Leu Asp Ile Ala Gly Leu
    1985                1990                1995

Lys Ile Pro Lys Ser Glu Leu Gln Gly Asn Val Leu Thr Phe Val
    2000                2005                2010

Pro Thr Lys Lys Leu Ala Ser Asp Thr Ala Lys Lys Leu Thr Thr
    2015                2020                2025

Gln Gly Tyr Asn Ala Gly Tyr Tyr Phe Ser Gly Glu Asp Pro Ser

```
            2030                2035                2040
Ser Leu Arg Thr Ile Thr Ser Lys Ser Pro Tyr Ile Ile Ile Ala
            2045                2050                2055

Thr Asn Ala Ile Glu Ser Gly Val Thr Leu Pro Asp Leu Asp Thr
            2060                2065                2070

Val Ile Asp Thr Gly Met Lys Cys Glu Lys Arg Val Arg Ile Glu
            2075                2080                2085

Asn Lys Ala Pro Tyr Ile Ile Thr Gly Leu Lys Arg Met Ala Ile
            2090                2095                2100

Thr Thr Gly Glu Gln Ala Gln Arg Lys Gly Arg Val Gly Arg Val
            2105                2110                2115

Lys Pro Gly Arg Tyr Leu Arg Gly Pro Glu Asn Ala Gly Gly Glu
            2120                2125                2130

Arg Asp Tyr His Tyr Asp Leu Leu Gln Ala Gln Arg Tyr Gly Leu
            2135                2140                2145

Gln Asp Ala Ile Asn Ile Thr Lys Ser Phe Arg Glu Met Asn Tyr
            2150                2155                2160

Asp Trp Ala Leu Tyr Glu Glu Asp Pro Leu Arg Ile Thr Gln Leu
            2165                2170                2175

Glu Val Leu Asn Thr Leu Leu Ile Ser Lys Asp Leu Pro Thr Val
            2180                2185                2190

Thr Lys Asn Leu Met Thr Arg Thr Thr His Pro Glu Pro Ile Gln
            2195                2200                2205

Leu Ala Tyr Asn Ser Ile Glu Thr Pro Val Pro Val Leu Phe Pro
            2210                2215                2220

Lys Val Lys Gly Gly Glu Val Thr Asp Ala Tyr Glu Thr Tyr Glu
            2225                2230                2235

Leu Met Met Cys Arg Lys Leu Asp Asn Asp Pro Pro Ile Tyr Leu
            2240                2245                2250

Tyr Ala Thr Glu Asp Glu Asp Leu Ala Val Asp Leu Leu Asn Leu
            2255                2260                2265

Lys Trp Pro Ala Val Ser Thr Ala Ser Ala Ile Glu Thr Glu Asp
            2270                2275                2280

Ala Leu Asn Lys Leu Ser Gly Leu Ser Ala Gly Glu Thr Ala Leu
            2285                2290                2295

Leu Val Ala Leu Leu Gly Trp Val Gly Tyr Glu Ala Leu Val Lys
            2300                2305                2310

Arg His Ile Pro Ile Val Thr Asp Ile Tyr Thr Ile Glu Asp Glu
            2315                2320                2325

Lys Leu Glu Asp Thr Thr His Leu Gln Tyr Ser Pro Asp Glu Leu
            2330                2335                2340

Gln Asn Thr Glu Thr Val Glu Leu Lys Asp Leu Ser Ala His Glu
            2345                2350                2355

Leu Lys Glu Ala Leu Glu Ser Gly Lys Ser Tyr Val Lys Asp Ala
            2360                2365                2370

Phe Glu Phe Val Lys Ser Gln Val Glu Lys Leu Pro Asp Thr Lys
            2375                2380                2385

Ile Tyr Lys Gln Val Gln Glu Lys Ser Pro Gly Leu Leu Glu Lys
            2390                2395                2400

Phe Leu Ala Tyr Leu Ser Glu His Ser Ser Asp Ile Lys Lys Tyr
            2405                2410                2415

Gly Leu Trp Gly Val His Thr Ser Leu Tyr Asn Ser Ile Lys Glu
            2420                2425                2430
```

-continued

```
Arg Leu Gly His Glu Thr Ala Phe Ala Ser Leu Ile Ile Lys Trp
2435                2440                2445

Ile Ala Phe Ser Ser Glu Gly Leu Pro Gly Met Val Lys Gln Ala
2450                2455                2460

Ala Val Asp Leu Val Val Tyr Tyr Leu Ile Asn Lys Pro Asp Phe
2465                2470                2475

Lys Gly Asp Lys Asp Thr Gln Asp Asp Gly Arg Lys Phe Val Gly
2480                2485                2490

Ala Leu Phe Val Ser Ala Leu Ala Asn Tyr Thr Phe Lys Asn Phe
2495                2500                2505

Asn Lys Ser Thr Leu Glu Gly Leu Val Met Pro Ala Leu Asn Tyr
2510                2515                2520

Leu Pro Tyr Ala Gly Ala Ala Leu Lys Ile Phe Val Pro Thr Lys
2525                2530                2535

Leu Glu Ser Leu Val Ile Leu Ser Thr Thr Ile Tyr Arg Thr Tyr
2540                2545                2550

Leu Ser Ile Lys Lys Gly Ser Ser Gln Gly Leu Ala Gly Leu Ala
2555                2560                2565

Val Ser Ser Gly Met Glu Ile Met Asn Gln Asn Pro Ile Ser Val
2570                2575                2580

Ala Ile Ala Val Ala Leu Gly Val Gly Ala Ile Ala Ala His Asn
2585                2590                2595

Ala Ile Glu Ser Ser Glu Ala Lys Arg Thr Leu Leu Met Lys Val
2600                2605                2610

Phe Val Lys Asn Phe Leu Asp Gln Ala Ala Thr Asp Glu Leu Val
2615                2620                2625

Lys Glu Asn Pro Glu Lys Ile Ile Met Ala Val Phe Glu Ala Ile
2630                2635                2640

Gln Thr Ala Gly Asn Pro Ile Arg Leu Ile Tyr His Leu Tyr Ala
2645                2650                2655

Met Phe Tyr Lys Gly Trp Asn Ala Ser Gln Ile Ala Asp Lys Thr
2660                2665                2670

Ala Gly Arg Asn Ile Phe Val Leu Thr Ile Phe Glu Gly Leu Glu
2675                2680                2685

Leu Leu Gly Leu Asp Lys Asp Ser Lys Trp Arg Asp Leu Ser Ser
2690                2695                2700

Asn Tyr Leu Val Asp Ala Ile Arg Lys Leu Ile Glu Lys Leu Thr
2705                2710                2715

Lys Ile Leu Arg Asn Thr Thr Lys Ser Leu Ile Lys Ser Leu Leu
2720                2725                2730

Pro Ala Pro Phe Ser Cys Thr Arg Phe Thr Arg Asp Asn Arg Ile
2735                2740                2745

Gly Trp Pro His Leu Asn Phe Asp Tyr Tyr Glu Ile Asn Cys Ala
2750                2755                2760

Cys Gly Tyr Arg Arg Arg Val Val Lys Thr Val Ile Asp Pro Val
2765                2770                2775

Thr Trp Glu Thr Leu Glu Glu Glu Gly Pro Glu Phe Cys Phe Asn
2780                2785                2790

Arg Gly Thr Asn Ala Leu Ala Asn Pro Arg Val Ala Ser Tyr Tyr
2795                2800                2805

Ser Ala Gly Glu Pro Val Leu Pro Val Val Lys Arg Glu Gly Val
2810                2815                2820
```

-continued

| | | | | | | | | | | | |
|---|---|---|---|---|---|---|---|---|---|---|---|
| Gly | Glu | Ile | Leu | Val | Arg | Gly | Val | Thr | Ile | Gln | Met | His | Tyr | Asp |
| 2825 | | | | | 2830 | | | | | 2835 | | | | |

Gly Glu Ile Leu Val Arg Gly Val Thr Ile Gln Met His Tyr Asp
 2825                2830               2835

His Asn Lys Ile Leu Ala Thr Asp Asn Trp Gln Val Pro Phe Gln
 2840                2845               2850

Ala Val Thr Lys Ile Phe Thr Asp Tyr Gln Gly Ile Gly Tyr Gln
 2855                2860               2865

Glu Ala Tyr Leu Gly Thr Gln Pro Asn Tyr Lys Ala Leu Val Lys
 2870                2875               2880

Arg Ser Ser Val Thr Ile Thr Lys Glu Gly Leu Lys Phe Ile Arg
 2885                2890               2895

Cys Lys Lys Gly Ile Ala Tyr Thr Thr Asn Leu Asn Leu Thr His
 2900                2905               2910

Ile Gln Lys Leu Val Gln Val Cys Arg Met Asn Glu Leu Gln Glu
 2915                2920               2925

Gly Val Ile Pro Glu Thr Leu Asp Gly Asp Thr Trp Ile Asn Tyr
 2930                2935               2940

Met Ala Ile Ile Glu Asp Val Gly Ala Thr Lys Pro Ser Leu Glu
 2945                2950               2955

Arg Glu Ser Tyr Pro Lys Pro Tyr Glu Glu Asp Pro Leu Glu Gly
 2960                2965               2970

Pro Ser Val Ile Val Glu Thr Gly Asp Val Asp Ile Thr Lys Val
 2975                2980               2985

Gly Val Asn Gln Gln Ser Ser Ser Ser Gly Thr Val Phe Gln Val
 2990                2995               3000

Val Glu Lys Ile Tyr Thr Lys Leu Val Asn Thr Asn Val Ile Lys
 3005                3010               3015

Ile Gly Phe Lys Glu Gly Cys Phe Pro Gly Pro Thr Lys Asn Val
 3020                3025               3030

Asn Ser Leu Asn Glu His Ile Glu Asp Lys Asp Ser Lys Pro Tyr
 3035                3040               3045

Ile Phe Ile Cys Ser Ser Asp Lys Ala Met Ser Asn Arg Val Lys
 3050                3055               3060

Thr Ala Arg Asn Ile Lys Lys Leu Asn Thr Asn Ser Ala Ile Val
 3065                3070               3075

Ala Arg Asn Leu Ala Arg Glu Gly Lys Leu Ile Ile Ile Val Leu
 3080                3085               3090

Gly Glu Lys Tyr His Glu Asp Ile Tyr Lys His Ala Asp Phe Lys
 3095                3100               3105

Gly Thr Phe Leu Asp Arg Lys Ala Leu Glu Ala Leu Ser Lys Ala
 3110                3115               3120

Lys Pro Val Lys Lys Asn Met Thr Arg Arg Glu Ala Gln Tyr Leu
 3125                3130               3135

Leu Glu Lys Lys Leu Ser Glu Asp Ile Glu Val Pro Glu Trp Leu
 3140                3145               3150

Gly Ser Glu Lys Pro Met Phe Leu Asp Val Thr Lys Ser Gly Glu
 3155                3160               3165

Thr Tyr His Leu Leu Gly Asp Leu Asn His Leu Lys Ala Gln Ala
 3170                3175               3180

Glu Gln Leu Gly Ala Lys Ala Thr Thr Thr Ile Asn Lys Val Gly
 3185                3190               3195

Lys Thr Tyr Thr Met Asn Leu Ser Thr Trp Trp Glu Ser Glu Arg
 3200                3205               3210

Thr Pro Thr Phe Arg Pro Leu Phe Gln Glu Leu Leu Leu Arg Cys

```
              3215                3220                3225
Arg Pro Cys Thr Arg Glu Glu Tyr Lys Ser Cys His Phe Val Gly
        3230                3235                3240

Ala Thr Gln Leu Ala Gly Gly Asn Trp Lys Pro Val Ala Pro Val
        3245                3250                3255

Val His Leu Gly Thr Ile Pro Ala Lys Arg Glu Lys Cys Leu Pro
        3260                3265                3270

Tyr Glu Ala Tyr Ile Ser Leu Lys Asn Met Val Glu Asn Leu Lys
        3275                3280                3285

Ile Glu Asn Pro Gly Val Cys Lys Lys His Gln Trp Leu Leu
        3290                3295                3300

Asn Lys Ile Lys Lys Gln Gly Glu Leu Gly Leu Lys Asn Leu Val
        3305                3310                3315

Ser Pro Gly Ser Val Gly Gly Ser Arg Gly Tyr Arg Lys Lys Glu
        3320                3325                3330

Phe Asn Ile Tyr Asn Lys Gln Ile Thr Ser Thr Met Leu Ala Val
        3335                3340                3345

Gly Ile Lys Pro Glu Lys Phe Pro Val Val Arg Ala Gln Thr Ser
        3350                3355                3360

Lys Arg Glu Phe His Gln Ala Ile Arg Glu Lys Ile Asp Lys Leu
        3365                3370                3375

Pro Asn Pro Gln Asn Arg Asp Leu His Lys Glu Leu Lys Glu Ile
        3380                3385                3390

Phe Asp Ser Val Cys Ala Val Lys Asp Leu Lys His Thr Tyr Glu
        3395                3400                3405

Glu Val Ser Trp Asp Val Leu Thr Val Gly Ile Asn Arg Lys Gly
        3410                3415                3420

Ala Ala Gly Tyr Phe Glu Lys Asn Val Gly Glu Ile Ile Asp
        3425                3430                3435

Thr Asp Arg Arg Gly Val Glu Lys Leu Ile Lys Val Met Lys Thr
        3440                3445                3450

Gly Gly Pro Ile Asp Tyr Tyr Glu Thr Ala Ile Pro Lys Asn Glu
        3455                3460                3465

Lys Arg Ala Val Val Asp Asp Trp Leu Glu Gly Asp Phe Val Glu
        3470                3475                3480

Glu Lys Lys Pro Arg Val Ile Gln Tyr Pro Glu Ala Lys Met Arg
        3485                3490                3495

Leu Ala Ile Thr Lys Val Met Tyr Asn Trp Val Lys Gln Lys Pro
        3500                3505                3510

Val Val Ile Pro Gly Tyr Glu Gly Lys Thr Pro Leu Phe Lys Val
        3515                3520                3525

Phe Asp Lys Val Phe Asp Glu Trp Lys Gln Leu Arg Asp Pro Val
        3530                3535                3540

Ala Val Ser Phe Asp Thr Lys Ala Trp Asp Thr Gln Val Thr Pro
        3545                3550                3555

Glu Asp Leu Gln Leu Ile Ser Glu Ile Gln Lys Tyr Tyr Phe Lys
        3560                3565                3570

Pro Lys Tyr His Lys Phe Ile Glu Thr Leu Thr Ala Glu Met Lys
        3575                3580                3585

Glu Val Pro Val Val Cys Gln Asp Gly Glu Val Tyr Ile Arg Leu
        3590                3595                3600

Gly Gln Arg Gly Ser Gly Gln Pro Asp Thr Ser Ala Gly Asn Ser
        3605                3610                3615
```

```
Met Leu Asn Val Leu Thr Met Ile Tyr Ala Phe Cys Lys Ser Asn
        3620                3625                3630

Asp Ile Pro Tyr Lys Ala Phe Arg Arg Val Ala Lys Ile His Val
        3635                3640                3645

Cys Gly Asp Asp Gly Phe Leu Ile Thr Glu Arg Arg Leu Gly Glu
        3650                3655                3660

Asn Phe Ala Ala Met Gly Pro Gln Ile Leu Met Glu Ala Gly Lys
        3665                3670                3675

Pro Gln Lys Leu Val Gly Glu Met Gly Leu Lys Leu Ala Tyr Lys
        3680                3685                3690

Phe Gln Asp Ile Glu Phe Cys Ser His Thr Pro Ile Gln Val Arg
        3695                3700                3705

Trp Asp Asp Asn Thr Thr Ser Tyr Leu Pro Gly Arg Asp Thr Ala
        3710                3715                3720

Thr Ile Leu Ala Lys Met Cys Thr Arg Leu Asp Ser Ala Gly Glu
        3725                3730                3735

Arg Gly Thr Ser Ser Tyr Glu Leu Ala Val Val Phe Ser Phe Leu
        3740                3745                3750

Leu Met Tyr Ser Trp Asn Pro Ile Val Arg Arg Ile Cys Leu Leu
        3755                3760                3765

Val Met Ala Thr Ile Gly Val Lys Asp Pro Asp Lys Ser Gly Thr
        3770                3775                3780

Ile Phe Thr Phe Ser Gly Asp Pro Leu Gly Ala Tyr Lys Glu Val
        3785                3790                3795

Ile Gly His Arg Leu Gly Gln Leu Lys Gln Thr Glu Phe Ser Lys
        3800                3805                3810

Leu Ala Ser Cys Asn Leu Ser Met Ser Leu Leu Gly Ile Tyr Ser
        3815                3820                3825

Arg His Thr Ser Lys Arg Ile Ile Glu Asp Cys Val Lys Ile Gly
        3830                3835                3840

Thr Leu Asn Arg Gln Ser Pro Val Asn Ala Asp Arg Leu Ile Ala
        3845                3850                3855

Lys Lys Thr Gly Phe Val Tyr Glu Pro Ser Arg Gly Ser Val Arg
        3860                3865                3870

Val Gly Lys His Tyr Glu Glu Leu Glu Leu Asp Lys Trp Lys Lys
        3875                3880                3885

Lys Thr Pro Leu Ile Glu Gly Ala Glu Arg Tyr Ile Pro Gly Pro
        3890                3895                3900

Ile Lys Thr Phe Ile Leu Lys Arg Leu Lys Val Leu Gln Met Ile
        3905                3910                3915

Gly Leu Lys Phe Phe
        3920

<210> SEQ ID NO 4
<211> LENGTH: 182
<212> TYPE: PRT
<213> ORGANISM: Porcine pestivirus

<400> SEQUENCE: 4

Met Glu Phe Lys Ile Leu Asn Asn Thr Lys Lys Lys Asn Asn Glu
 1               5                  10                  15

Glu Glu Ala Glu Gly Asn Met Phe Trp Arg Met Tyr Arg Arg Pro
            20                  25                  30

Pro Gly Cys Tyr Glu Pro Thr Tyr Asn Leu Ser Gly Thr Pro Ser Phe
```

```
            35                  40                  45
Gly Pro Met His Pro Leu Arg Lys Gly Ser Thr Leu Arg Leu Pro
    50                  55                  60

His Trp Arg Gly Ile Ala Thr Val Gly Cys Glu Leu Lys Asn Leu Pro
 65                  70                  75                  80

Arg Lys Gly Asp Cys Thr Lys Cys His Ala Asn Pro Thr Ser Gly Ile
                85                  90                  95

Tyr Leu Asn Leu Gly Ala Val Phe Tyr Lys Asp Tyr Glu Gly Glu Val
                100                 105                 110

Tyr His Arg Val Pro Leu Glu His Cys Glu Glu Gln Arg Cys Glu
            115                 120                 125

Val Val Lys Arg Val Gly Arg Met Thr Ala Ser Asp Gly Ser Leu Val
    130                 135                 140

Gly Val Leu Val Cys Ser Asp Asp Cys Val Leu Phe Glu Arg Arg
145                 150                 155                 160

Gly Glu His Thr Val Leu Lys Trp Val Lys Asn Pro Ile Gly Ala Pro
                165                 170                 175

Leu Trp Val Gln Ser Cys
            180

<210> SEQ ID NO 5
<211> LENGTH: 101
<212> TYPE: PRT
<213> ORGANISM: Porcine pestivirus

<400> SEQUENCE: 5

Ser Asp Glu Lys Gly Ala Lys Pro Lys Asn Lys Ser Lys Gln Gln Asn
 1               5                  10                  15

Asp Arg Met Ala Pro Gly Lys Met Val Thr Lys Pro Lys Glu Val Glu
                20                  25                  30

Ala Asp Gln Lys Thr Arg Pro Pro Asp Ala Thr Ile Val Val Asp Gly
            35                  40                  45

Gln Lys Tyr Gln Val Arg Lys Lys Gly Lys Ala Lys Pro Lys Thr Pro
    50                  55                  60

Asp Gly Leu Tyr His Asn Lys Asn Lys Pro Glu Ala Ser Arg Lys Lys
 65                  70                  75                  80

Leu Glu Lys Ala Leu Leu Ala Trp Ala Val Ile Ala Ile Ile Leu Ile
                85                  90                  95

Gln Gln Thr Thr Ala
                100

<210> SEQ ID NO 6
<211> LENGTH: 221
<212> TYPE: PRT
<213> ORGANISM: Porcine pestivirus

<400> SEQUENCE: 6

Asn Asn Val Thr Gln Trp Asn Leu Trp Asp Lys Asn Ala Thr Asp
 1               5                  10                  15

Val His Ser Val Met His Gln Arg Gln Ile Lys Arg Ser Leu His Gly
                20                  25                  30

Ile Trp Pro Glu Arg Ile Cys Lys Gly Val Pro Gly His Leu Ala Thr
            35                  40                  45

Asp Tyr Glu Leu Lys Arg Ile Glu Gly Met Leu Asp Ala Ser Glu Lys
    50                  55                  60

Thr Asn Phe Thr Cys Cys Arg Leu Gln Arg His Glu Trp Asn Lys His
```

```
                     65                  70                  75                  80
Gly Trp Cys Asn Trp Tyr Asn Ile Asp Pro Trp Val Ala Ile Met Asn
                    85                  90                  95

Arg Thr Gln Ala Leu Leu Ser Ser Gly Gln Asn Phe Thr Glu Cys Ala
                100                 105                 110

Val Thr Cys Arg Tyr Asp Thr Glu Gln Gln Ile Asn Ile Val Thr Gln
                115                 120                 125

Ala Arg Met Thr Pro Thr Ile Leu Thr Gly Cys Lys Lys Asp Val Asn
            130                 135                 140

Phe Ser Phe Ser Gly Glu Val Arg Thr Gly Pro Cys Asn Tyr Glu Leu
145                 150                 155                 160

Lys Pro Glu Asp Leu Met Arg Ile Leu Asp His Thr Asn Cys Lys Asp
                165                 170                 175

Phe Ser Tyr Phe Gly Glu Gly Leu Val Asp Asp Phe Thr Glu Ala Thr
                180                 185                 190

Glu Lys Ile Arg Ser Ser Gly Tyr Arg Ala Leu Ser Trp Leu Gln Asp
                195                 200                 205

Lys Leu Glu Lys Thr Lys Lys Val Phe Gly Ala Glu
210                 215                 220

<210> SEQ ID NO 7
<211> LENGTH: 198
<212> TYPE: PRT
<213> ORGANISM: Porcine pestivirus

<400> SEQUENCE: 7

Ala Thr Pro Tyr Cys Asn Val Thr Arg Arg Val Phe Asn Ile Ile Tyr
1               5                   10                  15

Thr Asn Asn Cys Thr Pro Ala Gly Leu Pro Asp Asn Thr Arg Ile Val
                20                  25                  30

Gly Pro Gly Thr Phe Asp Ile Ser Glu Met Glu Asn Lys Lys Leu Leu
            35                  40                  45

Pro Asn Leu Asp Tyr His Leu Ala Asp Phe Met Val Leu Gly Leu Val
        50                  55                  60

Ala Leu Ser Asp Phe Ala Pro Glu Thr Ala Ser Thr Ile Tyr Leu Val
65                  70                  75                  80

Leu His Tyr Trp Leu Pro Gln Ala Glu Val His Thr Leu Asp Thr Pro
                85                  90                  95

Leu Asp Thr Asn Lys Leu Asn Leu Thr Arg Asn Arg Gln Val Ser Ser
                100                 105                 110

Val Val Pro Asn Ser Ile Trp Leu Gly Gly Gln Leu Val Cys Val Lys
                115                 120                 125

Pro Arg Trp Trp Pro Tyr Ser Ala Glu Ile Thr Thr Val Ile Ser Gly
            130                 135                 140

Leu Thr Thr Val Thr Asp Leu Val Val Lys Thr Ile Glu Glu Leu Val
145                 150                 155                 160

Ser Leu Trp Thr Glu Ala Thr Ala Val Ala Phe Leu Ala Ala Leu Ile
                165                 170                 175

Lys Ile Phe Arg Gly Gln Pro Ile Gln Ala Leu Ala Trp Leu Ile Ile
                180                 185                 190

Ile Gly Gly Ala Gln Gly
            195

<210> SEQ ID NO 8
<211> LENGTH: 375
```

<212> TYPE: PRT
<213> ORGANISM: Porcine pestivirus

<400> SEQUENCE: 8

Leu Glu Cys Asn Phe Glu Leu Gln Tyr Ala Leu Ala Gly Asn Thr Ser
1               5                   10                  15

Met Ser Leu Leu Gly Pro Thr Ala Leu Lys Thr Gln Trp Tyr Gln Ala
            20                  25                  30

Ala Asp Gly Val Lys Ile Thr Asp Gly Val Val Thr Val Ile Cys Asn
        35                  40                  45

Lys Gly Ile Phe Ser Val Thr Pro Arg Cys Lys Glu Ala Pro Val Arg
    50                  55                  60

Tyr Leu Ala Ile Asn His Pro Arg Ser Leu Ser Thr Ser Ala Trp Phe
65                  70                  75                  80

Lys Lys Ile His Asp Pro Ala Asp His Pro Thr Glu Thr Leu Met Gly
                85                  90                  95

Glu Lys Gly Arg Ala Tyr Leu Cys Pro Cys Gly Ala Thr Pro Leu Pro
            100                 105                 110

Lys Pro Lys Val Pro Phe Asn Pro Ile Thr Ile Gln Gly Ser Ala Phe
        115                 120                 125

Ser Leu Thr Cys Pro Lys Asn Trp Gln Gly Asp Ile Glu Cys Asn Leu
    130                 135                 140

Leu Ser Pro Asp Thr Leu Ala Ile Glu Thr Ile Tyr Thr Phe Arg Lys
145                 150                 155                 160

His Lys Pro Tyr Lys Glu Glu Pro Tyr Cys Ser Tyr Thr Lys Val Val
                165                 170                 175

Asp Gly Tyr Leu Arg Asn Val His Leu Trp Gly His Asp Thr Cys Val
            180                 185                 190

Ala Gly Asp Ile Ile Asn Gly Ser Gln Asp Asp Ser Val Thr Lys Cys
        195                 200                 205

Lys Trp Cys Gly Tyr Glu Phe Asn Ser Ala Thr Asp Leu Pro Asp Tyr
    210                 215                 220

Pro Ile Gly Tyr Cys Thr Lys Arg Gly Thr Asn Tyr Leu Ile Arg Tyr
225                 230                 235                 240

Lys Gln Val Pro Cys Glu Val Gly Gly Val Arg Ile Gly Ser Gly Lys
                245                 250                 255

Val Glu Cys Thr Ile Gly Ser Thr Arg Val Lys Val Glu Gln Thr Ser
            260                 265                 270

Asn Glu Leu Gly Pro Met Pro Cys Lys Pro Ile Val Tyr Ser Ser Gln
        275                 280                 285

Gly Pro Pro Asn Pro Lys Thr Cys Thr Phe Lys Trp Ser Tyr Thr Leu
    290                 295                 300

Asn Asn Lys Tyr Tyr Glu Pro Arg Asp Glu Phe Gln Gln Tyr Ile
305                 310                 315                 320

Thr Ser Gly Gly Tyr Gln Tyr Trp Phe Asp Leu Thr Ala Lys Asp His
                325                 330                 335

Val Met Asp Trp Val Thr Arg Tyr Phe Pro Ile Ile Val Val Ala Leu
            340                 345                 350

Leu Gly Gly Arg Ala Val Leu Trp Ile Leu Ile Ala Tyr Glu Leu Leu
        355                 360                 365

Asn His Tyr Gln Val Gly Ala
    370                 375

<210> SEQ ID NO 9

```
<211> LENGTH: 75
<212> TYPE: PRT
<213> ORGANISM: Porcine pestivirus

<400> SEQUENCE: 9

Asp Gln Asn Thr Leu Leu Gln Ala Glu Ala Leu Val Ile Gly Asn Ile
1               5                   10                  15

Leu Met Thr Arg Asp Leu Glu Val Met Val Cys Phe Leu Leu Leu Met
            20                  25                  30

Val Leu Ile Arg Arg Gln Gln Ala Arg Arg Ala Leu Ala Leu Val Phe
        35                  40                  45

His Trp Met Val Met His Pro Ala Gln Ser Ala Ile Ala Thr Leu Val
    50                  55                  60

Tyr Val Ile Gly Ile Val Arg Ala Glu Glu Gly
65                  70                  75

<210> SEQ ID NO 10
<211> LENGTH: 456
<212> TYPE: PRT
<213> ORGANISM: Porcine pestivirus

<400> SEQUENCE: 10

Gln Val Asn Ser Asp Ser Ser Thr Gln Ala His Val Val Ala Ile Leu
1               5                   10                  15

Leu Phe Leu Ile Tyr His Thr Leu Lys Glu Arg Asp Leu His Thr Ala
            20                  25                  30

Met Thr Leu Leu Leu Thr Phe Ser Ile Lys Ser Thr Asp Tyr Val Asp
        35                  40                  45

Thr His Tyr Tyr Glu Ile Pro Met Leu Phe Thr Val Ile Ser Leu Val
    50                  55                  60

Ile Ser Ile Tyr Ile Phe Asn Ile His Ile Lys Thr Lys Trp Val Ala
65                  70                  75                  80

Leu Val Leu Ser Met Val Gly Met Val Thr Phe Ile Arg Cys Leu Trp
            85                  90                  95

Leu Ile Arg Asn Ile Gln Ile Thr Pro Pro Ser Ile Pro Leu Thr Tyr
        100                 105                 110

Ile Ser Pro Lys Ile Leu Ile Ile Ala Tyr Leu Val Ser Leu Thr Val
    115                 120                 125

Leu Val Asn Asn Asn Leu Asp Leu Ala Ser Tyr Val Ile Arg Ala Gly
    130                 135                 140

Pro Ile Leu Met Ser Tyr Leu Thr Leu Trp Val Asp Ile Leu Met Leu
145                 150                 155                 160

Leu Val Leu Leu Pro Trp Tyr Glu Leu Ile Lys Val Tyr Tyr Leu Lys
            165                 170                 175

Lys Lys Lys Asp Asp Ile Glu Asp Cys Phe Gln Tyr Ser Gly Ile Ala
        180                 185                 190

Thr Gln Gly Leu Ser Pro Tyr Asn Gln Asp Phe Val Asp Pro Lys Glu
    195                 200                 205

Gly Val His Leu Ile Pro Ser Gln Asn Lys Ser Asn Phe Thr Arg Thr
    210                 215                 220

Ala Tyr Leu Thr Ile Leu Arg Ala Leu Val Leu Thr Ala Phe Ser Ser
225                 230                 235                 240

Ile Trp Lys Pro Leu Ile Leu Ala Glu Leu Leu Leu Glu Ser Ile Tyr
            245                 250                 255

Trp Thr His Ile Lys Val Ala Lys Glu Val Ala Gly Ser Thr Arg Leu
        260                 265                 270
```

Ile Gly Arg Phe Val Ala Ala Leu Ile Glu Leu Asn Trp Val Phe Asp
        275                 280                 285

Asp Lys Glu Ala Ala Arg Tyr Lys Lys Phe Val Leu Thr Ser Arg
290                 295                 300

Val Arg Asp Leu Met Val Lys His Lys Val Gln Asn Asp Thr Met Arg
305                 310                 315                 320

Gln Trp Phe Glu Glu Thr Glu Ile Phe Gly Leu Gln Lys Val Ala Leu
                325                 330                 335

Val Val Arg Ala His Ser Leu Thr Ala Asp Ser Asn Ser Ile Leu Cys
            340                 345                 350

Ser Val Cys Glu Glu Lys Gln Asn Ile Glu Ala Lys Arg Val Cys Pro
        355                 360                 365

Lys Cys Gly Asn Arg Gly Thr Gly Ile Lys Cys Gly Met Thr Leu Ala
370                 375                 380

Glu Phe Glu Glu Lys Tyr Tyr Lys Lys Ile Tyr Leu Val Asp Gly Asp
385                 390                 395                 400

Asn Thr Gln Ala Tyr Arg Arg Glu Glu Arg Gly Glu Val Thr Tyr Thr
                405                 410                 415

Ala Arg Gly Ala Phe Phe Leu Arg Asn Leu Pro Ile Leu Ala Thr Lys
            420                 425                 430

Asn Lys Tyr Ile Leu Val Gly Asn Leu Gly Met Glu Leu Gln Asp Leu
        435                 440                 445

Glu Ser Met Gly Trp Ile Ile Arg
450                 455

<210> SEQ ID NO 11
<211> LENGTH: 683
<212> TYPE: PRT
<213> ORGANISM: Porcine pestivirus

<400> SEQUENCE: 11

Gly Pro Ala Val Cys Lys Lys Ile Val His Glu Arg Cys Arg Pro
1               5                   10                  15

Thr Ile Pro Asp Lys Leu Met Ala Phe Phe Gly Leu Met Pro Arg Gly
                20                  25                  30

Val Val Pro Arg Ala Pro Thr Arg Phe Pro Val Ser Leu Leu Lys Ile
            35                  40                  45

Lys Arg Gly Phe Glu Thr Gly Trp Ala Tyr Thr His Pro Gly Gly Ile
        50                  55                  60

Ser Ser Val Met His Val Thr Ala Gly Leu Asp Met Tyr Val Asn Asp
65                  70                  75                  80

Ala Met Gly Arg Thr Lys Val Gln Cys Gln Glu Arg Asn Lys Leu Thr
                85                  90                  95

Asp Glu Cys Glu Tyr Gly Ile Lys Thr Asp Ser Gly Cys Ser Glu Gly
            100                 105                 110

Ala Arg Cys Tyr Val Ile Asn Pro Glu Ala Val Asn Ile Ala Gly Thr
        115                 120                 125

Arg Gly Ala Met Val His Leu Arg Lys Thr Gly Pro Glu Phe Thr Cys
130                 135                 140

Val Thr Ala Gln Gly Thr Pro Ala Phe Tyr Asn Leu Arg Asn Leu Lys
145                 150                 155                 160

Gly Trp Ser Gly Leu Pro Ile Phe Glu Ala Ala Thr Gly Arg Val Val
                165                 170                 175

Gly Arg Val Lys Ala Gly Lys Asn Ala Glu Asp Ser Pro Thr Thr Ile

```
                180             185             190
Met Ser Gly Thr Gln Ala Ala Lys Pro Thr Glu Cys Asp Leu Glu Ser
            195                 200             205

Val Val Arg Lys Leu Glu Thr Met Asn Arg Gly Phe Lys Gln Val
        210              215             220

Val Leu Ala Thr Gly Ala Gly Lys Thr Thr Glu Leu Pro Arg Lys Leu
225                 230              235                 240

Ile Glu Ala Val Gly Arg His Lys Arg Val Leu Val Leu Ile Pro Leu
                245                 250                 255

Arg Ala Ala Ala Glu Gly Val Tyr Asn Tyr Met Arg Thr Lys His Pro
            260                 265             270

Ser Ile Ala Phe Asn Leu Arg Ile Gly Asp Leu Lys Glu Gly Asp Met
        275                 280             285

Ala Thr Gly Ile Thr Tyr Ala Ser Tyr Gly Tyr Phe Cys Gln Met Asp
        290                 295             300

Met Pro Arg Leu Asp Ala Ala Met Lys Glu Tyr Asn Tyr Ile Phe Leu
305             310              315                 320

Asp Glu Tyr His Cys Ala Thr Pro Glu Gln Leu Ala Val Met Ser Lys
                325             330             335

Ile His Arg Ile Ser Ala Asp Leu Arg Val Val Ala Met Thr Ala Thr
            340                 345             350

Pro Ala Gly Ala Val Ser Lys Val Gly Gln Lys Phe Ser Ile Glu Glu
            355             360             365

Val Val Val Pro Glu Val Met Lys Gly Glu Asp Leu Gly Glu Asp Tyr
        370             375             380

Leu Asp Ile Ala Gly Leu Lys Ile Pro Lys Ser Glu Leu Gln Gly Asn
385             390             395                 400

Val Leu Thr Phe Val Pro Thr Lys Lys Leu Ala Ser Asp Thr Ala Lys
                405             410             415

Lys Leu Thr Thr Gln Gly Tyr Asn Ala Gly Tyr Tyr Phe Ser Gly Glu
            420             425             430

Asp Pro Ser Ser Leu Arg Thr Ile Thr Ser Lys Ser Pro Tyr Ile Ile
            435             440             445

Ile Ala Thr Asn Ala Ile Glu Ser Gly Val Thr Leu Pro Asp Leu Asp
        450             455             460

Thr Val Ile Asp Thr Gly Met Lys Cys Glu Lys Arg Val Arg Ile Glu
465             470             475             480

Asn Lys Ala Pro Tyr Ile Ile Thr Gly Leu Lys Arg Met Ala Ile Thr
                485             490             495

Thr Gly Glu Gln Ala Gln Arg Lys Gly Arg Val Gly Arg Val Lys Pro
            500             505             510

Gly Arg Tyr Leu Arg Gly Pro Glu Asn Ala Gly Gly Glu Arg Asp Tyr
            515             520             525

His Tyr Asp Leu Leu Gln Ala Gln Arg Tyr Gly Leu Gln Asp Ala Ile
            530             535             540

Asn Ile Thr Lys Ser Phe Arg Glu Met Asn Tyr Asp Trp Ala Leu Tyr
545                 550             555             560

Glu Glu Asp Pro Leu Arg Ile Thr Gln Leu Glu Val Leu Asn Thr Leu
                565             570             575

Leu Ile Ser Lys Asp Leu Pro Thr Val Thr Lys Asn Leu Met Thr Arg
            580             585             590

Thr Thr His Pro Glu Pro Ile Gln Leu Ala Tyr Asn Ser Ile Glu Thr
            595             600             605
```

Pro Val Pro Val Leu Phe Pro Lys Val Lys Gly Gly Glu Val Thr Asp
    610                 615                 620

Ala Tyr Glu Thr Tyr Glu Leu Met Met Cys Arg Lys Leu Asp Asn Asp
625                 630                 635                 640

Pro Pro Ile Tyr Leu Tyr Ala Thr Glu Asp Glu Asp Leu Ala Val Asp
                645                 650                 655

Leu Leu Asn Leu Lys Trp Pro Ala Val Ser Thr Ala Ser Ala Ile Glu
            660                 665                 670

Thr Glu Asp Ala Leu Asn Lys Leu Ser Gly Leu
            675                 680

<210> SEQ ID NO 12
<211> LENGTH: 63
<212> TYPE: PRT
<213> ORGANISM: Porcine pestivirus

<400> SEQUENCE: 12

Ser Ala Gly Glu Thr Ala Leu Leu Val Ala Leu Leu Gly Trp Val Gly
1               5                   10                  15

Tyr Glu Ala Leu Val Lys Arg His Ile Pro Ile Val Thr Asp Ile Tyr
            20                  25                  30

Thr Ile Glu Asp Glu Lys Leu Glu Asp Thr Thr His Leu Gln Tyr Ser
        35                  40                  45

Pro Asp Glu Leu Gln Asn Thr Glu Thr Val Glu Leu Lys Asp Leu
    50                  55                  60

<210> SEQ ID NO 13
<211> LENGTH: 347
<212> TYPE: PRT
<213> ORGANISM: Porcine pestivirus

<400> SEQUENCE: 13

Ser Ala His Glu Leu Lys Glu Ala Leu Glu Ser Gly Lys Ser Tyr Val
1               5                   10                  15

Lys Asp Ala Phe Glu Phe Val Lys Ser Gln Val Glu Lys Leu Pro Asp
            20                  25                  30

Thr Lys Ile Tyr Lys Gln Val Gln Glu Lys Ser Pro Gly Leu Leu Glu
        35                  40                  45

Lys Phe Leu Ala Tyr Leu Ser Glu His Ser Ser Asp Ile Lys Lys Tyr
    50                  55                  60

Gly Leu Trp Gly Val His Thr Ser Leu Tyr Asn Ser Ile Lys Glu Arg
65                  70                  75                  80

Leu Gly His Glu Thr Ala Phe Ala Ser Leu Ile Ile Lys Trp Ile Ala
                85                  90                  95

Phe Ser Ser Glu Gly Leu Pro Gly Met Val Lys Gln Ala Ala Val Asp
            100                 105                 110

Leu Val Val Tyr Tyr Leu Ile Asn Lys Pro Asp Phe Lys Gly Asp Lys
        115                 120                 125

Asp Thr Gln Asp Asp Gly Arg Lys Phe Val Gly Ala Leu Phe Val Ser
    130                 135                 140

Ala Leu Ala Asn Tyr Thr Phe Lys Asn Phe Asn Lys Ser Thr Leu Glu
145                 150                 155                 160

Gly Leu Val Met Pro Ala Leu Asn Tyr Leu Pro Tyr Ala Gly Ala Ala
                165                 170                 175

Leu Lys Ile Phe Val Pro Thr Lys Leu Glu Ser Leu Val Ile Leu Ser
            180                 185                 190

```
Thr Thr Ile Tyr Arg Thr Tyr Leu Ser Ile Lys Lys Gly Ser Ser Gln
            195                 200                 205

Gly Leu Ala Gly Leu Ala Val Ser Ser Gly Met Glu Ile Met Asn Gln
            210                 215                 220

Asn Pro Ile Ser Val Ala Ile Ala Val Ala Leu Gly Val Gly Ala Ile
225                 230                 235                 240

Ala Ala His Asn Ala Ile Glu Ser Ser Glu Ala Lys Arg Thr Leu Leu
            245                 250                 255

Met Lys Val Phe Val Lys Asn Phe Leu Asp Gln Ala Ala Thr Asp Glu
            260                 265                 270

Leu Val Lys Glu Asn Pro Glu Lys Ile Ile Met Ala Val Phe Glu Ala
            275                 280                 285

Ile Gln Thr Ala Gly Asn Pro Ile Arg Leu Ile Tyr His Leu Tyr Ala
            290                 295                 300

Met Phe Tyr Lys Gly Trp Asn Ala Ser Gln Ile Ala Asp Lys Thr Ala
305                 310                 315                 320

Gly Arg Asn Ile Phe Val Leu Thr Ile Phe Glu Gly Leu Glu Leu Leu
            325                 330                 335

Gly Leu Asp Lys Asp Ser Lys Trp Arg Asp Leu
            340                 345

<210> SEQ ID NO 14
<211> LENGTH: 504
<212> TYPE: PRT
<213> ORGANISM: Porcine pestivirus

<400> SEQUENCE: 14

Ser Ser Asn Tyr Leu Val Asp Ala Ile Arg Lys Leu Ile Glu Lys Leu
1               5                   10                  15

Thr Lys Ile Leu Arg Asn Thr Thr Lys Ser Leu Ile Lys Ser Leu Leu
            20                  25                  30

Pro Ala Pro Phe Ser Cys Thr Arg Phe Thr Arg Asp Asn Arg Ile Gly
            35                  40                  45

Trp Pro His Leu Asn Phe Asp Tyr Tyr Glu Ile Asn Cys Ala Cys Gly
            50                  55                  60

Tyr Arg Arg Arg Val Val Lys Thr Val Ile Asp Pro Val Thr Trp Glu
65                  70                  75                  80

Thr Leu Glu Glu Glu Gly Pro Glu Phe Cys Phe Asn Arg Gly Thr Asn
            85                  90                  95

Ala Leu Ala Asn Pro Arg Val Ser Tyr Tyr Ser Ala Gly Glu Pro
            100                 105                 110

Val Leu Pro Val Val Lys Arg Glu Gly Val Gly Glu Ile Leu Val Arg
            115                 120                 125

Gly Val Thr Ile Gln Met His Tyr Asp His Asn Lys Ile Leu Ala Thr
            130                 135                 140

Asp Asn Trp Gln Val Pro Phe Gln Ala Val Thr Lys Ile Phe Thr Asp
145                 150                 155                 160

Tyr Gln Gly Ile Gly Tyr Gln Glu Ala Tyr Leu Gly Thr Gln Pro Asn
            165                 170                 175

Tyr Lys Ala Leu Val Lys Arg Ser Ser Val Thr Ile Thr Lys Glu Gly
            180                 185                 190

Leu Lys Phe Ile Arg Cys Lys Lys Gly Ile Ala Tyr Thr Thr Asn Leu
            195                 200                 205

Asn Leu Thr His Ile Gln Lys Leu Val Gln Val Cys Arg Met Asn Glu
```

```
                210                 215                 220
Leu Gln Glu Gly Val Ile Pro Glu Thr Leu Asp Gly Asp Thr Trp Ile
225                 230                 235                 240

Asn Tyr Met Ala Ile Ile Glu Asp Val Gly Ala Thr Lys Pro Ser Leu
                245                 250                 255

Glu Arg Glu Ser Tyr Pro Lys Pro Tyr Glu Asp Pro Leu Glu Gly
            260                 265                 270

Pro Ser Val Ile Val Glu Thr Gly Asp Val Asp Ile Thr Lys Val Gly
            275                 280                 285

Val Asn Gln Gln Ser Ser Ser Gly Thr Val Phe Gln Val Val Glu
    290                 295                 300

Lys Ile Tyr Thr Lys Leu Val Asn Thr Asn Val Ile Lys Ile Gly Phe
305                 310                 315                 320

Lys Glu Gly Cys Phe Pro Gly Pro Thr Lys Asn Val Asn Ser Leu Asn
                325                 330                 335

Glu His Ile Glu Asp Lys Asp Ser Lys Pro Tyr Ile Phe Ile Cys Ser
            340                 345                 350

Ser Asp Lys Ala Met Ser Asn Arg Val Lys Thr Ala Arg Asn Ile Lys
            355                 360                 365

Lys Leu Asn Thr Asn Ser Ala Ile Val Ala Arg Asn Leu Ala Arg Glu
370                 375                 380

Gly Lys Leu Ile Ile Ile Val Leu Gly Glu Lys Tyr His Glu Asp Ile
385                 390                 395                 400

Tyr Lys His Ala Asp Phe Lys Gly Thr Phe Leu Asp Arg Lys Ala Leu
                405                 410                 415

Glu Ala Leu Ser Lys Ala Lys Pro Val Lys Lys Asn Met Thr Arg Arg
            420                 425                 430

Glu Ala Gln Tyr Leu Leu Glu Lys Lys Leu Ser Glu Asp Ile Glu Val
            435                 440                 445

Pro Glu Trp Leu Gly Ser Glu Lys Pro Met Phe Leu Asp Val Thr Lys
            450                 455                 460

Ser Gly Glu Thr Tyr His Leu Leu Gly Asp Leu Asn His Leu Lys Ala
465                 470                 475                 480

Gln Ala Glu Gln Leu Gly Ala Lys Ala Thr Thr Ile Asn Lys Val
            485                 490                 495

Gly Lys Thr Tyr Thr Met Asn Leu
            500

<210> SEQ ID NO 15
<211> LENGTH: 718
<212> TYPE: PRT
<213> ORGANISM: Porcine pestivirus

<400> SEQUENCE: 15

Ser Thr Trp Trp Glu Ser Glu Arg Thr Pro Thr Phe Arg Pro Leu Phe
1               5                   10                  15

Gln Glu Leu Leu Leu Arg Cys Arg Pro Cys Thr Arg Glu Glu Tyr Lys
                20                  25                  30

Ser Cys His Phe Val Gly Ala Thr Gln Leu Ala Gly Gly Asn Trp Lys
            35                  40                  45

Pro Val Ala Pro Val Val His Leu Gly Thr Ile Pro Ala Lys Arg Glu
        50                  55                  60

Lys Cys Leu Pro Tyr Glu Ala Tyr Ile Ser Leu Lys Asn Met Val Glu
65                  70                  75                  80
```

```
Asn Leu Lys Ile Glu Asn Pro Gly Val Cys Lys Lys His Gln Trp
                    85                  90                  95
Leu Leu Asn Lys Ile Lys Lys Gln Gly Glu Leu Gly Leu Lys Asn Leu
            100                 105                 110
Val Ser Pro Gly Ser Val Gly Gly Ser Arg Gly Tyr Arg Lys Lys Glu
            115                 120                 125
Phe Asn Ile Tyr Asn Lys Gln Ile Thr Ser Thr Met Leu Ala Val Gly
        130                 135                 140
Ile Lys Pro Glu Lys Phe Pro Val Val Arg Ala Gln Thr Ser Lys Arg
145                 150                 155                 160
Glu Phe His Gln Ala Ile Arg Glu Lys Ile Asp Lys Leu Pro Asn Pro
                165                 170                 175
Gln Asn Arg Asp Leu His Lys Glu Leu Lys Glu Ile Phe Asp Ser Val
            180                 185                 190
Cys Ala Val Lys Asp Leu Lys His Thr Tyr Glu Glu Val Ser Trp Asp
            195                 200                 205
Val Leu Thr Val Gly Ile Asn Arg Lys Gly Ala Ala Gly Tyr Phe Glu
        210                 215                 220
Lys Lys Asn Val Gly Glu Ile Ile Asp Thr Asp Arg Arg Gly Val Glu
225                 230                 235                 240
Lys Leu Ile Lys Val Met Lys Thr Gly Gly Pro Ile Asp Tyr Tyr Glu
                245                 250                 255
Thr Ala Ile Pro Lys Asn Glu Lys Arg Ala Val Val Asp Asp Trp Leu
            260                 265                 270
Glu Gly Asp Phe Val Glu Glu Lys Lys Pro Arg Val Ile Gln Tyr Pro
        275                 280                 285
Glu Ala Lys Met Arg Leu Ala Ile Thr Lys Val Met Tyr Asn Trp Val
    290                 295                 300
Lys Gln Lys Pro Val Val Ile Pro Gly Tyr Glu Gly Lys Thr Pro Leu
305                 310                 315                 320
Phe Lys Val Phe Asp Lys Val Phe Asp Glu Trp Lys Gln Leu Arg Asp
                325                 330                 335
Pro Val Ala Val Ser Phe Asp Thr Lys Ala Trp Asp Thr Gln Val Thr
            340                 345                 350
Pro Glu Asp Leu Gln Leu Ile Ser Glu Ile Gln Lys Tyr Tyr Phe Lys
        355                 360                 365
Pro Lys Tyr His Lys Phe Ile Glu Thr Leu Thr Ala Glu Met Lys Glu
    370                 375                 380
Val Pro Val Val Cys Gln Asp Gly Glu Val Tyr Ile Arg Leu Gly Gln
385                 390                 395                 400
Arg Gly Ser Gly Gln Pro Asp Thr Ser Ala Gly Asn Ser Met Leu Asn
                405                 410                 415
Val Leu Thr Met Ile Tyr Ala Phe Cys Lys Ser Asn Asp Ile Pro Tyr
            420                 425                 430
Lys Ala Phe Arg Arg Val Ala Lys Ile His Val Cys Gly Asp Asp Gly
        435                 440                 445
Phe Leu Ile Thr Glu Arg Arg Leu Gly Glu Asn Phe Ala Ala Met Gly
    450                 455                 460
Pro Gln Ile Leu Met Glu Ala Gly Lys Pro Gln Lys Leu Val Gly Glu
465                 470                 475                 480
Met Gly Leu Lys Leu Ala Tyr Lys Phe Gln Asp Ile Glu Phe Cys Ser
                485                 490                 495
His Thr Pro Ile Gln Val Arg Trp Asp Asp Asn Thr Thr Ser Tyr Leu
```

```
            500             505             510
Pro Gly Arg Asp Thr Ala Thr Ile Leu Ala Lys Met Cys Thr Arg Leu
            515                 520             525

Asp Ser Ala Gly Glu Arg Gly Thr Ser Ser Tyr Glu Leu Ala Val Val
        530                 535             540

Phe Ser Phe Leu Leu Met Tyr Ser Trp Asn Pro Ile Val Arg Arg Ile
545                 550                 555                 560

Cys Leu Leu Val Met Ala Thr Ile Gly Val Lys Asp Pro Asp Lys Ser
                565                 570             575

Gly Thr Ile Phe Thr Phe Ser Gly Asp Pro Leu Gly Ala Tyr Lys Glu
            580                 585             590

Val Ile Gly His Arg Leu Gly Gln Leu Lys Gln Thr Glu Phe Ser Lys
            595             600             605

Leu Ala Ser Cys Asn Leu Ser Met Ser Leu Leu Gly Ile Tyr Ser Arg
        610                 615             620

His Thr Ser Lys Arg Ile Ile Glu Asp Cys Val Lys Ile Gly Thr Leu
625                 630                 635             640

Asn Arg Gln Ser Pro Val Asn Ala Asp Arg Leu Ile Ala Lys Lys Thr
                645                 650             655

Gly Phe Val Tyr Glu Pro Ser Arg Gly Ser Val Arg Val Gly Lys His
            660                 665             670

Tyr Glu Glu Leu Glu Leu Asp Lys Trp Lys Lys Thr Pro Leu Ile
            675                 680             685

Glu Gly Ala Glu Arg Tyr Ile Pro Gly Pro Ile Lys Thr Phe Ile Leu
        690                 695             700

Lys Arg Leu Lys Val Leu Gln Met Ile Gly Leu Lys Phe Phe
705                 710             715

<210> SEQ ID NO 16
<211> LENGTH: 381
<212> TYPE: DNA
<213> ORGANISM: Porcine pestivirus

<400> SEQUENCE: 16
gtatagcagc agtagctcaa ggctgctata cgattggaca taccaaattc caattggtgt      60
tagggaccac ctaggtgaag gccgacgaca ggtagccatt cctgttagta ggacgaaccg     120
ttatggtgga ctggttgctc aggtgagcag gctgcaatgc gtaagtggtg agtacaccac     180
agccgtcaaa ggtgccactg gtaaggatca cccactggcg atgccttgtg acgggggcg     240 tgcccaacgc aatgttagcg gtggcggggg ctgccatcgt gaaagctagg tcttgatgga     300
ccttgttgcc tgtacagtct gataggatgc cggcggatgc cctgtgacag ccagtataaa     360
gaatatccgt tgtgattgca c                                                381

<210> SEQ ID NO 17
<211> LENGTH: 546
<212> TYPE: DNA
<213> ORGANISM: Porcine pestivirus

<400> SEQUENCE: 17
atggagttta aaattctcaa caacacaaag aaaaaaaata ataatgagga ggaagctgag      60
gggaacatgt tctggcggat gtaccgaaga cctccgcctg gttgctacga accaacttac     120
aacctaagtg ggacacctag cttcggaccc atgcacccac cactgaggaa agggagtaca     180
ttacgtttac cccactggag aggcatagcc acggttggat gtgagcttaa aaacctgcca     240
```

```
cgcaagggtg attgtactaa gtgccacgct aacccaacat ctggcatcta cctcaacctg    300
ggtgcggtgt tttataaaga ttacgagggg gaggtatacc atagagtccc ccttgaacac    360
tgtgaggaac agcagaggtg cgaagtcgtc aagcgtgtag ggagaatgac tgctagcgat    420
ggatccttgg tgggagtgct agtatgcagt gacgactgcg tgctgtttga gagaagaaga    480
ggggaacaca cagtgttgaa gtgggtaaag aaccctatcg gggcgccact ctgggtacag    540
agctgc                                                               546

<210> SEQ ID NO 18
<211> LENGTH: 303
<212> TYPE: DNA
<213> ORGANISM: Porcine pestivirus

<400> SEQUENCE: 18
tccgacgaga agggggccaa accaaaaaac aagtctaaac aacaaaacga tcgaatggca     60
ccgggtaaaa tggtgacaaa acctaaggaa gtggaagctg atcagaaaac tagaccgcca    120
gacgctacaa ttgtggtgga tgacagaaaa tatcaagtaa ggaagaaagg gaaggcaaaa    180
ccaaagacac cagatggcct gtaccacaat aaaaacaagc cggaggcatc tagaaagaaa    240
ttagaaaaag cgctactagc ttgggcagtc attgcaataa tattgattca gcagaccaca    300
gca                                                                  303

<210> SEQ ID NO 19
<211> LENGTH: 663
<212> TYPE: DNA
<213> ORGANISM: Porcine pestivirus

<400> SEQUENCE: 19
aacaatgtga cgcagtggaa cttgtgggac gacaagaacg caacagatgt gcactcagtg     60
atgcatcaga gacaaatcaa gcgcagcctc cacggcatct ggcctgaaag aatctgcaaa    120
ggggtcccag gtcatctggc tactgactat gagctaaaac ggatagaggg gatgttggat    180
gccagcgaaa aaactaattt tacctgttgc aggctgcaaa gacacgaatg gaacaaacat    240
ggctggtgta actggtacaa tatagacccc tgggtcgcca ttatgaacag gacccaagcc    300
cttctatcta gtggccaaaa cttttacagag tgtgccgtta catgtaggta tgacacagaa    360
cagcagataa acatagtaac tcaagcccgc atgacaccaa cgattttaac agggtgtaag    420
aaggacgtaa acttctcttt ctcaggggag gtgaggactg ggccttgcaa ctatgaactg    480
aagccagaag acttaatgag gattctggac cataccaact gcaaagattt cagctatttc    540
ggagaaggtc tggtggatga tttcacagaa gccacggaaa aaattagatc tagtgggtac    600
agggccctgt cgtggctgca agacaagcta gagaaaacta gaagaaggt gtttggagct    660 gaa                                                                  663

<210> SEQ ID NO 20
<211> LENGTH: 594
<212> TYPE: DNA
<213> ORGANISM: Porcine pestivirus

<400> SEQUENCE: 20
gcaacaccat actgcaatgt gacaaggagg gtttttcaaca tcatatacac caacaactgc     60 accccccgctg gactgccaga taacacgagg atagttgggc cagggacatt tgacatcagt    120
gaaatgaaaa taaaaaaact gttacccaac ttggactacc acttggcaga tttcatggta    180
ctgggcttag tggctttatc cgactttgcc ccagaaactg ctagtacaat ctatctggta    240
```

```
ttgcactact ggctgcctca ggcagaggtg catacattgg acaccccact tgacaccaac    300
aagctgaatc taacaaggaa caggcaggtt agtagtgtag tccctaattc aatatggttg    360
ggagggcagc tggtgtgcgt caagccaagg tggtggccct actcagcaga aattacaaca    420
gtgattagcg gactgaccac tgtaaccgac ctagtggtca agaccataga ggaacttgtg    480
agcttgtgga cagaggcaac agcagtagcc ttcttggcag ccctgataaa gatcttcaga    540
ggacaaccaa tacaagcact agcatggctc ataataatag ggggagccca gggt          594
```

<210> SEQ ID NO 21
<211> LENGTH: 1125
<212> TYPE: DNA
<213> ORGANISM: Porcine pestivirus

<400> SEQUENCE: 21

```
cttgaatgca acttcgaact gcaatacgct ctggccggga acacatccat gagcctacta     60
gggccaactg cctaaagac tcaatggtac caagcggcag acggggtcaa aataacggat    120
ggggtagtaa ctgtgatatg caacaagggc attttctcgg tgactcctag gtgcaaagag    180
gcacctgtaa ggtacctggc aatcaaccac cccaggtcct tatcaaccag tgcttggttc    240
aagaaaatac acgacccggc agaccatccg actgagacac tgatgggcga aaagggaagg    300
gcatacctct gcccttgcgg ggctacacca ctaccaaaac ccaaggttcc gtttaaccca    360
atcacaatac aaggttcggc gttctcccta acatgcccaa aaaactggca aggtgacata    420
gaatgcaatc tcttaagccc agacacacta gcaattgaaa ccatatacac cttcagaaaa    480
cataagccat acaaagaaga accctactgc tcgtacacta aggtagtgga cgggtacttg    540
cgcaacgtgc acctatgggg gcatgataca tgtgtggcag agatataat caatggcagt    600 caagatgaca gtgtgaccaa gtgcaaatgg tgtgggtatg agttcaattc agcaactgac    660
ttacctgact acccaattgg ttactgcacg aagcgaggca ccaattatct aatcaggtac    720
aagcaggtgc cttgtgaggt aggaggagtc cgcatcgggt caggaaaagt agagtgtacc    780
attggctcca cgagagtaaa agtagaacaa accagtaatg agttgggtcc gatgccctgc    840
aagccaatag tatattcatc tcaaggaccg cctaatccaa aaacgtgtac attcaaatgg    900
agctacacat taaacaacaa gtactacgag ccaagggatg aattcttcca acagtacata    960
acctcaggtg gctatcagta ttggtttgac ctgacagcaa aagatcacgt gatggattgg   1020
gtaacacgat acttccccat tatagttgta gcattactgg ggggtagagc agtgctgtgg   1080
atcctaattg cgtacgagtt gctaaatcac taccaagtgg gcgca                   1125
```

<210> SEQ ID NO 22
<211> LENGTH: 225
<212> TYPE: DNA
<213> ORGANISM: Porcine pestivirus

<400> SEQUENCE: 22

```
gaccagaaca cattgctgca ggccgaagca ctagtgatag gtaacatcct gatgacaaga     60
gacctggaag tgatggtgtg ctttctgttg ctgatggtct tgataagaag acagcaggct    120
agaagggctt tggccttggt tttccattgg atggtaatgc atcccgccca atcagccatc    180
gcaacattgg tgtacgtaat aggcatcgtg agagctgaag aggga                    225
```

<210> SEQ ID NO 23
<211> LENGTH: 1368
<212> TYPE: DNA

<213> ORGANISM: Porcine pestivirus

<400> SEQUENCE: 23

| | | | | | |
|---|---|---|---|---|---|
| caggttaact | ctgacagttc | tacgcaagca | cacgtggtgg | ccattttgtt | gtttctaatt | 60 |
| taccacacac | taaaagaaag | ggaccttcac | acagctatga | cattactgtt | gacatttttcc | 120 |
| ataaagagca | ctgactatgt | agacacacat | tattatgaaa | taccgatgct | cttcacagtt | 180 |
| atttcgttgg | tcatttccat | ttacatattc | aacatacaca | taaaaaccaa | gtgggtagct | 240 |
| ctggtgctca | gtatggtggg | catggtcacc | tttataaggt | gcctttggtt | gatcaggaac | 300 |
| atacaaataa | cacccccttc | cataccacta | acatacatca | gtccaaaaat | attgatcata | 360 |
| gcttacctgg | tttctctgac | tgtcttggtg | aataacaacc | tagacctcgc | cagctacgtg | 420 |
| atcagggctg | gcccgatact | aatgtcctac | ttaactttat | gggtggacat | cctgatgttg | 480 |
| ctagttctac | taccttggta | tgaattgatt | aaagtctatt | acctaaagaa | gaagaaagac | 540 |
| gacatagaag | actgcttcca | atacagcggg | atagccactc | aagggttatc | cccgtacaat | 600 |
| caggacttcg | tggacccaaa | agaggggta | cacttgatcc | cctcacaaaa | caagagcaat | 660 |
| ttcacccgga | ccgcatatct | gactatcctg | agggccctag | ttctcacagc | tttcagcagc | 720 |
| atttggaagc | ctctaatcct | agccgaactg | ctattggaat | ccatttattg | gacacacatc | 780 |
| aaagttgcaa | agaagtggc | gggatctacg | aggcttatag | gtaggtttgt | agcggccctg | 840 |
| atagaactaa | attgggtttt | tgatgacaag | gaagcagcaa | gatacaaaaa | attctttgtt | 900 |
| ttaacctcaa | gagtgagaga | cctcatggta | aaacacaagg | tgcagaacga | cacaatgagg | 960 |
| cagtggtttg | aagagacgga | aatattcggc | ttacaaaaag | ttgccttggt | ggtcagagca | 1020 |
| cactcactga | cagcagacag | caacagtata | ctatgctcag | tgtgtgagga | aaaacagaac | 1080 |
| atagaagcca | agagggtatg | tcccaagtgt | ggaaacagag | aacaggaat | caagtgcggg | 1140 |
| atgaccttgg | ctgagtttga | agaaaaatat | tacaaaaaga | tctatctagt | ggatggagac | 1200 |
| aatacgcaag | catatcgcag | agaggagaga | ggagaagtca | cgtacacagc | tagggggcgcc | 1260 |
| ttcttcttga | ggaacttacc | cattctggcc | acaaaaaaca | agtatatact | ggtaggtaac | 1320 |
| ttaggtatgg | aattacaaga | ccttgagtcc | atgggggtgga | ttatcagg | | 1368 |

<210> SEQ ID NO 24
<211> LENGTH: 2049
<212> TYPE: DNA
<213> ORGANISM: Porcine pestivirus

<400> SEQUENCE: 24

| | | | | | |
|---|---|---|---|---|---|
| ggcccagctg | tctgcaaaaa | gatagtgcac | catgaacgct | gcaggcccac | catccctgat | 60 |
| aaacttatgg | ctttctttgg | gctcatgcca | agaggcgtag | tccccccgggc | accaaccccgc | 120 |
| ttccctgtat | cattactgaa | aattaaaagg | ggtttcgaaa | cggggtgggc | atatacacac | 180 |
| cctggaggga | tcagcagcgt | aatgcatgta | acagcaggct | tggacatgta | cgtcaatgat | 240 |
| gccatgggta | gaaccaaggt | gcagtgccaa | gagagaaaca | agctgacaga | cgaatgtgag | 300 |
| tatggcatta | aaactgactc | aggctgctct | gaaggggcac | gctgctatgt | aataaatccc | 360 |
| gaagccgtca | acatagcagg | caccaggggc | gctatggtac | acctcagaaa | aacaggtcca | 420 |
| gaatttaccct | gtgtgacagc | ccaaggaacc | ccagccttct | acaatttgag | gaatcttaaa | 480 |
| ggttggtcag | ggctaccaat | attcgaggca | gctacgggaa | gggtggtagg | cagagtgaaa | 540 |
| gcaggcaaga | atgcagagga | tagtccaaca | actataatgt | ctggcaccca | ggcagccaaa | 600 |
| ccgacagagt | gtgacctgga | gtcggtcgta | aggaagctgg | aaaccatgaa | cagaggggag | 660 |

```
ttcaagcagg tggtgctagc aactgggca gggaagacaa cagaactgcc aaggaagcta      720
atagaagccg tggggcggca caagagggtt ttagtcctaa tccccctgag agcagcagca      780 gaggggttt ataactatat gagaacaaag catccaagca tagcattcaa cctgaggata      840
ggggacttaa aagaaggaga catggcaact ggtataactt atgcctcata tggttatttt      900
tgtcaaatgg acatgccacg gctagatgca gctatgaagg agtacaacta catattcctg      960
gacgaatatc attgtgcaac accagagcaa ttggctgtga tgtcaaaaat acacaggatc     1020
agtgctgacc taagagtggt ggccatgaca gctacccctg caggcgctgt gtcaaaggtg     1080
ggccagaaat tctccataga agaagtggtg gtgccagagg taatgaaagg ggaagaccta     1140
ggcgaggatt atttggacat agccggacta aaaataccaa aatcggaact acaagggaat     1200
gtcttaacgt ttgttccgac aaaaaagttg gcgtcagaca ctgctaagaa actaaccacc     1260
cagggctaca acgctgggta ttactttagt ggtgaagacc caagctcgct gcgcaccata     1320
acatcaaaat ccccgtacat cataatagcc accaatgcaa tagagtcagg ggtgacatta     1380
ccagacctag acacagtaat tgacacaggg atgaagtgtg aaaagagggt gagaatagag     1440
aacaaggctc catacataat aacaggccta aaaagaatgg ccatcaccac aggggagcaa     1500
gcccagagga agggaagagt aggtagagtc aaaccaggga gatacctaag agggcctgaa     1560
aatgcaggtg gagagagaga ttatcactat gacctgctgc aggcacaacg ttatgggctc     1620
caggatgcta tcaacatcac caaatcattc agggagatga actatgactg ggcactctat     1680
gaggaagacc cactgagaat aacacaattg gaggtattaa ataccctact catatccaaa     1740
gatctgccaa cagtcacaaa gaatttgatg accaggacca cacacccaga accaattcaa     1800
ttagcttaca atagcataga acccccgtc ccagtgctgt tcccgaaagt gaagggtgga     1860
gaggtgaccg atgcttatga gacctatgaa ctgatgatgt gtcggaagct ggataacgac     1920
cccccgattt atctgtatgc cacggaagat gaagacctag cagtggacct cctgaacctg     1980
aaatggcccg cagtgtcaac agcctcggcc atagaaacag aggacgccct caacaagtta     2040
tcggggctt                                                            2049

<210> SEQ ID NO 25
<211> LENGTH: 189
<212> TYPE: DNA
<213> ORGANISM: Porcine pestivirus

<400> SEQUENCE: 25
tcggcagggg aaacagccct gctagtggct ctgctaggtt gggtcggtta cgaggctctg       60
gtgaaaagac acataccaat agtgactgac atatatacaa ttgaagatga aaaacttgag      120
gacaccaccc acctccagta ttcaccagat gaactgcaaa acaccgagac agtggagctg      180
aaagacctg                                                              189

<210> SEQ ID NO 26
<211> LENGTH: 1041
<212> TYPE: DNA
<213> ORGANISM: Porcine pestivirus

<400> SEQUENCE: 26
tcggcacacg aactgaaaga agccctggaa agcggaaaaa gttatgtcaa agacgccttt       60
gaattcgtaa aatcacaggt tgagaagctc cccgacacaa aaatttacaa gcaagtccaa      120
gagaagtcac ccggtctttt agaaaaattt ttggcctatc tgtcagaaca cagtagtgac      180
```

```
ataaagaaat atggattgtg gggggtccat acctctctgt acaatagtat caaagagaga      240
ttggggcacg aaactgcctt cgcttcattg atcatcaagt ggatagcatt ttccagcgaa      300
gggctgcctg aatggtgaaa acaagctgct gtagacttgg tggtatatta tctgatcaac     360
aaaccagatt tcaaaggtga caaagacacc caagatgatg aaggaagtt cgtaggagcc      420 ctgttcgtgt cagctctggc caattacaca tttaaaaatt ttaataagtc aacacttgaa     480
ggcttagtaa tgccagcatt gaactaccta ccatatgcag gggctgcact aaaaatattt     540
gtgcctacta aattagagag cttagtaata ctgtcaacaa ccatctacag gacctacctc     600
tccattaaga aaggctctag tcaaggactg gctgggttag cagtgagctc aggtatggaa     660
attatgaatc agaatccaat atcagtggcc attgcggtgg cattgggagt cggtgccata    720
gctgcacaca atgcgatcga gagcagcgag gcaaagagga ccctgttgat gaaggtattt     780
gtgaaaaact ttctagacca ggcagcgaca gacgagctgg taaaagagaa cccagaaaaa     840
ataataatgg cagtatttga agcaatccag acagcaggta atccaataag gctaatatac    900
cacctatatg ccatgttcta caaaggttgg aacgcctccc agatagcaga taagacagcg     960
gggaggaaca tattcgtgct gacaatattc gagggtttag aactgttggg actagacaag   1020
gattccaagt ggagggattt g                                              1041

<210> SEQ ID NO 27
<211> LENGTH: 1512
<212> TYPE: DNA
<213> ORGANISM: Porcine pestivirus

<400> SEQUENCE: 27
agctcaaatt atttagtgga tgcaatcagg aagctcattg aaaaattgac taaaatactc     60
agaaacacca ccaagtcatt aatcaaatcc ttgctgccag ctccattctc ttgcacgaga    120
ttcacaagag acaacagaat tggatggcca catttaaatt ttgattatta cgagataaat    180
tgtgcatgtg ggtaccggag gagagtggta aaaactgtca tcgacccagt cacctgggag    240
actttggaag aagaaggccc tgagttctgc ttcaacaggg ggactaacgc cctggcaaac    300
ccaagagttg caagttatta ctcagctgga gagccagttc tcccagtggt aaaaagagag    360
ggggttggcg aaatcctggt aagggggtg acaatccaga tgcattatga ccacaacaag    420
atactcgcca ctgacaactg gcaagtgcca ttccaggcag tgacgaagat atttacagat   480
taccagggca tagggtacca agaagcatat ctgggaaccc agccaaacta caaagcactg   540
gtgaagaggt catccgtcac gattacaaaa gaaggcctga aatttataag atgcaagaaa   600
gggatcgcgt atacgaccaa tctaaactta acccacatcc aaaagctggt gcaggtgtgc   660
agaatgaatg aattgcaaga aggcgtcata cctgagacct tggatggcga cacctggatt   720
aactacatgg caatcatcga agatgtgggg gccacaaaac caagcttgga gagagagtca    780
tacccgaaac catacgagga ggatccccstc gaaggcccca gtgtgatcgt ggaaacaggg   840
gacgtggaca tcacaaaagt gggcgtaaat caacaatcca gttcatcagg aaccgtcttt    900
caagtagtgg agaagatcta tactaaactg gtcaatacaa atgtaataaa gataggattc    960
aaagaaggct gtttccccggg acccacaaag aatgtgaatt cattgaatga gcacatagaa   1020
gataaagaca gtaaaccata catcttcata tgctcttccg acaaagcaat gtccaacaga   1080
gtaaagactg caaggaacat taagaaactc aacacaaatt cggcaatagt agcccgtaat   1140
ttggccaggg aagggaaatt gatcataata gtactaggag agaagtacca tgaggacatc    1200
tacaaacatg ctgacttcaa ggggactttc ctcgacagga aggcactgga agccctgtcc   1260
```

```
aaggccaagc ctgtaaaaaa gaacatgact aggagagagg ctcaatatct gctggaaaag   1320
aagcttagtg aagacataga ggtaccagaa tggctgggat ctgaaaaacc tatgtttttg   1380
gatgtaacca aaagtggtga acataccat ctgttagggg atctaaatca cttgaaggca   1440
caagcggaac aacttggtgc caaggcaacc actacaataa ataaagtagg aagacgtat   1500 acaatgaacc tc                                                      1512

<210> SEQ ID NO 28
<211> LENGTH: 2154
<212> TYPE: DNA
<213> ORGANISM: Porcine pestivirus

<400> SEQUENCE: 28
agtacatggt gggagagtga aagaaccccc acattcagac ccctgttcca ggaactgctg     60
ttacgctgca ggccatgcac tagggaggag tataagagct gccattttgt aggggctaca    120
caattggccg gaggaaactg gaaaccagta gcccctgtgg tgcacctagg aactatacca    180
gcaaaaagag agaaatgcct gccatatgaa gcatatatat cacttaagaa tatggtggaa    240
aacctaaaaa tagagaatcc tggagtgtgc aagaagaaac atcagtggct cttaaataaa    300
attaaaaaac aaggggaatt aggcttgaag aatctcgtat ctcctgggag tgtagggga    360 tcacgtggtt acagaaagaa agaattcaac atttacaaca aacagattac gagcacaatg    420
ctggctgtgg ggatcaagcc agagaagttt ccagtcgtca gagctcaaac gtccaagaga    480
gaattccatc aagcaattag agagaagatt gataagctgc ccaaccccca gaataggga    540 ctccataagg aactgaaaga aatatttgac tcggtgtgcg ctgtaaaaga tttgaaacat    600
acctacgaag aagtcagctg ggatgtactg acggtgggga tcaacaggaa aggagcagct    660
ggctatttcg aaaagaagaa tgtgggtgag ataatagaca ctgacaggag aggggtcgag    720
aaacttatca aggtaatgaa aaccgggggga cctatagact actatgagac agcaatacct    780
aagaatgaga agagagcagt tgtagatgac tggctggaag gagatttcgt tgaagagaaa    840
aagccacgag tgatccaata cccagaagca aaaatgcgtt tggcaataac caaagttatg    900
tacaattggg tcaagcaaaa accagtggtg ataccccggggt acgaggggaa gacacctttg    960 ttttaaaagtgt tgataaggt ttttgatgaa tgggaacaac tgagagaccc ggttgcagtc   1020
agtttcgaca ctaaagcatg ggatacacaa gtgacacctg aggacttaca attgatatcg   1080
gaaatccaaa agtattactt taaaccaaaa taccacaaat ttattgaaac attgactgcg   1140
gagatgaaag aagtgccagt cgtgtgccag gatgggagg tttacatcag gctaggacag   1200
agaggaagtg gccagccaga taccagtgca ggaaatagca tgttgaatgt gttgacaatg   1260
atatatgctt tttgcaaatc caatgacatc ccgtacaagg cattccgaag ggtggcaaaa   1320
atacacgtct gtggcgacga tgggttccta attacagaga ggcgcctagg agagaacttt   1380
gctgcgatgg ggccacaaat actgatgaa gccggaaac cacagaaact ggtaggagag   1440
atgggactga agctagccta caagttccag gacatagagt tctgctccca cacgcctata   1500
caagtaaggt gggatgacaa cacaactagt tatttaccag gcagagacac ggcaaccatc   1560
ttagcaaaga tgtgtaccag gctggactcc gcaggggagc gggtaccag ttcctatgaa   1620 cttgctgttg tgtttagttt cctcctaatg tactcctgga acccaatagt tagaaggatc   1680
tgcctattag ttatggcaac aatcggagta aaagacccag ataaatcagg aacaatattc   1740
accttctctg gagacccact aggggcgtac aaggaagtaa taggacaccg attgggccaa   1800
```

```
ctaaaacaaa ctgaattttc aaaattggca agttgcaatt tatcaatgtc actgttaggg    1860
atttacagta ggcacacctc aaaaagaatc atagaggact gtgtgaagat tggaacccta    1920
aaccgacaga gccccgtgaa tgcagatcgc ttgatagcaa agaagactgg ttttgtatac    1980
gaaccgtcaa ggggcagtgt tagggtggga aaacactatg aagaattgga attggacaaa    2040
tggaaaaaga agacgccact catagaaggg gcggaaaggt acattccagg cccgattaag    2100
acctttatac tgaaaagact caaagtgtta cagatgatag gcctgaaatt cttc          2154
```

<210> SEQ ID NO 29
<211> LENGTH: 464
<212> TYPE: DNA
<213> ORGANISM: Porcine pestivirus

<400> SEQUENCE: 29

```
taatatatag ggagtacagg ttacagctgt gtttcacaga aagtgggtgg cgacacttac      60
ctctggagcc aacttgtaaa taggttagta atatttattt aatagacgtt atttacttat     120
ttatttattt atttgattat ttattaatta tttaaaaacg ctactgcatg agctggttag     180
tcagcttatg aaagtgggtt gtgtcacttg cgtcaggagc aaatacctca ataacaacgc     240
taccacatag cctgagacca ggttgtgaaa gagagttgcg cctcttgcgt tgggagctat     300
ctacctcaag tacccagctg ctgaagctgg ttacctcaat tccaatggat gaccgtagcc     360
attggtctta ttaattcggt catttataat tagcacttta aagctaattg ggacataaag     420
taaggacgtc ctagggagga ctacttacag ttccaagagg cccc                      464
```

<210> SEQ ID NO 30
<211> LENGTH: 4
<212> TYPE: PRT
<213> ORGANISM: Porcine pestivirus

<400> SEQUENCE: 30

Met Glu Phe Lys
1

<210> SEQ ID NO 31
<211> LENGTH: 4
<212> TYPE: PRT
<213> ORGANISM: Porcine pestivirus

<400> SEQUENCE: 31

Ser Cys Ser Asp
1

<210> SEQ ID NO 32
<211> LENGTH: 20
<212> TYPE: PRT
<213> ORGANISM: Artificial Sequence
<220> FEATURE:
<223> OTHER INFORMATION: Primer

<400> SEQUENCE: 32

Gly Thr Lys Ala Thr His Cys Ala Ala Thr Ala Cys Cys Cys Thr Gly
1               5                   10                  15

Ala Arg Gly Cys
            20

<210> SEQ ID NO 33
<211> LENGTH: 19
<212> TYPE: PRT
<213> ORGANISM: Artificial Sequence

```
<220> FEATURE:
<223> OTHER INFORMATION: Primer

<400> SEQUENCE: 33

Gly Gly Arg Thr Thr Cys Cys Ala Gly Gly Ala Arg Thr Ala Cys Ala
1               5                   10                  15

Thr Cys Ala

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
ggccacgcgt cgactagtac                                             20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ggccacgcgt cgactagtac                                             20

<210> SEQ ID NO 36
<211> LENGTH: 381
<212> TYPE: PRT
<213> ORGANISM: Bungowannah virus E2

<400> SEQUENCE: 36
```

Gln Thr Cys Asn Pro Glu Phe Met Tyr Ala Leu Ala Lys Asn Thr Ser
1               5                   10                  15

Ile Gly Ser Leu Gly Pro Glu Ser Leu Thr Thr Arg Trp Tyr Gln Leu
            20                  25                  30

Thr Ser Gly Phe Lys Leu Thr Asp Ser Thr Ile Glu Val Thr Cys Val
        35                  40                  45

Gly Ala Asn Met Arg Ile His Val Val Cys Pro Leu Val Ser Asp Arg
    50                  55                  60

Tyr Leu Ala Ile Asn His Pro Arg Ala Leu Pro Thr Thr Ala Trp Phe
65                  70                  75                  80

Arg Lys Ile His Thr Gln His Glu Val Pro Arg Glu Arg Ile Met Ser
                85                  90                  95

Glu Ser Lys Arg Arg Tyr Thr Cys Pro Cys Gly Ser Lys Pro Val Val
            100                 105                 110

Arg Ser Thr Thr Gln Phe Asn Pro Ile Ser Ile Ser Thr Pro Ser Phe
        115                 120                 125

Glu Leu Glu Cys Pro Arg Gly Trp Thr Gly Ala Val Glu Cys Thr Leu
    130                 135                 140

Val Ser Pro Ser Thr Leu Thr Thr Glu Thr Ile Phe Thr Tyr Arg Lys
145                 150                 155                 160

Pro Lys Pro Phe Gly Leu Glu Asn Trp Cys Lys Tyr Thr Val Val Glu
                165                 170                 175

Lys Gly Ile Leu Tyr Ser Cys Lys Phe Gly Gly Asn Ser Thr Cys Ile
            180                 185                 190

Lys Gly Leu Ile Val Lys Gly Gln Arg Glu Asp Lys Val Arg Tyr Cys

```
            195                 200                 205
Glu Trp Cys Gly Tyr Lys Phe Ser Ser Pro Asn Gly Leu Pro Gln Tyr
    210                 215                 220

Pro Leu Gly Leu Cys Glu Lys Glu Gln Ser Glu Gly Leu Arg Asp Tyr
225                 230                 235                 240

Gly Asp Phe Pro Cys Cys Asn Asn Gly Thr Cys Ile Asp Lys Glu Gly
                245                 250                 255

Ser Val Gln Cys Tyr Ile Gly Asp Lys Lys Val Thr Val Lys Leu Tyr
            260                 265                 270

Asn Ala Ser Leu Leu Ala Pro Met Pro Cys Lys Pro Ile Val Tyr Asn
        275                 280                 285

Ser Gln Gly Pro Pro Ala Pro Lys Thr Cys Thr Tyr Arg Trp Ala Ser
    290                 295                 300

Thr Leu Glu Asn Lys Tyr Tyr Glu Pro Arg Asp Ser Tyr Tyr Gln Gln
305                 310                 315                 320

Tyr Ile Ile Lys Ser Gly Tyr Gln Tyr Trp Phe Asp Leu Thr Ala Lys
                325                 330                 335

Asp His Val Ala Asp Trp Ile Thr Lys Tyr Phe Pro Ile Ile Ile Val
            340                 345                 350

Ala Leu Leu Gly Gly Arg Gly Thr Leu Trp Val Leu Ile Ala Tyr Glu
        355                 360                 365

Leu Leu Thr Gln Tyr Glu Val Val Gly Asp Glu Asn Ile
    370                 375                 380

<210> SEQ ID NO 37
<211> LENGTH: 371
<212> TYPE: PRT
<213> ORGANISM: Pronghorn pestivirus E2

<400> SEQUENCE: 37

Leu Glu Cys Asp Thr Asn Phe Gln Tyr Ala Leu Ala Lys Gly Thr Lys
1               5                   10                  15

Ile Gly Pro Leu Gly Ala Glu Glu Leu Thr Thr Thr Tyr Arg Arg Leu
                20                  25                  30

Gln Pro Gly Glu Gln Leu Thr Asp Gly Leu Val Thr Ile Thr Cys Thr
            35                  40                  45

Asn His Asp Ile Ile Ile His Asp Gln Cys Ser Ile Glu Arg Arg Trp
        50                  55                  60

Ile Ala Lys Ile His Pro Gln Ala Leu Pro Thr Ser Val Gln Phe Tyr
65                  70                  75                  80

Leu Ala Ala Glu Pro Lys Glu Ala Pro Lys Ile Ile Glu Met Ser Asp
                85                  90                  95

Glu Phe Glu Phe Ala Ile Cys Pro Cys Asp Ala Leu Pro Leu Val Lys
            100                 105                 110

Gly Asn Phe Asn Cys Thr Leu Thr Asn Ala Gln Ala Phe Gln Met Val
        115                 120                 125

Cys Pro Tyr Gly Trp Val Gly Thr Ile Glu Cys Val Lys Tyr Ser Pro
    130                 135                 140

Thr Thr Leu Ser Thr Thr Val Val Gln Val Tyr Lys Arg Gly Arg Pro
145                 150                 155                 160

Phe Pro Arg Arg Arg His Cys Thr Thr Glu Glu Val Phe Gln Gly Asn
                165                 170                 175

Tyr Tyr Thr Cys Glu Lys Gly Gly Asn Trp Thr Cys Gln Pro Gly His
            180                 185                 190
```

```
Ile Ser His Gly His Asn Ser Asp Glu Val Glu Cys Glu Trp Cys
        195                 200                 205
Gly Phe Arg Ser Leu Lys Pro Ser Ala Lys Leu Gly Arg Cys Ile Arg
210                 215                 220
Arg Gly Glu Lys Ala His Arg Leu Tyr Asp Thr Arg Pro Cys Lys Glu
225                 230                 235                 240
Lys Ala Phe Thr Phe Ser Pro Ala Gly Glu Val Glu Cys Leu Leu Gly
                245                 250                 255
Gly Phe Lys Val Arg Val Asp Arg Ser Asp Thr Thr Asn Glu Leu Leu
            260                 265                 270
Pro Met Pro Cys Asn Pro Ile Lys Val Gly Ser Gln Gly Pro Val Ser
        275                 280                 285
Arg Ala Ala Cys Thr Tyr Asn Tyr Ser Gln Val Leu Arg Asn Ser Tyr
    290                 295                 300
Tyr Glu Glu Arg Asp Lys Phe Trp Gln Gln Tyr Met Ile Lys Asp Gly
305                 310                 315                 320
Tyr Gln Tyr Trp Phe Asp Leu Glu Ala Asp His His Lys Asn Trp
                325                 330                 335
Phe Asn Glu Phe Leu Val Val Val Val Ala Leu Leu Gly Gly Arg
            340                 345                 350
Tyr Ile Leu Trp Leu Ile Ile Ile Tyr Met Thr Leu Thr Tyr Tyr Pro
        355                 360                 365
Asp Asp Ala
    370

<210> SEQ ID NO 38
<211> LENGTH: 374
<212> TYPE: PRT
<213> ORGANISM: Giraffe pestivirus E2

<400> SEQUENCE: 38

Ala Ile Thr Cys Glu Pro Glu Tyr Gln Tyr Ala Leu Ala Arg Ser Lys
1               5                   10                  15
Arg Ile Gly Pro Leu Gly Ala Glu Asp Leu Val Thr Thr Trp His Asp
            20                  25                  30
Tyr Lys Phe Asp Leu Lys Ile Gln Asp Pro Leu Val Met Val Tyr Cys
        35                  40                  45
Lys Asn Asp Gln Phe Phe Val Gly Lys Arg Cys Lys Ala Gly Glu Ala
    50                  55                  60
Arg Tyr Leu Ala Lys Ile His Trp Arg Ala Leu Pro Thr Ser Val Val
65                  70                  75                  80
Phe Glu Lys Val Leu Glu Glu Asn Pro Pro Glu Glu Leu Pro Leu Glu
                85                  90                  95
Asp Asn Phe Glu Phe Gly Leu Cys Pro Cys Asp Ser Arg Pro Val Val
            100                 105                 110
Lys Gly Asn Phe Asn Thr Thr Leu Ile Asn His Ser Ala Phe Gln Leu
        115                 120                 125
Val Cys Pro Ile Gly Trp Val Gly Thr Ile Glu Cys Thr Leu Val Asn
    130                 135                 140
Thr Asp Thr Leu Ala Thr Thr Val Val Lys Arg Tyr Thr Arg Thr Thr
145                 150                 155                 160
Pro Phe Pro Met Arg Ala Gly Cys Val Val Tyr Lys Leu Ile Gly Glu
                165                 170                 175
Asp Leu His His Cys Thr Leu Gly Gly Asn Trp Thr Cys Val Pro Glu
            180                 185                 190
```

```
Asp Asp Gly Thr Tyr Thr Gly Gly Glu Leu Glu Lys Cys Lys Trp Cys
            195                 200                 205
Gly Phe Lys Phe Arg Ile Pro Asp Gly Leu Pro Thr Tyr Pro Ile Gly
210                 215                 220
Arg Cys Met Lys Arg Gly Lys Ala Gly Tyr Arg Phe Val Ser Glu Glu
225                 230                 235                 240
Pro Cys Asn Arg Glu Gly Val Glu Ile Ser Thr Lys Gly Lys Leu Lys
                245                 250                 255
Cys Ile Ile Glu Lys Thr Gln Val Lys Val Tyr Ala Ala Asp Asn Thr
                260                 265                 270
Leu Gly Pro Met Pro Cys Lys Pro Met Glu Ile Ile Ser Ser Glu Gly
            275                 280                 285
Pro Val Ser Lys Thr Ala Cys Thr Phe Asn Tyr Thr Glu Thr Leu Glu
            290                 295                 300
Asn Lys Tyr Phe Glu Pro Arg Asp Glu Tyr Phe Gln Gln Tyr Met Leu
305                 310                 315                 320
Lys Gly Lys Tyr Gln Tyr Trp Phe Asp Leu Lys Ala Thr Asp Asn Arg
                325                 330                 335
Lys Asp Tyr Phe Ala Glu Phe Leu Val Ile Ala Val Val Ala Leu Leu
            340                 345                 350
Gly Gly Arg Tyr Val Leu Trp Leu Leu Val Thr Tyr Phe Val Ile Thr
            355                 360                 365
Glu Gln Glu Ala Ser Gly
370

<210> SEQ ID NO 39
<211> LENGTH: 373
<212> TYPE: PRT
<213> ORGANISM: BDV E2

<400> SEQUENCE: 39

Gln Phe Ala Cys Arg Glu Asp Tyr Arg Tyr Ala Leu Ala Arg Thr Lys
1               5                   10                  15
Glu Ile Gly Ala Leu Gly Ala Glu Ser Leu Thr Thr Thr Trp Thr Asp
            20                  25                  30
Tyr Arg Gly Asn Leu Glu Leu Asp Asp Gly Thr Val Arg Ala Thr Cys
        35                  40                  45
Ser Arg Gly Phe Phe Arg Phe Arg Gly His Cys Met Ile Gly Pro Arg
    50                  55                  60
Tyr Leu Ala Ser Leu His Leu Arg Ala Leu Pro Thr Ser Val Thr Phe
65                  70                  75                  80
Glu Leu Ile Pro Gly Gly Ser Ala Met Thr Glu Glu Glu Met Gly Asp
                85                  90                  95
Asp Phe Glu Phe Gly Leu Cys Pro Cys Asp Ser Arg Pro Val Val Lys
            100                 105                 110
Gly Lys Tyr Asn Thr Thr Leu Leu Asn Gly Ser Ala Phe Gln Leu Ile
        115                 120                 125
Cys Pro Tyr Gly Trp Val Gly Arg Val Glu Cys Thr Thr Val Ser Lys
130                 135                 140
Ser Thr Leu Ala Thr Glu Val Val Lys Ile Tyr Lys Lys Thr Lys Pro
145                 150                 155                 160
Phe Pro Gln Arg Val Gly Cys Asp His Thr Thr Val Tyr Lys Gln Asp
                165                 170                 175
Leu Tyr His Cys Gln Met Gly Gly Asn Trp Thr Cys Met Arg Gly Glu
```

```
                    180                 185                 190
Val Val Lys Tyr Val Gly Gly Pro Val Lys Lys Cys Glu Trp Cys Gly
                195                 200                 205

Tyr Val Phe Lys Lys Arg Glu Gly Leu Pro His Tyr Pro Ile Gly Arg
            210                 215                 220

Cys Met Leu Arg Asn Glu Thr Gly Tyr Arg Ser Val Asp Asp Thr Pro
225                 230                 235                 240

Cys Asp Arg Gly Gly Val Val Ile Ser Lys Thr Gly Glu Leu Glu Cys
                245                 250                 255

Leu Ile Gly Lys Thr Thr Val Lys Val Phe Ser Ser Asp Lys Lys Leu
            260                 265                 270

Gly Pro Met Pro Cys Arg Pro Lys Glu Val Ile Ser Ser Glu Gly Pro
                275                 280                 285

Val Ser Lys Ile Ala Cys Thr Phe Asn Tyr Ser Lys Thr Leu Glu Asn
            290                 295                 300

Lys Tyr Tyr Glu Pro Arg Asp Ser Tyr Phe Gln Gln Tyr Met Leu Lys
305                 310                 315                 320

Gly Gln Tyr Gln Tyr Trp Phe Asp Leu Glu Ala Thr Asp His His Ser
                325                 330                 335

Asp Tyr Phe Ala Glu Phe Ile Met Leu Ala Val Val Ala Leu Leu Gly
            340                 345                 350

Gly Arg Tyr Val Leu Trp Leu Met Val Val Tyr Met Ile Leu Ala Asp
        355                 360                 365

Gln Met Thr Ser Ala
    370

<210> SEQ ID NO 40
<211> LENGTH: 373
<212> TYPE: PRT
<213> ORGANISM: Reindeer pestivirus E2

<400> SEQUENCE: 40

Gln Phe Ser Cys Arg Glu Gly Tyr Arg Tyr Ala Leu Ala Lys Thr Lys
1               5                   10                  15

Asp Val Gly Pro Leu Gly Ala Glu Ser Leu Thr Thr Thr Trp Val Asp
            20                  25                  30

Tyr Lys Arg Asn Leu Gln Leu Asp Asp Gly Thr Val Arg Ala Val Cys
        35                  40                  45

Ser Asn Gly Tyr Phe Arg Ile Arg Pro Thr Cys Leu Ile Gly Ser Arg
    50                  55                  60

Phe Ile Ala Ser Leu His Gln Arg Ala Leu Pro Thr Ser Val Thr Phe
65                  70                  75                  80

Glu Leu Ile Pro Arg Gly Ser Ala Met Val Thr Glu Glu Met Asn Asp
                85                  90                  95

Ser Phe Glu Phe Gly Leu Cys Pro Cys Asp Ser Lys Pro Val Val Lys
            100                 105                 110

Gly Lys Tyr Asn Ala Thr Leu Leu Asn Gly Ser Ala Phe Gln Leu Val
        115                 120                 125

Cys Pro Phe Gly Trp Val Gly Arg Val Glu Cys Thr Ala Val Ser Thr
    130                 135                 140

Ser Thr Leu Ala Thr Glu Val Ile Lys Ile Tyr Lys Arg Ser Thr Pro
145                 150                 155                 160

Phe Pro Tyr Arg Thr Gly Cys Asp His Thr Thr Val Ile Asn Lys Asp
                165                 170                 175
```

Leu Tyr Arg Cys Ser Met Gly Gly Asn Trp Thr Cys Ile Lys Gly Glu
            180                 185                 190

Gln Val Arg Tyr Thr Gly Gly Val Val Thr Lys Cys Lys Trp Cys Asp
        195                 200                 205

Tyr Val Phe Lys Glu Gly Asp Gly Leu Asp His Tyr Pro Ile Gly Lys
        210                 215                 220

Cys Met Leu Lys Asn Glu Thr Gly Tyr Arg Leu Val Asp Asp Thr Pro
225                 230                 235                 240

Cys Asp Arg Gly Gly Val Val Ile Ser Lys Thr Gly Thr Leu Glu Cys
                245                 250                 255

Leu Ile Gly Lys Thr Thr Val Lys Val Tyr Ser Ser Asn Asp Lys Leu
            260                 265                 270

Gly Ala Met Pro Cys Lys Pro Lys Glu Ile Ile Ser Glu Gly Pro
        275                 280                 285

Ile Ser Lys Thr Ala Cys Thr Phe Asn Tyr Ser Lys Thr Leu Lys Asn
    290                 295                 300

Lys Tyr Tyr Glu Pro Arg Asp Ser Tyr Phe Gln Gln Tyr Met Leu Lys
305                 310                 315                 320

Gly Glu Tyr Gln Tyr Trp Phe Asp Leu Asp Ala Thr Asp His His Thr
                325                 330                 335

Asp Tyr Phe Ala Glu Phe Ile Val Leu Ala Val Val Ala Leu Leu Gly
            340                 345                 350

Gly Arg Tyr Val Leu Trp Leu Leu Val Ile Tyr Thr Val Leu Thr Glu
        355                 360                 365

Gln Met Ala Ala Ala
        370

<210> SEQ ID NO 41
<211> LENGTH: 373
<212> TYPE: PRT
<213> ORGANISM: Sheep pestivirus E2

<400> SEQUENCE: 41

Gln Phe Thr Cys Glu Lys Asn Tyr Arg Tyr Ala Ile Ala Lys Thr Thr
1               5                   10                  15

Asp Val Gly Leu Leu Gly Ala Glu Gly Leu Thr Thr Thr Trp Arg Glu
            20                  25                  30

Tyr Lys Asn Asn Phe Glu Leu Asp Asp Gly Leu Leu Arg Ala Val Cys
        35                  40                  45

Lys Ser Gly Phe Phe Thr Phe Arg Phe His Cys Asp Met Gly Thr Arg
    50                  55                  60

Tyr Leu Ala Lys Leu His Ala Gln Ala Leu Pro Thr Ser Val Val Phe
65                  70                  75                  80

Glu Lys Val Gly Gln Gln Pro Gly Ala Arg Ile Thr Met Glu Asp
            85                  90                  95

Asn Phe Glu Phe Gly Leu Cys Pro Cys Asp Ser Lys Pro Val Val Lys
        100                 105                 110

Gly Lys Tyr Asn Ala Thr Leu Leu Asn Gly Ser Ala Phe Asn Leu Val
    115                 120                 125

Cys Pro Ile Gly Trp Thr Gly Val Val Glu Cys Thr Val Ile Ser Glu
    130                 135                 140

Ser Thr Leu His Thr Glu Val Val Lys Val Phe Arg Arg Asp Lys Pro
145                 150                 155                 160

Phe Pro Ser Arg Lys Tyr Cys Val Asp Thr Lys Val Ile Gly Glu Asp
                165                 170                 175

Leu Phe His Cys Lys Leu Gly Gly Asn Trp Thr Cys Ile Pro Gly Glu
                180                 185                 190

Gln Val Ala Tyr Arg Gly Gly Gln Val Lys Asn Cys Lys Trp Cys Gly
            195                 200                 205

Phe Thr Phe Glu Thr Pro Glu Asp Leu Pro His Tyr Pro Ile Gly Lys
210                 215                 220

Cys Val Leu Ser Asn Glu Thr Gly Tyr Arg Leu Val Asp Gly Thr Thr
225                 230                 235                 240

Cys Asn Arg His Gly Val Ile Ile Asp Gln Thr Gly Ser His Glu Cys
                245                 250                 255

Leu Ile Gly Lys Thr Lys Ile Lys Val Tyr Pro Val Asp Asp Lys Leu
                260                 265                 270

Gly Pro Met Pro Cys Arg Pro Lys Glu Ile Ile Ser Ser Glu Gly Pro
            275                 280                 285

Ile Ser Lys Thr Ala Cys Thr Phe Asn Tyr Thr Lys Thr Leu Lys Asn
290                 295                 300

Lys Tyr Tyr Glu Pro Arg Asp Ser Tyr Phe Gln Gln Tyr Met Leu Lys
305                 310                 315                 320

Gly Glu Tyr Gln Tyr Trp Phe Asp Leu Asp Val Thr Asp His His Thr
                325                 330                 335

Asp Tyr Phe Ala Glu Phe Ile Val Val Val Val Ala Leu Leu Gly
                340                 345                 350

Gly Arg Tyr Val Leu Trp Leu Met Val Val Tyr Ile Val Leu Thr Asp
                355                 360                 365

Gln Met Ala Ser Gly
        370

<210> SEQ ID NO 42
<211> LENGTH: 373
<212> TYPE: PRT
<213> ORGANISM: CSFV E2

<400> SEQUENCE: 42

Gln Leu Ala Cys Lys Glu Asp Tyr Arg Tyr Ala Ile Ser Ser Thr Asn
1               5                   10                  15

Glu Ile Gly Leu Leu Gly Ala Gly Gly Leu Thr Thr Thr Trp Lys Glu
                20                  25                  30

Tyr Asn His Asp Leu Gln Leu Asn Asp Gly Thr Val Lys Ala Ile Cys
            35                  40                  45

Val Ala Gly Ser Phe Lys Val Thr Ala Leu Asn Val Val Ser Arg Arg
50                  55                  60

Tyr Leu Ala Ser Leu His Lys Glu Ala Leu Pro Thr Ser Val Thr Phe
65                  70                  75                  80

Glu Leu Leu Phe Asp Gly Thr Asn Pro Ser Thr Glu Glu Met Gly Asp
                85                  90                  95

Asp Phe Gly Phe Gly Leu Cys Pro Phe Asp Thr Ser Pro Val Val Lys
            100                 105                 110

Gly Lys Tyr Asn Thr Thr Leu Leu Asn Gly Ser Ala Phe Tyr Leu Val
            115                 120                 125

Cys Pro Ile Gly Trp Thr Gly Val Ile Glu Cys Thr Ala Val Ser Pro
            130                 135                 140

Thr Thr Leu Arg Thr Glu Val Val Lys Thr Phe Arg Arg Asp Lys Pro
145                 150                 155                 160

Phe Pro His Arg Met Asp Cys Val Thr Thr Thr Val Glu Asn Glu Asp

```
                        165                 170                 175
Leu Phe Tyr Cys Lys Leu Gly Gly Asn Trp Thr Cys Val Lys Gly Glu
            180                 185                 190

Pro Val Val Tyr Thr Gly Gly Leu Val Lys Gln Cys Arg Trp Cys Gly
            195                 200                 205

Phe Asp Phe Asn Glu Pro Asp Gly Leu Pro His Tyr Pro Ile Gly Lys
            210                 215                 220

Cys Ile Leu Ala Asn Glu Thr Gly Tyr Arg Ile Val Asp Ser Thr Asp
225                 230                 235                 240

Cys Asn Arg Asp Gly Val Val Ile Ser Thr Glu Gly Ser His Glu Cys
                245                 250                 255

Leu Ile Gly Asn Thr Thr Val Lys Val His Ala Ser Asp Glu Arg Leu
                260                 265                 270

Gly Pro Met Pro Cys Arg Pro Lys Glu Ile Val Ser Ser Ala Gly Pro
            275                 280                 285

Val Arg Lys Thr Ser Cys Thr Phe Asn Tyr Ala Lys Thr Leu Lys Asn
            290                 295                 300

Lys Tyr Tyr Glu Pro Arg Asp Ser Tyr Phe Gln Gln Tyr Met Leu Lys
305                 310                 315                 320

Gly Glu Tyr Gln Tyr Trp Phe Asp Leu Asp Val Thr Asp Arg His Ser
                325                 330                 335

Asp Tyr Phe Ala Glu Phe Val Val Leu Val Val Ala Leu Leu Gly
                340                 345                 350

Gly Arg Tyr Ile Leu Trp Leu Ile Val Thr Tyr Ile Val Leu Thr Glu
            355                 360                 365

Gln Leu Ala Ala Gly
            370

<210> SEQ ID NO 43
<211> LENGTH: 374
<212> TYPE: PRT
<213> ORGANISM: BVDV-1 E2

<400> SEQUENCE: 43

His Leu Asp Cys Lys Pro Glu Phe Ser Tyr Ala Ile Ala Lys Asp Glu
1               5                   10                  15

Arg Ile Gly Gln Leu Gly Ala Glu Gly Leu Thr Thr Thr Trp Lys Glu
            20                  25                  30

Tyr Ser Pro Gly Met Lys Leu Glu Asp Thr Met Val Ile Ala Trp Cys
            35                  40                  45

Glu Asp Gly Lys Leu Met Tyr Leu Gln Arg Cys Thr Arg Glu Thr Arg
50                  55                  60

Tyr Leu Ala Ile Leu His Thr Arg Ala Leu Pro Thr Ser Val Val Phe
65                  70                  75                  80

Lys Lys Leu Phe Asp Gly Arg Lys Gln Glu Asp Val Val Glu Met Asn
                85                  90                  95

Asp Asn Phe Glu Phe Gly Leu Cys Pro Cys Asp Ala Lys Pro Ile Val
            100                 105                 110

Arg Gly Lys Phe Asn Thr Thr Leu Leu Asn Gly Pro Ala Phe Gln Met
            115                 120                 125

Val Cys Pro Ile Gly Trp Thr Gly Thr Val Ser Cys Thr Ser Phe Asn
            130                 135                 140

Met Asp Thr Leu Ala Thr Thr Val Val Arg Thr Tyr Arg Arg Ser Lys
145                 150                 155                 160
```

-continued

```
Pro Phe Pro His Arg Gln Gly Cys Ile Thr Gln Lys Asn Leu Gly Glu
            165                 170                 175

Asp Leu His Asn Cys Ile Leu Gly Gly Asn Trp Thr Cys Val Pro Gly
            180                 185                 190

Asp Gln Leu Leu Tyr Lys Gly Gly Ser Ile Glu Ser Cys Lys Trp Cys
            195                 200                 205

Gly Tyr Gln Phe Lys Glu Ser Glu Gly Leu Pro His Tyr Pro Ile Gly
            210                 215                 220

Lys Cys Lys Leu Glu Asn Glu Thr Gly Tyr Arg Leu Val Asp Ser Thr
225                 230                 235                 240

Ser Cys Asn Arg Glu Gly Val Ala Ile Val Pro Gln Gly Thr Leu Lys
            245                 250                 255

Cys Lys Ile Gly Lys Thr Thr Val Gln Val Ile Ala Met Asp Thr Lys
            260                 265                 270

Leu Gly Pro Met Pro Cys Arg Pro Tyr Glu Ile Ile Ser Ser Glu Gly
            275                 280                 285

Pro Val Glu Lys Thr Ala Cys Thr Phe Asn Tyr Thr Lys Thr Leu Lys
            290                 295                 300

Asn Lys Tyr Phe Glu Pro Arg Asp Ser Tyr Phe Gln Gln Tyr Met Leu
305                 310                 315                 320

Lys Gly Glu Tyr Gln Tyr Trp Phe Asp Leu Glu Val Thr Asp His His
            325                 330                 335

Arg Asp Tyr Phe Ala Glu Ser Ile Leu Val Val Val Ala Leu Leu
            340                 345                 350

Gly Gly Arg Tyr Val Leu Trp Leu Leu Val Thr Tyr Met Val Leu Ser
            355                 360                 365

Glu Gln Lys Ala Leu Gly
            370

<210> SEQ ID NO 44
<211> LENGTH: 372
<212> TYPE: PRT
<213> ORGANISM: BVDV-2 E2

<400> SEQUENCE: 44

Phe Pro Glu Cys Lys Glu Gly Phe Gln Tyr Ala Ile Ser Lys Asp Arg
1               5                   10                  15

Lys Met Gly Leu Leu Gly Pro Glu Ser Leu Thr Thr Thr Trp His Arg
            20                  25                  30

Pro Thr Lys Lys Leu Val Asp Ser Met Val Gln Val Trp Cys Glu Gly
            35                  40                  45

Lys Asp Leu Lys Ile Leu Lys Thr Cys Pro Lys Glu Glu Arg Tyr Leu
        50                  55                  60

Val Ala Val His Glu Arg Ala Leu Ser Thr Ser Ala Glu Phe Met Pro
65                  70                  75                  80

Ile Ser Asp Gly Thr Ile Gly Pro Asp Val Ile Asp Met Pro Asp Asp
            85                  90                  95

Phe Glu Phe Gly Leu Cys Pro Cys Asp Ala Lys Pro Val Ile Lys Gly
            100                 105                 110

Lys Phe Asn Ala Ser Leu Leu Asn Gly Pro Ala Phe Gln Met Val Cys
            115                 120                 125

Pro Gln Gly Trp Thr Gly Thr Ile Glu Cys Thr Leu Ala Asn Gln Asp
            130                 135                 140

Thr Leu Asp Thr Thr Val Val Arg Thr Tyr Arg Arg Thr Thr Pro Phe
145                 150                 155                 160
```

```
Gln Arg Arg Lys Trp Cys Ser Tyr Glu Lys Ile Ile Gly Glu Asp Ile
                165                 170                 175

His Glu Cys Ile Leu Gly Gly Asn Trp Thr Cys Ile Thr Gly Asp His
            180                 185                 190

Ser Lys Leu Lys Asp Gly Pro Ile Lys Cys Lys Trp Cys Gly Tyr
        195                 200                 205

Asp Phe Val Asn Ser Glu Gly Leu Pro His Tyr Pro Ile Gly Lys Cys
    210                 215                 220

Met Leu Ile Asn Glu Ser Gly Tyr Arg Tyr Val Asp Asp Thr Ser Cys
225                 230                 235                 240

Asp Arg Gly Gly Val Ala Ile Val Pro Thr Gly Thr Val Lys Cys Arg
                245                 250                 255

Ile Gly Asp Val Thr Val Gln Val Val Ala Ser Asn Asn Asp Leu Gly
                260                 265                 270

Pro Met Pro Cys Ser Pro Ala Glu Val Ile Ala Ser Glu Gly Pro Val
            275                 280                 285

Glu Lys Thr Ala Cys Thr Phe Asn Tyr Ser Arg Thr Leu Pro Asn Lys
    290                 295                 300

Tyr Tyr Glu Pro Arg Asp Arg Tyr Phe Gln Gln Tyr Met Leu Lys Gly
305                 310                 315                 320

Glu Trp Gln Tyr Trp Phe Asp Leu Asp His Val Asp His His Lys Asp
                325                 330                 335

Tyr Phe Ser Glu Phe Ile Ile Ile Ala Val Val Ala Leu Leu Gly Gly
                340                 345                 350

Lys Tyr Val Leu Trp Leu Leu Ile Thr Tyr Thr Ile Leu Ser Glu Gln
        355                 360                 365

Met Ala Met Gly
        370

<210> SEQ ID NO 45
<211> LENGTH: 372
<212> TYPE: PRT
<213> ORGANISM: BVDV-3 E2

<400> SEQUENCE: 45

Leu Ser Cys Lys Pro Glu Phe Gln Tyr Ala Ile Ser Glu Thr Asp Glu
1                5                  10                  15

Ile Asn Leu Leu Gly Pro Thr Gly Leu Thr Thr Thr Trp His Ala Tyr
                20                  25                  30

Ser Glu Lys Leu His Ile Thr Asp Ser Ser Val Asp Leu Thr Cys Val
            35                  40                  45

Asp Gly Asn Phe Leu Val Tyr Arg Arg Cys Val Arg Lys Arg Arg Tyr
        50                  55                  60

Leu Ala Thr Val His Glu Arg Ala Leu Ser Thr Ser Val Arg Phe Thr
65                  70                  75                  80

Leu Val Ala Asp Pro Gln Asp Leu Glu Asp Val Gln Met Gly Asp Asp
                85                  90                  95

Phe Glu Phe Gly Leu Cys Pro Cys Asp Ser Val Pro Ile Ile Arg Gly
            100                 105                 110

Lys Phe Asn Thr Thr Leu Leu Asn Gly Ser Ala Phe Gln Leu Val Cys
        115                 120                 125

Pro Tyr Gly Trp Thr Gly Thr Ile Glu Cys Thr Val Val Ser Asp Ser
    130                 135                 140

Thr Leu Lys Thr Gln Val Val Lys Arg Phe Ala Arg Tyr Lys Pro Phe
```

```
145                 150                 155                 160

Pro His Arg Lys His Cys Met Asp Gln Met Val Val Gly Glu Asp Leu
                165                 170                 175

Tyr Glu Cys Leu Tyr Gly Gly Asn Trp Thr Cys Ile Pro Gly Asp Arg
            180                 185                 190

Val Leu Tyr Gln Gly Gly Glu Val Lys Asp Cys Lys Trp Cys Gly Phe
        195                 200                 205

Thr Phe Glu Glu Pro Ser Asp Leu Pro His Phe Pro Leu Gly Lys Cys
    210                 215                 220

Arg Leu Thr Asn Glu Thr Gly Tyr Arg Tyr Val Asp Asn Thr Thr Cys
225                 230                 235                 240

Asp Arg Asp Gly Val Ala Ile Met Glu Gln Gly Thr Leu Lys Cys Lys
                245                 250                 255

Ile Gly Lys Val Glu Val Arg Val Ser Ala Leu Asn Lys Asn Leu Gly
            260                 265                 270

Pro Met Pro Cys Lys Pro Ser His Val Thr Gln Ser Glu Gly Pro Val
        275                 280                 285

Ser Lys Thr Ala Cys Thr Phe Asn Trp Thr Glu Thr Leu Glu Asn Lys
    290                 295                 300

Tyr Phe Glu Pro Arg Asp Asn Tyr Phe Gln Gln Tyr Met Leu Lys Gly
305                 310                 315                 320

Lys Tyr Gln Tyr Trp Phe Asp Leu Glu Ala Thr Asp His His Gln Asp
                325                 330                 335

Tyr Phe Ala Glu Phe Ile Val Ile Ile Val Val Ala Leu Leu Gly Gly
            340                 345                 350

Arg Tyr Val Leu Trp Leu Leu Ile Val Tyr Tyr Val Ala Thr Glu Gln
        355                 360                 365

Gly Ala Arg Gly
    370

<210> SEQ ID NO 46
<211> LENGTH: 379
<212> TYPE: PRT
<213> ORGANISM: Norway rat pestivirus E2

<400> SEQUENCE: 46

Arg Tyr Asn Gln Val Lys Val Asp Arg Pro Asp Trp His Thr Leu Leu
1               5                   10                  15

Gln Lys Asp Leu Lys Gly Val Leu Ser Gly Lys Asp Gly Leu Tyr Ile
            20                  25                  30

Leu Arg Ser Asn Lys Val Trp Thr Gly Gly Ser Val Ile Ile Thr Asp
        35                  40                  45

Glu Phe Ala Val Thr Thr Phe Ile Gly Asp His Thr Gly Asn Phe Lys
    50                  55                  60

Phe Ser Val Lys Val Met Thr Thr Pro Ile Glu Met Asp Tyr Cys Ile
65                  70                  75                  80

Lys Val Ile Asp Thr Ala Lys Phe Phe Cys Val Met Val Gly Thr Pro
                85                  90                  95

Thr Gln Arg Asp Leu Val Lys Pro Pro Glu Met Leu Cys Gly Cys Gly
            100                 105                 110

Ala Leu Glu Val Gln Asp Asn Asn Ser Thr Gly Leu Ile Ser Pro Gly
        115                 120                 125

Asn Val Leu Pro Ser Lys Cys Ile Asn Gly Trp Thr Gly Val Val Thr
    130                 135                 140
```

Cys His Cys Pro Tyr Thr Asp Ile Lys Met Lys Phe Leu Glu Asn Thr
145                 150                 155                 160

Thr Pro Gln Lys Tyr Ser Lys Asn Cys Pro Gly Thr Tyr Leu Ser Asp
            165                 170                 175

Gln Asn Phe His His Asp Cys Lys Tyr Gly Ser Gln Glu Ser Cys Ile
                180                 185                 190

Asp Pro Glu Pro Thr Lys Leu Pro Pro Glu Thr Tyr Glu Asp Ile Gln
            195                 200                 205

Glu Cys Phe Trp Cys Ser Tyr Tyr Ile Lys Asp Ala Asn Phe Thr Pro
        210                 215                 220

His Lys Gly Pro Leu Gly Trp Cys Arg Val Gly Glu Asn Glu Pro Tyr
225                 230                 235                 240

Tyr Leu Thr Asn Arg Lys Ser Cys Val Gln Gly Gly Val Gln Ile Gly
                245                 250                 255

Ser Gly Glu Val Thr Cys Leu Ile Gly Thr Thr Lys Ile Lys Val Gly
            260                 265                 270

Asn Phe Asn Glu Thr Ala Ile Ser Phe Met Pro Cys Asn Pro Ile Lys
                275                 280                 285

Glu Ala Ser Arg Gly Pro Pro Ser Arg Thr Thr Cys Thr Tyr Lys Tyr
290                 295                 300

Ala Lys Thr Leu Lys Asn Lys Ile Tyr Asp Glu Lys Asp Arg Tyr Trp
305                 310                 315                 320

Gly Gln Tyr Met Val Lys Gly Glu Tyr Gln Tyr Trp Phe Asp Leu Glu
                325                 330                 335

Gln Asp Asp His Val Thr Gly Gly Leu Leu Lys Tyr Leu Pro Leu Ile
            340                 345                 350

Met Val Leu Leu Leu Gly Gly Lys Met Val Ala Trp Leu Leu Thr Ala
        355                 360                 365

Tyr Tyr Leu Met Glu Val Val Glu Ala Thr Arg
370                 375

<210> SEQ ID NO 47
<211> LENGTH: 246
<212> TYPE: PRT
<213> ORGANISM: Rhinolophus affinis pestivirus E2

<400> SEQUENCE: 47

Asn Cys Ile Thr Arg Val Asp Tyr Tyr Asn Tyr Ser Leu Lys Val Glu
1               5                   10                  15

Lys Asn Thr Gly Asn Glu Val Thr Ala Tyr Asp Gly Thr Tyr Phe Val
            20                  25                  30

Ile Thr Leu Lys Asp Glu Glu Pro Lys Leu Met Glu Lys Val Val Lys
        35                  40                  45

Val Asn Gly Asn Ala Thr Lys Asp Glu Tyr Cys Tyr Gln Ala Ile Asn
    50                  55                  60

Ile Thr Lys Trp Asn Arg Lys Pro Asp Lys Leu Arg Trp Cys Gly Gln
65                  70                  75                  80

Thr Phe Pro Tyr Trp Leu Gly Asp Thr Val Asn Gly Glu Ala Tyr Phe
                85                  90                  95

Gln Lys Gly Tyr Trp Val Asn Ile Thr Thr Glu Pro Asn Cys Glu
            100                 105                 110

Leu Arg Lys Gly Val Phe Leu Ser Lys Asn Gly Ala Val Ser Cys Thr
        115                 120                 125

Arg Asn Gly Thr Arg Leu Val Leu Gln Leu Lys Asn Leu Asn Ser Thr
    130                 135                 140

```
Asn Lys Glu Glu Ile Pro Cys Asp Pro Ile Glu Thr Ser Ser Leu Gly
145                 150                 155                 160

Pro Ala Glu Asn Gly Ala Cys Val Tyr Thr Trp Ala Pro Ala Pro Glu
            165                 170                 175

Gly Trp Tyr Tyr Asp Lys Lys Asp Asp Tyr Trp Leu Gln Tyr Val Lys
            180                 185                 190

Lys Gly Gly Tyr Gln Tyr Trp Thr Gln Ile Pro Ser Leu Glu Ser Ser
            195                 200                 205

Ala Asn Ile Tyr Arg His Leu Leu Pro Ile Leu Ile Ala Cys Leu Leu
            210                 215                 220

Gly Gly Arg Leu Ser Val Trp Ile Leu Ala Met Ile Leu Ser Leu Gln
225                 230                 235                 240

Val Glu Ala Ser Glu Val
                245

<210> SEQ ID NO 48
<211> LENGTH: 243
<212> TYPE: PRT
<213> ORGANISM: Porcine pestivirus

<400> SEQUENCE: 48

Ser Cys His Lys Arg Gln Asp Tyr Tyr Ser Ile Gln Leu Val Val Asp
1               5                   10                  15

Gly Lys Thr Gly Val Glu Lys Arg Ser Ile Val Gly Lys Trp Thr Val
            20                  25                  30

Ile Thr Arg Glu Gly Arg Glu Pro Arg Leu Met Glu Gln Ile Ser Met
            35                  40                  45

Val Ser Asn Asp Ser Leu Ser Glu Thr Tyr Cys Tyr Asn Arg Leu Asn
50                  55                  60

Thr Ser Ser Trp Gly Arg Gln Pro Ala Arg Gln Arg Gly Cys Gly Gln
65                  70                  75                  80

Thr Val Pro Phe Trp Pro Gly Asp Asn Val Leu Glu Glu Gln Tyr Tyr
                85                  90                  95

Ser Thr Gly Tyr Trp Val Asn Ala Thr Gly Gly Cys Gln Leu Arg Glu
            100                 105                 110

Gly Val Trp Leu Ser Arg Lys Gly Asn Val Gln Cys Gln Arg Asn Gly
            115                 120                 125

Ser Ser Leu Ile Leu Gln Leu Ala Ile Lys Glu Glu Asn Asp Thr Met
            130                 135                 140

Glu Ile Pro Cys Asp Pro Val Glu Thr Glu Ser Met Gly Pro Val Thr
145                 150                 155                 160

Gln Gly Thr Cys Val Tyr Ser Trp Ala Phe Ala Pro Arg Gly Trp Tyr
            165                 170                 175

Tyr Asn Arg Lys Asp Gly Tyr Trp Leu Gln Tyr Val Lys Lys Asn Asp
            180                 185                 190

Tyr Gln Tyr Trp Thr Lys Met Pro Thr Ala Ser Ser Ala Thr Thr Met
            195                 200                 205

Tyr Arg His Leu Leu Pro Leu Leu Val Ala Cys Leu Met Gly Gly Arg
            210                 215                 220

Ile Ser Val Trp Ile Val Ala Met Leu Leu Ser Leu Gln Val Glu Ala
225                 230                 235                 240

Ser Glu Val

<210> SEQ ID NO 49
```

<211> LENGTH: 3897
<212> TYPE: PRT
<213> ORGANISM: Pronghorn pestivirus

<400> SEQUENCE: 49

```
Met Glu Val Val Glu Phe Leu Asn Leu His Lys Ile Gly Arg Gln Gly
1               5                   10                  15

Pro Pro Gly Ala Leu Glu Pro Val Phe Asp Lys Asn Gly Thr Pro Leu
            20                  25                  30

Phe Gly Asp Tyr Val Glu Ile His His Gln Ser Thr Leu Lys Leu Pro
        35                  40                  45

His Trp Arg Gly Glu Ala Asn Val Gln Val Ser Asp Lys Tyr Leu Pro
    50                  55                  60

Lys Lys Gly Asp Cys Arg Thr Gly Asn Lys Phe Gly Pro Val Ser Gly
65                  70                  75                  80

Ile Tyr Leu Glu Leu Gly Pro Lys Phe Tyr Gln Asp Tyr Thr Gly Tyr
                85                  90                  95

Val Tyr His Arg Ala Pro Leu Glu Phe Cys Ser Arg Ser Gln Met Cys
            100                 105                 110

Glu Val Thr Arg Leu Ile Gly Arg Ile Thr Gly Ser Asp Gly Val Leu
        115                 120                 125

Tyr His Leu Phe Thr Cys Val Asp Gly Cys Val Leu Leu Lys Gln Ala
    130                 135                 140

Thr Arg Asp Asn Pro Lys Val Phe Lys Trp Val Lys Asn Pro Leu Arg
145                 150                 155                 160

Cys Pro Leu Trp Val Thr Ser Cys Ser Asp Glu Gly Gly Ala Lys Gln
                165                 170                 175

Lys Lys Thr Asp Asn Asp Arg Met Lys Lys Gly Ala Leu Lys Tyr Lys
            180                 185                 190

Pro Gln Glu Gln Glu Lys Asp Val Arg Lys Pro Pro Asp Ala Thr
        195                 200                 205

Ile Val Val Asp Gly Val Lys Tyr Gln Val Thr Lys Lys Gly Lys Val
    210                 215                 220

Arg Ser Glu Lys Thr Lys Asp Gly Leu Tyr His Asn Lys Asn Lys Pro
225                 230                 235                 240

Ala Glu Ser Arg Lys Lys Leu Glu Lys Ala Leu Leu Ala Trp Ala Phe
                245                 250                 255

Leu Ala Met Leu His Ile Cys Thr Ala Val Asn Ile Thr Gln Trp Asn
            260                 265                 270

Leu Ala Asp Glu Gly Thr Glu Gly Val His Arg Val Met Phe Glu Arg
        275                 280                 285

Gly Ile Asn Arg Ser Leu His Gly Ile Trp Pro Gln Gln Ile Cys His
    290                 295                 300

Gly Ile Pro Ser Tyr Asn Pro Thr Asn Arg Glu Leu Ser Met Ile Val
305                 310                 315                 320

Gly Met Val Asp Ala Ser Ile Arg Thr Asn Tyr Thr Cys Cys Asn Leu
                325                 330                 335

Gln Arg His Glu Trp Asn Lys His Gly Trp Cys Asn Trp Tyr Asn Ile
            340                 345                 350

Ile Pro Trp Ile Lys Val Met Asn Tyr Ser Gln Arg Asn Leu Thr Glu
        355                 360                 365

Gly Thr Tyr Gly Lys Glu Cys Ala Val Thr Cys Arg His Asp Ser Ile
    370                 375                 380

Leu Asp Ile Asn Ile Val Thr Gln Ala Arg Asn Gln Pro Thr Met Leu
```

-continued

```
            385                 390                 395                 400
        Thr Gly Cys Lys Ile Gly Lys Asn Phe Ser Phe Ser Gly Glu Ile Arg
                        405                 410                 415
        Glu Lys Pro Cys Asn Tyr Asp Ile Gln Pro Glu Ile Leu His Leu
                        420                 425                 430
        Pro His Glu Cys Gly Glu Trp Tyr Ser Glu Ile Ser His Gln Ala Val
                        435                 440                 445
        Asp Met Ile Thr Asn Gly Leu Glu Ala Ser Arg Asn Ser Ala Ala Lys
                    450                 455                 460
        Val Leu Ser Trp Ile Gly Arg Lys Leu Glu Arg Ile Gly Lys Arg Ala
        465                 470                 475                 480
        Gln Ala Lys Ser Lys Thr Trp Phe Gly Ala Gln Ala Ser Glu Val Tyr
                        485                 490                 495
        Cys Lys Val Glu Lys Arg Val Gly Ser Leu Trp Tyr Thr Arg Asn Cys
                        500                 505                 510
        Thr Pro Ala Cys Leu Pro Gly His Thr Glu Ile Leu Gly Ala Gly Val
                        515                 520                 525
        Phe Asp Thr Asn Pro Gln Gly Arg Ser Leu Ile Pro Arg Leu Pro Gly
                    530                 535                 540
        His Ile Thr Glu Ala Val Ile Leu Ser Leu Val Ala Leu Ser Glu Val
        545                 550                 555                 560
        Met Pro Glu Thr Ser Ser Ala Leu Tyr Ile Ala Leu His Tyr Phe Leu
                        565                 570                 575
        His Pro Met Asn Glu Thr Ile Gly Tyr Cys Asp Lys Asn Gln Leu Asn
                        580                 585                 590
        Leu Thr Ile Thr Thr Thr Val Asp Lys Val Ile Pro Asn Ser Val Tyr
                    595                 600                 605
        Val Leu Gly Gln Trp Val Cys Val Lys Pro Gly Trp Trp Pro Tyr Asp
                    610                 615                 620
        Ser Glu Val Thr Leu Val Val Asn Glu Val Ile Asn Val Leu Asp Ile
        625                 630                 635                 640
        Gly Gly Arg Ala Ala Arg Val Leu Leu Gln Val Trp Asp Ala Ala Thr
                        645                 650                 655
        Ala Ile Ala Val Leu Ile Phe Ile Met Lys Val Ala Arg Gly Gln Leu
                        660                 665                 670
        Ile Gln Gly Leu Ile Trp Leu Leu Leu Thr Gly Thr Glu Ala Leu
                        675                 680                 685
        Glu Cys Asp Thr Asn Phe Gln Tyr Ala Leu Ala Lys Gly Thr Lys Ile
                        690                 695                 700
        Gly Pro Leu Gly Ala Glu Glu Leu Thr Thr Thr Tyr Arg Arg Leu Gln
        705                 710                 715                 720
        Pro Gly Glu Gln Leu Thr Asp Gly Leu Val Thr Ile Thr Cys Thr Asn
                        725                 730                 735
        His Asp Ile Ile Ile His Asp Gln Cys Ser Ile Glu Arg Arg Trp Ile
                        740                 745                 750
        Ala Lys Ile His Pro Gln Ala Leu Pro Thr Ser Val Gln Phe Tyr Leu
                        755                 760                 765
        Ala Ala Glu Pro Lys Glu Ala Pro Lys Ile Ile Glu Met Ser Asp Glu
                        770                 775                 780
        Phe Glu Phe Ala Ile Cys Pro Cys Asp Ala Leu Pro Leu Val Lys Gly
        785                 790                 795                 800
        Asn Phe Asn Cys Thr Leu Thr Asn Ala Gln Ala Phe Gln Met Val Cys
                        805                 810                 815
```

-continued

Pro Tyr Gly Trp Val Gly Thr Ile Glu Cys Val Lys Tyr Ser Pro Thr
             820                 825                 830

Thr Leu Ser Thr Thr Val Val Gln Val Tyr Lys Arg Gly Arg Pro Phe
        835                 840                 845

Pro Arg Arg Arg His Cys Thr Thr Glu Glu Val Phe Gln Gly Asn Tyr
    850                 855                 860

Tyr Thr Cys Glu Lys Gly Gly Asn Trp Thr Cys Gln Pro Gly His Ile
865                 870                 875                 880

Ser His Gly His Asn Ser Asp Glu Val Glu Glu Cys Glu Trp Cys Gly
                885                 890                 895

Phe Arg Ser Leu Lys Pro Ser Ala Lys Leu Gly Arg Cys Ile Arg Arg
            900                 905                 910

Gly Glu Lys Ala His Arg Leu Tyr Asp Thr Arg Pro Cys Lys Glu Lys
        915                 920                 925

Ala Phe Thr Phe Ser Pro Ala Gly Glu Val Glu Cys Leu Leu Gly Gly
    930                 935                 940

Phe Lys Val Arg Val Asp Arg Ser Asp Thr Thr Asn Glu Leu Leu Pro
945                 950                 955                 960

Met Pro Cys Asn Pro Ile Lys Val Gly Ser Gln Gly Pro Val Ser Arg
                965                 970                 975

Ala Ala Cys Thr Tyr Asn Tyr Ser Gln Val Leu Arg Asn Ser Tyr Tyr
            980                 985                 990

Glu Glu Arg Asp Lys Phe Trp Gln Gln Tyr Met Ile Lys Asp Gly Tyr
        995                 1000                1005

Gln Tyr Trp Phe Asp Leu Glu Ala Asp Asp His His Lys Asn Trp
    1010                1015                1020

Phe Asn Glu Phe Leu Val Val Val Val Ala Leu Leu Gly Gly
    1025                1030                1035

Arg Tyr Ile Leu Trp Leu Ile Ile Tyr Met Thr Leu Thr Tyr
    1040                1045                1050

Tyr Pro Asp Asp Ala Ala Leu Val Asn Thr Gly Asp Thr Val Ala
    1055                1060                1065

Ile Gly Asn Ile Leu Phe Ser Asn Asn Phe Glu Val Val Ser Tyr
    1070                1075                1080

Phe Leu Leu Ile Tyr Val Leu Leu Lys Asn Glu Pro Ser Lys Arg
    1085                1090                1095

Trp Val Ile Leu Leu Tyr His Thr Leu Val Gln His Pro Leu Lys
    1100                1105                1110

Thr Leu Thr Ala Leu Thr Leu Thr Val Val Asp Met Val Lys Gly
    1115                1120                1125

Asp Thr Asn Glu Thr Ser Ala Asn Gln Tyr Asp Phe Met Pro Met
    1130                1135                1140

Ala Ala Leu Val Val Ala Gly Leu Val Ser Leu Lys Val Arg Asp
    1145                1150                1155

Phe Ser Leu Ile Pro Ala Leu Val Leu Thr Leu Ala Thr Asn Thr
    1160                1165                1170

Leu His Leu Cys Asn Asn Met Gln Ala Asp Val Thr Ile Cys Ile
    1175                1180                1185

Leu Leu Thr Leu Val Val Leu Trp Thr Tyr Ile Thr Pro Cys Phe
    1190                1195                1200

Lys Tyr Ser Arg Val Phe Arg Leu Val Val Ser Leu Leu Tyr Leu
    1205                1210                1215

```
Val Phe Leu Val Arg Ala Leu Ser His Ile Gly Ser Ile His Thr
1220                1225                1230

Pro Ala Ile Glu Leu Pro Arg Val Arg Pro Ile Val Ile Ile Leu
1235                1240                1245

Ser Tyr Phe Thr Met Thr Val Leu Ala Val Asn Val Asn Ile Asp
1250                1255                1260

Val Ala Ser Thr Ile Leu Ser Ile Thr Pro Thr Ile Met Thr Leu
1265                1270                1275

Cys Thr Leu Trp Ala Asp Met Leu Thr Val Leu Val Val Leu Pro
1280                1285                1290

Ser Tyr Glu Val Thr Lys Leu Tyr Tyr Leu Glu Lys Val Lys Glu
1295                1300                1305

Asn Glu Thr Lys Pro Trp Val Arg Phe Gly Leu Lys Lys Val Lys
1310                1315                1320

Ile Lys Thr Leu Gly Glu Ile Glu Arg Glu Leu Val Asp Gly Lys
1325                1330                1335

Glu Lys Val Phe Glu Leu Pro Ser Leu Ser Thr Gly Asn Ser Gln
1340                1345                1350

Lys Ser Ser Leu Val Ser Ile Val Arg Cys Cys Leu Ile Ala Cys
1355                1360                1365

Val Ser Ser His Trp Arg Ser Phe Tyr Leu Leu Tyr Leu Ile Leu
1370                1375                1380

Glu Leu Ser Tyr Trp Ala His Ser Arg Ile Ile Lys Glu Val Ala
1385                1390                1395

Gly Ser Thr Asn Trp Leu Ser Arg Thr Ile Ala Thr Met Ile Glu
1400                1405                1410

Met Asn Trp Val Met Asp Ser Asp Asp Val Lys Gly Leu Lys Lys
1415                1420                1425

Phe Phe Ile Leu Ser Gly Arg Phe Arg Asp Leu Met Leu Lys His
1430                1435                1440

Lys Val Ala Asn Asp Arg Ile Arg Asp Trp Tyr Ser Glu Gly Glu
1445                1450                1455

Val Phe Gly Met Pro Lys Ile Leu Tyr Ile Thr Lys Ile Ala Ser
1460                1465                1470

Leu Ser Asn Ser Asn Gln His Met Val Cys Thr Val Cys Glu Thr
1475                1480                1485

Arg Ala Trp Val Asn Arg Arg Ser Thr Cys Pro Lys Cys Gly Gly
1490                1495                1500

Leu Gly Pro Pro Val Lys Cys Gly Met Ser Leu Ala Asp Phe Glu
1505                1510                1515

Glu Lys Lys Tyr Lys Arg Ile Phe Ile Arg Glu Phe Asp Glu Pro
1520                1525                1530

Gly Thr Phe Arg Glu Glu Gln Asp Gly Tyr Leu Ala Tyr Thr Ala
1535                1540                1545

Lys Gly Ser Leu Phe Leu Arg Asn Leu Pro Ile Leu Ala Thr Lys
1550                1555                1560

Met Lys Met Val Met Val Gly Asn Leu Gly Ser Glu Leu Ser Asp
1565                1570                1575

Leu Glu His Leu Gly Trp Ile Leu Arg Gly Pro Ala Val Cys Lys
1580                1585                1590

Lys Ile Val Cys His Glu Lys Thr Lys Pro Thr Val Met Asp Lys
1595                1600                1605

Leu Ser Cys Phe Phe Gly Leu Met Pro Arg Gly Ser Thr Pro Arg
```

```
                 1610                1615               1620

Ala Pro Val Arg Phe Pro Thr Ala Ile Ile Lys Val Arg Arg Gly
        1625                1630                1635

Leu Glu Val Gly Trp Ala Tyr Thr His Gln Gly Gly Ile Ser Ser
        1640                1645                1650

Val Glu His Val Thr Ser Gly Lys Asp Leu Phe Val Ser Asp Ser
        1655                1660                1665

Met Gly Arg Thr Arg Val Leu Cys Gln Ser Ser Asn Lys Asn Thr
        1670                1675                1680

Asp Glu Thr Glu Tyr Gly Ile Lys Thr Asp Ser Ser Cys Ala Glu
        1685                1690                1695

Gly Ser Arg Cys Tyr Val Phe Asn Pro Glu Ala Thr Asn Ile Ala
        1700                1705                1710

Gly Thr Arg Gly Ala Leu Val His Leu Arg Lys Gln Gly Cys Ser
        1715                1720                1725

Tyr Thr Cys Val Thr Ala Leu Gly Thr Pro Ala Phe Tyr Asp Leu
        1730                1735                1740

Lys Asn Leu Arg Gly Trp Ser Gly Leu Pro Ile Phe Glu Ala Ser
        1745                1750                1755

Thr Gly Lys Val Val Gly Arg Val Lys Val Gly Val Asn Glu Glu
        1760                1765                1770

Ser Lys Pro Thr Ala Ile Leu Ser Gly Thr Arg Ala Val Ser Ser
        1775                1780                1785

Lys Ala Ala Asp Leu Glu Val Val Val Lys Lys Leu Glu Asn Met
        1790                1795                1800

Ala Arg Gly Glu Phe Lys Gln Ile Thr Leu Ala Thr Gly Ala Gly
        1805                1810                1815

Lys Thr Thr Glu Leu Pro Arg Gly Leu Ile Glu Arg Ile Gly Arg
        1820                1825                1830

His Lys Arg Val Leu Val Leu Ile Pro Leu Arg Ala Ala Ala Glu
        1835                1840                1845

Ser Val Tyr Gln Tyr Met Arg Gln Lys His Pro Ser Ile Ala Phe
        1850                1855                1860

Asn Leu Arg Ile Gly Asp Leu Lys Glu Gly Asp Met Ala Thr Gly
        1865                1870                1875

Ile Thr Tyr Ala Ser Tyr Gly Tyr Phe Cys Gln Met Thr Gln Pro
        1880                1885                1890

Lys Leu Arg Ser Ala Leu Val Glu Tyr Ser Tyr Ile Phe Leu Asp
        1895                1900                1905

Glu Tyr His Cys Ala Thr Pro Glu Gln Leu Ala Val Met Ser Lys
        1910                1915                1920

Met His Arg Phe Ser Asp Gln Leu Arg Val Val Ala Met Thr Ala
        1925                1930                1935

Thr Pro Ala Gly Thr Val Thr Tyr Thr Gly Gln Lys Phe Pro Ile
        1940                1945                1950

Glu Glu Val Ile Ile Pro Asp Thr Met Lys Gly Glu Asp Leu Gly
        1955                1960                1965

Glu Asn Phe Leu Asp Ile Ala Gly Leu Lys Val Pro Arg Asp Glu
        1970                1975                1980

Met Lys Asn Asn Val Leu Val Phe Val Pro Thr Arg Asn Met Ala
        1985                1990                1995

Leu Glu Thr Ala Lys Asn Leu Lys Ala Lys Gly Tyr Asn Ser Gly
        2000                2005                2010
```

Tyr Tyr Tyr Ser Gly Glu Asp Pro Glu Gly Leu Arg Ser Ile Thr
2015                2020                2025

Ser Gln Ser Pro Tyr Ile Ile Ile Ala Thr Asn Ala Ile Glu Ser
2030                2035                2040

Gly Val Thr Leu Pro Asp Leu Asp Thr Val Ile Asp Thr Gly Leu
2045                2050                2055

Lys Cys Glu Lys Arg Val Arg Ile Ala Lys Lys Pro Pro Tyr Ile
2060                2065                2070

Val Thr Gly Leu Lys Arg Met Ala Ile Thr Ile Gly Glu Gln Ala
2075                2080                2085

Gln Arg Arg Gly Arg Val Gly Arg Val Lys Pro Gly Lys Tyr Tyr
2090                2095                2100

Arg Ser Gln Glu Thr Ala Ala Gly Ser Lys Asp Tyr His Tyr Asp
2105                2110                2115

Leu Leu Gln Ala Gln Lys Tyr Gly Val Glu Asp Gly Ile Asn Ile
2120                2125                2130

Thr Lys Ser Phe Arg Glu Met Asn Tyr Asp Trp Ser Leu Tyr Glu
2135                2140                2145

Glu Asp Thr Met Val Ile Ala Gln Leu Glu Val Leu Asn Asn Leu
2150                2155                2160

Leu Ile Ser Asp Glu Leu Gly Leu Ala Thr Arg Asn Ile Met Ala
2165                2170                2175

Arg Thr Thr Asn Pro Glu Pro Ile Gln Ile Ala Tyr Asn Ser Tyr
2180                2185                2190

Glu Thr Gln Val Pro Val Leu Phe Pro Arg Ile Val Arg Gly Glu
2195                2200                2205

Val Thr Asn Thr Tyr Glu Asp His Asn Tyr Ile Asn Cys Arg Lys
2210                2215                2220

Leu Ala Glu Asp Val Pro Cys Tyr Ile Tyr Ala Thr Glu Asp Glu
2225                2230                2235

Asp Leu Ala Val Asp Leu Leu Gly Leu Glu Trp Pro Asp Ala Ser
2240                2245                2250

Asn Gln Thr Val Lys Gly Val Glu Gln Ala Leu Glu Gln Ile Val
2255                2260                2265

Gly Leu Ser Thr Gly Glu Thr Ala Leu Leu Val Ala Leu Phe Gly
2270                2275                2280

Tyr Val Gly Tyr Gln Ala Leu Ser Lys Arg His Ile Pro Val Val
2285                2290                2295

Thr Asp Ile Tyr Thr Ile Glu Asp Gln Lys Ile Glu Asp Thr Ser
2300                2305                2310

Pro Leu Gln Phe Ala Pro Asp Ser Leu Ala Ser Pro Thr Ile Glu
2315                2320                2325

Met Arg Glu Leu Ala Val Gly Asp Val Glu Arg Val Lys Glu Glu
2330                2335                2340

Ile Met Thr Tyr Ala Lys Lys Gly Ile Asp Phe Ile Gln Met Gln
2345                2350                2355

Ala Glu Lys Met Thr Lys Ser Thr Thr Tyr Asn Thr Ser Lys Glu
2360                2365                2370

Thr Val Leu Glu Tyr Met Lys Lys Phe Leu Glu Ala Ile Lys Glu
2375                2380                2385

Asn Glu Asp Gln Ile Ile Arg Tyr Ser Leu Trp Gly Cys His Thr
2390                2395                2400

```
Ala Leu  Tyr Lys Ser Ile Lys  Glu Arg Leu Gly His  Glu Thr Ala
    2405                 2410                 2415

Phe Ala  Thr Leu Val Val Lys  Trp Leu Ala Phe Gly  Glu Pro Ser
    2420                 2425                 2430

Ile Asp  Gly His Ile Lys Gln  Ala Ala Thr Asp Leu  Val Val Tyr
    2435                 2440                 2445

Tyr Ile  Ile Asn Arg Pro Lys  Phe Glu Gly Asp Thr  Gln Thr Met
    2450                 2455                 2460

Asp Glu  Gly Arg Arg Phe Val  Ala Ala Leu Leu Val  Ser Thr Leu
    2465                 2470                 2475

Ala Ser  Tyr Thr Tyr Lys Ser  Tyr Asn Tyr Glu His  Leu Gly Lys
    2480                 2485                 2490

Leu Val  Glu Pro Val Leu Asn  Tyr Leu Pro Tyr Ser  Ala Ser Val
    2495                 2500                 2505

Leu Arg  Met Phe Ser Pro Gly  Arg Leu Glu Ser Val  Val Ile Leu
    2510                 2515                 2520

Ser Ser  Thr Ile Tyr Lys Ser  Tyr Leu Ala Ile Lys  Lys Gly Arg
    2525                 2530                 2535

Ser Asp  Gly Leu Ala Gly Ala  Gly Ile Ser Ala Ala  Met Glu Ile
    2540                 2545                 2550

Met Thr  Gln Asn Pro Val Thr  Ile Gly Ile Ala Val  Leu Leu Gly
    2555                 2560                 2565

Val Gly  Ala Ile Ala Ala His  Asn Ala Ile Glu Ser  Ser Glu Gln
    2570                 2575                 2580

Lys Arg  Thr Leu Leu Met Lys  Val Phe Val Lys Asn  Phe Leu Asp
    2585                 2590                 2595

Gln Ala  Ala Thr Asp Glu Leu  Val Lys Glu Ser Pro  Glu Lys Ile
    2600                 2605                 2610

Ile Met  Ala Leu Phe Glu Ala  Ile Gln Thr Val Gly  Asn Pro Leu
    2615                 2620                 2625

Arg Leu  Ile Phe His Leu Tyr  Ala Cys Tyr Tyr Lys  Lys Trp Asp
    2630                 2635                 2640

Ala Lys  Glu Ile Ala Glu Arg  Thr Ala Gly Arg Asn  Leu Phe Met
    2645                 2650                 2655

Leu Ile  Ile Tyr Glu Gly Leu  Glu Leu Leu Gly Val  Asp Ser Glu
    2660                 2665                 2670

Gly Lys  Met Arg Gln Leu Ser  Gly Asn Tyr Ile Met  Asp Leu Ile
    2675                 2680                 2685

His Arg  Val Ile Ser Asn Val  Ser Asn Ser Thr Asn  Arg Cys Leu
    2690                 2695                 2700

Lys Asn  Leu Leu Trp Arg Ile  Ala Pro Ala Pro Ile  Ser Cys Asp
    2705                 2710                 2715

Trp Ser  Asn Phe Asp Glu Arg  Ile Gly Leu Pro Thr  Leu Gln Tyr
    2720                 2725                 2730

Asp Arg  Thr Glu Thr Lys Cys  Thr Cys Gly Tyr Thr  Lys Ser Met
    2735                 2740                 2745

Met Lys  Thr Ser Asp Gly Arg  Trp Asn Val Leu Glu  Glu Lys Gly
    2750                 2755                 2760

Pro Val  Leu Cys Arg Asn Arg  Gly Glu Val Gly Leu  Leu Asn Tyr
    2765                 2770                 2775

Lys Val  Thr Ser Tyr Tyr Asn  Gln Arg Glu Lys Val  Asn Pro Val
    2780                 2785                 2790

Ile Lys  Leu Lys Gly Glu Val  Glu Leu Tyr Tyr Ser  Gly Gly Thr
```

-continued

```
                 2795                 2800                 2805
Tyr Lys Leu Ile Cys Ser His Asn Gln Arg Thr Ile Val Ala Thr
        2810                 2815                 2820

Ser Lys Trp Gln Val Gln His Ser Glu Val Ser Arg Leu Leu Thr
        2825                 2830                 2835

Arg Phe Ser Gly Phe Gly Val Gly Gly Ser Ser Leu Gly Asp Gln
        2840                 2845                 2850

Pro Asp Tyr Asp Ala Leu Val His Arg Lys Cys Ala Thr Ile Thr
        2855                 2860                 2865

Lys Thr Ser Val Val Phe Val Lys Leu Glu Lys Gly Cys Ala Phe
        2870                 2875                 2880

Thr Thr Asp Leu Thr Ile Gln Asn Leu Thr Lys Leu Ile Glu Leu
        2885                 2890                 2895

Val His Lys Asn Lys Leu Glu Asp Gln Ala Leu Pro Glu Val Ile
        2900                 2905                 2910

Thr Gly Thr Ile Trp Leu Ala Phe Asn Val Val Asn Ala Asn Ile
        2915                 2920                 2925

Gly Tyr Ile Lys Pro Thr Phe Gly Glu Lys Ile Ile Pro Glu Pro
        2930                 2935                 2940

Glu Glu Ala Thr Phe Met Glu Glu Val Ile Gln Ile Lys Gln Ser
        2945                 2950                 2955

Lys Ala Asn Ile Thr Cys Val Gly Glu Ala Glu Val Met Thr Thr
        2960                 2965                 2970

Gly Val Thr Lys Phe Thr Asn Val Gln Glu Thr Glu Asn Gln His
        2975                 2980                 2985

Asn Gln Val Glu Ile Gly Ile Glu Lys Gly Gln Phe Pro Gly Pro
        2990                 2995                 3000

Tyr Arg Gln Thr Ser Arg Leu Glu Glu Val Ile Glu Gln Lys Asp
        3005                 3010                 3015

Gly Arg Pro Tyr Leu Leu Val Ile Gly Lys Arg Thr Ser Met Ser
        3020                 3025                 3030

Met Arg Ala Arg Thr Ala Lys Asn Ile Lys Phe Phe Thr Gly Arg
        3035                 3040                 3045

Ser Glu Ile Leu Leu Arg Asp Leu Met Glu Gln Gly Lys Val Ile
        3050                 3055                 3060

Thr Val Ala Leu Cys Glu Leu Glu Asp Asp Leu Ile Pro Tyr Ile
        3065                 3070                 3075

Asp Tyr Lys Gly Ser Tyr Leu Asn Arg Glu Ala Leu Glu Ala Leu
        3080                 3085                 3090

Ala Arg Gly Gln Pro Lys Lys Lys Ile Thr Lys Ala Ile Ala
        3095                 3100                 3105

Arg Arg Leu Leu Gln Pro Glu Glu Asp Thr Ser Leu Pro Glu
        3110                 3115                 3120

Trp Leu His Val Asp Gln Pro Phe Gln Leu Thr Ile Thr Arg Lys
        3125                 3130                 3135

Gln Glu Ser Tyr His Ile Ile Gly Asp Leu Gln Ser Val Lys Glu
        3140                 3145                 3150

Lys Ala Lys Gln Leu Gly Ala Ser Glu Asn Thr Lys Ile Val Lys
        3155                 3160                 3165

Glu Lys Asn Ala Thr Ile Tyr Thr Met Lys Leu Ser Asn Trp Leu
        3170                 3175                 3180

Ser Tyr Glu Ser Lys Tyr Arg Asn Cys Asp Leu Thr Ala Leu Phe
        3185                 3190                 3195
```

-continued

| | | | | | | | | | | | |
|---|---|---|---|---|---|---|---|---|---|---|---|
| Glu | Glu | Leu | Leu | Leu | Arg | Cys | Thr | Pro | Ile | Ser | Glu | Arg | Lys | Asp |
| | 3200 | | | | 3205 | | | | 3210 | | | |

Glu Glu Leu Leu Leu Arg Cys Thr Pro Ile Ser Glu Arg Lys Asp
    3200                3205              3210

Leu His Met Ala Ser Pro Val Gln Met Ala Asn Gly Asn Trp Trp
    3215                3220              3225

Pro Leu Arg Ala Glu Val His Phe Gly Arg Ile Pro Cys Ile Arg
    3230                3235              3240

Arg Lys Thr His Pro Tyr Glu Ala Tyr Val Glu Leu Lys Glu Leu
    3245                3250              3255

Val Glu Arg Lys Glu Ser Ser Lys Leu Leu Gly Glu His Ser Leu
    3260                3265              3270

Arg Gln His Asn His Trp Ile Leu Lys Lys Ile Ser Glu Pro Gly
    3275                3280              3285

Thr Leu Asn Thr Lys Met Met Leu Asn Pro Gly Lys Ile Gly Gly
    3290                3295              3300

Gly Val Arg Lys Glu Lys Arg Lys Asn Asn Val Tyr Asn Ser Arg
    3305                3310              3315

Ile Gly Ala Ile Met His Ser Ile Gly Ile Lys Met Glu Lys Leu
    3320                3325              3330

Pro Val Val Arg Ala Gln Thr Asp Thr Arg Ser Phe His Ser Ala
    3335                3340              3345

Ile Lys Glu Lys Ile Asp Lys Lys Glu Asn Glu Gln Glu Pro Asn
    3350                3355              3360

Met His Pro Glu Leu Tyr Lys Ile Phe Glu Val Phe Ser Lys Gly
    3365                3370              3375

Glu Leu Ala Ser Thr Tyr Asp Glu Val Thr Trp Glu Glu Leu Glu
    3380                3385              3390

Asn Gly Ile Asn Arg Lys Gly Ala Ala Gly Val Leu Glu Asp Leu
    3395                3400              3405

Asn Ile Gly Glu Ile Leu Leu Lys Asp Lys Ala Gly Val Thr Lys
    3410                3415              3420

Ile Ile Arg Asp Leu Arg Ala Gly Lys Lys Ile Lys Tyr Tyr Glu
    3425                3430              3435

Thr Ala Ile Pro Lys Asn Glu Lys Arg Asp Val Thr Asp Asp Trp
    3440                3445              3450

Val Thr Gly Asp Tyr Val Glu Glu Lys Lys Pro Arg Val Ile Gln
    3455                3460              3465

Tyr Pro Glu Ala His Val Arg Leu Ala Ile Thr Lys Val Met Tyr
    3470                3475              3480

Ser Trp Val Lys Gln Lys Pro Val Val Ile Pro Gly Tyr Glu Gly
    3485                3490              3495

Lys Thr Pro Leu Phe Asn Val Phe Asn Lys Val His Lys Glu Trp
    3500                3505              3510

Lys Gly Phe Gln Asp Pro Val Ala Val Ser Phe Asp Thr Lys Ala
    3515                3520              3525

Trp Asp Thr Gln Val Thr Thr Lys Asp Leu Leu Leu Ile Ala Arg
    3530                3535              3540

Ile Gln Lys Phe Tyr Phe Lys Gln Lys Trp His Lys Phe Ile Asp
    3545                3550              3555

Thr Ile Thr Glu His Met Cys Glu Val Pro Val Val Thr Glu Asp
    3560                3565              3570

Gly Glu Val Tyr Ile Arg Gln Gly Gln Arg Gly Ser Gly Gln Pro
    3575                3580              3585

Asp Thr Ser Ala Gly Asn Ser Met Leu Asn Val Leu Thr Met Val
3590 3595 3600

Leu Ala Phe Cys Arg Ala Thr Gly Ile Pro Tyr Lys Ser Phe Pro
3605 3610 3615

Arg Val Ala Lys Ile His Val Cys Gly Asp Asp Gly Phe Leu Ile
3620 3625 3630

Thr Glu Arg Pro Leu Ala Glu Arg Phe Ser Arg His Gly Val Gln
3635 3640 3645

Leu Leu His Glu Leu Gly Lys Pro Gln Lys Ile Thr Thr Glu Asn
3650 3655 3660

Asn Thr Met Lys Leu Ala Tyr Asn Phe Glu Asp Ile Glu Phe Cys
3665 3670 3675

Ser His Thr Pro Ile Gln Val Arg Trp Ser Asp Asn Ser Ser Ser
3680 3685 3690

Tyr Met Ala Gly Arg Glu Thr Ala Thr Ile Leu Ala Lys Met Ala
3695 3700 3705

Thr Arg Leu Asp Ser Ser Gly Glu Arg Gly Ser Glu Ala Tyr Glu
3710 3715 3720

Arg Ala Val Ala Phe Ser Phe Leu Leu Met Tyr Ser Trp Asn Pro
3725 3730 3735

Leu Val Arg Arg Ile Cys Leu Leu Val Leu Ser Ile Cys Asp Gln
3740 3745 3750

Pro Lys Met Ala Gln Thr Thr Met Phe Tyr Ser Glu Gly Asp Pro
3755 3760 3765

Val Ala Ala Tyr Glu Glu Val Val Gly His Lys Ile Thr Gln Leu
3770 3775 3780

Asn Arg Thr Glu Phe Arg Lys Leu Ala Lys Leu Asn Leu Ser Met
3785 3790 3795

Ser Ile Leu Gly Ile Trp Thr Lys His Thr Ser Lys Arg Leu Leu
3800 3805 3810

Glu Asp Cys Ile Lys Arg Gly Met Ala Glu Gly Asn His Leu Val
3815 3820 3825

Asn Ala Asp Arg Leu Val Ser Gln Lys Thr Gly Asn Ser Tyr Thr
3830 3835 3840

Gln Gly Thr Gly His Val Lys Gln Gly Lys His Tyr Glu Glu Leu
3845 3850 3855

Ile Ile Pro Ser Gly Arg Arg Ile Thr Thr Thr Ile Val Glu Arg
3860 3865 3870

Tyr Ser Leu Gly Pro Ile Lys Thr Phe Ile Leu Lys Arg Leu Arg
3875 3880 3885

Leu Leu Thr Ile Phe Leu Ser Asn Asn
3890 3895

<210> SEQ ID NO 50
<211> LENGTH: 3989
<212> TYPE: PRT
<213> ORGANISM: Giraffe pestivirus

<400> SEQUENCE: 50

Met Glu Leu Ile Lys Phe Glu Leu Leu Tyr Lys Thr Ser Lys Gln Lys
1 5 10 15

Pro Val Gly Val Glu Glu Pro Val Tyr Arg Arg Thr Gly Glu Pro Val
20 25 30

Phe Gly Glu Pro Ser Pro Ile His Pro Gln Ala Ser Leu Glu Leu Pro
35 40 45

```
His Gln Arg Gly Thr Arg Asp Ile Pro Thr Arg Leu Lys Asp Leu Pro
     50                  55                  60

Arg Lys Gly Asp Cys Arg Ser Gly Asn Asn Lys Gly Pro Val Ser Gly
 65                  70                  75                  80

Val Tyr Ile Lys Pro Gly Pro Val Tyr Tyr Gln Asp Tyr Ser Gly Pro
                     85                  90                  95

Val Tyr His Arg Ala Pro Leu Glu Leu Phe Glu Glu Ser Thr Met Cys
                100                 105                 110

Glu Val Thr Arg Arg Leu Gly Arg Thr Thr Gly Ser Asp Gly Leu Leu
            115                 120                 125

Tyr His Val Tyr Val Cys Leu Asp Gly Cys Ile Ile Ile Lys Thr Ala
        130                 135                 140

Ser Arg Ala Gln Gln Lys Val Leu Lys Trp Thr Lys Asn Thr Leu Asn
145                 150                 155                 160

Cys Pro Leu Trp Leu Thr Ser Cys Ser Asp Glu Gly Ala Lys Lys
                165                 170                 175

Lys Gln Val Lys Pro Asp Arg Val Glu Lys Gly Arg Met Gln Ile Lys
                180                 185                 190

Pro Lys Glu Ser Glu Lys Asp Ser Arg Thr Lys Pro Pro Asp Ala Thr
            195                 200                 205

Ile Val Leu Asp Gly Val Lys Tyr Gln Val Lys Lys Gly Lys Val
        210                 215                 220

Lys Ser Lys Ser Thr Ala Asp Gly Leu Tyr His Asn Lys Asn Lys Pro
225                 230                 235                 240

Glu Gln Ser Arg Lys Lys Leu Glu Lys Ala Leu Leu Ala Trp Ala Ile
                245                 250                 255

Leu Ala Val Leu Phe Gln Pro Val Ala Gly Glu Asn Ile Thr Gln Trp
                260                 265                 270

Asn Leu Ser Asp Asn Gly Thr Ser Gly Ile Gln His Ala Met Tyr Leu
            275                 280                 285

Arg Gly Val Asn Arg Ser Leu His Gly Ile Trp Pro Glu Lys Ile Cys
        290                 295                 300

Thr Gly Ile Pro Thr His Leu Ala Thr Asp Thr Glu Leu Lys Arg Ile
305                 310                 315                 320

Ser Gly Met Met Asp Ala Ser Glu Glu Thr Asn Tyr Thr Cys Cys Arg
                325                 330                 335

Leu Gln Arg His Glu Trp Asn Lys His Gly Trp Cys Asn Trp Phe Asn
                340                 345                 350

Ile Glu Pro Trp Ile Ala Leu Met Asn Arg Thr Gln Ala Asn Leu Thr
            355                 360                 365

Glu Gly Pro Pro Lys Glu Cys Ala Val Thr Cys Arg Tyr Asp Lys
        370                 375                 380

Asn Thr Glu Thr Asn Ile Val Thr Gln Ala Arg Asp Arg Pro Thr Met
385                 390                 395                 400

Leu Thr Gly Cys Lys Lys Gly Lys Asn Phe Ser Phe Ala Gly Thr Val
                405                 410                 415

Ile Lys Gly Pro Cys Asn Phe Asp Val Ser Leu Glu Asp Ile Leu Phe
            420                 425                 430

Lys Asp Glu Gly Cys Gly Asn Met Met Gln Asp Ala Ala Ile Gln Glu
        435                 440                 445

Val Asp Gly Ile Thr Asn Thr Val Glu Gly Ala Arg Gln Gly Ala Ala
    450                 455                 460
```

```
Lys Leu Thr Thr Trp Leu Gly Lys Gln Phe Arg Ile Leu Gly Arg Lys
465                 470                 475                 480

Leu Glu His Lys Ser Lys Thr Trp Phe Gly Ala His Ala Ala Ser Pro
            485                 490                 495

Tyr Cys Glu Val Asn Lys Lys Leu Gly Tyr Ile Trp Tyr Thr Asn Asn
            500                 505                 510

Cys Thr Pro Ala Cys Leu Pro Gly Asn Thr Lys Ile Ile Gly Pro Gly
            515                 520                 525

Lys Phe Asp Thr Asn Ala Glu Asp Gly Lys Ile Leu His Glu Leu Gly
    530                 535                 540

Gly His Leu Ser Glu Phe Ile Leu Leu Ser Leu Val Val Leu Ser Asp
545                 550                 555                 560

Phe Ala Pro Glu Thr Ala Ser Ala Ile Tyr Leu Val Leu His Tyr Thr
                565                 570                 575

Met Pro Gln Lys Tyr Glu Val Val Gly Ser Cys Asp Arg Asn Gln Leu
                580                 585                 590

Asn Leu Thr Val Lys Thr Arg Val Glu Asp Val Ile Pro Ser Ser Val
            595                 600                 605

Trp Asn Ile Gly Lys Tyr Val Cys Val Arg Pro Asp Trp Trp Pro Tyr
610                 615                 620

Glu Thr Thr Thr Val Phe Ile Phe Glu Glu Val Ser Gln Val Val Lys
625                 630                 635                 640

Leu Val Leu Arg Ala Leu Arg Asp Leu Thr Arg Ile Trp Asn Ala Ala
                645                 650                 655

Ser Thr Thr Ala Phe Leu Ile Cys Leu Val Lys Val Leu Arg Gly Gln
                660                 665                 670

Val Ile Gln Gly Ile Val Trp Leu Leu Leu Val Thr Gly Ala Gln Gly
            675                 680                 685

Ala Ile Thr Cys Glu Pro Glu Tyr Gln Tyr Ala Leu Ala Arg Ser Lys
            690                 695                 700

Arg Ile Gly Pro Leu Gly Ala Glu Asp Leu Val Thr Thr Trp His Asp
705                 710                 715                 720

Tyr Lys Phe Asp Leu Lys Ile Gln Asp Pro Leu Val Met Val Tyr Cys
                725                 730                 735

Lys Asn Asp Gln Phe Phe Val Gly Lys Arg Cys Lys Ala Gly Glu Ala
                740                 745                 750

Arg Tyr Leu Ala Lys Ile His Trp Arg Ala Leu Pro Thr Ser Val Val
            755                 760                 765

Phe Glu Lys Val Leu Glu Glu Asn Pro Pro Glu Glu Leu Pro Leu Glu
    770                 775                 780

Asp Asn Phe Glu Phe Gly Leu Cys Pro Cys Asp Ser Arg Pro Val Val
785                 790                 795                 800

Lys Gly Asn Phe Asn Thr Thr Leu Ile Asn His Ser Ala Phe Gln Leu
                805                 810                 815

Val Cys Pro Ile Gly Trp Val Gly Thr Ile Glu Cys Thr Leu Val Asn
            820                 825                 830

Thr Asp Thr Leu Ala Thr Thr Val Lys Arg Tyr Thr Arg Thr Thr
            835                 840                 845

Pro Phe Pro Met Arg Ala Gly Cys Val Val Tyr Lys Leu Ile Gly Glu
            850                 855                 860

Asp Leu His His Cys Thr Leu Gly Gly Asn Trp Thr Cys Val Pro Glu
865                 870                 875                 880

Asp Asp Gly Thr Tyr Thr Gly Gly Glu Leu Glu Lys Cys Lys Trp Cys
```

-continued

```
                885                 890                 895
Gly Phe Lys Phe Arg Ile Pro Asp Gly Leu Pro Thr Tyr Pro Ile Gly
                900                 905                 910

Arg Cys Met Lys Arg Gly Lys Ala Gly Tyr Arg Phe Val Ser Glu Glu
                915                 920                 925

Pro Cys Asn Arg Glu Gly Val Glu Ile Ser Thr Lys Gly Lys Leu Lys
                930                 935                 940

Cys Ile Ile Glu Lys Thr Gln Val Lys Val Tyr Ala Ala Asp Asn Thr
945                 950                 955                 960

Leu Gly Pro Met Pro Cys Lys Pro Met Glu Ile Ile Ser Ser Glu Gly
                965                 970                 975

Pro Val Ser Lys Thr Ala Cys Thr Phe Asn Tyr Thr Glu Thr Leu Glu
                980                 985                 990

Asn Lys Tyr Phe Glu Pro Arg Asp Glu Tyr Phe Gln Gln Tyr Met Leu
                995                 1000                1005

Lys Gly Lys Tyr Gln Tyr Trp Phe Asp Leu Lys Ala Thr Asp Asn
                1010                1015                1020

Arg Lys Asp Tyr Phe Ala Glu Phe Leu Val Ile Ala Val Val Ala
                1025                1030                1035

Leu Leu Gly Gly Arg Tyr Val Leu Trp Leu Leu Val Thr Tyr Phe
                1040                1045                1050

Val Ile Thr Glu Gln Glu Ala Ser Gly Leu Gln Leu Glu Pro Gly
                1055                1060                1065

Val Val Val Met Ile Gly Asn Leu Ile Thr Glu Asp Asn Ile Glu
                1070                1075                1080

Val Val Val Tyr Phe Leu Leu Leu Phe Leu Val Val Arg Asp Glu
                1085                1090                1095

Pro Val Lys Lys Trp Val Ile Cys Leu Tyr His Cys Leu Thr Met
                1100                1105                1110

Lys Pro Ile Lys Thr Ala Ala Val Leu Val Leu Leu Met Ser Asn
                1115                1120                1125

Val Val Asn Gly Glu Gly Gly Ser Lys Ala Gly Ala Gly Ile Asp
                1130                1135                1140

Leu Tyr Phe Leu Thr Thr Leu Gly Met Val Val Phe Leu Val Leu
                1145                1150                1155

Ala Arg Arg Asp Pro Met Leu Ile Pro Leu Val Val Ala Ile Ala
                1160                1165                1170

Thr Phe Lys Thr Thr Lys Tyr Thr Ala Gly Phe Ser Val Asp Val
                1175                1180                1185

Ala Leu Ala Val Leu Leu Ile Val Leu Leu Ile Cys Ser Tyr Thr
                1190                1195                1200

Ser Asp Tyr Phe Lys Tyr Arg Lys Leu Leu Gln Cys Leu Leu Ser
                1205                1210                1215

Ile Gly Ala Ala Val Phe Leu Ile Arg Ser Leu Lys Trp Leu Gly
                1220                1225                1230

Gly Val Gly Leu Pro Ser Ile Glu Leu Pro Thr Gln Arg Pro Leu
                1235                1240                1245

Phe Tyr Ile Leu Val Tyr Leu Ile Ala Thr Ala Leu Val Thr Ser
                1250                1255                1260

Trp Asn Leu Asp Ile Ala Gly Ser Leu Ile Gln Ala Val Pro Ile
                1265                1270                1275

Leu Leu Leu Ile Phe Thr Leu Trp Ala Asp Ile Leu Thr Leu Ile
                1280                1285                1290
```

```
Leu Val Leu Pro Thr Tyr Glu Leu Ala Lys Leu Tyr Tyr Leu Lys
1295                1300                1305

Met Val Lys Thr Asp Val Glu Lys Thr Trp Thr Gly Arg Val Arg
1310                1315                1320

Tyr Lys Arg Val Thr Thr Val Tyr Asp Leu Glu Gly Ser Gly Glu
1325                1330                1335

Gly Val Tyr Leu Phe Pro Ser Lys Met Gly Gly Arg Asp Gly Phe
1340                1345                1350

Asp Phe Thr Leu Pro Leu Leu Arg Ala Val Leu Ile Ser Cys Val
1355                1360                1365

Ser Ser Tyr Trp Gln Thr Phe Tyr Leu Met Tyr Leu Ala Ile Asp
1370                1375                1380

Leu Leu Tyr Tyr Val His Arg Lys Ile Ile Glu Glu Val Ala Gly
1385                1390                1395

Gly Thr Asn Leu Ala Ser Arg Leu Leu Ala Ala Leu Ile Glu Leu
1400                1405                1410

Asn Trp Thr Val Asp Ser Glu Glu Ser Lys Gly Leu Lys Lys Phe
1415                1420                1425

Phe Val Leu Thr Ser Arg Val Lys Asn Leu Val Met Lys His Lys
1430                1435                1440

Val Arg Asn Asp Leu Val Ala Lys Trp Tyr Glu Asp Glu Glu Ile
1445                1450                1455

Tyr Gly Met Pro Lys Leu Val Ser Ile Val Lys Ala Ala Ser Leu
1460                1465                1470

Ser Lys Thr Lys Ser Cys Ile Leu Cys Thr Val Cys Glu Asn Lys
1475                1480                1485

Asp Trp Lys Gly Val Asn Cys Pro Lys Cys Gly Gly Thr Gly Pro
1490                1495                1500

Pro Ile Ser Cys Gly Met Thr Leu Ala Asp Phe Glu Glu Arg His
1505                1510                1515

Tyr Lys Arg Ile Phe Ile Arg Glu Asp Ser Met Asn Thr Met Met
1520                1525                1530

Cys Asn Arg Cys Gln Gly Lys His Arg Arg Phe Glu Met Asp Arg
1535                1540                1545

Glu Pro Lys Ser Ala Arg Tyr Cys Ala Glu Cys Asn Arg Leu His
1550                1555                1560

Pro Ala Glu Glu Gly Asp Phe Trp Ala Glu Ser Ser Met Leu Gly
1565                1570                1575

Leu Lys Ile Thr Tyr Phe Ala Leu Met Asp Gly Lys Val Tyr Asp
1580                1585                1590

Ile Thr Glu Trp Ala Gly Cys Gln Arg Val Gly Ile Ser Pro Asp
1595                1600                1605

Thr His Arg Val Pro Tyr His Ile Pro Phe Gly Ser Arg Met Pro
1610                1615                1620

Gly Thr Ser Asp Gln Arg Glu Glu Cys Glu Gly Phe Leu Gln Tyr
1625                1630                1635

Arg Ala Arg Gly Gln Leu Phe Leu Arg Asn Leu Pro Ile Leu Ala
1640                1645                1650

Thr Lys Val Lys Phe Leu Met Val Gly Asn Leu Gly Ser Glu Val
1655                1660                1665

Gly Asp Leu Glu His Leu Gly Trp Val Leu Arg Gly Pro Ala Val
1670                1675                1680
```

```
Cys Lys Lys Ile Thr Ser His Glu Lys Cys His Thr Gly Ile Ala
1685                1690                1695

Asp Lys Leu Thr Ala Phe Phe Gly Ile Met Pro Arg Gly Thr Thr
1700                1705                1710

Pro Arg Ala Pro Val Arg Phe Pro Asn Ala Leu Leu Lys Ile Arg
1715                1720                1725

Arg Gly Leu Glu Thr Gly Trp Ala Tyr Thr His Gln Gly Gly Ile
1730                1735                1740

Ser Ser Val Asp His Val Thr Gly Gly Lys Asp Leu Leu Val Cys
1745                1750                1755

Asp Ser Met Gly Arg Thr Arg Val Val Cys Gln Ser Asn Asn Lys
1760                1765                1770

Met Thr Asp Glu Thr Glu Tyr Gly Ile Lys Thr Asp Ser Gly Cys
1775                1780                1785

Pro Asp Gly Ala Arg Cys Tyr Val Leu Asn Pro Glu Ala Pro Asn
1790                1795                1800

Ile Ser Gly Thr Lys Gly Ala Met Val His Leu Gln Lys Thr Gly
1805                1810                1815

Ser Glu Phe Thr Cys Val Thr Ala Ser Gly Thr Pro Ala Phe Phe
1820                1825                1830

Asp Leu Lys Asn Leu Arg Gly Trp Ser Gly Leu Pro Ile Phe Glu
1835                1840                1845

Ala Ser Ser Gly Arg Val Val Gly Arg Val Lys Val Gly Lys Asn
1850                1855                1860

Glu Gly Ala Lys Pro Thr Lys Leu Met Ser Gly Ile Gln Thr Val
1865                1870                1875

Ser Lys Ser Thr Ala Asp Ile Thr Glu Met Val Lys Lys Ile Val
1880                1885                1890

Ala Met Asn Arg Gly Glu Phe Lys Gln Ile Thr Leu Ala Thr Gly
1895                1900                1905

Ala Gly Lys Thr Thr Glu Leu Pro Arg Ser Val Val Glu Glu Ile
1910                1915                1920

Gly Arg His Lys Arg Val Leu Val Leu Ile Pro Leu Arg Ala Ala
1925                1930                1935

Ala Glu Ser Val Tyr Gln Tyr Met Arg His Lys Tyr Pro Ser Ile
1940                1945                1950

Ala Phe Asn Leu Arg Ile Gly Glu Met Lys Glu Gly Asp Met Ala
1955                1960                1965

Thr Gly Ile Thr Tyr Ala Ser Tyr Gly Tyr Phe Cys Gln Met Pro
1970                1975                1980

Gln Pro Lys Leu Arg Ala Ala Met Val Glu Tyr Ser Tyr Ile Phe
1985                1990                1995

Leu Asp Glu Tyr His Cys Ala Thr Ala Glu Gln Leu Ala Ile Ile
2000                2005                2010

Gly Lys Ile His Arg Phe Ser Asp Gln Leu Arg Val Val Ala Met
2015                2020                2025

Thr Ala Thr Pro Ala Gly Thr Val Thr Thr Thr Gly Gln Lys His
2030                2035                2040

Pro Ile Glu Glu Phe Ile Ala Pro Glu Val Met Arg Gly Glu Glu
2045                2050                2055

Leu Gly Ser Glu Phe Ile Asp Ile Ala Gly Leu Lys Ile Pro Thr
2060                2065                2070

Glu Glu Met Lys Gly Asn Met Leu Val Phe Val Pro Thr Arg Asn
```

```
              2075                2080                2085
Met Ala Val Glu Thr Ala Lys Lys Leu Lys Ala Lys Gly Tyr Asn
        2090                2095                2100

Ser Gly Tyr Tyr Tyr Ser Gly Glu Asp Pro Ala Asn Leu Lys Val
        2105                2110                2115

Val Thr Ser Gln Ser Pro Tyr Val Val Ala Thr Asn Ala Ile
        2120                2125                2130

Glu Ser Gly Val Thr Leu Pro Asp Leu Asp Val Val Asp Thr
        2135                2140                2145

Gly Leu Lys Cys Glu Lys Arg Val Arg Ile Ser Ser Lys Met Pro
        2150                2155                2160

Phe Ile Val Thr Gly Leu Lys Arg Met Ala Val Thr Ile Gly Glu
        2165                2170                2175

Gln Ala Gln Arg Arg Gly Arg Val Gly Arg Val Lys Pro Gly Lys
        2180                2185                2190

Tyr Tyr Arg Ser Gln Glu Thr Ala Thr Gly Ser Lys Asp Tyr His
        2195                2200                2205

Tyr Asp Leu Leu Gln Ala Gln Arg Tyr Gly Ile Glu Asp Gly Ile
        2210                2215                2220

Asn Val Thr Lys Ser Phe Arg Glu Met Asn Tyr Asp Trp Ser Leu
        2225                2230                2235

Tyr Glu Glu Asp Ser Leu Leu Ile Thr Gln Leu Glu Val Leu Asn
        2240                2245                2250

Asn Leu Leu Ile Ser Glu Asp Leu Pro Ala Ala Val Lys Asn Ile
        2255                2260                2265

Met Ala Arg Thr Asp His Pro Glu Pro Ile Gln Leu Ala Tyr Asn
        2270                2275                2280

Ser Tyr Glu Val Gln Val Pro Val Leu Phe Pro Lys Ile Arg Asn
        2285                2290                2295

Gly Glu Val Thr Asp Thr Tyr Glu Thr Tyr Thr Phe Leu Asn Ala
        2300                2305                2310

Arg Lys Leu Gly Glu Asp Val Pro Ala Tyr Ile Tyr Ala Thr Glu
        2315                2320                2325

Asp Glu Asp Leu Ala Val Asp Leu Leu Gly Leu Asp Trp Pro Asp
        2330                2335                2340

Pro Gly Val Gln Ser Thr Thr Glu Thr Ser Arg Ala Leu Lys Gln
        2345                2350                2355

Val Met Gly Leu Ser Thr Ala Glu Asn Ala Leu Leu Val Ala Leu
        2360                2365                2370

Phe Gly Tyr Val Gly Tyr Gln Ala Leu Ser Lys Arg His Ile Pro
        2375                2380                2385

Ile Val Thr Asp Ile Tyr Thr Val Glu Asp His Arg Leu Glu Asp
        2390                2395                2400

Thr Thr His Leu Gln Phe Ala Pro Asn Ala Ile Arg Thr Asp Gly
        2405                2410                2415

Lys Glu Thr Glu Leu Lys Glu Leu Ala Val Gly Asp Ile Asp Arg
        2420                2425                2430

Cys Thr Glu Ala Ile Ala Asp Tyr Thr Asn Lys Gly Ile Gln Phe
        2435                2440                2445

Ile Lys Ile Gln Ala Ala Asn Val Met Gly Ser Thr Ala Val Lys
        2450                2455                2460

Glu Val Ala Ser Glu Val Lys Asp Tyr Val Gln Lys Phe Ile Asp
        2465                2470                2475
```

```
Ala Leu Ser Glu Ser Lys Glu Glu Ile Leu Arg Tyr Gly Leu Trp
    2480            2485                2490

Gly Thr His Thr Ala Leu Tyr Lys Ser Ile Ala Ser Arg Leu Gly
    2495            2500                2505

His Glu Thr Ala Phe Ala Thr Leu Val Ile Lys Trp Leu Ala Phe
    2510            2515                2520

Gly Gly Glu Ser Ile Ser Asp His Ile Lys Gln Ala Ala Thr Asp
    2525            2530                2535

Leu Val Val Tyr Tyr Ile Met Asn Lys Pro His Phe Pro Gly Asp
    2540            2545                2550

Thr Glu Thr Gln Gln Glu Gly Arg Arg Phe Val Ala Ser Leu Leu
    2555            2560                2565

Val Ala Gly Leu Ala Thr Tyr Thr Tyr Lys Thr Trp Asn Tyr Asn
    2570            2575                2580

Asn Leu Ser Lys Val Val Glu Pro Ala Leu Ala Cys Leu Pro Tyr
    2585            2590                2595

Ala Ala Gln Ala Leu Lys Leu Phe Thr Pro Thr Arg Leu Glu Ser
    2600            2605                2610

Val Val Ile Leu Ser Thr Ala Ile Tyr Lys Thr Tyr Leu Ser Ile
    2615            2620                2625

Arg Lys Gly Lys Ser Asp Gly Leu Leu Gly Thr Gly Val Ser Ala
    2630            2635                2640

Ala Met Glu Ile Met Ser Gln Asn Pro Val Ser Val Gly Val Ala
    2645            2650                2655

Val Met Leu Gly Val Gly Ala Val Ala Ala His Asn Ala Ile Glu
    2660            2665                2670

Ser Cys Glu Gln Lys Arg Thr Leu Leu Met Lys Val Phe Val Lys
    2675            2680                2685

Asn Phe Leu Asp Gln Ala Ala Thr Asp Glu Leu Val Lys Glu Ser
    2690            2695                2700

Pro Glu Lys Ile Ile Met Ala Leu Phe Glu Ala Val Gln Thr Ile
    2705            2710                2715

Gly Asn Pro Leu Arg Leu Ile Tyr His Ile Tyr Gly Val Phe Tyr
    2720            2725                2730

Lys Gly Trp Glu Thr Lys Asp Leu Ala Glu Arg Thr Ala Gly Arg
    2735            2740                2745

Asn Ile Phe Thr Leu Ile Met Phe Glu Ala Val Glu Leu Leu Gly
    2750            2755                2760

Val Asp Ser Glu Gly Lys Ile Arg Thr Leu Ser Ser Asn Tyr Ile
    2765            2770                2775

Leu Asp Ile Leu His Arg Leu Lys Asn Ser Leu Gln Ile Ser Ala
    2780            2785                2790

Arg Lys Val Ile Ile Gly Trp Ala Pro Ala Pro Phe Ser Cys Asp
    2795            2800                2805

Trp Thr Ala Ser Asp Asp Arg Ile His Leu Pro Ser Glu Asp Tyr
    2810            2815                2820

Gln His Ile Gln Thr Lys Cys Thr Cys Gly Tyr Glu Met Lys Ala
    2825            2830                2835

Val Lys Gly Ala Asp Gly Lys Ile Val Lys Val Glu Glu Lys Gly
    2840            2845                2850

Ser Phe Phe Cys Arg Asn Lys Tyr Gly Arg Gly Pro Ile Asn His
    2855            2860                2865
```

```
Lys Val Thr Arg Tyr Tyr Lys Gly Asp Met Ser Glu Val Lys Pro
2870             2875                 2880

Met Ala Lys Ile Gln Gly Val Val Asp Phe Tyr Tyr Lys Gly Ala
    2885             2890                 2895

Thr Ile Arg Val Asp Thr Gly Asn Gly Lys Thr Val Thr Ala Thr
2900             2905                 2910

Asp Lys Trp Glu Ile Asp His Ala Thr Ile Thr Arg Leu Leu Lys
2915             2920                 2925

Lys His Thr Gly Ile Gly Phe Asn Gly Ala Tyr Leu Gly Glu Glu
2930             2935                 2940

Pro Asn Tyr Lys Asp Leu Ile Gly Arg Asp Cys Ala Thr Ile Thr
2945             2950                 2955

Arg Asp Ser Val Gln Phe Leu Lys Met Lys Arg Gly Cys Ala Phe
2960             2965                 2970

Thr Tyr Asp Leu Thr Leu Ser Asn Leu Val Lys Leu Ile Glu Leu
2975             2980                 2985

Val His Lys Asn Lys Leu Glu Glu Arg Glu Ile Pro Glu Val Thr
2990             2995                 3000

Val Thr Thr Trp Leu Ala Tyr Val Phe Val Asp Glu Asp Val Gly
3005             3010                 3015

Thr Ile Lys Pro Cys Leu Gly Glu Lys Val Ile Pro Glu Lys Thr
3020             3025                 3030

Gly Asp Val Ser Leu Gln Ser Glu Val Ile Leu Asp Thr Thr Ser
3035             3040                 3045

Val Gly Ile Ser Val Val Gly Gly Ser Asp Arg Ala Thr Thr Gly
3050             3055                 3060

Ile Thr Pro Val Val Ile Glu Lys Gln Ser Val Thr Gly Gly Asn
3065             3070                 3075

Gln Asn Ile Leu Lys Ile Gly Leu Ser Glu Gly Glu Tyr Pro Gly
3080             3085                 3090

Pro Gly Val Asn Arg Ala Ser Ile Ser Gln Ala Val Glu Glu Arg
3095             3100                 3105

Asp Asn Arg Pro Trp Val Leu Ile Leu Gly Ser Asp Lys Ala Thr
3110             3115                 3120

Ser Asn Arg Val Lys Thr Ala Arg Asn Val Arg Leu Tyr Lys Gly
3125             3130                 3135

Ser Asp Pro Val Glu Val Arg Arg Leu Met Arg Glu Gly Arg Leu
3140             3145                 3150

Leu Val Ile Ser Leu Arg Asp Thr Asp Lys Gly Leu His Gln Tyr
3155             3160                 3165

Ile Asp Phe Lys Gly Thr Tyr Leu Thr Arg Glu Thr Leu Glu Ala
3170             3175                 3180

Leu Ser Met Gly Thr Pro Lys Ala Lys Gln Ile Thr Lys Ala Glu
3185             3190                 3195

Val Arg Glu Leu Leu Ser Pro Pro Ser Glu Asp Ser Gly Leu Pro
3200             3205                 3210

Asp Trp Leu Thr Ala Glu Asn Pro Val Phe Leu Glu Ala Thr Ile
3215             3220                 3225

Arg Gln Glu Lys Tyr His Ile Val Gly Asp Val Asp Val Val Lys
3230             3235                 3240

Thr Lys Ala Lys Glu Leu Gly Ala Thr Asp Asp Thr Lys Ile Val
3245             3250                 3255

Lys Glu Val Gly Ala Arg Thr Tyr Thr Met Lys Leu Ser Ser Trp
```

```
            3260                3265                3270
Phe Thr Gln Gln Ser Asn Lys His His Ser Leu Leu Pro Leu Phe
        3275                3280                3285
Glu Glu Val Leu Leu Gln Cys Pro Pro Lys Asn Pro Asn Pro Arg
        3290                3295                3300
Val His Met Val Ser Ala Tyr Gln Leu Ala Gln Gly Asn Trp Glu
        3305                3310                3315
Pro Val Asp Cys Gly Val His Leu Gly Thr Ile Pro Ala Lys Arg
        3320                3325                3330
Ser Lys Thr His Pro Tyr Glu Ala Tyr Thr Lys Leu Lys Glu Leu
        3335                3340                3345
Leu Glu Glu His Lys Asn Ser Asn Glu Met Gly Cys Gly Met Val
        3350                3355                3360
Lys Glu His Asn Lys Trp Ile Leu Arg Lys Ile Lys His His Gly
        3365                3370                3375
Asn Leu Arg Thr Lys His Ile Leu Asn Pro Gly Lys Leu Ser Glu
        3380                3385                3390
Gln Leu Ala Arg Asp Gly Gly Lys His Asn Ile Tyr Asn Lys Ile
        3395                3400                3405
Ile Gly Ser Thr Met Thr Ser Ile Gly Ile Lys Leu Glu Lys Leu
        3410                3415                3420
Pro Val Val Arg Ala Gln Thr Asp Thr Thr Ser Phe His Asp Ala
        3425                3430                3435
Ile Arg Asp Lys Ile Asp Lys Lys Glu Asn Leu Gln Asn Pro Thr
        3440                3445                3450
Leu His Thr Lys Leu Lys Glu Ile Phe Asn Asn Leu Ser Arg Pro
        3455                3460                3465
Glu Leu Arg Glu Thr Tyr Asp Glu Val Asp Trp Gly Glu Leu Glu
        3470                3475                3480
Ile Gly Ile Asn Arg Lys Gly Ala Ala Gly Phe Leu Glu Lys Lys
        3485                3490                3495
Asn Ile Gly Glu Ile Leu Thr Thr Glu Lys Lys Ser Val Glu Glu
        3500                3505                3510
Ile Ile Lys Lys Leu Arg Gln Gly Arg Leu Ile Asn Tyr Tyr Glu
        3515                3520                3525
Thr Ala Ile Pro Lys Asn Glu Lys Arg Asp Val Asn Asp Asp Trp
        3530                3535                3540
Glu Ala Gly Asp Leu Val Thr Glu Lys Lys Pro Arg Val Ile Gln
        3545                3550                3555
Tyr Pro Glu Ala Lys Val Arg Leu Ala Ile Thr Lys Val Met Tyr
        3560                3565                3570
Lys Trp Val Lys Gln Lys Pro Val Val Ile Pro Gly Tyr Glu Gly
        3575                3580                3585
Lys Thr Pro Leu Phe Leu Ile Phe Asp Lys Val Lys Lys Glu Trp
        3590                3595                3600
Asp Gln Phe Gln Asp Pro Val Ala Val Ser Phe Asp Thr Lys Ala
        3605                3610                3615
Trp Asp Thr Gln Val Thr Ser Arg Asp Leu Glu Leu Ile Arg Asp
        3620                3625                3630
Ile Gln Lys Tyr Tyr Phe Lys Arg Lys Trp His Lys Phe Leu Asp
        3635                3640                3645
Ala Ile Thr Glu His Met Thr Gln Val Pro Val Ile Thr Ala Asp
        3650                3655                3660
```

Gly Glu Val Tyr Ile Arg Glu Gly Gln Arg Gly Ser Gly Gln Pro
    3665                3670                3675

Asp Thr Ser Ala Gly Asn Ser Met Leu Asn Val Leu Thr Met Ile
    3680                3685                3690

Tyr Ala Phe Cys Glu Ser Thr Gly Val Pro Tyr Arg Ser Phe Asn
    3695                3700                3705

Arg Val Ala Lys Ile His Val Cys Gly Asp Asp Gly Phe Leu Ile
    3710                3715                3720

Thr Glu Lys Ser Leu Gly Leu Lys Phe Ala Ser Arg Gly Ala Gln
    3725                3730                3735

Ile Leu His Glu Ala Gly Lys Pro Gln Lys Ile Leu Glu Gly Asp
    3740                3745                3750

Arg Met Lys Val Ser His Arg Phe Glu Asp Ile Glu Phe Cys Ser
    3755                3760                3765

His Thr Pro Val Pro Val Arg Trp Ala Asp His Thr Ser Ser Tyr
    3770                3775                3780

Met Ala Gly Arg Asn Thr Ala Thr Ile Leu Ser Lys Met Ala Thr
    3785                3790                3795

Arg Leu Asp Ser Ser Gly Asp Arg Gly Thr Ala Ala Tyr Glu Lys
    3800                3805                3810

Ala Val Ala Phe Ser Phe Leu Leu Met Tyr Ser Trp Asn Pro Leu
    3815                3820                3825

Val Arg Arg Leu Cys Leu Met Val Met Ser Lys Thr His Glu Val
    3830                3835                3840

Gln Pro Asn Lys Gln Ala Ile Tyr Cys Tyr Glu Gly Asp Pro Ile
    3845                3850                3855

Ala Ala Tyr Arg Asp Val Ile Gly His Asn Leu Tyr Glu Leu Lys
    3860                3865                3870

Arg Thr Gly Phe Glu Lys Leu Ala Ser Leu Asn Leu Ser Met Ser
    3875                3880                3885

Val Leu Gly Ile Trp Thr Lys His Thr Ser Lys Arg Leu Ile Gln
    3890                3895                3900

Asp Cys Ile Glu Val Gly Lys Gly Asp Gly Asn Gln Leu Val Asn
    3905                3910                3915

Ala Asp Arg Leu Val Ser Ser Lys Thr Gly His Ile Tyr Val Pro
    3920                3925                3930

Gly Ser Gly Tyr Val Val Gln Gly Arg His Tyr Glu Glu Leu Ser
    3935                3940                3945

Ile Thr Lys Arg Pro Asp Arg Gln Thr Ser Asn Gly Leu Glu Arg
    3950                3955                3960

Tyr Asn Leu Gly Pro Ile Val Asn Leu Val Leu Arg Arg Leu Arg
    3965                3970                3975

Val Met Leu Met Ala Ser Ile Gly Arg Gly Ile
    3980                3985

<210> SEQ ID NO 51
<211> LENGTH: 3895
<212> TYPE: PRT
<213> ORGANISM: BDV

<400> SEQUENCE: 51

Met Glu Leu Asn Lys Phe Glu Leu Leu Tyr Lys Thr Ser Lys Gln Lys
1               5                   10                  15

Pro Val Gly Val Thr Glu Pro Ile Tyr Asp Ser Ala Gly Asn Pro Ile

-continued

```
            20                  25                  30
Tyr Gly Glu Arg Ser Thr Ile His Pro Gln Ser Thr Leu Lys Leu Pro
             35                  40                  45

His Glu Arg Gly Val Ala Glu Val Thr Thr Leu Arg Asp Leu Pro
 50                  55                  60

Lys Lys Gly Asp Cys Arg Ser Gly Asn His Arg Gly Pro Val Ser Gly
 65                  70                  75                  80

Ile Tyr Ile Lys Pro Gly Pro Val Leu Tyr Gln Asp Tyr Lys Gly Pro
             85                  90                  95

Val Tyr His Arg Ala Pro Leu Glu Leu Phe Val Glu Thr Gln Phe Cys
                 100                 105                 110

Glu Val Thr Lys Arg Ile Gly Arg Val Thr Gly Ser Asp Gly Arg Leu
                 115                 120                 125

Tyr His Leu Tyr Ile Cys Ser Asp Gly Cys Ile Leu Leu Lys Thr Ala
             130                 135                 140

Ser Lys Thr Arg Ser Ala Val Leu Lys Trp Thr Arg Asn Ile Leu Asp
145                 150                 155                 160

Cys Pro Leu Trp Val Thr Ser Cys Ser Asp Asp Asn Lys Ser Glu Lys
                 165                 170                 175

Thr Asn Glu Lys Lys Pro Asp Arg Val Arg Arg Gly Ala Met Lys Ile
             180                 185                 190

Thr Pro Lys Glu Ser Glu Lys Asp Ser Arg Ser Lys Pro Pro Asp Ala
             195                 200                 205

Thr Ile Val Val Glu Gly Ile Lys Tyr Gln Val Lys Lys Gly Lys
             210                 215                 220

Val Lys Gly Lys Asn Thr Gln Asp Gly Leu Tyr His Asn Lys Asn Lys
225                 230                 235                 240

Pro Pro Glu Ser Arg Lys Lys Leu Glu Lys Ala Leu Leu Ala Trp Ala
                 245                 250                 255

Ile Ile Ala Ile Phe Met Trp Glu Pro Val Ala Pro Glu Asn Val Thr
             260                 265                 270

Gln Trp Asn Leu Ser Asp Asn Gly Thr Thr Gly Ile Gln Leu Leu Met
             275                 280                 285

Phe Gln Arg Gly Val Asn Arg Ser Leu His Gly Ile Trp Pro Glu Lys
         290                 295                 300

Ile Cys Thr Gly Val Pro Thr His Leu Ala Thr Asp Ala Glu Leu Lys
305                 310                 315                 320

Gly Ile Gln Gly Met Met Asp Ala Ser Glu Lys Thr Asn Tyr Thr Cys
                 325                 330                 335

Cys Arg Leu Gln Arg His Glu Trp Asn Lys Tyr Gly Trp Cys Asn Trp
             340                 345                 350

Tyr Asn Ile Asn Pro Trp Ile Trp Leu Met Asn Lys Thr Gln Ala Asn
             355                 360                 365

Leu Thr Glu Gly Pro Pro Glu Lys Glu Cys Ala Val Thr Cys Arg Phe
         370                 375                 380

Asp Lys Glu Ala Asp Ile Asn Ile Val Thr Gln Ala Arg Asp Arg Pro
385                 390                 395                 400

Thr Thr Leu Thr Gly Cys Lys Lys Gly Lys Lys Phe Ser Phe Ala Gly
                 405                 410                 415

Met Ile Ile Glu Gly Pro Cys Asn Phe Asn Val Ser Val Glu Asp Ile
             420                 425                 430

Leu Phe Gly Asp Asn Glu Cys Ser Ser Leu Phe Gln Asp Thr Ala Leu
             435                 440                 445
```

```
Tyr Val Val Asp Gly Val Thr Asn Thr Val Glu Asn Ala Arg Gln Gly
    450                 455                 460
Ala Ala Lys Leu Thr Ser Trp Leu Gly Lys Gln Leu Gly Ile Met Gly
465                 470                 475                 480
Lys Lys Leu Glu His Lys Ser Lys Thr Trp Phe Gly Ala Asn Ala Gln
                485                 490                 495
Ser Pro Tyr Cys Asn Val Thr Arg Lys Ile Gly Tyr Val Trp Tyr Thr
            500                 505                 510
Asn Asn Cys Thr Pro Ala Cys Leu Pro Lys Asn Thr Lys Ile Ile Gly
        515                 520                 525
Pro Gly Lys Phe Asp Thr Asn Ala Glu Asp Gly Lys Ile Leu His Glu
    530                 535                 540
Met Arg Gly His Ile Ser Glu Phe Ile Leu Leu Ser Leu Val Val Leu
545                 550                 555                 560
Ser Asp Phe Ala Pro Glu Thr Ala Ser Thr Leu Tyr Leu Val Leu His
                565                 570                 575
Phe Ala Leu Pro Gln Thr His Glu Val Pro Ser Val Cys Asp Thr Asn
            580                 585                 590
Gln Leu Asn Leu Thr Val Ser Leu Arg Val Asp Asp Val Ile Pro Ser
        595                 600                 605
Ser Val Trp Asn Leu Gly Lys Tyr Val Cys Val Arg Pro Asp Trp Trp
    610                 615                 620
Pro Tyr Glu Thr Thr Met Val Leu Leu Phe Glu Ala Gly Gln Val
625                 630                 635                 640
Val Lys Leu Val Leu Arg Ala Ile Arg Asp Leu Thr Arg Val Trp Asn
                645                 650                 655
Ser Ala Ser Thr Thr Ala Phe Leu Ile Cys Leu Val Lys Val Leu Arg
            660                 665                 670
Gly Gln Val Val Gln Gly Leu Val Trp Leu Leu Leu Val Thr Gly Ala
        675                 680                 685
Gln Gly Gln Phe Ala Cys Arg Glu Asp Tyr Arg Tyr Ala Leu Ala Arg
    690                 695                 700
Thr Lys Glu Ile Gly Ala Leu Gly Ala Glu Ser Leu Thr Thr Thr Trp
705                 710                 715                 720
Thr Asp Tyr Arg Gly Asn Leu Glu Leu Asp Asp Gly Thr Val Arg Ala
                725                 730                 735
Thr Cys Ser Arg Gly Phe Phe Arg Phe Arg Gly His Cys Met Ile Gly
            740                 745                 750
Pro Arg Tyr Leu Ala Ser Leu His Leu Arg Ala Leu Pro Thr Ser Val
        755                 760                 765
Thr Phe Glu Leu Ile Pro Gly Gly Ser Ala Met Thr Glu Glu Met
    770                 775                 780
Gly Asp Asp Phe Glu Phe Gly Leu Cys Pro Cys Asp Ser Arg Pro Val
785                 790                 795                 800
Val Lys Gly Lys Tyr Asn Thr Leu Leu Asn Gly Ser Ala Phe Gln
                805                 810                 815
Leu Ile Cys Pro Tyr Gly Trp Val Gly Arg Val Glu Cys Thr Thr Val
            820                 825                 830
Ser Lys Ser Thr Leu Ala Thr Glu Val Val Lys Ile Tyr Lys Lys Thr
        835                 840                 845
Lys Pro Phe Pro Gln Arg Val Gly Cys Asp His Thr Thr Val Tyr Lys
    850                 855                 860
```

```
Gln Asp Leu Tyr His Cys Gln Met Gly Gly Asn Trp Thr Cys Met Arg
865                 870                 875                 880

Gly Glu Val Val Lys Tyr Val Gly Pro Val Lys Lys Cys Glu Trp
                885                 890                 895

Cys Gly Tyr Val Phe Lys Lys Arg Glu Gly Leu Pro His Tyr Pro Ile
        900                 905                 910

Gly Arg Cys Met Leu Arg Asn Glu Thr Gly Tyr Arg Ser Val Asp Asp
            915                 920                 925

Thr Pro Cys Asp Arg Gly Val Val Ile Ser Lys Thr Gly Glu Leu
930                 935                 940

Glu Cys Leu Ile Gly Lys Thr Thr Val Lys Val Phe Ser Ser Asp Lys
945                 950                 955                 960

Lys Leu Gly Pro Met Pro Cys Arg Pro Lys Glu Val Ile Ser Ser Glu
                965                 970                 975

Gly Pro Val Ser Lys Ile Ala Cys Thr Phe Asn Tyr Ser Lys Thr Leu
                980                 985                 990

Glu Asn Lys Tyr Tyr Glu Pro Arg Asp Ser Tyr Phe Gln Gln Tyr Met
            995                 1000                1005

Leu Lys Gly Gln Tyr Gln Tyr Trp Phe Asp Leu Glu Ala Thr Asp
    1010                1015                1020

His His Ser Asp Tyr Phe Ala Glu Phe Ile Met Leu Ala Val Val
    1025                1030                1035

Ala Leu Leu Gly Gly Arg Tyr Val Leu Trp Leu Met Val Val Tyr
    1040                1045                1050

Met Ile Leu Ala Asp Gln Met Thr Ser Ala Ile Asn Leu Gly Gln
    1055                1060                1065

Gly Glu Val Val Leu Ile Gly Asn Leu Ile Thr His Glu Asp His
    1070                1075                1080

Glu Val Val Val Tyr Phe Leu Leu Leu Tyr Leu Ile Val Lys Asp
    1085                1090                1095

Glu Pro Val Lys Lys Trp Ile Leu Phe Leu Phe His Ala Met Thr
    1100                1105                1110

Asn Asn Pro Val Lys Thr Ile Ser Val Gly Leu Leu Met Leu Ser
    1115                1120                1125

Gly Leu Val Lys Gly Glu Gly Ala Gly Met Thr Tyr Trp Glu Gly
    1130                1135                1140

Leu Asp Leu Gln Phe Thr Leu Leu Val Met Ile Thr Ala Ser Leu
    1145                1150                1155

Leu Val Ala Arg Arg Asp Val Thr Thr Tyr Pro Leu Ile Ile Thr
    1160                1165                1170

Val Ile Ala Leu Lys Thr Thr Trp Val Asn Ser Gly Pro Gly Ile
    1175                1180                1185

Asp Ala Ala Ile Ala Thr Ile Thr Thr Gly Leu Leu Met Trp Thr
    1190                1195                1200

Phe Ile Ser Asp Tyr Tyr Lys Tyr Lys Gln Trp Thr Gln Phe Leu
    1205                1210                1215

Ile Ser Ile Val Ser Gly Ile Phe Leu Ile Arg Thr Leu Lys Trp
    1220                1225                1230

Ile Gly Gly Leu Glu Leu His Ala Pro Glu Leu Pro Ser Tyr Arg
    1235                1240                1245

Pro Leu Phe Phe Ile Leu Thr Tyr Leu Ile Ser Ala Ala Ile Val
    1250                1255                1260

Thr Arg Trp Asn Leu Asp Ile Ala Gly Val Leu Leu Gln Cys Val
```

```
             1265                1270                1275

Pro  Thr  Ile  Leu  Met  Val  Leu  Thr  Leu  Trp  Ala  Asp  Leu  Leu  Thr
             1280                1285                1290

Leu  Ile  Leu  Ile  Leu  Pro  Thr  Tyr  Glu  Leu  Ala  Lys  Leu  Tyr  Tyr
             1295                1300                1305

Leu  Lys  Gly  Val  Lys  Asn  Gly  Met  Glu  Arg  Asn  Trp  Leu  Gly  Arg
             1310                1315                1320

Ile  Thr  Tyr  Lys  Arg  Val  Ser  Asp  Val  Tyr  Glu  Ile  Asp  Glu  Ser
             1325                1330                1335

Gln  Glu  Ala  Val  Tyr  Leu  Phe  Pro  Ser  Lys  Gln  Lys  Glu  Gly  Thr
             1340                1345                1350

Ile  Thr  Gly  Gly  Leu  Leu  Pro  Leu  Ile  Lys  Ala  Ile  Leu  Ile  Ser
             1355                1360                1365

Cys  Ile  Ser  Ser  Lys  Trp  Gln  Cys  Phe  Tyr  Leu  Leu  Tyr  Leu  Val
             1370                1375                1380

Val  Glu  Val  Ser  Tyr  Tyr  Leu  His  Lys  Lys  Ile  Ile  Glu  Glu  Val
             1385                1390                1395

Ala  Gly  Gly  Thr  Asn  Leu  Ile  Ser  Arg  Leu  Val  Ala  Ala  Leu  Leu
             1400                1405                1410

Glu  Val  Asn  Trp  Arg  Phe  Asp  Asn  Glu  Glu  Thr  Lys  Gly  Leu  Lys
             1415                1420                1425

Lys  Phe  Tyr  Leu  Ile  Ser  Gly  Gln  Val  Lys  Asn  Leu  Ile  Ile  Lys
             1430                1435                1440

His  Lys  Val  Arg  Asn  Glu  Val  Val  Ala  His  Trp  Phe  Asn  Glu  Glu
             1445                1450                1455

Glu  Val  Tyr  Gly  Met  Pro  Lys  Leu  Val  Ser  Val  Val  Lys  Ala  Ala
             1460                1465                1470

Thr  Leu  Asn  Arg  Ser  Arg  His  Cys  Ile  Leu  Cys  Thr  Val  Cys  Glu
             1475                1480                1485

Ser  Arg  Asp  Trp  Lys  Gly  Glu  Thr  Cys  Pro  Lys  Cys  Gly  Arg  Phe
             1490                1495                1500

Gly  Pro  Ser  Leu  Ser  Cys  Gly  Met  Thr  Leu  Ser  Asp  Phe  Glu  Glu
             1505                1510                1515

Arg  His  Tyr  Lys  Lys  Ile  Phe  Ile  Arg  Glu  Asp  Gln  Ser  Asp  Gly
             1520                1525                1530

Pro  Phe  Arg  Glu  Glu  Tyr  Lys  Gly  Tyr  Leu  Gln  Tyr  Lys  Ala  Arg
             1535                1540                1545

Gly  Gln  Leu  Phe  Leu  Arg  Asn  Leu  Pro  Ile  Leu  Ala  Thr  Lys  Val
             1550                1555                1560

Lys  Leu  Leu  Leu  Val  Gly  Asn  Leu  Gly  Ser  Glu  Val  Gly  Asp  Leu
             1565                1570                1575

Glu  His  Leu  Gly  Trp  Ile  Leu  Arg  Gly  Pro  Ala  Val  Cys  Lys  Lys
             1580                1585                1590

Ile  Ile  Asp  His  Glu  Arg  Cys  His  Val  Ser  Ile  Met  Asp  Lys  Leu
             1595                1600                1605

Thr  Ala  Phe  Phe  Gly  Ile  Met  Pro  Arg  Gly  Thr  Thr  Pro  Arg  Ala
             1610                1615                1620

Pro  Ile  Arg  Phe  Pro  Thr  Ser  Leu  Leu  Arg  Ile  Arg  Arg  Gly  Leu
             1625                1630                1635

Glu  Thr  Gly  Trp  Ala  Tyr  Thr  His  Gln  Gly  Gly  Ile  Ser  Ser  Val
             1640                1645                1650

Asp  His  Val  Thr  Ala  Gly  Lys  Asp  Leu  Leu  Val  Cys  Asp  Ser  Met
             1655                1660                1665
```

```
Gly Arg Thr Arg Val Val Cys Gln Ser Asn Asn Arg Met Thr Asp
1670              1675                1680

Glu Thr Glu Tyr Gly Val Lys Thr Asp Ser Gly Cys Pro Glu Gly
1685              1690                1695

Ala Arg Cys Tyr Val Phe Asn Pro Glu Ala Val Asn Ile Ser Gly
1700              1705                1710

Thr Lys Gly Ala Met Val His Leu Gln Lys Thr Gly Gly Glu Phe
1715              1720                1725

Thr Cys Val Thr Ala Ser Gly Thr Pro Ala Phe Phe Asp Leu Lys
1730              1735                1740

Asn Leu Lys Gly Trp Ser Gly Leu Pro Ile Phe Glu Ala Ser Ser
1745              1750                1755

Gly Arg Val Val Gly Arg Val Lys Val Gly Lys Asn Glu Glu Ser
1760              1765                1770

Lys Pro Thr Lys Leu Met Ser Gly Ile Gln Thr Val Ser Lys Ser
1775              1780                1785

Thr Thr Asp Leu Thr Asp Met Val Lys Lys Ile Thr Thr Met Asn
1790              1795                1800

Arg Gly Glu Phe Lys Gln Ile Thr Leu Ala Thr Gly Ala Gly Lys
1805              1810                1815

Thr Thr Glu Leu Pro Arg Ala Val Ile Glu Glu Ile Gly Arg His
1820              1825                1830

Lys Arg Val Leu Val Leu Ile Pro Leu Arg Ala Ala Ala Glu Ser
1835              1840                1845

Val Tyr Gln Tyr Met Arg Gln Lys His Pro Ser Ile Ala Phe Asn
1850              1855                1860

Leu Arg Ile Gly Glu Met Lys Glu Gly Asp Met Ala Thr Gly Ile
1865              1870                1875

Thr Tyr Ala Ser Tyr Gly Tyr Phe Cys Gln Met Pro Gln Pro Lys
1880              1885                1890

Leu Arg Ala Ala Met Val Glu Tyr Ser Tyr Ile Phe Leu Asp Glu
1895              1900                1905

Tyr His Cys Ala Thr Pro Glu Gln Leu Ala Ile Ile Gly Lys Ile
1910              1915                1920

His Arg Phe Ser Glu Gln Leu Arg Val Val Ala Met Thr Ala Thr
1925              1930                1935

Pro Ala Gly Thr Val Thr Thr Thr Gly Gln Lys His Pro Ile Glu
1940              1945                1950

Glu Phe Ile Ala Pro Glu Val Met Lys Gly Glu Asp Leu Gly Ser
1955              1960                1965

Glu Phe Leu Glu Ile Ala Gly Leu Lys Ile Pro Thr Glu Glu Met
1970              1975                1980

Lys Gly Asn Met Leu Val Phe Val Pro Thr Arg Asn Met Ala Val
1985              1990                1995

Glu Thr Ala Lys Lys Leu Lys Ala Lys Gly Tyr Asn Ser Gly Tyr
2000              2005                2010

Tyr Tyr Ser Gly Glu Asp Pro Ala Asn Leu Arg Val Val Thr Ser
2015              2020                2025

Gln Ser Pro Tyr Val Val Ala Thr Asn Ala Ile Glu Ser Gly
2030              2035                2040

Val Thr Leu Pro Asp Leu Asp Val Val Val Asp Thr Gly Leu Lys
2045              2050                2055
```

```
Cys Glu Lys Arg Ile Arg Leu Ser Ser Lys Met Pro Phe Ile Val
2060                2065                2070

Thr Gly Leu Lys Arg Met Ala Val Thr Ile Gly Glu Gln Ala Gln
2075                2080                2085

Arg Arg Gly Arg Val Gly Arg Val Lys Pro Gly Arg Tyr Tyr Arg
2090                2095                2100

Ser Gln Glu Thr Ala Val Gly Ser Lys Asp Tyr His Tyr Asp Leu
2105                2110                2115

Leu Gln Ala Gln Arg Tyr Gly Ile Glu Asp Gly Ile Asn Ile Thr
2120                2125                2130

Lys Ser Phe Arg Glu Met Asn Tyr Asp Trp Ser Leu Tyr Glu Glu
2135                2140                2145

Asp Ser Leu Met Ile Thr Gln Leu Glu Ile Leu Asn Asn Leu Leu
2150                2155                2160

Ile Ser Glu Glu Leu Pro Val Ala Val Lys Asn Ile Met Ala Arg
2165                2170                2175

Thr Asp His Pro Glu Pro Ile Gln Leu Ala Tyr Asn Ser Tyr Glu
2180                2185                2190

Val Gln Val Pro Val Leu Phe Pro Lys Ile Arg Asn Gly Glu Val
2195                2200                2205

Thr Asp Ser Tyr Asp Ser Tyr Ser Phe Leu Asn Ala Arg Lys Leu
2210                2215                2220

Gly Asp Asp Val Pro Ala Tyr Val Tyr Ala Thr Glu Asp Glu Asp
2225                2230                2235

Leu Ala Val Glu Leu Leu Gly Met Asp Trp Pro Asp Pro Gly Asn
2240                2245                2250

Gln Gly Thr Val Glu Thr Gly Arg Ala Leu Lys Gln Val Thr Gly
2255                2260                2265

Leu Ser Ala Ala Glu Asn Ala Leu Leu Val Ala Leu Phe Gly Tyr
2270                2275                2280

Val Gly Tyr Gln Ala Leu Ser Lys Arg His Val Pro Met Val Thr
2285                2290                2295

Asp Ile Tyr Ser Ile Glu Asp His Arg Leu Glu Asp Thr Thr His
2300                2305                2310

Leu Gln Phe Ala Pro Asn Ala Ile Arg Thr Asp Gly Lys Glu Thr
2315                2320                2325

Glu Leu Lys Glu Leu Ala Gln Gly Asp Ile Gln Arg Cys Ala Glu
2330                2335                2340

Ala Met Val Gly Tyr Ala Gln Gln Gly Val Gln Phe Ile Lys Thr
2345                2350                2355

Gln Ala Leu Lys Val Gln Glu Asn His Val Phe Lys Asp Ser Ala
2360                2365                2370

Asp Thr Ile Val Glu Tyr Val Asp Lys Phe Met Lys Ala Ile Ala
2375                2380                2385

Glu Ser Lys Asp Asp Ile Leu Arg Tyr Gly Leu Trp Gly Ala His
2390                2395                2400

Thr Ala Leu Tyr Lys Ser Ile Gly Ala Arg Leu Gly Tyr Glu Thr
2405                2410                2415

Ala Phe Ala Thr Leu Val Ile Lys Trp Leu Ala Phe Gly Gly Glu
2420                2425                2430

Ser Ile Asn Asp His Val Lys Gln Ala Ala Thr Asp Leu Val Val
2435                2440                2445

Tyr Tyr Ile Ile Asn Arg Pro Gln Phe Pro Gly Asp Thr Glu Thr
```

```
              2450                2455                2460

Gln Gln Glu Gly Arg Lys Phe Val Ala Ser Leu Leu Val Ser Ala
          2465                2470                2475

Leu Ala Thr Tyr Thr Tyr Lys Ser Trp Asn Tyr Ser Asn Leu Ser
          2480                2485                2490

Lys Val Val Glu Pro Ala Leu Ala Cys Leu Pro Tyr Ala Ser Gln
          2495                2500                2505

Ala Leu Lys Leu Phe Ala Pro Thr Arg Leu Glu Ser Val Val Ile
          2510                2515                2520

Leu Ser Thr Ala Ile Tyr Lys Thr Tyr Leu Ala Ile Arg Arg Gly
          2525                2530                2535

Arg Ser Asp Gly Leu Leu Gly Thr Gly Val Ser Ala Ala Met Glu
          2540                2545                2550

Ile Met Ser Gln Asn Pro Val Ser Val Gly Ile Ala Val Met Leu
          2555                2560                2565

Gly Val Gly Ala Val Ala Ala His Asn Ala Ile Glu Ser Ser Glu
          2570                2575                2580

Gln Lys Arg Thr Leu Leu Met Lys Val Phe Val Lys Asn Phe Leu
          2585                2590                2595

Asp Gln Ala Ala Thr Asp Glu Leu Val Lys Glu Ser Pro Glu Lys
          2600                2605                2610

Ile Ile Thr Ala Leu Phe Glu Ala Val Gln Thr Val Gly Asn Pro
          2615                2620                2625

Leu Arg Leu Ile Tyr His Leu Tyr Gly Val Phe Tyr Lys Gly Trp
          2630                2635                2640

Glu Ala Lys Glu Val Ala Glu Lys Thr Ala Gly Arg Asn Leu Phe
          2645                2650                2655

Thr Leu Ile Met Phe Glu Ala Val Glu Leu Leu Gly Val Asp Ser
          2660                2665                2670

Glu Gly Lys Met Arg Arg Leu Ser Gly Asn Tyr Leu Ile Glu Leu
          2675                2680                2685

Leu Gln Lys Leu His Asp Gly Phe Arg Ile Ser Ile Lys Lys Phe
          2690                2695                2700

Ala Leu Gly Trp Ala Pro Gly Pro Phe Ser Cys Asn Trp Thr Pro
          2705                2710                2715

Ala Asp Asn Arg Ile Arg Leu Pro His Glu Asn Tyr Leu Arg Val
          2720                2725                2730

Val Thr Arg Cys Arg Cys Gly Tyr Arg Thr Lys Ala Val Lys Asn
          2735                2740                2745

Cys Ala Gly Glu Leu Ile Leu Glu Glu Glu Gly Ser Phe Phe
          2750                2755                2760

Cys Arg Asn Lys Phe Gly Arg Gly Ala Pro Asn Tyr Lys Val Thr
          2765                2770                2775

Lys Phe Tyr Asp Gly Asn Leu Glu Glu Ile Arg Ala Arg Leu Lys
          2780                2785                2790

Leu Glu Gly Gln Val Glu Met Tyr Tyr Lys Gly Ala Thr Ile Lys
          2795                2800                2805

Ile Asp Tyr Ser Asn Asn Lys Leu Ile Leu Ala Thr Asp Lys Trp
          2810                2815                2820

Glu Val Glu His Ser Tyr Ile Thr Arg Leu Thr Lys Arg Tyr Thr
          2825                2830                2835

Gly Ala Gly Tyr Lys Gly Ala Phe Leu Gly Asp Glu Pro Asn His
          2840                2845                2850
```

```
Lys Ser Leu Ile Glu Arg Thr Cys Ala Thr Val Cys Lys Asp Lys
2855                2860                2865

Ile Tyr Phe Ser Lys Met Lys Lys Gly Cys Ala Phe Thr Tyr Asp
2870                2875                2880

Leu Ser Leu Ser Asn Leu Val Arg Leu Val Asp Leu Val His Arg
2885                2890                2895

Asn Lys Leu Glu Glu Lys Asp Ile Pro Glu Arg Thr Val Thr Thr
2900                2905                2910

Trp Leu Ala Tyr Thr Phe Val Asn Glu Asp Val Gly Thr Ile Lys
2915                2920                2925

Pro Val Leu Gly Glu Lys Val Ile Pro Glu Glu Ser Asp Glu Ile
2930                2935                2940

Asn Leu Gln Pro Thr Val Thr Val Asn Met Ser Lys Cys Gln Val
2945                2950                2955

Thr Val Val Gly Glu Ala Lys Asn Met Thr Thr Gly Val Val Pro
2960                2965                2970

Leu Thr Val Thr Lys Glu Ala Cys Asn Gly Gln Asp Arg Ser Val
2975                2980                2985

Leu Asn Ile Gly Met Glu Glu Gly Glu Tyr Pro Gly Pro Ala Val
2990                2995                3000

Ser Thr Val Thr Val Gly Glu Ala Val Gln Ser Lys Asp Val Arg
3005                3010                3015

Pro Tyr Val Leu Val Ile Gly Ser Asn Lys Ala Thr Ser Asn Arg
3020                3025                3030

Ala Lys Thr Ala Lys Asn Val Lys Leu Tyr Lys Gly Gly Asp Ala
3035                3040                3045

Val Glu Val Arg Asp Leu Ile Lys Lys Gly Glu Met Leu Val Val
3050                3055                3060

Ala Leu Ala Asp Val Glu Gln Asp Leu Leu Glu Tyr Val Asp Tyr
3065                3070                3075

Lys Gly Thr Phe Leu Thr Arg Glu Thr Leu Glu Ala Leu Ser Leu
3080                3085                3090

Gly Lys Pro Lys Ala Lys Asn Ile Thr Lys Ala Asp Ala His Arg
3095                3100                3105

Leu Leu Asn Pro Glu Lys Glu Gln Ile Gly Leu Pro Asp Trp Phe
3110                3115                3120

Thr Ala Thr Glu Pro Ile Phe Leu Glu Ala Met Ile Lys Gln Glu
3125                3130                3135

Lys Tyr His Ile Thr Gly Asp Val Ala Thr Val Lys Asp Lys Ala
3140                3145                3150

Lys Gln Leu Gly Ala Thr Asp Ser Thr Arg Ile Val Lys Glu Val
3155                3160                3165

Gly Ala Arg Val Tyr Thr Met Lys Leu Asn Ser Trp Ala Leu Gln
3170                3175                3180

Ala Glu Arg Gly Asp Ala Asn Leu Lys Pro Leu Phe Glu Glu Leu
3185                3190                3195

Leu Leu Gln Cys Pro Pro Gly Arg Thr Val Lys Gly Gly Thr Met
3200                3205                3210

Val Ser Ala Tyr Gln Leu Ala Gln Gly Asn Trp Thr Pro Thr Ser
3215                3220                3225

Cys Lys Val Tyr Met Gly Thr Ile Thr Ala Lys Arg Val Lys Ile
3230                3235                3240
```

-continued

| | | | | | | | | | | | |
|---|---|---|---|---|---|---|---|---|---|---|---|
|His|Pro|Tyr|Glu|Ala|Tyr|Ile|Lys|Leu|Lys|Glu|Leu|Ile|Glu|Glu|
|3245| | | |3250| | | |3255| | | |
|Tyr|Asn|Met|Lys|Arg|Val|Thr|Gly|Asp|Thr|Gly|Leu|Lys|Arg|His|
|3260| | | |3265| | | |3270| | | |
|Asn|Glu|Trp|Ile|Leu|Lys|Arg|Ile|Lys|His|His|Gly|Asn|Leu|Arg|
|3275| | | |3280| | | |3285| | | |
|Thr|Lys|Lys|Ile|Leu|Asn|Pro|Gly|Lys|Val|Ala|Glu|Gln|Leu|Ser|
|3290| | | |3295| | | |3300| | | |
|Arg|Glu|Gly|His|Lys|His|Asn|Val|Tyr|Asn|Lys|Ile|Ile|Gly|Ser|
|3305| | | |3310| | | |3315| | | |
|Thr|Met|Ala|Ser|Val|Gly|Ile|Lys|Leu|Glu|Lys|Leu|Pro|Val|Val|
|3320| | | |3325| | | |3330| | | |
|Arg|Ala|Gln|Thr|Asp|Thr|Thr|Phe|Phe|His|Gln|Ala|Ile|Arg|Asp|
|3335| | | |3340| | | |3345| | | |
|Lys|Ile|Asp|Lys|Glu|Glu|Asn|Pro|Gln|Thr|Pro|Asp|Leu|His|Lys|
|3350| | | |3355| | | |3360| | | |
|Glu|Leu|Lys|Glu|Val|Phe|Asn|Ala|Leu|Lys|Ile|Pro|Glu|Leu|Ala|
|3365| | | |3370| | | |3375| | | |
|Ala|Thr|Tyr|Asp|Ala|Val|Glu|Trp|Glu|Glu|Leu|Glu|Thr|Gly|Ile|
|3380| | | |3385| | | |3390| | | |
|Asn|Arg|Lys|Gly|Ala|Ala|Gly|Phe|Phe|Glu|Arg|Lys|Asn|Ile|Gly|
|3395| | | |3400| | | |3405| | | |
|Glu|Ile|Leu|Asp|Thr|Glu|Lys|Asn|Lys|Val|Glu|Asp|Ile|Ile|Arg|
|3410| | | |3415| | | |3420| | | |
|Asp|Leu|Lys|Ser|Gly|Arg|Pro|Ile|Lys|Tyr|Tyr|Glu|Thr|Ala|Ile|
|3425| | | |3430| | | |3435| | | |
|Pro|Lys|Asn|Glu|Lys|Arg|Asp|Val|Asn|Asp|Asp|Trp|Glu|Ser|Gly|
|3440| | | |3445| | | |3450| | | |
|Asp|Phe|Val|Asp|Glu|Lys|Lys|Pro|Arg|Val|Ile|Gln|Tyr|Pro|Glu|
|3455| | | |3460| | | |3465| | | |
|Ala|Lys|Val|Arg|Leu|Ala|Ile|Thr|Lys|Val|Met|Tyr|Lys|Trp|Val|
|3470| | | |3475| | | |3480| | | |
|Lys|Gln|Lys|Pro|Val|Val|Ile|Pro|Gly|Tyr|Glu|Gly|Lys|Thr|Pro|
|3485| | | |3490| | | |3495| | | |
|Leu|Phe|Glu|Ile|Phe|Asp|Lys|Val|Lys|Lys|Glu|Trp|Gly|Ser|Phe|
|3500| | | |3505| | | |3510| | | |
|Asp|Asn|Pro|Val|Ala|Val|Ser|Phe|Asp|Thr|Lys|Ala|Trp|Asp|Thr|
|3515| | | |3520| | | |3525| | | |
|Gln|Val|Thr|Ser|Lys|Ser|Leu|Glu|Leu|Ile|Arg|Asp|Ile|Gln|Lys|
|3530| | | |3535| | | |3540| | | |
|Tyr|Tyr|Phe|Lys|Lys|Glu|Trp|His|Lys|Phe|Ile|Glu|Thr|Ile|Thr|
|3545| | | |3550| | | |3555| | | |
|Glu|His|Met|Val|Glu|Val|Pro|Val|Val|Thr|Ala|Asp|Gly|Glu|Val|
|3560| | | |3565| | | |3570| | | |
|Tyr|Ile|Ser|Glu|Gly|Gln|Arg|Gly|Ser|Gly|Gln|Pro|Asp|Thr|Ser|
|3575| | | |3580| | | |3585| | | |
|Ala|Gly|Asn|Ser|Met|Leu|Asn|Val|Leu|Thr|Met|Val|Tyr|Ala|Phe|
|3590| | | |3595| | | |3600| | | |
|Cys|Arg|Ala|Thr|Gly|Val|Pro|Tyr|Lys|Ser|Phe|Lys|Arg|Val|Ala|
|3605| | | |3610| | | |3615| | | |
|Lys|Ile|His|Val|Cys|Gly|Asp|Asp|Gly|Phe|Leu|Ile|Thr|Glu|Lys|
|3620| | | |3625| | | |3630| | | |
|Ser|Leu|Gly|Glu|Lys|Phe|Ala|Ser|Lys|Gly|Ile|Gln|Ile|Leu|His|

```
                    3635              3640              3645
Glu Ala Gly Lys Pro Gln Lys Ile Thr Glu Gly Asp Arg Met Lys
           3650              3655              3660

Val Ala Tyr Lys Phe Glu Asp Ile Glu Phe Cys Ser His Thr Pro
           3665              3670              3675

Val Pro Val Arg Trp Ser Asp Asn Thr Ser Tyr Met Pro Gly
           3680              3685              3690

Arg Asn Thr Ala Thr Ile Leu Ala Lys Met Ala Thr Arg Leu Asp
           3695              3700              3705

Ser Ser Gly Glu Arg Gly Thr Thr Ala Tyr Glu Lys Ala Val Ala
           3710              3715              3720

Phe Ser Phe Leu Leu Met Tyr Ser Trp Asn Pro Leu Val Arg Arg
           3725              3730              3735

Ile Cys Leu Leu Thr Leu Ser Ser Glu Leu Gly Thr Lys Pro Ser
           3740              3745              3750

Lys Arg Thr Thr Tyr Tyr Tyr Glu Gly Asp Pro Ile Ser Ala Tyr
           3755              3760              3765

Arg Glu Val Ile Gly His Asn Leu Leu Asp Leu Lys Arg Thr Gly
           3770              3775              3780

Leu Glu Lys Leu Ala Leu Leu Asn Leu Ser Met Ser Thr Leu Gly
           3785              3790              3795

Ile Trp Thr Lys His Ile Ser Lys Arg Leu Leu Gln Asp Cys Val
           3800              3805              3810

Asp Val Gly Ser Lys Asp Gly Asn Trp Leu Val Asn Ala Asp Arg
           3815              3820              3825

Pro Glu Ser Arg Lys Thr Gly Lys Val Tyr Leu Gln Ser Gly Gly
           3830              3835              3840

His Thr Val Arg Gly Arg His Tyr Glu Asp Leu Ile Leu Pro Arg
           3845              3850              3855

Met Val Lys Pro Thr Phe Gln Gly Val Asp Arg Tyr Lys Leu Gly
           3860              3865              3870

Pro Ile Val Asn Val Ile Phe Arg Arg Leu Arg Val Met Met Met
           3875              3880              3885

Ala Leu Val Gly Arg Gly Met
           3890              3895

<210> SEQ ID NO 52
<211> LENGTH: 3895
<212> TYPE: PRT
<213> ORGANISM: Reindeer pestivirus

<400> SEQUENCE: 52

Met Glu Val Ile Lys Phe Glu Leu Leu Tyr Lys Thr Ser Lys Gln Arg
1               5                   10                  15

Pro Val Gly Val Ile Glu Pro Val Tyr Asn Gln Ala Gly Glu Pro Leu
                20                  25                  30

Phe Gly Glu Ile Ser Glu Ile His Pro Gln Ser Thr Leu Lys Leu Pro
            35                  40                  45

His Asp Arg Gly Arg Ala Glu Ile Ala Ile Pro Met Lys Ser Leu Pro
        50                  55                  60

Lys Lys Gly Asp Cys Arg Ser Gly Asn Arg Arg Ala Pro Val Ser Gly
65                  70                  75                  80

Ile Tyr Ile Lys Pro Gly Pro Val Phe Tyr Gln Asp Tyr Gln Gly Pro
                85                  90                  95
```

```
Val Tyr His Arg Ala Pro Leu Glu Leu Phe Thr Arg Thr Gln Phe Cys
            100                 105                 110

Glu Val Thr Lys Arg Val Gly Arg Val Thr Gly Ser Asp Gly Lys Leu
        115                 120                 125

Tyr His Leu Tyr Val Cys Ile Asp Gly Cys Val Leu Leu Lys Ser Ala
    130                 135                 140

Ser Arg Ile Arg Gly Pro Ala Leu Lys Trp Thr His Asn Ile Leu Asp
145                 150                 155                 160

Cys Pro Leu Trp Val Thr Ser Cys Ser Asp Asp Asn Lys Gly Glu Lys
                165                 170                 175

Val Ser Asp Lys Lys Pro Asp Arg Val Lys Arg Gly Ala Met Lys Ile
            180                 185                 190

Thr Pro Lys Glu Ser Glu Lys Asp Ser Lys Ser Lys Pro Pro Asp Ala
        195                 200                 205

Thr Ile Val Val Glu Gly Ile Lys Tyr Gln Val Lys Lys Lys Gly Lys
    210                 215                 220

Val Arg Gly Lys Asn Thr Gln Asp Gly Leu Tyr His Asn Lys Asn Lys
225                 230                 235                 240

Pro Pro Glu Ser Arg Lys Lys Leu Glu Lys Ala Leu Leu Ala Trp Ala
                245                 250                 255

Leu Val Ala Ile Leu Ile Pro Leu Pro Val Leu Ser Glu Asn Ile Thr
            260                 265                 270

Gln Trp Asn Leu Ser Asp Asn Gly Thr Ser Gly Val Gln His Ala Met
        275                 280                 285

Tyr Leu Arg Gly Val Asn Arg Ser Leu His Gly Ile Trp Pro Glu Lys
    290                 295                 300

Ile Cys Thr Gly Val Pro Thr His Leu Ala Thr Asp Leu Glu Leu Lys
305                 310                 315                 320

Gly Ile Arg Gly Met Met Asp Ala Ser Glu Lys Thr Asn Tyr Thr Cys
                325                 330                 335

Cys Arg Leu Gln Arg His Glu Trp Asn Lys His Gly Trp Cys Asn Trp
            340                 345                 350

Tyr Asn Ile Asp Pro Trp Ile Trp Leu Met Asn Lys Thr Gln Ala Asn
        355                 360                 365

Leu Thr Asn Gly Pro Pro Glu Lys Glu Cys Ala Val Thr Cys Arg Tyr
    370                 375                 380

Asp Lys Glu Thr Asp Val Asn Ile Val Thr Gln Ala Arg Asp Arg Pro
385                 390                 395                 400

Thr Thr Leu Thr Gly Cys Lys Lys Gly Lys Lys Phe Ser Phe Ala Gly
                405                 410                 415

Val Val Leu Glu Gly Pro Cys Asn Phe Asn Val Ser Val Glu Asp Ile
            420                 425                 430

Leu Phe Gly Asp Asn Glu Cys Ser Thr Leu Phe Gln Asp Thr Ala Leu
        435                 440                 445

Tyr Val Val Asp Gly Val Thr Asn Thr Val Glu Asn Ala Arg Gln Gly
    450                 455                 460

Ala Ala Lys Leu Thr Ser Trp Leu Gly Lys Gln Leu Gly Ile Met Gly
465                 470                 475                 480

Lys Lys Leu Glu His Lys Ser Lys Thr Trp Phe Gly Ala Asn Ala Gln
                485                 490                 495

Ser Pro Tyr Cys Asn Val Thr Lys Lys Leu Gly Tyr Ile Trp Tyr Thr
            500                 505                 510

Asn Asn Cys Thr Pro Ala Cys Leu Pro Arg Asn Thr Lys Ile Val Gly
```

```
                515                 520                 525
Pro Gly Lys Phe Asp Thr Asn Ala Glu Asp Gly Lys Ile Leu His Glu
    530                 535                 540

Met Arg Gly His Ile Ser Glu Phe Leu Leu Leu Ser Leu Val Val Leu
545                 550                 555                 560

Ser Asp Phe Ala Pro Glu Thr Ala Ser Thr Leu Tyr Leu Ile Leu His
                565                 570                 575

Phe Thr Ile Pro Gln Ser His Glu Ala Pro Ser Glu Cys Asp Thr Asn
            580                 585                 590

Gln Leu Asn Leu Thr Ile Gly Leu Arg Val Asp Glu Val Val Pro Ser
        595                 600                 605

Ser Val Trp Asn Leu Gly Lys Tyr Val Cys Val Arg Pro Asp Trp Trp
    610                 615                 620

Pro Tyr Glu Thr Thr Val Val Leu Leu Cys Glu Ala Gly Gln Val
625                 630                 635                 640

Ile Lys Leu Val Leu Arg Ala Ile Arg Asp Leu Thr Arg Val Trp Asn
                645                 650                 655

Ser Ala Ser Thr Thr Ala Phe Leu Ile Cys Leu Ile Lys Val Leu Arg
            660                 665                 670

Gly Gln Ile Val Gln Gly Leu Ile Trp Leu Leu Leu Val Thr Gly Ala
        675                 680                 685

Asn Gly Gln Phe Ser Cys Arg Glu Gly Tyr Arg Tyr Ala Leu Ala Lys
    690                 695                 700

Thr Lys Asp Val Gly Pro Leu Gly Ala Glu Ser Leu Thr Thr Thr Trp
705                 710                 715                 720

Val Asp Tyr Lys Arg Asn Leu Gln Leu Asp Asp Gly Thr Val Arg Ala
                725                 730                 735

Val Cys Ser Asn Gly Tyr Phe Arg Ile Arg Pro Thr Cys Leu Ile Gly
            740                 745                 750

Ser Arg Phe Ile Ala Ser Leu His Gln Arg Ala Leu Pro Thr Ser Val
        755                 760                 765

Thr Phe Glu Leu Ile Pro Arg Gly Ser Ala Met Val Thr Glu Glu Met
    770                 775                 780

Asn Asp Ser Phe Glu Phe Gly Leu Cys Pro Cys Asp Ser Lys Pro Val
785                 790                 795                 800

Val Lys Gly Lys Tyr Asn Ala Thr Leu Leu Asn Gly Ser Ala Phe Gln
                805                 810                 815

Leu Val Cys Pro Phe Gly Trp Val Gly Arg Val Glu Cys Thr Ala Val
            820                 825                 830

Ser Thr Ser Thr Leu Ala Thr Glu Val Ile Lys Ile Tyr Lys Arg Ser
        835                 840                 845

Thr Pro Phe Pro Tyr Arg Thr Gly Cys Asp His Thr Thr Val Ile Asn
    850                 855                 860

Lys Asp Leu Tyr Arg Cys Ser Met Gly Gly Asn Trp Thr Cys Ile Lys
865                 870                 875                 880

Gly Glu Gln Val Arg Tyr Thr Gly Gly Val Val Thr Lys Cys Lys Trp
                885                 890                 895

Cys Asp Tyr Val Phe Lys Glu Gly Asp Gly Leu Asp His Tyr Pro Ile
            900                 905                 910

Gly Lys Cys Met Leu Lys Asn Glu Thr Gly Tyr Arg Leu Val Asp Asp
        915                 920                 925

Thr Pro Cys Asp Arg Gly Gly Val Val Ile Ser Lys Thr Gly Thr Leu
    930                 935                 940
```

-continued

Glu Cys Leu Ile Gly Lys Thr Thr Val Lys Val Tyr Ser Ser Asn Asp
945                 950                 955                 960

Lys Leu Gly Ala Met Pro Cys Lys Pro Lys Glu Ile Ile Ser Ser Glu
                965                 970                 975

Gly Pro Ile Ser Lys Thr Ala Cys Thr Phe Asn Tyr Ser Lys Thr Leu
            980                 985                 990

Lys Asn Lys Tyr Tyr Glu Pro Arg Asp Ser Tyr Phe Gln Gln Tyr Met
        995                 1000                1005

Leu Lys Gly Glu Tyr Gln Tyr Trp Phe Asp Leu Asp Ala Thr Asp
    1010                1015            1020

His His Thr Asp Tyr Phe Ala Glu Phe Ile Val Leu Ala Val Val
    1025                1030            1035

Ala Leu Leu Gly Gly Arg Tyr Val Leu Trp Leu Val Ile Tyr
    1040                1045            1050

Thr Val Leu Thr Glu Gln Met Ala Ala Ala Met Ser Leu Asp Gln
    1055                1060            1065

Gly Glu Val Val Leu Ile Gly Asn Leu Ile Thr His Glu Asn His
    1070                1075            1080

Glu Val Val Val Tyr Phe Phe Leu Leu Tyr Leu Val Met Lys Asp
    1085                1090            1095

Glu Pro Ile Lys Lys Trp Ile Leu Phe Leu Phe His Ala Met Thr
    1100                1105            1110

Asn Asn Pro Met Lys Thr Val Ala Val Gly Leu Leu Met Leu Ser
    1115                1120            1125

Gly Val Val Arg Gly Asp Thr Ala Glu Thr Val Glu Ala Gly Ser
    1130                1135            1140

Ile Asp Leu Gln Phe Ile Leu Leu Val Ala Ile Thr Ala Ser Leu
    1145                1150            1155

Leu Val Ala Arg Arg Asp Ala Thr Thr Tyr Pro Leu Ile Ile Thr
    1160                1165            1170

Val Val Ala Leu Arg Thr Thr Trp Val Asn Ser Gly Pro Gly Leu
    1175                1180            1185

Asp Val Ala Ile Ala Ser Leu Thr Thr Gly Leu Leu Met Trp Thr
    1190                1195            1200

Phe Ile Ser Asp Tyr His Lys Tyr Lys Arg Trp Leu Gln Phe Ser
    1205                1210            1215

Ile Ser Ile Val Ser Gly Ile Phe Ile Ile Arg Thr Leu Lys Trp
    1220                1225            1230

Val Gly Gly Ala Glu Leu Ser Val Pro Glu Leu Pro Ser Tyr Arg
    1235                1240            1245

Pro Leu Phe Phe Ile Leu Thr Tyr Leu Ile Ser Thr Ala Val Val
    1250                1255            1260

Thr Arg Trp Asn Leu Asp Ile Ala Gly Ala Leu Leu Gln Cys Val
    1265                1270            1275

Pro Thr Leu Leu Met Val Met Thr Leu Trp Ala Asp Leu Leu Thr
    1280                1285            1290

Leu Val Leu Ile Leu Pro Thr Tyr Glu Leu Thr Lys Leu Tyr Tyr
    1295                1300            1305

Leu Lys Gly Val Lys Gln Gly Met Glu Arg Asn Trp Leu Gly Lys
    1310                1315            1320

Val Ser Tyr Lys Arg Val Ser Asp Ile Tyr Glu Ile Asp Glu Ser
    1325                1330            1335

```
Gln Glu Ala Val Tyr Leu Phe Pro Ser Lys Gln Lys Gly Gly Ser
    1340                1345                1350

Ile Thr Gly Gly Leu Leu Pro Leu Leu Lys Ala Ile Leu Ile Ser
    1355                1360                1365

Cys Val Ser Ser Lys Trp Gln Cys Phe Tyr Leu Leu Tyr Leu Val
    1370                1375                1380

Ile Glu Leu Ser Tyr Tyr Leu His Lys Lys Ile Ile Glu Lys Ile
    1385                1390                1395

Ala Gly Gly Thr Asn Leu Ile Ser Arg Leu Ile Ala Ala Leu Leu
    1400                1405                1410

Glu Val Thr Trp Glu Phe Asp Asp Lys Glu Thr Arg Gly Leu Lys
    1415                1420                1425

Lys Phe Tyr Leu Leu Ser Ser Arg Val Arg Ser Leu Ile Ile Lys
    1430                1435                1440

His Lys Val Arg Asn Glu Val Met Val His Trp Phe Glu Glu Glu
    1445                1450                1455

Glu Val Tyr Gly Met Pro Lys Leu Val Ser Val Val Lys Ser Ala
    1460                1465                1470

Thr Leu Asn Lys Ser Arg His Cys Ile Leu Cys Thr Val Cys Glu
    1475                1480                1485

Asn Arg Glu Trp Lys Gly Glu Thr Cys Pro Lys Cys Gly Arg Cys
    1490                1495                1500

Gly Pro Pro Val Ser Cys Gly Met Thr Leu Ser Asp Phe Glu Glu
    1505                1510                1515

Arg His Tyr Lys Arg Ile Phe Val Arg Glu Asp Gln Ser Glu Gly
    1520                1525                1530

Pro Phe Arg Glu Glu Tyr Lys Gly Tyr Leu Gln Tyr Arg Ala Arg
    1535                1540                1545

Gly Gln Leu Phe Leu Arg Asn Leu Pro Ile Leu Ala Thr Lys Val
    1550                1555                1560

Lys Leu Leu Leu Val Gly Asn Leu Gly Ser Glu Val Gly Asp Leu
    1565                1570                1575

Glu His Leu Gly Trp Ile Leu Arg Gly Pro Ala Val Cys Lys Lys
    1580                1585                1590

Ile Thr Asp His Glu Lys Cys His Val Ser Ile Val Asp Lys Leu
    1595                1600                1605

Thr Ala Phe Phe Gly Ile Met Pro Arg Gly Thr Thr Pro Arg Ala
    1610                1615                1620

Pro Ile Arg Phe Pro Thr Ser Leu Leu Arg Ile Arg Arg Gly Leu
    1625                1630                1635

Glu Thr Gly Trp Ala Tyr Thr His Gln Gly Gly Ile Ser Ser Val
    1640                1645                1650

Asp His Val Thr Ala Gly Lys Asp Leu Leu Val Cys Asp Ser Met
    1655                1660                1665

Gly Arg Thr Arg Val Val Cys Gln Ser Asn Asn Lys Met Thr Asp
    1670                1675                1680

Glu Thr Glu Tyr Gly Val Lys Thr Asp Ser Gly Cys Pro Glu Glu
    1685                1690                1695

Gln Arg Cys Tyr Val Phe Asn Pro Glu Ala Val Asn Ile Ser Gly
    1700                1705                1710

Thr Lys Gly Ala Met Val His Leu Gln Lys Thr Gly Gly Glu Phe
    1715                1720                1725

Thr Cys Val Thr Ala Ser Gly Thr Pro Ala Phe Phe Asp Leu Lys
```

```
            1730                1735                1740
Asn Leu Lys Gly Trp Ser Gly Leu Pro Ile Phe Glu Ala Ser Ser
            1745                1750                1755
Gly Arg Val Val Gly Arg Val Lys Val Gly Lys Asn Glu Glu Ser
            1760                1765                1770
Lys Pro Thr Lys Leu Met Ser Gly Ile Gln Thr Val Ser Lys Ser
            1775                1780                1785
Thr Thr Asp Leu Thr Glu Met Val Lys Lys Ile Thr Ser Met Asn
            1790                1795                1800
Arg Gly Glu Phe Lys Gln Ile Thr Leu Ala Thr Gly Ala Gly Lys
            1805                1810                1815
Thr Thr Glu Leu Pro Arg Ala Val Ile Glu Glu Ile Gly Arg His
            1820                1825                1830
Lys Arg Val Leu Val Leu Ile Pro Leu Arg Ala Ala Ala Glu Ser
            1835                1840                1845
Val Tyr Gln Tyr Met Arg Gln Lys His Pro Ser Ile Ala Phe Asn
            1850                1855                1860
Leu Arg Ile Gly Glu Met Lys Glu Gly Asp Met Ala Thr Gly Ile
            1865                1870                1875
Thr Tyr Ala Ser Tyr Gly Tyr Phe Cys Gln Met Pro Gln Pro Lys
            1880                1885                1890
Leu Arg Ala Ala Met Val Glu Tyr Ser Tyr Ile Phe Leu Asp Glu
            1895                1900                1905
Tyr His Cys Ala Thr Pro Glu Gln Leu Ala Ile Ile Gly Lys Ile
            1910                1915                1920
His Arg Phe Ser Glu Gln Leu Arg Val Val Ala Met Thr Ala Thr
            1925                1930                1935
Pro Ala Gly Thr Val Thr Thr Thr Gly Gln Lys His Pro Ile Glu
            1940                1945                1950
Glu Phe Ile Ala Pro Glu Val Met Lys Gly Glu Asp Leu Gly Ser
            1955                1960                1965
Glu Phe Leu Glu Ile Ala Gly Leu Lys Ile Pro Thr Glu Glu Met
            1970                1975                1980
Lys Gly Asn Met Leu Val Phe Val Pro Thr Arg Asn Met Ala Val
            1985                1990                1995
Glu Thr Ala Lys Lys Leu Lys Ala Lys Gly Tyr Asn Ser Gly Tyr
            2000                2005                2010
Tyr Tyr Ser Gly Glu Asp Pro Ala Asn Leu Arg Val Val Thr Ser
            2015                2020                2025
Gln Ser Pro Tyr Val Val Val Ala Thr Asn Ala Ile Glu Ser Gly
            2030                2035                2040
Val Thr Leu Pro Asp Leu Asp Val Val Val Asp Thr Gly Leu Lys
            2045                2050                2055
Cys Glu Lys Arg Ile Arg Leu Ser Ser Lys Met Pro Phe Ile Val
            2060                2065                2070
Thr Gly Leu Lys Arg Met Ala Val Thr Ile Gly Glu Gln Ala Gln
            2075                2080                2085
Arg Arg Gly Arg Val Gly Arg Val Lys Pro Gly Arg Tyr Tyr Arg
            2090                2095                2100
Ser Gln Glu Thr Ala Val Gly Ser Lys Asp Tyr His Tyr Asp Leu
            2105                2110                2115
Leu Gln Ala Gln Arg Tyr Gly Ile Glu Asp Gly Ile Asn Ile Thr
            2120                2125                2130
```

-continued

```
Lys Ser Phe Arg Glu Met Asn Tyr Asp Trp Ser Leu Tyr Glu Glu
    2135                2140                2145

Asp Ser Leu Met Ile Thr Gln Leu Glu Ile Leu Asn Asn Leu Leu
    2150                2155                2160

Ile Ser Glu Glu Leu Pro Ile Ala Val Lys Asn Ile Met Ala Arg
    2165                2170                2175

Thr Asp His Pro Glu Pro Ile Gln Leu Ala Tyr Asn Ser Tyr Glu
    2180                2185                2190

Val Gln Val Pro Val Leu Phe Pro Lys Ile Arg Asn Gly Glu Val
    2195                2200                2205

Thr Asp Thr Tyr Asp Thr Tyr Thr Phe Leu Asn Ala Arg Lys Leu
    2210                2215                2220

Gly Asp Asp Val Pro Ala Tyr Val Tyr Ser Thr Glu Asp Glu Asp
    2225                2230                2235

Leu Ala Val Glu Leu Leu Gly Leu Asp Trp Pro Asp Pro Gly Asn
    2240                2245                2250

Gln Thr Thr Ala Glu Thr Gly Arg Ala Leu Lys Gln Val Thr Gly
    2255                2260                2265

Leu Ser Ala Ala Glu Asn Ala Leu Leu Val Ala Leu Phe Gly Tyr
    2270                2275                2280

Val Gly Tyr Gln Ala Leu Ser Lys Arg His Ile Pro Met Val Thr
    2285                2290                2295

Asp Ile Tyr Ser Ile Glu Asp His Arg Leu Glu Asp Thr Thr His
    2300                2305                2310

Leu Gln Phe Ala Pro Asn Ala Ile Arg Thr Asp Gly Lys Glu Thr
    2315                2320                2325

Glu Leu Lys Glu Leu Ala Gln Gly Asp Ile Gln Arg Cys Thr Glu
    2330                2335                2340

Ala Ile Val Glu Tyr Ala Gln Gln Gly Val Gln Phe Ile Lys Ser
    2345                2350                2355

Gln Ala Leu Lys Ile Gln Gly Glu Pro Ala Val Lys Ser Ser Met
    2360                2365                2370

Asp Ala Ile Met Asp Tyr Val Asp Lys Phe Leu Lys Ala Ile Ala
    2375                2380                2385

Glu Ser Lys Asp Glu Ile Leu Arg Tyr Gly Leu Trp Gly Ala His
    2390                2395                2400

Thr Ala Leu Tyr Lys Ser Ile Gly Ala Arg Leu Gly Tyr Glu Thr
    2405                2410                2415

Ala Phe Ala Thr Leu Val Val Lys Trp Leu Ala Phe Gly Gly Glu
    2420                2425                2430

Thr Ile Asn Asp His Ile Lys Gln Ala Ala Thr Asp Leu Val Val
    2435                2440                2445

Tyr Tyr Ile Ile Asn Arg Pro Gln Phe Pro Gly Asp Ser Glu Thr
    2450                2455                2460

Gln Gln Glu Gly Arg Lys Phe Val Ala Ser Leu Leu Val Ser Ala
    2465                2470                2475

Leu Ala Thr Tyr Thr Tyr Lys Ser Trp Asn Tyr Asn Asn Leu Ser
    2480                2485                2490

Lys Ile Val Glu Pro Ala Leu Ala Cys Leu Pro Tyr Ala Ser Gln
    2495                2500                2505

Ala Leu Lys Leu Phe Ser Pro Thr Arg Leu Glu Ser Val Val Ile
    2510                2515                2520
```

```
Leu Ser Thr Ala Ile Tyr Lys Thr Tyr Leu Ala Ile Arg Arg Gly
    2525            2530                2535

Lys Ser Asp Gly Leu Leu Gly Thr Gly Val Ser Ala Ala Met Glu
    2540            2545                2550

Ile Met Ser Gln Asn Pro Val Ser Val Gly Ile Ala Val Met Leu
    2555            2560                2565

Gly Val Gly Ala Val Ala Ala His Asn Ala Ile Glu Ser Ser Glu
    2570            2575                2580

Gln Lys Arg Thr Leu Leu Met Lys Val Phe Val Lys Asn Phe Leu
    2585            2590                2595

Asp Gln Ala Ala Thr Asp Glu Leu Val Lys Glu Ser Pro Glu Lys
    2600            2605                2610

Ile Ile Met Ala Leu Phe Glu Ala Val Gln Thr Val Gly Asn Pro
    2615            2620                2625

Leu Arg Leu Ile Tyr His Leu Tyr Gly Val Phe Tyr Lys Gly Trp
    2630            2635                2640

Glu Ala Lys Glu Val Ala Glu Arg Thr Ala Gly Arg Asn Leu Phe
    2645            2650                2655

Thr Leu Ile Met Phe Glu Ala Val Glu Leu Leu Gly Val Asp Ser
    2660            2665                2670

Glu Gly Lys Ile Arg Asn Leu Ser Gly Asn Tyr Leu Ile Asp Leu
    2675            2680                2685

Ile Gln Lys Leu His Asp Gly Phe Lys Val Ser Ile Lys Arg Leu
    2690            2695                2700

Ala Leu Ala Trp Ala Pro Ala Pro Ile Ser Cys Asp Trp Thr Pro
    2705            2710                2715

Ala Asp Glu Arg Ile Lys Leu Pro His Glu Asn Tyr Leu Arg Ala
    2720            2725                2730

Val Thr Arg Cys Pro Cys Gly Tyr Arg Met Lys Ala Val Lys Asn
    2735            2740                2745

Cys Ala Gly Glu Leu Val Leu Glu Glu Glu Glu Gly Pro Tyr Leu
    2750            2755                2760

Cys Arg Asn Lys Phe Lys Arg Ser Ala Ile Asn Tyr Lys Val Thr
    2765            2770                2775

Lys Phe Tyr Asp Asp Asp Leu Glu Glu Ile Lys Pro Val Leu Thr
    2780            2785                2790

Leu Glu Gly Gln Val Asp Met Tyr Tyr Lys Gly Val Thr Met Lys
    2795            2800                2805

Ile Asp Tyr Asp Asn Ser Lys Leu Ile Leu Ala Thr Asp Lys Trp
    2810            2815                2820

Glu Ile Glu His Ser Thr Leu Thr Arg Phe Thr Lys Lys Tyr Thr
    2825            2830                2835

Gly Ala Gly Tyr Asn Gly Ala Tyr Leu Gly Glu Lys Pro Asn His
    2840            2845                2850

Lys Asn Leu Ile Glu Arg Ser Cys Ala Thr Val Cys Arg Asp Lys
    2855            2860                2865

Ile Tyr Phe Ser Lys Met Lys Lys Gly Cys Ala Phe Thr Tyr Asp
    2870            2875                2880

Leu Thr Leu Ser Asn Leu Thr Arg Leu Val Glu Leu Val His Arg
    2885            2890                2895

Asn Lys Leu Glu Glu Lys Asp Ile Pro Ala Ala Thr Val Thr Thr
    2900            2905                2910

Trp Leu Ala Tyr Thr Phe Val Asn Glu Asp Ile Gly Thr Ile Lys
```

-continued

```
            2915                2920                2925

Pro Val Leu Gly Glu Lys Val Ile Pro Glu Gly Glu Glu Val
        2930                2935                2940

Asn Leu Gln Pro Thr Val Ala Leu Asp Met Ser Glu Cys Gln Ile
        2945                2950                2955

Thr Val Val Gly Glu Ala Ala Thr Met Thr Thr Gly Leu Thr Pro
        2960                2965                2970

Val Thr Thr Ser Gly Gly Val His Gly Lys Gln Gly Gln Pro Val
        2975                2980                2985

Leu Lys Ile Gly Met Gly Glu Gly Glu Phe Pro Gly Pro Gly Gln
        2990                2995                3000

Gln Glu Val Thr Val Gly Val Ala Ile Leu Ala Val Asp Ala Arg
        3005                3010                3015

Pro Thr Leu Leu Val Ile Gly Ser Gly Arg Ala Ile Ser Asn Arg
        3020                3025                3030

Ala Lys Thr Ala Lys Asn Ile Lys Leu Tyr Arg Gly Ser Asp Pro
        3035                3040                3045

Ile Ala Val Arg Asp Lys Ile Arg Asn Gly Glu Met Leu Val Val
        3050                3055                3060

Ala Leu Thr Asp Ile Glu Arg Asp Leu Leu Lys Tyr Val Asp Tyr
        3065                3070                3075

Lys Gly Thr Phe Leu Ser Arg Glu Thr Leu Glu Ala Leu Ser Leu
        3080                3085                3090

Gly Lys Pro Arg Ala Lys Glu Ile Thr Lys Ala Asp Ala Arg Arg
        3095                3100                3105

Leu Leu Asn Leu Glu Thr Glu Glu Val Ala Leu Pro Asp Trp Phe
        3110                3115                3120

Glu Ala Thr Glu Pro Ile Phe Leu Glu Ala Val Ile Lys Gln Asp
        3125                3130                3135

Lys Tyr His Leu Thr Gly Asp Val Ala Thr Val Lys Asp Lys Ala
        3140                3145                3150

Lys Gln Leu Gly Ala Thr Asp Ser Thr Arg Ile Val Lys Glu Ala
        3155                3160                3165

Gly Ala Arg Val Tyr Thr Met Lys Leu Ser Ser Trp Ala Ser Leu
        3170                3175                3180

Val Asp Ser Gly Tyr Gly Asp Leu Arg Pro Leu Phe Glu Glu Leu
        3185                3190                3195

Phe Leu Met Cys Pro Pro Gly Lys Leu Ser Arg Thr Glu His Met
        3200                3205                3210

Val Ser Ala Tyr Gln Leu Ala Gln Gly Asn Trp Val Gln Pro Ser
        3215                3220                3225

Cys Cys Val Tyr Leu Gly Thr Val Pro Ala Lys Arg Val Lys Thr
        3230                3235                3240

His Pro Tyr Glu Ala Tyr Val Glu Leu Lys Glu Leu Ile Glu Glu
        3245                3250                3255

Tyr Asn Met Lys Lys Val Thr Gly Asp Pro Gly Leu Arg Lys His
        3260                3265                3270

Asn Glu Trp Ile Leu Lys Lys Ile Arg His Gln Gly Asn Leu Arg
        3275                3280                3285

Thr Arg Asn Ile Leu Asn Pro Gly Lys Val Ala Glu Gln Leu Ser
        3290                3295                3300

Arg Glu Gly His Lys His Asn Val Tyr Asn Lys Ile Ile Gly Ser
        3305                3310                3315
```

Thr Met Val Ser Val Gly Ile Lys Leu Glu Lys Leu Pro Val Val
3320          3325              3330

Arg Ala Gln Thr Asp Thr Val Ser Phe His Gln Ala Ile Arg Asp
3335          3340              3345

Lys Ile Asp Lys Lys Glu Asn Leu Gln Thr Pro Asp Leu His Thr
3350          3355              3360

Gln Leu Arg Glu Val Phe Asn Ala Leu Lys Ile Pro Asp Leu Ala
3365          3370              3375

Ser Thr Tyr Asp Glu Val Thr Trp Glu Glu Leu Glu Val Gly Ile
3380          3385              3390

Asn Arg Lys Gly Ala Ala Gly Phe Phe Glu Lys Lys Asn Ile Gly
3395          3400              3405

Glu Ile Leu Gly Thr Glu Lys His Gln Val Glu Ser Ile Ile Arg
3410          3415              3420

Asp Leu Lys Asn Gly Lys Pro Ile Arg Tyr Tyr Glu Thr Ala Ile
3425          3430              3435

Pro Lys Asn Glu Lys Arg Asp Val Asn Asp Asp Trp Glu Ser Gly
3440          3445              3450

Asp Leu Val Asp Glu Lys Lys Pro Arg Val Ile Gln Tyr Pro Glu
3455          3460              3465

Ala Lys Val Arg Leu Ala Ile Thr Lys Val Met Tyr Lys Trp Val
3470          3475              3480

Lys Gln Lys Pro Val Val Ile Pro Gly Tyr Glu Gly Lys Thr Pro
3485          3490              3495

Leu Phe Glu Ile Phe Asn Lys Val Arg Lys Glu Trp Gly His Phe
3500          3505              3510

Gln Asp Pro Val Ala Val Ser Phe Asp Thr Lys Ala Trp Asp Thr
3515          3520              3525

Gln Val Thr Ser Arg Asp Leu Glu Leu Ile Arg Asp Ile Gln Lys
3530          3535              3540

Tyr Tyr Phe Lys Lys Glu Trp His Lys Phe Ile Asp Thr Leu Thr
3545          3550              3555

Glu His Met Val Glu Val Pro Val Ile Thr Ala Asp Gly Glu Val
3560          3565              3570

Tyr Ile Arg Arg Gly Gln Arg Gly Ser Gly Gln Pro Asp Thr Ser
3575          3580              3585

Ala Gly Asn Ser Met Leu Asn Val Leu Thr Met Ile Tyr Ala Phe
3590          3595              3600

Cys Lys Ala Thr Gly Val Pro Tyr Lys Ser Phe Gly Arg Val Ala
3605          3610              3615

Lys Ile His Val Cys Gly Asp Asp Gly Phe Leu Ile Thr Glu Lys
3620          3625              3630

Ser Leu Gly Glu Lys Phe Ala Ser Lys Gly Met Gln Ile Leu His
3635          3640              3645

Glu Ala Gly Lys Pro Gln Lys Ile Thr Glu Gly Glu Arg Met Lys
3650          3655              3660

Val Ala Tyr Arg Phe Glu Asp Ile Glu Phe Cys Ser His Thr Pro
3665          3670              3675

Val Pro Val Arg Trp Ser Asp Asn Thr Thr Ser Tyr Met Pro Gly
3680          3685              3690

Arg Asn Thr Ala Thr Val Leu Ala Lys Met Ala Ala Arg Leu Asp
3695          3700              3705

```
Ser Ser Gly Glu Arg Gly Thr Thr Ala Tyr Glu Lys Ala Val Ala
3710                3715                3720

Phe Ser Phe Leu Leu Met Tyr Ser Trp Asn Pro Leu Val Arg Arg
3725                3730                3735

Ile Cys Leu Leu Thr Leu Ser Ser Glu Pro Ser Ala Asn Pro Ser
3740                3745                3750

Lys Leu Gly Thr Phe Tyr Tyr Glu Gly Asp Pro Ile Ser Ala Tyr
3755                3760                3765

Arg Glu Val Ile Gly His Asn Leu Gln Asp Leu Lys Arg Thr Gly
3770                3775                3780

Phe Glu Lys Leu Ala Gln Leu Asn Leu Ser Met Ser Thr Leu Gly
3785                3790                3795

Ile Trp Thr Arg His Thr Ser Lys Arg Leu Leu Gln Asp Cys Val
3800                3805                3810

Val Met Gly Ser Arg Glu Gly Asn Trp Leu Val Asn Ala Asp Arg
3815                3820                3825

Leu Val Ser Ser Lys Thr Gly Arg Val Tyr Leu Pro Ser Glu Gly
3830                3835                3840

His Thr Met Gln Gly Lys His Tyr Glu Glu Leu Lys Leu Pro Arg
3845                3850                3855

Thr Ser Arg Ser Leu Thr Glu Gly Val Glu Arg Tyr Asn Leu Gly
3860                3865                3870

Pro Ile Val Asn Val Ile Leu Arg Arg Leu Lys Val Leu Met Met
3875                3880                3885

Thr Phe Thr Gly Lys Gly Met
3890                3895

<210> SEQ ID NO 53
<211> LENGTH: 3895
<212> TYPE: PRT
<213> ORGANISM: Sheep pestivirus

<400> SEQUENCE: 53

Met Glu Leu Asn Asn Phe Tyr Phe Leu Tyr Lys Thr Ser Lys Gln Lys
1               5                   10                  15

Pro Ala Gly Val Glu Glu Pro Val Tyr Asn Ala Ala Gly Val Pro Leu
                20                  25                  30

Phe Gly Glu Thr Ser Glu Ile His Pro Gln Ser Thr Leu Lys Leu Pro
            35                  40                  45

His Asp Arg Gly Arg Gly Glu Val Arg Thr Thr Leu Glu Lys Leu Pro
        50                  55                  60

Arg Lys Gly Asp Cys Arg Ser Gly Asn Gln Leu Gly Pro Val Ser Gly
65                  70                  75                  80

Ile Tyr Ile Lys Pro Gly Pro Ile Tyr Tyr Gln Asp Tyr Ala Gly Pro
                85                  90                  95

Val Tyr His Arg Ala Pro Leu Glu Leu Phe Ala Glu Thr Gln Phe Cys
            100                 105                 110

Glu Thr Thr Lys Arg Ile Gly Arg Val Thr Gly Ser Asp Gly Arg Leu
        115                 120                 125

Tyr His Leu Tyr Val Cys Ile Asp Gly Cys Ile Leu Val Lys Leu Ala
    130                 135                 140

Lys Arg Gly Glu Ser Lys Thr Leu Lys Trp Val Lys Asn Val Met Asp
145                 150                 155                 160

Ser Pro Leu Trp Val Thr Ser Cys Ser Asp Asp Asn Lys Asp Lys Glu
                165                 170                 175
```

-continued

```
Lys Ser Gln Lys Lys Pro Asp Arg Ile Lys Gln Gly Ala Met Lys Ile
            180                 185                 190

Ser Pro Arg Glu Asn Glu Lys Asp Ser Lys Val Lys Pro Asp Ala
        195                 200                 205

Thr Ile Val Val Glu Gly Val Lys Tyr Gln Val Lys Lys Gly Lys
    210                 215                 220

Val Lys Gly Lys Asn Thr Gln Asp Gly Leu Tyr His Asn Lys Asn Lys
225                 230                 235                 240

Pro Pro Glu Ser Arg Lys Lys Leu Glu Lys Ala Leu Leu Ala Trp Ala
                245                 250                 255

Val Ile Ala Ile Leu Val Tyr His Pro Val Met Ala Glu Asn Ile Thr
            260                 265                 270

Gln Trp Asn Leu Ser Asp Asn Gly Thr Thr Gly Ile Gln His Val Met
        275                 280                 285

Tyr Gln Arg Gly Val Asn Arg Ser Leu His Gly Ile Trp Pro Glu Arg
    290                 295                 300

Ile Cys Ala Gly Val Pro Thr His Leu Ala Thr Asp Val Glu Leu Lys
305                 310                 315                 320

Gly Ile Gln Gly Met Met Asp Ala Ser Glu Arg Thr Asn Tyr Thr Cys
                325                 330                 335

Cys Arg Leu Gln Arg His Glu Trp Asn Lys His Gly Trp Cys Asn Trp
            340                 345                 350

Tyr Asn Ile Glu Pro Trp Ile Trp Leu Met Asn Lys Thr Gln Ala Asn
        355                 360                 365

Leu Thr Glu Gly Gln Pro Asp Lys Glu Cys Ala Val Thr Cys Arg Tyr
    370                 375                 380

Asp Lys Glu Ser Asp Leu Asn Val Val Thr Gln Ala Arg Asp Arg Pro
385                 390                 395                 400

Thr Thr Leu Thr Gly Cys Lys Lys Gly Lys Lys Phe Ser Phe Ala Gly
                405                 410                 415

Ile Ile Met Glu Ser Pro Cys Asn Phe Asn Val Ser Ala Glu Asp Ile
            420                 425                 430

Leu Tyr Gly Asp Asn Gly Cys Gly Asn Leu Phe Gln Asp Thr Ala Leu
        435                 440                 445

Tyr Val Val Asp Gly Val Thr Asn Thr Val Glu Asn Ala Arg Gln Gly
    450                 455                 460

Ala Ala Lys Leu Thr Ser Trp Leu Gly Lys Gln Leu Gly Ile Met Gly
465                 470                 475                 480

Lys Lys Leu Glu His Lys Ser Lys Thr Trp Phe Gly Ala His Ala Gln
                485                 490                 495

Ser Pro Tyr Cys Asn Val Thr Arg Arg Ile Gly Tyr Ile Trp Tyr Thr
            500                 505                 510

Asn Asn Cys Thr Pro Ala Cys Leu Pro Arg Asn Thr Lys Ile Ile Gly
        515                 520                 525

Pro Gly Lys Phe Asp Thr Asn Ala Glu Asp Gly Lys Ile Leu His Glu
    530                 535                 540

Met Gly Gly His Ile Ser Glu Phe Leu Leu Leu Ser Leu Val Val Leu
545                 550                 555                 560

Ser Asp Phe Ala Pro Glu Thr Ala Ser Ala Ile Tyr Leu Val Leu His
                565                 570                 575

Phe Thr Ile Pro Gln Ser Tyr Glu Asn Pro Lys Asp Cys Asp Lys Asn
            580                 585                 590
```

-continued

Gln Leu Asn Leu Thr Ile Gly Leu Arg Thr Glu Asp Val Pro Ser
595                 600                 605

Ser Val Trp Asn Ile Gly Lys Tyr Val Cys Ile Arg Pro Asp Trp Trp
610                 615                 620

Pro Tyr Glu Thr Thr Val Val Leu Leu Phe Glu Glu Val Gly Gln Val
625                 630                 635                 640

Ile Lys Leu Ala Leu Arg Ala Leu Arg Asp Leu Thr Arg Val Trp Asn
                645                 650                 655

Ser Ala Ser Thr Thr Ala Phe Leu Ile Cys Leu Ile Lys Val Leu Arg
            660                 665                 670

Gly Gln Val Ile Gln Gly Ile Ile Trp Leu Leu Leu Val Thr Gly Ala
        675                 680                 685

Gln Gly Gln Phe Thr Cys Glu Lys Asn Tyr Arg Tyr Ala Ile Ala Lys
690                 695                 700

Thr Thr Asp Val Gly Leu Leu Gly Ala Glu Gly Leu Thr Thr Thr Trp
705                 710                 715                 720

Arg Glu Tyr Lys Asn Asn Phe Glu Leu Asp Asp Gly Leu Leu Arg Ala
                725                 730                 735

Val Cys Lys Ser Gly Phe Phe Thr Phe Arg Phe His Cys Asp Met Gly
            740                 745                 750

Thr Arg Tyr Leu Ala Lys Leu His Ala Gln Ala Leu Pro Thr Ser Val
        755                 760                 765

Val Phe Glu Lys Val Gly Gln Gln Pro Gly Ala Arg Glu Ile Thr Met
770                 775                 780

Glu Asp Asn Phe Glu Phe Gly Leu Cys Pro Cys Asp Ser Lys Pro Val
785                 790                 795                 800

Val Lys Gly Lys Tyr Asn Ala Thr Leu Leu Asn Gly Ser Ala Phe Asn
                805                 810                 815

Leu Val Cys Pro Ile Gly Trp Thr Gly Val Val Glu Cys Thr Val Ile
            820                 825                 830

Ser Glu Ser Thr Leu His Thr Glu Val Val Lys Val Phe Arg Arg Asp
        835                 840                 845

Lys Pro Phe Pro Ser Arg Lys Tyr Cys Val Asp Thr Lys Val Ile Gly
850                 855                 860

Glu Asp Leu Phe His Cys Lys Leu Gly Gly Asn Trp Thr Cys Ile Pro
865                 870                 875                 880

Gly Glu Gln Val Ala Tyr Arg Gly Gly Gln Val Lys Asn Cys Lys Trp
                885                 890                 895

Cys Gly Phe Thr Phe Glu Thr Pro Glu Asp Leu Pro His Tyr Pro Ile
            900                 905                 910

Gly Lys Cys Val Leu Ser Asn Glu Thr Gly Tyr Arg Leu Val Asp Gly
        915                 920                 925

Thr Thr Cys Asn Arg His Gly Val Ile Ile Asp Gln Thr Gly Ser His
930                 935                 940

Glu Cys Leu Ile Gly Lys Thr Lys Ile Lys Val Tyr Pro Val Asp Asp
945                 950                 955                 960

Lys Leu Gly Pro Met Pro Cys Arg Pro Lys Glu Ile Ile Ser Ser Glu
                965                 970                 975

Gly Pro Ile Ser Lys Thr Ala Cys Thr Phe Asn Tyr Thr Lys Thr Leu
            980                 985                 990

Lys Asn Lys Tyr Tyr Glu Pro Arg Asp Ser Tyr Phe Gln Gln Tyr Met
        995                 1000                1005

Leu Lys Gly Glu Tyr Gln Tyr Trp Phe Asp Leu Asp Val Thr Asp

-continued

```
                1010                1015                1020
His His Thr Asp Tyr Phe Ala Glu Phe Ile Val Val Val Val
        1025                1030                1035
Ala Leu Leu Gly Gly Arg Tyr Val Leu Trp Leu Met Val Val Tyr
        1040                1045                1050
Ile Val Leu Thr Asp Gln Met Ala Ser Gly Leu Gln Leu Gly Gln
        1055                1060                1065
Gly Glu Val Val Leu Ile Gly Asn Leu Ile Thr His Glu Asp Leu
        1070                1075                1080
Glu Val Val Val Tyr Phe Leu Leu Leu Tyr Leu Val Ile Arg Asp
        1085                1090                1095
Glu Pro Ile Lys Lys Trp Ile Leu Leu Leu Tyr His Ala Leu Thr
        1100                1105                1110
Asn Asn Pro Met Lys Thr Ala Thr Val Gly Val Leu Met Leu Ser
        1115                1120                1125
Gly Ala Val Asn Gly Ala Glu Ser Gly Glu Gly Gly Gln Ala Gly
        1130                1135                1140
Leu Asp Leu Gln Phe Leu Val Thr Val Gly Ile Val Val Ser Met
        1145                1150                1155
Leu Ile Ala Arg Arg Asp Pro Thr Thr Ile Pro Leu Ile Ile Thr
        1160                1165                1170
Val Val Thr Leu Arg Thr Thr Gly Leu Ala Gly Gly Leu Ala Thr
        1175                1180                1185
Asp Leu Ala Ile Ala Thr Val Thr Thr Val Leu Leu Met Trp Thr
        1190                1195                1200
Phe Ile Ser Asp Tyr Tyr Arg His Lys Val Trp Leu Gln Phe Leu
        1205                1210                1215
Ile Ser Thr Val Ser Gly Ile Phe Leu Ile Arg Ala Leu Lys Gly
        1220                1225                1230
Leu Gly Glu Ile Glu Ile His Ala Pro Glu Ile Pro Ser Ser Arg
        1235                1240                1245
Pro Leu Phe Phe Val Leu Thr Tyr Leu Ile Ser Ala Ala Ile Val
        1250                1255                1260
Thr Arg Trp Asn Leu Asp Ile Ala Gly Ala Leu Leu Gln Gly Ile
        1265                1270                1275
Pro Ile Leu Met Met Ala Met Thr Met Trp Ala Asp Leu Ile Thr
        1280                1285                1290
Leu Ile Leu Val Leu Pro Thr Tyr Glu Leu Thr Lys Leu Tyr Tyr
        1295                1300                1305
Leu Arg Glu Val Lys Thr Ile Thr Glu Arg Asn Trp Leu Gly Gly
        1310                1315                1320
Ile Lys Tyr Lys Arg Val Ser Asp Val Tyr Glu Val Asp Gln Ser
        1325                1330                1335
Cys Glu Gly Val Tyr Leu Phe Pro Ser Arg Gln Arg Thr Asp Asn
        1340                1345                1350
Thr Thr Glu Gly Met Leu Pro Leu Ile Lys Ala Ile Leu Ile Ser
        1355                1360                1365
Cys Val Ser Ser Arg Trp Gln Leu Ile Tyr Leu Leu Tyr Leu Val
        1370                1375                1380
Leu Glu Ile Ser Tyr Tyr Leu His Arg Lys Ile Ile Glu Glu Val
        1385                1390                1395
Ala Gly Gly Thr Asn Leu Leu Ser Arg Phe Met Ala Ala Leu Ile
        1400                1405                1410
```

```
Glu Thr Asn Trp Thr Leu Asp Asn Asn Glu Val Arg Gly Leu Lys
1415                1420                1425

Lys Phe Tyr Leu Leu Ser Ser Arg Val Arg Ser Leu Ile Val Lys
1430                1435                1440

His Lys Val Arg Asn Glu Val Val Ala Ser Trp Tyr Gly Glu Glu
1445                1450                1455

Glu Ile Phe Gly Met Pro Lys Leu Val Asn Leu Val Arg Ile Ala
1460                1465                1470

Thr Leu Ser Arg Ser Lys His Cys Ile Leu Cys Thr Val Cys Glu
1475                1480                1485

Asp Lys Thr Trp Lys Gly Glu Thr Cys Pro Lys Cys Gly Arg Phe
1490                1495                1500

Gly Pro Pro Ile Ser Cys Gly Met Thr Leu Ala Asp Phe Glu Glu
1505                1510                1515

Lys His Tyr Lys Lys Ile Phe Phe Arg Glu Asp Gln Glu Asp Gly
1520                1525                1530

Leu Phe Arg Glu Glu His Lys Gly Tyr Val Gln Tyr Arg Ala Arg
1535                1540                1545

Gly Gln Leu Phe Leu Arg Asn Leu Pro Ile Leu Ala Thr Lys Val
1550                1555                1560

Lys Leu Leu Leu Val Gly Asn Leu Gly Ala Glu Val Gly Asp Leu
1565                1570                1575

Glu His Leu Gly Trp Val Leu Arg Gly Pro Ala Val Cys Lys Lys
1580                1585                1590

Val Thr Asn His Glu Lys Cys His Thr Thr Ile Ala Asp Lys Leu
1595                1600                1605

Thr Ala Phe Phe Gly Ile Met Pro Arg Gly Thr Thr Pro Arg Ala
1610                1615                1620

Pro Val Arg Phe Pro Thr Ser Leu Leu Lys Ile Arg Arg Gly Leu
1625                1630                1635

Glu Thr Gly Trp Ala Tyr Thr His Gln Gly Gly Ile Ser Ser Val
1640                1645                1650

Asp His Val Thr Phe Gly Lys Asp Leu Leu Val Cys Asp Ser Met
1655                1660                1665

Gly Arg Thr Arg Val Val Cys Gln Asn Asn Asn Lys Met Thr Asp
1670                1675                1680

Glu Thr Glu Tyr Gly Val Lys Thr Asp Ser Gly Cys Pro Glu Gly
1685                1690                1695

Ala Arg Cys Tyr Val Phe Asn Pro Glu Ala Val Asn Ile Ala Gly
1700                1705                1710

Thr Lys Gly Ala Met Val His Leu Gln Lys Thr Gly Gly Glu Phe
1715                1720                1725

Ser Cys Val Thr Ala Ser Gly Thr Pro Ala Phe Phe Asp Leu Lys
1730                1735                1740

Asn Leu Arg Gly Trp Ser Gly Leu Pro Ile Phe Glu Ala Ser Ser
1745                1750                1755

Gly Arg Val Val Gly Arg Val Lys Val Gly Lys Asn Glu Glu Ser
1760                1765                1770

Lys Pro Thr Lys Leu Met Ser Gly Ile Gln Thr Val Ser Lys Asn
1775                1780                1785

Thr Thr Asp Leu Thr Asp Leu Val Arg Lys Ile Thr Ala Met Asn
1790                1795                1800
```

```
Arg Gly Glu Phe Lys Gln Ile Thr Leu Ala Thr Gly Ala Gly Lys
1805                1810                1815

Thr Thr Glu Leu Pro Arg Ser Val Ile Glu Glu Ile Gly Arg His
1820                1825                1830

Lys Arg Ile Leu Val Leu Ile Pro Leu Arg Ala Ala Ala Glu Ser
1835                1840                1845

Val Tyr Gln Tyr Met Arg Gln Lys His Pro Ser Ile Ser Phe Asn
1850                1855                1860

Leu Arg Ile Gly Glu Met Lys Glu Gly Asp Met Ala Thr Gly Ile
1865                1870                1875

Thr Tyr Ala Ser Tyr Gly Tyr Phe Cys Gln Met Pro Gln Pro Lys
1880                1885                1890

Leu Arg Ala Ala Met Val Glu Tyr Ser Tyr Ile Phe Leu Asp Glu
1895                1900                1905

Tyr His Cys Ala Thr Pro Glu Gln Leu Ala Ile Ile Gly Lys Ile
1910                1915                1920

His Arg Phe Ser Glu Asn Leu Arg Val Val Ala Met Thr Ala Thr
1925                1930                1935

Pro Ala Gly Thr Val Thr Thr Gly Gln Lys His Pro Ile Glu
1940                1945                1950

Glu Phe Ile Ala Pro Glu Val Met Lys Gly Glu Asp Leu Gly Ser
1955                1960                1965

Glu Phe Leu Asp Ile Ala Gly Leu Lys Ile Pro Thr Asp Glu Met
1970                1975                1980

Lys Gly Asn Met Leu Val Phe Val Pro Thr Arg Asn Met Ala Val
1985                1990                1995

Glu Thr Ala Lys Lys Leu Lys Ala Lys Gly Tyr Asn Ser Gly Tyr
2000                2005                2010

Tyr Tyr Ser Gly Glu Asp Pro Ala Asn Leu Arg Val Val Thr Ser
2015                2020                2025

Gln Ser Pro Tyr Val Val Ala Thr Asn Ala Ile Glu Ser Gly
2030                2035                2040

Val Thr Leu Pro Asp Leu Asp Val Val Asp Thr Gly Leu Lys
2045                2050                2055

Cys Glu Lys Arg Ile Arg Leu Ala Ser Lys Met Pro Phe Ile Val
2060                2065                2070

Thr Gly Leu Lys Arg Met Ala Val Thr Ile Gly Glu Gln Ala Gln
2075                2080                2085

Arg Arg Gly Arg Val Gly Arg Val Lys Pro Gly Arg Tyr Tyr Arg
2090                2095                2100

Ser Gln Glu Thr Ala Thr Gly Ser Lys Asp Tyr His Tyr Asp Leu
2105                2110                2115

Leu Gln Ala Gln Arg Tyr Gly Ile Glu Asp Gly Ile Asn Ile Thr
2120                2125                2130

Lys Ser Phe Arg Glu Met Asn Tyr Asp Trp Ser Leu Tyr Glu Glu
2135                2140                2145

Asp Ser Leu Met Ile Thr Gln Leu Glu Ile Leu Asn Asn Leu Leu
2150                2155                2160

Ile Ser Glu Asp Leu Pro Ile Ala Val Lys Asn Ile Met Ala Arg
2165                2170                2175

Thr Asp His Pro Glu Pro Ile Gln Leu Ala Tyr Asn Ser Tyr Glu
2180                2185                2190

Val Gln Val Pro Val Leu Phe Pro Lys Ile Arg Asn Gly Glu Val
```

```
                    2195                2200                2205
Thr Asp Ser Tyr Asp Asn Tyr Thr Phe Leu Asn Ala Arg Lys Leu
    2210                2215                2220

Gly Asp Asp Val Pro Ala Tyr Ile Tyr Ala Thr Glu Asp Glu Asp
    2225                2230                2235

Leu Ala Val Glu Leu Leu Gly Leu Asp Trp Pro Asp Pro Gly Asn
    2240                2245                2250

Gln Ser Thr Val Glu Thr Ser Arg Ala Leu Lys Gln Val Ala Gly
    2255                2260                2265

Leu Ser Ala Ala Glu Asn Ala Leu Leu Val Ala Leu Phe Gly Tyr
    2270                2275                2280

Val Gly Tyr Gln Ala Leu Ser Lys Arg His Ile Pro Ile Val Thr
    2285                2290                2295

Asp Ile Tyr Thr Val Glu Asp His Arg Leu Glu Asp Thr Thr Pro
    2300                2305                2310

Met Gln Tyr Ala Pro Asn Ala Ile Arg Thr Glu Gly Lys Glu Thr
    2315                2320                2325

Glu Leu Arg Glu Leu Ala Gln Asp Asp Ile Gln Lys Tyr Ala Glu
    2330                2335                2340

Ala Val Ala Asp Tyr Ala Lys Gln Gly Val Glu Phe Met Lys Thr
    2345                2350                2355

Gln Ala Leu Lys Ile Arg Glu Thr Pro Thr Phe Lys Asn Ser Val
    2360                2365                2370

Asp Thr Leu Ser Asp Tyr Val Arg Arg Phe Leu Asp Ser Leu Ala
    2375                2380                2385

Asp Ser Lys Glu Glu Ile Ile Arg Tyr Gly Leu Trp Gly Thr His
    2390                2395                2400

Thr Ala Leu Tyr Lys Ser Ile Gly Ala Arg Leu Gly Tyr Glu Thr
    2405                2410                2415

Ala Phe Ala Thr Leu Val Ile Lys Trp Leu Ala Phe Gly Gly Glu
    2420                2425                2430

Thr Leu Ser Asp His Ile Lys Gln Ala Ala Thr Asp Leu Val Val
    2435                2440                2445

Tyr Tyr Ile Ile Asn Arg Pro Gln Phe Pro Gly Asp Thr Glu Thr
    2450                2455                2460

Gln Gln Glu Gly Arg Lys Phe Val Ala Ser Leu Leu Val Ser Ala
    2465                2470                2475

Leu Ala Thr Tyr Thr Tyr Lys Ser Trp Asn Tyr Asn Asn Leu Ala
    2480                2485                2490

Lys Ile Val Glu Pro Ala Leu Ala Cys Leu Pro Tyr Ala Ser Gln
    2495                2500                2505

Ala Leu Lys Leu Phe Ala Pro Thr Arg Leu Glu Ser Val Val Ile
    2510                2515                2520

Leu Ser Thr Ala Ile Tyr Lys Thr Tyr Leu Ala Ile Arg Arg Gly
    2525                2530                2535

Arg Ser Asp Gly Leu Leu Gly Thr Gly Val Ser Ala Ala Met Glu
    2540                2545                2550

Ile Met Ser Gln Asn Pro Val Ser Val Gly Ile Ala Val Met Leu
    2555                2560                2565

Gly Val Gly Ala Val Ala Ala His Asn Ala Ile Glu Ser Ser Glu
    2570                2575                2580

Gln Lys Arg Thr Leu Leu Met Lys Val Phe Val Lys Asn Phe Leu
    2585                2590                2595
```

-continued

```
Asp Gln Ala Ala Thr Asp Glu Leu Val Lys Glu Ser Pro Glu Lys
2600                2605                2610
Ile Ile Met Ala Leu Phe Glu Ala Val Gln Thr Val Gly Asn Pro
2615                2620                2625
Leu Arg Leu Ile Tyr His Leu Tyr Gly Val Phe Tyr Lys Gly Trp
2630                2635                2640
Glu Ala Lys Glu Leu Ala Glu Arg Thr Ala Gly Arg Asn Leu Phe
2645                2650                2655
Thr Leu Ile Met Phe Glu Ala Val Glu Leu Leu Gly Val Asp Ser
2660                2665                2670
Glu Gly Lys Met Arg Asn Leu Ser Ser Asn Tyr Leu Met Glu Met
2675                2680                2685
Leu Asn Lys Ile His Glu Ser Ile Lys Val Asn Ile Arg Lys Leu
2690                2695                2700
Ala Ile Ser Trp Ala Pro Ala Pro Phe Ser Cys Asp Trp Thr Pro
2705                2710                2715
Ser Asp Arg Arg Ile Thr Leu Arg Cys Asp Asp Tyr Leu Arg Val
2720                2725                2730
Glu Thr Lys Cys Pro Cys Gly Tyr Arg Met Lys Ala Val Lys Asn
2735                2740                2745
Cys Ser Gly Glu Leu Arg Leu Leu Glu Glu Gly Ser Phe Leu
2750                2755                2760
Cys Arg Asn Lys Phe Gly Arg Gly Phe Asp Asn Tyr Arg Val Thr
2765                2770                2775
Lys Tyr Tyr Asp Asp Asn Leu Glu Glu Ile Arg Pro Gly Val Ile
2780                2785                2790
Met Glu Gly Gln Met Glu Leu Tyr Tyr Lys Gly Thr Thr Val Lys
2795                2800                2805
Val Asp Phe Asp Asn Ser Lys Thr Val Val Ser Thr Asp Lys Trp
2810                2815                2820
Glu Met Asp His Ala Thr Leu Thr Arg Leu Leu Arg Lys His Thr
2825                2830                2835
Gly Val Gly Cys Gly Gly Ala Tyr Met Gly Asp Gln Pro Ser Tyr
2840                2845                2850
Lys Asn Leu Ile Lys Arg Asp Cys Ala Thr Ile Ser Lys Asp Lys
2855                2860                2865
Val Tyr Phe Thr Lys Met Lys Lys Gly Cys Ala Phe Thr Tyr Asp
2870                2875                2880
Leu Ser Ile His Asn Leu Val Arg Leu Ile Glu Leu Val His Lys
2885                2890                2895
Asn Asn Leu Glu Glu Lys Glu Ile Pro Ala Ala Thr Val Thr Thr
2900                2905                2910
Trp Leu Ala Tyr Thr Phe Val Asn Glu Asp Ile Gly Thr Ile Lys
2915                2920                2925
Pro Val Leu Gly Glu Lys Val Ile Pro Glu Lys Val Glu Asp Val
2930                2935                2940
Cys Leu Gln Pro Thr Val Lys Val Asp Thr Ser Asn Ile Ser Val
2945                2950                2955
Thr Val Val Gly Glu Ala Pro Val Met Thr Thr Gly Gln Thr Pro
2960                2965                2970
Val Glu Phe Leu Asp Lys Pro Glu Asp Asn Ser Cys Gln Pro Asn
2975                2980                2985
```

-continued

Leu Lys Leu Gly Phe Glu Glu Gly Gln Tyr Pro Gly Pro Ser Gln
2990            2995                3000

Gln Met Ser Gly Ile Asn Glu Ala Val Ser Gly Gln Asp Glu Arg
3005            3010                3015

Pro Met Val Ile Ile Val Gly Ser Asn Lys Ala Thr Ser Asn Arg
3020            3025                3030

Val Lys Thr Ala Lys Asn Val Arg Val Tyr Lys Gly Asp Asn Pro
3035            3040                3045

Val Glu Val Arg Asn Leu Leu Arg Glu Gly Lys Ala Leu Val Val
3050            3055                3060

Ala Leu Ala Glu Val Glu Val Asp Leu Leu Arg Tyr Val Asp Tyr
3065            3070                3075

Lys Gly Thr Phe Leu Thr Arg Glu Thr Leu Glu Ala Leu Ser Leu
3080            3085                3090

Gly Arg Pro Lys Pro Lys Asp Leu Thr Lys Ala Glu Ala Met Arg
3095            3100                3105

Leu Leu His Pro Glu Ser Gly Leu Val Glu Leu Pro Asp Trp Phe
3110            3115                3120

Thr Ala Glu Glu Pro Leu Phe Leu Glu Ala Thr Ile Lys Gln Asp
3125            3130                3135

Lys Tyr His Leu Val Gly Asp Val Thr Thr Ile Arg Glu Lys Ala
3140            3145                3150

Lys Leu Leu Gly Ala Thr Asp Ser Thr Lys Ile Val Arg Gln Ala
3155            3160                3165

Gly Ser Lys Ala Tyr Thr Met Lys Leu Ser Asn Trp Ile Met Gln
3170            3175                3180

Val Glu Asn Lys His Asn Asn Leu Thr Pro Leu Phe Glu Glu Leu
3185            3190                3195

Met Leu Arg Cys Pro Pro Gly Lys Gln Met Arg Ser Glu His Met
3200            3205                3210

Val Thr Ala Tyr Gln Leu Ala Gln Gly Asn Trp Met Pro Thr Ser
3215            3220                3225

Cys Asn Val Phe Leu Gly Thr Ile Pro Ala Lys Arg Val Lys Thr
3230            3235                3240

His Pro Tyr Glu Ala Tyr Val Lys Leu Lys Asp Leu Leu Glu Glu
3245            3250                3255

His Gly Met Lys Thr Leu His Gly Gly Ser Gly Leu Arg Glu His
3260            3265                3270

Asn Asn Trp Ile Val Gly Lys Val Lys His Gln Gly Asn Leu Arg
3275            3280                3285

Thr Lys His Ile Leu Asn Pro Gly Arg Val Ala Glu Gln Leu Gln
3290            3295                3300

Arg Glu Gly His Lys His Asn Val Tyr Asn Lys Ile Ile Gly Ser
3305            3310                3315

Thr Met Thr Ala Val Gly Ile Arg Leu Glu Arg Leu Pro Val Val
3320            3325                3330

Arg Ala Gln Thr Asp Thr Thr Ser Phe His Gln Ala Ile Arg Asp
3335            3340                3345

Lys Ile Asp Lys Arg Glu Asn Leu Gln Thr Pro Gly Leu His Gly
3350            3355                3360

Lys Leu Leu Glu Ile Phe Asn Thr Leu Lys Lys Asn Asp Leu Ala
3365            3370                3375

Gln Thr Tyr Asp Ala Val Glu Trp Glu Glu Leu Glu Arg Gly Val

```
                3380            3385            3390
Asn Arg Lys Gly Ala Ala Gly Phe Phe Glu His Lys Asn Ile Gly
    3395            3400            3405
Glu Val Leu Asn Thr Glu Lys Glu Lys Val Glu Arg Leu Ile Lys
    3410            3415            3420
Asp Leu Lys Ser Gly Lys His Ile Lys Tyr Tyr Glu Thr Ala Ile
    3425            3430            3435
Pro Lys Asn Glu Lys Arg Asp Val Asn Asp Asp Trp Glu Ala Gly
    3440            3445            3450
Asp Tyr Val Glu Glu Lys Lys Pro Arg Val Ile Gln Tyr Pro Glu
    3455            3460            3465
Ala Lys Val Arg Leu Ala Ile Thr Lys Val Met Tyr Lys Trp Val
    3470            3475            3480
Lys Gln Lys Pro Val Val Ile Pro Gly Tyr Glu Gly Lys Thr Pro
    3485            3490            3495
Leu Phe Glu Val Phe Asp Lys Val Lys Lys Glu Trp Asp Gln Phe
    3500            3505            3510
His Asn Pro Val Ala Val Ser Phe Asp Thr Lys Ala Trp Asp Thr
    3515            3520            3525
Gln Val Thr Thr Lys Asp Leu Glu Leu Ile Gly Glu Ile Gln Lys
    3530            3535            3540
Tyr Tyr Phe Lys Lys Glu Trp His Arg Phe Ile Asp Thr Ile Thr
    3545            3550            3555
Gln His Met Val Glu Val Pro Val Ile Thr Ala Asp Gly Glu Val
    3560            3565            3570
Tyr Ile Arg Asn Gly Gln Arg Gly Ser Gly Gln Pro Asp Thr Ser
    3575            3580            3585
Ala Gly Asn Ser Met Leu Asn Val Leu Thr Met Ile Tyr Ala Phe
    3590            3595            3600
Cys Glu Ala Thr Gly Val Pro Tyr Lys Ser Phe Asn Arg Val Ala
    3605            3610            3615
Lys Ile His Val Cys Gly Asp Asp Gly Phe Leu Ile Thr Glu Arg
    3620            3625            3630
Ala Leu Gly Glu Lys Phe Ala Ser Arg Gly Val Gln Ile Leu Tyr
    3635            3640            3645
Glu Ala Gly Lys Pro Gln Lys Ile Thr Glu Gly Asp Tyr Met Lys
    3650            3655            3660
Val Ala Tyr Lys Phe Asp Asp Ile Glu Phe Cys Ser His Thr Pro
    3665            3670            3675
Ile Gln Val Arg Trp Ser Asp Asn Thr Ser Ser Tyr Met Pro Gly
    3680            3685            3690
Arg Asn Thr Ala Thr Ile Leu Ala Lys Met Ala Thr Arg Leu Asp
    3695            3700            3705
Ser Ser Gly Glu Arg Gly Thr Thr Ala Tyr Glu Lys Ala Val Ala
    3710            3715            3720
Phe Ser Phe Leu Leu Met Tyr Ser Trp Asn Pro Leu Val Arg Arg
    3725            3730            3735
Ile Cys Leu Leu Thr Leu Ser Thr Glu Pro Glu Val Lys Pro Ser
    3740            3745            3750
Lys Ala Thr Thr Tyr Tyr Tyr Glu Gly Asp Pro Ile Ser Ala Tyr
    3755            3760            3765
Lys Glu Val Ile Gly His Asn Leu Gln Asp Leu Lys Arg Thr Gly
    3770            3775            3780
```

```
Phe Glu Lys Leu Ala Gln Leu Asn Leu Ser Met Thr Thr Leu Gly
    3785            3790                3795

Ile Trp Thr Arg His Thr Ser Lys Arg Leu Leu Gln Asp Cys Val
3800            3805                3810

Asn Thr Gly Ala Ser Glu Gly Asn Trp Leu Val Asn Ala Asp Arg
    3815            3820                3825

Leu Val Ser Ser Lys Thr Leu Arg Thr Tyr Val Pro Gly Lys Gly
    3830            3835                3840

His Thr Leu Gln Gly Lys His Tyr Glu Glu Leu Met Leu Asn Lys
    3845            3850                3855

Arg Thr Leu Thr Ser Tyr Val Gly Thr Glu Arg Tyr Asn Leu Gly
    3860            3865                3870

Pro Ile Val Asn Ile Val Leu Arg Arg Leu Lys Val Leu Met Met
    3875            3880                3885

Ala Cys Ile Gly Val Arg Glu
    3890            3895

<210> SEQ ID NO 54
<211> LENGTH: 3898
<212> TYPE: PRT
<213> ORGANISM: CSFV

<400> SEQUENCE: 54

Met Glu Leu Asn His Phe Glu Leu Leu Tyr Lys Thr Asn Lys Gln Lys
1               5                   10                  15

Pro Met Gly Val Glu Glu Pro Val Tyr Asp Ala Thr Gly Lys Pro Leu
                20                  25                  30

Phe Gly Asp Pro Ser Glu Val His Pro Gln Ser Thr Leu Lys Leu Pro
            35                  40                  45

His Asp Arg Gly Arg Gly Asn Ile Lys Thr Thr Leu Lys Asn Leu Pro
        50                  55                  60

Arg Lys Gly Asp Cys Arg Ser Gly Asn His Leu Gly Pro Val Ser Gly
65                  70                  75                  80

Ile Tyr Val Lys Pro Gly Pro Val Phe Tyr Gln Asp Tyr Met Gly Pro
                85                  90                  95

Val Tyr His Arg Ala Pro Leu Glu Phe Phe Ser Glu Ala Gln Phe Cys
            100                 105                 110

Glu Val Thr Lys Arg Ile Gly Arg Val Thr Gly Ser Asp Gly Arg Leu
        115                 120                 125

Tyr His Ile Tyr Val Cys Ile Asp Gly Cys Ile Leu Leu Lys Leu Ala
    130                 135                 140

Lys Arg Gly Glu Pro Arg Thr Leu Lys Trp Ile Arg Asn Phe Thr Asp
145                 150                 155                 160

Cys Pro Leu Trp Val Thr Ser Cys Ser Asp Asp Gly Ala Ser Gly Ser
                165                 170                 175

Lys Glu Lys Lys Pro Asp Arg Ile Asn Lys Gly Lys Leu Lys Ile Ala
            180                 185                 190

Pro Lys Glu His Glu Lys Asp Ser Arg Thr Lys Pro Pro Asp Ala Thr
        195                 200                 205

Ile Val Val Glu Gly Val Lys Tyr Gln Val Lys Lys Gly Lys Val
    210                 215                 220

Lys Gly Lys Asn Thr Gln Asp Gly Leu Tyr His Asn Lys Asn Lys Pro
225                 230                 235                 240

Pro Glu Ser Arg Lys Lys Leu Glu Lys Ala Leu Leu Ala Trp Ala Val
```

```
                245                 250                 255
Ile Ala Ile Met Leu Tyr Gln Pro Val Glu Ala Glu Asn Ile Thr Gln
            260                 265                 270

Trp Asn Leu Ser Asp Asn Gly Thr Asn Gly Ile Gln His Ala Met Tyr
            275                 280                 285

Leu Arg Gly Ile Ser Arg Ser Leu His Gly Ile Trp Pro Glu Lys Ile
            290                 295                 300

Cys Lys Gly Val Pro Thr Tyr Leu Ala Thr Asp Thr Glu Leu Lys Glu
305                 310                 315                 320

Ile Gln Gly Met Met Asp Ala Ser Glu Gly Thr Asn Tyr Thr Cys Cys
            325                 330                 335

Lys Leu Gln Arg His Glu Trp Asn Lys His Gly Trp Cys Asn Trp Tyr
            340                 345                 350

Asn Ile Asp Pro Trp Ile Gln Leu Met Asn Arg Thr Gln Ala Asn Leu
            355                 360                 365

Ala Glu Gly Pro Pro Ala Lys Glu Cys Ala Val Thr Cys Arg Tyr Asp
            370                 375                 380

Lys Asp Ala Asp Val Asn Val Val Thr Gln Ala Arg Asn Arg Pro Thr
385                 390                 395                 400

Thr Leu Thr Gly Cys Lys Lys Gly Lys Asn Phe Ser Phe Ala Gly Thr
                405                 410                 415

Val Ile Glu Gly Pro Cys Asn Phe Asn Val Ser Val Gly Asp Ile Leu
                420                 425                 430

Tyr Gly Asp His Glu Cys Gly Ser Leu Leu Gln Asp Thr Ala Leu Tyr
            435                 440                 445

Leu Val Asp Gly Met Thr Asn Thr Ile Glu Asn Ala Arg Gln Gly Ala
450                 455                 460

Ala Arg Val Thr Ser Trp Leu Gly Arg Gln Leu Arg Ile Ala Gly Lys
465                 470                 475                 480

Arg Leu Glu Gly Arg Ser Lys Thr Trp Phe Gly Ala Tyr Ala Leu Ser
                485                 490                 495

Pro Tyr Cys Asn Val Thr Ser Lys Ile Gly Tyr Ile Trp Tyr Thr Asn
            500                 505                 510

Asn Cys Thr Pro Ala Cys Leu Pro Lys Asn Thr Lys Ile Ile Gly Pro
            515                 520                 525

Gly Lys Phe Asp Thr Asn Ala Glu Asp Gly Lys Ile Leu His Glu Met
            530                 535                 540

Gly Gly His Leu Ser Glu Phe Leu Leu Leu Ser Leu Val Val Leu Ser
545                 550                 555                 560

Asp Phe Ala Pro Glu Thr Ala Ser Ala Leu Tyr Leu Ile Leu His Tyr
                565                 570                 575

Val Ile Pro Gln Ser His Glu Glu Pro Glu Gly Cys Asp Thr Asn Gln
            580                 585                 590

Leu Asn Leu Thr Val Glu Leu Arg Thr Glu Asp Val Ile Pro Ser Ser
            595                 600                 605

Val Trp Asn Val Gly Lys Tyr Val Cys Val Arg Pro Asp Trp Trp Pro
            610                 615                 620

Tyr Glu Thr Lys Val Ala Leu Leu Phe Glu Glu Ala Gly Gln Val Val
625                 630                 635                 640

Lys Leu Ala Leu Arg Ala Leu Arg Asp Leu Thr Arg Val Trp Asn Ser
                645                 650                 655

Ala Ser Thr Thr Ala Phe Leu Ile Cys Leu Ile Lys Val Leu Arg Gly
                660                 665                 670
```

-continued

```
Gln Ile Val Gln Gly Val Ile Trp Leu Leu Val Thr Gly Ala Gln
            675                 680                 685

Gly Gln Leu Ala Cys Lys Glu Asp Tyr Arg Tyr Ala Ile Ser Ser Thr
        690                 695                 700

Asn Glu Ile Gly Leu Leu Gly Ala Gly Gly Leu Thr Thr Thr Trp Lys
705                 710                 715                 720

Glu Tyr Asn His Asp Leu Gln Leu Asn Asp Gly Thr Val Lys Ala Ile
                725                 730                 735

Cys Val Ala Gly Ser Phe Lys Val Thr Ala Leu Asn Val Val Ser Arg
            740                 745                 750

Arg Tyr Leu Ala Ser Leu His Lys Glu Ala Leu Pro Thr Ser Val Thr
        755                 760                 765

Phe Glu Leu Leu Phe Asp Gly Thr Asn Pro Ser Thr Glu Glu Met Gly
770                 775                 780

Asp Asp Phe Gly Phe Gly Leu Cys Pro Phe Asp Thr Ser Pro Val Val
785                 790                 795                 800

Lys Gly Lys Tyr Asn Thr Thr Leu Leu Asn Gly Ser Ala Phe Tyr Leu
                805                 810                 815

Val Cys Pro Ile Gly Trp Thr Gly Val Ile Glu Cys Thr Ala Val Ser
            820                 825                 830

Pro Thr Thr Leu Arg Thr Glu Val Val Lys Thr Phe Arg Arg Asp Lys
        835                 840                 845

Pro Phe Pro His Arg Met Asp Cys Val Thr Thr Val Glu Asn Glu
850                 855                 860

Asp Leu Phe Tyr Cys Lys Leu Gly Gly Asn Trp Thr Cys Val Lys Gly
865                 870                 875                 880

Glu Pro Val Val Tyr Thr Gly Gly Leu Val Lys Gln Cys Arg Trp Cys
                885                 890                 895

Gly Phe Asp Phe Asn Glu Pro Asp Gly Leu Pro His Tyr Pro Ile Gly
            900                 905                 910

Lys Cys Ile Leu Ala Asn Glu Thr Gly Tyr Arg Ile Val Asp Ser Thr
        915                 920                 925

Asp Cys Asn Arg Asp Gly Val Val Ile Ser Thr Glu Gly Ser His Glu
930                 935                 940

Cys Leu Ile Gly Asn Thr Thr Val Lys Val His Ala Ser Asp Glu Arg
945                 950                 955                 960

Leu Gly Pro Met Pro Cys Arg Pro Lys Glu Ile Val Ser Ser Ala Gly
                965                 970                 975

Pro Val Arg Lys Thr Ser Cys Thr Phe Asn Tyr Ala Lys Thr Leu Lys
            980                 985                 990

Asn Lys Tyr Tyr Glu Pro Arg Asp Ser Tyr Phe Gln Gln Tyr Met Leu
        995                 1000                1005

Lys Gly Glu Tyr Gln Tyr Trp Phe Asp Leu Asp Val Thr Asp Arg
        1010                1015                1020

His Ser Asp Tyr Phe Ala Glu Phe Val Leu Val Val Val Ala
        1025                1030                1035

Leu Leu Gly Gly Arg Tyr Ile Leu Trp Leu Ile Val Thr Tyr Ile
        1040                1045                1050

Val Leu Thr Glu Gln Leu Ala Ala Gly Leu Pro Leu Gly Gln Gly
        1055                1060                1065

Glu Val Val Leu Ile Gly Asn Leu Ile Thr His Thr Asp Ile Glu
        1070                1075                1080
```

-continued

```
Val Val Val Tyr Phe Leu Leu Leu Tyr Leu Val Met Arg Asp Glu
    1085                1090                1095

Pro Ile Lys Lys Trp Ile Leu Leu Leu Phe His Ala Met Thr Asn
    1100                1105                1110

Asn Pro Val Lys Thr Ile Thr Val Ala Leu Leu Met Val Ser Gly
    1115                1120                1125

Val Ala Arg Gly Gly Lys Ile Asp Gly Gly Trp Gln Arg Leu Pro
    1130                1135                1140

Glu Thr Ser Phe Asp Ile Gln Leu Ala Leu Thr Val Ile Val Val
    1145                1150                1155

Ala Val Met Leu Leu Ala Lys Arg Asp Pro Thr Thr Val Pro Leu
    1160                1165                1170

Val Val Thr Val Ala Thr Leu Arg Thr Ala Lys Met Thr Asn Gly
    1175                1180                1185

Leu Ser Thr Asp Ile Ala Ile Ala Thr Val Ser Thr Ala Leu Leu
    1190                1195                1200

Thr Trp Thr Tyr Ile Ser Asp Tyr Tyr Arg Tyr Lys Thr Trp Leu
    1205                1210                1215

Gln Tyr Leu Ile Ser Thr Val Thr Gly Ile Phe Leu Ile Arg Val
    1220                1225                1230

Leu Lys Gly Ile Gly Glu Leu Asp Leu His Thr Pro Thr Leu Pro
    1235                1240                1245

Ser Tyr Arg Pro Leu Phe Phe Ile Leu Val Tyr Leu Ile Ser Thr
    1250                1255                1260

Ala Val Val Thr Arg Trp Asn Leu Asp Ile Ala Gly Leu Leu Leu
    1265                1270                1275

Gln Cys Val Pro Thr Leu Leu Met Val Phe Thr Met Trp Ala Asp
    1280                1285                1290

Ile Leu Thr Leu Ile Leu Ile Leu Pro Thr Tyr Glu Leu Thr Lys
    1295                1300                1305

Leu Tyr Tyr Leu Lys Glu Val Lys Ile Gly Ala Glu Arg Gly Trp
    1310                1315                1320

Leu Trp Lys Thr Asn Phe Lys Arg Val Asn Asp Ile Tyr Glu Val
    1325                1330                1335

Asp Gln Ala Gly Glu Gly Val Tyr Leu Phe Pro Ser Lys Gln Lys
    1340                1345                1350

Thr Ser Ser Ile Thr Gly Thr Met Leu Pro Leu Ile Lys Ala Ile
    1355                1360                1365

Leu Ile Ser Cys Ile Ser Asn Lys Trp Gln Phe Ile Tyr Leu Leu
    1370                1375                1380

Tyr Leu Ile Phe Glu Val Ser Tyr Tyr Leu His Lys Lys Ile Ile
    1385                1390                1395

Asp Glu Ile Ala Gly Gly Thr Asn Phe Ile Ser Arg Leu Val Ala
    1400                1405                1410

Ala Leu Ile Glu Ala Asn Trp Ala Phe Asp Asn Glu Glu Val Arg
    1415                1420                1425

Gly Leu Lys Lys Phe Phe Leu Leu Ser Ser Arg Val Lys Glu Leu
    1430                1435                1440

Ile Ile Lys His Lys Val Arg Asn Glu Val Met Val His Trp Phe
    1445                1450                1455

Gly Asp Glu Glu Val Tyr Gly Met Pro Lys Leu Val Gly Leu Val
    1460                1465                1470

Lys Ala Ala Thr Leu Ser Lys Asn Lys His Cys Ile Leu Cys Thr
```

```
            1475                1480                1485

Val Cys Glu Asp Arg Glu Trp Arg Gly Glu Thr Cys Pro Lys Cys
    1490                1495                1500

Gly Arg Phe Gly Pro Pro Met Thr Cys Gly Met Thr Leu Ala Asp
    1505                1510                1515

Phe Glu Glu Lys His Tyr Lys Arg Ile Phe Phe Arg Glu Asp Gln
    1520                1525                1530

Ser Glu Gly Pro Val Arg Glu Glu Tyr Ala Gly Tyr Leu Gln Tyr
    1535                1540                1545

Arg Ala Arg Gly Gln Leu Phe Leu Arg Asn Leu Pro Val Leu Ala
    1550                1555                1560

Thr Lys Val Lys Met Leu Leu Val Gly Asn Leu Gly Thr Glu Val
    1565                1570                1575

Gly Asp Leu Glu His Leu Gly Trp Val Leu Arg Gly Pro Ala Val
    1580                1585                1590

Cys Lys Lys Val Thr Glu His Glu Lys Cys Thr Thr Ser Ile Met
    1595                1600                1605

Asp Lys Leu Thr Ala Phe Phe Gly Val Met Pro Arg Gly Thr Thr
    1610                1615                1620

Pro Arg Ala Pro Val Arg Phe Pro Thr Ser Leu Leu Lys Ile Arg
    1625                1630                1635

Arg Gly Leu Glu Thr Gly Trp Ala Tyr Thr His Gln Gly Gly Ile
    1640                1645                1650

Ser Ser Val Asp His Val Thr Cys Gly Lys Asp Leu Leu Val Cys
    1655                1660                1665

Asp Thr Met Gly Arg Thr Arg Val Val Cys Gln Ser Asn Asn Lys
    1670                1675                1680

Met Thr Asp Glu Ser Glu Tyr Gly Val Lys Thr Asp Ser Gly Cys
    1685                1690                1695

Pro Glu Gly Ala Arg Cys Tyr Val Phe Asn Pro Glu Ala Val Asn
    1700                1705                1710

Ile Ser Gly Thr Lys Gly Ala Met Val His Leu Gln Lys Thr Gly
    1715                1720                1725

Gly Glu Phe Thr Cys Val Thr Ala Ser Gly Thr Pro Ala Phe Phe
    1730                1735                1740

Asp Leu Lys Asn Leu Lys Gly Trp Ser Gly Leu Pro Ile Phe Glu
    1745                1750                1755

Ala Ser Ser Gly Arg Val Val Gly Arg Val Lys Val Gly Lys Asn
    1760                1765                1770

Glu Asp Ser Lys Pro Thr Lys Leu Met Ser Gly Ile Gln Thr Val
    1775                1780                1785

Ser Lys Ser Thr Thr Asp Leu Thr Glu Met Val Lys Lys Ile Thr
    1790                1795                1800

Thr Met Asn Arg Gly Glu Phe Arg Gln Ile Thr Leu Ala Thr Gly
    1805                1810                1815

Ala Gly Lys Thr Thr Glu Leu Pro Arg Ser Val Ile Glu Glu Ile
    1820                1825                1830

Gly Arg His Lys Arg Val Leu Val Leu Ile Pro Leu Arg Ala Ala
    1835                1840                1845

Ala Glu Ser Val Tyr Gln Tyr Met Arg Gln Lys His Pro Ser Ile
    1850                1855                1860

Ala Phe Asn Leu Arg Ile Gly Glu Met Lys Glu Gly Asp Met Ala
    1865                1870                1875
```

-continued

```
Thr Gly Ile Thr Tyr Ala Ser Tyr Gly Tyr Phe Cys Gln Met Pro
        1880            1885            1890

Gln Pro Lys Leu Arg Ala Ala Met Val Glu Tyr Ser Phe Ile Phe
        1895            1900            1905

Leu Asp Glu Tyr His Cys Ala Thr Pro Glu Gln Leu Ala Ile Met
        1910            1915            1920

Gly Lys Ile His Arg Phe Ser Glu Asn Leu Arg Val Val Ala Met
        1925            1930            1935

Thr Ala Thr Pro Ala Gly Thr Val Thr Thr Gly Gln Lys His
        1940            1945            1950

Pro Ile Glu Glu Phe Ile Ala Pro Glu Val Met Lys Gly Glu Asp
        1955            1960            1965

Leu Gly Ser Glu Tyr Leu Asp Ile Ala Gly Leu Lys Ile Pro Val
        1970            1975            1980

Glu Glu Met Lys Ser Asn Met Leu Val Phe Val Pro Thr Arg Asn
        1985            1990            1995

Met Ala Val Glu Thr Ala Lys Lys Leu Lys Ala Lys Gly Tyr Asn
        2000            2005            2010

Ser Gly Tyr Tyr Tyr Ser Gly Glu Asp Pro Ser Asn Leu Arg Val
        2015            2020            2025

Val Thr Ser Gln Ser Pro Tyr Val Val Ala Thr Asn Ala Ile
        2030            2035            2040

Glu Ser Gly Val Thr Leu Pro Asp Leu Asp Val Val Asp Thr
        2045            2050            2055

Gly Leu Lys Cys Glu Lys Arg Ile Arg Leu Ser Pro Lys Met Pro
        2060            2065            2070

Phe Ile Val Thr Gly Leu Lys Arg Met Ala Val Thr Ile Gly Glu
        2075            2080            2085

Gln Ala Gln Arg Arg Gly Arg Val Gly Arg Val Lys Pro Gly Arg
        2090            2095            2100

Tyr Tyr Arg Ser Gln Glu Thr Pro Val Gly Ser Lys Asp Tyr His
        2105            2110            2115

Tyr Asp Leu Leu Gln Ala Gln Arg Tyr Gly Ile Glu Asp Gly Ile
        2120            2125            2130

Asn Ile Thr Lys Ser Phe Arg Glu Met Asn Tyr Asp Trp Ser Leu
        2135            2140            2145

Tyr Glu Glu Asp Ser Leu Met Ile Thr Gln Leu Glu Ile Leu Asn
        2150            2155            2160

Asn Leu Leu Ile Ser Glu Glu Leu Pro Met Ala Val Lys Asn Ile
        2165            2170            2175

Met Ala Arg Thr Asp His Pro Glu Pro Ile Gln Leu Ala Tyr Asn
        2180            2185            2190

Ser Tyr Glu Thr Gln Val Pro Val Leu Phe Pro Lys Ile Lys Asn
        2195            2200            2205

Gly Glu Val Thr Asp Ser Tyr Asp Asn Tyr Thr Phe Leu Asn Ala
        2210            2215            2220

Arg Lys Leu Gly Asp Asp Val Pro Pro Tyr Val Tyr Ala Thr Glu
        2225            2230            2235

Asp Glu Asp Leu Ala Val Glu Leu Leu Gly Leu Asp Trp Pro Asp
        2240            2245            2250

Pro Gly Asn Gln Gly Thr Val Glu Ala Gly Arg Ala Leu Lys Gln
        2255            2260            2265
```

-continued

Val Val Gly Leu Ser Thr Ala Glu Asn Ala Leu Leu Val Ala Leu
2270                2275                2280

Phe Gly Tyr Val Gly Tyr Gln Ala Leu Ser Lys Arg His Ile Pro
2285                2290                2295

Val Val Thr Asp Ile Tyr Ser Ile Glu Asp His Arg Leu Glu Asp
2300                2305                2310

Thr Thr His Leu Gln Tyr Ala Pro Asn Ala Ile Lys Thr Glu Gly
2315                2320                2325

Lys Glu Thr Glu Leu Lys Glu Leu Ala Gln Gly Asp Val Gln Arg
2330                2335                2340

Cys Val Glu Ala Met Thr Asn Tyr Ala Arg Glu Gly Ile Gln Phe
2345                2350                2355

Met Lys Ser Gln Ala Leu Lys Val Lys Glu Thr Pro Thr Tyr Lys
2360                2365                2370

Glu Thr Met Asp Thr Val Thr Asp Tyr Val Lys Lys Phe Met Glu
2375                2380                2385

Ala Leu Thr Asp Ser Lys Glu Asp Ile Ile Lys Tyr Gly Leu Trp
2390                2395                2400

Gly Thr His Thr Ala Leu Tyr Lys Ser Ile Cys Ala Arg Leu Gly
2405                2410                2415

Ser Glu Thr Ala Phe Ala Thr Leu Val Val Lys Trp Leu Ala Phe
2420                2425                2430

Gly Gly Glu Ser Ile Ala Asp His Val Lys Gln Ala Ala Thr Asp
2435                2440                2445

Leu Val Val Tyr Tyr Ile Ile Asn Arg Pro Gln Phe Pro Gly Asp
2450                2455                2460

Thr Glu Thr Gln Gln Glu Gly Arg Lys Phe Val Ala Ser Leu Leu
2465                2470                2475

Val Ser Ala Leu Val Thr Tyr Thr Tyr Lys Ser Trp Asn Tyr Asn
2480                2485                2490

Asn Leu Ser Lys Ile Val Glu Pro Ala Leu Ala Thr Leu Pro Tyr
2495                2500                2505

Ala Ala Thr Ala Leu Lys Leu Phe Ala Pro Thr Arg Leu Glu Ser
2510                2515                2520

Val Val Ile Leu Ser Thr Ala Ile Tyr Lys Thr Tyr Leu Ser Ile
2525                2530                2535

Arg Arg Gly Lys Ser Asp Gly Leu Leu Gly Thr Gly Val Ser Ala
2540                2545                2550

Ala Met Glu Ile Met Ser Gln Asn Pro Val Ser Val Gly Ile Ala
2555                2560                2565

Val Met Leu Gly Val Gly Ala Val Ala Ala His Asn Ala Ile Glu
2570                2575                2580

Ala Ser Glu Gln Lys Arg Thr Leu Leu Met Lys Val Phe Val Lys
2585                2590                2595

Asn Phe Leu Asp Gln Ala Ala Thr Asp Glu Leu Val Lys Glu Ser
2600                2605                2610

Pro Glu Lys Ile Ile Met Ala Leu Phe Glu Ala Val Gln Thr Val
2615                2620                2625

Gly Asn Pro Leu Arg Leu Val Tyr His Leu Tyr Gly Val Phe Tyr
2630                2635                2640

Lys Gly Trp Glu Ala Lys Glu Leu Ala Gln Arg Thr Ala Gly Arg
2645                2650                2655

Asn Leu Phe Thr Leu Ile Met Phe Glu Ala Val Glu Leu Leu Gly

```
            2660                2665                2670

Val  Asp  Ser  Glu  Gly  Lys  Ile  Arg  Gln  Leu  Ser  Ser  Asn  Tyr  Ile
            2675                2680                2685

Leu  Glu  Leu  Leu  Tyr  Lys  Phe  Arg  Asp  Ser  Ile  Lys  Ser  Ser  Val
            2690                2695                2700

Arg  Glu  Met  Ala  Ile  Ser  Trp  Ala  Pro  Ala  Pro  Phe  Ser  Cys  Asp
            2705                2710                2715

Trp  Thr  Pro  Thr  Asp  Asp  Arg  Ile  Gly  Leu  Pro  Gln  Asp  Asn  Phe
            2720                2725                2730

Leu  Gln  Val  Glu  Thr  Lys  Cys  Pro  Cys  Gly  Tyr  Lys  Met  Lys  Ala
            2735                2740                2745

Val  Lys  Asn  Cys  Ala  Gly  Glu  Leu  Arg  Leu  Leu  Glu  Glu  Glu  Gly
            2750                2755                2760

Ser  Phe  Leu  Cys  Arg  Asn  Lys  Phe  Gly  Arg  Gly  Ser  Arg  Asn  Tyr
            2765                2770                2775

Arg  Val  Thr  Lys  Tyr  Tyr  Asp  Asp  Asn  Leu  Ser  Glu  Ile  Lys  Pro
            2780                2785                2790

Val  Ile  Arg  Met  Glu  Gly  His  Val  Glu  Leu  Tyr  Tyr  Lys  Gly  Ala
            2795                2800                2805

Thr  Ile  Lys  Leu  Asp  Phe  Asn  Asn  Ser  Lys  Thr  Ile  Leu  Ala  Thr
            2810                2815                2820

Asp  Lys  Trp  Glu  Val  Asp  His  Ser  Thr  Leu  Val  Arg  Val  Leu  Lys
            2825                2830                2835

Arg  His  Thr  Gly  Ala  Gly  Tyr  His  Gly  Ala  Tyr  Leu  Gly  Glu  Lys
            2840                2845                2850

Pro  Asn  His  Lys  His  Leu  Ile  Glu  Arg  Asp  Cys  Ala  Thr  Ile  Thr
            2855                2860                2865

Lys  Asp  Lys  Val  Cys  Phe  Leu  Lys  Met  Lys  Arg  Gly  Cys  Ala  Phe
            2870                2875                2880

Thr  Tyr  Asp  Leu  Ser  Leu  His  Asn  Leu  Thr  Arg  Leu  Ile  Glu  Leu
            2885                2890                2895

Val  His  Lys  Asn  Asn  Leu  Glu  Asp  Lys  Glu  Ile  Pro  Ala  Val  Thr
            2900                2905                2910

Val  Thr  Thr  Trp  Leu  Ala  Tyr  Thr  Phe  Val  Asn  Glu  Asp  Ile  Gly
            2915                2920                2925

Thr  Ile  Lys  Pro  Ala  Phe  Gly  Glu  Lys  Val  Thr  Pro  Glu  Met  Gln
            2930                2935                2940

Glu  Glu  Ile  Thr  Leu  Gln  Pro  Ala  Val  Val  Asp  Thr  Thr  Asp
            2945                2950                2955

Val  Thr  Val  Thr  Val  Val  Gly  Glu  Ala  Pro  Thr  Met  Thr  Thr  Gly
            2960                2965                2970

Glu  Thr  Pro  Thr  Ala  Phe  Thr  Ser  Ser  Gly  Ser  Asp  Pro  Lys  Gly
            2975                2980                2985

Gln  Gln  Val  Leu  Lys  Leu  Gly  Val  Gly  Glu  Gly  Gln  Tyr  Pro  Gly
            2990                2995                3000

Thr  Asn  Pro  Gln  Arg  Ala  Ser  Leu  His  Glu  Ala  Ile  Gln  Gly  Ala
            3005                3010                3015

Asp  Glu  Arg  Pro  Ser  Val  Leu  Ile  Leu  Gly  Ser  Asp  Lys  Ala  Thr
            3020                3025                3030

Ser  Asn  Arg  Val  Lys  Thr  Ala  Lys  Asn  Val  Lys  Val  Tyr  Arg  Gly
            3035                3040                3045

Arg  Asp  Pro  Leu  Glu  Val  Arg  Asp  Met  Met  Arg  Arg  Gly  Lys  Ile
            3050                3055                3060
```

```
Leu Val Ile Ala Leu Ser Arg Val Asp Asn Ala Leu Leu Lys Phe
3065            3070            3075

Val Asp Tyr Lys Gly Thr Phe Leu Thr Arg Glu Thr Leu Glu Ala
3080            3085            3090

Leu Ser Leu Gly Arg Pro Lys Lys Lys Asn Ile Thr Lys Ala Glu
3095            3100            3105

Ala Gln Trp Leu Leu Cys Leu Glu Asp Gln Met Glu Glu Leu Pro
3110            3115            3120

Asp Trp Phe Ala Ala Gly Glu Pro Ile Phe Leu Glu Ala Asn Ile
3125            3130            3135

Lys His Asp Arg Tyr His Leu Val Gly Asp Ile Ala Thr Ile Lys
3140            3145            3150

Glu Lys Ala Lys Gln Leu Gly Ala Thr Asp Ser Thr Lys Ile Ser
3155            3160            3165

Lys Glu Val Gly Ala Lys Val Tyr Ser Met Lys Leu Ser Asn Trp
3170            3175            3180

Val Met Gln Glu Glu Asn Lys Gln Gly Asn Leu Thr Pro Leu Phe
3185            3190            3195

Glu Glu Leu Leu Gln Gln Cys Pro Pro Gly Gly Gln Asn Lys Thr
3200            3205            3210

Ala His Met Val Ser Ala Tyr Gln Leu Ala Gln Gly Asn Trp Met
3215            3220            3225

Pro Thr Ser Cys His Val Phe Met Gly Thr Ile Ser Ala Arg Arg
3230            3235            3240

Thr Lys Thr His Pro Tyr Glu Ala Tyr Val Lys Leu Arg Glu Leu
3245            3250            3255

Val Glu Glu His Lys Met Lys Thr Leu Cys Pro Gly Ser Ser Leu
3260            3265            3270

Gly Lys His Asn Glu Trp Ile Ile Gly Lys Ile Lys Tyr Gln Gly
3275            3280            3285

Asn Leu Arg Thr Lys His Met Leu Asn Pro Gly Lys Val Ala Glu
3290            3295            3300

Gln Leu Cys Arg Glu Gly His Arg Arg Asn Val Tyr Asn Lys Thr
3305            3310            3315

Ile Gly Ser Val Met Thr Ala Thr Gly Ile Arg Leu Glu Lys Leu
3320            3325            3330

Pro Val Val Arg Ala Gln Thr Asp Thr Thr Asn Phe His Gln Ala
3335            3340            3345

Ile Arg Asp Lys Ile Asp Lys Glu Glu Asn Leu Gln Thr Pro Gly
3350            3355            3360

Leu His Lys Lys Leu Met Glu Val Phe Asn Ala Leu Lys Arg Pro
3365            3370            3375

Glu Leu Glu Ser Ser Tyr Asp Ala Val Glu Trp Glu Glu Leu Glu
3380            3385            3390

Arg Gly Ile Asn Arg Lys Gly Ala Ala Gly Phe Phe Glu Arg Lys
3395            3400            3405

Asn Ile Gly Glu Ile Leu Asp Ser Glu Lys Asn Lys Val Glu Glu
3410            3415            3420

Ile Ile Asp Asn Leu Lys Lys Gly Arg Asn Ile Lys Tyr Tyr Glu
3425            3430            3435

Thr Ala Ile Pro Lys Asn Glu Lys Arg Asp Val Asn Asp Asp Trp
3440            3445            3450
```

```
Thr Ser Gly Asp Phe Val Asp Glu Lys Lys Pro Arg Val Ile Gln
    3455                3460                3465

Tyr Pro Glu Ala Lys Thr Arg Leu Ala Ile Thr Lys Val Met Tyr
    3470                3475                3480

Lys Trp Val Lys Gln Lys Pro Val Val Ile Pro Gly Tyr Glu Gly
    3485                3490                3495

Lys Thr Pro Leu Phe Gln Ile Phe Asp Lys Val Lys Lys Glu Trp
    3500                3505                3510

Asp Gln Phe Gln Asn Pro Val Ala Val Ser Phe Asp Thr Lys Ala
    3515                3520                3525

Trp Asp Thr Gln Val Thr Thr Lys Asp Leu Glu Leu Ile Lys Asp
    3530                3535                3540

Ile Gln Lys Tyr Tyr Phe Lys Lys Lys Trp His Lys Phe Ile Asp
    3545                3550                3555

Thr Leu Thr Met His Met Ser Glu Val Pro Val Ile Ser Ala Asp
    3560                3565                3570

Gly Glu Val Tyr Ile Arg Lys Gly Gln Arg Gly Ser Gly Gln Pro
    3575                3580                3585

Asp Thr Ser Ala Gly Asn Ser Met Leu Asn Val Leu Thr Met Val
    3590                3595                3600

Tyr Ala Phe Cys Glu Ala Thr Gly Val Pro Tyr Lys Ser Phe Asp
    3605                3610                3615

Arg Val Ala Lys Ile His Val Cys Gly Asp Asp Gly Phe Leu Ile
    3620                3625                3630

Thr Glu Arg Ala Leu Gly Glu Lys Phe Ala Ser Lys Gly Val Gln
    3635                3640                3645

Ile Leu Tyr Glu Ala Gly Lys Pro Gln Lys Ile Thr Glu Gly Asp
    3650                3655                3660

Lys Met Lys Val Ala Tyr Gln Phe Asp Asp Ile Glu Phe Cys Ser
    3665                3670                3675

His Thr Pro Ile Gln Val Arg Trp Ser Asp Asn Thr Ser Ser Tyr
    3680                3685                3690

Met Pro Gly Arg Asn Thr Thr Thr Ile Leu Ala Lys Met Ala Thr
    3695                3700                3705

Arg Leu Asp Ser Ser Gly Glu Arg Gly Thr Ile Ala Tyr Glu Lys
    3710                3715                3720

Ala Val Ala Phe Ser Phe Leu Leu Met Tyr Ser Trp Asn Pro Leu
    3725                3730                3735

Ile Arg Arg Ile Cys Leu Leu Val Leu Ser Thr Glu Leu Gln Val
    3740                3745                3750

Lys Pro Gly Lys Ser Thr Thr Tyr Tyr Tyr Glu Gly Asp Pro Ile
    3755                3760                3765

Ser Ala Tyr Lys Glu Val Ile Gly His Asn Leu Phe Asp Leu Lys
    3770                3775                3780

Arg Thr Ser Phe Glu Lys Leu Ala Lys Leu Asn Leu Ser Met Ser
    3785                3790                3795

Val Leu Gly Ala Trp Thr Arg His Thr Ser Lys Arg Leu Leu Gln
    3800                3805                3810

Asp Cys Val Asn Met Gly Val Lys Glu Gly Asn Trp Leu Val Asn
    3815                3820                3825

Ala Asp Arg Leu Val Ser Ser Lys Thr Gly Asn Arg Tyr Ile Pro
    3830                3835                3840

Gly Glu Gly His Thr Leu Gln Gly Arg His Tyr Glu Glu Leu Val
```

```
            3845                3850                3855
Leu Ala Arg Lys Gln Ile Asn Asn Phe Gln Gly Thr Asp Arg Tyr
        3860                3865                3870

Asn Leu Gly Pro Ile Val Asn Met Val Leu Arg Arg Leu Arg Val
        3875                3880                3885

Met Met Met Thr Leu Ile Gly Arg Gly Val
        3890                3895

<210> SEQ ID NO 55
<211> LENGTH: 3988
<212> TYPE: PRT
<213> ORGANISM: BVDV-1

<400> SEQUENCE: 55

Met Glu Leu Ile Thr Asn Glu Leu Leu Tyr Lys Thr Tyr Lys Gln Lys
1               5                   10                  15

Pro Val Gly Val Glu Glu Pro Val Tyr Asp Gln Ala Gly Asp Pro Leu
                20                  25                  30

Phe Gly Glu Arg Gly Ala Val His Pro Gln Ser Thr Leu Lys Leu Pro
            35                  40                  45

His Lys Arg Gly Glu Arg Asp Val Pro Thr Asn Leu Ala Ser Leu Pro
    50                  55                  60

Lys Arg Gly Asp Cys Arg Ser Gly Asn Ser Arg Gly Pro Val Ser Gly
65                  70                  75                  80

Ile Tyr Leu Lys Pro Gly Pro Leu Phe Tyr Gln Asp Tyr Lys Gly Pro
                85                  90                  95

Val Tyr His Arg Ala Pro Leu Glu Leu Phe Glu Glu Gly Ser Met Cys
            100                 105                 110

Glu Thr Thr Lys Arg Ile Gly Arg Val Thr Gly Ser Asp Gly Lys Leu
        115                 120                 125

Tyr His Ile Tyr Val Cys Ile Asp Gly Cys Ile Ile Ile Lys Ser Ala
    130                 135                 140

Thr Arg Ser Tyr Gln Arg Val Phe Arg Trp Val His Asn Arg Leu Asp
145                 150                 155                 160

Cys Pro Leu Trp Val Thr Thr Cys Ser Asp Thr Lys Glu Glu Gly Ala
                165                 170                 175

Thr Lys Lys Lys Thr Gln Lys Pro Asp Arg Leu Glu Arg Gly Lys Met
            180                 185                 190

Lys Ile Val Pro Lys Glu Ser Glu Lys Asp Ser Lys Thr Lys Pro Pro
        195                 200                 205

Asp Ala Thr Ile Val Val Glu Gly Val Lys Tyr Gln Val Arg Lys Lys
    210                 215                 220

Gly Lys Thr Lys Ser Lys Asn Thr Gln Asp Gly Leu Tyr His Asn Lys
225                 230                 235                 240

Asn Lys Pro Gln Glu Ser Arg Lys Lys Leu Glu Lys Ala Leu Leu Ala
                245                 250                 255

Trp Ala Ile Ile Ala Ile Val Leu Phe Gln Val Thr Met Gly Glu Asn
            260                 265                 270

Ile Thr Gln Trp Asn Leu Gln Asp Asn Gly Thr Glu Gly Ile Gln Arg
        275                 280                 285

Ala Met Phe Gln Arg Gly Val Asn Arg Ser Leu His Gly Ile Trp Pro
    290                 295                 300

Glu Lys Ile Cys Thr Gly Val Pro Ser His Leu Ala Thr Asp Ile Glu
305                 310                 315                 320
```

```
Leu Lys Thr Ile His Gly Met Met Asp Ala Ser Glu Lys Thr Asn Tyr
                325                 330                 335

Thr Cys Cys Arg Leu Gln Arg His Glu Trp Asn Lys His Gly Trp Cys
            340                 345                 350

Asn Trp Tyr Asn Ile Glu Pro Trp Ile Leu Val Met Asn Arg Thr Gln
                355                 360                 365

Ala Asn Leu Thr Glu Gly Gln Pro Arg Glu Cys Ala Val Thr Cys
        370                 375                 380

Arg Tyr Asp Arg Ala Ser Asp Leu Asn Val Val Thr Gln Ala Arg Asp
385                 390                 395                 400

Ser Pro Thr Pro Leu Thr Gly Cys Lys Lys Gly Lys Asn Phe Ser Phe
                405                 410                 415

Ala Gly Ile Leu Met Arg Gly Pro Cys Asn Phe Glu Ile Ala Ala Ser
                420                 425                 430

Asp Val Leu Phe Lys Glu His Glu Arg Ile Ser Met Phe Gln Asp Thr
            435                 440                 445

Thr Leu Tyr Leu Val Asp Gly Leu Thr Asn Ser Leu Glu Gly Ala Arg
        450                 455                 460

Gln Gly Thr Ala Lys Leu Thr Thr Trp Leu Gly Lys Gln Leu Gly Ile
465                 470                 475                 480

Leu Gly Lys Lys Leu Glu Asn Lys Ser Lys Thr Trp Phe Gly Ala Tyr
                485                 490                 495

Ala Ala Ser Pro Tyr Cys Asp Val Asp Arg Lys Ile Gly Tyr Ile Trp
                500                 505                 510

Tyr Thr Lys Asn Cys Thr Pro Ala Cys Leu Pro Lys Asn Thr Lys Ile
            515                 520                 525

Val Gly Pro Gly Lys Phe Gly Thr Asn Ala Glu Asp Gly Lys Ile Leu
        530                 535                 540

His Glu Met Gly Gly His Leu Ser Glu Val Leu Leu Ser Leu Val
545                 550                 555                 560

Val Leu Ser Asp Phe Ala Pro Glu Thr Ala Ser Val Met Tyr Leu Ile
                565                 570                 575

Leu His Phe Ser Ile Pro Gln Ser His Val Asp Val Met Asp Cys Asp
            580                 585                 590

Lys Thr Gln Leu Asn Leu Thr Val Glu Leu Thr Thr Ala Glu Val Ile
        595                 600                 605

Pro Gly Ser Val Trp Asn Leu Gly Lys Tyr Val Cys Ile Arg Pro Asn
        610                 615                 620

Trp Trp Pro Tyr Glu Thr Thr Val Val Leu Ala Phe Glu Glu Val Ser
625                 630                 635                 640

Gln Val Val Lys Leu Val Leu Arg Ala Leu Arg Asp Leu Thr Arg Ile
                645                 650                 655

Trp Asn Ala Ala Thr Thr Thr Ala Phe Leu Val Cys Leu Val Lys Ile
                660                 665                 670

Val Arg Gly Gln Met Val Gln Gly Ile Leu Trp Leu Leu Leu Ile Thr
            675                 680                 685

Gly Val Gln Gly His Leu Asp Cys Lys Pro Glu Phe Ser Tyr Ala Ile
        690                 695                 700

Ala Lys Asp Glu Arg Ile Gly Gln Leu Gly Ala Glu Gly Leu Thr Thr
705                 710                 715                 720

Thr Trp Lys Glu Tyr Ser Pro Gly Met Lys Leu Glu Asp Thr Met Val
                725                 730                 735

Ile Ala Trp Cys Glu Asp Gly Lys Leu Met Tyr Leu Gln Arg Cys Thr
```

```
                740              745              750
Arg Glu Thr Arg Tyr Leu Ala Ile Leu His Thr Arg Ala Leu Pro Thr
            755              760              765
Ser Val Val Phe Lys Lys Leu Phe Asp Gly Arg Lys Gln Glu Asp Val
            770              775              780
Val Glu Met Asn Asp Asn Phe Glu Phe Gly Leu Cys Pro Cys Asp Ala
785              790              795              800
Lys Pro Ile Val Arg Gly Lys Phe Asn Thr Thr Leu Leu Asn Gly Pro
                805              810              815
Ala Phe Gln Met Val Cys Pro Ile Gly Trp Thr Gly Thr Val Ser Cys
            820              825              830
Thr Ser Phe Asn Met Asp Thr Leu Ala Thr Thr Val Arg Thr Tyr
            835              840              845
Arg Arg Ser Lys Pro Phe Pro His Arg Gln Gly Cys Ile Thr Gln Lys
            850              855              860
Asn Leu Gly Glu Asp Leu His Asn Cys Ile Leu Gly Asn Trp Thr
865              870              875              880
Cys Val Pro Gly Asp Gln Leu Leu Tyr Lys Gly Gly Ser Ile Glu Ser
                885              890              895
Cys Lys Trp Cys Gly Tyr Gln Phe Lys Glu Ser Glu Gly Leu Pro His
            900              905              910
Tyr Pro Ile Gly Lys Cys Lys Leu Glu Asn Glu Thr Gly Tyr Arg Leu
            915              920              925
Val Asp Ser Thr Ser Cys Asn Arg Glu Gly Val Ala Ile Val Pro Gln
            930              935              940
Gly Thr Leu Lys Cys Lys Ile Gly Lys Thr Thr Val Gln Val Ile Ala
945              950              955              960
Met Asp Thr Lys Leu Gly Pro Met Pro Cys Arg Pro Tyr Glu Ile Ile
                965              970              975
Ser Ser Glu Gly Pro Val Glu Lys Thr Ala Cys Thr Phe Asn Tyr Thr
            980              985              990
Lys Thr Leu Lys Asn Lys Tyr Phe Glu Pro Arg Asp Ser Tyr Phe Gln
            995              1000             1005
Gln Tyr Met Leu Lys Gly Glu Tyr Gln Tyr Trp Phe Asp Leu Glu
            1010             1015             1020
Val Thr Asp His His Arg Asp Tyr Phe Ala Glu Ser Ile Leu Val
            1025             1030             1035
Val Val Val Ala Leu Leu Gly Gly Arg Tyr Val Leu Trp Leu Leu
            1040             1045             1050
Val Thr Tyr Met Val Leu Ser Glu Gln Lys Ala Leu Gly Ile Gln
            1055             1060             1065
Tyr Gly Ser Gly Glu Val Val Met Met Gly Asn Leu Leu Thr His
            1070             1075             1080
Asn Asn Ile Glu Val Val Thr Tyr Phe Leu Leu Leu Tyr Leu Leu
            1085             1090             1095
Leu Arg Glu Glu Ser Val Lys Lys Trp Val Leu Leu Tyr His
            1100             1105             1110
Ile Leu Val Val His Pro Ile Lys Ser Val Ile Val Leu Leu
            1115             1120             1125
Met Ile Gly Asp Val Val Lys Ala Asp Ser Gly Gly Gln Glu Tyr
            1130             1135             1140
Leu Gly Lys Ile Asp Leu Cys Phe Thr Thr Val Val Leu Ile Val
            1145             1150             1155
```

-continued

```
Ile Gly Leu Ile Ile Ala Arg Arg Asp Pro Thr Ile Val Pro Leu
1160                1165                1170

Val Thr Ile Met Ala Ala Leu Arg Val Thr Glu Leu Thr His Gln
1175                1180                1185

Pro Gly Val Asp Ile Ala Val Ala Val Met Thr Ile Thr Leu Leu
1190                1195                1200

Met Val Ser Tyr Val Thr Asp Tyr Phe Arg Tyr Lys Lys Trp Leu
1205                1210                1215

Gln Cys Ile Leu Ser Leu Val Ser Ala Val Phe Leu Ile Arg Ser
1220                1225                1230

Leu Ile Tyr Leu Gly Arg Ile Glu Met Pro Glu Val Thr Ile Pro
1235                1240                1245

Asn Trp Arg Pro Leu Thr Leu Ile Leu Leu Tyr Leu Ile Ser Thr
1250                1255                1260

Thr Ile Val Thr Arg Trp Lys Val Asp Val Ala Gly Leu Leu Leu
1265                1270                1275

Gln Cys Val Pro Ile Leu Leu Leu Val Thr Thr Leu Trp Ala Asp
1280                1285                1290

Phe Leu Thr Leu Ile Leu Ile Leu Pro Thr Tyr Glu Leu Val Lys
1295                1300                1305

Leu Tyr Tyr Leu Lys Thr Val Arg Thr Asp Thr Glu Arg Ser Trp
1310                1315                1320

Leu Gly Gly Ile Asp Tyr Thr Arg Val Asp Ser Ile Tyr Asp Val
1325                1330                1335

Asp Glu Ser Gly Glu Gly Val Tyr Leu Phe Pro Ser Arg Gln Lys
1340                1345                1350

Ala Gln Gly Asn Phe Ser Ile Leu Leu Pro Leu Ile Lys Ala Thr
1355                1360                1365

Leu Ile Ser Cys Val Ser Ser Lys Trp Gln Leu Ile Tyr Met Ser
1370                1375                1380

Tyr Leu Thr Leu Asp Phe Met Tyr Tyr Met His Arg Lys Val Ile
1385                1390                1395

Glu Glu Ile Ser Gly Gly Thr Asn Ile Ile Ser Arg Leu Val Ala
1400                1405                1410

Ala Leu Ile Glu Leu Asn Trp Ser Met Glu Glu Glu Glu Ser Lys
1415                1420                1425

Gly Leu Lys Lys Phe Tyr Leu Leu Ser Gly Arg Leu Arg Asn Leu
1430                1435                1440

Ile Ile Lys His Lys Val Arg Asn Glu Thr Val Ala Ser Trp Tyr
1445                1450                1455

Gly Glu Glu Val Tyr Gly Met Pro Lys Ile Met Thr Ile Ile
1460                1465                1470

Lys Ala Ser Thr Leu Ser Lys Ser Arg His Cys Ile Ile Cys Thr
1475                1480                1485

Val Cys Glu Gly Arg Glu Trp Lys Gly Gly Thr Cys Pro Lys Cys
1490                1495                1500

Gly Arg His Gly Lys Pro Ile Thr Cys Gly Met Ser Leu Ala Asp
1505                1510                1515

Phe Glu Glu Arg His Tyr Lys Arg Ile Phe Ile Arg Glu Gly Asn
1520                1525                1530

Phe Glu Gly Met Cys Ser Arg Cys Gln Gly Lys His Arg Arg Phe
1535                1540                1545
```

-continued

| | | | | | | | | | | | |
|---|---|---|---|---|---|---|---|---|---|---|---|
|Glu|Met|Asp|Arg|Glu|Pro|Lys|Ser|Ala|Arg|Tyr|Cys|Ala|Glu|Cys|
| |1550| | | |1555| | | |1560| | |

Asn Arg Leu His Pro Ala Glu Glu Gly Asp Phe Trp Ala Glu Ser
     1565            1570            1575

Ser Met Leu Gly Leu Lys Ile Thr Tyr Phe Ala Leu Met Asp Gly
     1580            1585            1590

Lys Val Tyr Asp Ile Thr Glu Trp Ala Gly Cys Gln Arg Val Gly
     1595            1600            1605

Ile Ser Pro Asp Thr His Arg Val Pro Cys His Ile Ser Phe Gly
     1610            1615            1620

Ser Arg Met Pro Phe Arg Gln Glu Tyr Asn Gly Phe Val Gln Tyr
     1625            1630            1635

Thr Ala Arg Gly Gln Leu Phe Leu Arg Asn Leu Pro Val Leu Ala
     1640            1645            1650

Thr Lys Val Lys Met Leu Met Val Gly Asn Leu Gly Glu Glu Ile
     1655            1660            1665

Gly Asn Leu Glu His Leu Gly Trp Ile Leu Arg Gly Pro Ala Val
     1670            1675            1680

Cys Lys Lys Ile Thr Glu His Glu Lys Cys His Ile Asn Ile Leu
     1685            1690            1695

Asp Lys Leu Thr Ala Phe Phe Gly Ile Met Pro Arg Gly Thr Thr
     1700            1705            1710

Pro Arg Ala Pro Val Arg Phe Pro Thr Ser Leu Leu Lys Val Arg
     1715            1720            1725

Arg Gly Leu Glu Thr Ala Trp Ala Tyr Thr His Gln Gly Gly Ile
     1730            1735            1740

Ser Ser Val Asp His Val Thr Ala Gly Lys Asp Leu Leu Val Cys
     1745            1750            1755

Asp Ser Met Gly Arg Thr Arg Val Val Cys Gln Ser Asn Asn Arg
     1760            1765            1770

Leu Thr Asp Glu Thr Glu Tyr Gly Val Lys Thr Asp Ser Gly Cys
     1775            1780            1785

Pro Asp Gly Ala Arg Cys Tyr Val Leu Asn Pro Glu Ala Val Asn
     1790            1795            1800

Ile Ser Gly Ser Lys Gly Ala Val Val His Leu Gln Lys Thr Gly
     1805            1810            1815

Gly Glu Phe Thr Cys Val Thr Ala Ser Gly Thr Pro Ala Phe Phe
     1820            1825            1830

Asp Leu Lys Asn Leu Lys Gly Trp Ser Gly Leu Pro Ile Phe Glu
     1835            1840            1845

Ala Ser Ser Gly Arg Val Val Gly Arg Val Lys Val Gly Lys Asn
     1850            1855            1860

Glu Glu Ser Lys Pro Thr Lys Ile Met Ser Gly Ile Gln Thr Val
     1865            1870            1875

Ser Lys Asn Arg Ala Asp Leu Thr Glu Met Val Lys Lys Ile Thr
     1880            1885            1890

Ser Met Asn Arg Gly Asp Phe Lys Gln Ile Thr Leu Ala Thr Gly
     1895            1900            1905

Ala Gly Lys Thr Thr Glu Leu Pro Lys Ala Val Ile Glu Glu Ile
     1910            1915            1920

Gly Arg His Lys Arg Val Leu Val Leu Ile Pro Leu Arg Ala Ala
     1925            1930            1935

Ala Glu Ser Val Tyr Gln Tyr Met Arg Leu Lys His Pro Ser Ile

```
            1940                1945                1950
Ser Phe Asn Leu Arg Ile Gly Asp Met Lys Glu Gly Asp Met Ala
    1955                1960                1965
Thr Gly Ile Thr Tyr Ala Ser Tyr Gly Tyr Phe Cys Gln Met Pro
    1970                1975                1980
Gln Pro Lys Leu Arg Ala Ala Met Val Glu Tyr Ser Tyr Ile Phe
    1985                1990                1995
Leu Asp Glu Tyr His Cys Ala Thr Pro Glu Gln Leu Ala Ile Ile
    2000                2005                2010
Gly Lys Ile His Arg Phe Ser Glu Ser Ile Arg Val Val Ala Met
    2015                2020                2025
Thr Ala Thr Pro Ala Gly Ser Val Thr Thr Gly Gln Lys His
    2030                2035                2040
Pro Ile Glu Glu Phe Ile Ala Pro Glu Val Met Lys Gly Glu Asp
    2045                2050                2055
Leu Gly Ser Gln Phe Leu Asp Ile Ala Gly Leu Lys Ile Pro Val
    2060                2065                2070
Asp Glu Met Lys Gly Asn Met Leu Val Phe Val Pro Thr Arg Asn
    2075                2080                2085
Met Ala Val Glu Val Ala Lys Lys Leu Lys Ala Lys Gly Tyr Asn
    2090                2095                2100
Ser Gly Tyr Tyr Tyr Ser Gly Glu Asp Pro Ala Asn Leu Arg Val
    2105                2110                2115
Val Thr Ser Gln Ser Pro Tyr Val Ile Val Ala Thr Asn Ala Ile
    2120                2125                2130
Glu Ser Gly Val Thr Leu Pro Asp Leu Asp Thr Val Ile Asp Thr
    2135                2140                2145
Gly Leu Lys Cys Glu Lys Arg Val Arg Val Ser Ser Lys Ile Pro
    2150                2155                2160
Phe Ile Val Thr Gly Leu Lys Arg Met Ala Val Thr Val Gly Glu
    2165                2170                2175
Gln Ala Gln Arg Arg Gly Arg Val Gly Arg Val Lys Pro Gly Arg
    2180                2185                2190
Tyr Tyr Arg Ser Gln Glu Thr Ala Thr Gly Ser Lys Asp Tyr His
    2195                2200                2205
Tyr Asp Leu Leu Gln Ala Gln Arg Tyr Gly Ile Glu Asp Gly Ile
    2210                2215                2220
Asn Val Thr Lys Ser Phe Arg Glu Met Asn Tyr Asp Trp Ser Leu
    2225                2230                2235
Tyr Glu Glu Asp Ser Leu Leu Ile Thr Gln Leu Glu Ile Leu Asn
    2240                2245                2250
Asn Leu Leu Ile Ser Glu Asp Leu Pro Ala Ala Val Lys Asn Ile
    2255                2260                2265
Met Ala Arg Thr Asp His Pro Glu Pro Ile Gln Leu Ala Tyr Asn
    2270                2275                2280
Ser Tyr Glu Val Gln Val Pro Val Leu Phe Pro Lys Ile Arg Asn
    2285                2290                2295
Gly Glu Val Thr Asp Thr Tyr Glu Asn Tyr Ser Phe Leu Asn Ala
    2300                2305                2310
Arg Lys Leu Gly Glu Asp Val Pro Val Tyr Ile Tyr Ala Thr Glu
    2315                2320                2325
Asp Glu Asp Leu Ala Val Asp Leu Leu Gly Leu Asp Trp Pro Asp
    2330                2335                2340
```

```
Pro Gly Asn Gln Gln Val Val Glu Thr Gly Lys Ala Leu Lys Gln
    2345                2350                2355

Val Thr Gly Leu Ser Ser Ala Glu Asn Ala Leu Leu Val Ala Leu
    2360                2365                2370

Phe Gly Tyr Val Gly Tyr Gln Ala Leu Ser Lys Arg His Val Pro
    2375                2380                2385

Met Ile Thr Asp Ile Tyr Thr Ile Glu Asp Gln Arg Leu Glu Asp
    2390                2395                2400

Thr Thr His Leu Gln Tyr Ala Pro Asn Ala Ile Lys Thr Asp Gly
    2405                2410                2415

Thr Glu Thr Glu Leu Lys Glu Leu Ala Ser Gly Asp Val Glu Lys
    2420                2425                2430

Ile Met Gly Ala Ile Ser Asp Tyr Ala Ala Gly Leu Glu Phe
    2435                2440                2445

Val Lys Ser Gln Ala Glu Lys Ile Lys Thr Ala Pro Leu Phe Lys
    2450                2455                2460

Glu Asn Ala Glu Ala Ala Lys Gly Tyr Val Gln Lys Phe Ile Asp
    2465                2470                2475

Ser Leu Ile Glu Asn Lys Glu Glu Ile Ile Arg Tyr Gly Leu Trp
    2480                2485                2490

Gly Thr His Thr Ala Leu Tyr Lys Ser Ile Ala Ala Arg Leu Gly
    2495                2500                2505

His Glu Thr Ala Phe Ala Thr Leu Val Leu Lys Trp Leu Ala Phe
    2510                2515                2520

Gly Gly Glu Ser Val Ser Asp His Val Lys Gln Ala Ala Val Asp
    2525                2530                2535

Leu Val Val Tyr Tyr Val Met Asn Lys Pro Ser Phe Pro Gly Asp
    2540                2545                2550

Ser Glu Thr Gln Gln Glu Gly Arg Arg Phe Val Ala Ser Leu Phe
    2555                2560                2565

Ile Ser Ala Leu Ala Thr Tyr Thr Tyr Lys Thr Trp Asn Tyr His
    2570                2575                2580

Asn Leu Ser Lys Val Val Glu Pro Ala Leu Ala Tyr Leu Pro Tyr
    2585                2590                2595

Ala Thr Ser Ala Leu Lys Met Phe Thr Pro Thr Arg Leu Glu Ser
    2600                2605                2610

Val Val Ile Leu Ser Thr Thr Ile Tyr Lys Thr Tyr Leu Ser Ile
    2615                2620                2625

Arg Lys Gly Lys Ser Asp Gly Leu Leu Gly Thr Gly Ile Ser Ala
    2630                2635                2640

Ala Met Glu Ile Leu Ser Gln Asn Pro Val Ser Val Gly Ile Ser
    2645                2650                2655

Val Met Leu Gly Val Gly Ala Ile Ala Ala His Asn Ala Ile Glu
    2660                2665                2670

Ser Ser Glu Gln Lys Arg Thr Leu Leu Met Lys Val Phe Val Lys
    2675                2680                2685

Asn Phe Leu Asp Gln Ala Ala Thr Asp Glu Leu Val Lys Glu Asn
    2690                2695                2700

Pro Glu Lys Ile Ile Met Ala Leu Phe Glu Ala Val Gln Thr Ile
    2705                2710                2715

Gly Asn Pro Leu Arg Leu Ile Tyr His Leu Tyr Gly Val Tyr Tyr
    2720                2725                2730
```

-continued

Lys Gly Trp Glu Ala Lys Glu Leu Ser Glu Arg Thr Ala Gly Arg
2735                2740                2745

Asn Leu Phe Thr Leu Ile Met Phe Glu Ala Phe Glu Leu Leu Gly
2750                2755                2760

Met Asp Ser Gln Gly Lys Ile Arg Asn Leu Ser Gly Asn Tyr Ile
2765                2770                2775

Leu Asp Leu Ile Tyr Gly Leu His Lys Gln Ile Asn Arg Gly Leu
2780                2785                2790

Lys Lys Met Val Leu Gly Trp Ala Pro Ala Pro Phe Ser Cys Asp
2795                2800                2805

Trp Thr Pro Ser Asp Glu Arg Ile Arg Leu Pro Thr Asp Asn Tyr
2810                2815                2820

Leu Arg Val Glu Thr Arg Cys Pro Cys Gly Tyr Glu Met Lys Ala
2825                2830                2835

Phe Lys Asn Val Gly Gly Lys Leu Thr Lys Val Glu Glu Ser Gly
2840                2845                2850

Pro Phe Leu Cys Arg Asn Arg Pro Gly Arg Gly Pro Val Asn Tyr
2855                2860                2865

Arg Val Thr Lys Tyr Tyr Asp Asp Asn Leu Arg Glu Ile Lys Pro
2870                2875                2880

Val Ala Lys Leu Glu Gly Gln Val Glu His Tyr Tyr Lys Gly Val
2885                2890                2895

Thr Ala Lys Ile Asp Tyr Ser Lys Gly Lys Met Leu Leu Ala Thr
2900                2905                2910

Asp Lys Trp Glu Val Glu His Gly Val Ile Thr Arg Leu Ala Lys
2915                2920                2925

Arg Tyr Thr Gly Val Gly Phe Asn Gly Ala Tyr Leu Gly Asp Glu
2930                2935                2940

Pro Asn His Arg Ala Leu Val Glu Arg Asp Cys Ala Thr Ile Thr
2945                2950                2955

Lys Asn Thr Val Gln Phe Leu Lys Met Lys Lys Gly Cys Ala Phe
2960                2965                2970

Thr Tyr Asp Leu Thr Ile Ser Asn Leu Thr Arg Leu Ile Glu Leu
2975                2980                2985

Val His Arg Asn Asn Leu Glu Glu Lys Glu Ile Pro Thr Ala Thr
2990                2995                3000

Val Thr Thr Trp Leu Ala Tyr Thr Phe Val Asn Glu Asp Val Gly
3005                3010                3015

Thr Ile Lys Pro Val Leu Gly Glu Arg Val Ile Pro Asp Pro Val
3020                3025                3030

Val Asp Ile Asn Leu Gln Pro Glu Val Gln Val Asp Thr Ser Glu
3035                3040                3045

Val Gly Ile Thr Ile Ile Gly Arg Glu Thr Leu Met Thr Thr Gly
3050                3055                3060

Val Thr Pro Val Leu Glu Lys Val Glu Pro Asp Ala Ser Asp Asn
3065                3070                3075

Gln Asn Ser Val Lys Ile Gly Leu Asp Glu Gly Asn Tyr Pro Gly
3080                3085                3090

Pro Gly Ile Gln Thr His Thr Leu Thr Glu Glu Ile His Asn Arg
3095                3100                3105

Asp Ala Arg Pro Phe Ile Met Ile Leu Gly Ser Arg Asn Ser Ile
3110                3115                3120

Ser Asn Arg Ala Lys Thr Ala Arg Asn Ile Asn Leu Tyr Thr Gly

```
               3125                3130                3135

Asn Asp Pro Arg Glu Ile Arg Asp Leu Met Ala Ala Gly Arg Met
    3140                3145                3150

Leu Val Val Ala Leu Arg Asp Val Asp Pro Glu Leu Ser Glu Met
    3155                3160                3165

Val Asp Phe Lys Gly Thr Phe Leu Asp Arg Glu Ala Leu Glu Ala
    3170                3175                3180

Leu Ser Leu Gly Gln Pro Lys Pro Lys Gln Val Thr Lys Glu Ala
    3185                3190                3195

Val Arg Asn Leu Ile Glu Gln Lys Lys Asp Val Glu Ile Pro Asn
    3200                3205                3210

Trp Phe Ala Ser Asp Asp Pro Val Phe Leu Glu Val Ala Leu Lys
    3215                3220                3225

Asn Asp Lys Tyr Tyr Leu Val Gly Asp Val Gly Glu Leu Lys Asp
    3230                3235                3240

Gln Ala Lys Ala Leu Gly Ala Thr Asp Gln Thr Arg Ile Ile Lys
    3245                3250                3255

Glu Val Gly Ser Arg Thr Tyr Ala Met Lys Leu Ser Ser Trp Phe
    3260                3265                3270

Leu Lys Ala Ser Asn Lys Gln Met Ser Leu Thr Pro Leu Phe Glu
    3275                3280                3285

Glu Leu Leu Arg Cys Pro Pro Ala Thr Lys Ser Asn Lys Gly
    3290                3295                3300

His Met Ala Ser Ala Tyr Gln Leu Ala Gln Gly Asn Trp Glu Pro
    3305                3310                3315

Leu Gly Cys Gly Val His Leu Gly Thr Ile Pro Ala Arg Arg Val
    3320                3325                3330

Lys Ile His Pro Tyr Glu Ala Tyr Leu Lys Leu Lys Asp Phe Ile
    3335                3340                3345

Glu Glu Glu Glu Lys Lys Pro Arg Val Lys Asp Thr Val Ile Arg
    3350                3355                3360

Glu His Asn Lys Trp Ile Leu Lys Lys Ile Arg Phe Gln Gly Asn
    3365                3370                3375

Leu Asn Thr Lys Lys Met Leu Asn Pro Gly Lys Leu Ser Glu Gln
    3380                3385                3390

Leu Asp Arg Glu Gly Arg Lys Arg Asn Ile Tyr Asn His Gln Ile
    3395                3400                3405

Gly Thr Ile Met Ser Ser Ala Gly Ile Arg Leu Glu Lys Leu Pro
    3410                3415                3420

Ile Val Arg Ala Gln Thr Asp Thr Lys Thr Phe His Glu Ala Ile
    3425                3430                3435

Arg Asp Lys Ile Asp Lys Ser Glu Asn Arg Gln Asn Pro Glu Leu
    3440                3445                3450

His Asn Lys Leu Leu Glu Ile Phe His Thr Ile Ala Gln Pro Thr
    3455                3460                3465

Leu Lys His Thr Tyr Gly Glu Val Thr Trp Glu Gln Leu Glu Ala
    3470                3475                3480

Gly Val Asn Arg Lys Gly Ala Ala Gly Phe Leu Glu Lys Lys Asn
    3485                3490                3495

Ile Gly Glu Val Leu Asp Ser Glu Lys His Leu Val Glu Gln Leu
    3500                3505                3510

Val Arg Asp Leu Lys Ala Gly Arg Lys Ile Lys Tyr Tyr Glu Thr
    3515                3520                3525
```

```
Ala Ile Pro Lys Asn Glu Lys Arg Asp Val Ser Asp Asp Trp Gln
3530                3535                3540

Ala Gly Asp Leu Val Val Glu Lys Arg Pro Arg Val Ile Gln Tyr
3545                3550                3555

Pro Glu Ala Lys Thr Arg Leu Ala Ile Thr Lys Val Met Tyr Asn
3560                3565                3570

Trp Val Lys Gln Gln Pro Val Ile Pro Gly Tyr Glu Gly Lys
3575                3580                3585

Thr Pro Leu Phe Asn Ile Phe Asp Lys Val Arg Lys Glu Trp Asp
3590                3595                3600

Ser Phe Asn Glu Pro Val Ala Val Ser Phe Asp Thr Lys Ala Trp
3605                3610                3615

Asp Thr Gln Val Thr Ser Lys Asp Leu Gln Leu Ile Gly Glu Ile
3620                3625                3630

Gln Lys Tyr Tyr Tyr Lys Lys Glu Trp His Lys Phe Ile Asp Thr
3635                3640                3645

Ile Thr Asp His Met Thr Glu Val Pro Val Ile Thr Ala Asp Gly
3650                3655                3660

Glu Val Tyr Ile Arg Asn Gly Gln Arg Gly Ser Gly Gln Pro Asp
3665                3670                3675

Thr Ser Ala Gly Asn Ser Met Leu Asn Val Leu Thr Met Met Tyr
3680                3685                3690

Gly Phe Cys Glu Ser Thr Gly Val Pro Tyr Lys Ser Phe Asn Arg
3695                3700                3705

Val Ala Arg Ile His Val Cys Gly Asp Asp Gly Phe Leu Ile Thr
3710                3715                3720

Glu Lys Gly Leu Gly Leu Lys Phe Ala Asn Lys Gly Met Gln Ile
3725                3730                3735

Leu His Glu Ala Gly Lys Pro Gln Lys Ile Thr Glu Gly Glu Lys
3740                3745                3750

Met Lys Val Ala Tyr Arg Phe Glu Asp Ile Glu Phe Cys Ser His
3755                3760                3765

Thr Pro Val Pro Val Arg Trp Ser Asp Asn Thr Ser Ser His Met
3770                3775                3780

Ala Gly Arg Asp Thr Ala Val Ile Leu Ser Lys Met Ala Thr Arg
3785                3790                3795

Leu Asp Ser Ser Gly Glu Arg Gly Thr Thr Ala Tyr Glu Lys Ala
3800                3805                3810

Val Ala Phe Ser Phe Leu Leu Met Tyr Ser Trp Asn Pro Leu Val
3815                3820                3825

Arg Arg Ile Cys Leu Leu Val Leu Ser Gln Gln Pro Glu Thr Asp
3830                3835                3840

Pro Ser Lys His Ala Thr Tyr Tyr Tyr Lys Gly Asp Pro Ile Gly
3845                3850                3855

Ala Tyr Lys Asp Val Ile Gly Arg Asn Leu Ser Glu Leu Lys Arg
3860                3865                3870

Thr Gly Phe Glu Lys Leu Ala Asn Leu Asn Leu Ser Leu Ser Thr
3875                3880                3885

Leu Gly Val Trp Thr Lys His Thr Ser Lys Arg Ile Ile Gln Asp
3890                3895                3900

Cys Val Ala Ile Gly Lys Glu Glu Gly Asn Trp Leu Val Lys Pro
3905                3910                3915
```

```
Asp Arg Leu Ile Ser Ser Lys Thr Gly His Leu Tyr Ile Pro Asp
    3920                3925                3930

Lys Gly Phe Thr Leu Gln Gly Lys His Tyr Glu Gln Leu Gln Leu
    3935                3940                3945

Arg Thr Glu Thr Asn Pro Val Met Gly Val Gly Thr Glu Arg Tyr
    3950                3955                3960

Lys Leu Gly Pro Ile Val Asn Leu Leu Arg Arg Leu Lys Ile
    3965                3970                3975

Leu Leu Met Thr Ala Val Gly Val Ser Ser
    3980                3985

<210> SEQ ID NO 56
<211> LENGTH: 3973
<212> TYPE: PRT
<213> ORGANISM: BVDV-2

<400> SEQUENCE: 56

Met Glu Leu Phe Ser Asn Glu Leu Leu Tyr Lys Thr Tyr Lys Gln Lys
1               5                   10                  15

Pro Ala Gly Val Val Glu Pro Val Tyr Asp Val Asn Gly Arg Pro Leu
                20                  25                  30

Phe Gly Glu Ser Ser Asp Leu His Pro Gln Ser Thr Leu Lys Leu Pro
            35                  40                  45

His Gln Arg Gly Ser Ala Asn Ile Leu Thr Asn Ala Arg Ser Leu Pro
        50                  55                  60

Arg Lys Gly Asp Cys Arg Arg Gly Asn Val Asn Gly Ala Val Ser Gly
65                  70                  75                  80

Ile Tyr Ile Lys Pro Gly Pro Ile Tyr Tyr Gln Asp Tyr Met Gly Pro
                85                  90                  95

Val Tyr His Arg Ala Pro Leu Glu Leu Cys Arg Glu Ala Ser Met Cys
            100                 105                 110

Glu Thr Thr Arg Arg Ile Gly Arg Val Thr Gly Ser Asp Gly Lys Leu
        115                 120                 125

Tyr His Ile Tyr Ile Cys Ile Asp Gly Cys Val Leu Leu Lys Arg Ala
    130                 135                 140

Thr Arg Thr Gln Pro Glu Val Leu Lys Trp Val Tyr Asn Arg Leu Asn
145                 150                 155                 160

Cys Pro Leu Trp Val Thr Ser Cys Ser Asp Glu Gly Ser Lys Gly Ala
                165                 170                 175

Thr Ser Lys Lys Gln Pro Lys Pro Asp Arg Ile Glu Lys Gly Lys Met
            180                 185                 190

Lys Ile Ala Pro Lys Glu Ser Glu Lys Asp Cys Lys Thr Arg Pro Pro
        195                 200                 205

Asp Ala Thr Ile Val Val Glu Gly Val Lys Tyr Gln Val Lys Lys Lys
    210                 215                 220

Gly Lys Val Arg Gly Lys Asn Thr Gln Asp Gly Leu Tyr His Asn Lys
225                 230                 235                 240

Asn Lys Pro Pro Glu Ser Arg Lys Lys Leu Glu Lys Ala Leu Leu Ala
                245                 250                 255

Trp Ala Ile Leu Ala Ala Val Leu Leu Gln Leu Val Thr Gly Glu Asn
            260                 265                 270

Ile Thr Gln Trp Asn Leu Met Asp Asn Gly Thr Glu Gly Ile Gln Gln
        275                 280                 285

Ala Met Phe Leu Arg Gly Val Asn Arg Ser Leu His Gly Ile Trp Pro
    290                 295                 300
```

-continued

```
Glu Lys Ile Cys Thr Gly Val Pro Thr His Leu Ala Thr Asp Tyr Glu
305                 310                 315                 320
Leu Arg Glu Ile Val Gly Met Met Asp Ala Ser Glu Lys Thr Asn Tyr
            325                 330                 335
Thr Cys Cys Arg Leu Gln Arg His Glu Trp Asn Lys His Gly Trp Cys
        340                 345                 350
Asn Trp Phe His Ile Glu Pro Trp Ile Trp Leu Met Asn Lys Thr Gln
    355                 360                 365
Asn Asn Leu Thr Glu Gly Gln Pro Pro Lys Glu Cys Ala Val Thr Cys
370                 375                 380
Arg Tyr Asp Lys Glu Ala Glu Leu Asn Ile Val Thr Gln Ala Arg Asp
385                 390                 395                 400
Arg Pro Thr Thr Leu Thr Gly Cys Lys Lys Gly Lys Asn Phe Ser Phe
                405                 410                 415
Ala Gly Val Ile Leu Asp Gly Pro Cys Asn Phe Lys Val Ser Val Glu
            420                 425                 430
Asp Val Leu Phe Lys Glu His Asp Cys Gly Asn Met Leu Gln Glu Thr
        435                 440                 445
Ala Ile Gln Leu Leu Asp Gly Ala Thr Asn Thr Ile Glu Gly Ala Arg
    450                 455                 460
Val Gly Thr Ala Lys Leu Thr Thr Trp Leu Gly Lys Gln Leu Gly Ile
465                 470                 475                 480
Leu Gly Lys Lys Leu Glu Asn Lys Thr Lys Ala Trp Phe Gly Ala His
                485                 490                 495
Ala Ala Ser Pro Tyr Cys Gly Val Glu Arg Lys Ile Gly Tyr Val Trp
            500                 505                 510
Tyr Thr Lys Asn Cys Thr Pro Ala Cys Leu Pro Arg Asn Thr Lys Ile
        515                 520                 525
Ile Gly Pro Gly Lys Phe Asp Thr Asn Ala Glu Asp Gly Lys Ile Leu
    530                 535                 540
His Glu Met Gly Gly His Leu Ser Glu Phe Ala Leu Leu Ser Leu Val
545                 550                 555                 560
Val Leu Ser Asp Phe Ala Pro Glu Thr Ala Ser Val Ile Tyr Leu Val
                565                 570                 575
Leu His Phe Ala Ile Pro Gln Ser His Val Asp Val Asp Thr Cys Asp
            580                 585                 590
Lys Asn Gln Leu Asn Leu Thr Val Ala Thr Thr Val Ala Glu Val Ile
        595                 600                 605
Pro Gly Thr Val Trp Asn Leu Gly Lys Tyr Val Cys Ile Arg Pro Asp
    610                 615                 620
Trp Trp Pro Tyr Glu Thr Thr Val Phe Val Leu Glu Glu Ala Gly
625                 630                 635                 640
Gln Val Ile Lys Leu Gly Leu Arg Ala Ile Arg Asp Leu Thr Arg Ile
                645                 650                 655
Trp Asn Ala Ala Thr Thr Thr Ala Phe Leu Ile Phe Leu Val Lys Ala
            660                 665                 670
Leu Arg Gly Gln Leu Ile Gln Gly Leu Leu Trp Leu Met Leu Ile Thr
        675                 680                 685
Gly Ala Gln Gly Phe Pro Glu Cys Lys Glu Gly Phe Gln Tyr Ala Ile
    690                 695                 700
Ser Lys Asp Arg Lys Met Gly Leu Leu Gly Pro Glu Ser Leu Thr Thr
705                 710                 715                 720
```

-continued

Thr Trp His Arg Pro Thr Lys Lys Leu Val Asp Ser Met Val Gln Val
            725                 730                 735

Trp Cys Glu Gly Lys Asp Leu Lys Ile Leu Lys Thr Cys Pro Lys Glu
        740                 745                 750

Glu Arg Tyr Leu Val Ala Val His Glu Arg Ala Leu Ser Thr Ser Ala
    755                 760                 765

Glu Phe Met Pro Ile Ser Asp Gly Thr Ile Gly Pro Asp Val Ile Asp
    770                 775                 780

Met Pro Asp Asp Phe Glu Phe Gly Leu Cys Pro Cys Asp Ala Lys Pro
785                 790                 795                 800

Val Ile Lys Gly Lys Phe Asn Ala Ser Leu Leu Asn Gly Pro Ala Phe
                805                 810                 815

Gln Met Val Cys Pro Gln Gly Trp Thr Gly Thr Ile Glu Cys Thr Leu
                820                 825                 830

Ala Asn Gln Asp Thr Leu Asp Thr Thr Val Val Arg Thr Tyr Arg Arg
            835                 840                 845

Thr Thr Pro Phe Gln Arg Arg Lys Trp Cys Ser Tyr Glu Lys Ile Ile
    850                 855                 860

Gly Glu Asp Ile His Glu Cys Ile Leu Gly Gly Asn Trp Thr Cys Ile
865                 870                 875                 880

Thr Gly Asp His Ser Lys Leu Lys Asp Gly Pro Ile Lys Lys Cys Lys
                885                 890                 895

Trp Cys Gly Tyr Asp Phe Val Asn Ser Glu Gly Leu Pro His Tyr Pro
                900                 905                 910

Ile Gly Lys Cys Met Leu Ile Asn Glu Ser Gly Tyr Arg Tyr Val Asp
            915                 920                 925

Asp Thr Ser Cys Asp Arg Gly Gly Val Ala Ile Val Pro Thr Gly Thr
    930                 935                 940

Val Lys Cys Arg Ile Gly Asp Val Thr Val Gln Val Val Ala Ser Asn
945                 950                 955                 960

Asn Asp Leu Gly Pro Met Pro Cys Ser Pro Ala Glu Val Ile Ala Ser
                965                 970                 975

Glu Gly Pro Val Glu Lys Thr Ala Cys Thr Phe Asn Tyr Ser Arg Thr
            980                 985                 990

Leu Pro Asn Lys Tyr Tyr Glu Pro Arg Asp Arg Tyr Phe Gln Gln Tyr
        995                 1000                1005

Met Leu Lys Gly Glu Trp Gln Tyr Trp Phe Asp Leu Asp His Val
    1010                1015                1020

Asp His His Lys Asp Tyr Phe Ser Glu Phe Ile Ile Ile Ala Val
    1025                1030                1035

Val Ala Leu Leu Gly Gly Lys Tyr Val Leu Trp Leu Leu Ile Thr
    1040                1045                1050

Tyr Thr Ile Leu Ser Glu Gln Met Ala Met Gly Ala Gly Val Asn
    1055                1060                1065

Thr Glu Glu Ile Val Met Ile Gly Asn Leu Leu Thr His Ser Asp
    1070                1075                1080

Ile Glu Val Val Val Tyr Phe Leu Leu Leu Tyr Leu Ile Val Lys
    1085                1090                1095

Glu Glu Leu Val Arg Lys Trp Val Ile Leu Val Tyr His Ile Leu
    1100                1105                1110

Val Ala Asn Pro Met Lys Thr Ile Gly Val Ile Leu Leu Met Leu
    1115                1120                1125

Gly Gly Ala Val Lys Ala Ser Arg Ile Asp Ala Asp Asp Gln Ser

```
             1130                1135               1140

Ala Thr Asp Pro Cys Phe Leu Leu Val Thr Gly Ile Val Ala Val
    1145            1150               1155

Leu Met Thr Ala Met Val Tyr Phe Leu Leu Tyr Leu Ile Val
    1160            1165               1170

Lys Glu Glu Leu Val Arg Lys Trp Val Ile Leu Val Tyr His Ile
    1175            1180               1185

Leu Val Ala Asn Pro Met Lys Thr Ile Gly Val Ile Leu Leu Met
    1190            1195               1200

Pro Gly Gly Val Val Ile Ala Ser Arg Ile Asp Ala Gly Asp Gln
    1205            1210               1215

Ser Ala Thr Asp Pro Cys Phe Leu Leu Val Thr Gly Ile Val Ala
    1220            1225               1230

Val Leu Met Ile Ala Arg Arg Glu Pro Ala Thr Leu Pro Leu Ile
    1235            1240               1245

Ile Ala Leu Leu Ala Ile Arg Thr Ser Gly Phe Leu Leu Pro Ala
    1250            1255               1260

Ser Ile Asp Ile Thr Val Ala Val Val Leu Ile Ala Leu Leu Leu
    1265            1270               1275

Ala Ser Tyr Val Thr Asp Tyr Phe Arg Tyr Lys Lys Trp Leu Gln
    1280            1285               1290

Phe Ser Phe Ser Leu Ile Ala Gly Ile Phe Ile Ile Arg Ser Leu
    1295            1300               1305

Lys His Ile Asn Gln Met Glu Val Pro Glu Thr Ser Met Pro Asn
    1310            1315               1320

Trp Arg Pro Leu Val Leu Val Ile Phe Tyr Ile Thr Ser Thr Ala
    1325            1330               1335

Ile Thr Thr Asn Trp Asn Ile Asp Leu Ala Gly Phe Leu Leu Gln
    1340            1345               1350

Trp Ala Pro Ala Val Ile Met Met Ala Thr Met Trp Ala Asp Phe
    1355            1360               1365

Trp Thr Leu Ile Ile Val Leu Pro Ser Tyr Glu Leu Ser Lys Leu
    1370            1375               1380

Tyr Phe Leu Lys Asn Val Arg Thr Asp Val Glu Lys Asn Trp Leu
    1385            1390               1395

Gly Lys Val Lys Tyr Lys Gln Ile Ser Ser Val Tyr Asp Ile Cys
    1400            1405               1410

Asp Ser Glu Glu Ala Val Tyr Leu Phe Pro Ser Arg His Lys Ser
    1415            1420               1425

Gly Ser Arg Pro Asp Phe Ile Leu Pro Leu Leu Lys Ala Val Leu
    1430            1435               1440

Ile Ser Cys Ile Ser Ser Gln Trp Gln Val Val Tyr Ile Ser Tyr
    1445            1450               1455

Leu Ile Leu Glu Ile Thr Tyr Tyr Met His Arg Lys Ile Ile Asp
    1460            1465               1470

Glu Val Ser Gly Gly Pro Asn Phe Leu Ser Arg Leu Ile Ala Ala
    1475            1480               1485

Ile Ile Glu Leu Asn Trp Ala Ile Asp Asp Glu Cys Lys Gly
    1490            1495               1500

Leu Lys Lys Leu Tyr Leu Leu Ser Gly Arg Val Lys Asn Leu Ile
    1505            1510               1515

Val Lys His Lys Val Arg Asn Glu Ala Val His Arg Trp Phe Gly
    1520            1525               1530
```

```
Glu Glu Glu Ile Tyr Gly Ala Pro Lys Val Ile Ala Ile Ile Lys
    1535                1540                1545

Ala Ser Thr Leu Thr Lys Asn Arg His Cys Ile Ile Cys Thr Ile
    1550                1555                1560

Cys Glu Gly Lys Asp Trp Asn Gly Ala Asn Cys Pro Lys Cys Gly
    1565                1570                1575

Arg Gln Gly Lys Pro Ile Thr Cys Gly Met Thr Leu Ala Asp Phe
    1580                1585                1590

Glu Glu Lys His Tyr Lys Lys Ile Phe Ile Arg Glu Gly Cys His
    1595                1600                1605

Asp Gly Pro Ser Arg Glu Glu Tyr Lys Gly Tyr Val Gln Tyr Ile
    1610                1615                1620

Ala Arg Gly Gln Leu Phe Leu Arg Asn Leu Pro Ile Leu Ala Thr
    1625                1630                1635

Lys Met Lys Leu Leu Met Val Gly Asn Leu Gly Ala Glu Ile Gly
    1640                1645                1650

Asp Leu Glu His Leu Gly Trp Val Leu Arg Gly Pro Ala Val Cys
    1655                1660                1665

Lys Lys Ile Thr Asn His Glu Lys Cys His Val Asn Ile Met Asp
    1670                1675                1680

Lys Leu Thr Ala Phe Phe Gly Ile Met Pro Arg Gly Thr Thr Pro
    1685                1690                1695

Arg Ala Pro Val Arg Phe Pro Thr Ala Leu Leu Lys Val Arg Arg
    1700                1705                1710

Gly Leu Glu Thr Gly Trp Ala Tyr Thr His Gln Gly Gly Ile Ser
    1715                1720                1725

Ser Val Asp His Val Thr Ala Gly Lys Asp Leu Leu Val Cys Asp
    1730                1735                1740

Ser Met Gly Arg Thr Arg Val Val Cys His Ser Asn Asn Lys Met
    1745                1750                1755

Thr Asp Glu Thr Glu Tyr Gly Ile Lys Thr Asp Ser Gly Cys Pro
    1760                1765                1770

Glu Gly Ala Arg Cys Tyr Val Leu Asn Pro Glu Ala Val Asn Ile
    1775                1780                1785

Ser Gly Thr Lys Gly Ala Met Val His Leu Gln Lys Thr Gly Gly
    1790                1795                1800

Glu Phe Thr Cys Val Thr Ala Ser Gly Thr Pro Ala Phe Phe Asp
    1805                1810                1815

Leu Lys Asn Leu Lys Gly Trp Ser Gly Leu Pro Ile Phe Glu Ala
    1820                1825                1830

Ser Ser Gly Arg Val Val Gly Arg Val Lys Val Gly Lys Asn Glu
    1835                1840                1845

Asp Ser Lys Pro Thr Lys Leu Met Ser Gly Ile Gln Thr Val Ser
    1850                1855                1860

Lys Asn Gln Thr Asp Leu Ala Asp Ile Val Lys Lys Leu Thr Ser
    1865                1870                1875

Met Asn Arg Gly Glu Phe Lys Gln Ile Thr Leu Ala Thr Gly Ala
    1880                1885                1890

Gly Lys Thr Thr Glu Leu Pro Arg Ser Val Ile Glu Glu Ile Gly
    1895                1900                1905

Arg His Lys Arg Val Leu Val Leu Ile Pro Leu Arg Ala Ala Ala
    1910                1915                1920
```

Glu Ser Val Tyr Gln Tyr Met Arg Val Lys Asp Pro Ser Ile Ser
1925                1930                1935

Phe Asn Leu Arg Ile Gly Asp Met Lys Glu Gly Asp Met Ala Thr
1940                1945                1950

Gly Ile Thr Tyr Ala Ser Tyr Gly Tyr Phe Cys Gln Leu Pro Gln
1955                1960                1965

Pro Lys Leu Arg Ala Ala Met Val Glu Tyr Ser Tyr Ile Phe Leu
1970                1975                1980

Asp Glu Tyr His Cys Ala Thr Pro Glu Gln Leu Ala Ile Ile Gly
1985                1990                1995

Lys Ile His Arg Phe Ser Glu Asn Leu Arg Val Val Ala Met Thr
2000                2005                2010

Ala Thr Pro Ala Gly Thr Gly Thr Thr Thr Gly Gln Lys His Pro
2015                2020                2025

Ile Glu Glu Ser Ile Ala Pro Glu Val Met Lys Gly Glu Asp Leu
2030                2035                2040

Gly Ser Glu Tyr Leu Asp Ile Ala Gly Leu Lys Ile Pro Pro Glu
2045                2050                2055

Glu Met Lys Gly Asn Met Leu Val Phe Val Pro Thr Arg Asn Met
2060                2065                2070

Ala Val Glu Thr Ala Lys Lys Leu Lys Ala Lys Gly Tyr Asn Ser
2075                2080                2085

Gly Tyr Tyr Tyr Ser Gly Gly Asn Pro Glu Asn Leu Arg Val Val
2090                2095                2100

Thr Ser Gln Ser Pro Tyr Val Val Thr Thr Asn Ala Ile Glu
2105                2110                2115

Ser Gly Val Thr Leu Pro Asp Leu Asp Thr Val Val Asp Thr Gly
2120                2125                2130

Leu Lys Cys Glu Lys Arg Val Arg Ile Ser Ser Lys Met Pro Phe
2135                2140                2145

Ile Val Thr Gly Leu Lys Arg Met Ala Val Thr Ile Gly Glu Gln
2150                2155                2160

Ala Gln Arg Arg Gly Arg Val Gly Arg Val Lys Pro Gly Arg Tyr
2165                2170                2175

Tyr Arg Ser Gln Glu Thr Ala Ser Gly Ser Lys Asp Tyr His Tyr
2180                2185                2190

Asp Leu Leu Gln Ala Gln Arg Tyr Gly Ile Glu Asp Gly Ile Asn
2195                2200                2205

Val Thr Lys Ser Phe Arg Glu Met Asn Tyr Asp Trp Ser Leu Tyr
2210                2215                2220

Glu Glu Asp Ser Leu Met Ile Thr Gln Leu Glu Val Leu Asn Asn
2225                2230                2235

Leu Leu Ile Ser Glu Asp Leu Pro Ala Ala Val Lys Asn Ile Met
2240                2245                2250

Ala Arg Thr Asp His Pro Glu Pro Ile Gln Leu Ala Tyr Asn Ser
2255                2260                2265

His Glu Asn Gln Ile Pro Val Leu Leu Pro Lys Ile Lys Asn Gly
2270                2275                2280

Glu Val Thr Asp Ser Tyr Glu Asn Tyr Thr Tyr Leu Asn Ala Arg
2285                2290                2295

Lys Leu Gly Glu Asp Val Pro Val Tyr Val Tyr Ala Thr Glu Gly
2300                2305                2310

Glu Asp Leu Ala Val Asp Leu Leu Gly Met Asp Trp Ser Asp Ser

-continued

```
                2315                2320                2325

Gly Asn Gln Gln Val Val Glu Thr Gly Arg Ala Leu Lys Gln Val
        2330                2335                2340

Thr Gly Leu Ser Thr Ala Glu Asn Ala Leu Leu Ile Ala Leu Phe
        2345                2350                2355

Gly Tyr Val Gly Tyr Gln Thr Leu Ser Lys Arg His Ile Pro Met
        2360                2365                2370

Val Thr Asp Ile Tyr Thr Leu Glu Asp His Arg Leu Glu Asp Thr
        2375                2380                2385

Thr His Leu Gln Phe Ala Pro Asn Ala Ile Arg Thr Asp Gly Lys
        2390                2395                2400

Asp Ser Glu Leu Lys Glu Leu Ala Val Gly Asp Leu Asp Lys Tyr
        2405                2410                2415

Leu Asp Ala Leu Val Asp Tyr Ser Lys Gln Gly Met Lys Phe Ile
        2420                2425                2430

Lys Val Gln Ala Glu Lys Val Lys Asp Ser Gln Ser Thr Lys Glu
        2435                2440                2445

Gly Leu Gln Thr Ile Lys Glu Tyr Val Asp Lys Phe Ile Gln Ser
        2450                2455                2460

Leu Thr Glu Asn Lys Glu Glu Ile Ile Arg Tyr Gly Leu Trp Gly
        2465                2470                2475

Ala His Thr Ala Leu Tyr Lys Ser Leu Ala Ala Arg Leu Gly His
        2480                2485                2490

Glu Thr Ala Phe Ala Thr Leu Val Val Lys Trp Leu Ala Phe Gly
        2495                2500                2505

Gly Glu Thr Val Ser Ala His Ile Lys Gln Ala Ala Val Asp Leu
        2510                2515                2520

Val Val Tyr Tyr Ile Met Asn Lys Pro Ser Phe Pro Gly Asp Thr
        2525                2530                2535

Glu Thr Gln Gln Glu Gly Arg Arg Phe Val Ala Ser Leu Phe Ile
        2540                2545                2550

Ser Ala Leu Ala Thr Tyr Tyr Thr Glu Thr Trp Asn Tyr Asn Asn
        2555                2560                2565

Leu Ala Arg Val Val Glu Pro Thr Leu Ala Tyr Leu Pro Tyr Ala
        2570                2575                2580

Thr Ser Ala Leu Lys Leu Phe Thr Pro Thr Arg Leu Glu Ser Val
        2585                2590                2595

Val Ile Leu Ser Ser Thr Ile Tyr Lys Thr Tyr Leu Ser Ile Arg
        2600                2605                2610

Lys Gly Lys Ser Asp Gly Leu Leu Gly Thr Gly Ile Ser Ala Ala
        2615                2620                2625

Met Glu Ile Leu Asn Gln Asn Pro Ile Ser Val Gly Ile Ser Val
        2630                2635                2640

Met Leu Gly Val Gly Ala Ile Ala Ala His Asn Ala Ile Glu Ser
        2645                2650                2655

Ser Glu Gln Lys Arg Thr Leu Leu Met Lys Val Phe Val Lys Asn
        2660                2665                2670

Phe Leu Asp Gln Ala Ala Thr Asp Glu Leu Val Lys Glu Asn Pro
        2675                2680                2685

Glu Lys Ile Ile Met Ala Leu Phe Glu Ala Val Gln Thr Ile Gly
        2690                2695                2700

Asn Pro Leu Arg Leu Ile Tyr His Leu Tyr Gly Val Tyr Tyr Lys
        2705                2710                2715
```

-continued

```
Gly Trp Glu Ala Lys Glu Leu Ala Glu Lys Thr Ala Gly Arg Asn
2720                2725                2730
Leu Phe Thr Leu Ile Met Phe Glu Ala Phe Glu Leu Leu Gly Met
2735                2740                2745
Asp Ser Glu Gly Lys Ile Arg Asn Leu Ser Gly Asn Tyr Ile Leu
2750                2755                2760
Asp Leu Ile Phe Asn Leu His Asn Lys Leu Asn Lys Gly Leu Lys
2765                2770                2775
Lys Leu Val Leu Gly Trp Ala Pro Ala Pro Phe Ser Cys Asp Trp
2780                2785                2790
Thr Pro Ser Asp Glu Arg Ile Ser Leu Pro His Asn Asn Tyr Leu
2795                2800                2805
Arg Val Glu Thr Arg Cys Pro Cys Gly Tyr Glu Met Lys Ala Ile
2810                2815                2820
Lys Asn Val Ala Gly Lys Leu Thr Lys Val Glu Glu Lys Gly Pro
2825                2830                2835
Phe Leu Cys Arg Asn Arg Leu Gly Arg Gly Pro Pro Asn Phe Arg
2840                2845                2850
Val Thr Lys Phe Tyr Asp Asp Asn Leu Ala Glu Val Lys Pro Val
2855                2860                2865
Ala Lys Leu Glu Gly Gln Val Asp Leu Tyr Tyr Lys Gly Val Thr
2870                2875                2880
Ala Lys Leu Asp Tyr Asn Asn Gly Lys Val Leu Leu Ala Thr Asn
2885                2890                2895
Lys Trp Glu Val Asp His Ala Phe Leu Thr Arg Leu Val Lys Lys
2900                2905                2910
His Thr Gly Ile Gly Phe Lys Gly Ala Tyr Leu Gly Asp Arg Pro
2915                2920                2925
Asp His Gln Asp Leu Val Asp Arg Asp Cys Ala Thr Ile Thr Lys
2930                2935                2940
Asn Ser Val Gln Phe Leu Lys Met Lys Lys Gly Cys Ala Phe Thr
2945                2950                2955
Tyr Asp Leu Thr Ile Ser Asn Leu Val Arg Leu Ile Glu Leu Val
2960                2965                2970
His Lys Asn Asn Leu Gln Glu Arg Glu Ile Pro Thr Val Thr Val
2975                2980                2985
Thr Thr Trp Ile Ala Tyr Ser Phe Val Asn Glu Asp Leu Gly Ser
2990                2995                3000
Ile Lys Pro Val Leu Gly Glu Lys Val Ile Pro Glu Pro Pro Thr
3005                3010                3015
Glu Leu Ser Leu Gln Pro Thr Val Gly Leu Val Thr Thr Glu Thr
3020                3025                3030
Ala Ile Thr Ile Thr Gly Glu Ala Glu Val Met Thr Thr Gly Ile
3035                3040                3045
Thr Pro Val Val Glu Met Lys Glu Glu Pro Gln Leu Asp His Gln
3050                3055                3060
Ser Thr Thr Leu Lys Val Gly Leu Lys Glu Gly Glu Tyr Pro Gly
3065                3070                3075
Pro Gly Val Asn Pro Asn His Leu Val Glu Val Ile Asp Glu Lys
3080                3085                3090
Asp Asp Arg Pro Phe Val Leu Ile Ile Gly Asn Lys Ser Ser Thr
3095                3100                3105
```

```
Ser Asn Arg Ala Arg Thr Ala Lys Asn Ile Ser Leu Tyr Lys Gly
    3110                3115                3120

Asn Asn Pro Arg Glu Ile Arg Asp Leu Met Ser Gln Gly Arg Ile
    3125                3130                3135

Phe Asp Val Ala Leu Lys Glu Leu Asp Pro Glu Leu Lys Glu Leu
    3140                3145                3150

Val Asp Tyr Lys Gly Thr Phe Leu Asn Arg Glu Ala Leu Glu Ala
    3155                3160                3165

Leu Ser Leu Gly Lys Pro Ile Lys Arg Lys Thr Thr Thr Ala Met
    3170                3175                3180

Ile Arg Arg Leu Ile Glu Pro Glu Val Glu Glu Leu Pro Asp
    3185                3190                3195

Trp Phe Gln Ala Glu Glu Pro Leu Phe Leu Glu Ala Lys Ile Gln
    3200                3205                3210

Ala Asp Leu Tyr His Leu Ile Gly Ser Val Asp Ser Ile Lys Ser
    3215                3220                3225

Lys Ala Lys Glu Leu Gly Ala Thr Asp Asn Thr Lys Ile Val Lys
    3230                3235                3240

Glu Val Gly Ala Arg Thr Tyr Thr Met Lys Leu Ser Ser Trp Ser
    3245                3250                3255

Thr Gln Val Thr Lys Lys Gln Met Ser Leu Ala Pro Leu Phe Glu
    3260                3265                3270

Glu Leu Leu Ile Lys Cys Pro Pro Cys Ser Lys Ile Ser Lys Gly
    3275                3280                3285

His Met Val Ser Ala Tyr Gln Leu Ala Gln Gly Asn Trp Glu Pro
    3290                3295                3300

Leu Gly Cys Gly Val Tyr Met Gly Thr Ile Pro Ala Arg Arg Leu
    3305                3310                3315

Lys Ile His Pro Tyr Glu Ala Tyr Leu Lys Leu Lys Glu Leu Val
    3320                3325                3330

Glu Val Glu Leu Ser Arg Val Thr Ala Lys Glu Ser Ile Ile Arg
    3335                3340                3345

Glu His Asn Thr Trp Ile Leu Arg Lys Val Arg His Glu Gly Asn
    3350                3355                3360

Leu Arg Thr Lys Ser Met Ile Asn Pro Gly Lys Ile Ser Asp Gln
    3365                3370                3375

Leu Cys Arg Asp Gly His Lys Arg Asn Ile Tyr Asn Lys Ile Ile
    3380                3385                3390

Gly Ser Thr Met Gly Ser Ala Gly Ile Arg Leu Glu Lys Leu Pro
    3395                3400                3405

Val Val Arg Ala Gln Thr Asp Thr Thr Ser Phe His Gln Ala Ile
    3410                3415                3420

Arg Glu Lys Ile Asp Lys Pro Glu Asn Lys Gln Thr Pro Glu Leu
    3425                3430                3435

His Glu Glu Leu Met Lys Val Phe Asp Cys Leu Lys Ile Pro Glu
    3440                3445                3450

Leu Lys Glu Ser Phe Asp Glu Val Ser Trp Glu Gln Leu Glu Ala
    3455                3460                3465

Gly Ile Asn Arg Lys Gly Ala Ala Gly Tyr Leu Glu Ser Lys Asn
    3470                3475                3480

Ile Gly Glu Val Leu Asp Thr Glu Lys His Ile Val Glu Gln Leu
    3485                3490                3495

Ile Lys Asp Leu Arg Lys Gly Lys Lys Ile Arg Tyr Tyr Glu Thr
```

```
                    3500               3505               3510

Ala Ile Pro Lys Asn Glu Lys Arg Asp Val Ser Asp Asp Trp Glu
    3515               3520               3525

Ala Gly Glu Phe Val Asp Glu Lys Lys Pro Arg Val Ile Gln Tyr
    3530               3535               3540

Pro Asp Ala Lys Val Arg Leu Ala Ile Ala Lys Val Met Tyr Lys
    3545               3550               3555

Trp Val Lys Gln Lys Pro Val Val Ile Pro Gly Tyr Glu Gly Lys
    3560               3565               3570

Thr Pro Leu Phe Asp Ile Phe Asn Lys Val Lys Lys Glu Trp Asp
    3575               3580               3585

Ser Phe Gln Asp Pro Val Ala Val Ser Phe Asp Thr Lys Ala Trp
    3590               3595               3600

Asp Thr Gln Val Thr Ser Lys Asp Leu Met Leu Ile Lys Asp Ile
    3605               3610               3615

Gln Lys Tyr Tyr Phe Lys Arg Ser Thr His Lys Phe Leu Asp Thr
    3620               3625               3630

Ile Thr Glu His Met Val Glu Val Pro Val Ile Thr Ala Asp Gly
    3635               3640               3645

Glu Val Tyr Ile Arg Asn Gly Gln Arg Gly Ser Gly Gln Pro Asp
    3650               3655               3660

Thr Ser Ala Gly Asn Ser Met Leu Asn Val Leu Thr Met Ile Tyr
    3665               3670               3675

Ala Phe Cys Lys Ser Thr Gly Ile Pro Tyr Arg Gly Phe Ser Arg
    3680               3685               3690

Val Ala Arg Ile His Val Cys Gly Asp Asp Gly Phe Leu Ile Thr
    3695               3700               3705

Glu Arg Gly Leu Gly Leu Lys Phe Ser Glu Lys Gly Met Gln Ile
    3710               3715               3720

Leu His Glu Ala Gly Lys Pro Gln Lys Ile Thr Glu Gly Glu Lys
    3725               3730               3735

Met Lys Val Ala Tyr Arg Phe Glu Asp Ile Glu Phe Cys Ser His
    3740               3745               3750

Thr Pro Val Pro Val Arg Trp Ala Asp Asn Thr Ser Ser Tyr Met
    3755               3760               3765

Ala Gly Arg Ser Thr Ala Thr Ile Leu Ala Lys Met Pro Thr Arg
    3770               3775               3780

Leu Asp Ser Ser Gly Glu Arg Gly Ser Thr Ala Tyr Glu Lys Pro
    3785               3790               3795

Val Ala Phe Ser Phe Leu Leu Met Tyr Ser Trp Asn Pro Val Val
    3800               3805               3810

Arg Arg Ile Cys Leu Leu Val Leu Ser Gln Phe Pro Glu Ile Ser
    3815               3820               3825

Pro Ser Lys Asn Thr Ile Tyr Tyr Tyr Gln Gly Asp Pro Ile Ala
    3830               3835               3840

Ala Tyr Arg Glu Val Ile Gly Lys Gln Leu Cys Glu Leu Lys Arg
    3845               3850               3855

Thr Gly Phe Glu Lys Leu Ala Ser Leu Asn Leu Asn Met Thr Thr
    3860               3865               3870

Leu Gly Ile Trp Thr Lys His Thr Ser Lys Arg Leu Ile Gln Asp
    3875               3880               3885

Cys Val Glu Ile Gly Lys Arg Glu Gly Asn Trp Leu Val Asn Ala
    3890               3895               3900
```

Asp Arg Leu Ile Ala Gly Lys Thr Gly Lys Phe Tyr Ile Pro Ser
3905                3910                3915

Thr Gly Val Thr Leu Leu Gly Lys His Tyr Glu Glu Ile Asn Leu
3920                3925                3930

Lys Gln Lys Ala Ala Gln Ser Pro Ile Glu Gly Val Asp Arg Tyr
3935                3940                3945

Lys Leu Gly Pro Ile Val Asn Val Ile Leu Arg Arg Leu Arg Val
3950                3955                3960

Met Leu Met Thr Val Ala Ser Gly Ser Trp
3965                3970

<210> SEQ ID NO 57
<211> LENGTH: 3899
<212> TYPE: PRT
<213> ORGANISM: BVDV-3

<400> SEQUENCE: 57

Met Glu Leu Leu Asn Phe Glu Leu Leu Tyr Lys Thr Tyr Lys Gln Lys
1               5                   10                  15

Pro Ala Gly Val Gln Glu Pro Leu Tyr Asp Lys Asn Gly Ala Val Leu
                20                  25                  30

Phe Gly Glu Pro Ser Asp Thr His Pro Gln Ser Thr Leu Lys Leu Pro
            35                  40                  45

His Pro Arg Gly Glu Lys Glu Val Ile Val Gly Ile Arg Asp Leu Pro
        50                  55                  60

Arg Lys Gly Asp Cys Arg Thr Gly Asn Arg Leu Gly Pro Val Ser Gly
65                  70                  75                  80

Leu Phe Val Lys Pro Gly Pro Val Phe Tyr Gln Asp Tyr Ser Gly Pro
                85                  90                  95

Val Tyr His Arg Ala Pro Leu Glu Gln Phe Lys Gln Ala Pro Met Cys
            100                 105                 110

Glu Val Thr Lys Arg Ile Gly Arg Val Thr Gly Ser Asp Gly Asn Leu
        115                 120                 125

Tyr His Met Tyr Val Cys Thr Asp Gly Cys Ile Leu Val Lys Thr Ala
130                 135                 140

Lys Arg Glu Gly Gln Asp Val Leu Lys Trp Val Tyr Asn Val Leu Asp
145                 150                 155                 160

Ser Pro Ile Trp Val Ala Ser Cys Ser Asp Glu Lys Ala Gly Ala Lys
                165                 170                 175

Pro Lys Gly Lys Ser Lys Pro Asp Arg Val Gln Lys Gly Lys Met Gln
            180                 185                 190

Ile Ser Pro Lys Glu Thr Glu Arg Asp Ser Lys Thr Lys Pro Pro Asp
        195                 200                 205

Ala Thr Ile Val Val Glu Gly Val Lys Tyr Gln Val Lys Lys Lys Gly
        210                 215                 220

Lys Val Arg Gly Lys Asn Thr Gln Asp Gly Leu Tyr His Asn Lys Asn
225                 230                 235                 240

Lys Pro Glu Gln Ser Arg Lys Lys Leu Glu Lys Ala Leu Leu Ala Trp
                245                 250                 255

Ala Val Leu Ala Leu Val Leu Trp Gln Pro Val Gly Ala Glu Asn Ile
            260                 265                 270

Thr Gln Trp Asn Leu Lys Asp Asn Gly Thr Asn Gly Ile Gln His Ala
        275                 280                 285

Met Phe Val Arg Gly Val Asn Arg Ser Leu His Gly Ile Trp Pro Ser

-continued

```
            290                 295                 300
Lys Ile Cys Ser Gly Val Pro Thr His Leu Ala Thr Asp Ala Glu Leu
305                 310                 315                 320

Lys Gln Ile His Gly Met Met Asp Ala Ser Glu Lys Thr Asn Tyr Thr
                325                 330                 335

Cys Cys Arg Leu Gln Arg His Glu Trp Asn Lys His Gly Trp Cys Asn
                340                 345                 350

Trp Tyr Asn Ile Glu Pro Trp Ile Trp Leu Met Asn Lys Thr Gln Ala
                355                 360                 365

Asn Leu Thr Gly Gly Thr Pro Leu Lys Glu Cys Ala Val Thr Cys Arg
            370                 375                 380

Tyr Asp Lys Asp Lys Glu Ile Asn Ile Val Thr Gln Ala Arg Asp Arg
385                 390                 395                 400

Pro Thr Thr Leu Thr Gly Cys Lys Lys Gly Lys Arg Phe Ser Phe Ala
                405                 410                 415

Gly Glu Val Ile Asp Gly Pro Cys Asn Phe Asn Ile Ser Ala Glu Asp
                420                 425                 430

Met Leu Tyr Asp Glu Met Glu Cys Thr Gly Val Phe Gln Glu Met Ala
            435                 440                 445

Gln His Val Val Asp Gly Thr Thr Asn Thr Ile Glu Gly Ala Arg Gln
        450                 455                 460

Gly Ala Ala Lys Leu Thr Thr Trp Leu Gly Lys Gln Leu Arg Ile Leu
465                 470                 475                 480

Gly Lys Lys Leu Glu His Lys Ser Lys Thr Trp Phe Gly Ala His Ala
                485                 490                 495

Ala Thr Pro Tyr Cys Asn Ile Asn Lys Lys Ile Gly Tyr Val Trp Tyr
                500                 505                 510

Thr Asn Asn Cys Thr Pro Ala Cys Leu Pro Lys Asn Thr Arg Ile Val
            515                 520                 525

Gly Pro Gly Lys Phe Asp Thr Asn Gly Asp Asp Gly Lys Ile Leu His
        530                 535                 540

Glu Met Gly Ser His Leu Ser Glu Leu Ala Ile Leu Ala Leu Val Val
545                 550                 555                 560

Met Ser Asp Phe Ala Pro Glu Ser Ala Ser Val Leu Tyr Leu Ile Leu
                565                 570                 575

His Phe Ser Ile Pro Gln Ala His Glu Glu Val Asp Gln Cys Asp Arg
                580                 585                 590

Asn Gln Leu Asn Leu Thr Val Gly Leu Arg Thr Asp Glu Val Val Pro
            595                 600                 605

Ser Ser Val Trp Asn Leu Gly Lys Trp Val Cys Val Arg Pro Pro Trp
        610                 615                 620

Trp Pro Tyr Glu Thr Ala Thr Val Leu Ala Phe Glu Glu Ile Gly Gln
625                 630                 635                 640

Val Leu Lys Leu Ile Leu Arg Ala Leu Lys Asp Leu Thr Asn Met Trp
                645                 650                 655

Asn Ala Ala Ser Thr Thr Ala Phe Leu Val Cys Leu Val Lys Ile Leu
            660                 665                 670

Arg Gly Gln Ile Val Gln Gly Val Ile Trp Leu Leu Leu Ile Thr Gly
        675                 680                 685

Ala Gln Gly Asp Leu Ser Cys Lys Pro Glu Phe Gln Tyr Ala Ile Ser
    690                 695                 700

Glu Thr Asp Glu Ile Asn Leu Leu Gly Pro Thr Gly Leu Thr Thr Thr
705                 710                 715                 720
```

-continued

Trp His Ala Tyr Ser Glu Lys Leu His Ile Thr Asp Ser Ser Val Asp
            725                 730                 735

Leu Thr Cys Val Asp Gly Asn Phe Leu Val Tyr Arg Arg Cys Val Arg
            740                 745                 750

Lys Arg Arg Tyr Leu Ala Thr Val His Glu Arg Ala Leu Ser Thr Ser
            755                 760                 765

Val Arg Phe Thr Leu Val Ala Asp Pro Gln Asp Leu Glu Asp Val Gln
770                 775                 780

Met Gly Asp Asp Phe Glu Phe Gly Leu Cys Pro Cys Asp Ser Val Pro
785                 790                 795                 800

Ile Ile Arg Gly Lys Phe Asn Thr Thr Leu Leu Asn Gly Ser Ala Phe
            805                 810                 815

Gln Leu Val Cys Pro Tyr Gly Trp Thr Gly Thr Ile Glu Cys Thr Val
            820                 825                 830

Val Ser Asp Ser Thr Leu Lys Thr Gln Val Val Lys Arg Phe Ala Arg
            835                 840                 845

Tyr Lys Pro Phe Pro His Arg Lys His Cys Met Asp Gln Met Val Val
            850                 855                 860

Gly Glu Asp Leu Tyr Glu Cys Leu Tyr Gly Gly Asn Trp Thr Cys Ile
865                 870                 875                 880

Pro Gly Asp Arg Val Leu Tyr Gln Gly Gly Glu Val Lys Asp Cys Lys
                    885                 890                 895

Trp Cys Gly Phe Thr Phe Glu Glu Pro Ser Asp Leu Pro His Phe Pro
                    900                 905                 910

Leu Gly Lys Cys Arg Leu Thr Asn Glu Thr Gly Tyr Arg Tyr Val Asp
            915                 920                 925

Asn Thr Thr Cys Asp Arg Asp Gly Val Ala Ile Met Glu Gln Gly Thr
            930                 935                 940

Leu Lys Cys Lys Ile Gly Lys Val Glu Val Arg Val Ser Ala Leu Asn
945                 950                 955                 960

Lys Asn Leu Gly Pro Met Pro Cys Lys Pro Ser His Val Thr Gln Ser
                965                 970                 975

Glu Gly Pro Val Ser Lys Thr Ala Cys Thr Phe Asn Trp Thr Glu Thr
                980                 985                 990

Leu Glu Asn Lys Tyr Phe Glu Pro Arg Asp Asn Tyr Phe Gln Gln Tyr
            995                 1000                1005

Met Leu Lys Gly Lys Tyr Gln Tyr Trp Phe Asp Leu Glu Ala Thr
        1010                1015                1020

Asp His His Gln Asp Tyr Phe Ala Glu Phe Ile Val Ile Ile Val
        1025                1030                1035

Val Ala Leu Leu Gly Gly Arg Tyr Val Leu Trp Leu Leu Ile Val
        1040                1045                1050

Tyr Tyr Val Ala Thr Glu Gln Gly Ala Arg Gly Gln Gln Met Asn
        1055                1060                1065

Pro Gly Glu Val Val Leu Ile Gly Asp Met Ile Thr His Asp Ser
        1070                1075                1080

Ile Glu Val Ile Thr Tyr Phe Leu Leu Leu Tyr Leu Leu Ile Lys
        1085                1090                1095

Asp Glu Pro Val Lys Lys Trp Val Leu Leu Ile Tyr His Ala Ile
        1100                1105                1110

Thr Ala Ser Pro Arg Lys Thr Ile Ile Val Ala Val Leu Met Phe
        1115                1120                1125

```
Ser  Ser  Leu  Val  Arg  Gly  Asp  Asp  Gly  Arg  Ala  Thr  Gln  Gly  Asp
     1130                1135                     1140

Gly  Leu  Asp  Val  Trp  Phe  Tyr  Val  Val  Leu  Ala  Met  Val  Cys  Ile
     1145                1150                     1155

Leu  Leu  Met  Val  Lys  Arg  Asp  Pro  Thr  Thr  Ile  Pro  Ala  Val  Val
     1160                1165                     1170

Ile  Ile  Thr  Gly  Val  Lys  Thr  Arg  Gln  Tyr  Ala  Ala  Trp  Leu  Glu
     1175                1180                     1185

Leu  Asp  Ile  Ala  Leu  Ser  Ile  Val  Ala  Ala  Val  Val  Leu  Leu  His
     1190                1195                     1200

Ser  Tyr  Ile  Ser  Ser  Tyr  Tyr  Arg  Tyr  Lys  Gln  Trp  Leu  Gln  Cys
     1205                1210                     1215

Val  Ile  Ser  Leu  Leu  Ala  Gly  Phe  Phe  Ile  Ile  Arg  Thr  Leu  Lys
     1220                1225                     1230

Ala  Val  Gly  Glu  Tyr  Gln  Leu  Pro  Val  Ile  Thr  Val  Pro  Asn  Val
     1235                1240                     1245

Arg  Pro  Leu  Pro  Ile  Val  Phe  Ile  Tyr  Leu  Ile  Thr  Thr  Thr  Leu
     1250                1255                     1260

Val  Thr  His  Gln  Asn  Leu  Asp  Leu  Ala  Gly  Ile  Phe  Leu  Ser  Asn
     1265                1270                     1275

Ala  Pro  Ile  Val  Leu  Met  Val  Leu  Thr  Leu  Trp  Ala  Asp  Leu  Leu
     1280                1285                     1290

Thr  Leu  Ile  Leu  Val  Leu  Pro  Thr  Tyr  Glu  Leu  Thr  Lys  Leu  Tyr
     1295                1300                     1305

Tyr  Ile  Arg  Arg  Val  Lys  Lys  Asp  Val  Glu  Arg  Ser  Trp  Leu  Gly
     1310                1315                     1320

Ala  Thr  Asn  Phe  Thr  Arg  Val  Asp  Ser  Val  Tyr  Glu  Leu  Asp  Gly
     1325                1330                     1335

Ser  Glu  Glu  Gly  Val  Tyr  Leu  Phe  Pro  Ser  Arg  Leu  Gly  Pro  Gly
     1340                1345                     1350

Ala  Lys  Thr  Gly  Glu  Ile  Leu  Pro  Val  Leu  Arg  Cys  Val  Leu  Ile
     1355                1360                     1365

Ser  Cys  Ile  Ser  Ser  Tyr  Trp  Gln  Trp  Thr  Tyr  Leu  Thr  Tyr  Leu
     1370                1375                     1380

Val  Ile  Glu  Leu  Val  Tyr  Phe  Met  His  Arg  Arg  Val  Ile  Glu  Glu
     1385                1390                     1395

Ile  Ala  Gly  Gly  Thr  Asn  Ala  Leu  Ser  Arg  Thr  Ile  Ala  Gly  Leu
     1400                1405                     1410

Ile  Glu  Met  Ser  Trp  Ala  Leu  Asp  Glu  Glu  Ser  Lys  Gly  Leu
     1415                1420                     1425

Lys  Lys  Phe  Phe  Ile  Leu  Ser  Ala  Arg  Leu  Lys  Asn  Leu  Val  Leu
     1430                1435                     1440

Lys  His  Lys  Val  Arg  Asn  Glu  Thr  Ile  Arg  Ala  Trp  Tyr  Glu  Glu
     1445                1450                     1455

Glu  Glu  Ile  Tyr  Gly  Met  Pro  Lys  Val  Ile  Thr  Leu  Ile  Lys  Ala
     1460                1465                     1470

Ala  Ser  Leu  Ser  Gln  Ser  Lys  His  Cys  Ile  Leu  Cys  Thr  Val  Cys
     1475                1480                     1485

Glu  Arg  Arg  Asp  Trp  Lys  Gly  Gly  Ser  Cys  Pro  Lys  Cys  Gly  Arg
     1490                1495                     1500

Ser  Gly  Arg  Pro  Ile  Ser  Cys  Gly  Met  Thr  Leu  Ala  Asp  Phe  Glu
     1505                1510                     1515

Glu  Lys  His  Tyr  Lys  Arg  Ile  Phe  Ile  Arg  Glu  Gly  Glu  Leu  Asp
```

```
              1520                1525                1530

Gly Pro Phe Arg Gln Glu Ala Arg Gly Tyr Leu Gln Tyr Ile Ala
        1535                1540                1545

Arg Gly Gln Leu Phe Leu Arg Asn Leu Pro Ile Leu Ala Thr Lys
        1550                1555                1560

Val Lys Leu Leu Met Val Gly Asn Leu Gly Ser Glu Val Gly Asp
        1565                1570                1575

Leu Glu His Leu Gly Trp Val Leu Arg Gly Pro Ala Val Cys Lys
        1580                1585                1590

Lys Ile Val Ser His Glu Lys Cys His Thr Gly Ile Ala Asp Lys
        1595                1600                1605

Leu Thr Ala Phe Phe Gly Ile Met Pro Arg Gly Thr Thr Pro Arg
        1610                1615                1620

Ala Pro Val Arg Phe Pro Thr Ser Leu Ile Lys Ile Arg Arg Gly
        1625                1630                1635

Leu Glu Thr Gly Trp Ala Tyr Thr His Gln Gly Gly Ile Ser Ser
        1640                1645                1650

Val Asp His Val Thr Ala Gly Lys Asp Leu Leu Val Cys Asp Ser
        1655                1660                1665

Met Gly Arg Thr Arg Val Val Cys Gln Ser Asn Asn Lys Met Thr
        1670                1675                1680

Asp Glu Thr Glu Tyr Gly Ile Lys Thr Asp Ser Gly Cys Pro Glu
        1685                1690                1695

Gly Ala Arg Cys Tyr Val Leu Asn Pro Glu Ala Gln Asn Ile Ala
        1700                1705                1710

Gly Thr Arg Gly Ala Met Val His Leu Gln Lys Thr Gly Gly Glu
        1715                1720                1725

Phe Thr Cys Val Thr Ala Ser Gly Thr Pro Ala Phe Phe Asp Leu
        1730                1735                1740

Lys Asn Leu Lys Gly Trp Ser Gly Leu Pro Ile Phe Glu Ala Ser
        1745                1750                1755

Ser Gly Arg Val Val Gly Arg Val Lys Val Gly Lys Asn Glu Glu
        1760                1765                1770

Ser Lys Pro Thr Lys Leu Met Ser Gly Ile Gln Thr Val Ser Lys
        1775                1780                1785

Ser Thr Thr Asp Leu Thr Glu Met Val Lys Lys Ile Val Ala Met
        1790                1795                1800

Asn Arg Gly Glu Phe Lys Gln Ile Thr Leu Ala Thr Gly Ala Gly
        1805                1810                1815

Lys Thr Thr Glu Leu Pro Arg Ser Val Ile Glu Glu Ile Gly Arg
        1820                1825                1830

His Lys Arg Val Leu Val Leu Ile Pro Leu Arg Ala Ala Ala Glu
        1835                1840                1845

Ser Val Tyr Gln Tyr Met Lys Gln Lys His Pro Ser Ile Ala Phe
        1850                1855                1860

Asn Leu Arg Ile Gly Glu Met Lys Glu Gly Asp Met Ala Thr Gly
        1865                1870                1875

Ile Thr Tyr Ala Ser Tyr Gly Tyr Phe Cys Gln Met Pro Gln Pro
        1880                1885                1890

Lys Leu Arg Ala Ala Met Val Glu Tyr Ser Tyr Ile Phe Leu Asp
        1895                1900                1905

Glu Tyr His Cys Ala Thr Pro Glu Gln Leu Ala Ile Ile Gly Lys
        1910                1915                1920
```

Ile His Arg Phe Ser Glu Asn Leu Arg Val Val Ala Met Thr Ala
1925                1930                1935

Thr Pro Ala Gly Ser Val Thr Thr Thr Gly Gln Lys His Pro Ile
1940                1945                1950

Glu Glu Phe Ile Ala Pro Glu Val Met Lys Gly Glu Asp Leu Gly
1955                1960                1965

Ser Asn Phe Leu Asp Ile Ala Gly Leu Lys Ile Pro Thr Glu Glu
1970                1975                1980

Met Lys Gly Asn Met Leu Val Phe Val Pro Thr Arg Asn Met Ala
1985                1990                1995

Val Glu Val Ala Lys Lys Leu Lys Ala Lys Gly Tyr Asn Ser Gly
2000                2005                2010

Tyr Tyr Tyr Ser Gly Glu Asp Pro Ala Asn Leu Arg Val Val Thr
2015                2020                2025

Ser Gln Ser Pro Tyr Val Val Ala Thr Asn Ala Ile Glu Ser
2030                2035                2040

Gly Val Thr Leu Pro Asp Leu Asp Val Val Asp Thr Gly Leu
2045                2050                2055

Lys Cys Glu Lys Arg Val Arg Ile Ser Ser Lys Met Pro Phe Ile
2060                2065                2070

Val Thr Gly Leu Lys Arg Met Ala Val Thr Val Gly Glu Gln Ala
2075                2080                2085

Gln Arg Arg Gly Arg Val Gly Arg Val Lys Pro Gly Arg Phe Tyr
2090                2095                2100

Arg Ser Gln Glu Thr Ala Ser Gly Ser Lys Asp Tyr His Tyr Asp
2105                2110                2115

Leu Leu Gln Ala Gln Arg Tyr Gly Ile Glu Asp Gly Ile Asn Ile
2120                2125                2130

Thr Lys Ser Phe Arg Glu Met Asn Tyr Asp Trp Ser Leu Tyr Glu
2135                2140                2145

Glu Asp Ser Leu Leu Ile Thr Gln Leu Glu Val Leu Asn Asn Leu
2150                2155                2160

Leu Ile Ser Asp Asp Leu Pro Ala Ala Val Lys Asn Ile Met Ala
2165                2170                2175

Arg Thr Asp His Pro Glu Pro Ile Gln Leu Ala Tyr Asn Ser Tyr
2180                2185                2190

Glu Val Gln Val Pro Val Leu Phe Pro Lys Ile Arg Asn Gly Glu
2195                2200                2205

Val Thr Asn Glu Tyr Glu Ala Tyr Ser Phe Leu Asn Ala Arg Lys
2210                2215                2220

Leu Gly Glu Asp Val Pro Ala Tyr Ile Tyr Ala Thr Glu Asn Glu
2225                2230                2235

Asp Leu Ala Val Asp Leu Leu Gly Leu Asp Trp Pro Asp Pro Gly
2240                2245                2250

Ser Gln Gln Thr Asn Glu Thr Gly Lys Ala Leu Lys Gln Val Ser
2255                2260                2265

Gly Leu Ser Thr Ala Glu Asn Ala Leu Leu Val Ala Leu Phe Ser
2270                2275                2280

Tyr Val Gly Tyr Gln Ala Leu Ser Lys Arg His Ile Pro Val Val
2285                2290                2295

Thr Asp Ile Tyr Thr Ile Glu Asp Gln Arg Leu Glu Asp Thr Thr
2300                2305                2310

```
His Leu Gln Tyr Ala Pro Asn Ala Ile Arg Thr Asp Gly Lys Glu
    2315            2320                2325
Thr Lys Leu Glu Glu Leu Ala Ile Gly Asp Ile Glu Arg Cys Leu
    2330            2335                2340
Ser Thr Ala Lys Glu Tyr Ala Ser Arg Gly Val Glu Phe Ile Lys
    2345            2350                2355
Thr Gln Ala Leu Lys Val Asn Asp Ser Pro Lys Val Glu Glu Thr
    2360            2365                2370
Met Glu Ser Val His Gln Tyr Val Glu Lys Leu Leu Glu Thr Leu
    2375            2380                2385
Lys Glu Ser Arg Glu Asp Ile Ile Lys Tyr Gly Leu Trp Gly Cys
    2390            2395                2400
His Thr Ala Leu Tyr Lys Ser Ile Ala Ala Arg Leu Gly Asn Glu
    2405            2410                2415
Thr Ala Phe Ala Thr Leu Val Ile Lys Trp Leu Ala Phe Gly Gly
    2420            2425                2430
Glu Ser Leu Pro Ala His Val Lys Gln Ala Ala Val Asp Leu Val
    2435            2440                2445
Val Tyr Tyr Ile Ile Asn Lys Pro Ser Phe Pro Gly Asp Thr Glu
    2450            2455                2460
Thr Gln Gln Glu Gly Arg Arg Phe Val Ala Ser Leu Leu Val Ser
    2465            2470                2475
Ala Leu Ala Thr Tyr Thr Tyr Lys Thr Trp Asn Tyr Asn Asn Leu
    2480            2485                2490
Ala Lys Val Val Glu Pro Ala Leu Ala Tyr Leu Pro Tyr Ala Ser
    2495            2500                2505
Lys Ala Leu Ser Leu Phe Val Pro Thr Arg Leu Glu Ser Val Val
    2510            2515                2520
Ile Leu Ser Thr Ala Ile Tyr Lys Ser Tyr Leu Ala Ile Arg Lys
    2525            2530                2535
Gly Lys Ser Asp Gly Leu Met Gly Thr Gly Leu Ser Ala Ala Met
    2540            2545                2550
Glu Met Met Ser Gln Asn Pro Val Ser Val Gly Ile Ala Val Met
    2555            2560                2565
Leu Gly Val Gly Ala Val Ala Ala His Asn Ala Ile Glu Ser Ser
    2570            2575                2580
Glu Gln Lys Arg Thr Leu Leu Met Lys Val Phe Val Lys Asn Phe
    2585            2590                2595
Leu Asp Gln Ala Ala Thr Asp Glu Leu Val Lys Glu Asn Pro Glu
    2600            2605                2610
Lys Ile Ile Met Ala Met Phe Glu Ala Val Gln Thr Ile Gly Asn
    2615            2620                2625
Pro Leu Arg Leu Ile Tyr His Leu Tyr Gly Ile Phe Tyr Lys Lys
    2630            2635                2640
Trp Glu Ala Lys Glu Leu Ala Glu Arg Thr Ala Gly Arg Asn Leu
    2645            2650                2655
Phe Thr Leu Ile Met Phe Glu Ala Val Glu Leu Leu Gly Val Asp
    2660            2665                2670
Asn Glu Gly Lys Ile Arg Thr Leu Ser Ser Asn Tyr Val Leu Glu
    2675            2680                2685
Leu Leu Thr Lys Phe Cys Gly Asn Ile Asn Asn Lys Val Arg Asn
    2690            2695                2700
Leu Val Leu Gly Trp Ala Pro Ala Pro Phe Ser Cys Asp Trp Thr
```

-continued

```
              2705                2710                2715

Pro His Asp Glu Arg Ile Arg Leu Pro His Glu Asn Tyr Ala Leu
        2720                2725                2730

Val Val Thr Arg Cys Pro Cys Gly Tyr Glu Ser Arg Ser Arg Lys
        2735                2740                2745

Met Asp Thr Gly Glu Met Val Lys Leu Glu Glu Lys Gly Pro Phe
        2750                2755                2760

Leu Cys Arg Asn Arg Pro Gly Arg Asn Tyr Gly Asn Leu Arg Val
        2765                2770                2775

Thr Arg Tyr Tyr Asp Lys Asp Gly Ala Glu Leu Lys Pro Val Ile
        2780                2785                2790

Lys Leu Glu Lys Gln Ala Glu Leu Tyr Tyr Lys Gly Ala Thr Leu
        2795                2800                2805

Lys Val Asp Phe Ser Asn Gly Lys Ser Val Val Ala Thr Asp Lys
        2810                2815                2820

Trp Glu Val Asp His Ser Thr Ile Ala Arg Leu Glu Lys Arg Tyr
        2825                2830                2835

Thr Gly Ala Gly Tyr Lys Gly Ala Tyr Leu Gly Asp Arg Pro Asn
        2840                2845                2850

His Glu Ala Leu Val Glu Arg Lys Cys Ala Thr Ile Thr Arg Asp
        2855                2860                2865

Lys Val Gln Phe Ile Lys Met Ala Lys Gly Cys Ala Phe Thr Tyr
        2870                2875                2880

Asp Leu Ser Leu Ser Asn Leu Lys Arg Leu Ile Glu Leu Val His
        2885                2890                2895

Lys Asn Lys Leu Glu Glu Lys Glu Ile Pro Gln Ala Thr Val Thr
        2900                2905                2910

Thr Trp Leu Ala Tyr Thr Phe Val Asn Glu Asp Ile Gly Thr Ile
        2915                2920                2925

Arg Pro Ser Phe Gly Glu Arg Val Leu Pro Glu Ser Pro Ser Asp
        2930                2935                2940

Pro Ser Leu Gln Pro Ser Val Val Ile Asn Arg Ala Ala Ala Glu
        2945                2950                2955

Ile Thr Val Ile Gly Glu Ala Glu Gln Met Thr Thr Gly Val Thr
        2960                2965                2970

Pro Val Glu Leu Asn Asp Asn Gln Ala Gly Val Ser Ser Val Asn
        2975                2980                2985

Glu Leu Glu Ile Gly Leu Glu Arg Gly Gln Phe Pro Gly Pro Val
        2990                2995                3000

Pro Gln Gly Lys Ser Leu Glu Glu Ala Ile Glu Lys Asp Gly
        3005                3010                3015

Arg Pro Tyr Val Leu Ile Leu Gly Ser Lys His Ser Thr Ser Asn
        3020                3025                3030

Arg Val Lys Thr Ala Lys Asn Val Lys Val Tyr Lys Gly Asp Ser
        3035                3040                3045

Met Gln Glu Val Arg Gly Leu Met Arg Glu Gly Lys Leu Leu Val
        3050                3055                3060

Val Ala Leu Arg Glu Val Ser Lys Asp Leu Leu His Leu Val Asp
        3065                3070                3075

Tyr Lys Gly Thr Phe Leu Thr Arg Glu Ala Leu Glu Ala Leu Ser
        3080                3085                3090

Met Gly Arg Pro Arg Pro Lys Glu Ala Thr Arg Ala Glu Ile Thr
        3095                3100                3105
```

-continued

Arg Leu Leu Asn Pro Thr Glu Glu Asp Ile Glu Val Pro Glu Trp
3110            3115            3120

Phe Thr Ala Ser Glu Pro Val Phe Leu Asp Ala Gln Ile Lys Gly
3125            3130            3135

Gly Thr Tyr His Leu Val Gly Gly Ile Gln Gln Ile Lys Glu Lys
3140            3145            3150

Ala Lys Ala Leu Gly Ala Thr Asp Ser Thr Lys Ile Ile Gln Gly
3155            3160            3165

Leu Gly Ser Arg Val Tyr Thr Met Lys Leu Ser Ser Trp Ile His
3170            3175            3180

Gln Asn Thr Thr Lys Glu Asn Asp Leu Arg Pro Leu Phe Glu Glu
3185            3190            3195

Leu Leu Leu Gln Cys Pro Pro Ser Ser Arg Gln Thr Lys Gly His
3200            3205            3210

Val Val Ser Ala Tyr Gln Leu Ala Gln Gly Asn Trp Glu Pro Val
3215            3220            3225

Ser Cys Asn Val Tyr Met Gly Thr Ile Pro Ala Arg Arg Val Lys
3230            3235            3240

Thr His Pro Tyr Glu Ala Tyr Leu Lys Leu Lys Asp Leu Leu Ser
3245            3250            3255

Glu His Lys Met Arg Val Glu Thr Gly Phe Asp Asp Leu Lys Asp
3260            3265            3270

His Asn Arg Trp Ile Leu Arg Lys Val Lys His Gln Gly Asn Leu
3275            3280            3285

Arg Thr Lys His Ile Leu Asn Pro Gly Lys Leu Thr Glu Gln Leu
3290            3295            3300

Glu Arg Glu Gly Arg Lys His Asn Val Tyr Asn Lys Gln Ile Gly
3305            3310            3315

Ser Ile Met Thr Ser Ile Gly Ile Arg Met Glu Lys Leu Pro Ile
3320            3325            3330

Val Arg Ala Gln Thr Asp Thr Val Ser Phe His Gln Ala Ile Arg
3335            3340            3345

Asp Lys Ile Asp Lys Glu Glu Asn Ala Gln Ser Pro Asp Leu His
3350            3355            3360

Glu Lys Leu Trp Glu Val Phe Asp Thr Leu Lys Val Pro Glu Leu
3365            3370            3375

Lys Gly Val Tyr Asp Glu Val Ser Trp Glu Glu Leu Glu Thr Gly
3380            3385            3390

Ile Asn Arg Lys Gly Ala Ala Gly Phe Leu Glu Lys Lys Asn Ile
3395            3400            3405

Gly Glu Val Leu Ala Ser Glu Lys Asn Leu Val Glu Glu Ile Val
3410            3415            3420

Lys Asp Leu Lys Arg Gly Lys Lys Ile Asn Tyr Tyr Glu Thr Ala
3425            3430            3435

Ile Pro Lys Asn Glu Lys Arg Asp Val Asn Asp Asp Trp Glu Ala
3440            3445            3450

Gly Asp Leu Val Asp Glu Lys Lys Pro Arg Val Ile Gln Tyr Pro
3455            3460            3465

Asp Ala Lys Val Arg Leu Ala Ile Thr Lys Val Met Tyr Lys Trp
3470            3475            3480

Val Lys Gln Lys Pro Val Val Ile Pro Gly Tyr Glu Gly Lys Thr
3485            3490            3495

-continued

```
Pro Leu Phe Gln Ile Phe Asp Lys Val Lys Lys Glu Trp Asp Gly
    3500                3505                3510

Phe Asn Asp Pro Val Ala Val Ser Phe Asp Thr Lys Ala Trp Asp
    3515                3520                3525

Thr Gln Val Thr Ser Arg Asp Leu Arg Leu Ile Gly Arg Ile Gln
    3530                3535                3540

Lys Tyr Tyr Phe Lys Ser Arg Trp His Lys Phe Ile Asp Thr Leu
    3545                3550                3555

Thr Glu His Met Thr Glu Val Pro Val Ile Thr Ala Asp Gly Glu
    3560                3565                3570

Val Tyr Ile Arg Lys Gly Gln Arg Gly Ser Gly Gln Pro Asp Thr
    3575                3580                3585

Ser Ala Gly Asn Ser Met Leu Asn Val Leu Thr Met Val Tyr Ala
    3590                3595                3600

Phe Cys Glu Ser Thr Gly Val Pro Tyr Arg Ser Phe Asn Arg Val
    3605                3610                3615

Ala Arg Ile His Val Cys Gly Asp Asp Gly Phe Leu Ile Thr Glu
    3620                3625                3630

Arg Gly Leu Gly Leu Lys Phe Ala Ser Lys Gly Ala Gln Ile Leu
    3635                3640                3645

Tyr Glu Ser Gly Lys Pro Gln Lys Ile Leu Glu Gly Asp Lys Met
    3650                3655                3660

Lys Val Ala Tyr Arg Phe Glu Asp Ile Glu Phe Cys Ser His Thr
    3665                3670                3675

Pro Ile Pro Val Arg Trp Ser Asp Asn Ser Ser Gly Tyr Met Ala
    3680                3685                3690

Gly Arg Asn Thr Ala Thr Val Leu Ala Lys Met Ala Thr Arg Leu
    3695                3700                3705

Asp Ser Ser Gly Glu Arg Gly Thr Ala Ala Tyr Glu Lys Ala Val
    3710                3715                3720

Ala Phe Ser Phe Leu Leu Met Tyr Ser Trp Asn Pro Leu Ile Arg
    3725                3730                3735

Arg Ile Cys Leu Leu Thr Leu Ser Ser Lys Pro Glu Val Asp Pro
    3740                3745                3750

Ser Lys Gln Ala Thr Tyr Tyr Tyr Lys Gly Asp Pro Ile Gly Ala
    3755                3760                3765

Tyr Lys Glu Val Val Gly His Asn Leu His Asp Leu Lys Arg Val
    3770                3775                3780

Gly Phe Glu Lys Leu Ala Ser Leu Asn Leu Ser Met Ser Thr Leu
    3785                3790                3795

Gly Ile Trp Thr Arg His Thr Ser Lys Arg Leu Leu Glu Asp Cys
    3800                3805                3810

Val Lys Val Gly Lys Glu Glu Gly Asn Trp Leu Val Asn Ala Asp
    3815                3820                3825

Arg Leu Val Ser Ser Lys Thr Asn Lys Met Tyr Ile Pro Asp Glu
    3830                3835                3840

Gly His Thr Leu Gln Gly Lys Tyr Tyr Glu Glu Leu Arg Leu Leu
    3845                3850                3855

Gly Pro Gly Gly Pro Ile Leu Arg Val Gly Lys Asp Arg Tyr Arg
    3860                3865                3870

Leu Gly Pro Ile Val Asn Val Ile Leu Arg Arg Leu Arg Val Leu
    3875                3880                3885

Met Met Ala Ala Val Gly Glu Lys Ala Val Ile
```

3890 3895

<210> SEQ ID NO 58
<211> LENGTH: 3993
<212> TYPE: PRT
<213> ORGANISM: Norway rat pestivirus

<400> SEQUENCE: 58

Met Ser Gly Val Gln Gly Gln Pro Arg Arg Gly Ser Glu Lys Thr Val
1 5 10 15

Arg Met Arg Glu Tyr Lys Asp Ser Phe Gln Arg Gly Leu Tyr Val Glu
20 25 30

Ile Gly Pro Lys Leu Tyr Ser Ser Tyr Glu Gly Pro Val Tyr Asp Thr
35 40 45

Ile Pro Ile Lys Ile Thr Glu Glu Ile Gln Glu Leu Cys Thr Thr Gly
50 55 60

Tyr Gln Val Gly Thr Gly Arg Asp Glu Thr Gln Lys Glu Trp Glu Ile
65 70 75 80

Tyr Cys Cys Lys Cys His Pro Tyr Ile Thr Phe Leu Asp Lys Lys Thr
85 90 95

Gly Lys Ile Lys Ala Leu Lys Glu Glu Pro Leu Gly Cys Pro Ile Met
100 105 110

Ile Val Pro Glu Glu Gly Ala Thr Tyr Thr Lys Gly Cys Asp Asn Pro
115 120 125

Ala Asp Thr Leu Tyr Gly Ser Cys Gly Cys Thr Tyr Gly Lys Lys Pro
130 135 140

Arg Val Cys Thr Gly Arg Gly Val Thr Leu Arg Leu Pro His Pro Arg
145 150 155 160

Gly Lys Lys Thr Thr Pro Thr Gln Asp Ile Pro Arg Val Gly Asp Cys
165 170 175

Asn Asn Val Asp Thr Ser Gly Val Phe Leu Lys Val Gly Gly Ile Met
180 185 190

Tyr Arg Asp Tyr Gln Gly Leu Val Tyr His Arg Leu Pro Lys Glu Gln
195 200 205

Cys Arg Lys Thr Lys Gly Asn His Lys Pro Ile Ile Lys Leu Gly Lys
210 215 220

Val Tyr Ala Thr Asp Gly Lys Ile Tyr Lys Ile Gly Ile Arg Glu Gln
225 230 235 240

Thr Glu Val Val Ala Trp Arg Arg Asn Ile Leu Gly Ile Gln Val Phe
245 250 255

Tyr Asn Trp Val Thr Glu Pro Leu Gly Ile Pro Ile Trp Val Lys Thr
260 265 270

Cys Ser Asp Pro Asn Gly Asn Thr Lys Lys Lys Glu Glu Lys Thr Asp
275 280 285

Asp Arg Leu Lys Lys Gly Gly Leu Lys Cys Lys Pro Arg Glu Gln Glu
290 295 300

Pro Asp Ile Lys Arg Lys Pro Gly Pro Asp Ala Val Ile Val Ser Glu
305 310 315 320

Gly Lys Lys Tyr His Val Thr Cys Lys Gly Lys Val Lys Gly Glu Asn
325 330 335

Thr Lys Glu Gly Leu Tyr His Lys Lys Pro Lys Pro Gln Asp Ser Arg
340 345 350

Lys Lys Leu Glu Lys Ala Leu Leu Ala Trp Ala Ile Leu Ala Ile Leu
355 360 365

-continued

```
Thr Gly Leu Ala Thr Ser Asn Val Thr Gln Trp Asn Leu Ala Asp Glu
    370                 375                 380

Tyr Ser His Asp Met His Arg Val Met Phe Glu Arg Asn Ile Ser Arg
385                 390                 395                 400

Ser Ile His Gly Ile Trp Pro Val Lys Ile Cys Lys Gly Val Pro Asn
            405                 410                 415

Pro Met Ile Thr Asp Gln Gln Ala Lys Gln Ile Val Gly Met Val Asp
            420                 425                 430

Ala Ser Pro Ser Thr Asn Tyr Thr Cys Cys His Leu Gln Arg His Glu
        435                 440                 445

Trp Asn Lys His Gly Trp Cys Asn Trp Phe Asn Val Asp Pro Trp Ile
450                 455                 460

Thr Met Met Ile Tyr Gln Asn Gln Arg Ile Val Asn Lys Ile Gly Gln
465                 470                 475                 480

Glu Cys Ala Val Thr Cys Arg Tyr Asn His Thr Met Gly Thr Asn Ile
                485                 490                 495

Val Leu Gln Ala Arg Ser Ser Pro Thr Ser Thr Thr Gly Cys Lys Pro
            500                 505                 510

Gly Ala Lys Tyr Ser Phe Ala Gly Glu Ile Arg Lys Ser Lys Cys Lys
            515                 520                 525

Leu Glu Val Gly Met Glu Glu Leu Ile Glu Ser Leu Asp Thr Asp Trp
        530                 535                 540

Gln Arg His Thr Phe Ser Trp Glu Asp Tyr Ile Ile Asp Gly Ala Thr
545                 550                 555                 560

His Ile Ile Glu Gly Lys Arg Gln Leu Ile Thr Lys Leu Ile Asp Lys
                565                 570                 575

Val Glu Asn Gly Leu Asp Lys Ala Lys Gln Lys Leu Asn Lys Val Lys
            580                 585                 590

Lys Phe Phe Ser Ser Ala Thr Asn Thr Asp Ile Lys Asn Lys Ile Tyr
        595                 600                 605

Cys Glu Lys Phe His Val Leu Gly Asp Leu Val Tyr Val Asn Ser Cys
610                 615                 620

Leu Pro Met Gly Leu Pro Thr Gly Ala Arg Phe Val Ser Lys Asn Val
625                 630                 635                 640

Ile Ser Leu Glu Pro Glu Lys Thr Ala Gln Ile Ile Pro Arg Leu Thr
                645                 650                 655

His His Leu Asp Ser Gly Ile Leu Leu Val Leu Val Ala Met Ser Asp
            660                 665                 670

Phe Met Pro Glu Thr Ser Ser Ala Leu Tyr Leu Ile Leu His Phe Met
        675                 680                 685

Ile Pro Asn Ser Arg His Arg Thr Ile Ser Glu Glu Gly Leu Thr Met
690                 695                 700

Ala Leu Asn Leu Thr Ser Thr Glu Pro Val Ser Ser Val Ile Pro Thr
705                 710                 715                 720

Ser Val Tyr Val Glu Gly Gln Trp Thr Cys Trp Lys Pro Ser Trp Trp
                725                 730                 735

Pro Tyr Asn Ala Asp Ile Ala Leu Phe Phe Glu Gly Ala Phe Glu Met
            740                 745                 750

Leu Glu Leu Ile Ala Arg Ala Gly Asp Leu Met Lys Val Trp Thr
        755                 760                 765

Glu Ala Thr Ala Val Ala Phe Leu Cys Phe Leu Ile Lys Ala Phe Arg
770                 775                 780

Gly Gln Ile Leu Gln Gly Val Ile Leu Leu Leu Leu Ser Ser Ala
```

-continued

```
            785                 790                 795                 800
Glu Gly Arg Tyr Asn Gln Val Lys Val Asp Arg Pro Asp Trp His Thr
                    805                 810                 815
Leu Leu Gln Lys Asp Leu Lys Gly Val Leu Ser Gly Lys Asp Gly Leu
                820                 825                 830
Tyr Ile Leu Arg Ser Asn Lys Val Trp Thr Gly Gly Ser Val Ile Ile
                835                 840                 845
Thr Asp Glu Phe Ala Val Thr Thr Phe Ile Gly Asp His Thr Gly Asn
            850                 855                 860
Phe Lys Phe Ser Val Lys Val Met Thr Thr Pro Ile Glu Met Asp Tyr
865                 870                 875                 880
Cys Ile Lys Val Ile Asp Thr Ala Lys Phe Phe Cys Val Met Val Gly
                    885                 890                 895
Thr Pro Thr Gln Arg Asp Leu Val Lys Pro Pro Glu Met Leu Cys Gly
                900                 905                 910
Cys Gly Ala Leu Glu Val Gln Asp Asn Asn Ser Thr Gly Leu Ile Ser
                915                 920                 925
Pro Gly Asn Val Leu Pro Ser Lys Cys Ile Asn Gly Trp Thr Gly Val
            930                 935                 940
Val Thr Cys His Cys Pro Tyr Thr Asp Ile Lys Met Lys Phe Leu Glu
945                 950                 955                 960
Asn Thr Thr Pro Gln Lys Tyr Ser Lys Asn Cys Pro Gly Thr Tyr Leu
                    965                 970                 975
Ser Asp Gln Asn Phe His His Asp Cys Lys Tyr Gly Ser Gln Glu Ser
                    980                 985                 990
Cys Ile Asp Pro Glu Pro Thr Lys Leu Pro Pro Glu Thr Tyr Glu Asp
            995                 1000                1005
Ile Gln Glu Cys Phe Trp Cys Ser Tyr Tyr Ile Lys Asp Ala Asn
            1010                1015                1020
Phe Thr Pro His Lys Gly Pro Leu Gly Trp Cys Arg Val Gly Glu
            1025                1030                1035
Asn Glu Pro Tyr Tyr Leu Thr Asn Arg Lys Ser Cys Val Gln Gly
            1040                1045                1050
Gly Val Gln Ile Gly Ser Gly Glu Val Thr Cys Leu Ile Gly Thr
            1055                1060                1065
Thr Lys Ile Lys Val Gly Asn Phe Asn Glu Thr Ala Ile Ser Phe
            1070                1075                1080
Met Pro Cys Asn Pro Ile Lys Glu Ala Ser Arg Gly Pro Pro Ser
            1085                1090                1095
Arg Thr Thr Cys Thr Tyr Lys Tyr Ala Lys Thr Leu Lys Asn Lys
            1100                1105                1110
Ile Tyr Asp Glu Lys Asp Arg Tyr Trp Gly Gln Tyr Met Val Lys
            1115                1120                1125
Gly Glu Tyr Gln Tyr Trp Phe Asp Leu Glu Gln Asp Asp His Val
            1130                1135                1140
Thr Gly Gly Leu Leu Lys Tyr Leu Pro Leu Ile Met Val Leu Leu
            1145                1150                1155
Leu Gly Gly Lys Met Val Ala Trp Leu Leu Thr Ala Tyr Tyr Leu
            1160                1165                1170
Met Glu Val Val Glu Ala Thr Arg Asp Ile Ala Ser His Thr Ala
            1175                1180                1185
Val Val Met Gly Pro Leu Ile Lys Cys Val Asp Tyr Asp Thr Val
            1190                1195                1200
```

-continued

```
Cys Val Leu Ala Leu Ile Phe Leu Leu Ile Lys Asn Asn Thr Ser
    1205                1210                1215

Arg Leu Val Val Ile Ser Leu Tyr Ser Ile Met Lys Gly Lys Ile
    1220                1225                1230

Leu Ile Pro Leu Leu Ile Ala Met Ser Ile Ile Ile Gln Gly Thr
    1235                1240                1245

Met Ala His Glu Cys Glu Met Glu Thr Thr Glu Gly Ser Asn Leu
    1250                1255                1260

Phe Pro Met Ala Cys Val Val Phe Tyr Cys Ile Val Ser Phe Leu
    1265                1270                1275

Lys Phe Gly Glu Ala Thr Gly Val Val Val Leu Ile Leu Leu Gly
    1280                1285                1290

Val Met Lys Met Ala Gln Asn Leu Ser Val Gly Val Ser Ala Val
    1295                1300                1305

Leu Val Leu Ala Trp Ala Val Leu Gly Thr Val Ile Tyr Leu Ser
    1310                1315                1320

Thr Arg Lys His His Val Ser Pro Ile Met Thr Ser Leu Val Ala
    1325                1330                1335

Leu Thr Leu Thr Ala Gln Leu Ala Gly Leu Val Thr Asn Thr Val
    1340                1345                1350

Gln Gln Leu Ser Asp Val Val Met Glu Leu Arg Pro Val Glu Ile
    1355                1360                1365

Thr Thr Val His Lys Ile Phe Leu Val Tyr Ile Phe Tyr Leu Val
    1370                1375                1380

Tyr Ile Val Thr Tyr Lys Lys Glu Gly Thr Asp Phe Phe Thr Tyr
    1385                1390                1395

Leu Leu Asp Leu Leu Leu Ile Lys Met Tyr Leu Val Val Ser
    1400                1405                1410

Leu Asp Cys Val Ser Phe Leu Ser Asn Phe Cys Ser Asp Val
    1415                1420                1425

Val Arg Tyr Lys Leu Ile Thr Lys Lys Leu Gly Val Pro Glu Glu
    1430                1435                1440

Leu Gln Asn Leu Ser Leu Asn Ser Asp Met Glu Ala Leu Glu Lys
    1445                1450                1455

Ser Gly Ala Tyr Leu Arg Pro Tyr Ser Lys Asn Arg Lys Leu Leu
    1460                1465                1470

Glu Cys Arg Glu Val Val Tyr Ile Leu Ala Arg Ala Leu Leu Leu
    1475                1480                1485

Thr Ala Leu Gly Arg Leu Trp Phe Pro Phe Val Phe Leu Asp Leu
    1490                1495                1500

Phe Phe Ser Ile Leu Leu His Ala His Lys Gln Leu Leu Arg Glu
    1505                1510                1515

Val Ala Ser Ser Lys Thr Leu Ile Ala Ser Leu Leu Ala Ser Thr
    1520                1525                1530

Val Asn Ala Val Met Ile Leu Lys Tyr Pro Gly Met Thr Lys Thr
    1535                1540                1545

Glu Lys Leu Tyr Gln Val Trp Thr Thr Val Arg Arg Glu Ile Leu
    1550                1555                1560

Lys His Glu Val Gln Asn Pro Val Leu Lys Asn Trp Tyr Glu Asp
    1565                1570                1575

Thr Glu Ser Met His Arg Gly Val Met Ala Phe Ile Val Lys Val
    1580                1585                1590
```

-continued

| | | | | | | | | | |
|---|---|---|---|---|---|---|---|---|---|
|Val|Gly|Lys|Asp|Ser|Ile|Leu|Cys|Ser|Asn|Cys|Glu|Gln|Glu|Asn|
|1595| | | | |1600| | | | |1605| | | | |
|Lys|Tyr|Pro|Cys|Pro|Ala|Cys|Gly|Ala|Glu|Ser|Pro|Arg|Ile|Arg|
|1610| | | | |1615| | | | |1620| | | | |
|Cys|Gly|Trp|Thr|Leu|Lys|Asp|Leu|Glu|Tyr|Thr|Arg|Leu|Ser|Lys|
|1625| | | | |1630| | | | |1635| | | | |
|Ala|Glu|Glu|Lys|Ile|Gly|Gly|Val|Tyr|Lys|Phe|Arg|Arg|Thr|Asn|
|1640| | | | |1645| | | | |1650| | | | |
|Ile|Glu|Phe|Asp|Phe|Gly|Thr|Ala|Ser|His|Ser|Leu|Lys|Lys|Tyr|
|1655| | | | |1660| | | | |1665| | | | |
|Ile|Gln|Met|Leu|Pro|Ile|Leu|Ala|Thr|Arg|Gln|Asn|Leu|Ile|Leu|
|1670| | | | |1675| | | | |1680| | | | |
|Val|Gly|Asn|Leu|Gly|Tyr|Glu|Val|Glu|Thr|Leu|Ile|Lys|Ala|Gly|
|1685| | | | |1690| | | | |1695| | | | |
|Trp|Lys|Leu|Arg|Ala|Pro|Ala|Ile|Ile|Pro|Lys|Ile|Val|Glu|Thr|
|1700| | | | |1705| | | | |1710| | | | |
|Leu|Gln|Gly|Glu|Asn|Ser|Val|Leu|Asp|Lys|Leu|Gln|Leu|Phe|Phe|
|1715| | | | |1720| | | | |1725| | | | |
|Gly|Ile|Thr|Pro|Met|Gly|Val|Thr|Pro|Lys|Asn|Pro|Thr|Arg|Leu|
|1730| | | | |1735| | | | |1740| | | | |
|Pro|Thr|Ser|Leu|Ile|Lys|Ile|Lys|Arg|Gly|Phe|Glu|Thr|Gly|Trp|
|1745| | | | |1750| | | | |1755| | | | |
|Ala|Tyr|Thr|His|Pro|Gly|Gly|Leu|Ser|Ser|Val|Glu|His|Val|Thr|
|1760| | | | |1765| | | | |1770| | | | |
|Gly|Lys|Asn|Asp|Ile|Phe|Cys|Ser|Asp|Ser|Asn|Gly|Arg|Thr|Thr|
|1775| | | | |1780| | | | |1785| | | | |
|Ile|Lys|Ile|Thr|Ser|Ser|Asn|Ser|Lys|Thr|Asp|Glu|Thr|Glu|Tyr|
|1790| | | | |1795| | | | |1800| | | | |
|Gly|Ile|Lys|Thr|Asp|Met|Asn|Thr|Ser|Glu|Gly|Ala|Arg|Cys|Leu|
|1805| | | | |1810| | | | |1815| | | | |
|Val|Tyr|Asn|Pro|Glu|Ala|Thr|Asn|Ile|Ser|Gly|Ser|Lys|Gly|Ala|
|1820| | | | |1825| | | | |1830| | | | |
|Val|Val|His|Leu|Arg|Lys|Cys|Gly|Ser|Asp|Phe|Lys|Cys|Ile|Thr|
|1835| | | | |1840| | | | |1845| | | | |
|Ala|Asp|Gly|Thr|Pro|Ala|Tyr|Tyr|Asn|Leu|Asn|Leu|Lys|Gly|
|1850| | | | |1855| | | | |1860| | | | |
|Trp|Ser|Gly|Leu|Pro|Ile|Phe|Asp|Leu|Gly|Thr|Gly|Lys|Ile|Val|
|1865| | | | |1870| | | | |1875| | | | |
|Gly|Arg|Val|Lys|Ala|Gly|Ser|Asn|Val|Thr|Glu|Gly|Asn|Thr|Glu|
|1880| | | | |1885| | | | |1890| | | | |
|Ile|Ile|Gly|Gly|Thr|Thr|Ser|Val|Leu|Pro|Glu|Ser|Cys|Asp|Leu|
|1895| | | | |1900| | | | |1905| | | | |
|Asp|Ser|Thr|Val|Lys|Gln|Ile|Gln|Lys|Met|Glu|Arg|Gly|Met|Phe|
|1910| | | | |1915| | | | |1920| | | | |
|Leu|Ser|Val|Thr|Leu|Ala|Thr|Gly|Ala|Gly|Lys|Thr|Thr|Glu|Leu|
|1925| | | | |1930| | | | |1935| | | | |
|Pro|Arg|Lys|Leu|Ile|Glu|Lys|Ile|Gly|Thr|His|Lys|Arg|Val|Leu|
|1940| | | | |1945| | | | |1950| | | | |
|Val|Leu|Ile|Pro|Leu|Arg|Ala|Ala|Ile|Gly|Val|His|Arg|Tyr|
|1955| | | | |1960| | | | |1965| | | | |
|Met|Gln|Val|Lys|Tyr|Pro|His|Ile|Asn|Phe|Asn|Leu|Arg|Val|Gly|
|1970| | | | |1975| | | | |1980| | | | |
|Asp|Leu|Lys|Glu|Gly|Asp|Met|Ser|Thr|Gly|Ile|Thr|Tyr|Ala|Ser|

```
                1985                1990                1995

Tyr Gly Tyr Met Cys Gln Met Glu Met Pro Lys Ile Arg Glu Met
        2000                2005                2010

Ala Ala Thr Tyr Asn Tyr Ile Phe Leu Asp Glu Tyr His Cys Ala
        2015                2020                2025

Thr Pro Glu Gln Leu Ala Ile Ile Ala Lys Ile His Arg Val Ala
        2030                2035                2040

Glu Thr Val Arg Val Ile Ala Met Thr Ala Thr Pro Val Gly Val
        2045                2050                2055

Val Ala Ser Lys Gly Gln Lys Phe Asp Ile Lys Glu Glu Glu Leu
        2060                2065                2070

Ala Glu Val Leu Lys Gly Glu Asn Leu Gly Glu Asn Tyr Leu Asn
        2075                2080                2085

Val Ala Gly Leu Lys Val Ala Arg Thr Ile Leu Lys Glu Asn Thr
        2090                2095                2100

Leu Val Phe Val Pro Thr Arg Arg Gln Ala Glu Asp Thr Ala Lys
        2105                2110                2115

Lys Leu Arg Gln Glu Gly Val Asn Ala Gly Phe Tyr Tyr Ser Gly
        2120                2125                2130

Met Glu Pro Glu Ser Ile Val Lys Asn Thr Ser Arg Glu Pro Tyr
        2135                2140                2145

Cys Ile Val Ala Thr Asn Ala Ile Glu Ser Gly Val Thr Leu Pro
        2150                2155                2160

Asn Leu Thr Asn Val Ile Asp Thr Cys Leu Lys Cys Glu Lys Arg
        2165                2170                2175

Val Arg Ile Gln Thr Arg Ala Pro His Ile Val Thr Gly Leu Lys
        2180                2185                2190

Lys Ile Val Ile Thr Pro Gly Glu Ala Ala Gln Arg Arg Gly Arg
        2195                2200                2205

Val Gly Arg Thr Lys Pro Gly Asn Tyr Tyr Lys Ala Pro Val Ala
        2210                2215                2220

Val Gln Gly Glu Gln Asp Tyr His Phe Asn Leu Leu Gln Ala Gln
        2225                2230                2235

Leu Tyr Gly Leu Pro Asp Gly Ile Asn Ile Thr Ala Gln Phe Arg
        2240                2245                2250

Lys Met Asn Asn Glu Trp Ala Leu Tyr Glu Glu Asp Lys Val Leu
        2255                2260                2265

Leu Thr Gln Leu Glu Val Cys Asn Asn Tyr Leu Leu Ser Asp Asp
        2270                2275                2280

Leu Pro Gln Leu Thr Lys Asn Ile Leu Ala Arg Thr Thr His Pro
        2285                2290                2295

Glu Lys Ile Gln Leu Ala Tyr Asn Cys Phe Glu Thr Pro Val Pro
        2300                2305                2310

Ile Ile Phe Pro Glu Val Lys Asn Gly Glu Val Thr Ser Val Tyr
        2315                2320                2325

Pro Asp Tyr Asn Leu Val Ser Tyr Lys Val Leu Lys Asp Gln Ala
        2330                2335                2340

Pro Phe Ser Phe Tyr Cys Thr Glu Asp Glu Asp Leu Ala Leu Asp
        2345                2350                2355

Leu Met Asn Met Glu Trp Gln Ser Pro Asn Met Glu Gln Thr Val
        2360                2365                2370

Glu Thr Gly Lys Ala Leu Glu Lys Met Ala Lys Leu Ser Lys Leu
        2375                2380                2385
```

```
Glu Thr Ala Leu Val Gly Gly Leu Ile Thr Tyr Ile Gly Tyr Lys
    2390            2395                2400

Ala Leu Glu Lys Arg His Lys Pro Phe Val Glu Ala Ile Tyr Ser
    2405            2410                2415

Tyr Gln Met Glu Gln Val Glu Asp Leu Val Leu Cys Gln Val Cys
    2420            2425                2430

Pro Asp Asp Ile Val Pro Lys Leu Val Glu Glu Val Lys Leu
    2435            2440                2445

Asn Gln Asn Ile Ile Asp Glu Lys Ile Leu Lys Ile Lys Glu Trp
    2450            2455                2460

Ile Lys Glu Leu Asn Cys Phe Thr Gln Ala Thr Thr Asp Arg Thr
    2465            2470                2475

Asn Phe Lys Leu Glu Ser Ser Asn Asp Ile Phe Glu Tyr Trp Lys
    2480            2485                2490

Lys Phe Lys Glu Tyr Leu Tyr Lys Asn Glu Lys Asn Ile Ala Lys
    2495            2500                2505

Tyr Gly Gly Trp Gly Leu His Thr Ala Leu His Asn Ser Ile Ser
    2510            2515                2520

Ala Arg Leu Gly Thr Glu Val Ala Thr Ala Leu Val Val Leu Lys
    2525            2530                2535

Trp Met Ala Phe Gly Gly Ile Glu Ala Gly Asp Tyr Val Lys Gln
    2540            2545                2550

Ala Ala Val Asp Val Ile Val Tyr Tyr Ile Ile Asn Thr Pro Arg
    2555            2560                2565

Phe Asp Gly Asp Glu Glu Thr Ala Ser Arg Gly Arg Lys Tyr Val
    2570            2575                2580

Ala Thr Val Leu Ile Ser Ala Leu Ala Lys Tyr Ile Tyr Thr Asn
    2585            2590                2595

Gly Tyr Gly Asp Leu His Ser Leu Leu Glu Pro Ile Leu Ser Tyr
    2600            2605                2610

Leu Pro Tyr Ala Thr Asn Leu Leu Gln Trp Phe Arg Pro Asn Gln
    2615            2620                2625

Leu Glu Asn Val Val Val Thr Gly His Leu Ile Tyr Lys Leu Phe
    2630            2635                2640

Leu Ser Val Lys Thr Gly Ser Asn Lys Gly Leu Val Gly Leu Ser
    2645            2650                2655

Ile Ser Ser Gly Met Glu Leu Tyr Ser Met Asn Pro Ile Thr Leu
    2660            2665                2670

Cys Val Ala Leu Val Leu Gly Val Gly Ala Ile Ala Ala His Thr
    2675            2680                2685

Val Leu Glu Gln Ser Glu Asn Lys Arg Thr Leu Leu Met Lys Val
    2690            2695                2700

Phe Val Lys Asn Phe Leu Asp Gln Ala Ala Thr Asp Glu Leu Cys
    2705            2710                2715

Lys Ser Asp Pro Glu Thr Ile Ile Ser Ala Val Phe Glu Thr Leu
    2720            2725                2730

His Thr Ala Ser Asn Pro Ile Arg Val Ile Phe His Leu Tyr Met
    2735            2740                2745

His Phe His Lys Lys Tyr Asp Ile Lys Lys Ile Ile Glu Met Thr
    2750            2755                2760

Ala Gly Lys Asn Ile Leu Val Leu Val Val Leu Glu Cys Leu Glu
    2765            2770                2775
```

| | | | | | | | | | | | |
|---|---|---|---|---|---|---|---|---|---|---|---|
| Ile | Met | Glu | Leu | Asp | Lys | Glu | Ser | Lys | Leu | Lys | Thr | Leu | Ser | Thr |
| 2780 | | | | | 2785 | | | | | 2790 | | | | |
| Asn | Tyr | Ile | Val | Asp | Trp | Ile | Lys | Asn | Tyr | Leu | Lys | Lys | Leu | Lys |
| 2795 | | | | | 2800 | | | | | 2805 | | | | |
| Arg | Met | Ala | Thr | Thr | His | Leu | Ile | Lys | Thr | Ile | Val | Pro | Ala | Pro |
| 2810 | | | | | 2815 | | | | | 2820 | | | | |
| Phe | Ser | Cys | Lys | Val | Tyr | Lys | Pro | Ser | Tyr | Arg | Val | Lys | Leu | Ile |
| 2825 | | | | | 2830 | | | | | 2835 | | | | |
| Gly | Gln | Glu | Asn | Cys | Thr | Arg | Ala | Glu | His | Arg | Cys | Thr | Cys | Gly |
| 2840 | | | | | 2845 | | | | | 2850 | | | | |
| Ser | Glu | Thr | Ile | Val | Tyr | Asn | Thr | Gly | Asn | Arg | Trp | Glu | Val | Val |
| 2855 | | | | | 2860 | | | | | 2865 | | | | |
| Gln | Arg | Lys | Gly | Ser | Thr | Trp | Cys | Arg | Asn | Asn | Ser | Val | Glu | Arg |
| 2870 | | | | | 2875 | | | | | 2880 | | | | |
| Val | Leu | Ser | Asp | Leu | Gln | Asn | Thr | Asp | Phe | Tyr | Asp | Glu | Lys | Asn |
| 2885 | | | | | 2890 | | | | | 2895 | | | | |
| Asn | Leu | Leu | Ala | Ile | Glu | Val | Asp | Lys | Thr | Ser | Thr | Val | Ile | Tyr |
| 2900 | | | | | 2905 | | | | | 2910 | | | | |
| Glu | Arg | Asn | Gly | Lys | Thr | Val | Ser | Leu | Glu | Asn | His | Gly | Glu | Thr |
| 2915 | | | | | 2920 | | | | | 2925 | | | | |
| Leu | Thr | Gly | Thr | Ser | Ala | Val | Thr | Ile | Ser | Tyr | Arg | Asp | Leu | Val |
| 2930 | | | | | 2935 | | | | | 2940 | | | | |
| Asp | Val | Phe | Asn | Gly | Arg | Tyr | Asp | Gly | Phe | Thr | Ile | Glu | Gly | Phe |
| 2945 | | | | | 2950 | | | | | 2955 | | | | |
| Ser | Arg | Gly | Phe | Ile | Glu | Pro | Lys | Glu | Val | Tyr | Asn | Arg | Asn | Glu |
| 2960 | | | | | 2965 | | | | | 2970 | | | | |
| Ala | Tyr | Phe | Leu | Asn | Gly | Val | Val | Tyr | Phe | Tyr | Lys | Ile | Glu | Lys |
| 2975 | | | | | 2980 | | | | | 2985 | | | | |
| Cys | Gln | Ala | Ala | Thr | Lys | Leu | Leu | Thr | Asn | Asp | Asn | Ile | Lys | Lys |
| 2990 | | | | | 2995 | | | | | 3000 | | | | |
| Ile | Ile | Ser | Thr | Ile | Asn | Arg | Arg | Lys | Leu | Gln | Pro | Glu | Lys | Thr |
| 3005 | | | | | 3010 | | | | | 3015 | | | | |
| Pro | Lys | Glu | Phe | Leu | Ile | Asn | Trp | Tyr | Pro | Glu | Asn | Leu | Ile | Thr |
| 3020 | | | | | 3025 | | | | | 3030 | | | | |
| Asp | Cys | His | Arg | Ile | Ile | Lys | Pro | Cys | Phe | Gly | Glu | Lys | Leu | Val |
| 3035 | | | | | 3040 | | | | | 3045 | | | | |
| Cys | Val | Gly | Asp | Ala | Thr | His | Asp | Glu | His | His | Leu | Gly | Glu | Ser |
| 3050 | | | | | 3055 | | | | | 3060 | | | | |
| Thr | Cys | Glu | Glu | Glu | Pro | Asp | Val | Trp | Val | Leu | Ala | Pro | Glu | Glu |
| 3065 | | | | | 3070 | | | | | 3075 | | | | |
| Met | Thr | Val | Arg | Glu | Gly | Thr | His | Arg | Val | Ala | Gly | Gln | Val | Val |
| 3080 | | | | | 3085 | | | | | 3090 | | | | |
| Lys | Val | Glu | Lys | Ile | Gln | Thr | Lys | Pro | Asn | Glu | Arg | Lys | Ile | Gly |
| 3095 | | | | | 3100 | | | | | 3105 | | | | |
| Tyr | Glu | Gln | Asn | Gln | Ile | Pro | Gly | Asn | Lys | Ile | Ser | Leu | Thr | Arg |
| 3110 | | | | | 3115 | | | | | 3120 | | | | |
| Ser | Leu | Val | His | Cys | Gln | Ala | Glu | Arg | Glu | Lys | Lys | Thr | Ile | Leu |
| 3125 | | | | | 3130 | | | | | 3135 | | | | |
| Ile | Phe | Gly | Asn | Pro | Arg | Leu | Met | Ser | Ala | Thr | Ala | Lys | His | Leu |
| 3140 | | | | | 3145 | | | | | 3150 | | | | |
| Leu | Lys | Lys | Phe | Leu | Val | Ile | Tyr | Pro | Glu | Lys | Leu | Thr | Glu | Ala |
| 3155 | | | | | 3160 | | | | | 3165 | | | | |
| Asn | Gly | Pro | Gly | Val | Ser | Ile | Tyr | Ile | Gly | Glu | Glu | Lys | Phe | Gly |

-continued

```
            3170                3175                3180

Ile Phe Asp Ile Glu Thr Lys Phe Leu Thr Ser Lys Gln Leu Lys
            3185                3190                3195

Arg Asn Leu Thr Glu Arg Gln His Asp Leu Asn Val Glu Glu Phe
            3200                3205                3210

Phe Ser Thr Lys Gln Ser Tyr Cys Glu Ile Pro Asp Tyr His Gln
            3215                3220                3225

Ala Glu Asn Pro Val Phe Ile Thr Glu Glu Gln Asn Ser Glu Asn
            3230                3235                3240

Ile Tyr His His Ile Gly Glu Lys Phe Phe Leu Leu Lys Leu Met
            3245                3250                3255

Lys Gly Lys Gly Tyr Asn Val Met Thr Lys Gln Glu Thr Gly Phe
            3260                3265                3270

Lys Val Lys Leu Ser Trp Asn Gly Gln Lys Glu Leu Val Arg Thr
            3275                3280                3285

Leu Glu Pro Leu Ile Arg Glu Gln Ile Leu Asp Val Asp Ile Gln
            3290                3295                3300

Lys Leu Lys Asn Cys His Tyr Ile Ser Thr Arg Glu Phe Ala Asn
            3305                3310                3315

Gly Gly Trp Arg Pro Leu Asp Ala Ser Thr Tyr Asn Gly Lys Ile
            3320                3325                3330

Pro Cys Lys Arg Glu Gly Ser Leu Thr Pro Val Gln Ala Tyr Leu
            3335                3340                3345

Glu Leu Arg Gln Leu Lys Gln Glu Ile Lys Lys Asn Lys Glu Ser
            3350                3355                3360

Lys Leu Gly Tyr Ser Asn Leu Lys Gly Lys Glu Trp Leu Leu Asn
            3365                3370                3375

Arg Ile Arg Glu Pro Pro Arg Leu Met Leu Lys His Leu Ala Asn
            3380                3385                3390

Pro Gly Gly Leu Ser Lys Gly Gly Val Arg Thr Lys Tyr Asn Tyr
            3395                3400                3405

Asn Ile Tyr Asn Lys Lys Ile Cys Gly Leu Met Gln Glu Ile Gly
            3410                3415                3420

Ile Asn Ile Ser Arg Leu Pro Thr Val Arg Ala Gln Cys Ser Thr
            3425                3430                3435

Ala Asp Thr His Glu Ala Ile Arg Thr Lys Ile Asp Lys Glu Pro
            3440                3445                3450

Asn Lys Gln His Pro Glu Leu His Glu Asp Leu Phe Lys Ile Phe
            3455                3460                3465

Leu His Asn Ile Asp Ser Lys Tyr Gln His Lys Phe Glu Glu Val
            3470                3475                3480

Gly Trp Glu Lys Leu Glu Pro Gly Leu Asn Arg Lys Gly Ala Pro
            3485                3490                3495

Gly Phe Leu Glu Asp Ile Asn Lys Leu Gly Asp Tyr Leu Thr Pro
            3500                3505                3510

Glu Gly Lys Lys Gln Ile Asp Lys Leu Val Arg Lys Met Leu Arg
            3515                3520                3525

Gly Asp Ile Pro Gln Tyr Tyr Glu Thr Ala Ile Pro Lys Asn Glu
            3530                3535                3540

Lys Arg Asp Val Thr Asp Asp Leu Leu Glu Leu Gly Glu Trp Pro
            3545                3550                3555

Glu Lys Lys Pro Arg Ile Ile Gln Tyr Pro Glu Ala Lys Met Arg
            3560                3565                3570
```

-continued

Ile Ala Ile Thr Lys Ile Met Tyr Asn Trp Val Lys Gln Gln Pro
3575                3580                3585

Ile Leu Ile Pro Gly Tyr Glu Gly Lys Thr Pro Ile Phe Asn Val
3590                3595                3600

Phe Asn Lys Val Lys Lys Glu Trp Asp Gln Phe Gln Lys Pro Ala
3605                3610                3615

Ile Ile Ser Phe Asp Thr Lys Ala Trp Asp Thr Gln Val Thr Pro
3620                3625                3630

Asn Asp Leu Asp Leu Val Ala Arg Ile Gln Lys Trp Leu Tyr Lys
3635                3640                3645

Lys Lys Tyr His Lys Phe Ile Asp Arg Leu Thr Glu Glu Met Lys
3650                3655                3660

Glu Val Val Val Ile Thr Glu Asp Gly Gln Val Tyr Ile Arg Lys
3665                3670                3675

Gly Gln Arg Gly Ser Gly Gln Pro Asp Thr Ser Ala Gly Asn Ser
3680                3685                3690

Ile Leu Asn Val Leu Thr Met Ala Trp Ala Phe Cys Arg Ala Asn
3695                3700                3705

Asn Leu Glu Tyr Arg Thr Phe Ser Lys Val Ala Lys Ile His Val
3710                3715                3720

Cys Gly Asp Asp Gly Phe Leu Ile Thr Glu Asp Tyr Leu Ala Arg
3725                3730                3735

Lys Phe Ser Glu Glu Gly Pro Arg Leu Leu Gln Glu Ala Gly Lys
3740                3745                3750

Pro Gln Lys Leu Leu Thr Gly Asn Thr Met Lys Ile Ser Ser Asn
3755                3760                3765

Phe Ser Asp Leu Glu Phe Cys Ser His Thr Pro Ile Lys Val Arg
3770                3775                3780

Leu Ser Asn Gly Ala Thr Thr Tyr Met Ala Gly Arg Asp Thr Ala
3785                3790                3795

Val Ile Leu Ser Lys Met Ala Thr Lys Leu Asp Glu Ser Gly Val
3800                3805                3810

Arg Ser Thr Glu Glu Tyr Glu Asn Gln Val Ala Phe Cys Phe Leu
3815                3820                3825

Leu Leu Tyr Pro Trp Asn Pro Leu Ile Arg Arg Ile Cys Leu Tyr
3830                3835                3840

Thr Leu Ser Thr Thr Val Tyr Asp Lys Pro Asn Pro Asn Lys Pro
3845                3850                3855

Ile Leu Val Gln Tyr Arg Gly Asp Pro Ile Gly Ala Phe Lys Asp
3860                3865                3870

Val Tyr Gly Phe Asp Leu Arg Ala Ile Glu Arg Thr Glu Leu Ser
3875                3880                3885

Lys Leu Ser Gln Leu Asn Leu Asn Met Thr Ile Leu Thr Ile Trp
3890                3895                3900

His Arg Lys Thr Ser Gln Arg Ile Leu Glu Lys Cys Leu Glu Ile
3905                3910                3915

Ala Lys Pro Ala Ser Pro Val Thr Ser Asp Arg Leu Val Glu Lys
3920                3925                3930

Lys Thr Gly Ile Ile Tyr Ile Pro Met Glu Gly His Val Ile Gln
3935                3940                3945

Gly Lys Tyr Tyr Glu Lys Leu Asp Leu Gly Val Lys Asn Gln Arg
3950                3955                3960

```
Ile Thr Arg Ala Ile Glu Gly Leu Glu Arg Tyr Lys Glu Gly Pro
    3965                3970                3975

Ile Tyr Gly Ile Phe Tyr Lys Ile Arg Asn Leu Leu Met Met Leu
    3980                3985                3990

<210> SEQ ID NO 59
<211> LENGTH: 1710
<212> TYPE: PRT
<213> ORGANISM: Rhinolophus affinis pestivirus

<400> SEQUENCE: 59

Glu Ser Trp Val Glu Thr Leu Phe Ser Glu Ala Trp His Ile Leu His
1               5                   10                  15

Ile Leu Thr Ser Ala Ile Val Asn Ile Phe Gln Ala Leu Ile Ser Leu
            20                  25                  30

Glu Ile Val Tyr Leu Val Ile Ile Met Leu Lys Ile Ala Arg Gly Asn
        35                  40                  45

Leu Ile Gly Ala Val Leu Trp Cys Leu Leu Leu Ser Gly Ala Glu Ala
    50                  55                  60

Asn Cys Ile Thr Arg Val Asp Tyr Tyr Asn Tyr Ser Leu Lys Val Glu
65                  70                  75                  80

Lys Asn Thr Gly Asn Glu Val Thr Ala Tyr Asp Gly Thr Tyr Phe Val
                85                  90                  95

Ile Thr Leu Lys Asp Glu Glu Pro Lys Leu Met Glu Lys Val Val Lys
            100                 105                 110

Val Asn Gly Asn Ala Thr Lys Asp Glu Tyr Cys Tyr Gln Ala Ile Asn
        115                 120                 125

Ile Thr Lys Trp Asn Arg Lys Pro Asp Lys Leu Arg Trp Cys Gly Gln
    130                 135                 140

Thr Phe Pro Tyr Trp Leu Gly Asp Thr Val Asn Gly Glu Ala Tyr Phe
145                 150                 155                 160

Gln Lys Gly Tyr Trp Val Asn Ile Thr Thr Glu Pro Asp Asn Cys Glu
                165                 170                 175

Leu Arg Lys Gly Val Phe Leu Ser Lys Asn Gly Ala Val Ser Cys Thr
            180                 185                 190

Arg Asn Gly Thr Arg Leu Val Leu Gln Leu Lys Asn Leu Asn Ser Thr
        195                 200                 205

Asn Lys Glu Glu Ile Pro Cys Asp Pro Ile Glu Thr Ser Ser Leu Gly
    210                 215                 220

Pro Ala Glu Asn Gly Ala Cys Val Tyr Thr Trp Ala Pro Ala Pro Glu
225                 230                 235                 240

Gly Trp Tyr Tyr Asp Lys Lys Asp Asp Tyr Trp Leu Gln Tyr Val Lys
                245                 250                 255

Lys Gly Gly Tyr Gln Tyr Trp Thr Gln Ile Pro Ser Leu Glu Ser Ser
            260                 265                 270

Ala Asn Ile Tyr Arg His Leu Leu Pro Ile Leu Ile Ala Cys Leu Leu
        275                 280                 285

Gly Gly Arg Leu Ser Val Trp Ile Leu Ala Met Ile Leu Ser Leu Gln
    290                 295                 300

Val Glu Ala Ser Glu Val Gly Ala Lys Gln Leu Ala Thr Thr Leu Thr
305                 310                 315                 320

Leu Trp Lys Leu Asp Trp Thr Asp Leu Leu Phe Tyr Leu Val Leu Met
                325                 330                 335

Val Ile Val Lys Glu Glu Leu Ile Lys Lys Met Ile Thr Leu Val Leu
            340                 345                 350
```

-continued

```
Ile Leu Val Lys Asn Ser Pro Leu Ala Leu Thr Phe Leu Val Leu
            355                 360                 365

Arg Leu Ala Gly Gly Thr Glu Ala Leu Pro Val Gly Ile Leu Leu Glu
370                 375                 380

Arg Met Ser Ile Gly Gln Pro Glu Phe Gly Thr Pro Phe Ile His Tyr
385                 390                 395                 400

Ile Trp Asp Asn Trp Lys Trp Thr Ala Leu Thr Ser Phe Ala Ala Leu
                405                 410                 415

Asn Cys Glu Arg Thr Val Ser Ile Thr Lys Lys Leu Leu Ala Thr
                420                 425                 430

His Ile Phe Ala Leu Leu Leu Thr Gly Ile Ser Asp Tyr Ala Phe Leu
                435                 440                 445

Val Val Leu Ala Met Leu Asn Phe Phe Ala Lys Leu Met Ile Tyr Gly
            450                 455                 460

Leu Gly Cys Phe Leu Asn Trp Val Glu Leu Glu Lys Lys Lys Leu Leu
465                 470                 475                 480

Ala Lys Arg Met Ala Lys Arg Lys Ile Phe Lys Asp Thr Lys Gln Glu
                485                 490                 495

Ile Asp Asn Gly Asn Ser Asp Ser Thr Lys Phe Asn Arg Ile Glu Leu
                500                 505                 510

Asn Gly Glu Phe Thr Pro Val Lys Leu Glu Val Leu Gln Leu Cys Arg
                515                 520                 525

Ala Phe Ile Thr Ser Ala Met Phe Thr Tyr Tyr Lys Pro Leu Leu Tyr
            530                 535                 540

Leu Glu Thr Thr Leu Thr Ile Val Leu Leu Thr Val His Glu Tyr Arg
545                 550                 555                 560

Val Ala Met Ala Arg Gly Arg Ser Leu Ile His Lys Phe Leu Ser Val
                565                 570                 575

Ala Tyr Ala Phe Tyr Leu Gln Ile Gln Gly Gly Ser Phe Ser Arg Ala
                580                 585                 590

Ala Ile Gln Asp Phe Phe Ser Ser Pro Arg Lys Ile Met Lys His Thr
            595                 600                 605

Ile Glu Asn Pro Ile Ile Lys Gln Met Trp Arg Gly Glu Thr Glu Ile
            610                 615                 620

Phe Asn Gln Gly Val His Leu Ser Lys Leu Val Lys Pro Lys Glu Leu
625                 630                 635                 640

Gly Met Asp Asp Leu Lys Arg Gly Met Cys Gly Leu Pro Thr Ile Val
                645                 650                 655

Gln Asn Leu Val Ile Phe Ala Lys Gln His Asp Lys Leu Ile Val Gly
                660                 665                 670

Glu Val Gly Tyr Ser Pro Thr Glu Leu Thr Glu Glu Gly Trp Glu Ile
            675                 680                 685

Leu Gly Pro Gly Lys Ile Pro Lys Ile Thr Lys Ile Glu Thr Ala Lys
690                 695                 700

Met Asp Leu Leu Ser Ser Phe Met Thr Phe Ile Gly Leu Glu Thr Thr
705                 710                 715                 720

Arg Val Pro Arg Thr Pro Ile His Ser Thr Pro Lys Leu Leu Lys Ile
                725                 730                 735

Val Lys Gly Leu Glu Ser Gly Trp Gly Tyr Thr His Thr Gly Gly Ile
                740                 745                 750

Ser Thr Ala Lys His Val Thr Gly Glu Lys Asn Leu Met Ser His Met
            755                 760                 765
```

```
Glu Gly Arg Lys Gly Lys Tyr Leu Leu Gln Asn Gln Asp His Ala Ser
        770             775                 780

Asp Glu Val Glu Tyr Gly Ile Arg Thr Asp Gln Lys Ala Pro Glu Asn
785             790                 795                 800

Ser Leu Cys Tyr Cys Phe Asn Pro Glu Ala Ile Asn Ile Lys Gly Glu
                805                 810                 815

Lys Gly Ala Leu Val Phe Leu Lys Lys Lys Ala Asn Lys Trp Thr Leu
                820                 825                 830

Val Thr Ser Asp Gly Asn Lys Ala Tyr Tyr Asn Val Ser Asn Leu Lys
            835                 840                 845

Gly Trp Ser Gly Leu Pro Ile Met Leu His Ser Thr Gly Thr Ile Val
850                 855                 860

Gly Arg Ile Lys Ala Ala Tyr Pro Thr Glu Glu Asn Phe Val Glu Glu
865                 870                 875                 880

Leu Ile Asp Ser Lys Ile Leu Asn Thr Gly Lys Ala Val Pro Leu Glu
                885                 890                 895

Ile Ala Val Arg Glu Leu Glu Glu Met Gly Arg Gly Glu Phe Arg Ser
                900                 905                 910

Ile Thr Leu Gly Thr Gly Ala Gly Lys Thr Thr Glu Leu Pro Lys Asp
                915                 920                 925

Tyr Leu Ser Ala Ile Gly Thr His Lys Ser Val Leu Val Leu Val Pro
930                 935                 940

Leu Lys Ala Pro Ala Glu Ser Val Cys Lys Tyr Met Lys Lys Lys Tyr
945                 950                 955                 960

Pro Met Ile Asn Phe Ser Leu Arg Val Gly Asp His Lys Glu Gly Asp
                965                 970                 975

Leu Gln Ser Gly Ile Thr Tyr Ala Thr Tyr Gly Phe Ala Cys Gln Leu
                980                 985                 990

Asn Ile Ile Gln Leu Lys Glu Trp Val Ala Lys Phe Ser Met Val Phe
            995                 1000                1005

Phe Asp Glu Tyr His Ala Gly Thr Pro Glu Gln Leu Ala Val Ile
    1010                1015                1020

Ser Lys Val Tyr Ala Ser Lys Ala Lys Ser Arg Phe Val Ala Met
    1025                1030                1035

Ser Ala Thr Pro Pro Gly Thr Val Thr Thr Glu Gly Arg Lys Tyr
    1040                1045                1050

Asp Ile Glu Glu Ile Gly Val Ser Thr Leu Glu Arg Asn Glu Glu
    1055                1060                1065

Pro Lys His Gly Arg Leu Gly Val Ala Gly Leu Gln Val Pro Ala
    1070                1075                1080

Glu Asp Leu Thr Ser Lys Asn Cys Leu Val Phe Val Ala Thr Arg
    1085                1090                1095

Lys Glu Ala Glu Gln Val Ser Lys Glu Leu Arg Asp Lys Gly Val
    1100                1105                1110

Asn Ser His Tyr Tyr Tyr Ser Gly Leu Asp Pro Asn Thr Leu Ile
    1115                1120                1125

Gln Ala Met Thr Asn Gln Pro Tyr Thr Ile Val Ser Thr Asn Ala
    1130                1135                1140

Ile Glu Ser Gly Ile Thr Cys Pro Asp Leu Asp Val Val Val Asp
    1145                1150                1155

Thr Met Gln Lys Tyr Glu Lys Thr Val Asn Phe Ser Ala Lys Leu
    1160                1165                1170

Pro Phe Ile Thr Thr Ser Leu Val Arg Lys Arg Ile Thr Arg Glu
```

-continued

|  |  |  |  | 1175 |  |  |  | 1180 |  |  |  | 1185 |  |  |
|---|---|---|---|---|---|---|---|---|---|---|---|---|---|---|

Glu Gln Gly Gln Arg Lys Gly Arg Val Gly Arg Gln Lys Lys Gly
            1190                1195                1200

Tyr Tyr Tyr His Pro Thr Gly Ala Ala Pro Thr Gly Ser Arg Asp
            1205                1210                1215

Leu Ser Tyr Leu Leu Leu Gln Ala Gln Glu Tyr Gly Leu Leu Asp
            1220                1225                1230

Gln Met Asn Ile Thr Glu Gln Phe Ile Leu Met Asn Glu Asp Trp
            1235                1240                1245

Gly Leu Tyr Asp Val Asp Glu Val Glu Val Arg Ile Leu Glu Arg
            1250                1255                1260

Leu Asn Lys Glu Ile Leu Leu Pro Ile Gly Ile Val Glu Arg Gln
            1265                1270                1275

Ile Leu Glu Arg Ser Thr His Pro Glu Lys Ile Ser Leu Leu Tyr
            1280                1285                1290

Asn Lys Met Val Gln Gln Asn Pro Leu Val Tyr Pro Lys Ile Lys
            1295                1300                1305

Glu Gly Glu Leu Ala Arg Glu Tyr Glu Thr Tyr Asn Leu Ala Val
            1310                1315                1320

Tyr Asp Lys Val Lys Asp Thr Asn Pro Cys Ala Leu Tyr Ile Met
            1325                1330                1335

Ala Glu Glu Lys Ile Val Asp Met Leu Gly Leu Glu Phe Glu
            1340                1345                1350

Ser Leu Pro Thr Asn Leu Pro Gln Glu Val Ile Ser Leu His Ser
            1355                1360                1365

Asp Ile Gly Arg Tyr Thr Lys Leu Ser Gly Leu Thr Glu Lys Phe
            1370                1375                1380

Leu Leu Gly Thr Met Ile Gly Tyr Leu Gly Tyr Lys Ala Leu Thr
            1385                1390                1395

Arg Asn His Val Pro Trp Val Lys Ala Glu Tyr Gln Tyr Glu Leu
            1400                1405                1410

Val Asp Ser Ser Asp Thr Tyr Asp Gln Thr Tyr Ala Pro Leu Asp
            1415                1420                1425

Ile Glu Met Glu Glu Leu Gly Lys Glu Lys Ser Lys Val Asn Leu
            1430                1435                1440

Asn Ile Asn Ser Ala Glu Glu Leu Leu Lys Lys Thr Leu Glu Asn
            1445                1450                1455

Thr Asn Asn Trp Ala Lys Gly Leu Lys Glu Val Ile Met Thr Arg
            1460                1465                1470

Ile Asn Pro Glu Lys Ser Lys Lys Ile Trp Glu Lys Ile Tyr Glu
            1475                1480                1485

Tyr Leu Lys Thr His Gln Lys Asp Leu Thr Ala Ala Ala Trp
            1490                1495                1500

Gly Thr Ala Thr Ala Leu His Asp Ser Ile Lys Ser Arg Leu Gly
            1505                1510                1515

Asp Glu Val Ala Thr Ala Val Ile Leu Ile Lys Tyr Leu Ala Phe
            1520                1525                1530

Gly Asp Arg Asp Leu Gln Gly Leu Ser Arg Gln Val Leu Ile Asp
            1535                1540                1545

Ile Val Val Tyr Tyr Ile Met Asn Arg Pro Arg Phe Glu Gly Asp
            1550                1555                1560

Asp Tyr Thr Lys Arg Lys Gly Arg Arg Leu Val Val Glu Val Leu
            1565                1570                1575

Ile Gly Ala Ile Ala Ala Tyr Ser Val Ser Asn Phe Trp Gly Val
       1580            1585                1590

Ser Ile Lys Lys Ile Leu Glu Pro Ile Ser Asp Tyr Leu Pro Tyr
       1595            1600                1605

Ala Thr Ala Ala Leu Gly Tyr Leu Arg Pro Thr Phe Met Glu Ser
       1610            1615                1620

Ala Val Val Val Ala Ala Ser Ile Tyr Arg Ala Phe Leu Ser Ile
       1625            1630                1635

Lys His Ala Glu Asn Arg Ser Leu Ile Thr Gln Ile Ala Ser Ala
1640            1645                1650

Ala Leu Glu Val Met Gly Leu Thr Pro Val Ser Ala Gly Ile Gly
       1655            1660                1665

Val Leu Leu Gly Leu Gly Leu Cys Val Leu His Asn Ala Ile Glu
       1670            1675                1680

Lys Asn Glu Glu Lys Arg Val Leu Ile Leu Lys Met Phe Val Lys
       1685            1690                1695

Asn Phe Ile Asp Gln Ala Ala Leu Asp Gly Glu Ser
       1700            1705                1710

<210> SEQ ID NO 60
<211> LENGTH: 3635
<212> TYPE: PRT
<213> ORGANISM: Atypical porcine pestivirus

<400> SEQUENCE: 60

Met Glu Lys Gln Ile Ala His Tyr Leu Lys Lys Glu Lys Gln Arg Asn
1               5                   10                  15

Gly Trp Thr Glu Leu Val Val Gly Ser His Thr Lys Ile Thr Thr
            20                  25                  30

Leu Ser Gly Lys Thr Tyr Arg Gly Thr Trp Glu Met Glu Lys Arg Pro
        35                  40                  45

Asn Pro Tyr Gly Thr Tyr Phe Pro Arg Pro Ser Pro Gln Gln Leu Thr
    50                  55                  60

Ala Leu His Pro His Pro Val Val Asn Cys Lys Val Ile Glu Tyr Lys
65                  70                  75                  80

Gly Thr Asp Pro Asn Tyr Gly Asp Cys Pro Asn Thr Asn Gly Val Phe
                85                  90                  95

Ile Asp Glu Lys Gly Arg Arg Leu Ser Ser Pro Leu Gly Ile Trp
            100                 105                 110

Lys Ile Arg Leu Asp Tyr Ser Asp Leu Ile Asn Ile Asn Arg Pro Val
        115                 120                 125

Pro Thr Arg Gly Glu Asn Ser Tyr Arg Val Glu Thr Cys Ser Gly Glu
    130                 135                 140

Leu Ala Thr Val Met Leu Val His Asn Arg Val Leu Val Glu Asp Cys
145                 150                 155                 160

Arg Gly Leu Tyr Gln Trp Lys Pro Asn Cys Glu Gly Ile Val Leu Tyr
                165                 170                 175

Val Lys Thr Cys Ser Asp Trp Ala Asp Gln Val Glu Lys Gln Glu Lys
            180                 185                 190

Gly Ser Pro Pro Lys Pro Gln Arg Pro Arg Arg Asp Pro Arg Lys
        195                 200                 205

Gly Leu Gln Pro Gln Val Pro Arg Glu Thr Glu Val Thr Glu Lys Lys
    210                 215                 220

Arg Gln Pro Ser Val Thr Leu Val Ala Gly Gly Gln Lys Ala Gln Ile

```
                225                 230                 235                 240
Ile Tyr Lys Gly Arg Thr Lys Asn Lys Lys Thr Pro Asp Gly Val Tyr
                245                 250                 255
Lys Tyr Pro Gly Ala Lys Glu Gly Asp Val Lys Val Arg Lys Met
            260                 265                 270
Leu Lys Asn Trp His Ile Ala Leu Ile Met Tyr Leu Ile Tyr Ile Ile
            275                 280                 285
Thr Pro Gly Phe Ala Lys Val Gln Trp Phe Leu Lys Asp Glu Asn Ser
            290                 295                 300
Thr Gly Ile Asn Gln Ile Leu Trp Gln Arg Gln Ile Asn Arg Thr Leu
305                 310                 315                 320
His Gly Glu Trp Pro Asn Gln Ile Cys His Gly Met Pro Asn Glu Thr
                325                 330                 335
Ile Thr Asp Glu Glu Leu Arg Ser Leu Gly Met Ile Asp Thr Ser Pro
            340                 345                 350
Arg Thr Asn Tyr Thr Cys Cys Gln Leu Gln Tyr His Glu Trp Lys Lys
            355                 360                 365
His Gly Trp Cys Asn Tyr Pro Gln Lys Gln Val Trp Ile Arg Arg Ile
            370                 375                 380
Thr Ala Leu Gln Ala Asn Leu Thr Gly Ala Tyr Glu Gly Pro Glu Cys
385                 390                 395                 400
Ala Val Ile Cys Arg Phe Asn Gly Ser Tyr Asn Ile Val Lys Gln Ala
                405                 410                 415
Arg Asp Glu Val Ser Pro Leu Thr Gly Cys Lys Glu Gly His Pro Phe
            420                 425                 430
Leu Phe Ser Gly Glu Arg Ser Asp Thr Ser Cys Leu Arg Pro Pro Ser
            435                 440                 445
Thr Ser Trp Val Arg Pro Val Lys Met Asp Glu Ala Ser Leu Ala Asp
            450                 455                 460
Ser Phe Ala His Gly Val Asp Lys Ala Ile Ile Leu Ile Arg Lys Gly
465                 470                 475                 480
Ala Ser Gly Ile Ile Asn Phe Leu Asp Thr Ile Gly Arg Trp Leu Pro
                485                 490                 495
Val Ala Glu Ala Ala Ile Val Pro Tyr Cys Glu Thr Tyr Thr Val Thr
            500                 505                 510
Gly Met Tyr Val His Val Lys Asn Cys Leu Pro Arg Gly Leu Pro Lys
            515                 520                 525
His Ser Lys Ile Ile Ser Pro Thr Ile Tyr Leu Gly Glu Gly Asp
            530                 535                 540
Pro Ala His Asn Ile Gln His Leu Phe Gly Ser Gly Ile Ala Lys Trp
545                 550                 555                 560
Val Leu Val Leu Leu Gly Val Leu Gly Glu Trp Tyr Gly Glu Leu Ala
                565                 570                 575
Ser Thr Ile Tyr Leu Leu Glu Tyr Gly Ser Glu Trp Leu Glu His
            580                 585                 590
Glu Ser Leu Val Thr Glu Gly Leu Ile Pro Gly Ile Asn Thr Ile
            595                 600                 605
Glu Leu Pro Ala Ser His Thr Val Pro Gly Trp Val Trp Val Ala Gly
            610                 615                 620
Arg Trp Val Cys Val Lys Pro Asp Trp Pro Thr Gln Ile Trp Ile
625                 630                 635                 640
Glu Thr Ile Val Ala Glu Val Trp His Ile Leu Lys Ile Leu Ala Ser
                645                 650                 655
```

-continued

```
Ala Leu Val Asn Ile Val Thr Ala Phe Val Asn Leu Glu Leu Val Tyr
                660             665             670

Leu Val Ile Ile Leu Val Lys Ile Ser Lys Gly Asn Leu Ile Gly Ala
            675             680             685

Ile Leu Trp Cys Leu Leu Leu Ser Gly Ala Glu Gly Ser Cys His Lys
        690             695             700

Arg Gln Asp Tyr Tyr Ser Ile Gln Leu Val Val Asp Gly Lys Thr Gly
705             710             715             720

Val Glu Lys Arg Ser Ile Val Gly Lys Trp Thr Val Ile Thr Arg Glu
            725             730             735

Gly Arg Glu Pro Arg Leu Met Glu Gln Ile Ser Met Val Ser Asn Asp
            740             745             750

Ser Leu Ser Glu Thr Tyr Cys Tyr Asn Arg Leu Asn Thr Ser Ser Trp
            755             760             765

Gly Arg Gln Pro Ala Arg Gln Arg Gly Cys Gly Gln Thr Val Pro Phe
            770             775             780

Trp Pro Gly Asp Asn Val Leu Glu Glu Gln Tyr Tyr Ser Thr Gly Tyr
785             790             795             800

Trp Val Asn Ala Thr Gly Gly Cys Gln Leu Arg Glu Gly Val Trp Leu
            805             810             815

Ser Arg Lys Gly Asn Val Gln Cys Gln Arg Asn Gly Ser Ser Leu Ile
            820             825             830

Leu Gln Leu Ala Ile Lys Glu Glu Asn Asp Thr Met Glu Ile Pro Cys
            835             840             845

Asp Pro Val Glu Thr Glu Ser Met Gly Pro Val Thr Gln Gly Thr Cys
850             855             860

Val Tyr Ser Trp Ala Phe Ala Pro Arg Gly Trp Tyr Tyr Asn Arg Lys
865             870             875             880

Asp Gly Tyr Trp Leu Gln Tyr Val Lys Lys Asn Asp Tyr Gln Tyr Trp
            885             890             895

Thr Lys Met Pro Thr Ala Ser Ser Ala Thr Thr Met Tyr Arg His Leu
            900             905             910

Leu Pro Leu Leu Val Ala Cys Leu Met Gly Gly Arg Ile Ser Val Trp
            915             920             925

Ile Val Ala Met Leu Leu Ser Leu Gln Val Glu Ala Ser Glu Val Gly
            930             935             940

Thr Lys Gln Leu Ala Val Thr Leu Thr Leu Trp Lys Met Asp Trp Thr
945             950             955             960

Glu Leu Leu Phe Tyr Ile Val Ile Met Leu Ala Val Lys Glu Glu Leu
                965             970             975

Ile Lys Lys Ile Val Thr Ala Ser Leu Val Ala Leu Lys Asn Ser Pro
            980             985             990

Val Ala Leu Ser Phe Leu Ile Val Leu Arg Leu Val Gly Gly Ser Glu
            995             1000            1005

Ala Leu  Pro Val Gly Leu Leu  Leu Glu Lys Met Cys  Ile Asp Gln
    1010            1015            1020

Pro Glu  Phe Gly Thr Pro Phe  Leu Ile Tyr Leu Trp  Asp Asn Trp
    1025            1030            1035

Lys Trp  Thr Val Leu Val Ser  Phe Ser Ala Leu Asn  His Glu Lys
    1040            1045            1050

Thr Ile  Lys Leu Ala Arg Lys  Leu Leu Leu Ala Thr  His Ile Thr
    1055            1060            1065
```

```
Ala Leu Thr Leu Thr Gly Leu Ser Asp Ser Ile Phe Tyr Met Met
    1070            1075             1080

Leu Ile Met Thr Asn Leu Leu Ile Lys Thr Phe Ile Tyr Leu Leu
    1085            1090             1095

Gly Ala Ser Ile Asn Trp Val Glu Arg Glu Lys Lys Lys Leu Leu
    1100            1105             1110

Val Lys Arg Thr Leu Ile Tyr Lys Lys Ala Ala Ile Cys Ser Gln
    1115            1120             1125

Asp Gly Asn Glu Leu Glu Asn Lys Phe Asn Lys Ile Thr Val Asn
    1130            1135             1140

Ala Asp Phe Thr Pro Cys Lys Leu Glu Leu Leu Gln Leu Leu Arg
    1145            1150             1155

Ala Phe Leu Val Ser Leu Cys Phe Ser Tyr Tyr Lys Pro Leu Leu
    1160            1165             1170

Tyr Ala Glu Thr Thr Leu Thr Val Ile Val Ile Gly Val Gln Glu
    1175            1180             1185

Tyr Asn Val Ala Met Ala Arg Gly Arg Ser Val Val His Arg Leu
    1190            1195             1200

Leu Ala Met Ala Tyr Tyr Ile Tyr Gly Arg Ile Gln Gly Asp Met
    1205            1210             1215

Phe Gln Leu Ala Thr Ile Gln Cys Leu Leu Ser Ser Pro Arg Lys
    1220            1225             1230

Ile Met Lys His Met Ile Glu Asn Pro Thr Leu Lys Lys Leu Trp
    1235            1240             1245

Gln Gly Glu Thr Glu Leu Phe Asn Gln Gly Val Ser Gln Ser Lys
    1250            1255             1260

Ile Val Asn Pro Lys Ser Ile Gly Leu Glu Glu Leu His Lys Gly
    1265            1270             1275

Met Cys Gly Leu Pro Thr Val Val Gln Asn Leu Val Ile Tyr Ala
    1280            1285             1290

Lys Lys Asn Asp Ser Leu Ile Leu Gly Glu Leu Gly Tyr Pro Pro
    1295            1300             1305

Gly Asp Leu Thr Ser Asp Gly Trp Glu Ile Leu Gly Pro Gly Arg
    1310            1315             1320

Ile Pro Lys Ile Thr Asn Val Glu Ser Ala Lys Met Asp Leu Leu
    1325            1330             1335

Ser Lys Leu Met Thr Phe Leu Gly Val Glu Ser Ser Arg Val Pro
    1340            1345             1350

Arg Thr Pro Val His Ser Thr Arg Lys Leu Leu Lys Ile Val Arg
    1355            1360             1365

Gly Leu Glu Thr Gly Trp Gly Tyr Thr His Ala Gly Gly Ile Ser
    1370            1375             1380

Ser Ala Lys His Val Thr Gly Glu Lys Asn Leu Met Thr His Met
    1385            1390             1395

Glu Gly Arg Lys Gly Lys Tyr Ile Leu Gln Ser Gln Glu His Gly
    1400            1405             1410

Ala Asp Glu Val Glu Tyr Gly Val Lys Thr Asp Gln Lys Ala Pro
    1415            1420             1425

Asp Asn Ala Leu Cys Tyr Cys Phe Asn Pro Glu Ala Thr Asn Ile
    1430            1435             1440

Lys Gly Glu Thr Gly Ala Met Val Phe Met Lys Lys Ile Gly Lys
    1445            1450             1455

Lys Trp Thr Leu Val Thr Ser Asp Gly Asn Lys Ala Tyr Tyr Asn
```

-continued

```
              1460                1465                1470
Val  Asn  Asn  Leu  Lys  Gly  Trp  Ser  Gly  Leu  Pro  Ile  Met  Leu  His
              1475                1480                1485

Ser  Thr  Gly  Ala  Ile  Val  Gly  Arg  Ile  Lys  Ser  Ala  Tyr  Ser  Asp
              1490                1495                1500

Glu  Asn  Asp  Leu  Val  Glu  Glu  Leu  Ile  Asp  Ser  Arg  Thr  Ile  Ser
              1505                1510                1515

Lys  Ser  Asn  Glu  Ala  Asn  Leu  Asp  His  Leu  Ile  Lys  Glu  Leu  Ala
              1520                1525                1530

Asp  Met  Arg  Arg  Gly  Glu  Phe  Arg  Ser  Ile  Thr  Leu  Gly  Thr  Gly
              1535                1540                1545

Ala  Gly  Lys  Thr  Thr  Glu  Leu  Pro  Arg  Gln  Tyr  Leu  Thr  Thr  Val
              1550                1555                1560

Gly  Ala  His  Lys  Ser  Val  Leu  Val  Leu  Val  Pro  Leu  Lys  Ala  Pro
              1565                1570                1575

Ala  Glu  Ser  Val  Cys  Arg  Phe  Met  Arg  Ser  Lys  Tyr  Pro  Thr  Ile
              1580                1585                1590

Asn  Phe  Ser  Leu  Arg  Val  Gly  Glu  Arg  Lys  Glu  Gly  Asp  Val  Ser
              1595                1600                1605

Ser  Gly  Ile  Thr  Tyr  Ala  Thr  Tyr  Gly  Phe  Cys  Cys  Gln  Leu  Asn
              1610                1615                1620

Leu  Val  Gln  Leu  Lys  Glu  Trp  Ile  Ser  Arg  Tyr  Ser  Met  Val  Phe
              1625                1630                1635

Phe  Asp  Glu  Tyr  His  Thr  Ala  Thr  Pro  Glu  Gln  Ile  Ala  Ile  Ile
              1640                1645                1650

Ser  Lys  Ile  His  Ala  Leu  Lys  Val  Lys  Thr  Arg  Ile  Val  Ala  Met
              1655                1660                1665

Ser  Ala  Thr  Pro  Pro  Gly  Thr  Val  Thr  Thr  Glu  Gly  Arg  Lys  Phe
              1670                1675                1680

Asp  Ile  Glu  Glu  Val  Gly  Val  Ala  Thr  Ile  Glu  Lys  Gly  Glu  Glu
              1685                1690                1695

Pro  Lys  Arg  Gly  Arg  Ile  Ala  Val  Ala  Gly  Met  Gln  Val  Pro  Leu
              1700                1705                1710

Glu  Asp  Leu  Thr  Gly  Lys  Asn  Cys  Leu  Val  Phe  Val  Ala  Thr  Lys
              1715                1720                1725

Glu  Ala  Ala  Glu  Thr  Glu  Ala  Lys  Glu  Leu  Arg  Ala  Arg  Gly  Val
              1730                1735                1740

Asn  Ala  Thr  Tyr  Tyr  Tyr  Ser  Gly  Ile  Asp  Pro  Lys  Thr  Leu  Glu
              1745                1750                1755

His  Gly  Met  Thr  Asn  Gln  Pro  Tyr  Cys  Ile  Val  Ala  Thr  Asn  Ala
              1760                1765                1770

Ile  Glu  Ser  Gly  Ile  Thr  Cys  Pro  Asp  Leu  Asp  Val  Val  Ile  Asp
              1775                1780                1785

Thr  Met  Gln  Lys  Tyr  Glu  Lys  Val  Val  Asn  Phe  Ser  Ala  Lys  Leu
              1790                1795                1800

Pro  Leu  Ile  Val  Thr  Ser  Leu  Val  Lys  Lys  Lys  Ile  Thr  Arg  Glu
              1805                1810                1815

Glu  Gln  Gly  Gln  Arg  Lys  Gly  Arg  Val  Gly  Arg  Gln  Lys  Lys  Gly
              1820                1825                1830

Lys  Tyr  Tyr  Tyr  Pro  Ser  Gly  Val  Val  Pro  Asn  Gly  Ser  Lys  Asp
              1835                1840                1845

Leu  Ser  Tyr  Leu  Ile  Leu  Gln  Ala  Gln  Glu  Tyr  Gly  Ile  Leu  Glu
              1850                1855                1860
```

-continued

```
Gln Val Asn Ile Thr Glu Tyr Phe Ile Ile Met Asn Glu Asp Trp
    1865                1870                1875

Gly Leu Tyr Asp Val Asp Glu Val Glu Val Arg Ile Leu Glu Arg
    1880                1885                1890

Met Asn Lys Glu Ile Leu Leu Pro Leu Gly Ile Val Glu Lys Gln
    1895                1900                1905

Ile Leu Glu Arg Ser Thr His Pro Glu Lys Val Ala Leu Leu Tyr
    1910                1915                1920

Asn Lys Leu Val Gln Lys Asn Pro Ile Val Tyr Pro Lys Val Gln
    1925                1930                1935

Glu Gly Glu Val Ser Lys Glu Tyr Asn Thr His Asn Leu Ala Val
    1940                1945                1950

Tyr Asp Lys Leu Lys Asp Val Asn Pro Gln Ala Ile Tyr Val Leu
    1955                1960                1965

Ala Glu Glu Glu Arg Ala Thr Glu Met Met Gly Leu Glu Phe Glu
    1970                1975                1980

Gln Asp Pro Ser Asp Leu Gln Asp Ser Val Ala Gln Leu Cys Glu
    1985                1990                1995

Asp Ile Lys Arg Tyr Thr Lys Leu Ser Gly Ile Thr Glu Lys Leu
    2000                2005                2010

Leu Val Gly Thr Met Val Gly Tyr Ile Gly Tyr Lys Ala Leu Thr
    2015                2020                2025

Arg Asn His Val Pro Trp Val Ser Lys Glu Tyr Ser Tyr Glu Leu
    2030                2035                2040

Thr Asp Ser Pro Asp Thr Tyr Glu Asn Ser Phe Ala Pro Leu Asp
    2045                2050                2055

Val Asp Val Gln Asn Pro Gly Glu Gly Lys His Pro Glu Gln Leu
    2060                2065                2070

Ala Asp His Gln Leu Arg Gln Leu Leu Glu Thr Gly Arg Asp Lys
    2075                2080                2085

Ala Ile Asp Phe Leu Lys Gly Ile Arg Glu Phe Ala Ser Gly Ala
    2090                2095                2100

Ile Asn Ser Pro Lys Ala Leu Ser Ile Trp Glu Lys Met Tyr Gln
    2105                2110                2115

Tyr Leu Arg Lys His Gln Gly Glu Ile Ile Ala Ser Ala Ala Trp
    2120                2125                2130

Gly Ser Ala Thr Ala Leu His Asp Ser Ile Lys Ser Arg Leu Gly
    2135                2140                2145

Asp Glu Val Ala Thr Ala Val Ile Ile Leu Lys Tyr Leu Ala Phe
    2150                2155                2160

Gly Glu Arg Glu Leu Ser Gly Leu Thr Arg Gln Val Leu Ile Asp
    2165                2170                2175

Ile Ile Val Tyr Tyr Ile Val Asn Lys Pro Arg Phe Glu Gly Asp
    2180                2185                2190

Asp Tyr Ala Lys Arg Lys Gly Arg Arg Leu Val Ile Glu Val Leu
    2195                2200                2205

Met Gly Ala Leu Ala Thr Tyr Ala Val Ser Asn Phe Trp Gly Val
    2210                2215                2220

Ser Ile Asn Lys Ile Leu Gln Pro Ile Ser Asp Tyr Leu Pro Tyr
    2225                2230                2235

Ala Thr Ala Thr Leu Ala Phe Leu Arg Pro Thr Phe Met Glu Ser
    2240                2245                2250
```

```
Ala Val Val Val Ala Ser Ser Ile Tyr Arg Ala Phe Leu Ser Ile
        2255                2260                2265

Lys His Ala Glu Asn Arg Ser Leu Val Thr Gln Val Ala Ser Ala
2270                2275                2280

Ala Leu Glu Val Met Gly Leu Thr Pro Val Ser Ala Gly Leu Gly
        2285                2290                2295

Val Leu Leu Gly Leu Gly Leu Cys Val Leu His Met Asn Ile Asp
2300                2305                2310

Lys Asn Glu Glu Lys Arg Thr Leu Ile Leu Lys Met Phe Val Lys
        2315                2320                2325

Asn Phe Ile Asp Gln Ala Ala Leu Asp Glu Leu Asp Lys Leu Glu
2330                2335                2340

Pro Glu Lys Ile Ile Leu Ser Leu Leu Glu Gly Ile Gln Thr Cys
        2345                2350                2355

Thr Asn Pro Val Arg Ala Ile Met Ile Leu Tyr Arg Val Tyr Tyr
2360                2365                2370

Lys Gly Glu Ser Phe Thr Glu Ala Leu Ser Lys Met Ala Gly Lys
        2375                2380                2385

Ser Leu Ile Val Met Val Ile Val Glu Phe Leu Glu Leu Thr Gly
2390                2395                2400

Gln Thr Gln Gly Gly Tyr Ile Asp Leu Ser Ala Asn Leu Leu Thr
        2405                2410                2415

Leu Leu Leu Glu Lys Leu Lys Lys Met Thr Asn Leu Ala Ile Gly
2420                2425                2430

Glu Ala Arg Lys Val Leu Leu Pro Ile Pro Tyr Leu Tyr Cys Glu
        2435                2440                2445

Thr Trp Gln Ser Asp Ala Arg Ile Lys Ala Pro Glu Ser Tyr Asp
2450                2455                2460

Gln Val Val Val Glu Cys Lys Cys Gly Ala Ser Ala Arg Tyr Ser
        2465                2470                2475

Phe Arg His Gly Val His Glu Ile Leu Glu Glu Lys Arg Thr Lys
2480                2485                2490

Trp Cys Lys Asn Phe Phe Leu Trp Gly Pro Asn Phe His Asn Pro
        2495                2500                2505

Asp Pro Lys Arg Met Thr Phe Tyr Glu Phe Gly Gln Ala Lys Lys
2510                2515                2520

Cys Pro Val Val Ile Met Gly Glu Asp Ile Thr Phe Gly Lys Tyr
        2525                2530                2535

Gly Ile Tyr Ile Lys Phe Gly His Lys Pro Asp Gly Gly Arg Leu
2540                2545                2550

Ile Arg Gly Thr Thr His Ala Thr Ile Ser Arg Glu Glu Leu Leu
        2555                2560                2565

Glu Ile Leu Thr Ala Pro Ser Gln Val Ala Ile Gly Lys Val Lys
2570                2575                2580

Leu Thr Asp Tyr Cys Asn Gln Lys Gly Ile Ile Asp Arg Lys Leu
        2585                2590                2595

Ala Val Leu Glu Gly Asp Lys Ile His Phe Trp Lys Ala His Arg
2600                2605                2610

Gly Ser Lys Ile Thr Asp Gln Leu Thr Ile Glu Ser Leu Thr Asp
        2615                2620                2625

Asp Leu Gly Ser Glu Ile Arg Asp Ile Thr Trp Glu Leu Tyr Thr
2630                2635                2640

Gly Gly Thr Cys Thr Val Lys Gly Ile Ser Leu Arg Ser Cys Ala
```

|  |  |  |  |  |  |  |  |  |  |
|---|---|---|---|---|---|---|---|---|---|
|  |  | 2645 |  |  | 2650 |  |  | 2655 |  |
| Pro | Gly | Gln | Arg | Asn | Lys | Ala | Thr | Val | Leu | Cys | Asp | Cys | Thr | Asp |
|  |  | 2660 |  |  |  | 2665 |  |  | 2670 |
| Val | Leu | Ser | Pro | Cys | Tyr | Leu | Val | Asn | Gly | Arg | Arg | Pro | Ser | Pro |
|  |  | 2675 |  |  |  | 2680 |  |  | 2685 |
| Phe | Asp | Val | Val | Glu | Gly | Tyr | Glu | Cys | His | His | Arg | Lys | Pro | Arg |
|  |  | 2690 |  |  |  | 2695 |  |  | 2700 |
| Ala | Thr | Tyr | Glu | Asp | Leu | Glu | Met | Glu | Glu | Ile | Leu | Lys | Arg | Arg |
|  |  | 2705 |  |  |  | 2710 |  |  | 2715 |
| Val | Pro | Val | Tyr | Asp | Pro | Leu | Ser | Leu | Phe | Asp | Thr | Asp | Ser | Lys |
|  |  | 2720 |  |  |  | 2725 |  |  | 2730 |
| Leu | Leu | Pro | Pro | Asp | Thr | Tyr | Tyr | Leu | Glu | Glu | Asp | Gln | Glu | Asp |
|  |  | 2735 |  |  |  | 2740 |  |  | 2745 |
| Phe | Glu | Tyr | Ala | Leu | Arg | Cys | Trp | Gly | Leu | Gly | Val | Tyr | Val | Thr |
|  |  | 2750 |  |  |  | 2755 |  |  | 2760 |
| Asp | Gly | Pro | Ala | Ile | Ser | Pro | Pro | Asp | Ile | Arg | Val | His | His | Ser |
|  |  | 2765 |  |  |  | 2770 |  |  | 2775 |
| Ser | Val | Leu | Leu | Leu | Leu | Thr | Pro | Gly | Val | Asp | Ser | Glu | Leu | Pro |
|  |  | 2780 |  |  |  | 2785 |  |  | 2790 |
| Leu | Gln | Tyr | Ile | Arg | Cys | Tyr | Ser | His | Gln | Val | Glu | Val | Asp | Ile |
|  |  | 2795 |  |  |  | 2800 |  |  | 2805 |
| Tyr | Ile | Arg | Gly | Gln | Leu | Leu | Glu | Glu | Glu | Asp | Thr | Ala | Thr | Glu |
|  |  | 2810 |  |  |  | 2815 |  |  | 2820 |
| Ala | Glu | Asp | Ser | Gln | Glu | Asp | Ser | Asp | Glu | Gly | Met | Gly | Asp | Val |
|  |  | 2825 |  |  |  | 2830 |  |  | 2835 |
| Val | Ile | Lys | Asp | Glu | Asp | Thr | Leu | Ser | Thr | Thr | Glu | Ser | Ile | Pro |
|  |  | 2840 |  |  |  | 2845 |  |  | 2850 |
| Pro | Leu | Glu | Glu | Glu | Glu | Gly | Gly | Glu | Glu | Pro | Ile | Thr | Tyr | Val |
|  |  | 2855 |  |  |  | 2860 |  |  | 2865 |
| Val | Ile | Arg | Gly | Leu | Gln | Glu | Glu | Arg | Tyr | Thr | Ser | His | Leu | Lys |
|  |  | 2870 |  |  |  | 2875 |  |  | 2880 |
| Leu | Ser | Asp | Trp | Ile | Ser | Glu | Asn | Ile | Ser | Glu | Pro | His | Arg | Val |
|  |  | 2885 |  |  |  | 2890 |  |  | 2895 |
| Gln | Ile | Met | Leu | Asp | Gly | Thr | Val | Arg | Val | Thr | Ile | Lys | Glu | Gly |
|  |  | 2900 |  |  |  | 2905 |  |  | 2910 |
| Lys | Val | Lys | His | Leu | Phe | Gly | Val | Tyr | Arg | Ile | Glu | Asn | Ser | Leu |
|  |  | 2915 |  |  |  | 2920 |  |  | 2925 |
| Glu | Ala | Met | Phe | Lys | Glu | Thr | Ile | Ala | Asp | Leu | Pro | Val | Ala | Thr |
|  |  | 2930 |  |  |  | 2935 |  |  | 2940 |
| Gln | Pro | Pro | Arg | Gly | Pro | Ile | Tyr | Thr | Ala | Lys | Glu | Leu | Ala | Gln |
|  |  | 2945 |  |  |  | 2950 |  |  | 2955 |
| Gly | Asn | Ile | Ala | Pro | Ile | Gln | Pro | Ala | Ala | Asn | Phe | Tyr | Gly | Met |
|  |  | 2960 |  |  |  | 2965 |  |  | 2970 |
| Ile | Glu | Gly | Arg | Gly | Asp | Pro | Met | Thr | Ala | Phe | Glu | Ala | Leu | Ser |
|  |  | 2975 |  |  |  | 2980 |  |  | 2985 |
| Val | Leu | Arg | Ser | Gln | Lys | Val | Ser | Ala | Lys | Glu | Val | Lys | Met | Asn |
|  |  | 2990 |  |  |  | 2995 |  |  | 3000 |
| Thr | Arg | Arg | Ala | Gln | Ala | Phe | Leu | Asn | Lys | Val | Arg | Gly | Thr | Ala |
|  |  | 3005 |  |  |  | 3010 |  |  | 3015 |
| Glu | Val | Arg | Ala | Ser | Glu | Leu | Thr | Leu | Lys | Cys | Leu | Pro | Ala | Leu |
|  |  | 3020 |  |  |  | 3025 |  |  | 3030 |
| Gly | Lys | Val | Asn | Gly | Arg | Lys | Leu | Ile | Arg | Glu | Glu | Thr | Asn | Ile |
|  |  | 3035 |  |  |  | 3040 |  |  | 3045 |

```
Pro Asn Gln Arg Leu Ala Ser Ile Met Thr Ser Ile Gly Ile Arg
3050                3055                3060

Leu Glu Lys Leu Pro Val Val Arg Ala Asn Thr Ser Gly Ser Lys
3065                3070                3075

Phe Arg Gln Ser Ile Leu Glu Lys Met Asp Lys Tyr Glu Asn Glu
3080                3085                3090

Gln Val Pro Gly Leu His Glu Lys Met Trp Ala Ala Phe Leu Ala
3095                3100                3105

Thr Ala Arg Gln Asp Leu Arg Asn Thr Tyr Glu Glu Val Thr Tyr
3110                3115                3120

Leu Glu Leu Glu Thr Gly Ile Asn Arg Lys Gly Ala Pro Gly Phe
3125                3130                3135

Phe Glu Lys Glu Ser Ser Ile Gly Glu Val Leu Glu Arg Lys Gly
3140                3145                3150

Lys Ile Asp Val Val Ile Gln Glu Ile Glu Lys Gly Asn His Leu
3155                3160                3165

Tyr Tyr Glu Thr Ala Met Pro Lys Asn Glu Lys Arg Asp Val Leu
3170                3175                3180

Asp Asp Trp Leu Ser Glu Asp Phe Val Thr Tyr Lys Lys Pro Arg
3185                3190                3195

Val Ile Gln Tyr Pro Glu Ala Val Thr Arg Leu Ala Ile Thr Lys
3200                3205                3210

Ile Met Tyr Lys Trp Val Lys Gln Lys Pro Ile Val Ile Pro Gly
3215                3220                3225

Tyr Glu Gly Lys Thr Pro Ile Phe Glu Ile Phe Glu Lys Val Ser
3230                3235                3240

Ala Asp Trp Ala Gln Phe Arg Asn Pro Val Ala Val Ser Phe Asp
3245                3250                3255

Thr Lys Ala Trp Asp Thr Gln Val Thr Arg Glu Asp Leu Arg Leu
3260                3265                3270

Val Gly Arg Ile Gln Lys Tyr Tyr Tyr Lys Lys Lys Tyr Trp Lys
3275                3280                3285

Phe Ile Asp Asn Leu Thr Ala Met Met Glu Glu Val Pro Val Ile
3290                3295                3300

Thr Val Glu Gly Asp Met Phe Leu Arg Val Gly Gln Arg Gly Ser
3305                3310                3315

Gly Gln Pro Asp Thr Ser Ala Gly Asn Ser Ile Leu Asn Val Leu
3320                3325                3330

Thr Met Leu Val Ala Phe Ser Glu Ser Thr Asn Leu Pro Ile Ala
3335                3340                3345

Ala Ala Trp Lys Ala Cys Arg Ile His Val Cys Gly Asp Asp Gly
3350                3355                3360

Phe Leu Ile Thr Glu Ser Glu Leu Gly Arg Lys Phe Ala Glu Lys
3365                3370                3375

Gly Val Pro Leu Leu Ala Ala Phe Gly Lys Pro Gln Lys Ile Thr
3380                3385                3390

Glu Gly Ala Ser Leu Lys Ile Thr Ser Asn Phe Asp Gly Ile Glu
3395                3400                3405

Phe Cys Ser His Ser Pro Ile Arg Val Gln Thr Pro Asn Ile Arg
3410                3415                3420

Trp Met Pro Ala Arg Pro Thr Ala Thr Ile Leu Gly Lys Met Ser
3425                3430                3435
```

-continued

```
Thr Arg Leu Gly Glu Gly Ala Thr Arg Ser Gly Glu Glu Tyr Glu
    3440            3445            3450

Lys Gln Val Ala Phe Ala Tyr Leu Leu Met Tyr Pro Trp Asn Pro
3455            3460            3465

Leu Val Arg Arg Ile Ser Leu Leu Leu Ser Thr Thr Asp Pro
    3470            3475            3480

Met Gly Arg Glu Glu Thr Pro Cys Ser Asp Glu Gly Val Lys Tyr
    3485            3490            3495

Val Gly Asp Pro Ile Ala Ala Tyr Arg Asp Val Trp Gly His Lys
    3500            3505            3510

Leu Glu Asp Val Gly His Val Asp Gln Pro Gln Leu Ser Arg Met
    3515            3520            3525

Asn Tyr Ser Met Thr Tyr Leu Gly Ile Trp Lys Pro Lys Thr Ser
    3530            3535            3540

Gln Arg Leu Val Glu Gln Cys Cys Arg Leu Ala Glu Lys Asn Asn
    3545            3550            3555

Cys Val Ala Arg Ala Asp Ser Leu Ile Lys Lys Val Lys Ile
    3560            3565            3570

Thr Tyr Asp Pro Gly Ile Gly Ala Ala Gln Val Ile Arg Arg Trp
    3575            3580            3585

Glu Glu Leu Glu Trp Thr Arg Arg Lys Pro Glu Pro Ser Asn Ala
    3590            3595            3600

Thr Ala Glu Asp Asp Ile Phe Leu Val Leu Trp Lys Arg Phe Ser
    3605            3610            3615

Lys Tyr Ile Phe Gln Lys Met Lys Phe Met Gln Arg Met Leu Ala
    3620            3625            3630

Pro Tyr
    3635

<210> SEQ ID NO 61
<211> LENGTH: 3918
<212> TYPE: PRT
<213> ORGANISM: Bungowannah virus

<400> SEQUENCE: 61

Met Asn Thr Phe Thr Phe Asn Thr Tyr Gly Gly Ser Glu Glu Gly Asn
1               5                   10                  15

Met Phe Phe Arg Thr Ala Pro Thr Pro Pro Gly Cys Gln Glu Pro
            20                  25                  30

Val Tyr Thr Ser Thr Met Arg Pro Ile Phe Gly Glu Pro His Pro Pro
            35                  40                  45

Leu His Lys His Ser Thr Leu Lys Leu Pro His Trp Arg Gly Ile Lys
50                  55                  60

Thr Ile Arg Val Lys Lys Arg Glu Leu Pro Lys Gly Asp Cys Ser
65                  70                  75                  80

Asn Ser Thr Thr Ala Pro Thr Ser Gly Val Tyr Val Glu Leu Gly Ala
            85                  90                  95

Val Phe Tyr Lys Asp Tyr Thr Gly Thr Val Tyr His Arg Val Pro Leu
            100                 105                 110

Glu Leu Cys Thr Asn Gln Glu Arg Cys Glu Gly Ser Lys Cys Val Gly
            115                 120                 125

Arg Met Thr Gly Ser Asp Gly Arg Leu Tyr Asn Val Leu Val Cys Pro
    130                 135                 140

Asp Asp Cys Ile Leu Phe Glu Arg His Cys Arg Gly Gln Thr Val Val
145                 150                 155                 160
```

```
Leu Lys Trp Ile Ser Asn Pro Leu Thr Ser Pro Leu Trp Val Gln Ser
                165                 170                 175

Cys Ser Asp Asp Lys Gly Ala Lys Pro Lys Val Lys Pro Lys Asp Asp
            180                 185                 190

Arg Met Lys Gln Gly Lys Ile Val Thr Lys Pro Lys Glu Thr Glu Ala
        195                 200                 205

Asp Gln Lys Thr Arg Pro Pro Asp Ala Thr Ile Val Val Asp Gly Gln
    210                 215                 220

Lys Tyr Gln Val Arg Lys Gly Lys Ala Lys Pro Lys Thr Gln Asp
225                 230                 235                 240

Gly Leu Tyr His Asn Lys Asn Lys Pro Glu Ala Ser Arg Lys Lys Leu
                245                 250                 255

Glu Lys Ala Leu Leu Ala Trp Ala Ile Leu Ala Cys Leu Leu Val Val
            260                 265                 270

Pro Val Gly Ser Thr Asn Val Thr Gln Trp Asn Leu Trp Asp Asn Lys
        275                 280                 285

Ser Thr Thr Asp Ile His Ser Val Met Phe Ser Arg Gly Ile Lys Arg
    290                 295                 300

Ser Leu His Gly Ile Trp Pro Thr Gln Ile Cys Lys Gly Ile Pro Thr
305                 310                 315                 320

His Leu Ala Ala Asp Tyr Glu Leu Lys Arg Ile His Gly Met Val Asp
                325                 330                 335

Ala Ser Pro Met Thr Asn Phe Thr Cys Cys Arg Leu Gln Arg His Glu
            340                 345                 350

Trp Asn Lys His Gly Trp Cys Asn Trp Tyr Asn Ile Glu Pro Trp Ile
        355                 360                 365

Asn Leu Met Asn Asn Thr Gln Gly Leu Leu Asn Thr Gly Asp Asn Phe
    370                 375                 380

Thr Glu Cys Ala Val Thr Cys Arg Tyr Asp Ala Asp Leu Gly Val Asn
385                 390                 395                 400

Ile Val Thr Gln Ala Arg Thr Thr Pro Thr Ile Leu Thr Gly Cys Lys
                405                 410                 415

Lys Gly His Asn Phe Ser Phe Ser Gly Glu Val Arg Ala Ser Pro Cys
            420                 425                 430

Asn Phe Glu Leu Thr Ala Glu Asp Leu Leu Arg Ile Met Asp His Thr
        435                 440                 445

Asn Cys Glu Gly Phe Thr Tyr Phe Gly Glu Gly Ile Val Asp Gly Tyr
    450                 455                 460

Thr Glu Val Val Glu Lys Ala Arg Ser Ser Gly Phe Arg Ala Leu Thr
465                 470                 475                 480

Trp Leu Ser Ser Lys Ile Glu Asn Thr Lys Lys Ile Phe Gly Ala
                485                 490                 495

Glu Ala Ser Pro Tyr Cys Pro Val Ala Lys Arg Val Phe Asn Ile Ile
            500                 505                 510

Tyr Thr Asn Asn Cys Thr Pro Leu Gly Leu Pro Asp Lys Ser Lys Ile
        515                 520                 525

Ile Gly Pro Gly Thr Phe Asp Ile Ser Gly Arg Asp Glu Phe Ile Phe
    530                 535                 540

Pro Lys Leu Pro Tyr His Val Asp Asp Phe Ile Leu Leu Ser Leu Ile
545                 550                 555                 560

Ala Met Ser Asp Phe Ala Pro Glu Thr Ser Ser Ile Ile Tyr Leu Ala
                565                 570                 575
```

-continued

```
Leu His Tyr Leu Met Pro Ser Asn Asp Asn Arg Asp Phe Val Met Asp
            580                 585                 590

Leu Asp Pro Asn Lys Leu Asn Leu Thr Ala Thr Lys Ser Val Ala Ser
        595                 600                 605

Val Val Pro Thr Ser Val Asn Val Leu Gly Glu Trp Val Cys Val Lys
    610                 615                 620

Pro Ser Trp Trp Pro Tyr Ser Ala Glu Ile Thr Asn Leu Ile Gly Gly
625                 630                 635                 640

Val Ile Thr Val Ala Asp Leu Val Ile Lys Thr Ile Glu Glu Leu Leu
                645                 650                 655

Asn Leu Trp Thr Glu Ala Thr Ala Val Ala Phe Leu Ala Ala Leu Ile
            660                 665                 670

Lys Ile Phe Arg Gly Gln Pro Ile Gln Ala Val Ala Trp Leu Ile Ile
        675                 680                 685

Ile Gly Gly Ala Gln Ala Gln Thr Cys Asn Pro Glu Phe Met Tyr Ala
    690                 695                 700

Leu Ala Lys Asn Thr Ser Ile Gly Ser Leu Gly Pro Glu Ser Leu Thr
705                 710                 715                 720

Thr Arg Trp Tyr Gln Leu Thr Ser Gly Phe Lys Leu Thr Asp Ser Thr
                725                 730                 735

Ile Glu Val Thr Cys Val Gly Ala Asn Met Arg Ile His Val Val Cys
            740                 745                 750

Pro Leu Val Ser Asp Arg Tyr Leu Ala Ile Asn His Pro Arg Ala Leu
        755                 760                 765

Pro Thr Thr Ala Trp Phe Arg Lys Ile His Thr Gln His Glu Val Pro
    770                 775                 780

Arg Glu Arg Ile Met Ser Glu Ser Lys Arg Arg Tyr Thr Cys Pro Cys
785                 790                 795                 800

Gly Ser Lys Pro Val Val Arg Ser Thr Thr Gln Phe Asn Pro Ile Ser
                805                 810                 815

Ile Ser Thr Pro Ser Phe Glu Leu Glu Cys Pro Arg Gly Trp Thr Gly
            820                 825                 830

Ala Val Glu Cys Thr Leu Val Ser Pro Ser Thr Leu Thr Thr Glu Thr
        835                 840                 845

Ile Phe Thr Tyr Arg Lys Pro Lys Pro Phe Gly Leu Glu Asn Trp Cys
    850                 855                 860

Lys Tyr Thr Val Val Glu Lys Gly Ile Leu Tyr Ser Cys Lys Phe Gly
865                 870                 875                 880

Gly Asn Ser Thr Cys Ile Lys Gly Leu Ile Val Lys Gly Gln Arg Glu
                885                 890                 895

Asp Lys Val Arg Tyr Cys Glu Trp Cys Gly Tyr Lys Phe Ser Ser Pro
            900                 905                 910

Asn Gly Leu Pro Gln Tyr Pro Leu Gly Leu Cys Glu Lys Glu Gln Ser
        915                 920                 925

Glu Gly Leu Arg Asp Tyr Gly Asp Phe Pro Cys Cys Asn Asn Gly Thr
    930                 935                 940

Cys Ile Asp Lys Glu Gly Ser Val Gln Cys Tyr Ile Gly Asp Lys Lys
945                 950                 955                 960

Val Thr Val Lys Leu Tyr Asn Ala Ser Leu Leu Ala Pro Met Pro Cys
                965                 970                 975

Lys Pro Ile Val Tyr Asn Ser Gln Gly Pro Ala Pro Lys Thr Cys
            980                 985                 990

Thr Tyr Arg Trp Ala Ser Thr Leu  Glu Asn Lys Tyr Tyr  Glu Pro Arg
```

```
                995               1000              1005
Asp Ser Tyr Tyr Gln Gln Tyr Ile Ile Lys Ser Gly Tyr Gln Tyr
    1010            1015            1020

Trp Phe Asp Leu Thr Ala Lys Asp His Val Ala Asp Trp Ile Thr
    1025            1030            1035

Lys Tyr Phe Pro Ile Ile Ile Val Ala Leu Leu Gly Gly Arg Gly
    1040            1045            1050

Thr Leu Trp Val Leu Ile Ala Tyr Glu Leu Leu Thr Gln Tyr Glu
    1055            1060            1065

Val Val Gly Asp Glu Asn Ile Val Ala Gln Ala Glu Ala Leu Val
    1070            1075            1080

Ile Gly Asn Ile Leu Met Ser Leu Asp Leu Glu Ile Ile Ser Cys
    1085            1090            1095

Phe Leu Leu Leu Leu Ile Val Val Lys Lys Gln Ala Val Arg Arg
    1100            1105            1110

Thr Leu Ala Leu Leu Phe His Trp Ile Thr Met Asn Pro Phe Gln
    1115            1120            1125

Ser Val Met Ile Thr Val Val Tyr Phe Val Gly Leu Val Arg Ala
    1130            1135            1140

Glu Glu Gly Thr Lys Glu Gly Ser Thr Ser Gly Pro Pro Ile His
    1145            1150            1155

Val Val Ala Ile Leu Leu Phe Leu Leu Tyr His Thr Val Lys Tyr
    1160            1165            1170

Lys Asp Phe Asn Ile Ala Met Ile Leu Leu Ile Thr Leu Ser Leu
    1175            1180            1185

Lys Ser Ser Ser Tyr Ile His Thr Ser Leu Tyr Glu Ile Pro Leu
    1190            1195            1200

Leu Val Ala Val Ile Ser Leu Thr Cys Ser Ile Tyr Ile Phe Asp
    1205            1210            1215

Leu Gln Val Lys Ser Lys Leu Val Ala Pro Thr Ile Gly Ile Ile
    1220            1225            1230

Gly Val Thr Leu Ala Met Arg Val Leu Trp Leu Val Arg Gln Met
    1235            1240            1245

Thr Ile Pro Thr Pro Ser Val Ser Ile Ser Leu Ile Asp Pro Lys
    1250            1255            1260

Met Val Ile Ile Leu Tyr Leu Ile Ser Leu Thr Ile Thr Val Asn
    1265            1270            1275

His Asn Leu Asp Leu Ala Ser Tyr Cys Leu Lys Leu Gly Pro Phe
    1280            1285            1290

Ile Leu Ser Phe Leu Thr Met Trp Val Asp Val Val Ile Leu Leu
    1295            1300            1305

Leu Met Leu Pro Trp Tyr Glu Leu Val Lys Val Tyr Tyr Leu Lys
    1310            1315            1320

Lys Lys Lys Glu Asp Val Glu Thr Trp Phe Gln Asn Ser Gly Ile
    1325            1330            1335

Ser Thr Gln Glu Thr Ser Pro Tyr Gly Phe Asp Phe Ser Ser Pro
    1340            1345            1350

Gly Glu Gly Val His Thr Leu Pro Met Gln Asn Lys Thr Lys Phe
    1355            1360            1365

Cys Arg Thr Ala Tyr Met Thr Val Leu Arg Ala Leu Val Ile Thr
    1370            1375            1380

Ala Ile Ser Ser Val Trp Lys Pro Ile Ile Leu Ala Glu Leu Leu
    1385            1390            1395
```

```
Ile Glu Ala Val Tyr Trp Thr His Ile Lys Ile Ala Lys Glu Leu
    1400                1405                1410

Ala Gly Ser Ser Arg Phe Val Ala Arg Phe Ile Ala Ser Ile Ile
    1415                1420                1425

Glu Leu Asn Trp Ala Met Asp Glu Lys Glu Ala Ser Arg Tyr Lys
    1430                1435                1440

Arg Phe Tyr Leu Leu Ser Ser Lys Ile Thr Asp Leu Met Val Lys
    1445                1450                1455

His Lys Ile Gln Asn Glu Thr Val Lys Ser Trp Phe Glu Glu Thr
    1460                1465                1470

Glu Ile Phe Gly Ile Gln Lys Val Ala Met Val Ile Arg Ala His
    1475                1480                1485

Ser Leu Ser Leu Glu Pro Asn Ala Ile Leu Cys Ser Val Cys Glu
    1490                1495                1500

Glu Lys Gln Asn Gln Lys Ala Lys Arg Pro Cys Pro Lys Cys Gly
    1505                1510                1515

Ser Arg Gly Thr Gln Ile Lys Cys Gly Leu Thr Leu Ala Glu Phe
    1520                1525                1530

Glu Glu Glu His Tyr Lys Lys Ile Tyr Ile Leu Glu Gly Gln Asp
    1535                1540                1545

Glu Thr Pro Met Arg Lys Glu Glu Arg Gln Gln Val Thr Tyr Val
    1550                1555                1560

Ser Arg Gly Ala Leu Phe Leu Arg Asn Leu Pro Ile Leu Ala Ser
    1565                1570                1575

Lys Asn Lys Tyr Leu Leu Val Gly Asn Leu Gly Met Glu Leu Gln
    1580                1585                1590

Asp Leu Glu Ser Met Gly Trp Ile Ile Arg Gly Pro Ala Val Cys
    1595                1600                1605

Lys Lys Ile Ile His His Glu Lys Cys Arg Pro Ser Ile Pro Asp
    1610                1615                1620

Lys Leu Met Ala Phe Phe Gly Ile Met Pro Arg Gly Val Thr Pro
    1625                1630                1635

Arg Ala Pro Thr Arg Phe Pro Val Ser Leu Leu Lys Ile Arg Arg
    1640                1645                1650

Gly Phe Glu Thr Gly Trp Ala Tyr Thr His Pro Gly Gly Val Ser
    1655                1660                1665

Ser Val Met His Val Thr Ala Gly Ser Asp Ile Tyr Val Asn Asp
    1670                1675                1680

Ser Ile Gly Arg Thr Lys Ile Gln Cys Gln Asp Lys Asn Thr Thr
    1685                1690                1695

Thr Asp Glu Cys Glu Tyr Gly Val Lys Thr Asp Ser Gly Cys Ser
    1700                1705                1710

Asp Gly Ala Arg Cys Tyr Val Ile Asn Pro Glu Ala Thr Asn Ile
    1715                1720                1725

Ala Gly Thr Lys Gly Ala Met Val His Leu Arg Lys Ala Gly Gly
    1730                1735                1740

Glu Phe Asn Cys Val Thr Ala Gln Gly Thr Pro Ala Phe Tyr Asn
    1745                1750                1755

Leu Lys Asn Leu Lys Gly Trp Ser Gly Leu Pro Ile Phe Glu Ala
    1760                1765                1770

Ala Thr Gly Arg Val Val Gly Arg Val Lys Ala Gly Lys Asn Thr
    1775                1780                1785
```

```
Asp Asn Ala Pro Thr Thr Ile Met Ser Gly Thr Gln Val Ala Lys
    1790                1795                1800

Pro Ser Glu Cys Asp Leu Glu Ser Val Val Arg Lys Leu Glu Thr
    1805                1810                1815

Met Asn Arg Gly Glu Phe Lys Gln Val Thr Leu Ala Thr Gly Ala
    1820                1825                1830

Gly Lys Thr Thr Met Leu Pro Lys Leu Leu Ile Glu Ser Ile Gly
    1835                1840                1845

Arg His Lys Arg Val Leu Val Leu Ile Pro Leu Arg Ala Ala Ala
    1850                1855                1860

Glu Gly Val Tyr Gln Tyr Met Arg Thr Lys His Pro Ser Ile Ser
    1865                1870                1875

Phe Asn Leu Arg Ile Gly Asp Leu Lys Glu Gly Asp Met Ala Thr
    1880                1885                1890

Gly Ile Thr Tyr Ala Ser Tyr Gly Tyr Phe Cys Gln Met Asp Met
    1895                1900                1905

Pro Arg Leu Glu Asn Ala Met Lys Glu Tyr His Tyr Ile Phe Leu
    1910                1915                1920

Asp Glu Tyr His Cys Ala Thr Pro Glu Gln Leu Ala Val Met Ser
    1925                1930                1935

Lys Ile His Arg Phe Gly Glu Ser Val Arg Val Ile Ala Met Thr
    1940                1945                1950

Ala Thr Pro Ser Gly Thr Val Ser Thr Thr Gly Gln Lys Phe Thr
    1955                1960                1965

Ile Glu Glu Val Val Val Pro Glu Val Met Lys Gly Glu Asp Leu
    1970                1975                1980

Ala Asp Asp Tyr Ile Glu Ile Ala Gly Leu Lys Val Pro Lys Lys
    1985                1990                1995

Glu Leu Glu Gly Asn Val Leu Thr Phe Val Pro Thr Arg Lys Met
    2000                2005                2010

Ala Ser Glu Thr Ala Lys Lys Leu Thr Thr Gln Gly Tyr Asn Ala
    2015                2020                2025

Gly Tyr Tyr Phe Ser Gly Glu Asp Pro Ser Ser Leu Arg Thr Thr
    2030                2035                2040

Thr Ser Lys Ser Pro Tyr Ile Val Val Ala Thr Asn Ala Ile Glu
    2045                2050                2055

Ser Gly Val Thr Leu Pro Asp Leu Asp Thr Val Ile Asp Thr Gly
    2060                2065                2070

Met Lys Cys Glu Lys Arg Leu Arg Ile Glu Asn Lys Ala Pro Tyr
    2075                2080                2085

Ile Val Thr Gly Leu Lys Arg Met Ala Ile Thr Thr Gly Glu Gln
    2090                2095                2100

Ala Gln Arg Lys Gly Arg Val Gly Arg Val Lys Pro Gly Arg Tyr
    2105                2110                2115

Leu Arg Gly Pro Glu Asn Thr Ala Gly Glu Lys Asp Tyr His Tyr
    2120                2125                2130

Asp Leu Leu Gln Ala Gln Arg Tyr Gly Ile Gln Asp Ser Ile Asn
    2135                2140                2145

Ile Thr Lys Ser Phe Arg Glu Met Asn Tyr Asp Trp Ala Leu Tyr
    2150                2155                2160

Glu Glu Asp Pro Leu Lys Ile Ala Gln Leu Glu Leu Leu Asn Thr
    2165                2170                2175

Leu Leu Ile Ser Arg Asp Leu Pro Val Val Thr Lys Asn Leu Met
```

-continued

```
            2180                2185                2190

Ala Arg Thr Thr His Pro Glu Pro Ile Gln Leu Ala Tyr Asn Ser
        2195                2200                2205

Leu Glu Thr Pro Val Pro Val Ala Phe Pro Lys Val Lys Asn Gly
        2210                2215                2220

Glu Val Thr Asp Ala His Glu Thr Tyr Glu Leu Met Thr Cys Arg
        2225                2230                2235

Lys Leu Glu Lys Asp Pro Pro Ile Tyr Leu Tyr Ala Thr Glu Glu
        2240                2245                2250

Glu Asp Leu Val Val Asp Ile Leu Gly Leu Lys Trp Pro Asp Ala
        2255                2260                2265

Thr Glu Arg Ala Val Leu Glu Val Gln Asp Ala Leu Gly Gln Ile
        2270                2275                2280

Thr Gly Leu Ser Ala Gly Glu Thr Ala Leu Leu Ile Ala Leu Leu
        2285                2290                2295

Gly Trp Val Gly Tyr Glu Ala Leu Val Lys Arg His Val Pro Met
        2300                2305                2310

Val Thr Asp Ile Tyr Thr Leu Glu Asp Glu Lys Leu Glu Asp Thr
        2315                2320                2325

Thr His Leu Gln Phe Ala Pro Asp Asp Leu Asn Asn Ser Asp Thr
        2330                2335                2340

Ile Glu Leu Gln Asp Leu Ser Asn His Gln Ile Gln Gln Ile Leu
        2345                2350                2355

Glu Gly Gly Lys Glu Tyr Val Gly Gln Ala Tyr Gln Phe Leu Arg
        2360                2365                2370

Leu Gln Ala Glu Arg Ala Ala Asn Ser Asp Lys Gly Lys Lys Ala
        2375                2380                2385

Met Ala Ala Ala Pro Leu Leu Ala His Lys Phe Leu Glu Tyr Leu
        2390                2395                2400

Gln Glu His Ala Gly Asp Ile Lys Lys Tyr Gly Leu Trp Gly Val
        2405                2410                2415

His Thr Ala Leu Tyr Asn Ser Ile Lys Glu Arg Leu Gly His Glu
        2420                2425                2430

Thr Ala Phe Ala Ser Leu Val Ile Lys Trp Ile Ala Phe Ser Ser
        2435                2440                2445

Asp Gly Val Pro Gly Met Ile Lys Gln Ala Ala Val Asp Leu Val
        2450                2455                2460

Val Tyr Tyr Ile Ile Asn Arg Pro Glu Tyr Gln Gly Asp Lys Glu
        2465                2470                2475

Thr Gln Asn Ala Gly Arg Gln Phe Val Gly Ser Leu Phe Val Ser
        2480                2485                2490

Cys Leu Ala Glu Tyr Thr Phe Lys Asn Phe Asn Lys Ser Ala Leu
        2495                2500                2505

Glu Gly Leu Ile Glu Pro Leu Ser Tyr Leu Pro Tyr Ala Ser
        2510                2515                2520

Ser Ala Leu Lys Leu Phe Leu Pro Thr Arg Leu Glu Ser Val Val
        2525                2530                2535

Ile Leu Ser Thr Thr Ile Tyr Arg Thr Tyr Leu Ser Ile Arg Lys
        2540                2545                2550

Gly Ser Ser Gln Gly Leu Ala Gly Leu Ala Val Ser Ser Ala Met
        2555                2560                2565

Glu Ile Met Asn Gln Asn Pro Ile Ser Val Ala Ile Ala Leu Ala
        2570                2575                2580
```

```
Leu Gly Val Gly Ala Ile Ala Ala His Asn Ala Ile Glu Ser Ser
    2585                2590                2595

Glu Ala Lys Arg Thr Leu Leu Met Lys Val Phe Val Lys Asn Phe
    2600                2605                2610

Leu Asp Gln Ala Ala Thr Asp Glu Leu Val Lys Glu Asn Pro Glu
    2615                2620                2625

Lys Ile Ile Met Ala Val Phe Glu Gly Ile Gln Thr Ala Gly Asn
    2630                2635                2640

Pro Leu Arg Leu Val Tyr His Leu Tyr Ala Met Phe Tyr Lys Gly
    2645                2650                2655

Trp Thr Ala Ala Glu Ile Ala Glu Lys Thr Ala Gly Arg Asn Ile
    2660                2665                2670

Phe Val Leu Thr Ile Phe Glu Gly Leu Glu Met Leu Gly Leu Asp
    2675                2680                2685

Ala Asp Ser Lys Trp Arg Asn Leu Ser Ser Asn Tyr Leu Ile Asp
    2690                2695                2700

Ala Val Lys Lys Ile Ile Glu Lys Met Thr Lys Thr Ala Thr Ser
    2705                2710                2715

Phe Thr Tyr Ser Phe Leu Lys Ser Leu Leu Pro Ala Pro Phe Ser
    2720                2725                2730

Cys Thr Lys Ser Glu Arg Asp Pro Arg Ile Gly Trp Pro Gln Lys
    2735                2740                2745

Asp Tyr Asp Tyr Leu Glu Val Arg Cys Ala Cys Gly Tyr Asn Arg
    2750                2755                2760

Arg Ala Ile Lys Arg Asp Ser Gly Pro Val Leu Trp Glu Thr Leu
    2765                2770                2775

Glu Glu Thr Gly Pro Glu Tyr Cys His Asn Arg Gly Glu Arg Gly
    2780                2785                2790

Leu Ser Asn Val Lys Thr Thr Arg Cys Phe Val Gln Gly Glu Glu
    2795                2800                2805

Ile Pro Pro Ile Ala Leu Arg Lys Gly Val Gly Glu Met Leu Val
    2810                2815                2820

Lys Gly Val Ser Phe Arg Ile Asp Phe Asp Lys Asp Lys Ile Leu
    2825                2830                2835

Ser Thr Asp Lys Trp Lys Val Pro His Arg Ala Val Thr Ser Ile
    2840                2845                2850

Phe Glu Asp Trp Gln Gly Ile Gly Tyr Arg Glu Ala Tyr Leu Gly
    2855                2860                2865

Thr Lys Pro Asp Tyr Gly Gly Leu Val Pro Arg Ser Cys Val Thr
    2870                2875                2880

Val Thr Lys Gln Gly Leu Thr Phe Leu Lys Thr Ala Arg Gly Met
    2885                2890                2895

Ala Phe Thr Thr Asp Leu Thr Ile Gln Asn Ile Lys Met Leu Ile
    2900                2905                2910

Ala Thr Cys Phe Lys Asn Lys Val Lys Glu Gly Glu Ile Pro Ala
    2915                2920                2925

Thr Ile Glu Gly Glu Thr Trp Ile Asn Ile Pro Leu Val Asn Glu
    2930                2935                2940

Asp Thr Gly Thr Ile Lys Pro Ser Phe Gly Glu Arg Val Ile Pro
    2945                2950                2955

Glu Pro Tyr Glu Glu Asp Pro Leu Glu Gly Pro Ser Val Ile Val
    2960                2965                2970
```

-continued

| | | | | | | | | | | | | |
|---|---|---|---|---|---|---|---|---|---|---|---|---|
| Glu | Thr | Gly | Gly | Ile | Ala | Ile | Asn | Gln | Ile | Gly | Val | Asn Pro Gln |
| 2975 | | | | | 2980 | | | | | 2985 | | |
| Ser | Ser | Thr | Cys | Gly | Thr | Val | Phe | Thr | Ala | Val | Lys | Asp Leu Cys |
| 2990 | | | | | 2995 | | | | | 3000 | | |
| Gln | Thr | Val | Ser | Asn | Lys | Ala | Lys | Asn | Ile | Lys | Ile | Gly Phe Ser |
| 3005 | | | | | 3010 | | | | | 3015 | | |
| Glu | Gly | Gln | Tyr | Pro | Gly | Pro | Gly | Val | Ala | Lys | Lys | Thr Leu Asn |
| 3020 | | | | | 3025 | | | | | 3030 | | |
| Gln | Leu | Ile | Gln | Asp | Glu | Asp | Pro | Lys | Pro | Phe | Ile | Phe Val Cys |
| 3035 | | | | | 3040 | | | | | 3045 | | |
| Gly | Ser | Asp | Lys | Ser | Met | Ser | Asn | Arg | Ala | Lys | Thr | Ala Arg Asn |
| 3050 | | | | | 3055 | | | | | 3060 | | |
| Ile | Lys | Arg | Ile | Thr | Thr | Thr | Pro | Glu | Lys | Phe | Arg | Asp Leu |
| 3065 | | | | | 3070 | | | | | 3075 | | |
| Ala | Lys | Asn | Lys | Lys | Leu | Ile | Ile | Val | Leu | Leu | Gly | Asp Arg Tyr |
| 3080 | | | | | 3085 | | | | | 3090 | | |
| His | Glu | Asp | Ile | Glu | Lys | Tyr | Ala | Asp | Phe | Lys | Gly | Thr Phe Leu |
| 3095 | | | | | 3100 | | | | | 3105 | | |
| Thr | Arg | Gln | Thr | Leu | Glu | Ala | Leu | Ala | Ser | Ala | Lys | Ala Val Glu |
| 3110 | | | | | 3115 | | | | | 3120 | | |
| Lys | Asp | Met | Thr | Lys | Lys | Glu | Ala | Ala | Arg | Val | Leu | Ala Met Glu |
| 3125 | | | | | 3130 | | | | | 3135 | | |
| Glu | Lys | Asp | Glu | Leu | Glu | Leu | Pro | Gly | Trp | Leu | His | Thr Asp Ala |
| 3140 | | | | | 3145 | | | | | 3150 | | |
| Pro | Lys | Phe | Leu | Asp | Ile | Thr | Lys | Asp | Asn | Ile | Thr | His His Leu |
| 3155 | | | | | 3160 | | | | | 3165 | | |
| Ile | Gly | Asp | Met | Gln | Ser | Leu | Arg | Glu | Arg | Ala | Gly | Glu Ile Gly |
| 3170 | | | | | 3175 | | | | | 3180 | | |
| Ala | Lys | Ala | Thr | Thr | Gln | Ile | Thr | Lys | Lys | Gly | Ser | Val Tyr Thr |
| 3185 | | | | | 3190 | | | | | 3195 | | |
| Ile | Asn | Leu | Ser | Thr | Trp | Trp | Glu | Ser | Glu | Arg | Leu | Ala Ser Leu |
| 3200 | | | | | 3205 | | | | | 3210 | | |
| Glu | Pro | Leu | Phe | Arg | Glu | Leu | Leu | Ser | Lys | Cys | Arg | Pro Val Asp |
| 3215 | | | | | 3220 | | | | | 3225 | | |
| Arg | Glu | Thr | Tyr | Lys | Asn | Cys | His | Phe | Ala | Thr | Ala | Ala Gln Leu |
| 3230 | | | | | 3235 | | | | | 3240 | | |
| Ala | Gly | Gly | Asn | Trp | Val | Pro | Val | Ala | Pro | Val | Val | His Leu Gly |
| 3245 | | | | | 3250 | | | | | 3255 | | |
| Glu | Ile | Pro | Val | Lys | Lys | Lys | Lys | Thr | Leu | Pro | Tyr | Glu Ala Tyr |
| 3260 | | | | | 3265 | | | | | 3270 | | |
| Lys | Leu | Leu | Lys | Glu | Met | Val | Asp | Ser | Glu | Lys | Glu | Phe His Lys |
| 3275 | | | | | 3280 | | | | | 3285 | | |
| Pro | Val | Ser | Arg | Glu | Lys | His | Gln | Trp | Ile | Leu | Asn | Lys Val Lys |
| 3290 | | | | | 3295 | | | | | 3300 | | |
| Thr | Gly | Gly | Asp | Leu | Gly | Leu | Lys | Asn | Leu | Val | Cys | Pro Gly Arg |
| 3305 | | | | | 3310 | | | | | 3315 | | |
| Val | Gly | Glu | Pro | Ile | Leu | Arg | Glu | Lys | Lys | Phe | Asn | Ile Tyr |
| 3320 | | | | | 3325 | | | | | 3330 | | |
| Asn | Lys | Arg | Ile | Thr | Ser | Thr | Met | Leu | Ser | Val | Gly | Ile Arg Pro |
| 3335 | | | | | 3340 | | | | | 3345 | | |
| Glu | Lys | Leu | Pro | Val | Val | Arg | Ala | Gln | Thr | Ser | Thr | Lys Glu Phe |
| 3350 | | | | | 3355 | | | | | 3360 | | |
| His | Glu | Ala | Ile | Arg | Asp | Lys | Ile | Asp | Lys | Lys | Ala | Asn Thr Gln |

```
            3365                3370                3375

Thr Pro Gly Leu His Lys Glu Leu Leu Glu Ile Phe Asn Ser Ile
    3380                3385                3390

Cys Ala Ile Pro Glu Leu Arg Asn Thr Tyr Lys Glu Val Asp Trp
    3395                3400                3405

Asp Val Leu Thr Ser Gly Ile Asn Arg Lys Gly Ala Ala Gly Tyr
    3410                3415                3420

Phe Glu Lys Met Asn Ile Gly Glu Ile Asp Ser Asp Lys Lys
    3425                3430                3435

Ser Val Glu Gln Leu Ile Lys Arg Met Lys Ser Gly Leu Glu Phe
    3440                3445                3450

Asn Tyr Tyr Glu Thr Ala Ile Pro Lys Asn Glu Lys Arg Ala Val
    3455                3460                3465

Val Asp Asp Trp Met Glu Gly Asp Tyr Val Glu Glu Lys Arg Pro
    3470                3475                3480

Arg Val Ile Gln Tyr Pro Glu Ala Lys Met Arg Leu Ala Ile Thr
    3485                3490                3495

Lys Val Met Tyr Asn Trp Val Lys Gln Lys Pro Ile Val Ile Pro
    3500                3505                3510

Gly Tyr Glu Gly Lys Thr Pro Leu Phe His Val Phe Asp Lys Val
    3515                3520                3525

His Lys Glu Trp Lys Asn Phe Asn Ser Pro Val Ala Val Ser Phe
    3530                3535                3540

Asp Thr Lys Ala Trp Asp Thr Gln Val Thr Pro Lys Asp Leu Leu
    3545                3550                3555

Leu Ile Ser Glu Ile Gln Lys Tyr Tyr Lys Lys Glu Tyr His
    3560                3565                3570

Arg Phe Ile Asp Asn Leu Thr Glu Lys Met Val Glu Val Pro Val
    3575                3580                3585

Val Cys Glu Asp Gly Asn Val Tyr Ile Arg Glu Gly Gln Arg Gly
    3590                3595                3600

Ser Gly Gln Pro Asp Thr Ser Ala Gly Asn Ser Met Leu Asn Val
    3605                3610                3615

Leu Thr Met Ile Tyr Ala Phe Cys Lys Ala Asn Ser Ile Pro Tyr
    3620                3625                3630

Ser Ala Phe His Arg Val Ala Lys Ile His Val Cys Gly Asp Asp
    3635                3640                3645

Gly Phe Leu Ile Thr Glu Lys Ser Phe Gly Glu Ala Phe Ala Ile
    3650                3655                3660

Lys Gly Pro Gln Ile Leu Met Glu Ala Gly Lys Pro Gln Lys Leu
    3665                3670                3675

Ile Gly Glu Phe Gly Leu Lys Leu Ala Tyr Lys Phe Asp Asp Ile
    3680                3685                3690

Glu Phe Cys Ser His Thr Pro Ile Lys Val Arg Trp Ala Asp Asn
    3695                3700                3705

Asn Thr Ser Tyr Met Pro Gly Arg Asp Thr Ala Thr Ile Leu Ala
    3710                3715                3720

Lys Met Ala Thr Arg Leu Asp Ser Ser Gly Glu Arg Gly Thr Glu
    3725                3730                3735

Gly Tyr Glu Leu Ala Val Ala Phe Ser Phe Leu Leu Met Tyr Ser
    3740                3745                3750

Trp Asn Pro Leu Val Arg Arg Ile Cys Leu Leu Val Met Ser Thr
    3755                3760                3765
```

-continued

```
Ile Asp Thr Lys Glu Ala Ser Gln Asn Asn Thr Ile Tyr Thr Phe
    3770            3775            3780

Arg Gly Asp Pro Ile Gly Ala Tyr Thr Glu Val Ile Gly Tyr Arg
    3785            3790            3795

Leu Asp Gln Leu Lys Gln Thr Glu Phe Ser Lys Leu Ala Gln Leu
    3800            3805            3810

Asn Leu Ser Met Ala Ile Leu Gln Ile Tyr Asn Lys Asn Thr Thr
    3815            3820            3825

Lys Arg Leu Ile Glu Asp Cys Val Lys Leu Gly Asn Gln Asn Lys
    3830            3835            3840

Gln Ile Leu Val Asn Ala Asp Arg Leu Ile Ser Lys Lys Thr Gly
    3845            3850            3855

Tyr Thr Tyr Glu Pro Thr Ala Gly His Thr Lys Ile Gly Lys His
    3860            3865            3870

Tyr Glu Glu Ile Asn Leu Leu Lys Asp Thr Pro Gln Lys Thr Val
    3875            3880            3885

Tyr Gln Gly Thr Glu Arg Tyr Val Pro Gly Pro Ile Arg Asp Phe
    3890            3895            3900

Ile Leu Arg Arg Leu Lys Ile Leu Glu Ile Val Gly Leu Lys Phe
    3905            3910            3915
```